(12) United States Patent
Nishida et al.

(10) Patent No.: US 8,642,582 B2
(45) Date of Patent: Feb. 4, 2014

(54) MORPHOLINONE COMPOUNDS AS FACTOR IXA INHIBITORS

(75) Inventors: Hidemitsu Nishida, Tokyo (JP);
Fumihiko Saitoh, Tokyo (JP);
Tomokazu Hirabayashi, Tokyo (JP);
Samuel Chackalamannil, Califon, NJ (US); Tin-Yau Chan, Edison, NJ (US);
Mariappan V. Chelliah, Edison, NJ (US); Martin C. Clasby, Plainsboro, NJ (US); Michael Dwyer, Scotch Plains, NJ (US); William J. Greenlee, Teaneck, NJ (US); Yan Xia, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 498 days.

(21) Appl. No.: 12/744,736

(22) PCT Filed: Dec. 3, 2009

(86) PCT No.: PCT/US2009/066548
§ 371 (c)(1),
(2), (4) Date: May 26, 2010

(87) PCT Pub. No.: WO2010/065717
PCT Pub. Date: Jun. 10, 2010

(65) Prior Publication Data
US 2011/0059958 A1    Mar. 10, 2011

Related U.S. Application Data

(60) Provisional application No. 61/120,328, filed on Dec. 5, 2008, provisional application No. 61/150,955, filed on Feb. 9, 2009, provisional application No. 61/165,214, filed on Mar. 31, 2009, provisional application No. 61/238,455, filed on Aug. 31, 2009.

(51) Int. Cl.
*A61K 31/535*    (2006.01)

(52) U.S. Cl.
USPC ........................................ 514/183; 514/228.8

(58) Field of Classification Search
None
See application file for complete search history.

(56) References Cited

U.S. PATENT DOCUMENTS

| | | | | |
|---|---|---|---|---|
| 6,958,402 B2 * | 10/2005 | Allerton et al. | ............ | 548/340.1 |
| 7,652,020 B2 * | 1/2010 | Guo et al. | .................. | 514/265.1 |
| 2006/0252778 A1 * | 11/2006 | Guo et al. | .................. | 514/265.1 |
| 2011/0135650 A1 * | 6/2011 | Chackalamannil et al. | ......................... | 424/145.1 |

FOREIGN PATENT DOCUMENTS

| | | |
|---|---|---|
| DE | 103 15 377 A1 | 10/2004 |
| EP | 1 182 202 A1 | 2/2002 |
| EP | 1 447 401 A1 | 8/2004 |
| EP | 1864971 A1 | 12/2007 |
| WO | WO03005824 A2 | 1/2003 |
| WO | WO 03/061652 A1 | 7/2003 |
| WO | WO 2005/026165 | 3/2005 |
| WO | 2005/073201 | 8/2005 |
| WO | WO2008/031508 A1 | 3/2008 |
| WO | 2010/065717 A1 | 6/2010 |

OTHER PUBLICATIONS

Matsunaga S, Shibasaki M et al. : "Sc3+-Catalyzed Aldol-Type Additions of N-Benzolycyclopropanecarboxamides via Iodide-Mediated Ring-Opening: Stereoselective Synthesis of gamma-Lactams", Organic Letters, vol. 10, No. 8, Mar. 18, 2008, pp. 1661-1664, XP002573322, the general formula of the products in the abstract; entry 5 in table 2.

Tsukada, Hidetaka et al: "Synthesis and lateral root-inducting activity of N-benzyl-3-substituted-2-piperidones" Journal of the Faculty of Agriculture Kyushu Univerisity, Kyushu Daigaku Nogakubu, Fukuoka, JP, vol. 44, No. 1-2, Jan. 1, 1999, pp. 119-126, XP009131017, ISSN: 0023-6152, compounds 25-30 in table 1.

Bellesia, Franco et al. "Rearrangement of N-allyl-.alpha.,.alpha.-dichloroamides,.beta.- or .gamma.—functionalized, to substituted analogues of the .gamma.-aminobutyric acid (GABA) "Synthetic Communications, Taylor & Francis Group, Philadelphia, PA, vol. 29, No. 21, Mar. 19, 1999, pp. 3739-3748, XP009131002, ISSN: 0039-7911, compound G5 on p. 3746; scheme 2; table.

Lee, Jin Soo et al.: "Synthesis and structure-activity relationships of 1 .beta.-Methyl-2-( .alpha.-functionalized lactamyl) Carbapenems" Korean Journal of Medicinal Chemistry, Korean Chemical Society, Seoul, KR, vol. 8, No. 2, Jan. 1, 1998, pp. 102-116, XP009131001 ISSN: 1225-0058 , Compounds 7f, 7g in scheme 1, table 1 and on pp. 114-115.

J.M. Smallheer et al: "SAR and factor IXa crystal structure of a dual inhibitor of factors IXa and Xa" Bioorganic & Medicinal Chemistry Letters, Pergamon, Elsevier Science, GB LNKD-DOI:10.1016/J/BMCL. 2004.08.034, vol. 14, No. 21, Nov. 1, 2004 5263-5267-XP004580511 ISSN: 0960-894X. The Whole Document.

International Search Report for PCT/US2009/066548; Performed by the European Patent Office; Completed Mar. 23, 2010.

International Search Report for PCT/US2010/036853; Performed by the European Patent Office; Completed Jul. 8, 2010.

* cited by examiner

*Primary Examiner* — Craig Ricci
*Assistant Examiner* — Jared D Barsky
(74) *Attorney, Agent, or Firm* — Nicole M. Beeler; Catherine D. Fitch

(57) ABSTRACT

The present invention provides a compound of Formula (I)

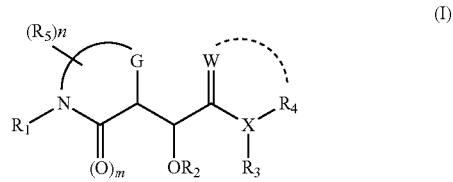

as described herein, or a pharmaceutically acceptable salt or a solvate thereof. The present invention also provides pharmaceutical compositions comprising one or more said compounds, and methods for using said compounds for treating or preventing a thromboses, embolisms, hypercoagulability or fibrotic changes.

19 Claims, No Drawings

MORPHOLINONE COMPOUNDS AS FACTOR IXA INHIBITORS

CROSS REFERENCE TO RELATED APPLICATIONS

This application is a U.S. National Phase application under 35 U.S.C. §371 of PCT Application No. PCT/US2009/066548 filed Dec. 3, 2009, which claims priority under 35 U.S.C. §119(e) from U.S. Provisional Application(s) No. 61/120,328, filed on Dec. 5, 2008 and U.S. Provisional Application No. 61/150,955, filed on Feb. 9, 2009 and U.S. Provisional Application No. 61/165,214 filed on Mar. 31, 2009, and U.S. Provisional Application No. 61/238,455 filed on Aug. 31, 2009.

FIELD OF THE INVENTION

The invention relates to novel compounds of the Formula (I) having antithrombotic activity which, in particular, inhibit blood clotting factor IXa, to processes for their preparation and to use thereof as medicaments.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, as shown in the Patent Document 1, and the subsequent dissolution of the clot after wound healing has taken place commences after vascular damage and can be divided into four phases:
1. The phase of vasoconstriction or vasocontraction: By means of this the blood loss in the damaged area is decreased.
2. The next phase is platelet activation by thrombin. The platelets attach to the site of the vessel wall damage and form a platelet aggregate. The protein fibrinogen is responsible here for the crosslinkage of the platelets by means of appropriate surface receptors. Platelets also bind to exposed collagen of the extracellular matrix of the damaged vessel wall and are activated by this means. After activation of the platelets, a number of messenger substances are secreted, which induce the activation of further platelets. At the same time, a membrane lipid, phosphatidylserine, is transported from the inside of the membrane of the platelets to the outside, on which complexes of clotting factors can accumulate. The platelets accelerate blood clotting by means of this mechanism.
3. The formation of these clotting complexes leads to the massive formation of thrombin, which converts soluble fibrinogen to fibrin by cleavage of two small peptides. Fibrin monomers spontaneously form threadlike strands, from which, after crosslinkage by clotting factor XIII, a stable protein network forms. The initially even looser platelet aggregate is stabilized by this fibrin network; platelet aggregates and fibrin network are the two essential constituents of a thrombus.
4. After wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors.

The intrinsic pathway requires the clotting factors V, VIII, IX, X, XI and XII and also prekallikrein, high molecular weight kininogen, calcium ions and phospholipids from platelets.

The intrinsic pathway is initiated when prekallikrein, high molecular weight kininogen factor XI and XII bind to a negatively charged surface. This point in time is designated as the contact phase. Exposure to vessel wall collagen is the primary stimulus of the contact phase. The result of the processes of the contact phase is the conversion of prekallikrein to kallikrein, which in turn activates factor XII. Factor XIIa hydrolyzes further prekallikrein to kallikrein, such that activation is the result. With increasing activation of factor XII, activation of factor XI occurs, which leads to a release of bradykinin, a vasodilator. As a result, the ending of the initial phase of vasoconstriction occurs. Bradykinin is formed from high molecular weight kininogen. In the presence of $Ca^{2+}$ ions, factor XIa activates factor IX. Factor IX is a proenzyme, which contains vitamin K-dependent, γ-carboxyglutamic acid (GLA) residues. The serine protease activity becomes noticeable after binding of $Ca^{2+}$ to these GLA residues. A number of the serine proteases of the blood clotting cascade (factors II, VII, IX and X) contain such vitamin K-dependent GLA residues. Factor IXa cleaves factor X and leads to activation to factor Xa. The prerequisite for the formation of factor IXa is the formation of a tenase complex from $Ca^{2+}$ and the factors VIIIa, IXa and X on the surface of activated platelets. One of the reactions of activated platelets is the presentation of phosphatidylserine and phosphatidylinositol along the surfaces. The exposure of these phospholipids first makes the formation of the tenase complex possible. Factor VIII in this process has the function of a receptor for the factors IXa and X. Factor VIII is therefore a cofactor in the clotting cascade. The activation of factor VIII with formation of factor VIIIa, the actual receptor, needs only a minimal amount of thrombin. With increase in the concentration of thrombin, factor VIIIa is finally cleaved further and inactivated by thrombin. This dual activity of thrombin in relation to factor VIII leads to a self-restriction of tenase complex formation and thus to a limitation of blood clotting.

The extrinsic pathway requires a tissue factor (TF) and clotting factors V, VII, VIII, IX and X. In the case of a vessel injury, the tissue factor (TF) accumulates with the clotting factor VII and the latter is activated. The complex of TF and clotting factor VII has two substrates, clotting factors X and IX.

Clotting factor IX can be activated by means of the intrinsic pathway and the extrinsic pathway. The activation of factor IXa is thus a central point of intersection between the two pathways of activation of clotting.

Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445).

Recently, compounds having a Factor IXa antagonism are being studied. Known compounds each having an amide bond are disclosed in, for example, PCT Publication No. 08/031,508 pamphlet (Patent Document 1), PCT Publication No. 08/031,509 pamphlet (Patent Document 2). However, these patent documents do not disclose cyclic morpholinone derivatives.

In the development of pharmaceuticals, it is required to satisfy strict criteria for not only target pharmacological activity but also absorption, distribution, metabolism, excretion, and the like. With respect to drug interactions, desensitization or tolerance, digestive absorption in oral administration, the rate of transfer to a small intestine, the rate of absorption and first-pass effect, an organ barrier, protein binding, induction of a drug-metabolizing enzyme, an excretion pathway and body clearance, a method of administration (an application site, a method, and purpose), and the like, various agenda are required. However, a drug that satisfies these requirements is seldom discovered.

These comprehensive problems in drug development might also exist for Factor IXa antagonists, and Factor IXa antagonists have not yet been released onto the market. More specifically, known compounds having a Factor IXa antagonism may also include problems in terms of usefulness and safety. For example, these compounds may have low absorption, and oral administration of these compounds may be difficult; these compounds also may exhibit inhibitory activity of the human ether-a-go-go related gene (hERG) channel, which may cause arrhythmia, and pharmacokinetics of these compounds might not satisfactory.

Accordingly, a compound in which these problems are solved and which has high activity has been desired.

DOCUMENT LIST (Patent Document 1) PCT Publication No. 08/031,508 pamphlet
(Patent Document 2) PCT Publication No. 08/031,509 pamphlet

SUMMARY OF THE INVENTION

In its many embodiments, the present invention provides a novel class of cyclic morpholine compounds or its analogue, pharmaceutical compositions comprising one or more said compounds, and methods for using said compounds for treating or preventing a thromboses, embolisms, hypercoagulability or fibrotic changes.

The compounds of the Formula (I) according to the invention are suitable for prophylactic and for therapeutic administration to humans who suffer from diseases which accompany thromboses, embolisms, hypercoagulability or fibrotic changes. They can be employed for secondary prevention and are suitable both for acute and for long-term therapy.

The invention therefore relates to a compound of Formula (I)

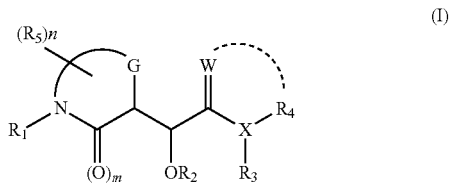

or a pharmaceutically acceptable salt or a solvate thereof; wherein:

R1 is selected from the group consisting of
1) —$(C_6\text{-}C_{14})$-aryl, which is unsubstituted or substituted independently with one to four Y;
2) -(three- to fifteen-membered heterocyclic ring), which is unsubstituted or substituted independently with one to four Y;
3) —$(C_6\text{-}C_{14})$-aryl-U—$(C_6\text{-}C_{14})$-aryl, wherein each of said —$(C_6\text{-}C_{14})$-aryl-independently is unsubstituted or substituted independently with one to four Y;
4) —$(C_6\text{-}C_{14})$-aryl-U—$(C_3\text{-}C_{12})$-cycloalkyl, wherein said —$(C_6\text{-}C_{14})$-aryl and —$(C_3\text{-}C_{12})$-cycloalkyl independently are unsubstituted or substituted independently with one to four Y;
5) —$(C_6\text{-}C_{14})$-aryl-U-(three- to fifteen-membered heterocyclic ring), wherein said —$(C_6\text{-}C_{14})$-aryl and said (three- to fifteen-membered heterocyclic ring) are independently unsubstituted or substituted independently with one to four Y;
6) -(three- to fifteen-membered heterocyclic ring)-U—$(C_6\text{-}C_{14})$-aryl, wherein said —$(C_6\text{-}C_{14})$-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) —(three- to fifteen-membered heterocyclic ring)-U—$(C_3\text{-}C_{12})$-cycloalkyl, wherein said —$(C_3\text{-}C_{12})$-cycloalkyl, and said -(three- to fifteen-membered heterocyclic ring)- are independently unsubstituted or substituted independently with one to four Y;
9) —V—$(C_6\text{-}C_{14})$-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —$(C_1\text{-}C_6)$-alkyl, wherein
each R6 independently is selected from the group consisting of hydrogen atom, —$(C_1\text{-}C_6)$-alkyl, —$(C_3\text{-}C_8)$-cycloalkyl, —$(C_6\text{-}C_{14})$-aryl and a three- to fifteen-membered heterocyclic ring;

R3 is absent, or selected from the group consisting of hydrogen atom and —$(C_1\text{-}C_4)$-alkyl, R4 is selected from the group consisting of:
1) —$(C_6\text{-}C_{14})$-aryl-Z, wherein said Z is a basic nitrogen-containing group and wherein said —$(C_6\text{-}C_{14})$-aryl is unsubstituted or substituted independently with one to four Y;

2) —($C_3$-$C_{12}$)-cycloalkyl-Z, wherein said Z is a basic nitrogen-containing group and wherein said —($C_3$-$C_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —($C_6$-$C_{14}$)-aryl, which is unsubstituted or substituted independently with one to four Y;
6) —($C_3$-$C_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;

each R5 independently is selected from the group consisting of:
1) halogen;
2) —($C_1$-$C_6$)-alkyl, which is unsubstituted or substituted independently with one to four —($C_1$-$C_3$)-haloalkyl, —N—C(O)—OH, —N—C(O)—($C_1$-$C_4$)-alkyl, or —C(O)OR7;
3) —($C_1$-$C_3$)-haloalkyl;
4) —($C_3$-$C_8$)-cycloalkyl;
5) —OH;
6) —O—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)-C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) =O (oxo);
20) —C(O)OR7; and
21) C(O)R7
wherein each of R7 and R8 is independently selected from the group consisting of hydrogen atom, —($C_6$-$C_{14}$)-aryl, —($C_3$-$C_8$)-cycloalkyl, and —($C_1$-$C_6$)-alkyl, wherein said —($C_1$-$C_6$)-alkyl is unsubstituted or substituted with at least one substituent selected from the group consisting of OH, —O—($C_1$-$C_4$)-alkyl, —($C_1$-$C_3$)-fluoroalkyl, —O—($C_1$-$C_3$)-haloalkyl, C(O)OH, and C(O)O—($C_1$-$C_6$)-alkyl;

each U independently is selected from the group consisting of a covalent bond, —($C_1$-$C_4$)-alkylene, —NH—, —N(($C_1$-$C_4$)-alkyl)-, —O—, —$SO_2$— or —S—,
wherein said —($C_1$-$C_4$)-alkylene or —($C_1$-$C_4$)-alkyl is unsubstituted or substituted independently with one to four T, or wherein geminal hydrogens in said —($C_1$-$C_4$)-alkylene or —($C_1$-$C_4$)-alkyl can be replaced by a ($C_3$-$C_8$)-cycloalkyl to form a spiro cyclic ring;

each V independently is selected from the group consisting of —($C_1$-$C_4$)-alkylene, —$SO_2$—, —C(O)—, —C(O)—NH— and —$SO_2$—NH—,
wherein the carbon atom of said —C(O)—NH— or the sulfur atom of said —$SO_2$—NH— is connected to a nitrogen atom of the morpholinone ring, and wherein said —($C_1$-$C_4$)-alkylene is unsubstituted or substituted independently with one to four T,
or wherein geminal hydrogens in said —($C_1$-$C_4$)-alkylene can be replaced by a ($C_3$-$C_8$)-cycloalkyl to form a spiro cyclic ring;

each T independently is selected from the group consisting of:
1) halogen;
2) —($C_1$-$C_6$)-alkyl, which is unsubstituted or substituted independently with one to four substituents selected from the group consisting of OH, —O—($C_1$-$C_4$)-alkyl, —($C_1$-$C_3$)-haloalkyl, —O—($C_1$-$C_3$)-haloalkyl, —N—C(O)—OH and —N—C(O)—($C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)—C(O)—R7;
13) —N(R8)—$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo); and
22) —C(O)OR7;
23) —C(O)OR7;
24) —N—C(O)—OR7
wherein each of R7 and R8 independently is selected from the group consisting of a hydrogen atom, —($C_3$-$C_8$)-cycloalkyl, halogen and —($C_1$-$C_6$)-alkyl, wherein said —($C_1$-$C_6$)-alkyl is optionally substituted with at least one substituent selected from the group consisting of OH, —O—($C_1$-$C_4$)-alkyl, —($C_1$-$C_3$)-fluoroalkyl, and —O—($C_1$-$C_3$)-haloalkyl;

G is selected from the group consisting of oxygen atom, imino, sulfur atom, sulfoxide, sulfone and methylene;
W is selected from the group consisting of oxygen atom, nitrogen atom and carbon atom;
X is selected from the group consisting of nitrogen atm, carbon atom and oxygen atom;
Y is selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_6$)-alkyl;
7) —O—($C_1$-$C_3$)-haloalkyl;
8) —$NO_2$;

9) —CN;
10) —N(R7)(R8);
11) —C(O)—N(R7)(R8);
12) —N(R8)—C(O)—R7;
13) —N(R8)—SO$_2$—R7;
14) —SO$_2$—(C$_1$-C$_4$)-alkyl;
15) —SO$_2$—N(R7)(R8);
16) —SO$_2$—(C$_1$-C$_3$)-haloalkyl;
17) —S—(C$_1$-C$_4$)-alkyl;
18) —S—(C$_1$-C$_3$)-haloalkyl;
19) —(C$_1$-C$_6$)-alkyl-N(R7)(R8);
20) —N(R8)—C(O)—N(R7)(R8);
21) =O (oxo);
22) —SF$_5$;
23) —C(O)OR7;
24) —N—C(O)—OR7
25) —N(R8)—C(O)—(C$_1$-C$_4$)-alkyl-O—(C$_1$-C$_4$)-alkyl-(C$_6$-C$_{14}$)-aryl, wherein said —(C$_6$-C$_{14}$)-aryl is unsubstituted or substituted independently with one to four Y selected from (1) to (24) as set forth above;
26) —N(R8)—C(O)—(C$_1$-C$_4$)-alkyl-O—(C$_1$-C$_4$)-alkyl-(three- to fifteen-membered heterocyclic ring), wherein said -(three- to fifteen-membered heterocyclic ring) is unsubstituted or substituted independently with one to four Y selected from (1) to (24) as set forth above;
wherein said —(C$_1$-C$_4$)-alkyl part or —(C$_1$-C$_6$)-alkyl part of 2), 6), 14), 17), 19), 25) or 26) of said Y is unsubstituted or substituted independently with one to four T;
wherein each of R7 and R8 of 10), 11), 12), 13), 15), 19), 20), 23), 24), 25) or 26) of said Y independently is selected from the group consisting of hydrogen atom, —(C$_3$-C$_8$)-cycloalkyl, and —(C$_1$-C$_6$)-alkyl, wherein said —(C$_1$-C$_6$)-alkyl is optionally substituted with OH, —O—(C$_1$-C$_4$)-alkyl, —(C$_1$-C$_3$)-fluoroalky, —O—(C$_1$-C$_3$)-haloalkyl, —C(O)OH, or C(O)O—(C$_1$-C$_6$)-alkyl;
m is 0 or 1,
n is 0, 1, 2, 3 or 4,
the linkage between G atom and Nitrogen atom of the substructure (II)

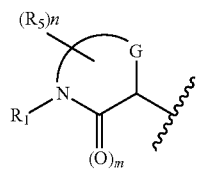

(II)

in Formula (I) comprises one to four carbon atoms to form alkylene chain, wherein said alkylene chain or G (imino or methylene) is unsubstituted or substituted independently with one to four R5;
the dotted linkage between W and R4 of the substructure (III)

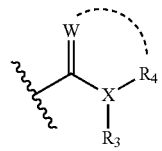

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

In another aspect, the present invention relates to a compound of Formula (I)-(A)

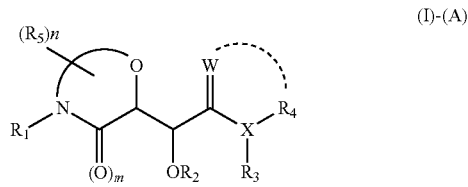

(I)-(A)

or a pharmaceutically acceptable salt or a solvate thereof;
wherein:
R1 is selected from the group consisting of:
1) —(C$_6$-C$_{14}$)-aryl, which is unsubstituted or substituted independently with one to four Y;
2) -(three- to fifteen-membered heterocyclic ring), which is unsubstituted or substituted independently with one to four Y;
3) —(C$_6$-C$_{14}$)-aryl-U—(C$_6$-C$_{14}$)-aryl, wherein each of said —(C$_6$-C$_{14}$)-aryl-independently is unsubstituted or substituted independently with one to four Y;
4) —(C$_6$-C$_{14}$)-aryl-U—(C$_3$-C$_{12}$)-cycloalkyl, wherein said —(C$_6$-C$_{14}$)-aryl and —(C$_3$-C$_{12}$)-cycloalkyl independently are unsubstituted or substituted independently with one to four Y;
5) —(C$_6$-C$_{14}$)-aryl-U-(three- to fifteen-membered heterocyclic ring), wherein said —(C$_6$-C$_{14}$)-aryl and said (three- to fifteen-membered heterocyclic ring) are independently unsubstituted or substituted independently with one to four Y;
6) -(three- to fifteen-membered heterocyclic ring)-U—(C$_6$-C$_{14}$)-aryl, wherein said —(C$_6$-C$_{14}$)-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;

8) -(three- to fifteen-membered heterocyclic ring)-U—($C_3$-$C_{12}$)-cycloalkyl, wherein said —($C_3$-$C_{12}$)-cycloalkyl, and said -(three- to fifteen-membered heterocyclic ring)- are independently unsubstituted or substituted independently with one to four Y;
9) —V—($C_6$-$C_{14}$)-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —($C_1$-$C_6$)-alkyl, wherein each R6 independently is selected from the group consisting of hydrogen atom, —($C_1$-$C_6$)-alkyl, —($C_3$-$C_8$)-cycloalkyl, —($C_6$-$C_{14}$)-aryl and a three- to fifteen-membered heterocyclic ring;

R3 is absent, or selected from the group consisting of hydrogen atom and —($C_1$-$C_4$)-alkyl, R4 is selected from the group consisting of:
1) —($C_6$-$C_{14}$)-aryl-Z, wherein said Z is a basic nitrogen-containing group and wherein said —($C_6$-$C_{14}$)-aryl is unsubstituted or substituted independently with one to four Y;
2) —($C_3$-$C_{12}$)-cycloalkyl-Z, wherein said Z is a basic nitrogen-containing group and wherein said —($C_3$-$C_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —($C_6$-$C_{14}$)-aryl, which is unsubstituted or substituted independently with one to four Y;
6) —($C_3$-$C_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;

each R5 independently is selected from the group consisting of:
1) halogen;
2) —($C_1$-$C_6$)-alkyl, which is unsubstituted or substituted independently with one to four —($C_1$-$C_3$)-haloalkyl, —N—C(O)—OH or —N—C(O)—($C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl;
7) —O—($C_1$-$C_3$)-haloalkyl;
8) —NO$_2$;
9) —CN;
10) —N(R7)(R8);
11) —C(O)—NH—R7;
12) —NH—C(O)—R7;
13) —NH—SO$_2$—R7;
14) —SO$_2$—($C_1$-$C_4$)-alkyl;
15) —SO$_2$—NH—R7;
16) —SO$_2$—($C_1$-$C_3$)-haloalkyl;
17) —S—($C_1$-$C_4$)-alkyl;
18) —S—($C_1$-$C_3$)-haloalkyl; and
19) =O (oxo);
wherein each of R7 and R8 is independently selected from the group consisting of hydrogen atom, —($C_3$-$C_8$)-cycloalkyl, halogen and —($C_1$-$C_6$)-alkyl, wherein said —($C_1$-$C_6$)-alkyl is unsubstituted or substituted with at least one substituent selected from the group consisting of OH, —O—($C_1$-$C_4$)-alkyl, —($C_1$-$C_3$)-fluoroalky, and —O—($C_1$-$C_3$)-haloalkyl;

each U independently is selected from the group consisting of a covalent bond, —($C_1$-$C_4$)-alkylene, —NH—, —N(($C_1$-$C_4$)-alkyl)-, —O—, —SO$_2$— or —S—, wherein said —($C_1$-$C_4$)-alkylene or —($C_1$-$C_4$)-alkyl is unsubstituted or substituted independently with one to four T,
or wherein geminal hydrogens in said —($C_1$-$C_4$)-alkylene or —($C_1$-$C_4$)-alkyl can be replaced by a ($C_3$-$C_8$)-cycloalkyl to form a spiro cyclic ring;

each V independently is selected from the group consisting of —($C_1$-$C_4$)-alkylene, —SO$_2$—, —C(O)—, —C(O)—NH— and —SO$_2$—NH—,
wherein the carbon atom of said —C(O)—NH— or the sulfur atom of said —SO$_2$—NH— is connected to a nitrogen atom of the morpholinone ring, and wherein said —($C_1$-$C_4$)-alkylene is unsubstituted or substituted independently with one to four T,
or wherein geminal hydrogens in said —($C_1$-$C_4$)-alkylene can be replaced by a ($C_3$-$C_8$)-cycloalkyl to form a spiro cyclic ring;

each T independently is selected from the group consisting of:
1) halogen;
2) —($C_1$-$C_6$)-alkyl, which is unsubstituted or substituted independently with one to four substituents selected from the group consisting of OH, —O—($C_1$-$C_4$)-alkyl, —($C_1$-$C_3$)-haloalkyl, —O—($C_1$-$C_3$)-haloalkyl, —N—C(O)—OH and —N—C(O)—($C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —NO$_2$;
9) —CN;
10) —N(R7)(R8);
11) —C(O)—NH—R7;
12) —NH—C(O)—R7;
13) —NH—SO$_2$—R7;
14) —SO$_2$—($C_1$-$C_4$)-alkyl;
15) —SO$_2$—NH—R7;
16) —SO$_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo); and
22) —C(O)OR7;
wherein each of R7 and R8 independently is selected from the group consisting of a hydrogen atom, —($C_3$-$C_8$)-cycloalkyl, halogen and —($C_1$-$C_6$)-alkyl, wherein said —(C$_1$-C$_6$)-alkyl is optionally substituted with at least one substituent selected from the group consisting of OH, —O—(C$_1$-C$_4$)-alkyl, —(C$_1$-C$_3$)-fluoroalky, and —O—(C$_1$-C$_3$)-haloalkyl;

W is selected from the group consisting of oxygen atom, nitrogen atom and carbon atom;

X is selected from the group consisting of nitrogen atom, carbon atom and oxygen atom;

Y is selected from the group consisting of
1) halogen;
2) —(C$_1$-C$_6$)-alkyl;
3) —(C$_1$-C$_3$)-haloalkyl;
4) —(C$_3$-C$_8$)-cycloalkyl;
5) —OH;
6) —O—(C$_1$-C$_4$)-alkyl, which is unsubstituted or mono substituted with OH, —O—(C$_1$-C$_4$)-alkyl, —(C$_1$-C$_3$)-haloalkyl, —O—(C$_1$-C$_3$)-haloalkyl, —N—C(O)—OH or —N—C(O)—(C$_1$-C$_4$)-alkyl;
7) —O—(C$_1$-C$_3$)-haloalkyl;
8) —NO$_2$;
9) —CN;
10) —N(R7)(R8);
11) —C(O)—NH—R7;
12) —NH—C(O)—R7;
13) —NH—SO$_2$—R7;
14) —SO$_2$—(C$_1$-C$_4$)-alkyl;
15) —SO$_2$—NH—R7;
16) —SO$_2$—(C$_1$-C$_3$)-haloalkyl;
17) —S—(C$_1$-C$_4$)-alkyl;
18) —S—(C$_1$-C$_3$)-haloalkyl;
19) —(C$_1$-C$_6$)-alkyl-N(R7)(R8);
20) —NH—C(O)—N(R7)(R8);
21) =O (oxo);
22) —NH—C(O)—(C$_1$-C$_4$)-alkyl-O—(C$_1$-C$_4$)-alkyl-(C$_6$-C$_{14}$)-aryl, wherein said —(C$_6$-C$_{14}$)-aryl is unsubstituted or substituted independently with one to four Y selected from (1) to (21) as set forth above;
23) —NH—C(O)—(C$_1$-C$_4$)-alkyl-O—(C$_1$-C$_4$)-alkyl-(three- to fifteen-membered heterocyclic ring), wherein said -(three- to fifteen-membered heterocyclic ring) is unsubstituted or substituted independently with one to four Y selected from (1) to (21) as set forth above;

wherein said —(C$_1$-C$_4$)-alkyl or —(C$_1$-C$_6$)-alkyl of said 2), 6), 10), 14), 17), 19), 22) or 23) of said Y is unsubstituted or substituted independently with one to four T;

wherein each of R7 and R8 independently is selected from the group consisting of hydrogen atom, —(C$_3$-C$_8$)-cycloalkyl, halogen and —(C$_1$-C$_6$)-alkyl, wherein said —(C$_1$-C$_6$)-alkyl is optionally substituted with OH, —O—(C$_1$-C$_4$)-alkyl, —(C$_1$-C$_3$)-fluoroalky, or —O—(C$_1$-C$_3$)-haloalkyl;

m is 0 or 1,
n is 0, 1, 2, 3 or 4,
the linkage between Oxygen atom and Nitrogen atom of the substructure (II)

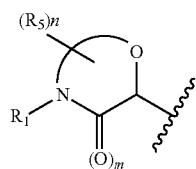

(II)

in Formula (I) comprises one to four carbon atoms, wherein said linkage is unsubstituted or substituted independently with one to four R5;

the dotted linkage between W and R4 of the substructure (III)

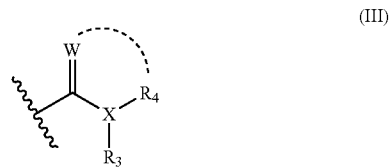

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
4) present such that substructure (III) is a (three- to fifteen-membered heterocyclic ring), wherein said (three- to fifteen-membered heterocyclic ring) is unsubstituted or substituted independently with one to four Y;
5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

In another aspect, the present invention relates to a compound of Formula (I)-(B)

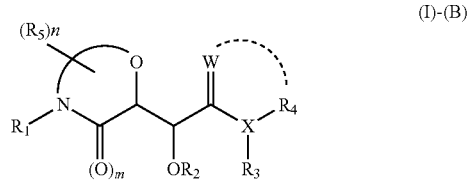

(I)-(B)

or a pharmaceutically acceptable salt or a solvate thereof;
wherein:
R1 is
1) —(C$_5$-C$_{14}$)-aryl, in which aryl is unsubstituted or substituted independently with one to four Y,
2) -(three- to fifteen-membered heterocyclic ring), in which ring is unsubstituted or substituted independently with one to four Y,
3) —(C$_6$-C$_{14}$)-aryl-U—(C$_6$-C$_{14}$)-aryl, in which the two aryls in each case independently of one another are unsubstituted or substituted independently with one to four Y,
4) —(C$_6$-C$_{14}$)-aryl-U—(C$_3$-C$_{12}$)-cycloalkyl, in which aryl and cycloalkyl in each case independently of one another are unsubstituted or substituted independently with one to four Y, 5) —($C_6$-$C_{14}$)-aryl-U-(three- to fifteen-membered heterocyclic ring), in which aryl and (three- to fifteen-membered heterocyclic ring) in each case independently of one another are unsubstituted or substituted independently with one to four Y, 6) -(three- to fifteen-membered heterocyclic ring)-U—($C_6$-$C_{14}$)-aryl, in which aryl and (three- to fifteen-membered heterocyclic ring) in each case independently of one another are unsubstituted or substituted independently with one to four Y, 7) -(three- to fifteen-membered heterocyclic ring)-U-(three- to fifteen-membered heterocyclic ring), in which the two heterocyclic ring radicals in each case independently of one another are unsubstituted or substituted independently with one to four Y, 8) -(three- to fifteen-membered heterocyclic ring)-U—($C_3$-$C_{12}$)-cycloalkyl, in which ($C_3$-$C_{12}$)-cycloalkyl, and (three- to fifteen-membered heterocyclic ring) in each case independently of one another are unsubstituted or substituted independently with one to four Y, 9) —V—($C_6$-$C_{14}$)-aryl, in which aryl is unsubstituted or substituted independently with one to four Y, 10) —V-(three- to fifteen-membered heterocyclic ring), in which (three- to fifteen-membered heterocyclic ring) is unsubstituted or substituted independently with one to four Y, R2 is independently selected from hydrogen atom, —C(O)—R6, —C(O)—O—R6, —C(O)—NH—R6, —C(O)—N(R6)$_2$, —P(O)(OR6)$_2$ or —($C_1$-$C_6$)-alkyl, in which R6 is independently selected from hydrogen atom, —($C_1$-$C_6$)-alkyl, —($C_3$-$C_8$)-cycloalkyl, —($C_6$-$C_{14}$)-aryl or three- to fifteen-membered heterocyclic ring, R3 is independently selected from absent, hydrogen atom or —($C_1$-$C_4$)-alkyl, R4 is
1) —($C_6$-$C_{14}$)-aryl-Z, in which Z is a basic nitrogen-containing group and in which aryl is unsubstituted or substituted independently with one to four
2) —($C_3$-$C_{12}$)-cycloalkyl-Z, in which Z is a basic nitrogen-containing group and in which cycloalkyl is unsubstituted or substituted independently with one to four Y,
3) -(three- to fifteen-membered heterocyclic ring)-Z, in which Z is a basic nitrogen-containing group and in which (three- to fifteen-membered heterocyclic ring) is unsubstituted or additionally substituted independently with one to four Y,
4) -(three- to fifteen-membered heterocyclic ring)-U-(three- to fifteen-membered heterocyclic ring)-Z, in which Z is a basic nitrogen-containing group and in which the two (three- to fifteen-membered heterocyclic ring) radicals in each case independently of one another are unsubstituted or additionally substituted independently with one to four Y,
5) —($C_6$-$C_{14}$)-aryl, in which aryl is unsubstituted or substituted independently with one to four Y,
6) —($C_3$-$C_{12}$)-cycloalkyl, in which cycloalkyl is unsubstituted or substituted independently with one to four Y,
7) -(three- to fifteen-membered heterocyclic ring), in which heterocyclic ring is unsubstituted or substituted independently with one to four Y,
8) -(three- to fifteen-membered heterocyclic ring)-U-(three- to fifteen-membered heterocyclic ring), in which the two (three- to fifteen-membered heterocyclic ring) radicals in each case independently of one another are unsubstituted or substituted independently with one to four Y, R5 is
1) halogen,
2) —($C_1$-$C_6$)-alkyl, in which alkyl is unsubstituted or substituted independently with one to four —($C_1$-$C_3$)-haloalkyl, —N—C(O)—OH or —N—C(O)—($C_1$-$C_4$)-alkyl,
3) —($C_1$-$C_3$)-haloalkyl,
4) —($C_3$-$C_8$)-cycloalkyl,
5) —OH,
6) —O—($C_1$-$C_4$)-alkyl,
7) —O—($C_1$-$C_3$)-haloalkyl,
8) —NO$_2$,
9) —CN,
10) —N(R7)(R8),
11) —C(O)—NH—R7,
12) —NH—C(O)—R7,
13) —NH—SO$_2$—R7,
14) —SO$_2$—($C_1$-$C_4$)-alkyl,
15) —SO$_2$—NH—R7,
16) —SO$_2$—($C_1$-$C_3$)-haloalkyl,
17) —S—($C_1$-$C_4$)-alkyl or
18) —S—($C_1$-$C_3$)-haloalkyl,
19) =O
in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH, —O—($C_1$-$C_4$)-alkyl, —($C_1$-$C_3$)-fluoroalky, or —O—($C_1$-$C_3$)-haloalkyl, U is independently selected from a covalent bond, —($C_1$-$C_4$)-alkylene, —NH—, —N(($C_1$-$C_4$)-alkyl)-, —O—, —SO$_2$— or —S—,
in which —($C_1$-$C_4$)-alkylene or —($C_1$-$C_4$)-alkyl is unsubstituted or substituted independently with one to four T,
or substituted geminal hydrogens by ($C_3$-$C_8$)-cycloalkyl to form a spiro cyclic ring, V is independently selected from —($C_1$-$C_4$)-alkylene, —SO$_2$—, —C(O)—, —C(O)—NH— and —SO$_2$—NH—,
in which carbon atom or sulfur atom of —C(O)—NH— and —SO$_2$—NH— is connected to a nitrogen atom of the morpholinone ring,
in which —($C_1$-$C_4$)-alkylene is unsubstituted or substituted independently with one to four T,
or substituted geminal hydrogens by ($C_3$-$C_8$)-cycloalkyl to form a spiro cyclic ring, T is
1) halogen,
2) —($C_1$-$C_6$)-alkyl, in which alkyl is unsubstituted or substituted independently with one to four substituents selected from OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
3) —($C_1$-$C_3$)-haloalkyl,
4) —($C_3$-$C_8$)-cycloalkyl,
5) —OH,
6) —O—($C_1$-$C_4$)-alkyl, in which alkyl is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl,
7) —O—($C_1$-$C_3$)-haloalkyl,
8) —NO$_2$,
9) —CN,
10) —N(R7)(R8),
11) —C(O)—NH—R7, 12) —NH—C(O)—R7,
13) —NH—SO₂—R7,
14) —SO₂—(C₁-C₄)-alkyl,
15) —SO₂—NH—R7,
16) —SO₂—(C₁-C₃)-haloalkyl,
17) —S—(C₁-C₄)-alkyl,
18) —S—(C₁-C₃)-haloalkyl,
19) —(C₁-C₆)-alkyl-N(R7)(R8),
20) —NH—C(O)—N(R7)(R8),
21) =O
22) —C(O)OR7
in which R7 and R8 independently of one another are a hydrogen atom, —(C₃-C₈)-cycloalkyl, halogen or —(C₁-C₆)-alkyl, in which —(C₁-C₆)-alkyl is optionally substituted with OH, —O—(C₁-C₄)-alkyl, —(C₁-C₃)-fluoroalky, or —O—(C₁-C₃)-haloalkyl, W is independently selected from oxygen atom, nitrogen atom or carbon atom,
X is independently selected from nitrogen atom, carbon atom or oxygen atom,
Y is
1) halogen,
2) —(C₁-C₆)-alkyl,
3) —(C₁-C₃)-haloalkyl,
4) —(C₃-C₈)-cycloalkyl,
5) —OH,
6) —O—(C₁-C₄)-alkyl, in which alkyl is unsubstituted or mono substituted with OH, —O—(C₁-C₄)-alkyl, —(C₁-C₃)-haloalkyl, —O—(C₁-C₃)-haloalkyl, —N—C(O)—OH or —N—C(O)—(C₁-C₄)-alkyl,
7) —O—(C₁-C₃)-haloalkyl,
8) —NO₂,
9) —CN,
10) —N(R7)(R8),
11) —C(O)—NH—R7,
12) —NH—C(O)—R7,
13) —NH—SO₂—R7,
14) —SO₂—(C₁-C₄)-alkyl,
15) —SO₂—NH—R7,
16) —SO₂—(C₁-C₃)-haloalkyl,
17) —S—(C₁-C₄)-alkyl,
18) —S—(C₁-C₃)-haloalkyl,
19) —(C₁-C₆)-alkyl-N(R7)(R8),
20) —NH—C(O)—N(R7)(R8),
21) =0
22) —NH—C(O)—(C₁-C₄)-alkyl-O—(C₁-C₄)-alkyl-(C₆-C₁₄)-aryl, in which aryl is unsubstituted or substituted independently with one to four Y (selected from (1) to (21)),
23) —NH—C(O)—(C₁-C₄)-alkyl-O—(C₁-C₄)-alkyl-(three- to fifteen-membered heterocyclic ring), in which -(three- to fifteen-membered heterocyclic ring) is unsubstituted or substituted independently with one to four Y (selected from (1) to (21)),
in which —(C₁-C₄)-alkyl or —(C₁-C₆)-alkyl of 2), 6), 10), 14), 17), 19), 22) or 23) is unsubstituted or substituted independently with one to four T,
in which R7 and R8 independently of one another are a hydrogen atom, —(C₃-C₈)-cycloalkyl, halogen or —(C₁-C₆)-alkyl, in which —(C₁-C₆)-alkyl is optionally substituted with OH, —O—(C₁-C₄)-alkyl, —(C₁-C₃)-fluoroalky, or —O—(C₁-C₃)-haloalkyl, T is
1) halogen,
2) —(C₁-C₆)-alkyl, in which alkyl is unsubstituted or substituted independently with one to four substituents selected from OH, —O—(C₁-C₄)-alkyl, —(C₁-C₃)-haloalkyl, —O—(C₁-C₃)-haloalkyl, —N—C(O)—OH or —N—C(O)—(C₁-C₄)-alkyl,
3) —(C₁-C₃)-haloalkyl,
4) —(C₃-C₈)-cycloalkyl,
5) —OH,
6) —O—(C₁-C₄)-alkyl, in which alkyl is unsubstituted or mono substituted with OH, —O—(C₁-C₄)-alkyl, —(C₁-C₃)-haloalkyl, —O—(C₁-C₃)-haloalkyl, —N—C(O)—OH or —N—C(O)—(C₁-C₄)-alkyl,
7) —O—(C₁-C₃)-haloalkyl,
8) —NO₂,
9) —CN,
10) —N(R7)(R8),
11) —C(O)—NH—R7,
12) —NH—C(O)—R7,
13) —NH—SO₂—R7,
14) —SO₂—(C₁-C₄)-alkyl,
15) —SO₂—NH—R7,
16) —SO₂—(C₁-C₃)-haloalkyl,
17) —S—(C₁-C₄)-alkyl,
18) —S—(C₁-C₃)-haloalkyl,
19) —(C₁-C₆)-alkyl-N(R7)(R8),
20) —NH—C(O)—N(R7)(R8),
21) =O
22) —C(O)OR7
in which R7 and R8 independently of one another are a hydrogen atom, —(C₃-C₈)-cycloalkyl, halogen or —(C₁-C₆)-alkyl, in which —(C₁-C₆)-alkyl is optionally substituted with OH, —O—(C₁-C₄)-alkyl, —(C₁-C₃)-fluoroalky, or —O—(C₁-C₃)-haloalkyl, m is 0 or 1,
n is 0, 1, 2, 3 or 4,
the linkage between Oxygen atom and Nitrogen atom of the substructure (II)

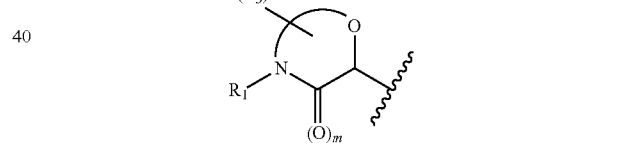

(II)

in Formula (I) describes one to four carbon atoms, which is unsubstituted or substituted independently with one to four R5,
the dotted linkage between W and R4 of the substructure (III)

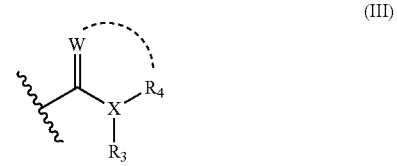

(III)

in Formula (I) is
1) absent,
2) attached to form (three- to fifteen-membered heterocyclic ring)-Z as a whole of the substructure (III), in which Z is a basic nitrogen-containing group and in which (three- to fifteen-membered heterocyclic ring) is unsubstituted or additionally substituted independently with one to four Y, 3) attached to form (three- to fifteen-membered heterocyclic ring)-U-(three- to fifteen-membered heterocyclic ring)-Z as a whole of the substructure (III), in which Z is a basic nitrogen-containing group and in which the two (three- to fifteen-membered heterocyclic ring) radicals in each case independently of one another are unsubstituted or additionally substituted independently with one to four Y, 4) attached to form (three- to fifteen-membered heterocyclic ring) as a whole of the substructure (III), in which (three- to fifteen-membered heterocyclic ring) is unsubstituted or substituted independently with one to four Y, 5) attached to form (three- to fifteen-membered heterocyclic ring)-U-(three- to fifteen-membered heterocyclic ring), as a whole of the substructure (III), in which the two (three- to fifteen-membered heterocyclic ring) radicals in each case independently of one another are unsubstituted or substituted independently with one to four Y.

In another aspect, the present invention relates to a compound of Formula (I)-(C)

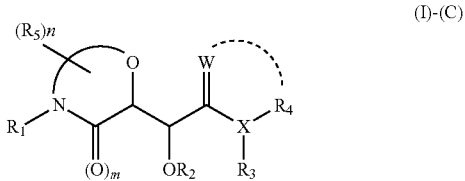

(I)-(C)

or a pharmaceutically acceptable salt or solvate thereof;
wherein:
R1 is
1) $(C_6-C_{14})$-aryl, in which aryl is unsubstituted or substituted independently with one to four Y,
2) four- to fifteen-membered heterocyclic ring, in which ring is unsubstituted or substituted independently with one to four Y,
3) $(C_6-C_{14})$-aryl-U—$(C_6-C_{14})$-aryl, in which the two aryls in each case independently of one another are unsubstituted or substituted independently with one to four Y,
4) $(C_6-C_{14})$-aryl-U—$(C_3-C_{12})$-cycloalkyl, in which aryl and cycloalkyl in each case independently of one another are unsubstituted or substituted independently with one to four Y,
5) $(C_6-C_{14})$-aryl-U-(four- to fifteen-membered heterocyclic ring), in which aryl and (four- to fifteen-membered heterocyclic ring) in each case independently of one another are unsubstituted or substituted independently with one to four Y,
6) (four- to fifteen-membered heterocyclic ring)-U—$(C_6-C_{14})$-aryl, in which aryl and (four- to fifteen-membered heterocyclic ring) in each case independently of one another are unsubstituted or substituted independently with one to four Y,
7) (four- to fifteen-membered heterocyclic ring)-U-(four- to fifteen-membered heterocyclic ring), in which the two heterocyclic ring radicals in each case independently of one another are unsubstituted or substituted independently with one to four Y,
8) —V—$(C_6-C_{14})$-aryl, in which aryl is unsubstituted or substituted independently with one to four Y,
9) —V-(four- to fifteen-membered heterocyclic ring), in which (four- to fifteen-membered heterocyclic ring) is unsubstituted or substituted independently with one to four Y,
R2 is hydrogen atom, —C(O)—R6, —C(O)—O—R6, —C(O)—NH—R6, —P(O)(OR6)$_2$ or —$(C_1-C_4)$-alkyl, in which R6 is —$(C_1-C_6)$-alkyl, —$(C_3-C_8)$-cycloalkyl, —$(C_6-C_{14})$-aryl or four- to fifteen-membered heterocyclic ring,
R3 is hydrogen atom or —$(C_1-C_4)$-alkyl,
R4 is 1) —$(C_6-C_{14})$-aryl-Z, in which Z is a basic nitrogen-containing group and in which aryl is unsubstituted or substituted independently with one to four Y,
2) —$(C_3-C_{12})$-cycloalkyl-Z, in which Z is a basic nitrogen-containing group and in which cycloalkyl is unsubstituted or substituted independently with one to four Y,
3) (four- to fifteen-membered heterocyclic ring)-Z, in which Z is a basic nitrogen-containing group and in which (four- to fifteen-membered heterocyclic ring) is unsubstituted or additionally substituted independently with one to four Y,
4) (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
5) —$(C_6-C_{14})$-aryl, in which aryl is unsubstituted or substituted independently with one to four Y,
6) —$(C_3-C_{12})$-cycloalkyl, in which cycloalkyl is unsubstituted or substituted independently with one to four Y,
7) A four- to fifteen-membered heterocyclic ring, in which heterocyclic ring is unsubstituted or substituted independently with one to four Y,
8) (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y,
R5 is
1) halogen,
2) —$(C_1-C_6)$-alkyl, in which alkyl is unsubstituted or substituted independently with one to four —$(C_1-C_3)$-fluoroalkyl, —N═C(O)—OH or —N═C(O)—$(C_1-C_4)$-alkyl,
3) —$(C_1-C_3)$-fluoroalkyl,
4) —$(C_3-C_3)$-cycloalkyl,
5) —OH,
6) —O—$(C_1-C_4)$-alkyl,
7) —O—$(C_1-C_3)$-fluoroalkyl,
8) —NO$_2$,
9) —CN,
10) —N(R7)(R8), in which R7 and R8 independently of one another are a hydrogen atom, —$(C_3-C_8)$-cycloalkyl, halogen or —$(C_1-C_6)$-alkyl, in which —$(C_1-C_6)$-alkyl is optionally substituted with OH,
11) —C(O)—NH—R7,
12) —NH—C(O)—R7,
13) —N1-1-SO$_2$—R7,
14) —SO$_2$—$(C_1-C_4)$-alkyl,
15) —SO$_2$—NH—R7,
16) —SO$_2$—$(C_1-C_3)$-fluoroalkyl,
17) —S—$(C_1-C_4)$-alkyl or
18) —S—$(C_1-C_3)$-fluoroalkyl,
U is a covalent bond, —$(C_1-C_4)$-alkylene, —NH—, —N(($C_1-C_4$)-alkyl)-, —O—, —SO$_2$— or —S—,
V is —$(C_1-C_4)$-alkylene, —SO$_2$—, —C(O)—NH— and —SO$_2$—NH—,
W is oxygen atom, nitrogen atom or carbon atom,
X is nitrogen atom, carbon atom or oxygen atom,
Y is
1) halogen,
2) —$(C_1-C_6)$-alkyl, in which alkyl is unsubstituted or substituted independently with one to four —$(C_1-C_3)$-fluoroalkyl, —N═C(O)—OH or —N═C(O)—$(C_1-C_4)$-alkyl,
3) —$(C_1-C_3)$-fluoroalkyl, 4) —($C_3$-$C_8$)-cycloalkyl,
5) —OH,
6) —O—($C_1$-$C_4$)-alkyl, in which alkyl is unsubstituted or mono substituted with OH,
7) —O—($C_1$-$C_3$)-fluoroalkyl,
8) —$NO_2$,
9) —CN,
10) —N(R7)(R8), in which R7 and R8 independently of one another are a hydrogen atom, —($C_3$-$C_8$)-cycloalkyl, halogen or —($C_1$-$C_6$)-alkyl,
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-fluoroalkyl,
17) —S—($C_1$-$C_4$)-alkyl or
18) —S—($C_1$-$C_3$)-fluoroalkyl,
19) —($C_1$-$C_6$)-alkyl-N(R7)(R8),
m is 0 or 1,
n is 0 to 4,

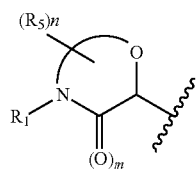

(II)

the linkage between Oxygen atom and Nitrogen atom of the substructure (II) describes one to four carbon atoms, which is unsubstituted or substituted independently with one to four R5,

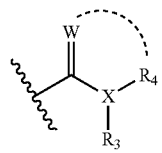

(III)

the linkage between W and R4 of the substructure (III) is
1) absent,
2) attached to form (four- to fifteen-membered heterocyclic ring)-Z, in which Z is a basic nitrogen-containing group and in which (four- to fifteen-membered heterocyclic ring) is unsubstituted or additionally substituted independently with one to four Y,
3) attached to form (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
4) attached to form (four- to fifteen-membered heterocyclic ring) in which (four- to fifteen-membered heterocyclic ring) is unsubstituted or substituted independently with one to four Y,
5) attached to form (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y, wherein,
each nitrogen atom of Z in Formula (I) is unsubstituted or substituted independently with —OH, —O—($C_1$-$C_4$)-alkyl group, —(CO)—($C_1$-$C_4$)-alkyl, or —O(CO)—($C_1$-$C_4$)-alkyl group.

In another aspect, the present invention relates to a compound of Formula (I)-(D)

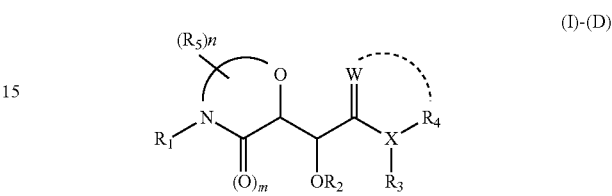

(I)-(D)

or a pharmaceutically acceptable salt or solvate thereof;
wherein:
R1 is
1) ($C_6$-$C_{14}$)-aryl, in which aryl is unsubstituted or substituted independently with one to four Y,
2) four- to fifteen-membered heterocyclic ring, in which ring is unsubstituted or substituted independently with one to four Y,
3) ($C_6$-$C_{14}$)-aryl-U—($C_6$-$C_{14}$)-aryl, in which the two aryls in each case independently of one another are unsubstituted or substituted independently with one to four Y,
4) ($C_6$-$C_{14}$)-aryl-U—($C_3$-$C_{12}$)-cycloalkyl, in which aryl and cycloalkyl in each case independently of one another are unsubstituted or substituted independently with one to four Y,
5) ($C_6$-$C_{14}$)-aryl-U-(four- to fifteen-membered heterocyclic ring), in which aryl and (four- to fifteen-membered heterocyclic ring) in each case independently of one another are unsubstituted or substituted independently with one to four Y,
6) (four- to fifteen-membered heterocyclic ring)-U—($C_6$-$C_{14}$)-aryl, in which aryl and (four- to fifteen-membered heterocyclic ring) in each case independently of one another are unsubstituted or substituted independently with one to four Y,
7) (four- to fifteen-membered heterocyclic ring)-U-(four- to fifteen-membered heterocyclic ring), in which the two heterocyclic ring radicals in each case independently of one another are unsubstituted or substituted independently with one to four Y,
8) —V—($C_6$-$C_{14}$)-aryl, in which aryl is unsubstituted or substituted independently with one to four Y,
9) —V-(four- to fifteen-membered heterocyclic ring), in which (four- to fifteen-membered heterocyclic ring) is unsubstituted or substituted independently with one to four Y,
R2 is hydrogen atom, —C(O)—R6, —C(O)—O—R6, —C(O)—NH—R6, —P(O)(OR6)$_2$ or —($C_1$-$C_4$)-alkyl, in which
R6 is —($C_1$-$C_6$)-alkyl, —($C_3$-$C_8$)-cycloalkyl, —($C_6$-$C_{14}$)-aryl or four- to fifteen-membered heterocyclic ring,
R3 is hydrogen atom or —($C_1$-$C_4$)-alkyl,
R4 is
1) —($C_6$-$C_{14}$)-aryl-Z, in which Z is a basic nitrogen-containing group and in which aryl is unsubstituted or substituted independently with one to four Y, 2) —($C_3$-$C_{12}$)-cycloalkyl-Z, in which Z is a basic nitrogen-containing group and in which cycloalkyl is unsubstituted or substituted independently with one to four Y,
3) (four- to fifteen-membered heterocyclic ring)-Z, in which Z is a basic nitrogen-containing group and in which (four- to fifteen-membered heterocyclic ring) is unsubstituted or additionally substituted independently with one to four Y,
4) (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
5) —($C_6$-$C_{14}$)-aryl, in which aryl is unsubstituted or substituted independently with one to four Y,
6) —($C_3$-$C_{12}$)-cycloalkyl, in which cycloalkyl is unsubstituted or substituted independently with one to four Y,
7) A four- to fifteen-membered heterocyclic ring, in which heterocyclic ring is unsubstituted or substituted independently with one to four Y,
8) (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y, R5 is
1) halogen,
2) —($C_1$-$C_6$)-alkyl, in which alkyl is unsubstituted or substituted independently with one to four —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_8$)-cycloalkyl,
5) —OH,
6) —O—($C_1$-$C_4$)-alkyl,
7) —O—($C_1$-$C_3$)-fluoroalkyl,
8) —$NO_2$,
9) —CN,
10) —N(R7)(R8), in which R7 and R8 independently of one another are a hydrogen atom, —($C_3$-$C_8$)-cycloalkyl, halogen or —($C_1$-$C_6$)-alkyl, in which —($C_1$-$C_6$)-alkyl is optionally substituted with OH,
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-fluoroalkyl,
17) —S—($C_1$-$C_4$)-alkyl or
18) —S—($C_1$-$C_3$)-fluoroalkyl, U is a covalent bond, —($C_1$-$C_4$)-alkylene, —NH—, —N(($C_1$-$C_4$)-alkyl)-, —O—, —$SO_2$— or —S—,
V is —($C_1$-$C_4$)-alkylene, —$SO_2$—, —C(O)—NH— and —$SO_2$—NH—,
W is nitrogen atom or carbon atom,
X is nitrogen atom, carbon atom or oxygen atom,
Y is
1) halogen,
2) —($C_1$-$C_6$)-alkyl, in which alkyl is unsubstituted or substituted independently with one to four —($C_1$-$C_3$)-fluoroalkyl, —N—C(O)—OH or —N—C(O)—($C_1$-$C_4$)-alkyl,
3) —($C_1$-$C_3$)-fluoroalkyl,
4) —($C_3$-$C_8$)-cycloalkyl,
5) —OH,
6) —O—($C_1$-$C_4$)-alkyl, in which alkyl is unsubstituted or mono substituted with OH,
7) —O—($C_1$-$C_3$)-fluoroalkyl,
8) —$NO_2$,
9) —CN,
10) —N(R7)(R8), in which R7 and R8 independently of one another are a hydrogen atom, —($C_3$-$C_8$)-cycloalkyl, halogen or —($C_1$-$C_6$)-alkyl,
11) —C(O)—NH—R7,
12) —NH—C(O)—R7,
13) —NH—$SO_2$—R7,
14) —$SO_2$—($C_1$-$C_4$)-alkyl,
15) —$SO_2$—NH—R7,
16) —$SO_2$—($C_1$-$C_3$)-fluoroalkyl,
17) —S—($C_1$-$C_4$)-alkyl or
18) —S—($C_1$-$C_3$)-fluoroalkyl,
19) —($C_1$-$C_6$)-alkyl-N(R7)(R8),
m is 0 or 1,
n is 0 to 4,

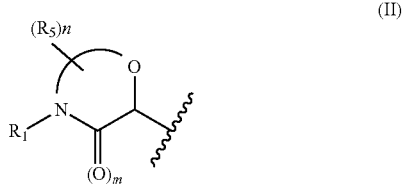

the linkage between Oxygen atom and Nitrogen atom of the substructure (II) describes one to four carbon atoms, which is unsubstituted or substituted independently with one to four R5,

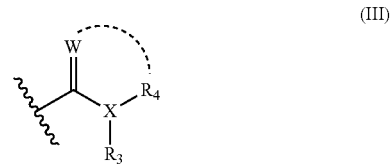

the linkage between W and R4 of the substructure (III) is
1) absent,
2) attached to form (four- to fifteen-membered heterocyclic ring)-Z, in which Z is a basic nitrogen-containing group and in which (four- to fifteen-membered heterocyclic ring) is unsubstituted or additionally substituted independently with one to four Y,
3) attached to form (four- to fifteen-membered heterocyclic ring)-U-(four- to fifteen-membered heterocyclic ring)-Z, in which Z is a basic nitrogen-containing group and in which the two (four- to fifteen-membered heterocyclic ring) radicals in each case independently of one another are unsubstituted or additionally substituted independently with one to four Y,
4) attached to form (four- to fifteen-membered heterocyclic ring) in which (four- to fifteen-membered heterocyclic ring) is unsubstituted or substituted independently with one to four Y,
5) attached to form (four- to fifteen-membered heterocyclic ring)-U-(four- to fifteen-membered heterocyclic ring), in which the two (four- to fifteen-membered heterocyclic ring) radicals in each case independently of one another are unsubstituted or substituted independently with one to four Y, wherein,
    each nitrogen atom of Z in Formula (I) is unsubstituted or substituted independently with —OH, —O—($C_1$-$C_4$)-alkyl group, —(CO)—($C_1$-$C_4$)-alkyl, or —(CO)—($C_1$-$C_4$)-alkyl group.

In another aspect, compounds of the Formula (I), or (I)(A)-(I)(D) or a pharmaceutical acceptable salt or a solvate thereof can be useful for treating or preventing a disorder or disease mediated by factor IXa, or a thromboembolic disorder (each disorder being a "Condition").

In another aspect, the present invention provides pharmaceutical compositions comprising at least one compound of the Formula (I) or (I)(A)-(I)(D) or a pharmaceutically acceptable carrier. The composition can be useful for treating or preventing a Condition.

In another aspect, the present invention provides a method for treating a Condition, the method comprising administering to a patient an effective amount of at least one compound of Formula (I) or (I)(A)-(I)(D) or a pharmaceutically acceptable salt or a solvate thereof.

DETAILED DESCRIPTION OF THE INVENTION

In an embodiment, the present invention provides compounds of Formula (I) or (I)(A)-(I)(D) and/or pharmaceutically acceptable salts, solvates and prodrugs thereof. The compounds of Formula (I) or (I)(A)-(I)(D) can be useful for treating or preventing a Condition in a patient.

As used above, and throughout this disclosure, the following terms, unless otherwise indicated, shall be understood to have the following meanings: the linkage between G atom and Nitrogen atom of the substructure (II)

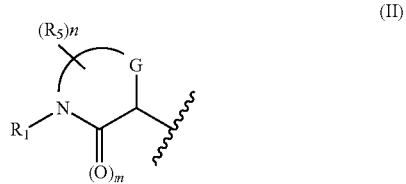

(II)

in Formula (I) comprises one to four carbon atoms to form alkylene chain, wherein said alkylene chain or G (imino or methylene) is unsubstituted or substituted independently with one to four R5,
the dotted linkage between W and R4 of the substructure (III)

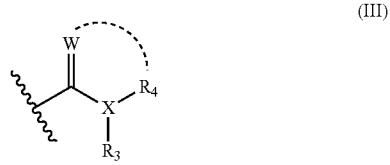

(III)

in Formula (I) is
1) absent,
2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;

3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;

4) present such that substructure (III) is a (three- to fifteen-membered heterocyclic ring), wherein said (three- to fifteen-membered heterocyclic ring) is unsubstituted or substituted independently with one to four Y;

5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

When the substructure (III) denotes the oxazole-Z as a whole, for example, W represents nitrogen atom, X represents oxygen atom and R3 represents absent and R4 and the dotted line represents ethylene carbon atoms, one of which is substituted with —Z, to form oxazole as a whole.

The term "($C_a$-$C_b$)-alkyl", in which a and b is each independently integers representing 1 to 6, is understood as meaning hydrocarbon radicals whose carbon chain are each straight-chain or branched and contains a to b carbon atoms, for example methyl, ethyl, propyl, isopropyl, butyl, isobutyl, tertiary-butyl, pentyl, isopentyl, neopentyl, hexyl, 2,3-dimethylbutyl or neohexyl.

The term "—($C_0$-$C_4$)-alkylene" is understood as meaning a bond or hydrocarbon radicals whose carbon chain is straight-chain or branched and contains 1 to 4 carbon atoms, for example methylene, ethylene, propylene, isopropylene, isobutylene, butylene or tertiary-butylene. "—$C_0$-alkylene" is a covalent bond. The term "—($C_1$-$C_4$)-alkylene" is understood as meaning hydrocarbon radicals whose carbon chain is straight-chain or branched and contains 1 to 4 carbon atoms, for example methylene (—$CH_2$—), ethylene (—$CH_2$—$CH_2$—), (—$CH_2(CH_3)$—), propylene (—$CH_2$—$CH_2$—$CH_2$—), isopropylene, isobutylene, butylene or tertiary-butylene.

The term "—($C_3$-$C_{12}$)-cycloalkyl" is understood as meaning rings of 3 to 12 carbon atoms such as compounds which partially have monocycles having 3 to 8 carbon atoms in the ring such as cyclopropane, cyclobutane, cyclopentane, cyclohexane, cycloheptane or cyclooctane, which are derived from the bicycles bicyclo[4.2.0]octane, octahydroindene, decahydronaphthalene, decahydroazulene, decahydrobenzocycloheptene or dodecahydroheptalene or from the bridged cycles such as spiro[2.5]octane, spiro[3.4]octane, spiro[3.5]nonane, bicyclo[3.1.1]heptane, bicyclo[2.2.1]heptane or bicyclo[2.2.2]octane.

The term "—($C_3$-$C_8$)-cycloalkyl" is understood as meaning radicals which are derived from monocycles having 3 to 8 carbon atoms in the ring such as cyclopropane, cyclobutane, cyclopentane, cyclohexane, cyclo-heptane or cyclooctane.

The term "—($C_6$-$C_{14}$)-aryl" is understood as meaning aromatic hydrocarbon radicals having 6 to 14 carbon atoms in the ring. —($C_6$-$C_{14}$)-aryl radicals are, for example, phenyl, 1-naphthyl, 2-naphthyl, anthryl or fluorenyl. Naphthyl radicals and in particular phenyl radicals are preferred aryl radicals.

The term "three- to fifteen-membered heterocyclic ring" is understood as meaning ring systems having 3 to 15 carbon atoms, which are present in one, two or three ring systems connected to one another and in which one, two, three or four identical or different heteroatoms from the group consisting of oxygen, nitrogen or sulfur can replace the respective carbon atoms.

One of the examples of "three- to fifteen-membered heterocyclic ring" is a bicyclic ring system represented by Formula (a):

In the bicyclic ring system represented by Formula (a);

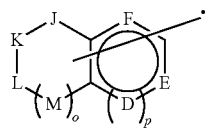

Formula (a)

wherein Formula (a) is unsubstituted or substituted independently with one to four Y; and wherein:

o and p are independently selected from 0 or 1;

J, K, L and M are independently selected from the group consisting of CH2, C(O), NH, O and S(O)q, wherein q is 0, 1 or 2;

D, E and F are independently selected from the group consisting of carbon atom, nitrogen atom, oxygen atom and sulfur atom.

Examples of three- to fifteen-membered heterocyclic ring are the radicals acridinyl, azepinyl, azetidinyl, aziridinyl, benzimidazolinyl, benzimidazolyl, benzisoxazole, benzofuranyl, benzothiofuranyl, benzothiophenyl, benzoxazolyl, benzothiazolyl, benzotriazolyl, benzotetrazolyl, benzisoxazolyl, benzisothiazolyl, carbazolyl, 4H-carbazolyl, carbolinyl, beta-carbolinyl, chromanyl, chromenyl, cinnolinyl, deca-hydroquinolinyl, dibenzofuranyl, dibenzothiophenyl, dihydrofuran[2,3-b]-tetrahydrofuranyl, dihydrofuranyl, 1,1-dioxido-2H-1,2,4-benzothiadiazinyl, dioxolyl, dioxanyl, dioxolenyl, 2H, 6H-1,5,2-dithiazinyl, furanyl, furazanyl, imidazolidinyl, imidazolinyl, imidazolyl, 1H-indazolyl, indolinyl, indolizinyl, indolyl, isobenzofuranyl, isoquinolinyl, isochromanyl, isoindazolyl, isoindolinyl, isoindolyl, isothiazolidinyl, 2-isothiazolinyl, isothiazolyl, isoxazolyl, isoxazolidinyl, 2-isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxiranyl, oxothiolanyl, phenanthridinyl, phenanthrenyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridothiophenyl, pyridyl, pyrimidinyl, pyrrolidinyl, pyrrolinyl, pyrrolyl, 2H-pyrrolyl, quinazolinyl, quinolinyl, quinolizinyl, 4H-quinolizinyl, quinoxalinyl, quinuclidinyl, tetrahydrofuranyl, tetrahydroisoquinolinyl, tetrahydroquinolinyl, tetrahydropyridinyl, tetrazolyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazinyl, thiazolyl, thienyl, thienoimidazolyl, thienooxazolyl, thienopyridinyl, thienopyrrolyl, thienothiazolyl, thienothiophenyl, thiomorpholinyl, thiopyranyl, triazinyl, 1,2,3-triazolyl, 1,2,4-triazolyl, 1,2,5-triazolyl, 1,3,4-triazolyl, xanthenyl, oxindolyl, benzimidazolinyl, benzoxalonyl, 1,3-dihydro-benzisothiazolyl, 3,4-dihydro-2,3-benzothiazinyl, 2,3-dihydro-isoindolyl, 1,4-dihydro-isoquinolinonyl, 3,4-dihydro-quinolinonyl or 3,4-dihydro-benzothiadiazinyl.

The term "—($C_1$-$C_3$)-haloalkyl" is understood as meaning a partially or completely fluorinated or chlorinated alkyl radical which is selected, for example, from the following radical —$CF_3$, —$CHF_2$, —$CH_2F$, —$CHF$—$CF_3$, —$CHF$—$CHF_2$, —$CHF$—$CH_2F$, —$CH_2$—$CF_3$, —$CH_2$—$CHF_2$, —$CH_2$—$CH_2F$, —$CF_2$—$CF_3$, —$CF_2$—$CHF_2$, —$CF_2$—$CH_2F$, —$CH_2$—$CHF$—$CF_3$, —$CH_2$—$CHF$—$CHF_2$, —$CH_2$—$CHF$—$CH_2F$, —$CH_2$—$CH_2$—$CF_3$, —$CH_2$—$CH_2$—$CHF_2$, —$CH_2$—$CH_2$—$CH_2F$, —$CH_2$—$CF_2$—$CF_3$, —$CH_2$—$CF_2$—$CHF_2$, —$CH_2$—$CF_2$—$CH_2F$, —$CHF$—$CHF$—$CF_3$, —$CHF$—$CHF$—$CHF_2$, —$CHF$—$CHF$—$CH_2F$, —$CHF$—$CH_2$—$CF_3$, —$CHF$—$CH_2$—$CHF_2$, —$CHF$—$CH_2$—$CH_2F$, —$CHF$—$CF_2$—$CF_3$, —$CHF$—$CF_2$—$CHF_2$, —$CHF$—$CF_2$—$CH_2F$, —$CF_2$—$CHF$—$CF_3$, —$CF_2$—$CHF$—$CHF_2$, —$CF_2$—$CHF$—$CH_2F$, —$CF_2$—$CH_2$—$CF_3$, —$CF_2$—$CH_2$—$CHF_2$, —$CF_2$—$CH_2$—$CH_2F$, —$CF_2$—$CF_2$—$CF_3$, —$CF_2$—$CF_2$—$CHF_2$ or —$CF_2$—$CF_2$—$CH_2F$.

The term "halogen" is understood as meaning fluorine, chlorine, bromine or iodine; fluorine, chlorine or bromine is preferred, in particular fluorine or chlorine is preferred.

The term "a basic nitrogen-containing group" is understood as meaning radicals where the conjugated acid of this group has a pKa of approximately 5 to 15, and preferably 7 to 12, of which nitrogen group can be optionally substituted by one or two the same or different ($C_1$-$C_6$) alkyl group.

Examples of this basic nitrogen-containing group are amino, imino, aminomethyl, amidino (carbamidoyl), guanidino, azetidinyl, pyrrolidinyl, piperidinyl, pyridinyl or aminopyridinyl, and any of the nitrogen atom of these basic nitrogen-containing group can be substituted independently with one or two ($C_1$-$C_3$)-alkyl group.

Examples of —($C_6$-$C_{14}$)-aryl-Z, wherein Z is a basic nitrogen-containing group and wherein —($C_6$-$C_{14}$)-aryl is unsubstituted or substituted independently with one to four Y, are amidino phenyl (preferably 4-amidino phenyl), amidino chloro phenyl (preferably 4-amidino-2-chloro phenyl), amidino fluoro phenyl (preferably 4-amidino-2-fluoro-phenyl or 4-amidino-3-fluoro-phenyl), amidino methyl phenyl (preferably 4-amidino-2-methyl-phenyl), and aminomethyl phenyl (preferably 4-aminomethyl phenyl).

Examples of (three- to fifteen-membered heterocyclic ring)-Z, wherein Z is a basic nitrogen-containing group and wherein (three- to fifteen-membered heterocyclic ring) is unsubstituted or additionally substituted independently with one to four Y, are 1-aminoisoquinolinyl (preferably 1-aminoisoquinolin-6-yl), 1-imino-2,3-dihydroisoindolyl (preferably 1-imino-2,3-dihydroisoindol-5-yl), 2-amino-3H-benzimidazolyl (preferably 2-amino-3H-benzimidazol-5-yl), 3-amino-benzoisoxazolyl (preferably 3-amino-benzoisoxazole-6-yl), 3-amino-indazolyl (preferably 3-amino-indazole-6-yl), 4-amino-quinazolinyl (preferably 4-amino-quinazoline-7-yl).

Examples of the substructure (III) in Formula (I),

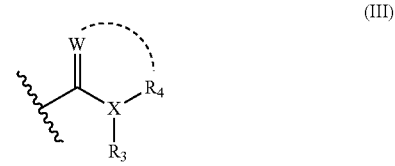

(III)

wherein the dotted linkage between W and R4 is present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y, are 6-amidino-benzimidazole-2-yl, 7-amidino-1,1-dioxo-2H-1,2,4-benzothiadiazin-3-yl.

Functional groups of the intermediates used, for example amino or carboxyl groups, can be masked here by suitable protective groups. Suitable protective groups for amino functions are, for example, para methoxy benzyl, benzyl, t-butoxycarbonyl, benzyloxycarbonyl, phthaloyl, trityl or tosyl protective group. Suitable protective groups for the carboxyl function are, for example, alkyl, aryl or arylalkyl esters. Protective groups can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme). The term protective group can also include polymer-bound protective groups. Such masked compounds according to Formula (I) or (I)(A)-(I)(D), in which, for example, the functional groups of the radicals R1, R2, R3 or R4 can optionally also be masked, can, although optionally themselves not pharmacologically active, optionally be converted after administration to mammals by metabolization to the pharmacologically active compounds according to the invention.

When any variable (e.g., aryl, R1, etc.) occurs more than one time in any constituent or in Formula (I) or (I)(A)-(I)(D), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

In the embodiments described below in [1-1] to [8-1] of the present invention, unless otherwise noted, R1, R2, R3, R4, R5, G, W, X, m, n or other definitions, for example, R6, R7, R8, V, Y, Z, T, U, etc in the substituents as well as D, E, F, J, K, L, M, or p etc in the sub-Formulae, shown in the each descriptions are the same as defined above for the Formula (I) or (I)(A)-(I)(D). In the embodiments, compounds having Factor IXa antagonistic activity (determined by, for example, pharmacological examples described below: a measurement of fluorescence value using microtiter plate reader, ARVO 1420 Multilabel Counter) of 30 µM or less, preferably 1 µM or less, more preferably 100 nM or less, and the most preferably 50 nM or less in terms of an IC50 value are preferably used.

In the embodiments described in this description, "agent" or "drug" means a material which is used for improvement of disease or symptom, not only for treatment of disease or symptom.

In all the above embodiments, when the term "compound" is used, the term also refers to pharmaceutically acceptable salts thereof. The compounds of the present invention have asymmetric carbon atoms. Accordingly, the compounds of the present invention include mixtures of various stereoisomers, such as geometrical isomers, tautomers, such as keto- and enol-tautomers, or amidino- and imidino-tautomers, and optical isomers, and isolated isomers, for example, (R,R), (S,S), (R,S) and (S,R) isomers. (R,R) isomer is preferred. Specific example of (R,R) isomer compound is, for example, (2R)—N-(4-amidinophenyl)-2-hydroxy-2-[(2R)-3-oxo-4-p-tolylmorpholin-2-yl]acetamide hydrochloride (Example 7). The isolation and the purification of such stereoisomers can be performed by those skilled in the art with a known technique such as optical resolution using preferential crystallization or column chromatography, or asymmetric synthesis.

The compounds represented by Formula (I) or (I)(A)-(I)(D) of the present invention may form acid addition salts. Alternatively, these compounds may form salts with a base according to the type of substituent. These salts are not particularly limited as long as the salts are pharmaceutically acceptable salts. Specific examples of the salts include acid addition salts with a mineral acid such as hydrochloric acid, hydrobromic acid, hydroiodic acid, sulfuric acid, nitric acid, or phosphoric acid; an organic carboxylic acid such as an aliphatic monocarboxylic acid, e.g., formic acid, acetic acid, trifluoroacetic acid (TFA), propionic acid, butyric acid, valeric acid, enanthic acid, capric acid, myristic acid, palmitic acid, stearic acid, lactic acid, sorbic acid, or mandelic acid, an aromatic monocarboxylic acid, e.g., benzoic acid or salicylic acid, an aliphatic dicarboxylic acid, e.g., oxalic acid, malonic acid, succinic acid, fumaric acid, maleic acid, malic acid, or tartaric acid, and an aliphatic tricarboxylic acid e.g., citric acid; an organic sulfonic acid such as an aliphatic sulfonic acid, e.g., methanesulfonic acid, ethanesulfonic acid, trifluoromethanesulfonic acid, or 2-hydroxyethanesulfonic acid, or an aromatic sulfonic acid, e.g., benzenesulfonic acid or p-toluenesulfonic acid; or an acidic amino acid, e.g., aspartic acid or glutamic acid; salts with a metal such as an alkali metal, e.g., sodium or potassium, or an alkaline earth metal, e.g., magnesium or calcium; salts with an organic base such as methylamine, ethylamine, ethanolamine, pyridine, lysine, arginine, or ornithine; and ammonium salts.

These salts can be obtained by a known method, for example, by mixing a compound of the present invention with an equivalent amount and a solution containing a desired acid, base, or the like, and then collecting the desired salt by filtering the salt or distilling off the solvent.

The compounds of the present invention and salts thereof can form solvates with a solvent such as water, ethanol, or glycerol.

The salts of a compound of the present invention include monosalts and di-salts. The compounds of the present invention can form an acid addition salt and a salt with a base at the same time according to the type of substituent of the side chain.

Furthermore, the present invention includes hydrates, pharmaceutically acceptable various solvates, and crystal polymorphism of the compounds represented by Formula (I) or (I)(A)-(I)(D) of the present invention. The present invention is not limited to the compounds described in examples below and includes all compounds represented by Formula (I) or (I)(A)-(I)(D) of the present invention and pharmaceutically acceptable salts thereof.

Prodrugs and solvates of the compounds of the invention are also contemplated herein. A discussion of prodrugs is provided in T. Higuchi and V. Stella, Pro-drugs as Novel Delivery Systems, 14, 1987, of the A.C.S. Symposium Series, and in Bioreversible Carriers in Drug Design, 1987, Edward B. Roche, ed., American Pharmaceutical Assosiation and Pergamon Press. The term "prodrug" means a compound (e.g, a drug precursor) that is transformed in vivo to yield a compound of Formula (I) or (I)(A)-(I)(D) or a pharmaceutically acceptable salt, hydrate or a solvate of the compound. The transformation may occur by various mechanisms (e.g., by metabolic or chemical processes), such as, for example, through hydrolysis in blood. A discussion of the use of pro-drugs is provided by T. Higuchi and W. Stella, "Pro-drugs as Nobel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or (I)(A)-(I)(D) or a pharmaceutically acceptable salt, hydrate or a solvate of the compound contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal from of a carbohydrate), and the like.

If a compound of Formula (I) or (I)(A)-(I)(D) incorporates an amine functional group or imine functional group, for example, such as a part of amidino group, a prodrug can be formed by the replacement of a hydrogen atom of the amine group or imine group with a group such as, for example, hydroxyl group, RO-, R-carbonyl, RO-carbonyl, NRR'-carbonyl where R and R' are each independently hydrogen atom, ($C_1$-$C_{10}$)alkyl, ($C_3$-$C_7$)cycloalkyl, benzyl, or R-carbonyl is a natural α-aminoacyl or natural β-aminoacyl, —CH(OY2)Y3 wherein Y2 is ($C_1$-$C_4$) alkyl and Y3 is ($C_1$-$C_6$)alkyl, carboxy ($C_1$-$C_6$)alkyl, amino($C_1$-$C_4$)alkyl or mono-N- or di-N,N—($C_1$-$C_6$)alkylaminoalkyl, —CH(Y4)Y5 wherein Y4 is H or methyl and Y5 is mono-N- or $C_1$-$C_6$)alkylamino morpholino, piperidin-1-yl or pyrrolidin-1-yl and the like.

Morpholinone Compounds of the Invention

[1-1] The invention therefore relates to a compound of Formula (I)

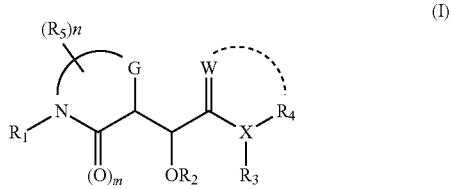

(I)

or a pharmaceutically acceptable salt or a solvate thereof;
wherein:
R1 is selected from the group consisting of:
1) —($C_6$-$C_{14}$)-aryl, which is unsubstituted or substituted independently with one to four Y;
2) -(three- to fifteen-membered heterocyclic ring), which is unsubstituted or substituted independently with one to four Y;
3) —($C_6$-$C_{14}$)-aryl-U—($C_6$-$C_{14}$)-aryl, wherein each of said —($C_6$-$C_{14}$)-aryl-independently is unsubstituted or substituted independently with one to four Y;
4) —($C_6$-$C_{14}$)-aryl-U—($C_3$-$C_{12}$)-cycloalkyl, wherein said —($C_6$-$C_{14}$)-aryl and —($C_3$-$C_{12}$)-cycloalkyl independently are unsubstituted or substituted independently with one to four Y;
5) —($C_6$-$C_{14}$)-aryl-U-(three- to fifteen-membered heterocyclic ring), wherein said —($C_6$-$C_{14}$)-aryl and said (three- to fifteen-membered heterocyclic ring) are independently unsubstituted or substituted independently with one to four Y;
6) -(three- to fifteen-membered heterocyclic ring)-U—($C_6$-$C_{14}$)-aryl, wherein said —($C_6$-$C_{14}$)-aryl and said (three- to fifteen-membered heterocyclic ring) are independently unsubstituted or substituted independently with one to four Y;
7) -(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) -(three- to fifteen-membered heterocyclic ring)-U—($C_3$-$C_{12}$)-cycloalkyl, wherein said —($C_3$-$C_{12}$)-cycloalkyl, and said -(three- to fifteen-membered heterocyclic ring)- are independently unsubstituted or substituted independently with one to four Y;
9) —V—($C_6$-$C_{14}$)-aryl, which is unsubstituted or substituted independently with one to four Y; and
10) —V-(three- to fifteen-membered heterocyclic ring), which is unsubstituted or substituted independently with one to four Y;

R2 is selected from the group consisting of hydrogen atom, —C(O)—R6, —C(O)—O—R6, —C(O)—NH—R6, —C(O)—N(R6)$_2$, —P(O)(OR6)$_2$ and —($C_1$-$C_6$)-alkyl, wherein
each R6 independently is selected from the group consisting of hydrogen atom, —($C_1$-$C_6$)-alkyl, —($C_3$-$C_8$)-cycloalkyl, —($C_6$-$C_{14}$)-aryl and a three- to fifteen-membered heterocyclic ring;

R3 is absent, or selected from the group consisting of hydrogen atom and —($C_1$-$C_4$)-alkyl, R4 is selected from the group consisting of:
1) —($C_6$-$C_{14}$)-aryl-Z, wherein said Z is a basic nitrogen-containing group and wherein said —($C_6$-$C_{14}$)-aryl is unsubstituted or substituted independently with one to four Y;
2) —($C_3$-$C_{12}$)-cycloalkyl-Z, wherein said Z is a basic nitrogen-containing group and wherein said —($C_3$-$C_{12}$)-cycloalkyl is unsubstituted or substituted independently with one to four Y;
3) -(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) -(three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;
5) —($C_6$-$C_{14}$)-aryl, which is unsubstituted or substituted independently with one to four Y;
6) —($C_3$-$C_{12}$)-cycloalkyl, which is unsubstituted or substituted independently with one to four Y;
7) -(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;

each R5 independently is selected from the group consisting of
1) halogen;
2) —($C_1$-$C_6$)-alkyl, which is unsubstituted or substituted independently with one to four —($C_1$-$C_3$)-haloalkyl, —N—C(O)—OH, —N—C(O)—($C_1$-$C_4$)-alkyl, or —C(O)OR7;
3) —($C_1$-$C_3$)-haloalkyl;
4) —($C_3$-$C_8$)-cycloalkyl;
5) —OH;
6) —O—($C_1$-$C_4$)-alkyl;
7) —O—($C_1$-$C_3$)-haloalkyl;
8) —NO$_2$;

9) —CN;
10) —N(R7)(R8);
11) —C(O)—N(R7)(R8);
12) —N(R8)—C(O)—R7;
13) —N(R8)—SO$_2$—R7;
14) —SO$_2$—(C$_1$-C$_4$)-alkyl;
15) —SO$_2$—N(R7)(R8);
16) —SO$_2$—(C$_1$-C$_3$)-haloalkyl;
17) —S—(C$_1$-C$_4$)-alkyl;
18) —S—(C$_1$-C$_3$)-haloalkyl;
19) =O (oxo);
20) —C(O)OR7; and
21) C(O)R7
wherein each of R7 and R8 is independently selected from the group consisting of hydrogen atom, —(C$_6$-C$_{14}$)-aryl, —(C$_3$-C$_8$)-cycloalkyl, and —(C$_1$-C$_6$)-alkyl, wherein said —(C$_1$-C$_6$)-alkyl is unsubstituted or substituted with at least one substituent selected from the group consisting of OH, —O—(C$_1$-C$_4$)-alkyl, —(C$_1$-C$_3$)-fluoroalky, —O—(C$_1$-C$_3$)-haloalkyl, C(O)OH, and C(O)O—(C$_1$-C$_6$)-alkyl;

each U independently is selected from the group consisting of a covalent bond, —(C$_1$-C$_4$)-alkylene, —NH—, —N((C$_1$-C$_4$)-alkyl)-, —O—, —SO$_2$— or —S—,
wherein said —(C$_1$-C$_4$)-alkylene or —(C$_1$-C$_4$)-alkyl is unsubstituted or substituted independently with one to four T,
or wherein geminal hydrogens in said —(C$_1$-C$_4$)-alkylene or —(C$_1$-C$_4$)-alkyl can be replaced by a (C$_3$-C$_8$)-cycloalkyl to form a spiro cyclic ring;

each V independently is selected from the group consisting of —(C$_1$-C$_4$)-alkylene, —SO$_2$—, —C(O)—, —C(O)—NH— and —SO$_2$—NH—,
wherein the carbon atom of said —C(O)—NH— or the sulfur atom of said —SO$_2$—NH— is connected to a nitrogen atom of the morpholinone ring, and wherein said —(C$_1$-C$_4$)-alkylene is unsubstituted or substituted independently with one to four T,
or wherein geminal hydrogens in said —(C$_1$-C$_4$)-alkylene can be replaced by a (C$_3$-C$_8$)-cycloalkyl to form a Spiro cyclic ring;

each T independently is selected from the group consisting of:
1) halogen;
2) —(C$_1$-C$_6$)-alkyl, which is unsubstituted or substituted independently with one to four substituents selected from the group consisting of OH, —O—(C$_1$-C$_4$)-alkyl, —(C$_1$-C$_3$)-haloalkyl, —O—(C$_1$-C$_3$)-haloalkyl, —N—C(O)—OH and —N—C(O)—(C$_1$-C$_4$)-alkyl;
3) —(C$_1$-C$_3$)-haloalkyl;
4) —(C$_3$-C$_8$)-cycloalkyl;
5) —OH;
6) —O—(C$_1$-C$_4$)-alkyl, which is unsubstituted or mono substituted with OH, —O—(C$_1$-C$_4$)-alkyl, —(C$_1$-C$_3$)-haloalkyl, —O—(C$_1$-C$_3$)-haloalkyl, —N—C(O)—OH or —N—C(O)—(C$_1$-C$_4$)-alkyl;
7) —O—(C$_1$-C$_3$)-haloalkyl;
8) —NO$_2$;
9) —CN;
10) —N(R7)(R8);
11) —C(O)—N(R7)(R8);
12) —N(R8)—C(O)—R7;
13) —N(R8)—SO$_2$—R7;
14) —SO$_2$—(C$_1$-C$_4$)-alkyl;
15) —SO$_2$—N(R7)(R8);
16) —SO$_2$—(C$_1$-C$_3$)-haloalkyl;
17) —S—(C$_1$-C$_4$)-alkyl;
18) —S—(C$_1$-C$_3$)-haloalkyl;
19) —(C$_1$-C$_6$)-alkyl-N(R7)(R8);
20) —NH—C(O)—N(R7)(R8);
21) =O (oxo); and
22) —C(O)OR7;
23) —C(O)OR7;
24) —N—C(O)—OR7
wherein each of R7 and R8 independently is selected from the group consisting of a hydrogen atom, —(C$_3$-C$_8$)-cycloalkyl, halogen and —(C$_1$-C$_6$)-alkyl, wherein said —(C$_1$-C$_6$)-alkyl is optionally substituted with at least one substituent selected from the group consisting of OH, —O—(C$_1$-C$_4$)-alkyl, —(C$_1$-C$_3$)-fluoroalky, and —O—(C$_1$-C$_3$)-haloalkyl;

G is selected from the group consisting of oxygen atom, imino, sulfur atom, sulfoxide, sulfone and methylene;
W is selected from the group consisting of oxygen atom, nitrogen atom and carbon atom;
X is selected from the group consisting of nitrogen atm, carbon atom and oxygen atom;
Y is selected from the group consisting of:
1) halogen;
2) —(C$_1$-C$_6$)-alkyl;
3) —(C$_1$-C$_3$)-haloalkyl;
4) —(C$_3$-C$_8$)-cycloalkyl;
5) —OH;
6) —O—(C$_1$-C$_6$)-alkyl;
7) —O—(C$_1$-C$_3$)-haloalkyl;
8) —NO$_2$;
9) —CN;
10) —N(R7)(R8);
11) —C(O)—N(R7)(R8);
12) —N(R8)—C(O)—R7;
13) —N(R8)—SO$_2$—R7;
14) —SO$_2$—(C$_1$-C$_4$)-alkyl;
15) —SO$_2$—N(R7)(R8);
16) —SO$_2$—(C$_1$-C$_3$)-haloalkyl;
17) —S—(C$_1$-C$_4$)-alkyl;
18) —S—(C$_1$-C$_3$)-haloalkyl;
19) —(C$_1$-C$_6$)-alkyl-N(R7)(R8);
20) —N(R8)—C(O)—N(R7)(R8);
21) =O (oxo);
22) —SF$_5$;
23) —C(O)OR7;
24) —N—C(O)—OR7
25) —N(R8)—C(O)—(C$_1$-C$_4$)-alkyl-O—(C$_1$-C$_4$)-alkyl-(C$_6$-C$_{14}$)-aryl, wherein said —(C$_6$-C$_{14}$)-aryl is unsubstituted or substituted independently with one to four Y selected from (1) to (24) as set forth above;
26) —N(R8)—C(O)—(C$_1$-C$_4$)-alkyl-O—(C$_1$-C$_4$)-alkyl-(three- to fifteen-membered heterocyclic ring), wherein said -(three- to fifteen-membered heterocyclic ring) is unsubstituted or substituted independently with one to four Y selected from (1) to (24) as set forth above;
wherein said —(C$_1$-C$_4$)-alkyl part or —(C$_1$-C$_6$)-alkyl part of 2), 6), 14), 17), 19), 25) or 26) of said Y is unsubstituted or substituted independently with one to four T;
wherein each of R7 and R8 of 10), 11), 12), 13), 15), 19), 20), 23), 24), 25) or 26) of said Y independently is selected from the group consisting of hydrogen atom, —(C$_3$-C$_8$)-cycloalkyl, and —(C$_1$-C$_6$)-alkyl, wherein said —(C$_1$-C$_6$)-alkyl is optionally substituted with OH, —O—(C$_1$-C$_4$)-alkyl, —(C$_1$-C$_3$)-fluoroalky, —O—(C$_1$-C$_3$)-haloalkyl, —C(O)OH, or C(O)O—(C$_1$-C$_6$)-alkyl;

m is 0 or 1, n is 0, 1, 2, 3 or 4, the linkage between G atom and Nitrogen atom of the substructure (II)

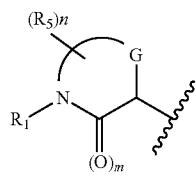
(II)

in Formula (I) comprises one to four carbon atoms to form alkylene chain, wherein said alkylene chain or G (imino or methylene) is unsubstituted or substituted independently with one to four R5;

the dotted linkage between W and R4 of the substructure (III)

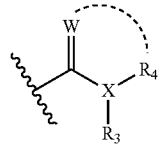
(III)

in Formula (I) is 1) absent, 2) present such that substructure (III) is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;

3) present such that substructure (III) is a (three- to fifteen-membered heterocyclic ring)-U-(three- to fifteen-membered heterocyclic ring)-Z, wherein said Z is a basic nitrogen-containing group and wherein each of said (three- to fifteen-membered heterocyclic ring) is independently unsubstituted or additionally substituted independently with one to four Y;

4) present such that substructure (III) is a (three- to fifteen-membered heterocyclic ring), wherein said (three- to fifteen-membered heterocyclic ring) is unsubstituted or substituted independently with one to four Y;

5) present such that substructure (III) is a (three- to fifteen-membered heterocyclic ring)-U-(three- to fifteen-membered heterocyclic ring), wherein each of said (three- to fifteen-membered heterocyclic ring) is independently unsubstituted or substituted independently with one to four Y.

[1-2] In another aspect, the present invention provides compounds of the Formula (I), wherein m is 1 and n is 0.

[1-3] In another aspect, the present invention provides compounds of the Formula (I), wherein m is 1 and n is 1.

[1-4] In another aspect, the present invention provides compounds of the Formula (I), wherein m is 0 and n is 0.

[1-5] In another aspect, the present invention provides compounds of the Formula (I), wherein m is 0 and n is 1.

[2-1] In another aspect, the present invention provides compounds of the Formula (I), wherein Formula (II),

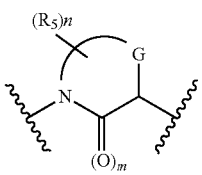
(II)

in Formula (I) is (IIa)

(IIb)

(IIc)

or (IId)

[2-2] In another aspect, the present invention provides compounds of the Formula (I),
wherein Formula (II),

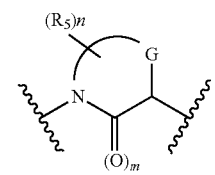
(II)

in Formula (I) is,

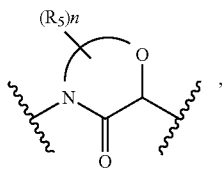
(IIa)

and preferably,

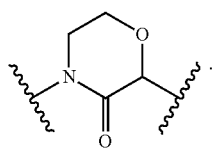
(IIa1)

[2-3] In another aspect, the present invention provides compounds of the Formula (I), wherein Formula (III),

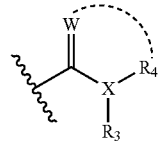
(III)

in Formula (I) is

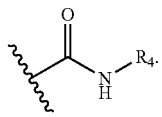

[2-4] In another aspect, the present invention provides compounds of the Formula (I'),

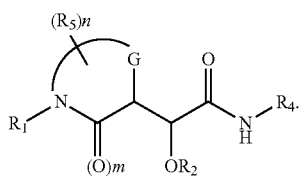
(I')

[2-5] In another aspect, the present invention provides compounds of the Formula (I"),

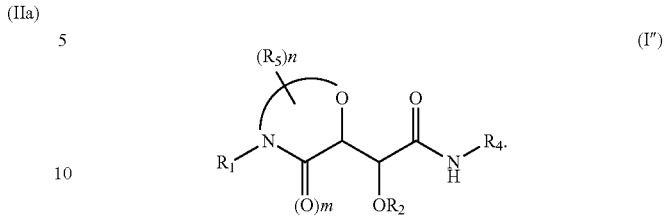
(I")

[2-6] In another aspect, the present invention provides compounds of the Formula (I'''),

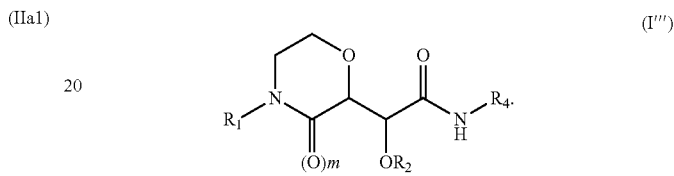
(I''')

[3-1] In another aspect, the present invention provides compounds of the Formula (I), wherein:
R1 is selected from the group consisting of
1) —$(C_6\text{-}C_{14})$-aryl, which is unsubstituted or substituted independently with one to four Y;
2) -(three- to fifteen-membered heterocyclic ring), which is unsubstituted or substituted independently with one to four Y;
3) —$(C_6\text{-}C_{14})$-aryl-U—$(C_6\text{-}C_{14})$-aryl, wherein each of said —$(C_6\text{-}C_{14})$-aryl independently is unsubstituted or substituted independently with one to four Y;
5) —$(C_6\text{-}C_{14})$-aryl-U-(three- to fifteen-membered heterocyclic ring), in which said —$(C_6\text{-}C_{14})$-aryl and said (three- to fifteen-membered heterocyclic ring) are independently unsubstituted or substituted independently with one to four Y; and
9) —V—$(C_6\text{-}C_{14})$-aryl, wherein said —V—$(C_6\text{-}C_{14})$-aryl is unsubstituted or substituted independently with one to four Y.

[3-2] In another aspect, the present invention provides compounds of the Formula (I), wherein:
R1 is: 1) —$(C_6\text{-}C_{14})$-aryl, which is unsubstituted or substituted independently with one to four Y

[3-3] In another aspect, the present invention provides compounds of the Formula (I), wherein:
R1 is: 2) -(three- to fifteen-membered heterocyclic ring), which is unsubstituted or substituted independently with one to four Y

[3-4] In another aspect, the present invention provides compounds of the Formula (I), wherein:
R1 is: 3) —$(C_6\text{-}C_{14})$-aryl-U—$(C_6\text{-}C_{14})$-aryl, wherein each of said —$(C_6\text{-}C_{14})$-aryl independently is unsubstituted or substituted independently with one to four Y

[3-5] In another aspect, the present invention provides compounds of the Formula (I), wherein:
R1 is: 5) —$(C_6\text{-}C_{14})$-aryl-U-(three- to fifteen-membered heterocyclic ring), in which said —$(C_6\text{-}C_{14})$-aryl and said (three- to fifteen-membered heterocyclic ring) are independently unsubstituted or substituted independently with one to four Y

[3-5-1] In another aspect, the present invention provides compounds of the Formula (I), wherein:
R1 is: 5) —$(C_6\text{-}C_{14})$-aryl-U-(three- to fifteen-membered heterocyclic ring), in which said —$(C_6\text{-}C_{14})$-aryl and said (three- to fifteen-membered heterocyclic ring) are independently unsubstituted or substituted independently with one to four Y wherein U is a covalent bond.

[3-5-2] In another aspect, the present invention provides compounds of the Formula (I), wherein:

R1 is: 5) —($C_6$-$C_{14}$)-aryl-U-(three- to fifteen-membered heterocyclic ring), in which said —($C_6$-$C_{14}$)-aryl and said (three- to fifteen-membered heterocyclic ring) are independently unsubstituted or substituted independently with one to four Y;

wherein U is methylene which is substituted with oxo to form carbonyl group (—C(O)—).

[3-6] In another aspect, the present invention provides compounds of the Formula (I), wherein:

R1 is: 9) —V—($C_6$-$C_{14}$)-aryl, wherein said —V—($C_6$-$C_{14}$)-aryl is unsubstituted or substituted independently with one to four Y.

[3-7] In another aspect, the present invention provides compounds of the Formula (I), wherein R1 is a phenyl group, which is unsubstituted or substituted independently with one to four Y.

[3-8] In another aspect, the present invention provides compounds of the Formula (I), wherein said three- to fifteen-membered heterocyclic ring of R1 is represented by the Formula (a)

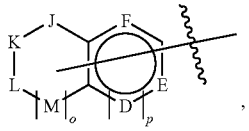

Formula (a)

wherein Formula (a) is unsubstituted or substituted independently with one to four Y; and wherein:

o and p are independently selected from 0 or 1;

J, K, L and M are independently selected from the group consisting of CH2, C(O), NH, O and S(O)q, wherein q is 0, 1 or 2;

D, E and F are independently selected from the group consisting of carbon atom, nitrogen atom, oxygen atom and sulfur atom.

[4-1] In another aspect, the present invention provides compounds of the Formula (I), wherein Z represents a radical whose conjugate acid has a pKa of 5 to 15.

[4-2] In another aspect, the present invention provides compounds of the Formula (I), wherein Z represents a radical whose conjugate acid has a pKa of 7 to 12.

[4-3] In another aspect, the present invention provides compounds of the Formula (I), wherein Z represents a radical selected from the group consisting of amino, imino, aminomethyl, amidino (carbamimidoyl), guanidino, azetidinyl, pyrrolidinyl, piperidinyl, pyridinyl and aminopyridinyl, and wherein any nitrogen atom of each of said aforementioned Z radicals is unsubstituted or substituted independently with one or two ($C_{1-3}$) alkyl.

[5-1] In another aspect, the present invention provides compounds of the Formula (I), wherein the substructure Formula (III)

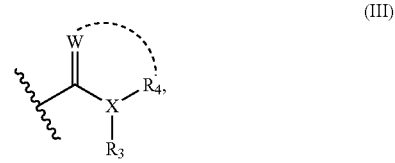

(III)

W is oxygen atom, X(R3) is NH, the dotted linkage is absent, and R4 is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y.

[5-2] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is —($C_6$-$C_{14}$)-aryl-Z, wherein Z is a basic nitrogen-containing group and wherein said —($C_6$-$C_{14}$)-aryl is unsubstituted or additionally substituted independently with one to four Y.

[5-3] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -benzimidazole-Z, wherein Z is a basic nitrogen-containing group and wherein said benzimidazole is unsubstituted or additionally substituted independently with one to four Y.

[5-4] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted independently with one to four Y.

[5-5] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
 1) halogen;
 2) —($C_1$-$C_6$)-alkyl;
 3) —($C_1$-$C_3$)-haloalkyl;
 4) —($C_3$-$C_8$)-cycloalkyl;
 5) —OH;
 6) —O—($C_1$-$C_6$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
 7) —O—($C_1$-$C_3$)-haloalkyl;
 8) —$NO_2$;
 9) —CN;
 10) —N(R7)(R8);
 11) —C(O)—N(R7)(R8);
 12) —N(R8)—C(O)—R7;
 13) —N(R8)—$SO_2$—R7;

[5-6] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
1) halogen;
2) —($C_1$-$C_6$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl; and
7) —O—($C_1$-$C_3$)-haloalkyl

[5-7] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is -phenyl-Z, wherein Z is a basic nitrogen-containing group and wherein said phenyl is unsubstituted or additionally substituted with Y selected from the group consisting of:
1) halogen;
2) —($C_1$-$C_6$)-alkyl;
3) —($C_1$-$C_3$)-haloalkyl;
4) —($C_3$-$C_8$)-cycloalkyl.

[5-8] In another aspect, the present invention provides compounds of the Formula (I), wherein W of the substructure Formula (III) is oxygen atom, X(R3) of the substructure Formula (III) is NH, the dotted linkage between W and R4 of the substructure Formula (III) is absent, and R4 is 1-imino-2,3-dihydroisoindol-5-yl.

[6] In another aspect, the present invention provides compounds of combination at least two embodiments selected from aforementioned [1-1] to [5-7] as a preferable sub embodiment. For example, the compounds drawn from the combination embodiment [2-3] and [3-8] is shown with the formula:

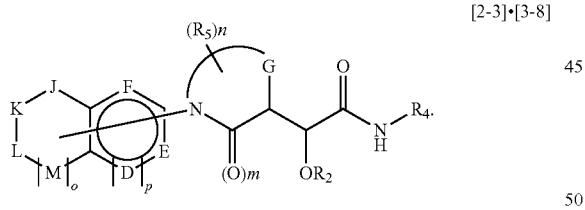

[2-3]·[3-8]

[7-1] In another aspect, the present invention provides compounds of the Formula (IV):

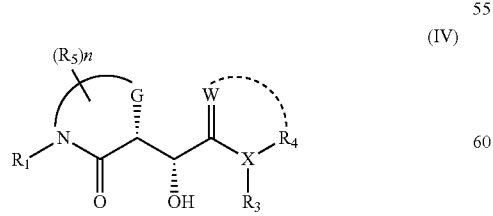

(IV)

((R,R) isomer) or a pharmaceutically acceptable salt or solvate thereof, wherein $R_1$ is a group selected from the group consisting of:

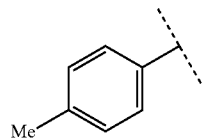

a1

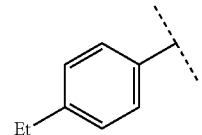

a2

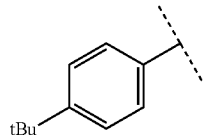

a3

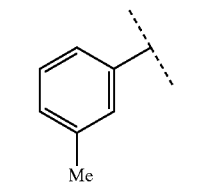

a4

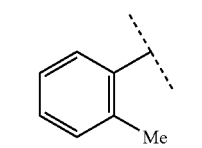

a5

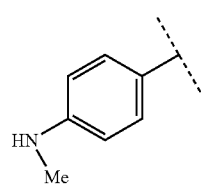

a6

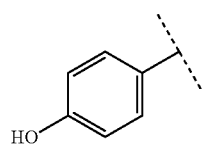

a7

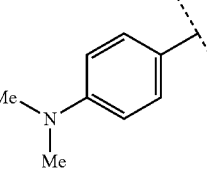

a8

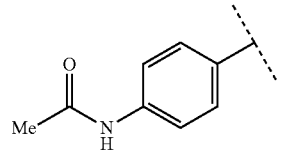

a9

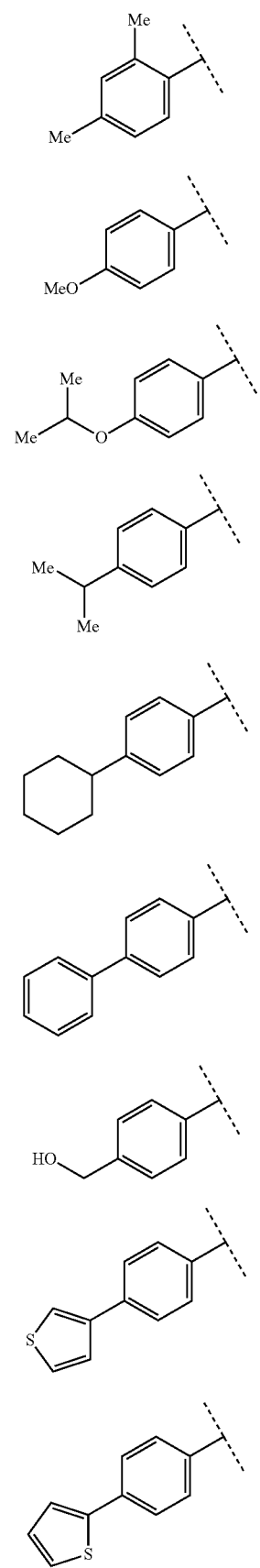
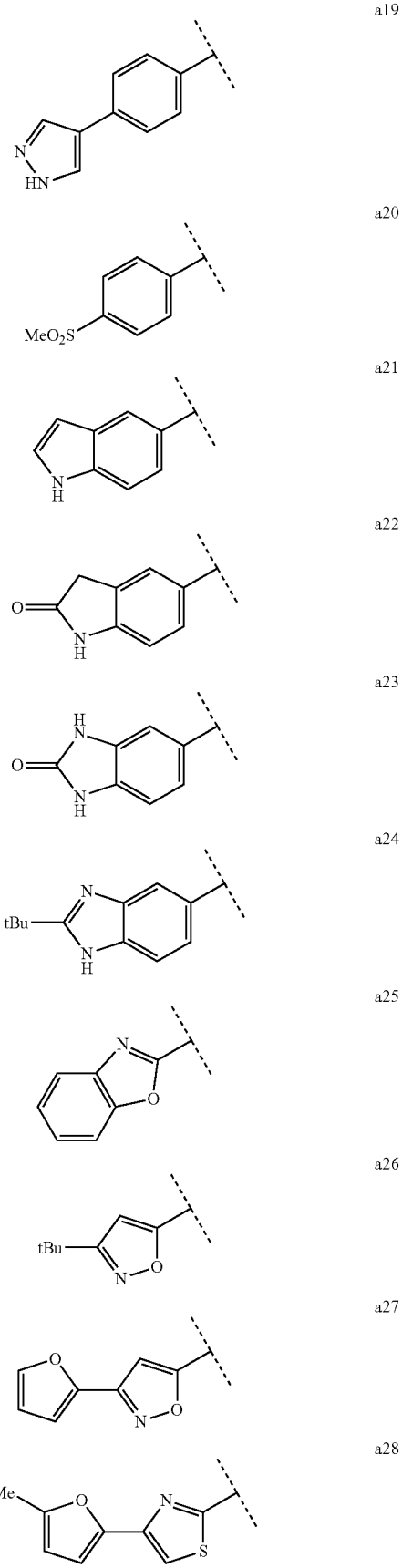

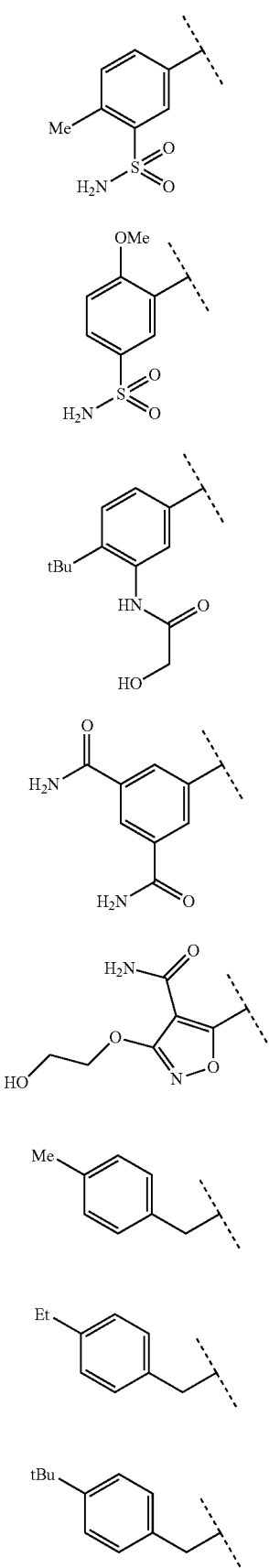
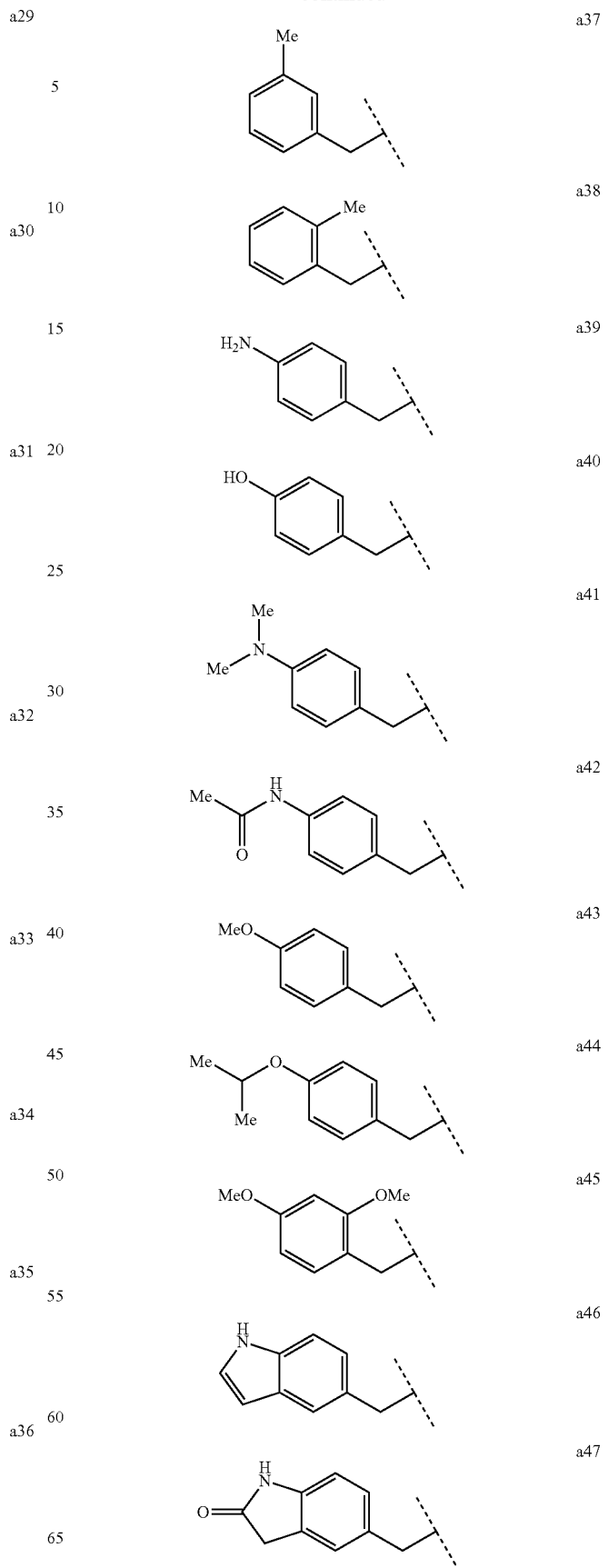

| | |
|---|---|
| a48 | a57 |
| a49 | a58 |
| a50 | a59 |
| a51 | a60 |
| a52 | a61 |
| a53 | a62 |
| a54 | a63 |
| a55 | a64 |
| a56 | a65 | a66 a67 a68 a69 a70 a71 a72 a73 a74 a75 a76 a77 a78 a79 a80 a81 a82 a83 a84 a85

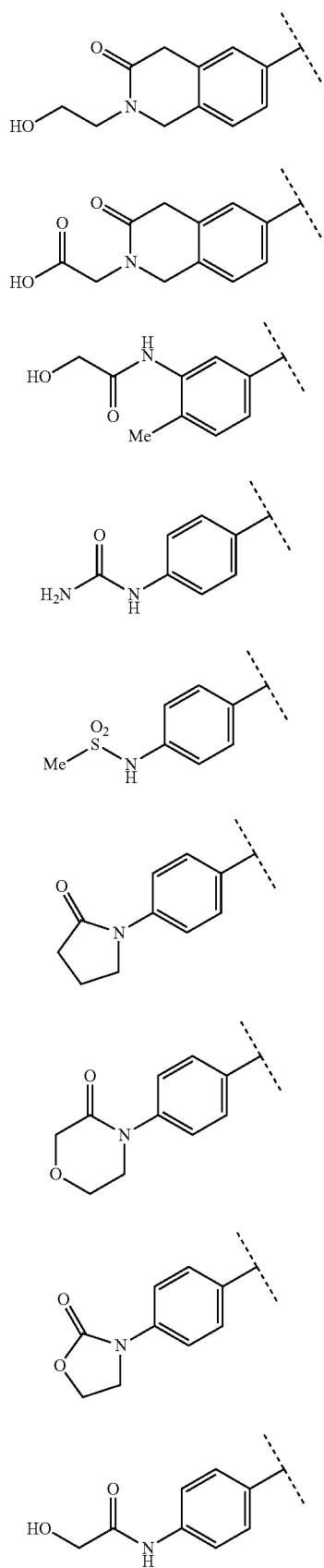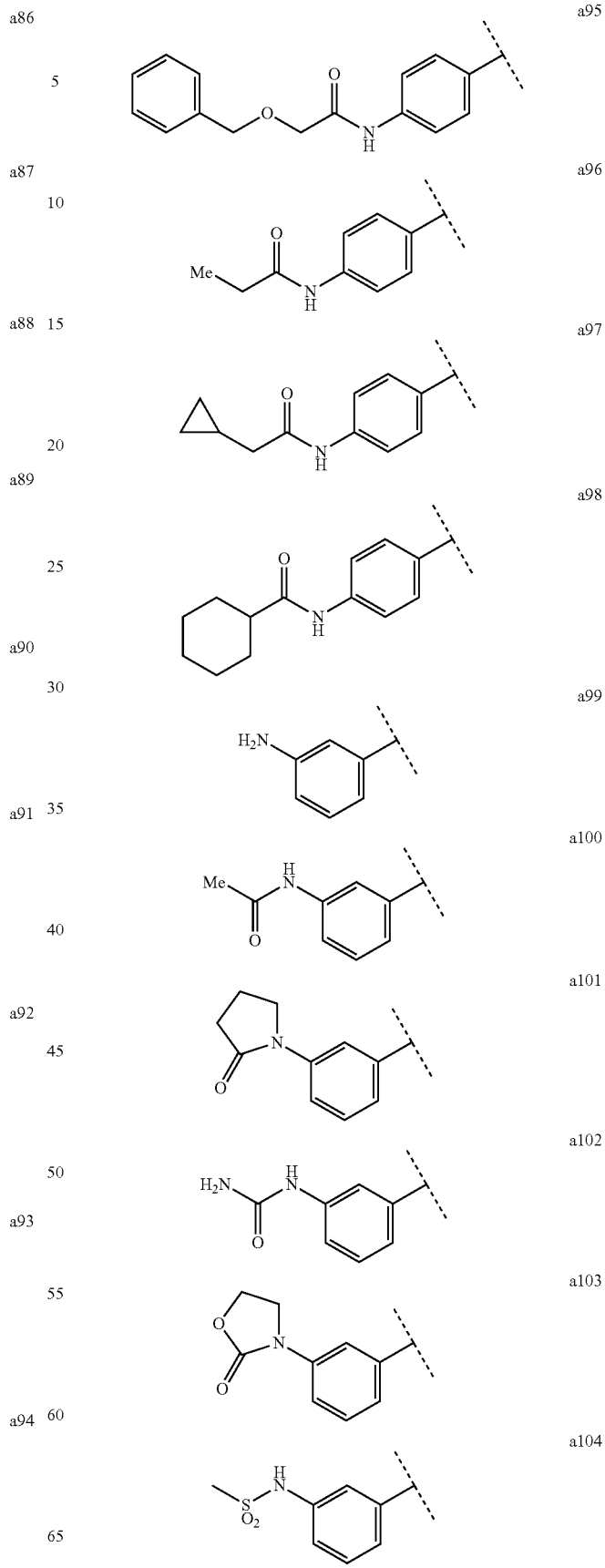

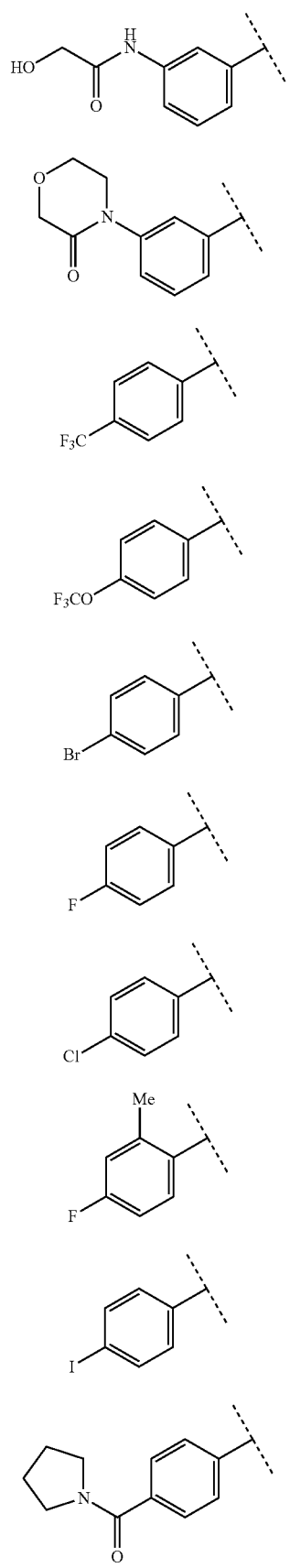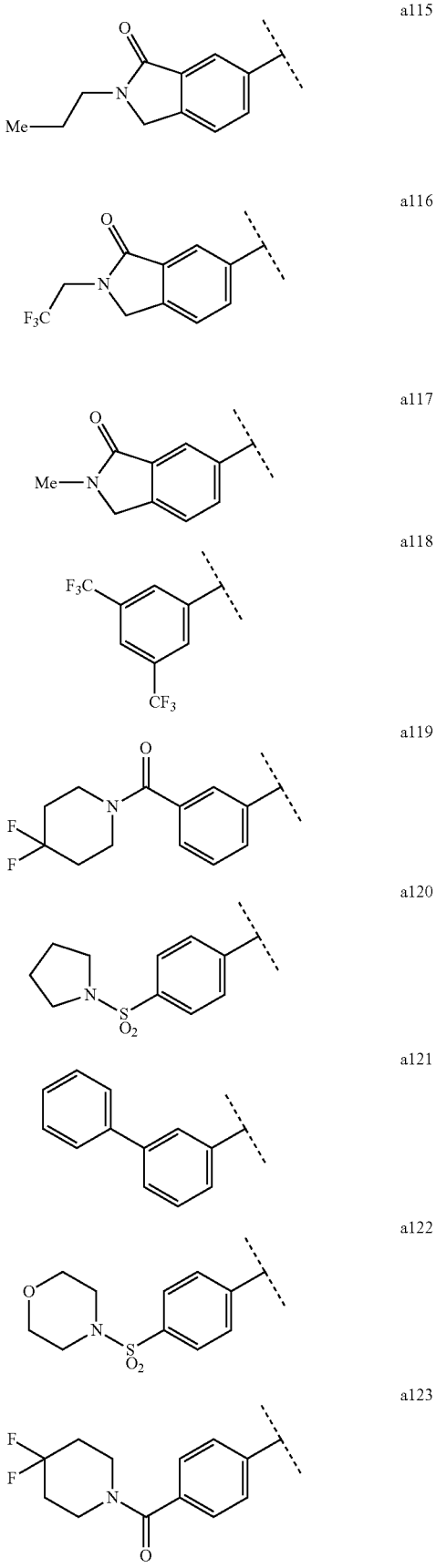

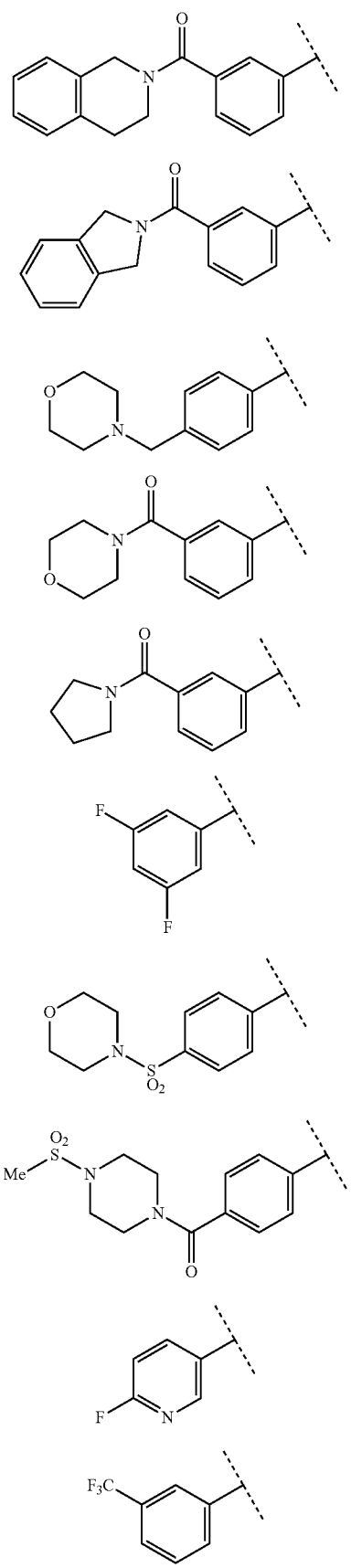
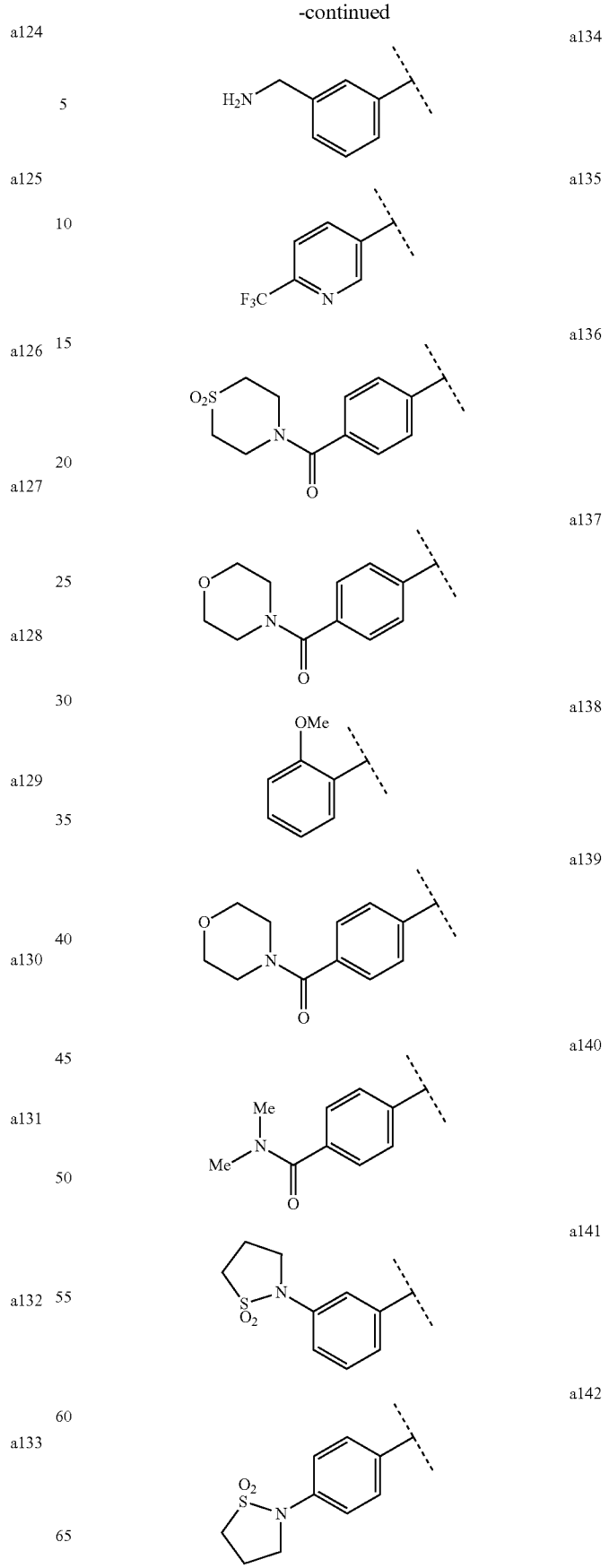

-continued
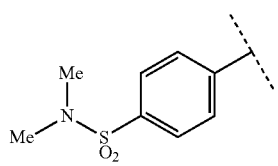  a143
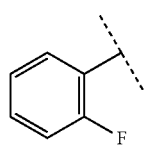  a144
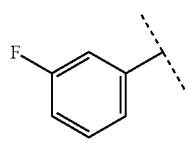  a145
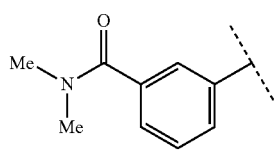  a146
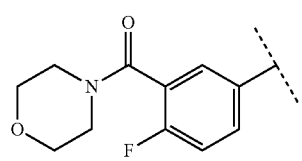  a147
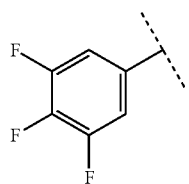  a148
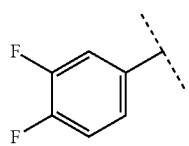  a149
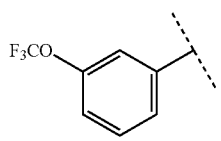  a150
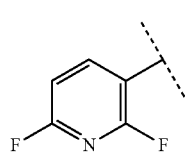  a151
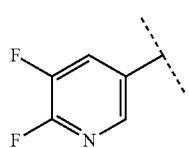  a152
-continued
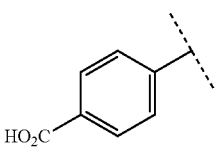  a153
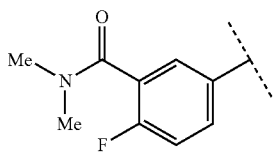  a154
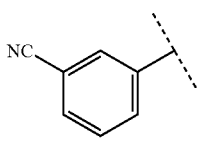  a155
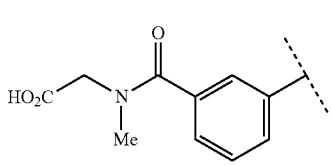  a156
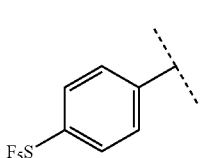  a157
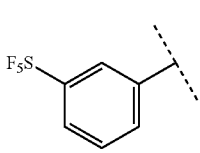  a158
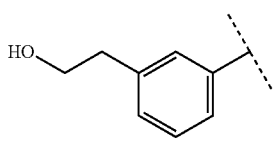  a159
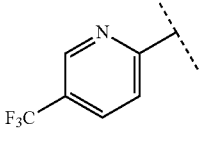  a160
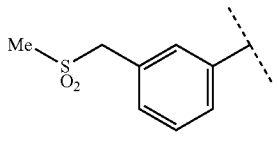  a161
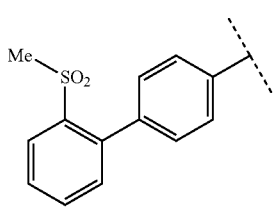  a162

| | |
|---|---|
| 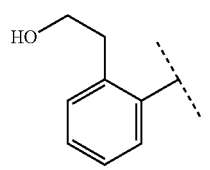 | a163 |
| 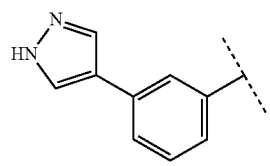 | a164 |
| 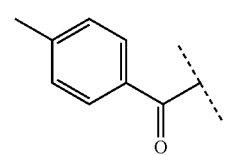 | a165 |
| 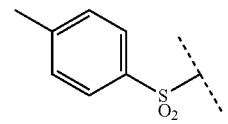 | a166 |
| 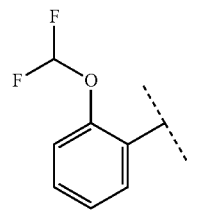 | a167 |
| 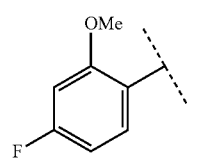 | a168 |
| 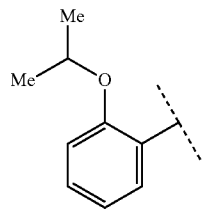 | a169 |
| 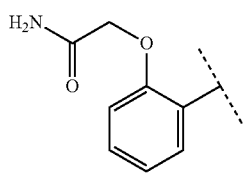 | a170 |
| 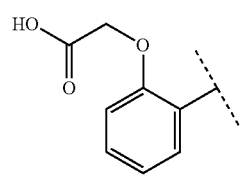 | a171 |
| 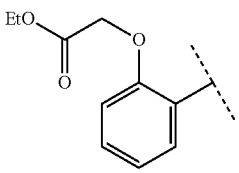 | a172 |
| 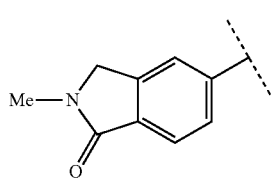 | a173 |
| 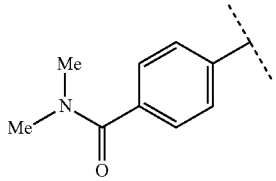 | a174 |
| 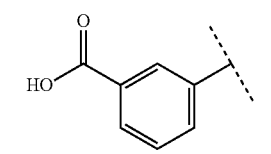 | a175 |
| 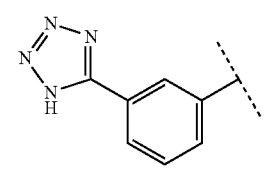 | a176 |
| 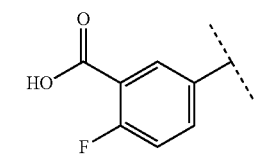 | a177 |
| 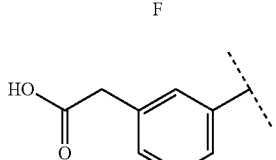 | a178 |
| 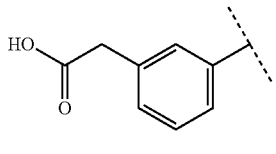 | a179 |
| 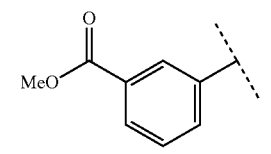 | a180 |

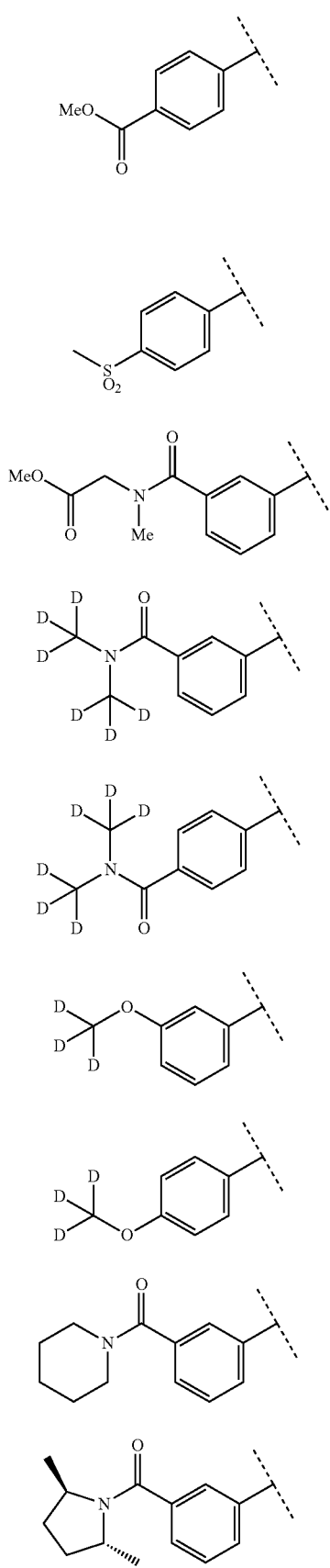
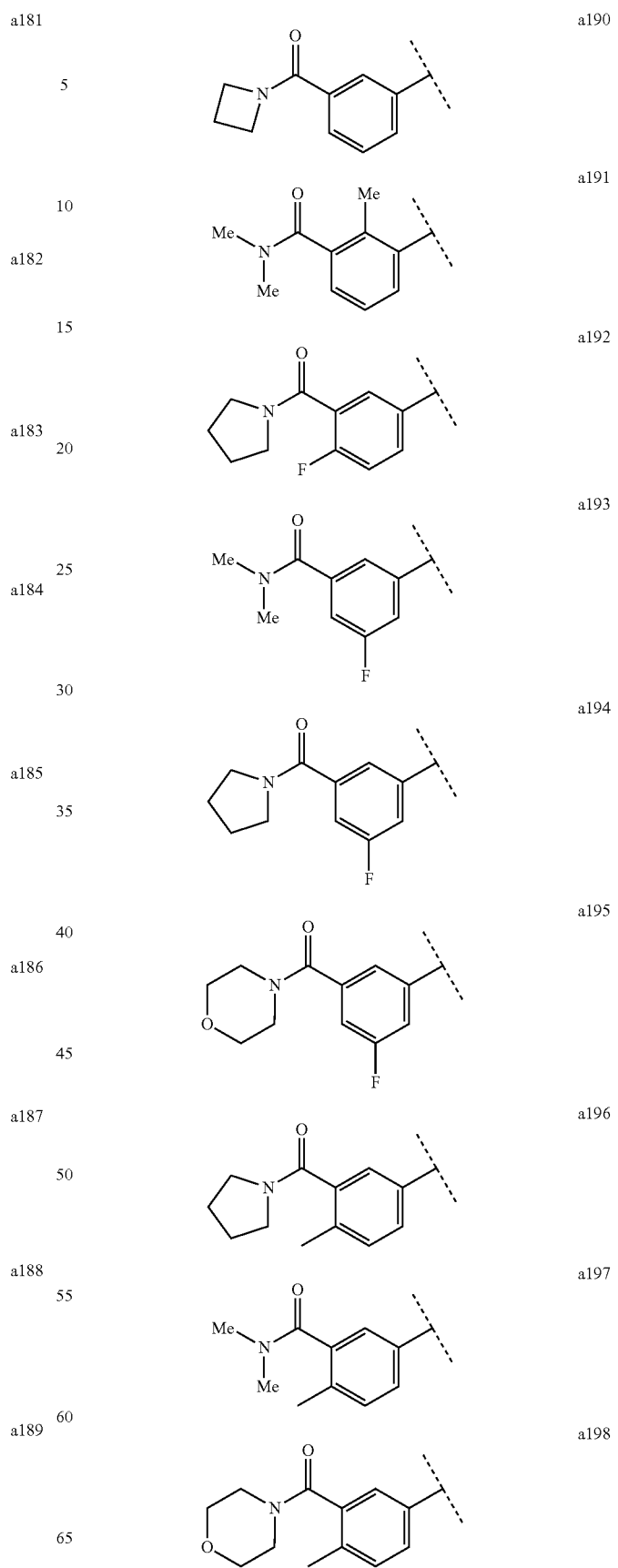

-continued
a199 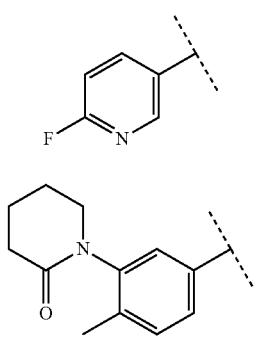
a200 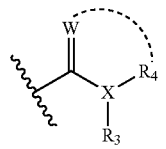
and wherein
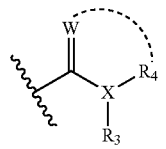
is selected from the group consisting of
b1 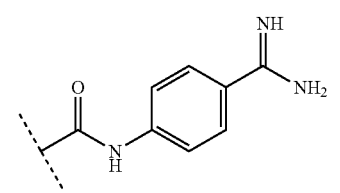
b2 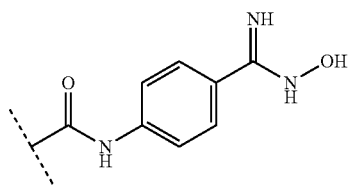
b3 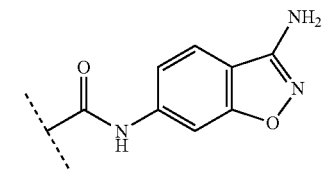
b4 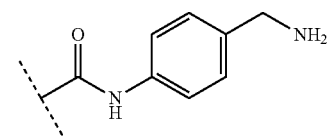
b5 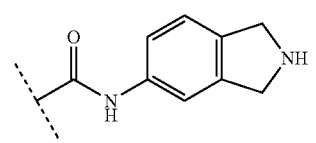
-continued
b6 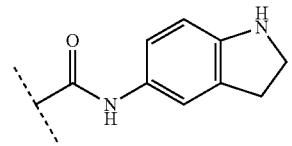
b7 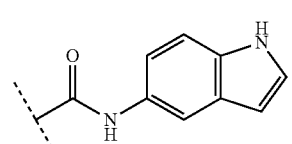
b8 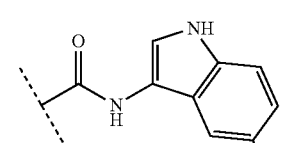
b9 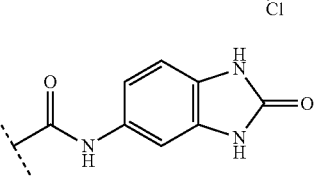
b10 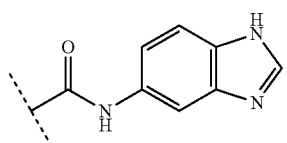
b11 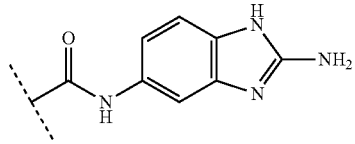
b12 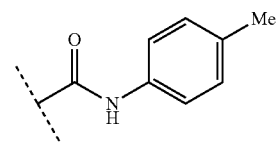
b13 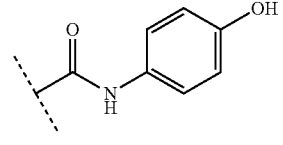
b14 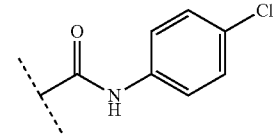
b15 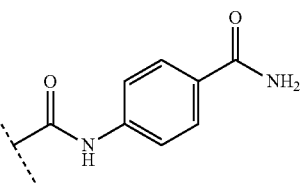

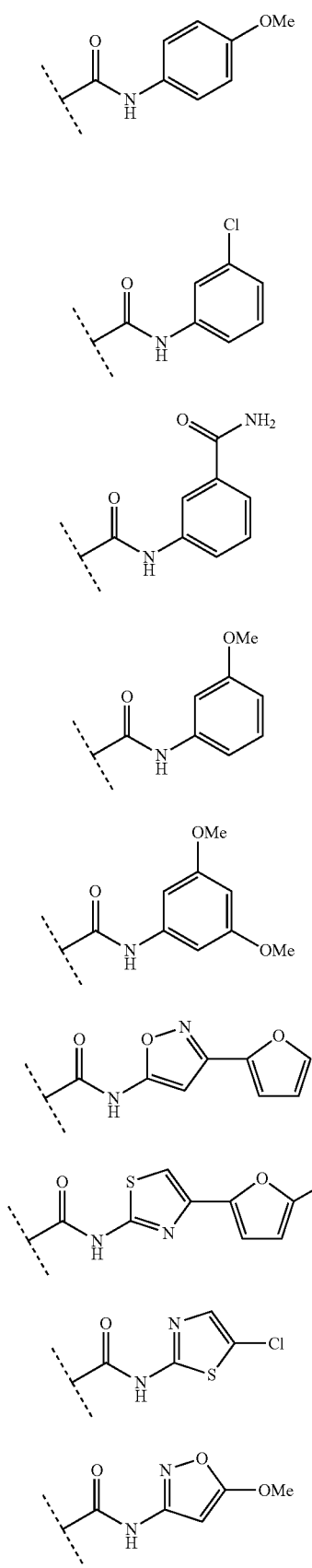
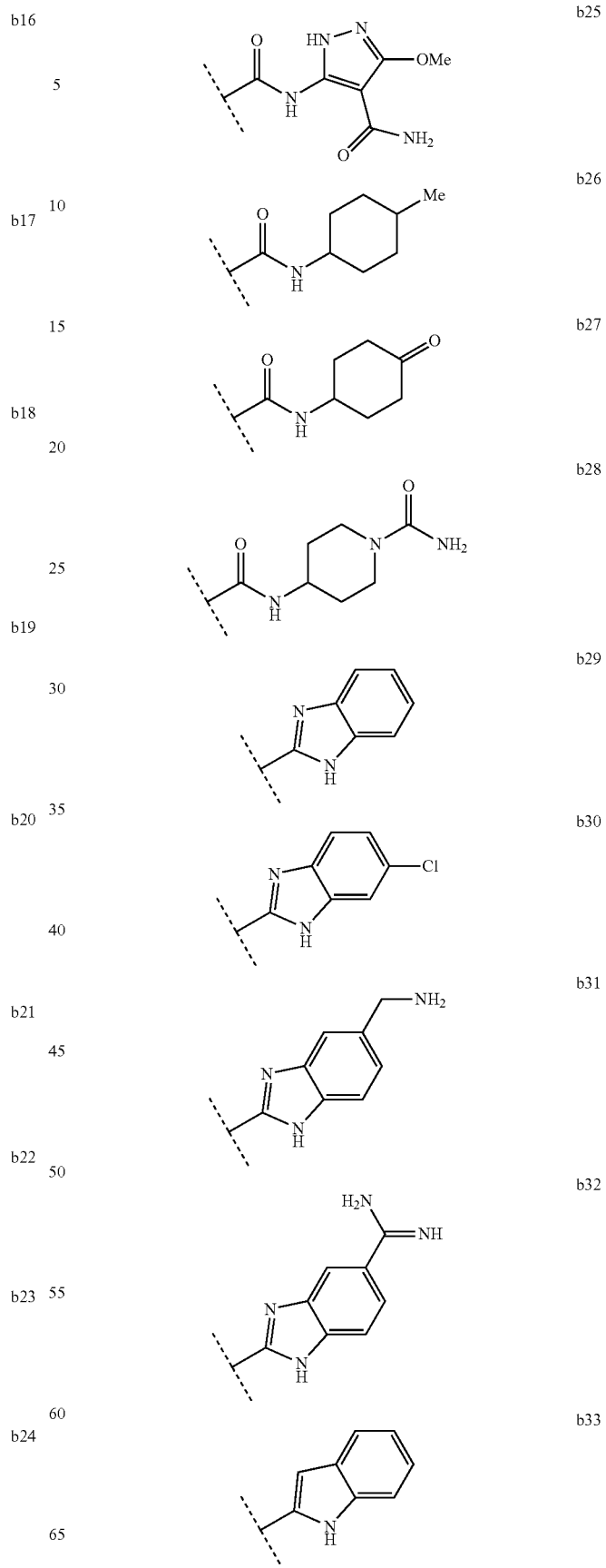

-continued
b34 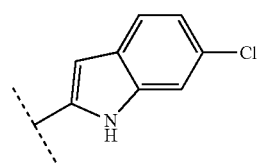
b35 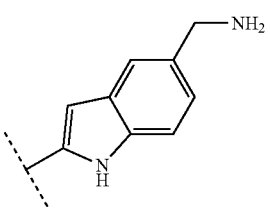
b36 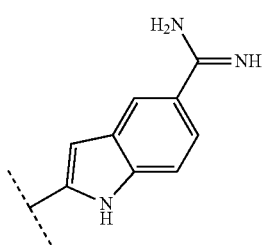
b37 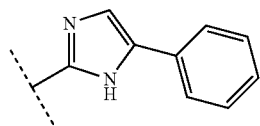
b38 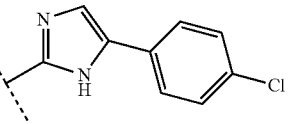
b39 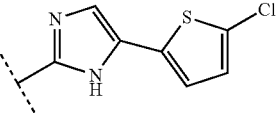
b40 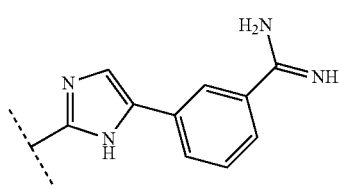
b41 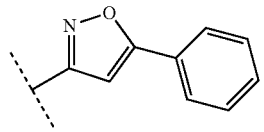
b42 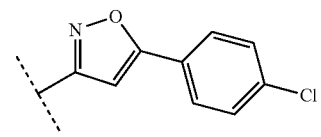
-continued
b43 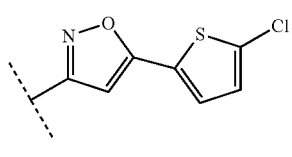
b44 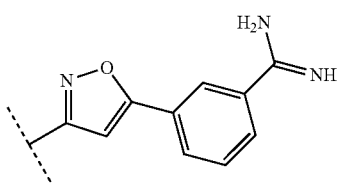
b45 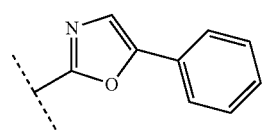
b46 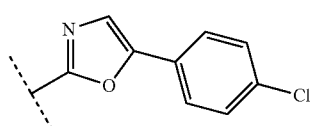
b47 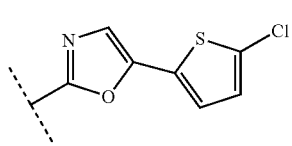
b48 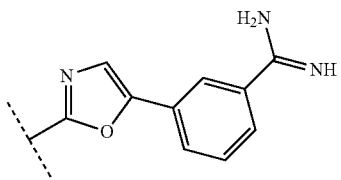
b49 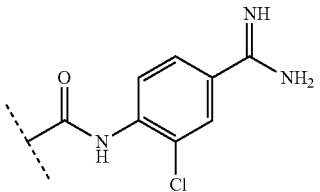
b50 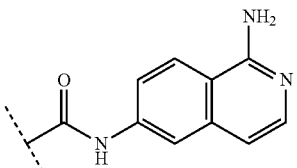
b51 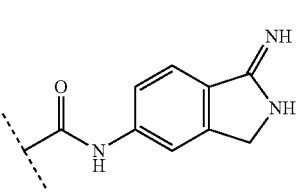

| | |
|---|---|
| b52 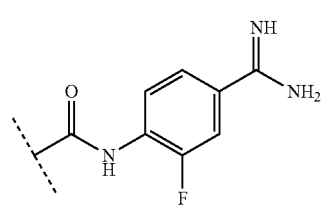 | b60 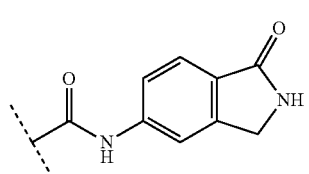 |
| b53 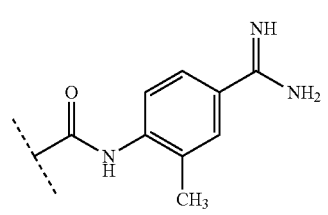 | b61 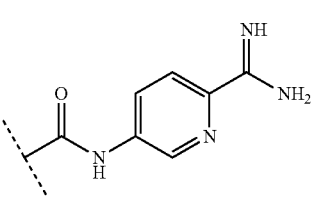 |
| b54 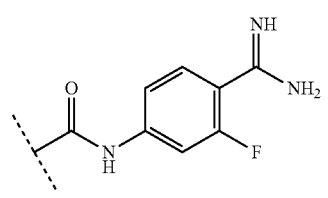 | b62 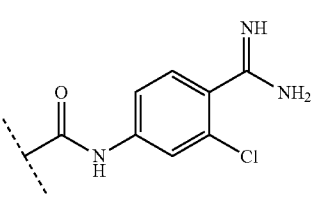 |
| b55 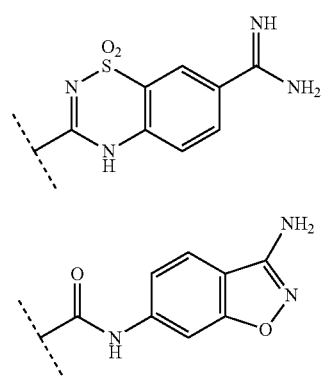 | b63 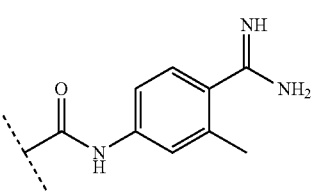 |
| b56 | |
| b57 | b64 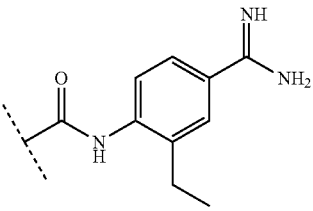 |
| b58 | b65 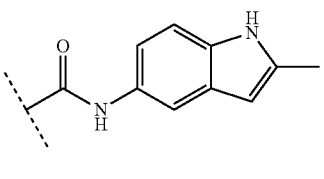 |
| b59 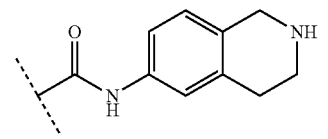 | b66 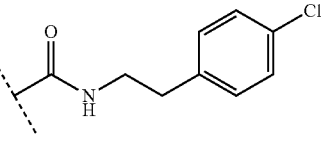 | b67
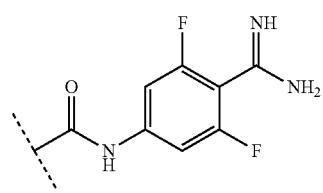
and wherein the substructure of the Formula (IV)
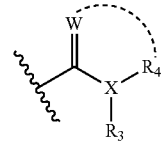
is selected from the group consisting of
b1, b4, b49 to b61.
[7-1-1] In another aspect, the present invention provides compounds of [7-1] wherein
R₁ is a group selected from the group consisting of:
a1 to a33, a64 to a164,
[7-2] In another aspect, the present invention provides compounds selected from the group consisting of:
1
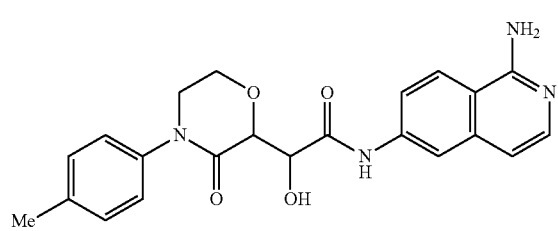
2
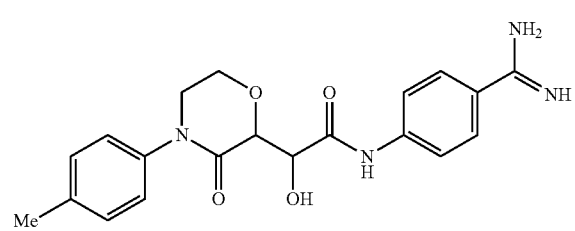
3
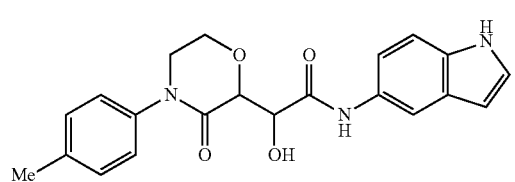
4
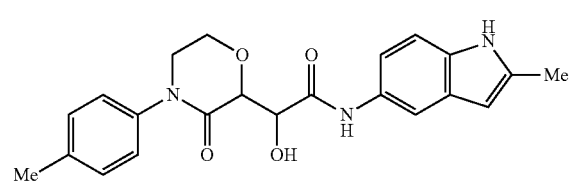
5
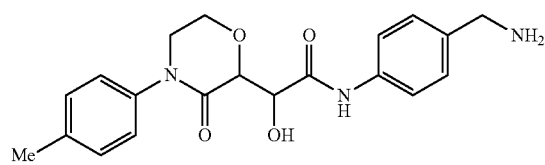
6
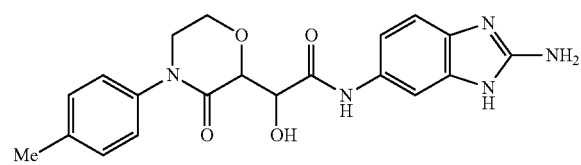
7
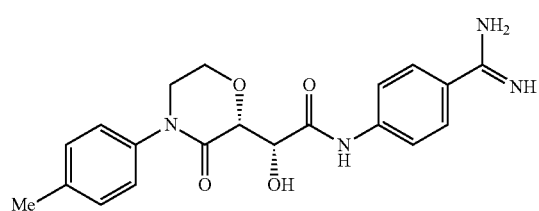
8
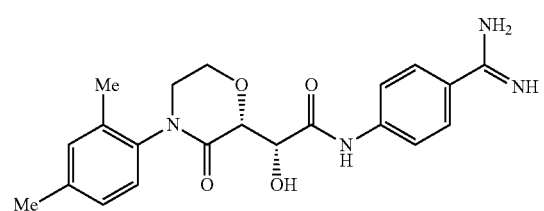
9
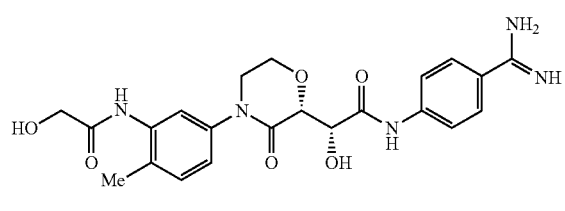
10
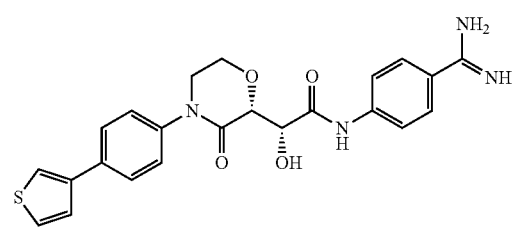

-continued
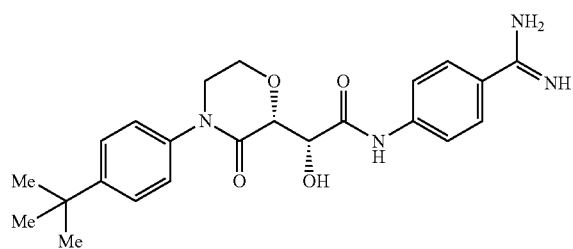
11
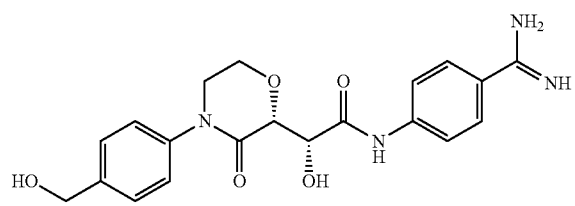
12
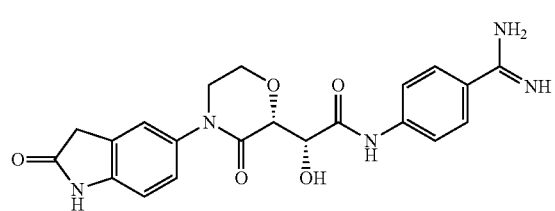
13
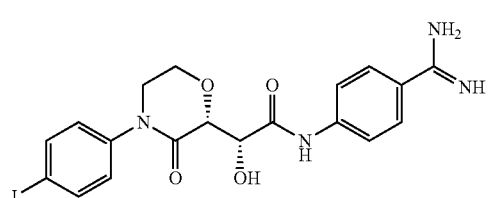
14
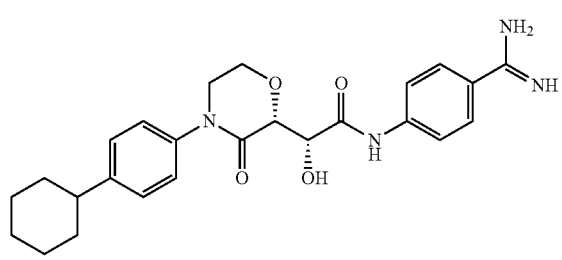
15
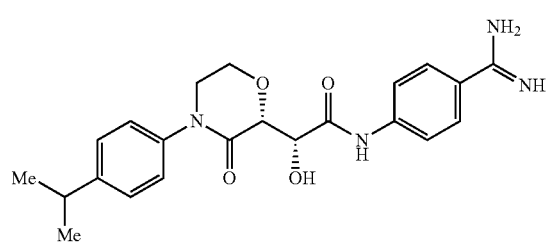
16
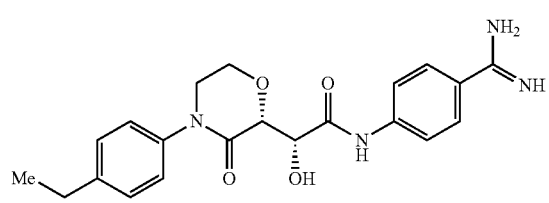
17
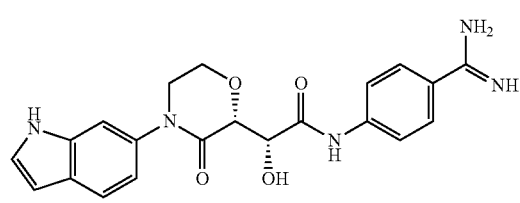
18
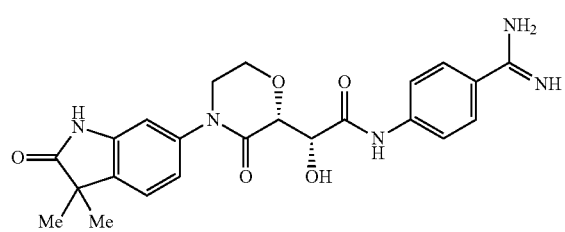
19
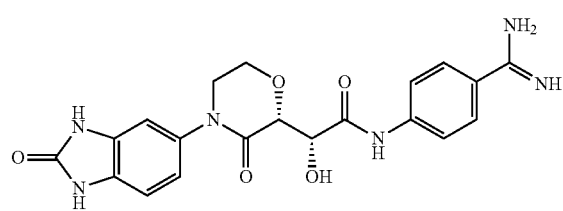
20
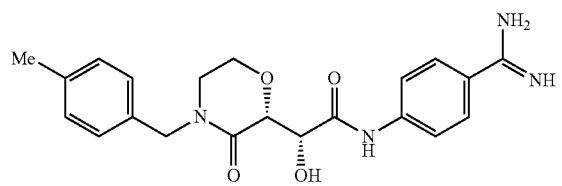
21
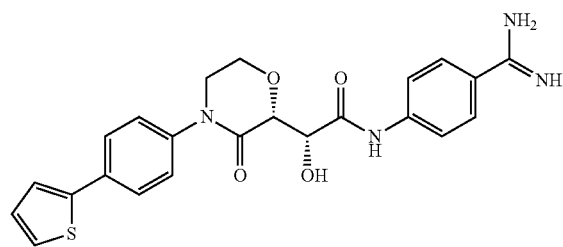
22

-continued
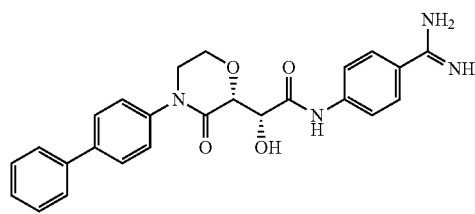
23
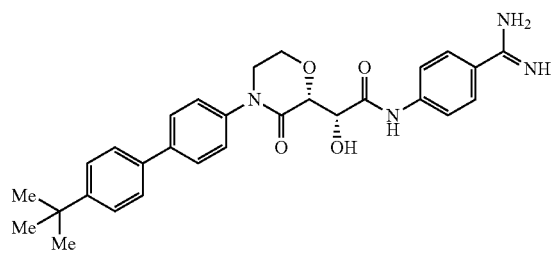
24
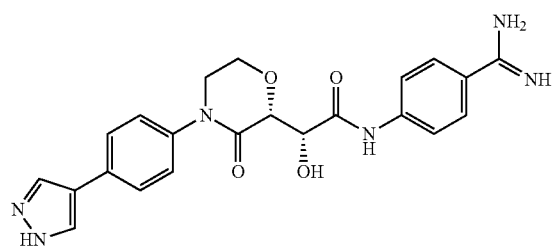
25
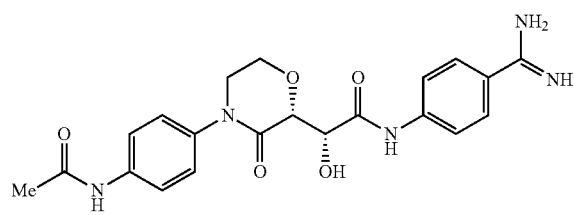
26
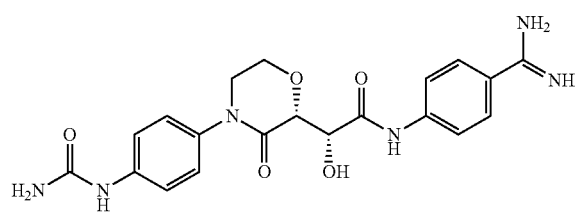
27
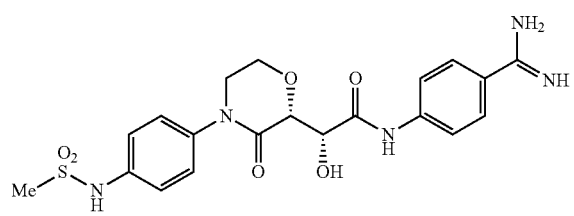
28
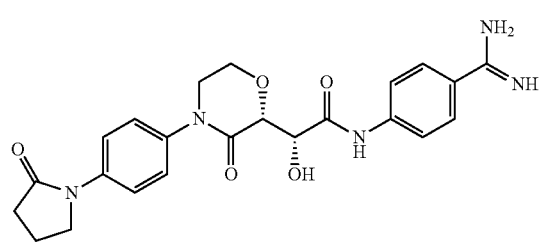
29
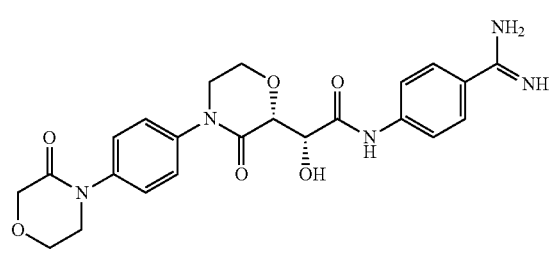
30
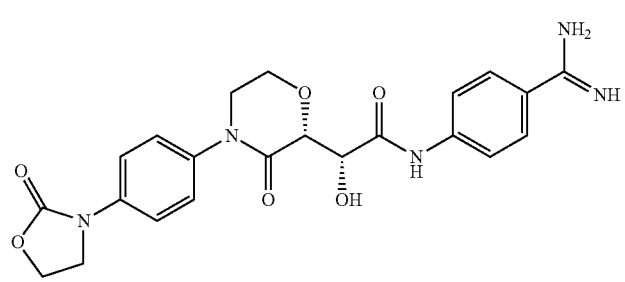
31
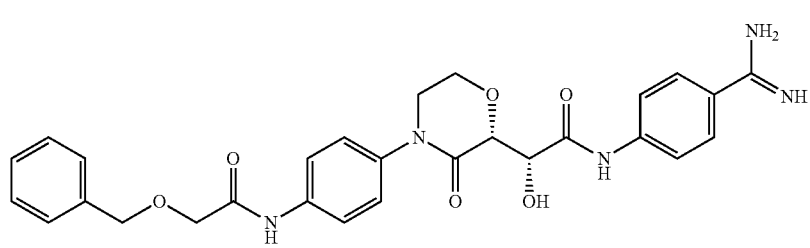
32

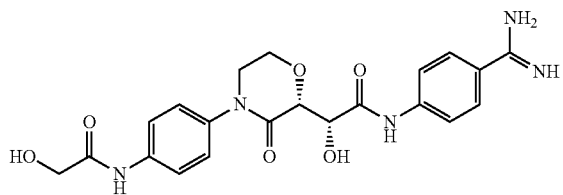

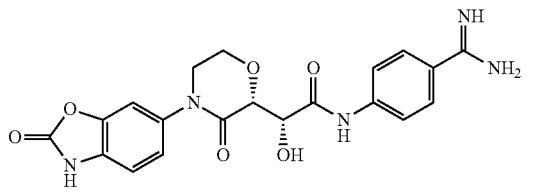

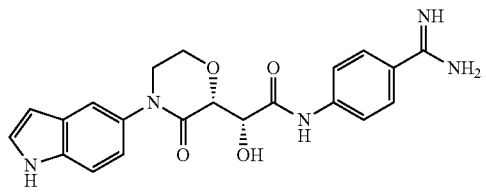

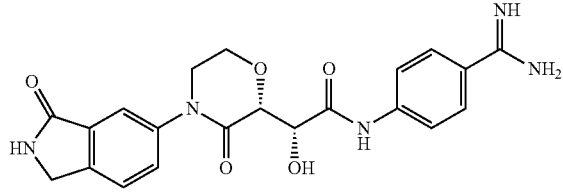

or its pharmaceutically acceptable salt or a solvate thereof.

Each compound name from example 1 to example 37 is,

1: N-(1-aminoisoquinolin-6-yl)-2-hydroxy-2-(3-oxo-4-p-tolylmorpholin-2-yl)acetamide;
2: N-(4-amidinophenyl)-2-hydroxy-2-(3-oxo-4-p-tolylmorpholin-2-yl)acetamide;
3: 2-hydroxy-N-(1H-indol-5-yl)-2-(3-oxo-4-p-tolylmorpholin-2-yl)acetamide;
4: 2-hydroxy-N-(2-methyl-1H-indol-5-yl)-2-(3-oxo-4-p-tolylmorpholin-2-yl)acetamide;
5: N-[4-(aminomethyl)phenyl]-2-hydroxy-2-(3-oxo-4-p-tolylmorpholin-2-yl)acetamide;
6: N-(2-amino-3H-benzimidazol-5-yl)-2-hydroxy-2-(3-oxo-4-p-tolylmorpholin-2-yl)-acetamide;
7: (2R)—N-(4-amidinophenyl)-2-hydroxy-2-[(2R)-3-oxo-4-p-tolylmorpholin-2-yl]acetamide;
8: (2R)—N-(4-amidinophenyl)-2-hydroxy-2-[(2R)-4-(2,4-dimethylphenyl)-3-oxomorpholin-2-yl]-2-hydroxyacetamide;
9: (2R)—N-(4-amidinophenyl)-2-hydroxy-2-[(2R)-4-[3-[(2-hydroxyacetyl)amino]-4-methylphenyl]-3-oxomorpholin-2-yl]acetamide;
10: (2R)—N-(4-amidinophenyl)-2-hydroxy-2-[(2R)-3-oxo-4-(4-thiophen-3-ylphenyl)-morpholin-2-yl]acetamide;
11: (2R)—N-(4-amidinophenyl)-2-[(2R)-4-(4-tert-butylphenyl)-3-oxomorpholin-2-yl]-2-hydroxyacetamide;
12: (2R)—N-(4-amidinophenyl)-2-hydroxy-2-[(2R)-4-[4-(hydroxymethyl)phenyl]-3-oxo morpholin-2-yl]acetamide;
13: (2R)—N-(4-amidinophenyl)-2-hydroxy-2-[(2R)-3-oxo-4-(2-oxo-1,3-dihydroindol-5-yl)-morpholin-2-yl]acetamide;
14: (2R)—N-(4-amidinophenyl)-2-hydroxy-2-[(2R)-4-(4-iodophenyl)-3-oxomorpholin-2-yl]-acetamide;
15: (2R)—N-(4-amidinophenyl)-2-[(2R)-4-(4-cyclohexylphenyl)-3-oxomorpholin-2-yl]-2-hydroxyacetamide;
16: (2R)—N-(4-amidinophenyl)-2-hydroxy-2-[(2R)-3-oxo-4-(4-propan-2-ylphenyl)-morpholin-2-yl]acetamide;
17: (2R)—N-(4-amidinophenyl)-2-[(2R)-4-(4-ethylphenyl)-3-oxomorpholin-2-yl]-2-hydroxyacetamide;
18: (2R)—N-(4-amidinophenyl)-2-hydroxy-2-[(2R)-4-(1H-indol-6-yl)-3-oxomorpholin-2-yl]-acetamide;
19: (2R)—N-(4-amidinophenyl)-2-[(2R)-4-(3,3-dimethyl-2-oxo-1H-indol-6-yl)-3-oxomorpholin-2-yl]-2-hydroxyacetamide;
20: (2R)—N-(4-amidinophenyl)-2-hydroxy-2-[(2R)-3-oxo-4-(2-oxo-1,3-dihydrobenzimidazol-5-yl)morpholin-2-yl] acetamide;
21: (2R)—N-(4-amidinophenyl)-2-hydroxy-2-[(2R)-3-oxo-4-p-tolylmethylmorpholin-2-yl]-acetamide;
22: (2R)—N-(4-amidinophenyl)-2-hydroxy-2-[(2R)-3-oxo-4-(4-thiophen-2-ylphenyl)-morpholin-2-yl]acetamide;
23: (2R)—N-(4-amidinophenyl)-2-[(2R)-4-biphenyl-3-oxomorpholin-2-yl]-2-hydroxy-acetamide;
24: (2R)—N-(4-amidinophenyl)-2-[(2R)-4-(4'-tert-butylbiphenyl)-3-oxomorpholin-2-yl]-2-hydroxyacetamide;
25: (2R)—N-(4-amidinophenyl)-2-hydroxy-2-[(2R)-3-oxo-4-[4-(1H-pyrazol-4-yl)phenyl]-morpholin-2-yl]acetamide;
26: (2R)-2-[(2R)-4-(4-acetamidophenyl)-3-oxomorpholin-2-yl]-N-(4-amidinophenyl)-2-hydroxyacetamide;
27: (2R)—N-(4-amidinophenyl)-2-[(2R)-4-[4-(carbamoylamino)phenyl]-3-oxomorpholin-2-yl]-2-hydroxyacetamide;
28: (2R)—N-(4-amidinophenyl)-2-hydroxy-2-[(2R)-4-[4-(methanesulfonamido)phenyl]-3-oxomorpholin-2-yl]acetamide;
29: (2R)—N-(4-amidinophenyl)-2-hydroxy-2-[(2R)-3-oxo-4-[4-(2-oxopyrrolidin-1-yl)phenyl]morpholin-2-yl]acetamide;
30: (2R)—N-(4-amidinophenyl)-2-hydroxy-2-[(2R)-3-oxo-4-[4-(3-oxomorpholin-4-yl)phenyl]morpholin-2-yl]acetamide;
31: (2R)—N-(4-amidinophenyl)-2-hydroxy-2-[(2R)-3-oxo-4-[4-(2-oxo-1,3-oxazolidin-3-yl)-phenyl]morpholin-2-yl] acetamide;
32: (2R)—N-(4-amidinophenyl)-2-hydroxy-2-[(2R)-3-oxo-4-[4-[(2-phenylmethoxyacetyl)-amino]phenyl]morpholin-2-yl]acetamide;

33: (2R)—N-(4-amidinophenyl)-2-hydroxy-2-[(2R)-4-[4-[(2-hydroxyacetyl)amino]phenyl]-3-oxomorpholin-2-yl]acetamide;

34: (2R)—N-(4-amidinophenyl)-2-[(2R)-4-(3,3-dimethyl-2-oxo-1H-indol-5-yl)-3-oxomorpholin-2-yl]-2-hydroxyacetamide;

35: (2R)—N-(4-amidinophenyl)-2-hydroxy-2-[(2R)-4-(1H-indol-5-yl)-3-oxomorpholin-2-yl]-acetamide;

36: (2R)—N-(4-amidinophenyl)-2-hydroxy-2-[(2R)-3-oxo-4-(2-oxo-3H-1,3-benzoxazol-6-yl)morpholin-2-yl]acetamide;

and

37: (2R)—N-(4-amidinophenyl)-2-hydroxy-2-[(2R)-3-oxo-4-(3-oxo-1,2-dihydroisoindol-5-yl)morpholin-2-yl]acetamide.

[7-3] In another aspect, the present invention also provides a compound selected from the group consisting of:

1p

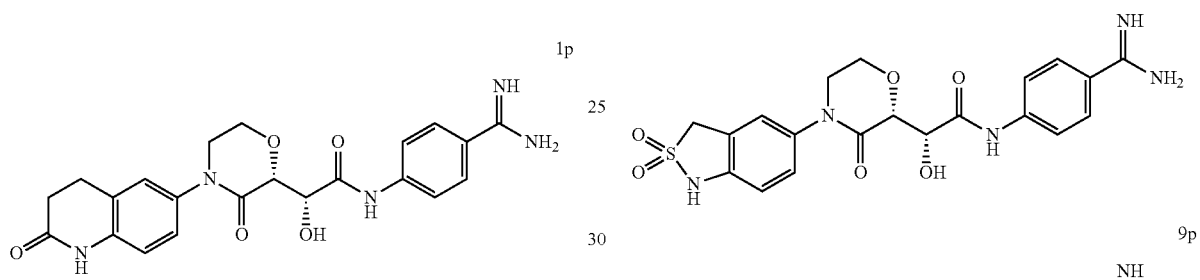

2p

3p

4p

5p

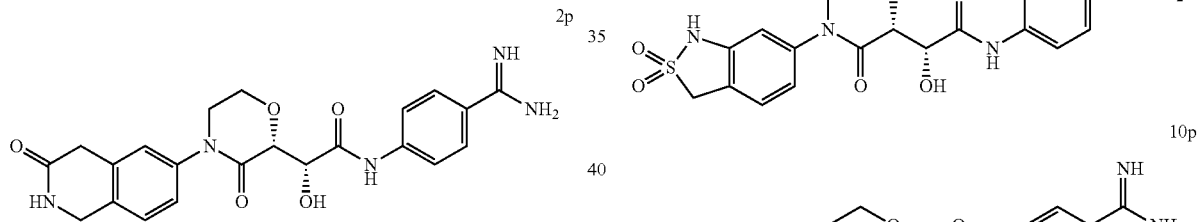

6p

7p

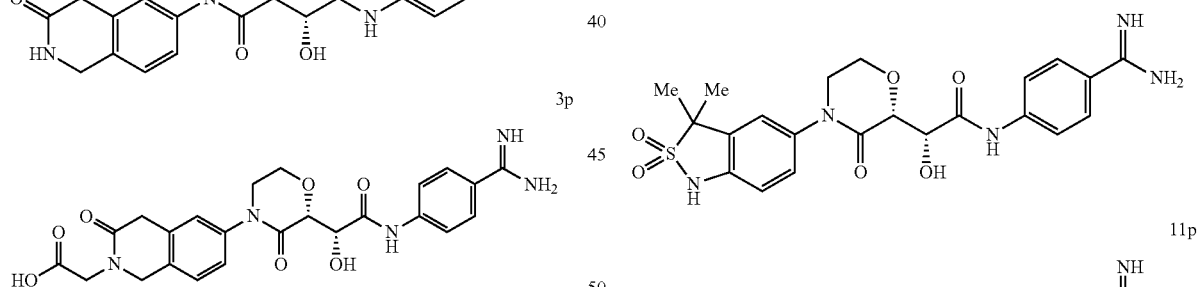

8p

9p

10p

11p

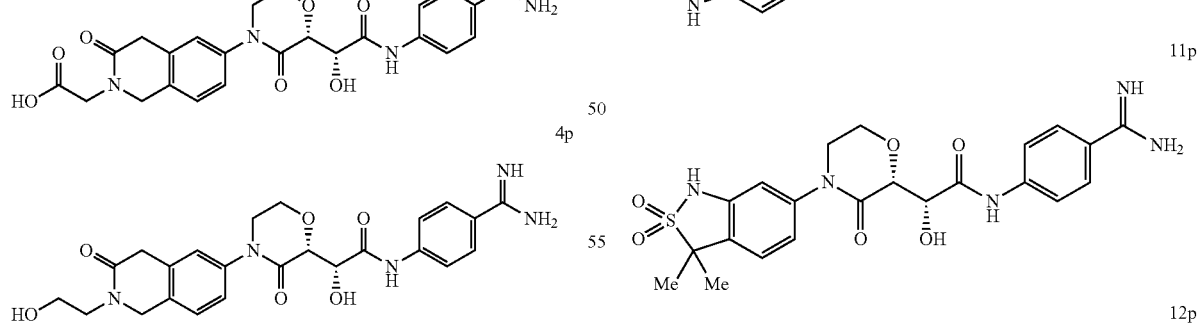

12p

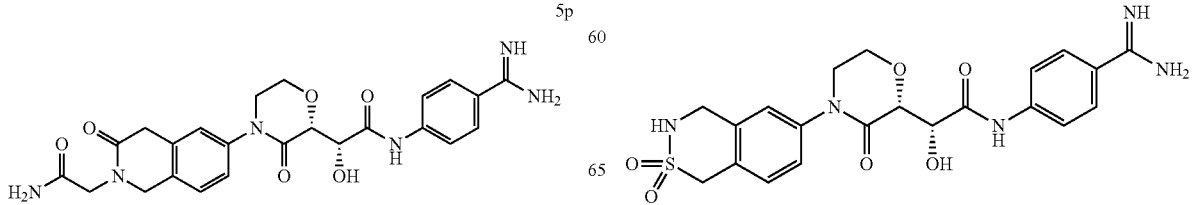

13p
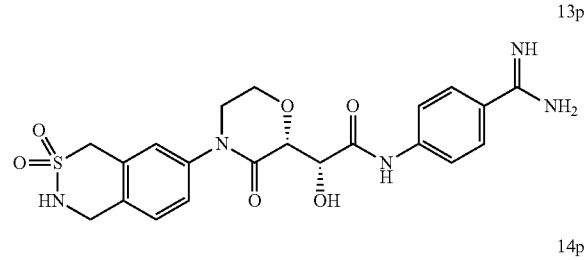

14p
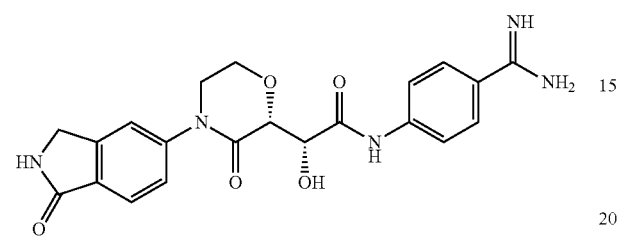

15p
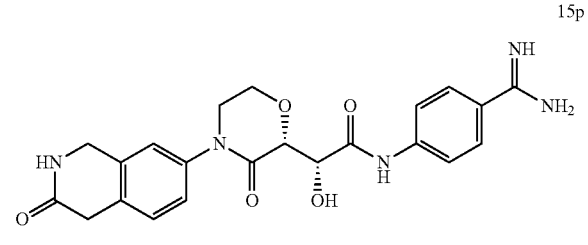

16p
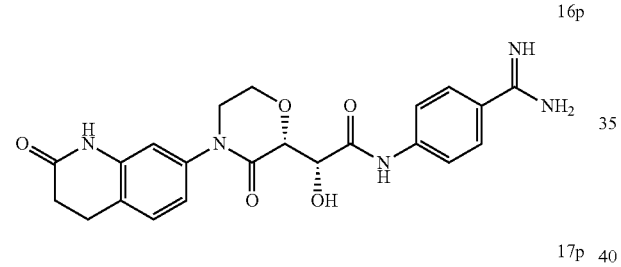

17p
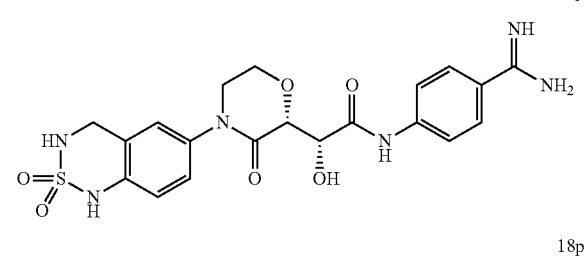

18p
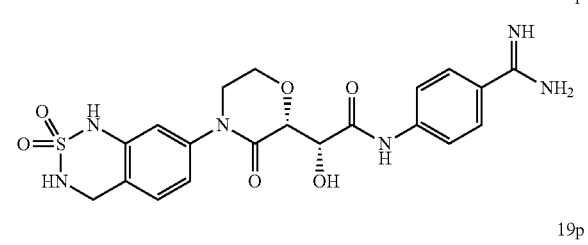

19p
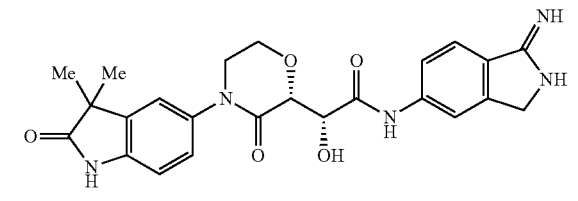

20p
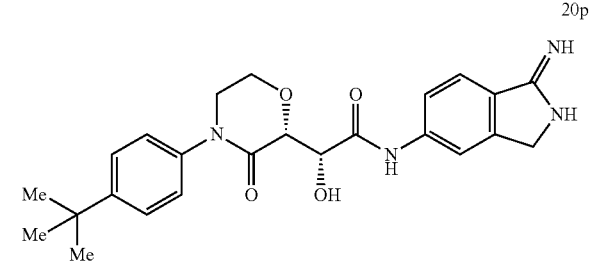

21p
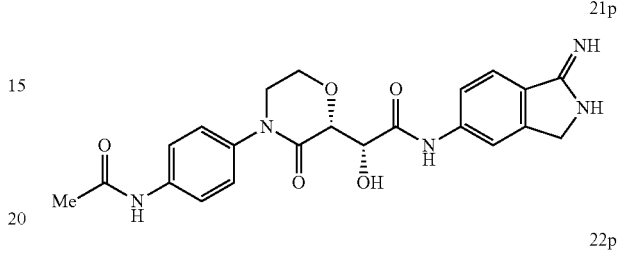

22p
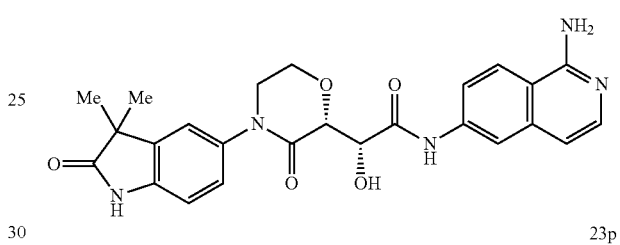

23p
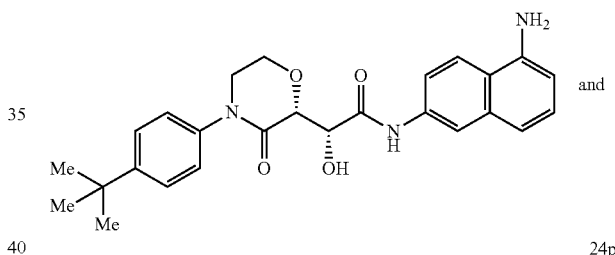

and

24p
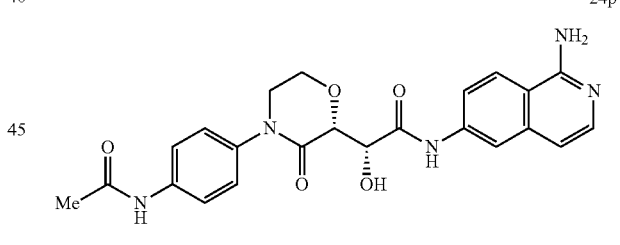

or a pharmaceutically acceptable salt or solvate thereof.

Each compound name from example 1p to example 24p is,

1p: (2R)—N-(4-amidinophenyl)-2-hydroxy-2-[(2R)-3-oxo-4-(2-oxo-3,4-dihydro-1H-quinolin-6-yl)morpholin-2-yl]acetamide;

2p: (2R)—N-(4-amidinophenyl)-2-hydroxy-2-[(2R)-3-oxo-4-(3-oxo-2,4-dihydro-1H-isoquinolin-6-yl)morpholin-2-yl]acetamide;

3p: 2-[6-[(2R)-2-[(1R)-2-(4-amidinoanilino)-1-hydroxy-2-oxoethyl]-3-oxomorpholin-4-yl]-3-oxo-1,4-dihydroisoquinolin-2-yl]acetic acid;

4p: (2R)—N-(4-amidinophenyl)-2-hydroxy-2-[(2R)-4-[2-(2-hydroxyethyl)-3-oxo-1,4-dihydroisoquinolin-6-yl]-3-oxomorpholin-2-yl]acetamide;

5p: (2R)—N-(4-amidinophenyl)-2-[(2R)-4-[2-(2-amino-2-oxoethyl)-3-oxo-1,4-dihydroisoquinolin-6-yl]-3-oxomorpholin-2-yl]-2-hydroxyacetamide;

6p: (2R)—N-(4-amidinophenyl)-2-hydroxy-2-[(2R)-3-oxo-4-(2-oxo-3H-1,3-benzoxazol-5-yl)morpholin-2-yl]acetamide;

7p: (2R)—N-(4-amidinophenyl)-2-[(2R)-4-(1H-benzimidazol-5-yl)-3-oxomorpholin-2-yl]-2-hydroxyacetamide;

8p: (2R)—N-(4-amidinophenyl)-2-[(2R)-4-(2,2-dioxo-1,3-dihydro-2,1-benzothiazol-5-yl)-3-oxomorpholin-2-yl]-2-hydroxyacetamide;

9p: (2R)—N-(4-amidinophenyl)-2-[(2R)-4-(2,2-dioxo-1,3-dihydro-2,1-benzothiazol-6-yl)-3-oxomorpholin-2-yl]-2-hydroxyacetamide;

10p: (2R)—N-(4-amidinophenyl)-2-[(2R)-4-(3,3-dimethyl-2,2-dioxo-1H-2,1-benzothiazol-5-yl)-3-oxomorpholin-2-yl]-2-hydroxyacetamide;

11p: (2R)—N-(4-amidinophenyl)-2-[(2R)-4-(3,3-dimethyl-2,2-dioxo-1H-2,1-benzothiazol-6-yl)-3-oxomorpholin-2-yl]-2-hydroxyacetamide;

12p: (2R)—N-(4-amidinophenyl)-2-[(2R)-4-(2,2-dioxo-3,4-dihydro-1H-benzo[d]thiazin-6-yl)-3-oxomorpholin-2-yl]-2-hydroxyacetamide;

13p: (2R)—N-(4-amidinophenyl)-2-[(2R)-4-(2,2-dioxo-3,4-dihydro-1H-benzo[d]thiazin-7-yl)-3-oxomorpholin-2-yl]-2-hydroxyacetamide;

14p: (2R)—N-(4-amidinophenyl)-2-hydroxy-2-[(2R)-3-oxo-4-(1-oxo-2,3-dihydroisoindol-5-yl)morpholin-2-yl]acetamide;

15p: (2R)—N-(4-amidinophenyl)-2-hydroxy-2-[(2R)-3-oxo-4-(3-oxo-2,4-dihydro-1H-isoquinolin-7-yl)morpholin-2-yl]acetamide;

16p: (2R)—N-(4-amidinophenyl)-2-hydroxy-2-[(2R)-3-oxo-4-(2-oxo-3,4-dihydro-1H-quinolin-7-yl)morpholin-2-yl]acetamide;

17p: (2R)—N-(4-amidinophenyl)-2-[(2R)-4-(2,2-dioxo-3,4-dihydro-1H-benzo[c][1,2,6]thia-diazin-6-yl)-3-oxomorpholin-2-yl]-2-hydroxyacetamide;

18p: (2R)—N-(4-amidinophenyl)-2-[(2R)-4-(2,2-dioxo-3,4-dihydro-1H-benzo[c][1,2,6]thia-diazin-7-yl)-3-oxomorpholin-2-yl]-2-hydroxyacetamide;

19p: (2R)-2-[(2R)-4-(3,3-dimethyl-2-oxo-1H-indol-5-yl)-3-oxomorpholin-2-yl]-2-hydroxy-N-(1-imino-2,3-dihydroisoindol-5-yl)acetamide;

20p: (2R)-2-[(2R)-4-(4-tert-butylphenyl)-3-oxomorpholin-2-yl]-2-hydroxy-N-(1-imino-2,3-dihydroisoindol-5-yl)acetamide;

21p: (2R)-2-[(2R)-4-(4-acetamidophenyl)-3-oxomorpholin-2-yl]-2-hydroxy-N-(1-imino-2,3-dihydroisoindol-5-yl)acetamide;

22p: (2R)—N-(1-aminoisoquinolin-6-yl)-2-[(2R)-4-(3,3-dimethyl-2-oxo-1H-indol-5-yl)-3-oxomorpholin-2-yl]-2-hydroxyacetamide;

23p: (2R)—N-(1-aminoisoquinolin-6-yl)-2-[(2R)-4-(4-tert-butylphenyl)-3-oxomorpholin-2-yl]-2-hydroxyacetamide;

and

24p: (2R)-2-[(2R)-4-(4-acetamidophenyl)-3-oxomorpholin-2-yl]-N-(1-aminoisoquinolin-6-yl)-2-hydroxyacetamide.

[7-4] In another aspect, the present invention provides a compound selected from the group consisting of:

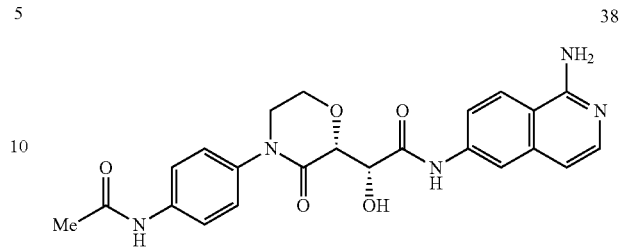

38

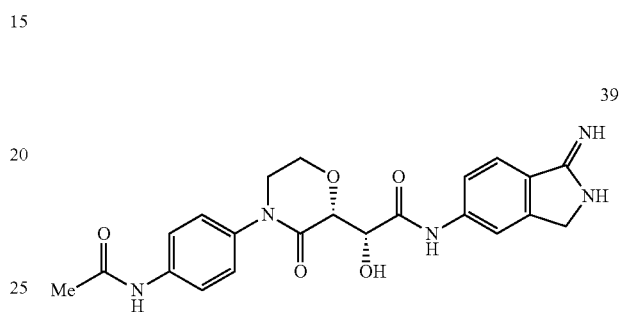

39

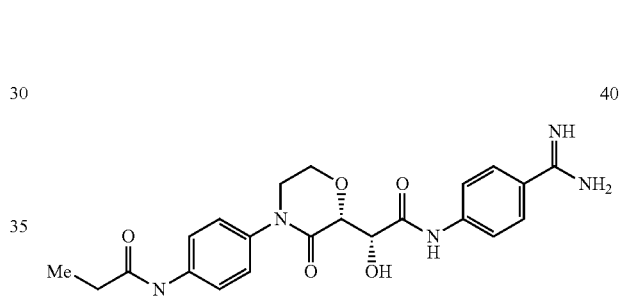

40

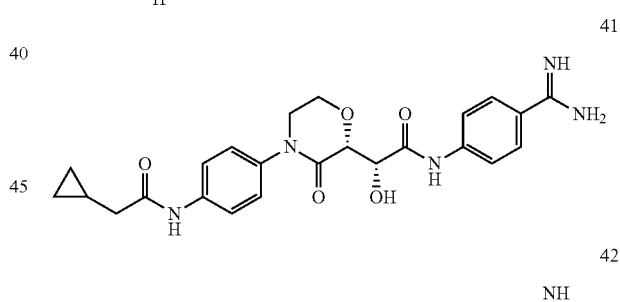

41

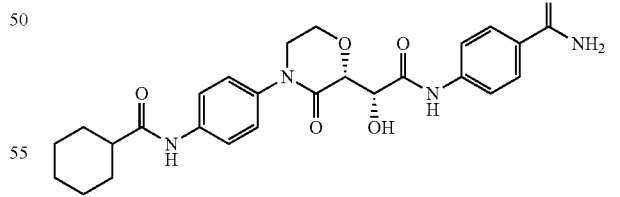

42

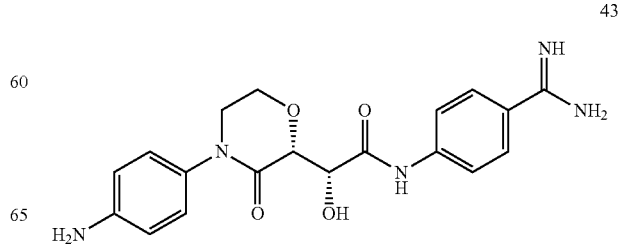

43

44
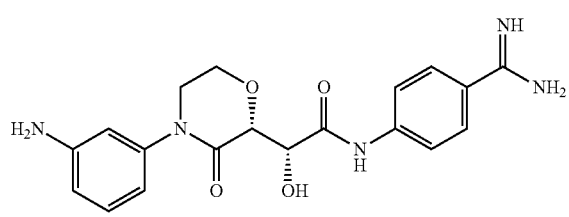
45
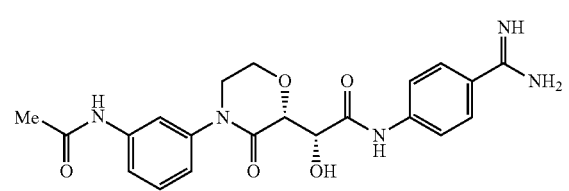
46
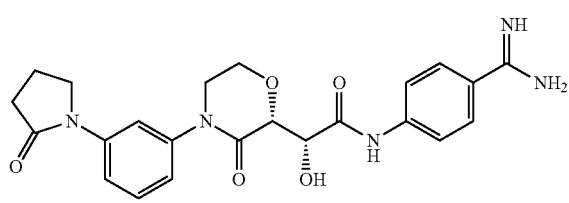
47
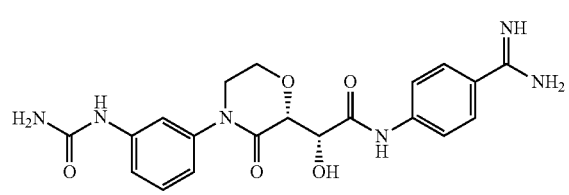
48
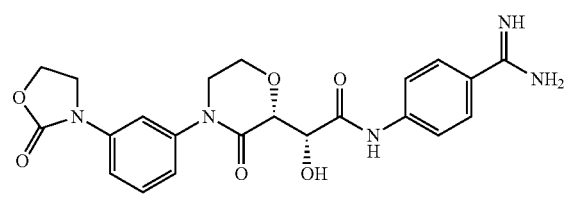
49
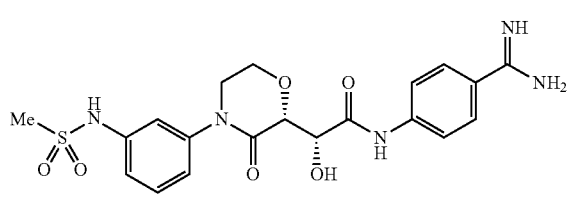
50
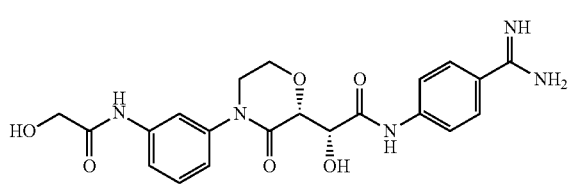
51
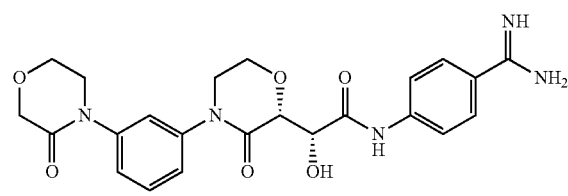
52
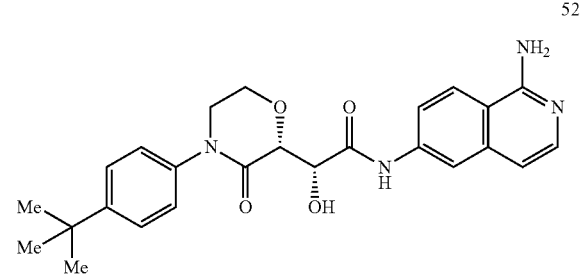
53
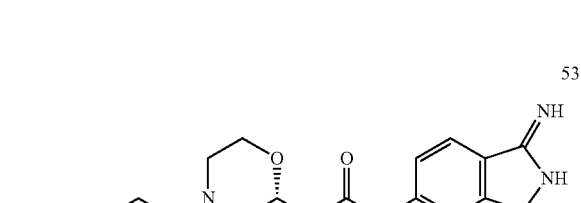
54
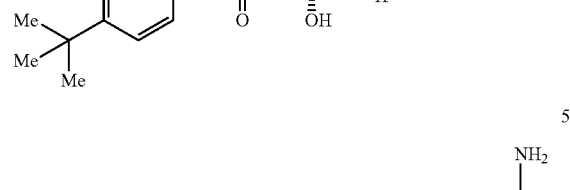
55
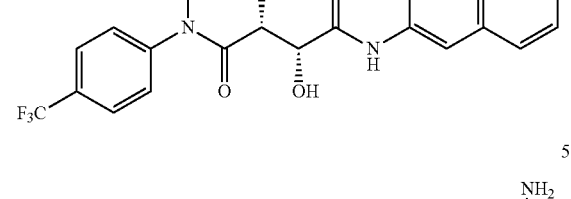
56
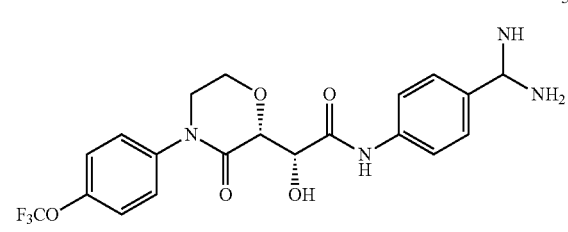

57
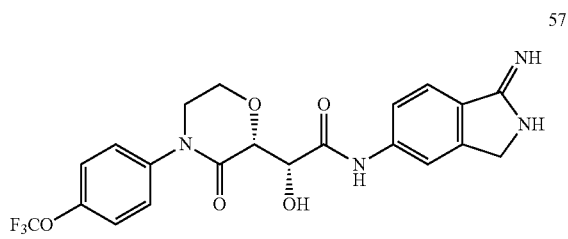

58
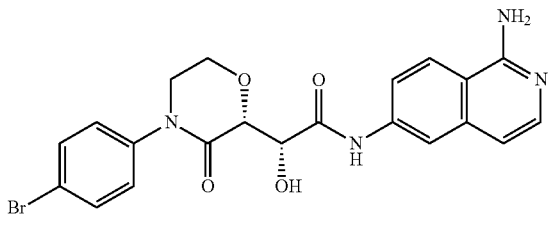

59
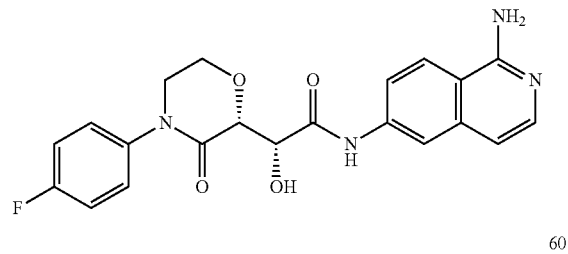

60
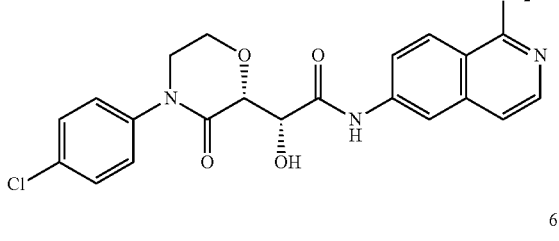

61
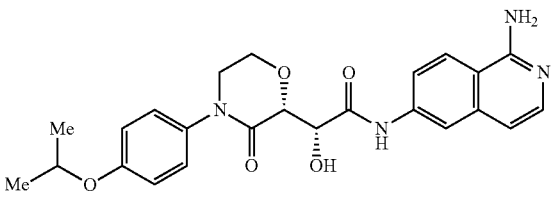

62
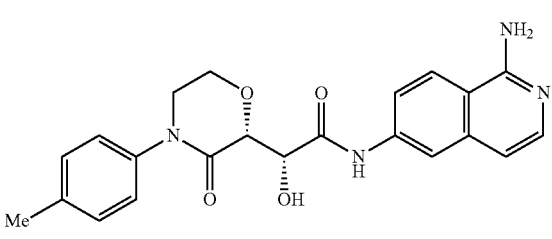

63
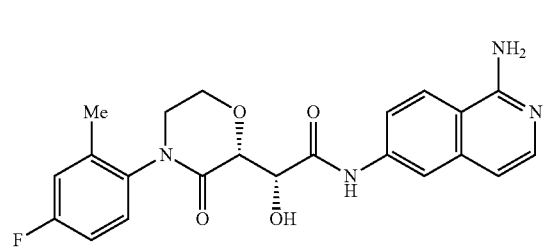

64
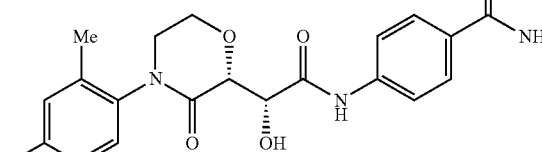

65
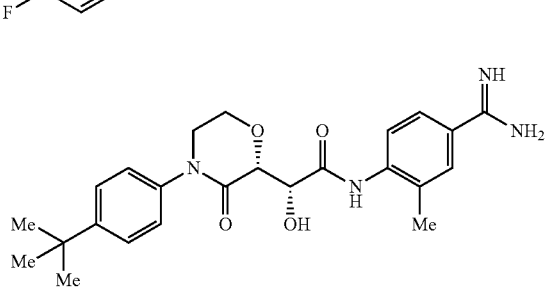

66

67
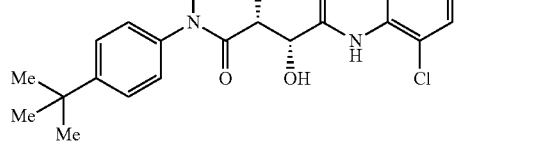

or a pharmaceutically acceptable salt or solvate thereof.

Each compound name from example 38 to example 67 is,

38: (2R)-2-[(2R)-4-(4-Acetamidophenyl)-3-oxomorpholin-2-yl]-N-(1-aminoisoquinolin-6-yl)-2-hydroxyacetamide;

39: (2R)-2-[(2R)-4-(4-Acetamidophenyl)-3-oxomorpholin-2-yl]-2-hydroxy-N-(1-imino-2,3-dihydroisoindol-5-yl)acetamide;

40: N-[4-[(2R)-2-[(1R)-2-(4-amidinoanilino)-1-hydroxy-2-oxoethyl]-3-oxomorpholin-4-yl]phenyl]propanamide;

41: (2R)—N-(4-Amidinophenyl)-2-[(2R)-4-[4-[(2-cyclopropylacetyl)amino]phenyl]-3-oxomorpholin-2-yl]-2-hydroxyacetamide;

42: N-[4-[(2R)-2-[(1R)-2-(4-Amidinoanilino)-1-hydroxy-2-oxoethyl]-3-oxomorpholin-4-yl]phenyl]cyclohexanecarboxamide;

43: (2R)—N-(4-Amidinophenyl)-2-[(2R)-4-(4-aminophenyl)-3-oxomorpholin-2-yl]-2-hydroxyacetamide;
44: (2R)—N-(4-Amidinophenyl)-2-[(2R)-4-(3-aminophenyl)-3-oxomorpholin-2-yl]-2-hydroxyacetamide;
45: (2R)-2-[(2R)-4-(3-Acetamidophenyl)-3-oxomorpholin-2-yl]-N-(4-amidinophenyl)-2-hydroxyacetamide;
46: (2R)—N-(4-Amidinophenyl)-2-hydroxy-2-[(2R)-3-oxo-4-[3-(2-oxopyrrolidin-1-yl)phenyl]morpholin-2-yl]acetamide;
47: (2R)—N-(4-Amidinophenyl)-2-[(2R)-4-[3-(carbamoylamino)phenyl]-3-oxomorpholin-2-yl]-2-hydroxyacetamide;
48: (2R)—N-(4-Amidinophenyl)-2-hydroxy-2-[(2R)-3-oxo-4-[3-(2-oxo-1,3-oxazolidin-3-yl)phenyl]morpholin-2-yl]acetamide;
49: (2R)—N-(4-Amidinophenyl)-2-hydroxy-2-[(2R)-4-[3-(methanesulfonamido)phenyl]-3-oxomorpholin-2-yl]acetamide;
50: (2R)—N-(4-Amidinophenyl)-2-hydroxy-2-[(2R)-4-[3-[(2-hydroxyacetyl)amino]phenyl]-3-oxomorpholin-2-yl]acetamide;
51: (2R)—N-(4-Amidinophenyl)-2-hydroxy-2-[(2R)-3-oxo-4-[3-(3-oxomorpholin-4-yl)phenyl]morpholin-2-yl]acetamide;
52: (2R)—N-(1-Aminoisoquinolin-6-yl)-2-[(2R)-4-(4-tert-butylphenyl)-3-oxomorpholin-2-yl]-2-hydroxyacetamide;
53: (2R)-2-[(2R)-4-(4-tert-Butylphenyl)-3-oxomorpholin-2-yl]-2-hydroxy-N-(1-imino-2,3-dihydroisoindol-5-yl)acetamide;
54: (2R)—N-(1-Aminoisoquinolin-6-yl)-2-hydroxy-2-[(2R)-3-oxo-4-[4-(trifluoromethyl)phenyl]morpholin-2-yl]acetamide;
55: (2R)—N-(1-Aminoisoquinolin-6-yl)-2-hydroxy-2-[(2R)-3-oxo-4-[4-(trifluoromethoxy)phenyl]morpholin-2-yl]acetamide;
56: (2R)—N-(4-Amidinophenyl)-2-hydroxy-2-[(2R)-3-oxo-4-[4-(trifluoromethoxy)phenyl]morpholin-2-yl]acetamide;
57: (2R)-2-Hydroxy-N-(1-imino-2,3-dihydroisoindol-5-yl)-2-[(2R)-3-oxo-4-[4-(trifluoromethoxy)phenyl]morpholin-2-yl]acetamide;
58: (2R)—N-(1-Aminoisoquinolin-6-yl)-2-[(2R)-4-(4-bromophenyl)-3-oxomorpholin-2-yl]-2-hydroxyacetamide;
59: (2R)—N-(1-Aminoisoquinolin-6-yl)-2-[(2R)-4-(4-fluorophenyl)-3-oxomorpholin-2-yl ]-2-hydroxyacetamide;
60: (2R)—N-(1-Aminoisoquinolin-6-yl)-2-[(2R)-4-(4-chlorophenyl)-3-oxomorpholin-2-yl]-2-hydroxyacetamide;
61: (2R)—N-(1-Aminoisoquinolin-6-yl)-2-hydroxy-2-[(2R)-4-(4-isopropyloxyphenyl)-3-oxomorpholin-2-yl]acetamide;
62: (2R)—N-(1-Aminoisoquinolin-6-yl)-2-hydroxy-2-[(2R)-3-oxo-4-p-tolylmorpholin-2-yl]acetamide;
63: (2R)—N-(1-Aminoisoquinolin-6-yl)-2-[(2R)-4-(4-fluoro-o-tolyl)-3-oxomorpholin-2-yl]-2-hydroxyacetamide;
64: (2R)—N-(4-Amidinophenyl)-2-[(2R)-4-(4-fluoro-o-tolyl)-3-oxomorpholin-2-yl]-2-hydroxyacetamide;
65: (2R)—N-(4-Amidino-o-tolyl)-2-[(2R)-4-(4-tert-butylphenyl)-3-oxomorpholin-2-yl]-2-hydroxyacetamide;
66: (2R)—N-(4-Amidino-2-chlorophenyl)-2-[(2R)-4-(4-tert-butylphenyl)-3-oxomorpholin-2-yl]-2-hydroxyacetamide;
and
67: (2R)—N-(4-Amidino-2-fluorophenyl)-2-[(2R)-4-(4-tert-butylphenyl)-3-oxomorpholin-2-yl]-2-hydroxyacetamide;

[7-5] In another aspect, the present invention provides a compound selected from the group consisting of:

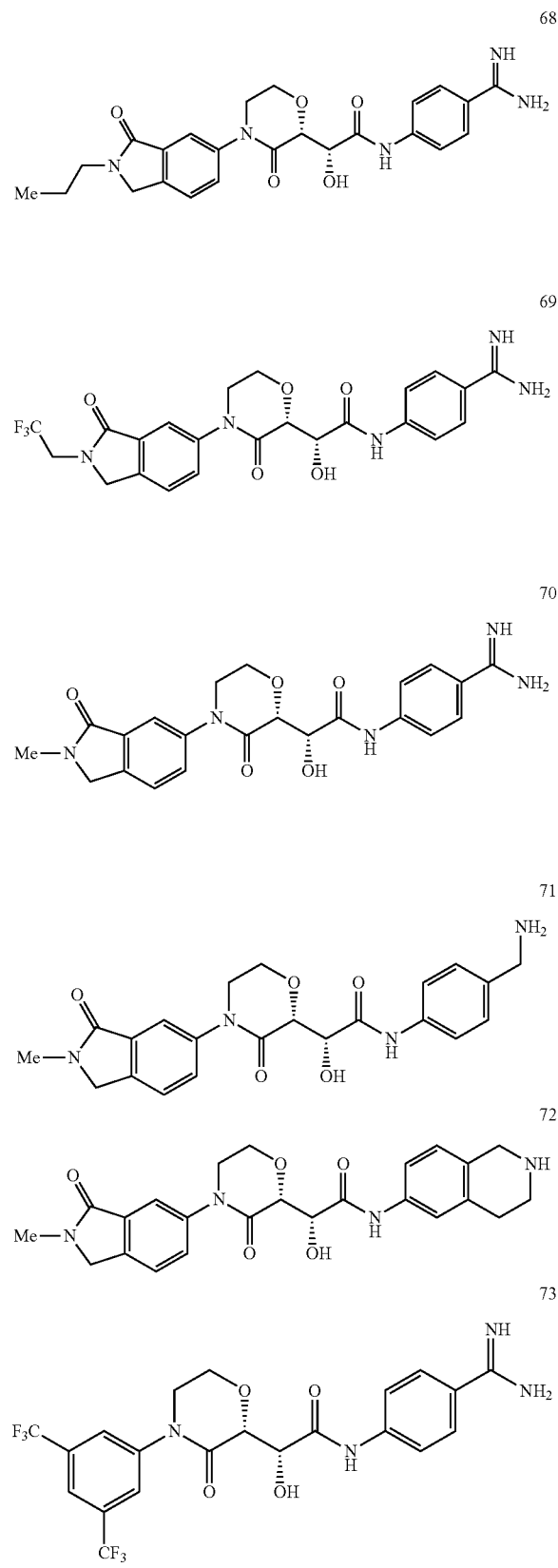

-continued
74
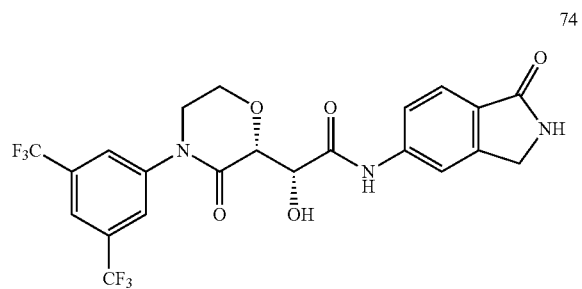
75
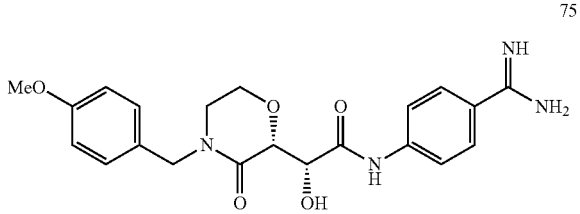
76
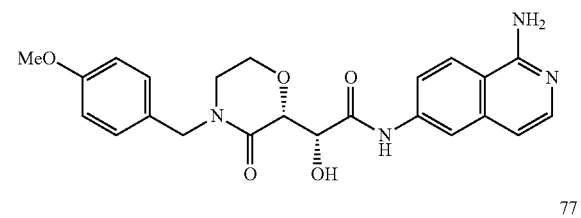
77
78
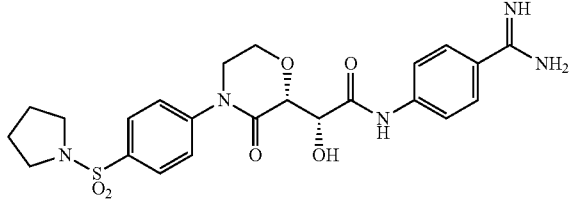
79
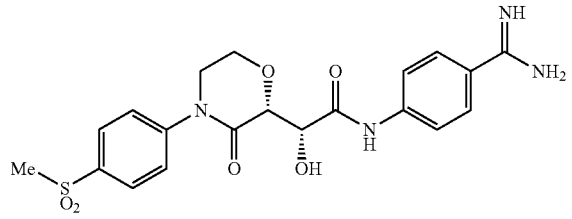
80
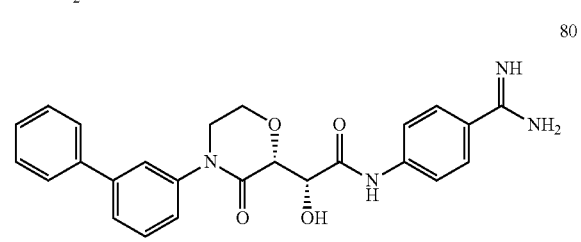
-continued
81
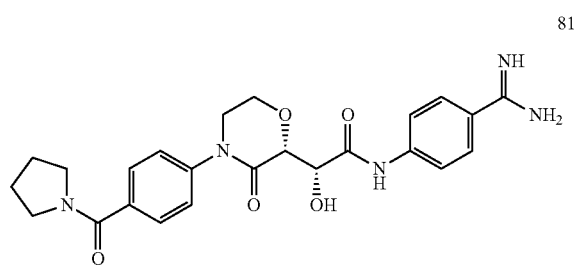
82
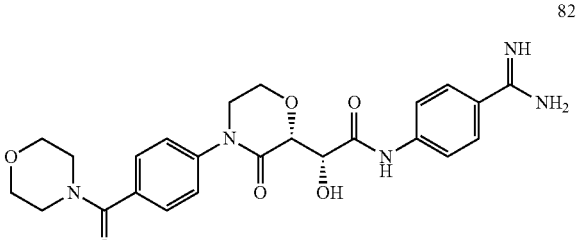
83
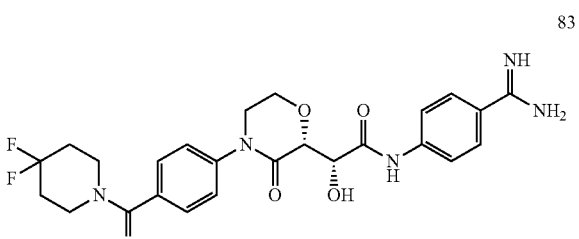
84
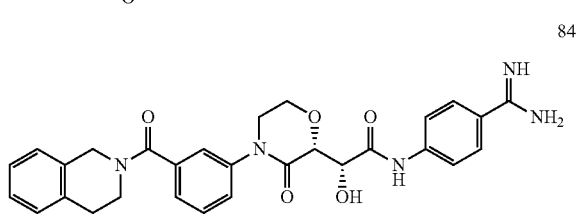
85
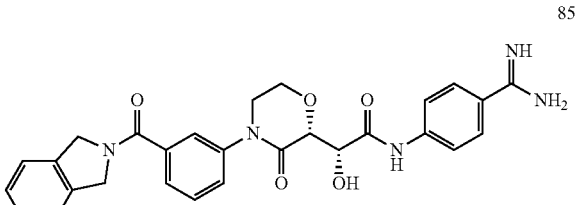
86
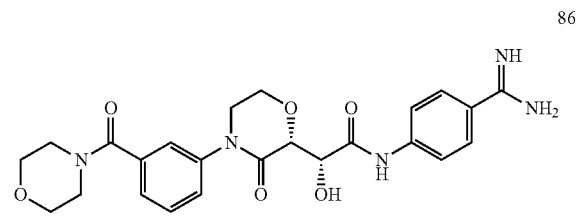
87
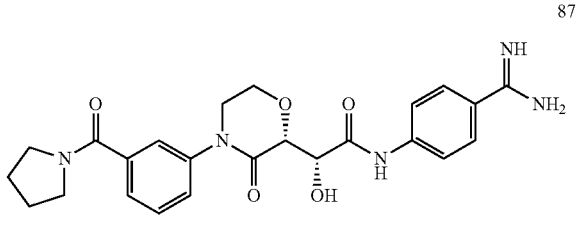

88
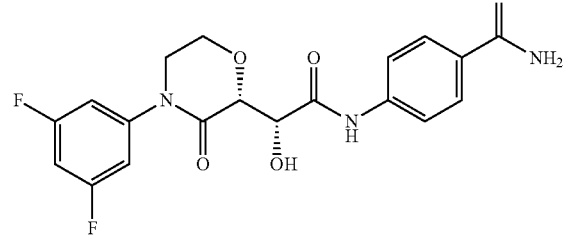
89
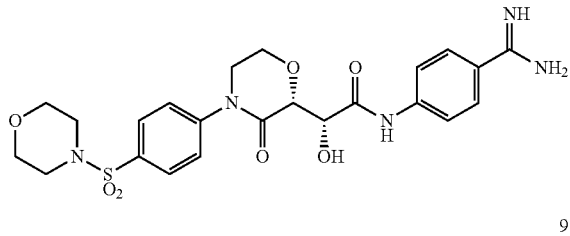
90
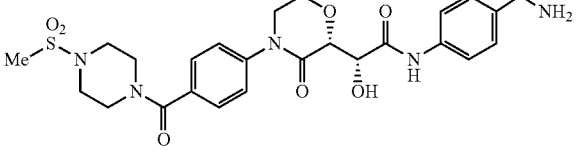
91
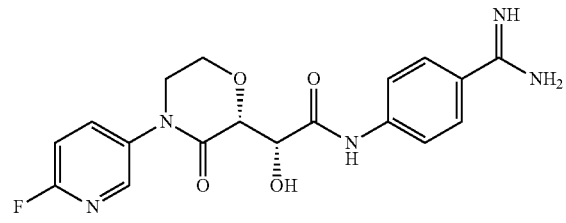
92
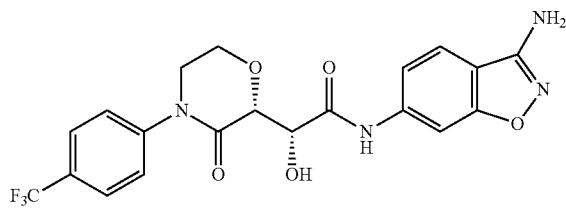
93
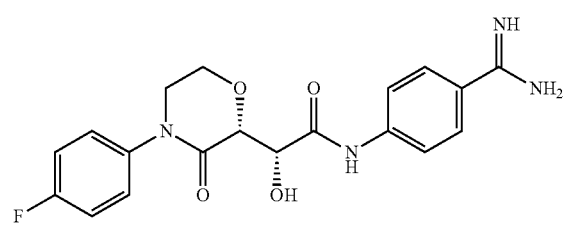
94
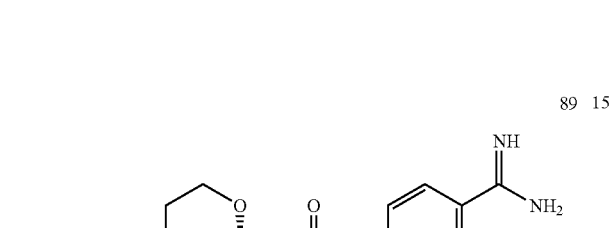
95
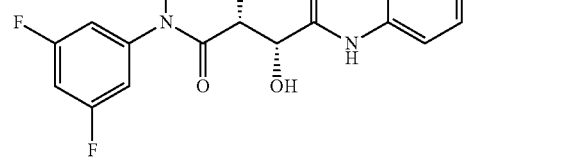
96
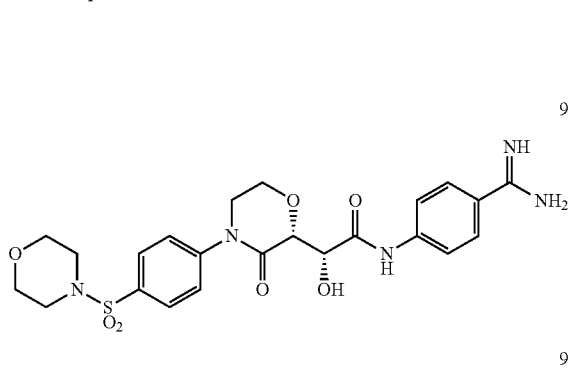
97
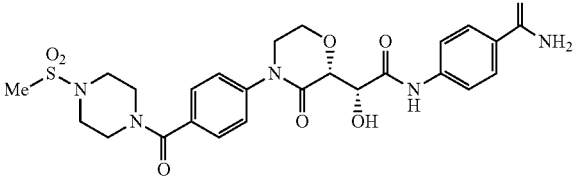
98
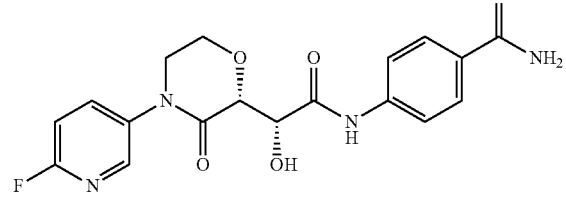
99
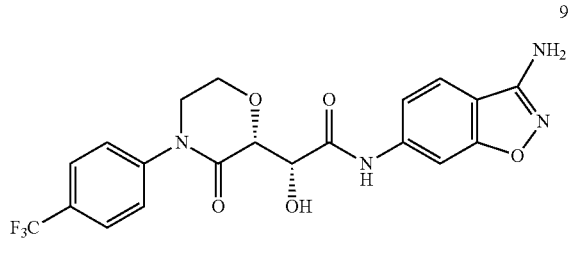
100

101 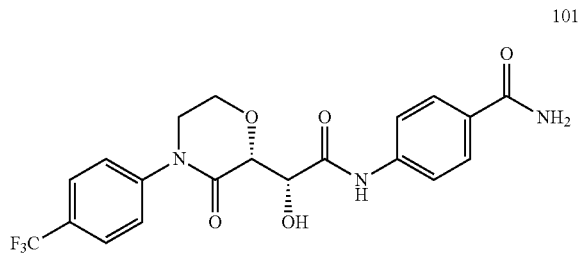
107 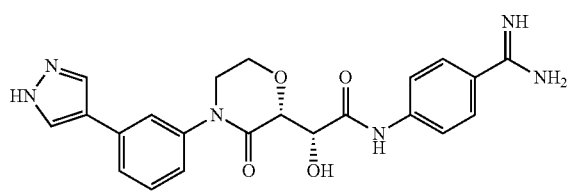
102 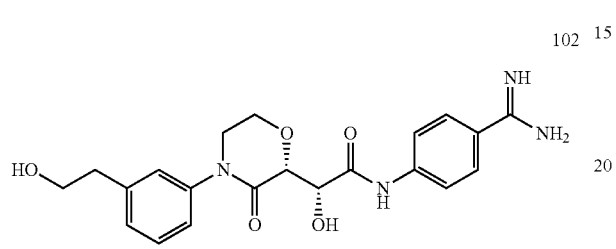
108 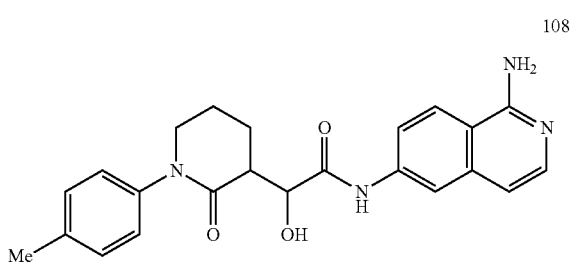
103 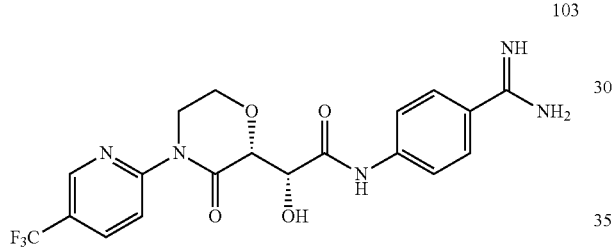
109 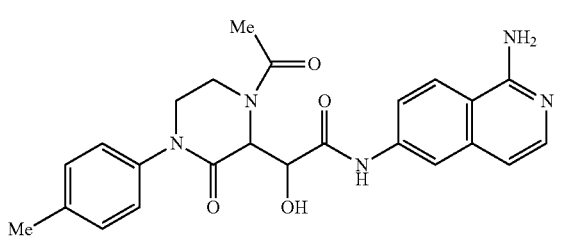
104 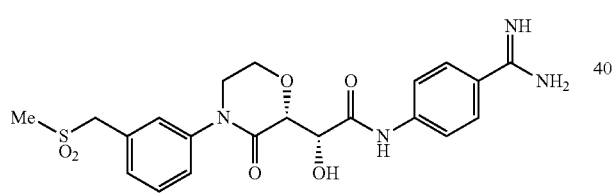
110 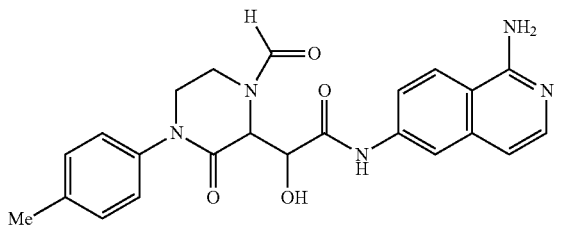
105 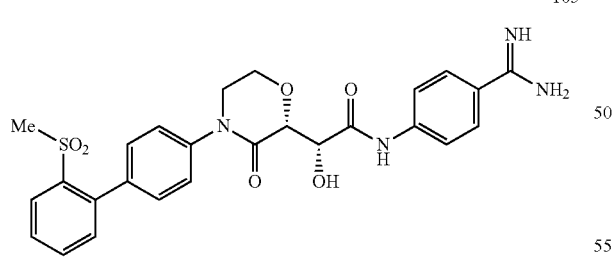
111 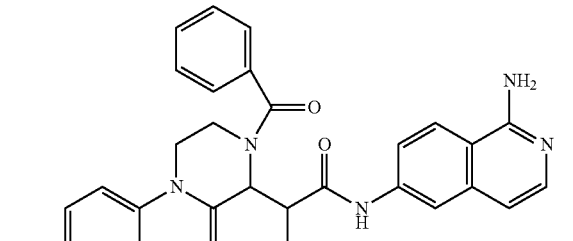
106 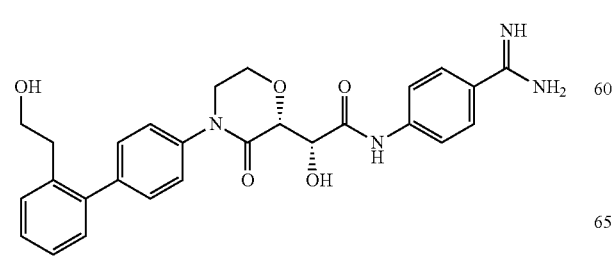
112 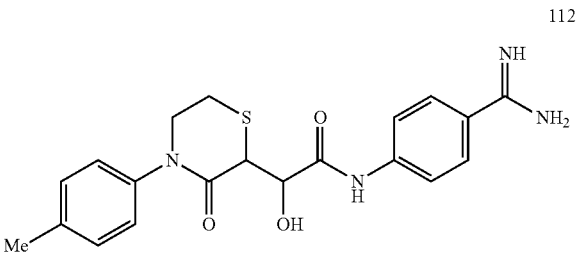

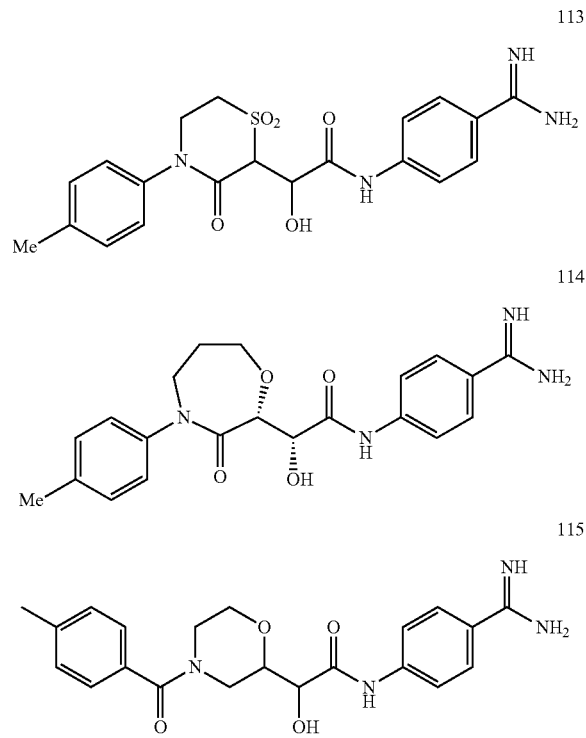
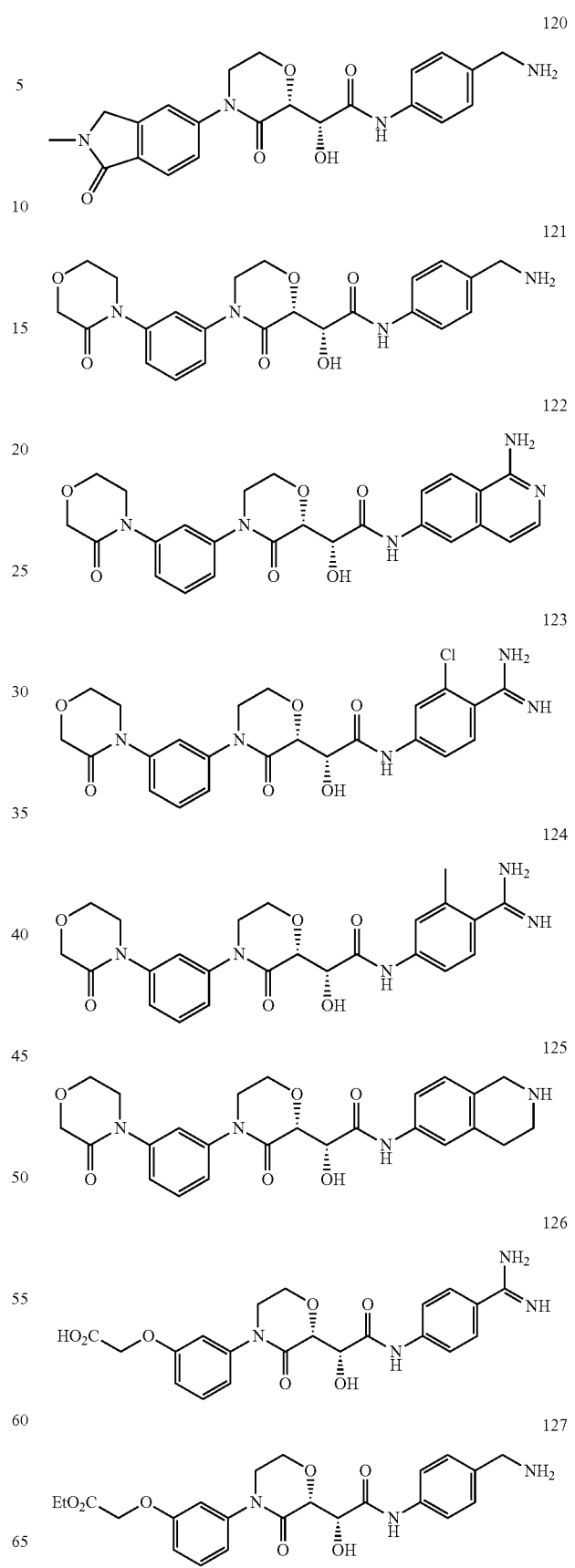

-continued

128

129

130

131

132

133

134

-continued

135

136

137

138

139

140

141

142
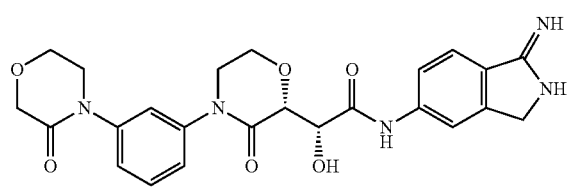
143
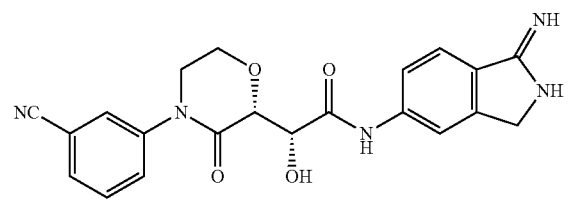
144
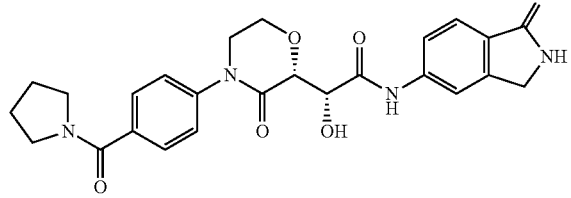
145
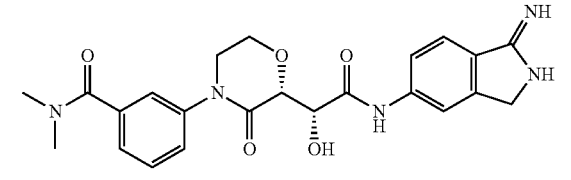
146
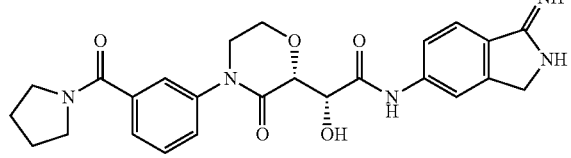
147
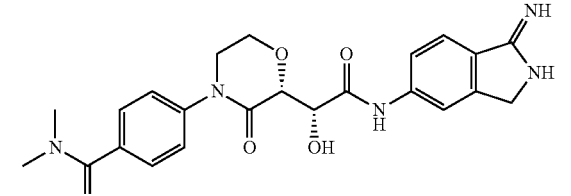
148

149
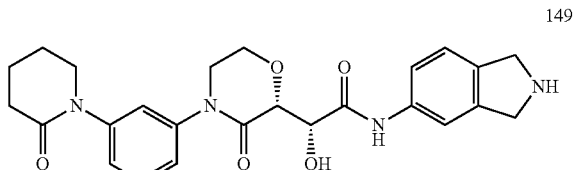
150
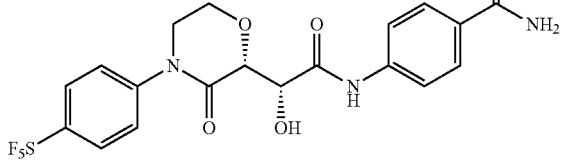
151
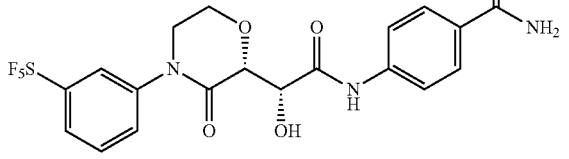
152
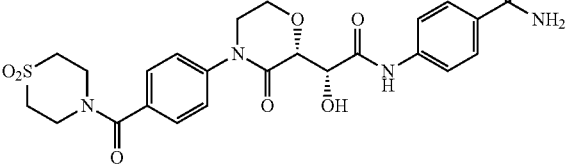
153
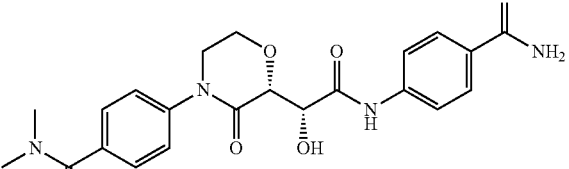
154
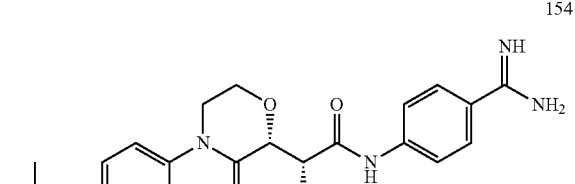
155
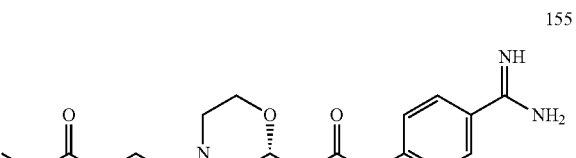

156
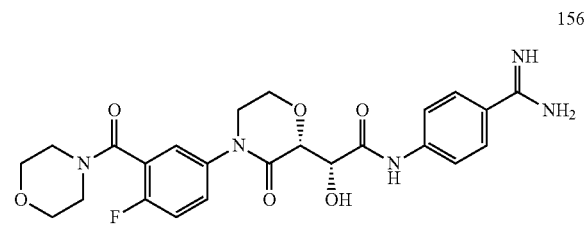
157
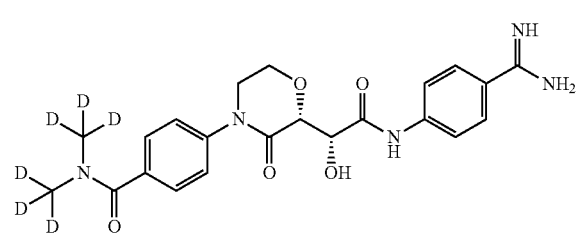
158
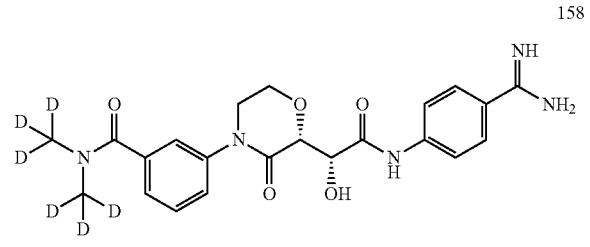
159
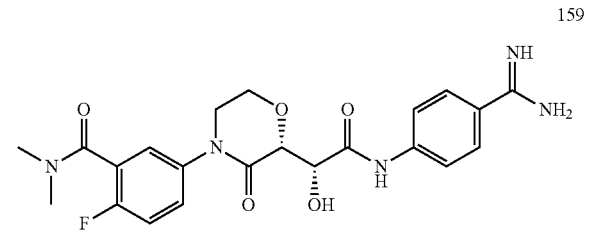
160
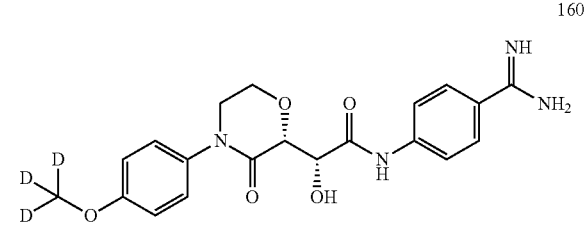
161

162
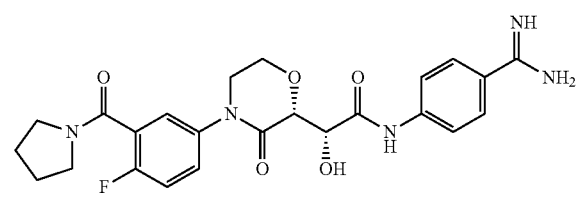
163
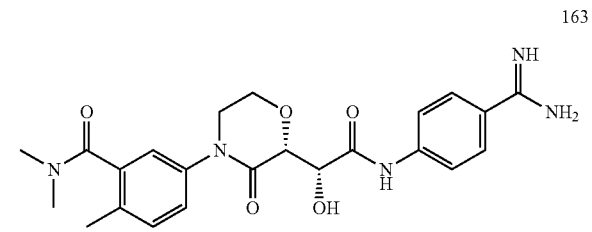
164
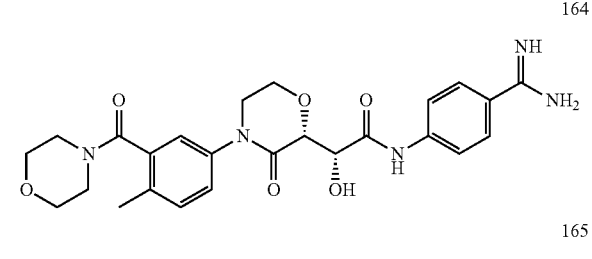
165
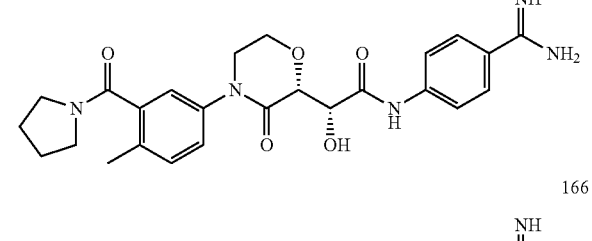
166
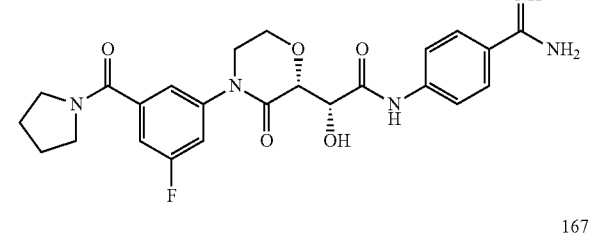
167
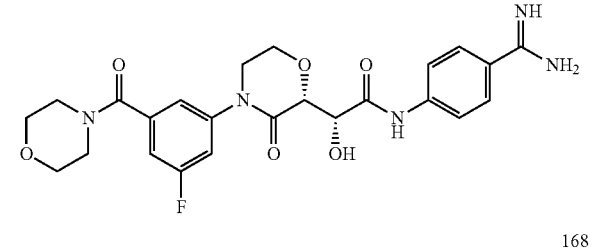
168
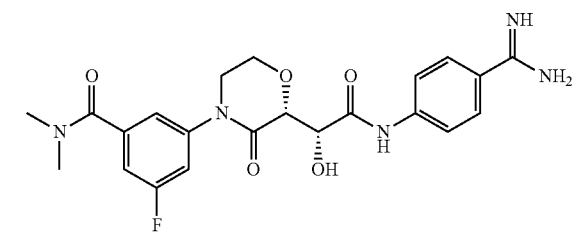
169
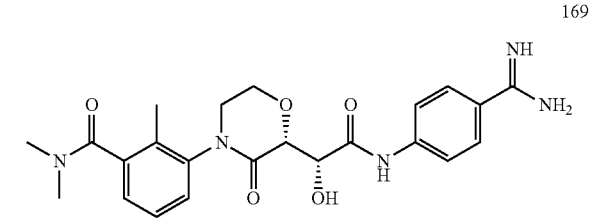

103
-continued
170
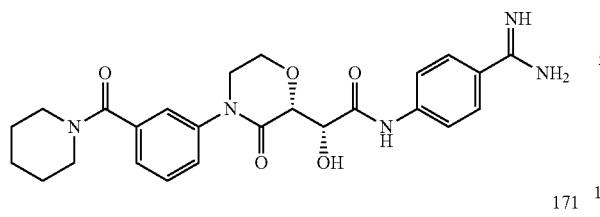
171
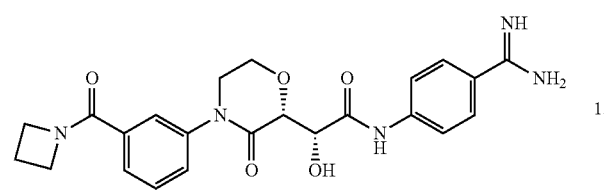
172
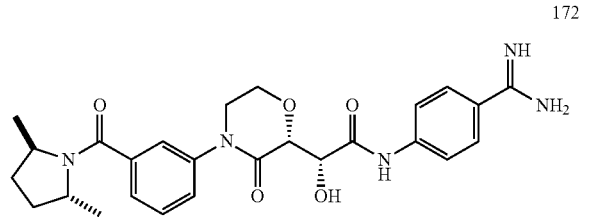
173
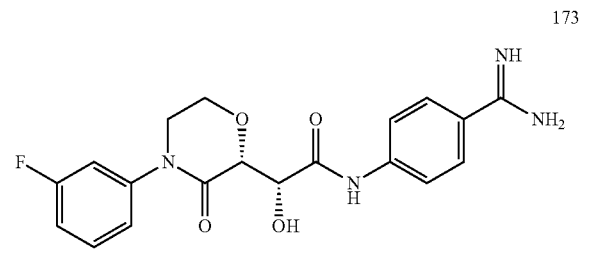
174
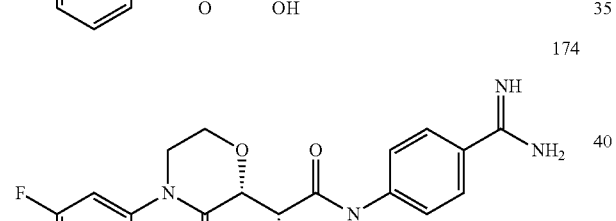
175
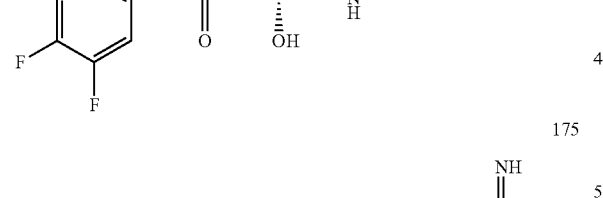
176
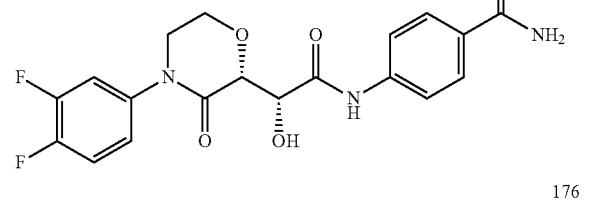
104
-continued
177
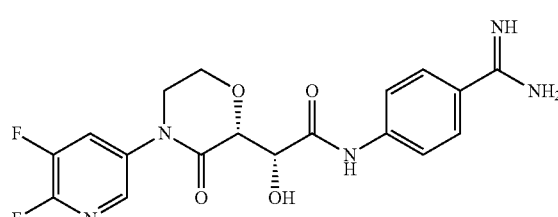
178
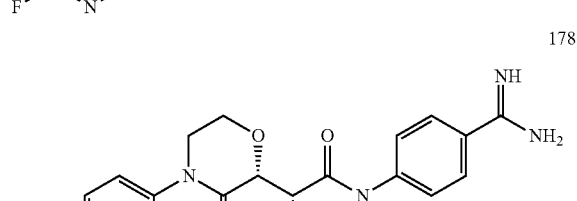
179
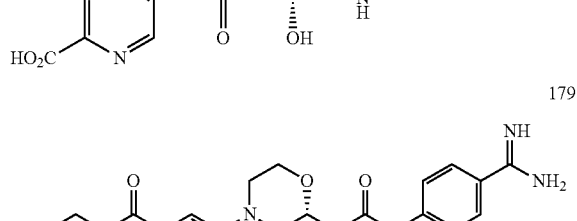
180
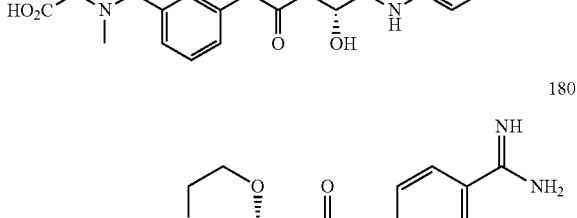
181
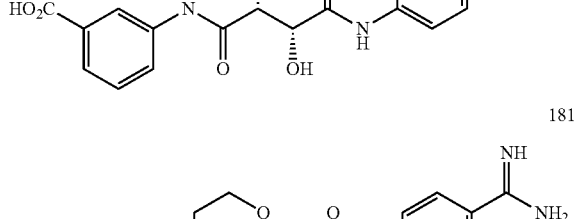
182
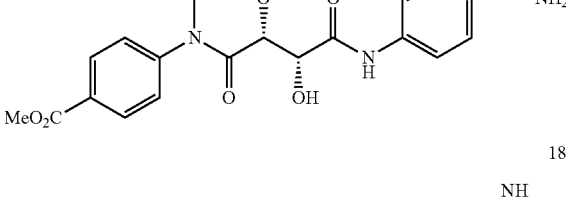
183
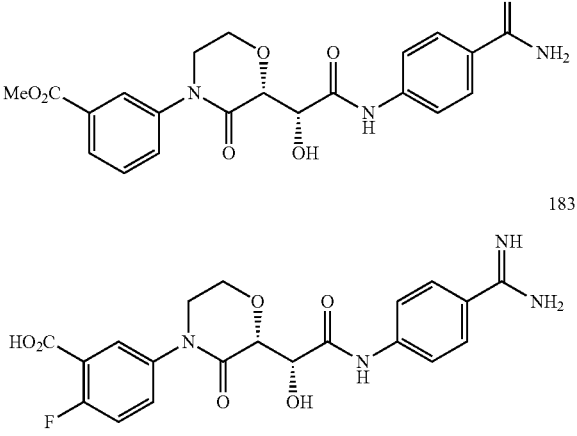

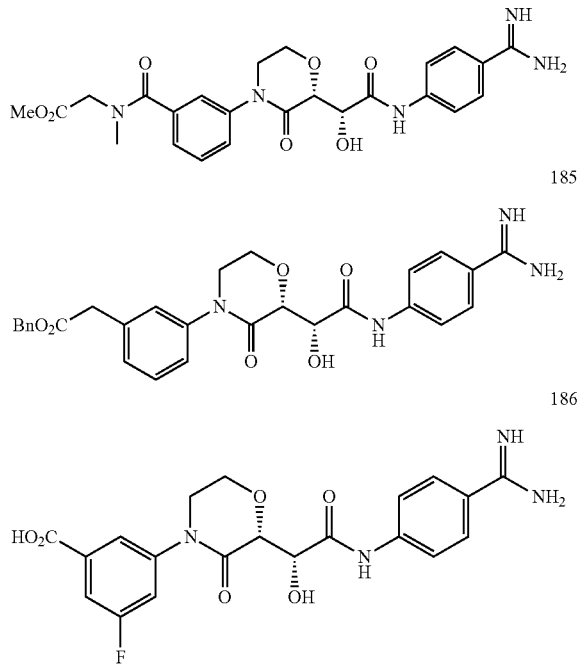

or a pharmaceutically acceptable salt or solvate thereof.

Each compound name from example 68 to example 217 is,

68: (R)—N-(4-carbamimidoylphenyl)-2-hydroxy-2-((R)-3-oxo-4-(3-oxo-2-propylisoindolin-5-yl)morpholin-2-yl)acetamide;
69: (R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide;
70: (R)—N-(4-carbamimidoylphenyl)-2-hydroxy-2-((R)-4-(2-methyl-3-oxoisoindolin-5-yl)-3-oxomorpholin-2-yl)acetamide;
71: (R)—N-(4-(aminomethyl)phenyl)-2-hydroxy-2-((R)-4-(2-methyl-3-oxoisoindolin-5-yl)-3-oxomorpholin-2-yl)acetamide;
72: (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide;
73: (R)-2-((R)-4-(3,5-bis(trifluoromethyl)phenyl)-3-oxomorpholin-2-yl)-N-(4-carbamimidoylphenyl)-2-hydroxyacetamide;
74: (R)-2-((R)-4-(3,5-bis(trifluoromethyl)phenyl)-3-oxomorpholin-2-yl)-2-hydroxy-N-(1-oxoisoindolin-5-yl)acetamide;
75: (R)—N-(4-carbamimidoylphenyl)-2-hydroxy-2-((R)-4-(4-methoxybenzyl)-3-oxomorpholin-2-yl)acetamide;
76: (R)—N-(1-aminoisoquinolin-6-yl)-2-hydroxy-2-((R)-4-(4-methoxybenzyl)-3-oxomorpholin-2-yl)acetamide;
77: (2R)—N-(4-amidinophenyl)-2-hydroxy-2-[(2R)-3-oxo-4-(3-(4,4-difluoropiperidin-1-ylcarbonyl)phenyl)morpholin-2-yl]acetamide;
78: (2R)—N-(4-amidinophenyl)-2-hydroxy-2-[(2R)-3-oxo-4-(4-(pyrrolidin-1-ylsulfonyl)phenyl)morpholin-2-yl]acetamide;
79: (2R)—N-(4-amidinophenyl)-2-hydroxy-2-[(2R)-3-oxo-4-(4-(methylsulfonyl)phenyl) morpholin-2-yl]acetamide;
80: (2R)—N-(4-amidinophenyl)-2-hydroxy-2-[(2R)-3-oxo-4-(3-phenylphenyl)morpholin-2-yl]acetamide;
81: (2R)—N-(4-amidinophenyl)-2-hydroxy-2-[(2R)-3-oxo-4-(4-(pyrrolidin-1-ylcarbonyl)phenyl)morpholin-2-yl]acetamide;
82: (2R)—N-(4-amidinophenyl)-2-hydroxy-2-[(2R)-3-oxo-4-(4-(morpholin-4-ylcarbonyl)phenyl)morpholin-2-yl]acetamide;
83: (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide;
84: (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide;
85: (2R)—N-(4-amidinophenyl)-2-hydroxy-2-[(2R)-3-oxo-4-(3-(isoindolin-2-ylcarbonyl)phenyl)morpholin-2-yl]acetamide;
86: (2R)—N-(4-amidinophenyl)-2-hydroxy-2-[(2R)-3-oxo-4-(3-(morpholin-4-ylcarbonyl)phenyl)morpholin-2-yl]acetamide;
87: (2R)—N-(4-amidinophenyl)-2-hydroxy-2-[(2R)-3-oxo-4-(3-(pyrrolidin-1-ylcarbonyl)phenyl)morpholin-2-yl]acetamide;
88: (2R)—N-(4-amidinophenyl)-2-hydroxy-2-[(2R)-3-oxo-4-(4-fluorophenyl)morpholin-2-yl]acetamide;
89: (2R)—N-(4-amidinophenyl)-2-hydroxy-2-[(2R)-3-oxo-4-(3,5-difluorophenyl)morpholin-2-yl]acetamide;
90: (2R)—N-(4-amidinophenyl)-2-hydroxy-2-[(2R)-3-oxo-4-(4-(morpholin-1-ylsulfonyl)phenyl)morpholin-2-yl]acetamide;
91: (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide;
92: (2R)—N-(4-amidinophenyl)-2-hydroxy-2-[(2R)-3-oxo-4-(2-fluoropyridin-5-yl)morpholin-2-yl]acetamide;
93: (R)—N-(3-aminobenzo[d]isoxazol-6-yl)-2-hydroxy-2-((R)-3-oxo-4-(4-(trifluoromethyl)phenyl)morpholin-2-yl)acetamide;
94: (R)—N-(3-amino-1H-indazol-6-yl)-2-hydroxy-2-((R)-3-oxo-4-(4-(trifluoromethyl)phenyl)morpholin-2-yl)acetamide;
95: (R)—N-(4-carbamimidoyl-3-fluorophenyl)-2-hydroxy-2-((R)-3-oxo-4-(4-(trifluoromethyl)phenyl)morpholin-2-yl)acetamide;
96: (R)—N-(4-carbamimidoylphenyl)-2-hydroxy-2-{(R)-3-oxo-4-[4-(trifluoromethyl)phenyl]morpholin-2-yl}acetamide;
97: (R)—N-(4-carbamimidoylphenyl)-2-hydroxy-2-((R)-3-oxo-4-(3-(trifluoromethyl)phenyl)morpholin-2-yl)acetamide;
98: N-(4-amino-7-quinazolinyl)-alpha(R)-hydroxy-3-oxo-4-[4-(trifluoromethyl)phenyl]-2(R)-morpholineacetamide;
99: N-[4-(aminomethyl)phenyl]-alpha(R)-hydroxy-3-oxo-4-[4-(trifluoromethyl)phenyl]-2(R)-morpholineacetamide;
100: N-[4-(aminoiminomethyl)phenyl]-4-[3-(aminomethyl)phenyl]-alpha(R)-hydroxy-3-oxo-2(R)-morpholineacetamide; and
101: N-[4-(aminocarbonyl)phenyl]-alpha(R)-hydroxy-3-oxo-4-[4-(trifluoromethyl)phenyl]-2(R)-morpholineacetamide;
102: (2R)—N-(4-amidinophenyl)-2-hydroxy-2-[(2R)-4-[3-(2-hydroxyethyl)phenyl]-3-oxomorpholin-2-yl]acetamide;
103: (2R)—N-(4-amidinophenyl)-2-hydroxy-2-[(2R)-3-oxo-4-[5-(trifluoromethyl)-2-pyridyl]morpholin-2-yl]acetamide;
104: (2R)—N-[4-amidinophenyl]-2-hydroxy-2-[(2R)-4-[3-(methylsulfonylmethyl)phenyl]-3-oxomorpholin-2-yl]acetamide;

105: (2R)—N-(4-amidinophenyl)-2-hydroxy-2-[(2R)-4-[4-(2-methylsulfonylphenyl)phenyl]-3-oxomorpholin-2-yl]acetamide;
106: (2R)—N-(4-amidinophenyl)-2-hydroxy-2-[(2R)-4-[4-[2-(2-hydroxyethyl)phenyl]phenyl]-3-oxomorpholin-2-yl]acetamide;
107: (2R)—N-(4-amidinophenyl)-2-hydroxy-2-[(2R)-3-oxo-4-[3-(1H-pyrazol-4-yl)phenyl]morpholin-2-yl]acetamide;
108: N-(1-amino-6-isoquinolyl)-2-hydroxy-2-[2-oxo-1-(p-tolyl)-3-piperidyl]acetamide;
109: 2-[1-acetyl-3-oxo-4-(p-tolyl)piperazin-2-yl]-N-(1-amino-6-isoquinolyl)-2-hydroxy-acetamide;
110: N-(1-amino-6-isoquinolyl)-2-[1-formyl-3-oxo-4-(p-tolyl)piperazin-2-yl]-2-hydroxyacetamide;
111: N-(1-amino-6-isoquinolyl)-2-[1-benzoyl-3-oxo-4-(p-tolyl)piperazin-2-yl]-2-hydroxyacetamide;
112: N-(4-amidinophenyl)-2-hydroxy-2-[3-oxo-4-(p-tolyl)thiomorpholin-2-yl]acetamide;
113: N-(4-amidinophenyl)-2-hydroxy-2-[1,1,3-trioxo-4-(p-tolyl)-1,4-thiazinan-2-yl]acetamide;
114: (2R)—N-(4-amidinophenyl)-2-hydroxy-2-[(2R)-3-oxo-4-(p-tolyl)-1,4-oxazepan-2-yl]acetamide;
115: N-(4-amidinophenyl)-2-hydroxy-2-[4-(4-methylbenzoyl)morpholin-2-yl]acetamide;
116: N-(4-amidinophenyl)-2-hydroxy-2-[4-(p-tolylsulfonyl)morpholin-2-yl]acetamide;
117: N-(1-amino-6-isoquinolyl)-2-hydroxy-2-[4-(p-tolyl)morpholin-2-yl]acetamide ditrifluoroacetate;
118: (R)—N-(4-Carbamimidoylphenyl)-2-hydroxy-2-((R)-3-oxo-4-(3-(trifluoromethoxy)phenyl)morpholin-2-yl)acetamide;
119: (R)—N-(4-Carbamimidoylphenyl)-2-hydroxy-2-((R)-4-(2-methyl-3-oxoisoindolin-5-yl)-3-oxomorpholin-2-yl)acetamide;
120: (R)—N-(4-(Aminomethyl)phenyl)-2-hydroxy-2-((R)-4-(2-methyl-1-oxoisoindolin-5-yl)-3-oxomorpholin-2-yl)acetamide;
121: (R)—N-(4-(Aminomethyl)phenyl)-2-hydroxy-2-((R)-3-oxo-4-(3-(3-oxomorpholino)phenyl)morpholin-2-yl)acetamide;
122: (R)—N-(1-Aminoisoquinolin-6-yl)-2-hydroxy-2-((R)-3-oxo-4-(3-(3-oxomorpholino)phenyl)morpholin-2-yl)acetamide;
123: (R)—N-(4-Carbamimidoyl-3-chlorophenyl)-2-hydroxy-2-((R)-3-oxo-4-(3-(3-oxomorpholino)phenyl)morpholin-2-yl)acetamide;
124: (R)—N-(4-Carbamimidoyl-3-methylphenyl)-2-hydroxy-2-((R)-3-oxo-4-(3-(3-oxomorpholino)phenyl)morpholin-2-yl)acetamide;
125: (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide;
126: 2-(3-((R)-2-((R)-2-(4-Carbamimidoylphenylamino)-1-hydroxy-2-oxoethyl)-3-oxo morpholino)phenoxy)acetic acid;
127: Ethyl 2-(3-((R)-2-((R)-2-(4-(aminomethyl)phenylamino)-1-hydroxy-2-oxoethyl)-3-oxomorpholino)phenoxy)acetate;
128: (R)—N-(4-carbamimidoyl-2-ethylphenyl)-2-hydroxy-2-((R)-4-(2-methyl-3-oxoisoindolin-5-yl)-3-oxomorpholin-2-yl)acetamide;
129: (R)-2-Hydroxy-N-(2-methyl-1H-indol-5-yl)-2-((R)-3-oxo-4-(3-(3-oxomorpholino)phenyl)morpholin-2-yl)acetamide;
130: (R)—N-(4-Chlorophenethyl)-2-hydroxy-2-((R)-3-oxo-4-(3-(3-oxomorpholino)phenyl)morpholin-2-yl)acetamide;
131: (R)—N-(4-carbamimidoylphenyl)-2-hydroxy-2-((R)-4-(2-methoxyphenyl)-3-oxomorpholin-2-yl)acetamide;
132: (R)—N-(4-carbamimidoylphenyl)-2-hydroxy-2-((R)-4-(2-fluorophenyl)-3-oxomorpholin-2-yl)acetamide;
133: (R)—N-(4-carbamimidoylphenyl)-2-hydroxy-2-((R)-4-(2-(difluoromethoxy)phenyl)-3-oxomorpholin-2-yl)acetamide;
134: (R)—N-(6-carbamimidoylpyridin-3-yl)-2-hydroxy-2-((R)-3-oxo-4-(3-(3-oxomorpholino)phenyl)morpholin-2-yl)acetamide;
135: N-[4-(aminoiminomethyl)phenyl]-4-[3-(1,1-dioxido-2-isothiazolidinyl)phenyl]alpha(R)-hydroxy-3-oxo-2(R)-morpholineacetamide;
136: (R)—N-(4-carbamimidoylphenyl)-2-((R)-4-(4-fluoro-2-methoxyphenyl)-3-oxomorpholin-2-yl)-2-hydroxyacetamide;
137: (R)—N-(4-carbamimidoylphenyl)-2-hydroxy-2-((R)-4-(2-isopropoxyphenyl)-3-oxomorpholin-2-yl)acetamide;
138: (R)-2-((R)-4-(2-(2-amino-2-oxoethoxy)phenyl)-3-oxomorpholin-2-yl)-N-(4-carbamimidoylphenyl)-2-hydroxyacetamide;
139: (R)—N-(4-carbamimidoyl-3-fluorophenyl)-2-hydroxy-2-((R)-3-oxo-4-(3-(3-oxomorpholino)phenyl)morpholin-2-yl)acetamide;
140: (R)—N-(4-carbamimidoyl-3,5-difluorophenyl)-2-hydroxy-2-((R)-3-oxo-4-(3-(3-oxomorpholino)phenyl)morpholin-2-yl)acetamide;
141: 3-((R)-2-((R)-2-(4-carbamimidoyl-3-fluorophenylamino)-1-hydroxy-2-oxoethyl)-3-oxomorpholino)benzoic acid;
142: N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide;
143: 4-(3-Cyanophenyl)-N-(2,3-dihydro-1-imino-1H-isoindol-5-yl)-alpha(R)-hydroxy-3-oxo-2(R)-morpholineacetamide;
144: N-(2,3-Dihydro-1-imino-1H-isoindol-5-yl)-alpha(R)-hydroxy-3-oxo-4-[4-(1-pyrrolidinylcarbonyl)phenyl]-2(R)-morpholineacetamide;
145: N-(2,3-Dihydro-1-imino-1H-isoindol-5-yl)-4-[3-[(dimethylamino)carbonyl]phenyl]-alpha(R)-hydroxy-3-oxo-2(R)-morpholineacetamide;
146: n-(2,3-Dihydro-1-imino-1H-isoindol-5-yl)-alpha(R)-hydroxy-3-oxo-4-[3-(1-pyrrolidinylcarbonyl)phenyl]-2(R)-morpholineacetamide;
147: N-(2,3-Dihydro-1-imino-1H-isoindol-5-yl)-4-[4-[(dimethylamino)carbonyl]phenyl]-alpha(R)-hydroxy-3-oxo-2(R)-morpholineacetamide;
148: N-[4-(Aminoiminomethyl)phenyl]-alpha(R)-hydroxy-3-oxo-4-[3-(1h-tetrazol-5-yl)phenyl]-2(R)-morpholineacetamide;
149: N-(2,3-dihydro-1H-isoindol-5-yl)-alpha(R)-hydroxy-3-oxo-4-[3-(3-oxo-4-morpholinyl)phenyl]-2(R)-morpholineacetamide;
150: [4-[2(R)-[2-[[4-(Aminoiminomethyl)phenyl]amino]-1(R)-hydroxy-2-oxoethyl]-3-oxo-4-morpholinyl]phenyl] pentafluorosulfur;
151: [3-[2(R)-[2-[[4-(Aminoiminomethyl)phenyl]amino]-1(R)-hydroxy-2-oxoethyl]-3-oxo-4-morpholinyl]phenyl] pentafluorosulfur;
152: (2R)—N-(4-amidinophenyl)-2-hydroxy-2-[(2R)-3-oxo-4-(4-(1,1-dioxothiomorpholin-4-ylcarbonyl)phenyl)morpholin-2-yl]acetamide;

153: (2R)—N-(4-amidinophenyl)-2-hydroxy-2-[(2R)-3-oxo-4-(4-(dimethylaminocarbonyl)phenyl)morpholin-2-yl]acetamide;

154: (2R)—N-(4-amidinophenyl)-2-hydroxy-2-[(2R)-3-oxo-4-(4-(dimethylaminolsulfonyl)phenyl)morpholin-2-yl]acetamide;

155: (2R)—N-(4-amidinophenyl)-2-hydroxy-2-[(2R)-3-oxo-4-(3-(dimethylaminocarbonyl)phenyl)morpholin-2-yl]acetamide;

156: (2R)—N-(4-amidinophenyl)-2-hydroxy-2-[(2R)-3-oxo-4-(4-fluoro-3-(morpholin-4-ylcarbonyl)phenyl)morpholin-2-yl]acetamide;

157: (2R)—N-(4-amidinophenyl)-2-hydroxy-2-[(2R)-3-oxo-4-(4-(dimethyl-$D_6$-aminocarbonyl)phenyl)morpholin-2-yl]acetamide;

158: (2R)—N-(4-amidinophenyl)-2-hydroxy-2-[(R2)-3-oxo-4-(3-(dimethyl-$D_6$-aminocarbonyl)phenyl)morpholin-2-yl]acetamide;

159: (2R)—N-(4-amidinophenyl)-2-hydroxy-2-[(2R)-3-oxo-4-(3-(dimethylaminocarbonyl)-4-fluorophenyl)morpholin-2-yl]acetamide;

160: (2R)—N-(4-amidinophenyl)-2-hydroxy-2-[(2R)-3-oxo-4-(4-methoxy-$D_3$-phenyl)morpholin-2-yl]acetamide;

161: (2R)—N-(4-amidinophenyl)-2-hydroxy-2-[(2R)-3-oxo-4-(3-methoxy-$D_3$-phenyl)morpholin-2-yl]acetamide;

162: (2R)—N-(4-amidinophenyl)-2-hydroxy-2-[(2R)-3-oxo-4-(4-fluoro-3-(pyrrolidin-1-ylcarbonyl)phenyl)morpholin-2-yl]acetamide;

163: (2R)—N-(4-amidinophenyl)-2-hydroxy-2-[(2R)-3-oxo-4-(3-(dimethylaminocarbonyl)-4-methylphenyl)morpholin-2-yl]acetamide;

164: (2R)—N-(4-amidinophenyl)-2-hydroxy-2-[(2R)-3-oxo-4-(4-methyl-3-(morpholin-4-ylcarbonyl)phenyl)morpholin-2-yl]acetamide;

165: (2R)—N-(4-amidinophenyl)-2-hydroxy-2-[(2R)-3-oxo-4-(4-methyl-3-(pyrrolidin-1-ylcarbonyl)phenyl)morpholin-2-yl]acetamide;

166: (2R)—N-(4-amidinophenyl)-2-hydroxy-2-[(2R)-3-oxo-4-(3-fluoro-5-(pyrrolidin-1-ylcarbonyl)phenyl)morpholin-2-yl]acetamide;

167: (2R)—N-(4-amidinophenyl)-2-hydroxy-2-[(2R)-3-oxo-4-(3-fluoro-5-(morpholin-4-ylcarbonyl)phenyl)morpholin-2-yl]acetamide;

168: (2R)—N-(4-amidinophenyl)-2-hydroxy-2-[(2R)-3-oxo-4-(3-(dimethylaminocarbonyl)-5-fluorophenyl)morpholin-2-yl]acetamide;

169: (2R)—N-(4-amidinophenyl)-2-hydroxy-2-[(2R)-3-oxo-4-(3-(dimethylaminocarbonyl)-2-methylphenyl)morpholin-2-yl]acetamide;

170: (2R)—N-(4-amidinophenyl)-2-hydroxy-2-[(2R)-3-oxo-4-(3-(piperidin-1-ylcarbonyl)phenyl)morpholin-2-yl]acetamide;

171: (2R)—N-(4-amidinophenyl)-2-hydroxy-2-[(2R)-3-oxo-4-(3-(azetidin-1-ylcarbonyl)phenyl)morpholin-2-yl]acetamide;

172: (2R)—N-(4-amidinophenyl)-2-hydroxy-2-[(2R)-3-oxo-4-(3-((2R,5R)-(−)-trans-dimethylpyrrolidin-1-ylcarbonyl)phenyl)morpholin-2-yl]acetamide;

173: (2R)—N-(4-amidinophenyl)-2-hydroxy-2-[(2R)-3-oxo-4-(3-fluorophenyl)morpholin-2-yl]acetamide;

174: (2R)—N-(4-amidinophenyl)-2-hydroxy-2-[(2R)-3-oxo-4-(3,4,5-trifluorophenyl)morpholin-2-yl]acetamide;

175: (2R)—N-(4-amidinophenyl)-2-hydroxy-2-[(2R)-3-oxo-4-(3,4-difluorophenyl)morpholin-2-yl]acetamide;

176: (2R)—N-(4-amidinophenyl)-2-hydroxy-2-[(2R)-3-oxo-4-(2,4-difluoropyridin-3-yl)morpholin-2-yl]acetamide;

177: (2R)—N-(4-amidinophenyl)-2-hydroxy-2-[(2R)-3-oxo-4-(4,5-difluoropyridin-3-yl)morpholin-2-yl]acetamide;

178: (2R)—N-(4-amidinophenyl)-2-hydroxy-2-[(2R)-3-oxo-4-(4-carboxylphenyl)morpholin-2-yl]acetamide;

179: (2R)—N-(4-amidinophenyl)-2-hydroxy-2-[(2R)-3-oxo-4-(3-(carboxymethyl)(methyl)carbamoylphenyl) morpholin-2-yl]acetamide;

180: (2R)—N-(4-amidinophenyl)-2-hydroxy-2-[(2R)-3-oxo-4-(3-carboxylphenyl)morpholin-2-yl]acetamide;

181: (2R)—N-(4-amidinophenyl)-2-hydroxy-2-[(2R)-3-oxo-4-(4-methoxycarbonylphenyl)morpholin-2-yl]acetamide;

182: (2R)—N-(4-amidinophenyl)-2-hydroxy-2-[(2R)-3-oxo-4-(3-methoxycarbonylphenyl)morpholin-2-yl]acetamide;

183: (2R)—N-(4-amidinophenyl)-2-hydroxy-2-[(2R)-3-oxo-4-(3-carboxy-4-fluorophenyl)morpholin-2-yl]acetamide;

184: (2R)—N-(4-amidinophenyl)-2-hydroxy-2-[(2R)-3-oxo-4-(3-(methoxycarbonylmethyl)(methyl)carbamoylphenyl)morpholin-2-yl]acetamide;

185: (2R)—N-(4-amidinophenyl)-2-hydroxy-2-[(2R)-3-oxo-4-(3-carboxymethylphenyl) morpholin-2-yl]acetamide; and 186: (2R)—N-(4-amidinophenyl)-2-hydroxy-2-[(2R)-3-oxo-4-(3-carboxy-5-fluorophenyl)morpholin-2-yl]acetamide.

[7-6] In another aspect, the present invention provides a compound of the Formula (V):

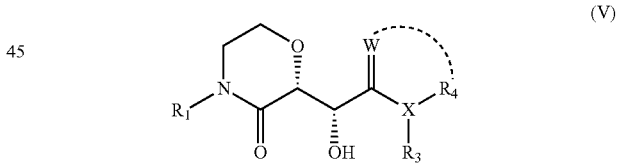

((R,R) isomer) or a pharmaceutically acceptable salt or solvate thereof, wherein $R_1$ is a group selected from the group consisting of a1 to a166 described in [7-1], and wherein formula (III) in the formula (V)

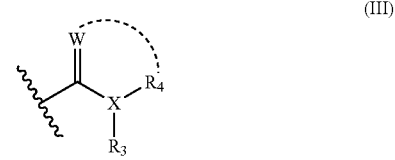

is selected from the group consisting of b1 to b61 described in [7-1].

[7-6-1] In another aspect, the present invention provides compounds of [7-6] wherein R₁ is a group selected from the group consisting of:
a1 to a33, a64 to a199,
and wherein the substructure of the Formula (V)

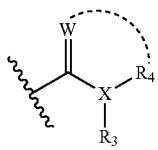

is selected from the group consisting of:
b1, b4, b49 to b67.

[8-1] In another aspect, the present invention provides (R,R) optically active isomers of compounds selected from the group consisting of compounds represented by Formula (I), Example compounds 1 to 208, Example compounds 1p to 24p, combination compounds represented by Formula (IV), or a pharmaceutically acceptable salt or a solvate thereof. Combination compounds represented by Formula (IV) are expressed as general Compound (a1, b1) (IV) to Compound (a200, b67) (IV) as total 13400 subformula. For example, Compound (a1, b1) (IV) corresponds to the structure of:

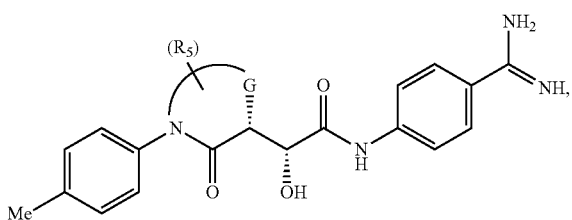

wherein n, G and R5 is the same definition as Formula (I).
Combination compounds represented by Formula (V) are expressed as Compound (a1, b1) to Compound (a200, b67) as total 13400 compounds. For example, Compound (a1, b1) corresponds to the structure of

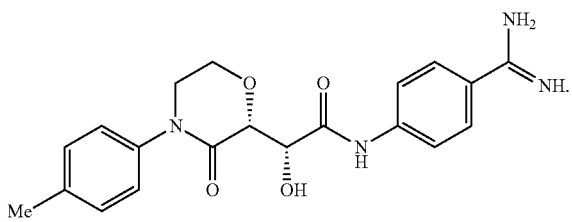 [SMILES: Cc1ccc(N2CCO[C@H]([C@@H](O)C(=O)Nc3ccc(C(=N)N)cc3)C2=O)cc1]

Methods for Making the Compounds of Present Invention
General Methods

The compounds represented by Formula (I) and salts thereof, which are the compounds of the present invention can be readily produced from known compounds or commercially available compounds by, for example, known processes described in published documents, and produced by production processes described below. The present invention is not limited to the production processes described below.

Unless otherwise noted, R1, R2, R3, R4, R5, G, W, X, m, and n in the formulae shown in the description of the production method are as defined above for the Formula (I). The alkylene group in the side chain or ring of the compound may be substituted with the substituents defined for the Formula (I). R4' and R in the formulae shown in the description of the production method are defined in the corresponding part.

Unless otherwise noted, each of $P^1$, $P^2$, $P^3$, $P^4$ or $P^5$ in the production method independently designate protecting group, and exemplary appropriate protecting groups include typical an arylmethyl group such as benzyl group, para methoxy benzyl group or triphenylmethyl group; acyl protecting groups, namely, an alkanoyl group such as acetyl group; an alkoxycarbonyl group such as methoxycarbonyl group, ethoxycarbonyl group, or t-butoxycarbonyl group; an arylmethoxycarbonyl group such as benzyloxycarbonyl group, paramethoxybenzyloxycarbonyl group, or para(ortho)nitrobenzyloxycarbonyl group; or an aroyl group such as benzoyl group. The method used for deprotecting such protecting group differs depending on the chemical nature of the protecting group employed, and in the case of an arylmethyl group such as para methoxy benzyl group or benzyl group, the deprotection can be accomplished by hydrogenation using a palladium-carbon catalyst for conversion into nitrogen-hydrogen bond, or alternatively, by Birch reduction using metal sodium in liquid ammonia, or by oxidative condition using such as CAN (ceric ammonium nitrate) or DDQ (2,3-dichloro-5,6-dicyano-p-benzoquinone). The triphenylmethyl group can be removed by using an appropriate acid such as acetic acid, hydrochloric acid, hydrobromic acid, sulfuric acid, phosphoric acid, trifluoroacetic acid, trifluoromethanesulfonic acid, or a combination thereof, or alternatively, or by Birch reduction using metal sodium in liquid ammonia.

In the case of an acyl protecting group such as an alkanoyl group, an alkoxycarbonyl group, or aroyl group, the deprotection can be accomplished by the hydrolysis using an appropriate base such as an alkaline metal hydroxide such as lithium hydroxide, sodium hydroxide, or potassium hydroxide.

The substituted methoxycarbonyl protecting group such as t-butoxycarbonyl group or paramethoxybenzyloxycarbonyl group can be removed by an appropriate acid such as acetic acid, hydrochloric acid, hydrobromic acid, sulfuric acid, phosphoric acid, trifluoroacetic acid, trifluoromethanesulfonic acid, or a combination thereof.

The arylmethoxycarbonyl group such as benzyloxycarbonyl group, paramethoxybenzyloxycarbonyl group, or para (ortho)nitrobenzyloxycarbonyl group can be removed by the hydrolysis using a palladium-carbon catalyst. The protecting groups $P^1$, $P^2$, $P^3$, $P^4$ or $P^5$ of the imino group (—NH—) can be independently or simultaneously deprotected by adequately selecting the type of the protecting group and deprotection conditions, and if desired, the protecting group can be re-introduced.

Unless otherwise noted, each of $L_1$, $L_2$, $L_3$, $L_4$, $L_5$, $L_6$, $L_7$ or $L_8$ in the production method designates a leaving group such as a halogen atom (for example, fluorine, chlorine, bromine, or iodine), methanesulfonyloxy group, or p-toluenesulfonyloxy group, or a replaceable substituent such as hydroxy group or an alkoxy group.

It should be noted that, when the derivative of the Formula (I) of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et.

al., "Protective Groups in Organic Synthesis", 2007, 4th Ed., Wiley, New York, or Kocienski, P., "Protecting Groups" 1994, Thieme. The required starting materials, such as (i-a), (i-b), (i-c), (i-d), (i-e), (i-f), (i-g), (ii-a), (iii-a), (iii-b), (v-b), (viii-a), (viii-b), (viii-c), (viii-d), (viii-e), (ix-a), (xvi-a), or (xvii-a) are either commercially available, or capable of being readily synthesized by the method commonly used in the organic chemistry from commercially available products. Unless otherwise noted, the reaction conditions employed in the production method are as described below:

Reaction temperature is in the range of −78° C. to the solvent-reflux temperature, and reaction time is the time sufficient for required progress of the reaction. Solvent which is not involved in the reaction may be any of the aromatic hydrocarbon solvents such as toluene and benzene; polar solvents such as water, methanol, DMF, and DMSO; basic solvents such as triethylamine and pyridine; halogen solvents such as chloroform, methylene chloride, and 1,2-dichloroethane; ethereal solvent such as diethylether, tetrahydrofuran, and dioxane; and mixed solvents thereof; and the solvent used may be adequately selected depending on the reaction conditions. Base may be any of inorganic bases such as potassium carbonate, cesium carbonate, sodium hydroxide, potassium hydroxide, and sodium hydride; and organic bases such as triethylamine, pyridine, N,N-dialkylaniline, lithium diisopropylamide and lithium hexamethyldisilazide; and acid may be any of mineral acids such as hydrochloric acid, and sulfuric acid; and organic acids such as methanesulfonic acid, trifluoroacetic acid and p-toluenesulfonic acid. The base and the acid are not necessarily limited to those mentioned above. The production processes will now be described in detail.

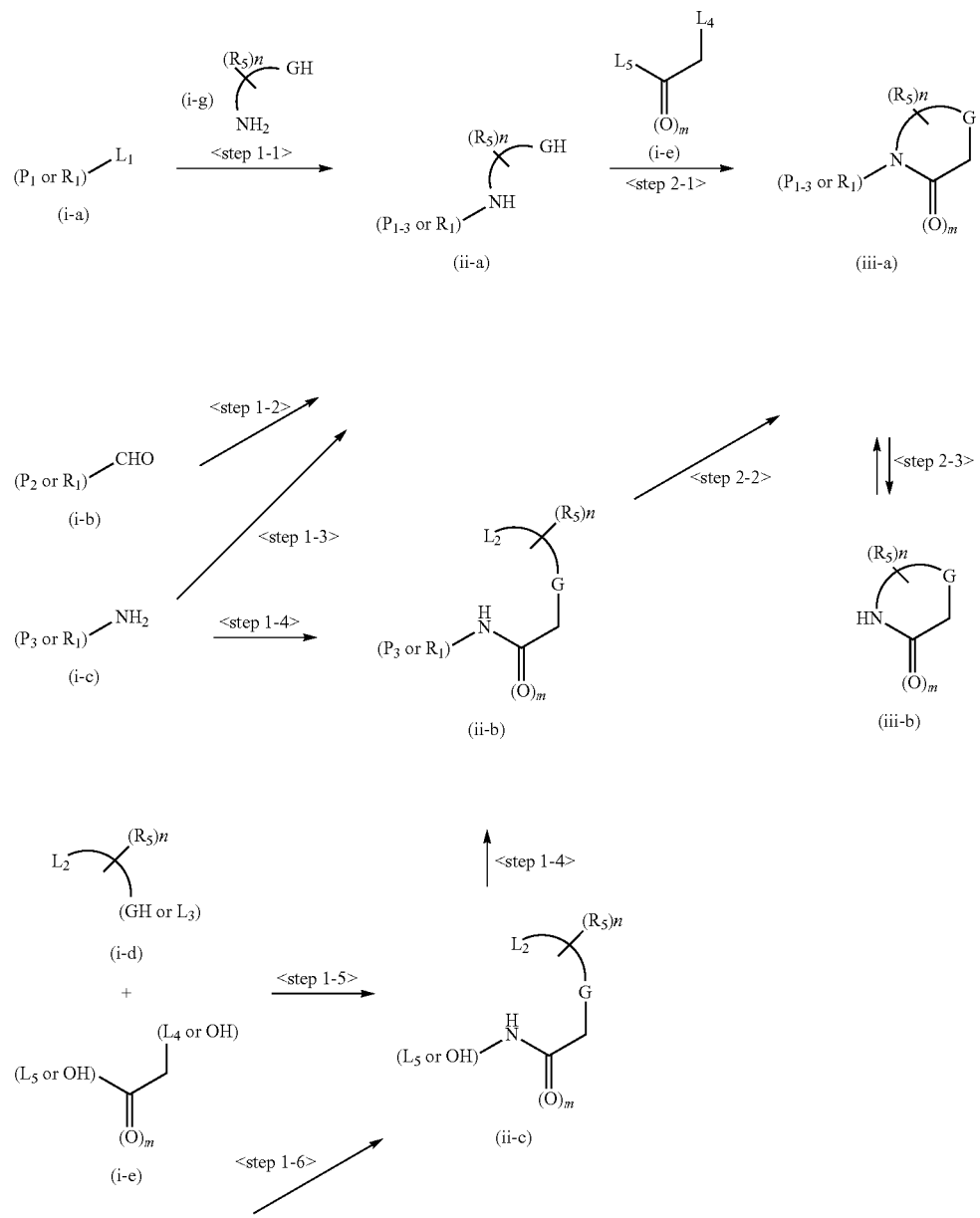

Scheme 1
Synthetic route of the key intermediate (iii-a)
(Reaction scheme 1)

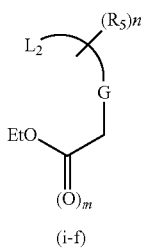

(i-f)

G represents O or S in the Scheme 1

<Step 1-1>

A compound represented by formula (ii-a) can be produced by allowing a compound represented by formula (i-a) to react with a commercially available aminoalcohol or aminothiol (i-g), readily prepared aminoalcohol or aminothiol from known compounds by a process similar to that described in published documents, for example, *Organic Synthesis, Collective Vol.* 5, pp. 88 1973, in the presence of a base such as potassium tert-buthoxide, sodium hydride, lithium hydroxide, sodium hydroxide, potassium hydroxide, lithium carbonate, sodium carbonate, or potassium carbonate using a solvent which is inactive to the reaction, such as methanol, ethanol, acetone, N,N-dimethylformamide, dioxane or tetrahydrofuran, or a mixed solvent thereof at a temperature in the range of room temperature to the solvent-reflux temperature.

<Step 1-2>

Alternatively, a compound represented by formula (ii-a) can be produced by conducting a reaction using a compound represented by formula (i-b) by a process of reductive amination. After a compound represented by formula (i-b) is converted to an imine with a suitable aminoalcohol (i-g), an aminothiol (i-g) using a solvent which is inactive to the reaction, such as a halogenated solvent, e.g., dichloromethane or chloroform, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature, a compound represented by formula (ii-a) can be produced by a process similar to that described in published documents, for example, Journal of Medical Chemistry, 23(12), pp. 1405-1410, 1980 in the presence of a reductive reagent such as sodium borohydride using a solvent which is inactive to the reaction, such as an alcoholic solvent, e.g., methanol, ethanol, 2-propanol, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature.

Alternatively, hydrogen gas can be used to an imine with a suitable process similar to that described in published documents, for example, Jikken Kagaku Koza (Experimental Chemistry Series), 4th edition, 26, Organic synthesis VIII, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide ($PtO_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid at a temperature in the range of room temperature to the solvent-reflux temperature, thereby producing a compound represented by formula (ii-a).

<Step 1-3>

Alternatively, a compound represented by formula (ii-a) can be produced by conducting a reaction using a compound represented by formula (i-c) by a process similar to that of <step 1-1> with a suitable alcohol or thiol in the presence of copper iodide and cesium carbonate using a solvent which is inactive to the reaction, such as acetonitrile.

Step <1-4>

A compound represented by formula (ii-b) can be produced by conducting a reaction using a compound represented by formula (ii-c) and a compound represented by formula (i-c) (for example, a known amine) as follows. When a compound represented by formula (ii-c) is a carboxylic acid, a compound represented by formula (ii-b) can be produced by allowing a compound represented by formula (ii-c) to react with a compound represented by formula (i-c) by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl) carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (ii-c) is an acid halide, a compound represented by formula (ii-b) can be similarly produced by conducting a reaction with a compound represented by formula (i-c) by a process similar to that described in, for example, Jikken Kagaku Koza (Experimental Chemistry Series), 4th edition, 22, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

Step <1-5>

A compound represented by formula (ii-c) can be produced by the same process as that used in <Step 1-1> of (Reaction Scheme 1) using a compound represented by formula (i-d) and compound represented by formula (i-e).

Step <1-6>

A compound represented by formula (ii-c) can be produced from a compound represented by formula (i-f) by a process similar to that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of a base such as lithium hydroxide, sodium hydroxide, potassium hydroxide, lithium carbonate, sodium carbonate, or potassium carbonate using water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

Step <2-1>

A compound represented by formula (iii-a) can be produced by a process similar to that described in published documents, for example, *Zhurnal Organicheskoi Khimii*, (6), 1305-8, 1970, or by a similar process as that used in <Step 1-4> and <step 1-5> of (Reaction Scheme 1) using a compound represented by formula (i-e) as an acid halide, and compound represented by formula (ii-a) as a suitable aminoalcohol or aminothiol. When aminothiol (ii-a) was used, cyclization process of producing a compound represented by formula (iii-a) can be also conducted step by step process using different base or different solvent system.

Step <2-2>

Alternatively, a compound represented by formula (iii-a) can be produced by the same process as that used in <Step 2-1> of (Reaction Scheme 1) using a compound represented by formula (ii-b).

Step <2-3>

Protective groups of a compound represented by formula (iii-a) can be introduced and removed between (iii-a) and (iii-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Scheme 2
Synthetic route of Example compounds and combination compounds.
(Reaction scheme 2)

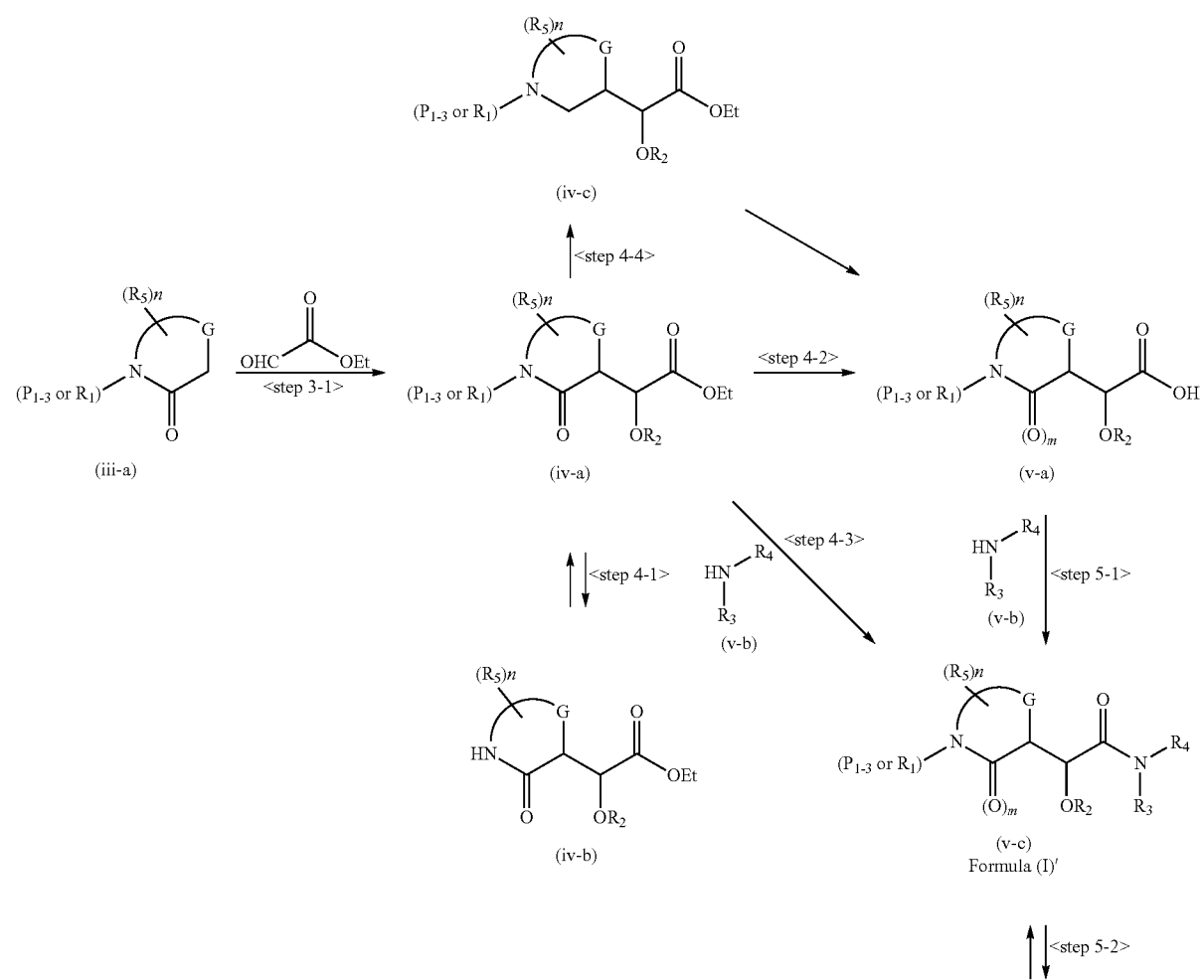

-continued

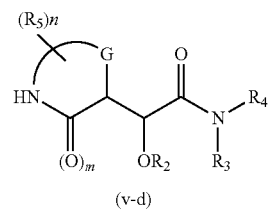

(v-d)

G represents O, S, NH, or CH$_2$ in the Scheme 2

Step <3-1>

A compound represented by formula (iv-a) can be produced by allowing a compound represented by formula (iii-a) or (iii-b), which was produced in the Reaction scheme 1 or commercially available, to react with alkyl glyoxylate, such as ethyl glyoxylate by a process similar to that described in published documents, for example, *Journal of Medicinal Chemistry,* 31(1), pp. 230-243, 1988, in the presence of a base such as lithium hexamethyldisilazide, sodium hydride, lithium hydroxide, sodium hydroxide, potassium hydroxide, lithium carbonate, sodium carbonate, or potassium carbonate using a solvent which is inactive to the reaction, such as tetrahydrofuran, N,N-dimethylformamide, dioxane, or a mixed solvent thereof at a temperature in the range of room temperature to the solvent-reflux temperature. The resulting alcoholic compound (iv-a) wherein R2 represents hydrogen can be protected in any step described hereafter by techniques which are well-known or described here (see Greene, T. W., et. al., *Protective Groups in Organic Synthesis* (2007), 4th Ed., Wiley, New York, or Kocienski, P., *Protecting Groups* (1994), Thieme), to be, for example, alkoxy groups or ester groups.

Step <4-1>

Protective groups of a compound represented by formula (iv-a) can be introduced and removed between (iv-a) and (iv-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <4-2>

A compound represented by formula (v-a) can be produced by the same process as that used in <Step 1-6> of (Reaction Scheme 1) using a compound represented by formula (iv-a) or (iv-c).

Step <4-3>

A compound represented by formula (v-c) can be produced by allowing a compound represented by formula (iv-a) to react with a compound represented by formula (v-b) by a process similar to that described in published documents, for example, Organic synthesis IV, Acids, amino acids, and peptides, pp. 191-309, 1992, Maruzen Co., Ltd., in the presence of a condensing agent, in a solvent which is inactive to the reaction, such as an alcoholic solvent, e.g., methanol, ethanol, or 2-propanol, in the presence or absence of a base such as triethylamine or pyridine at a temperature in the range of 0° C. to the solvent-reflux temperature.

Step <4-4>

A compound represented by formula (iv-c) can be produced by a process similar to that described in published documents, for example, Organic synthesis, Collective Vol. 7, pp. 221, 1990, Organic synthesis, Collective Vol. 7, pp. 530, 1990, *Jikken Kagaku Koza (Experimental Chemistry Series),* *4th edition,* 26, Reduction by borane, hydrazine or diimide pp 237-248, using a compound represented by formula (iv-a) in the presence of borane-THF complex, borane-diethyl ether complex, borane-dimethyl sulfide complex, hydradine or hydroxylamine using a solvent such as an ethereal solvent, e.g., diethyl ether or tetrahydrofuran at a temperature in the range of −78° C. to the solvent-reflux temperature.

Step <5-1>

A compound represented by formula (v-c) can be produced by allowing a compound represented by formula (v-a) to react with a compound represented by formula (v-b) by a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (v-a) is converted to an acid halide, a compound represented by formula (v-c) can be similarly produced by conducting a reaction by a process similar to that described in, for example, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

Alternatively, a compound represented by formula (v-c) can be produced by using triphosgene by a process similar to that described in published documents, for example, *Letters in Organic Chemistry,* 4, 20-22, 2007, in the presence of a base such as triethyl amine using a solvent which is inactive to the reaction, such as tetrahydrofuran, N,N-dimethylformamide, dioxane, CH2Cl2 or a mixed solvent thereof at a temperature in the range of room temperature to the solvent-reflux temperature.

Step <5-2>

Protective groups of a compound represented by formula (v-c) can be introduced and removed between (v-c) and (v-d) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

3-1> of (Reaction Scheme 2) using a compound represented by formula (iii-a) and a compound represented by formula (vi-b).

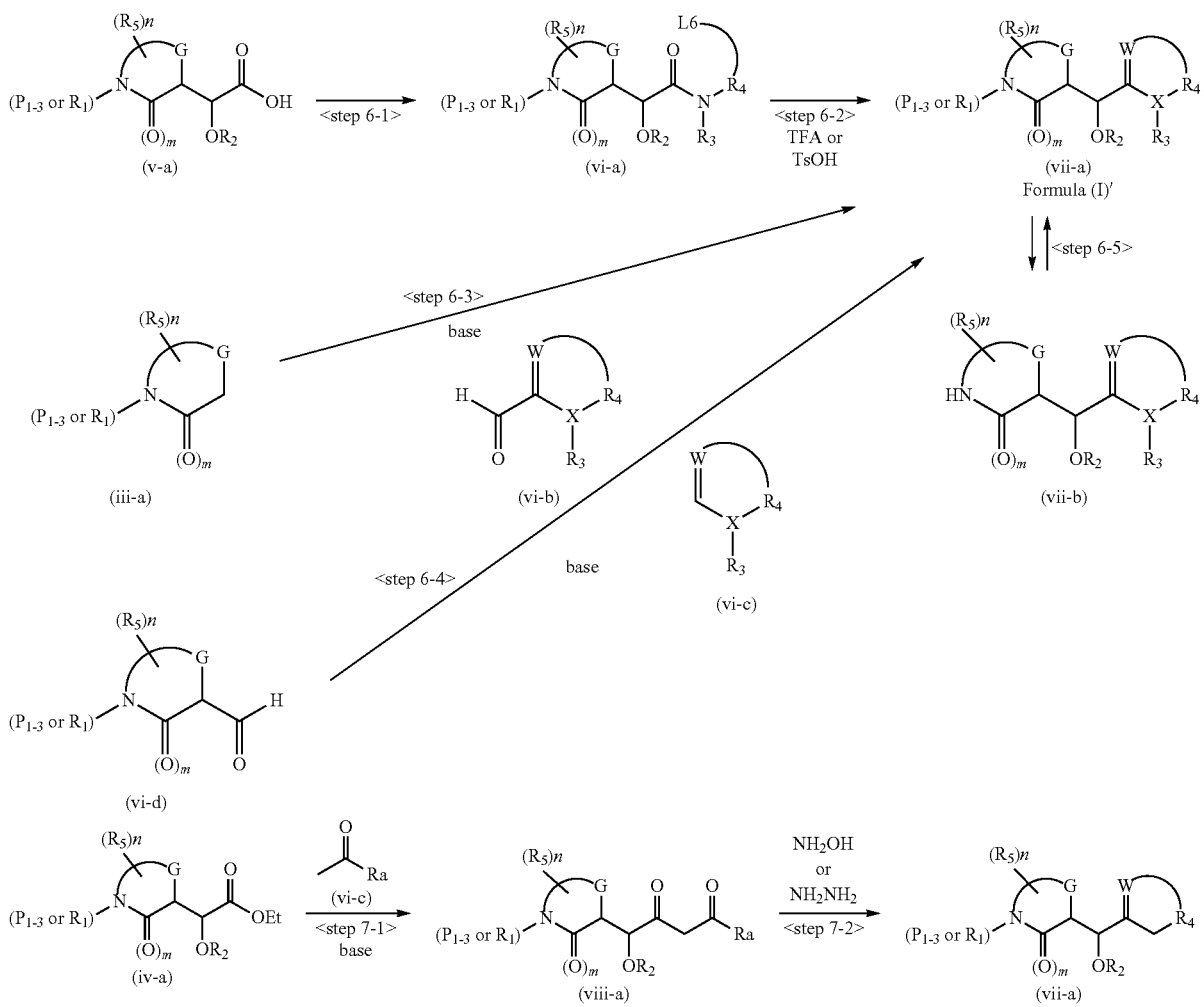

G represents O, S, NH, or $CH_2$ in the Scheme 3

Step <6-1>

A compound represented by formula (vi-d) can be produced by the similar process as that used in <Step 5-1> of (Reaction Scheme 2) using a compound represented by formula (v-a).

Step <6-2>

A compound represented by formula (vii-a) can be produced by allowing a compound represented by formula (vi-a) to react with by a process similar to that described in published documents, for example, *Synthetic Communications*, 37(24), 2007, in the presence of an acid such as acetic acid, trifluoroacetic acid or p-toluenesulfonic acid using a solvent such as acetic acid, trifluoroacetic acid, or a mixed solvent thereof at a temperature in the range of room temperature to the solvent-reflux temperature.

Step <6-3>

Alternately, a compound represented by formula (vii-a) can be produced by the similar process as that used in <Step Step <6-4>

Alternatively, a compound represented by formula (vii-a) can be produced by a process similar to that described in published documents, for example, *Bioorganic & Medicinal Chemistry Letters*, 17(14), 2007, 3860 using a compound represented by formula (vi-d) and a compound represented by formula (vi-c), wherein Ra represents a suitable substituent.

Step <6-5>

Protective groups of a compound represented by formula (vi-a) can be introduced and removed between (vii-a) and (vii-b) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <7-1>

A compound represented by formula (viii-a) can be produced by allowing a compound represented by formula (Iv-a)

to react with by a process similar to that described in published documents, for example, Organic synthesis, Collective Vol 1, pp. 238, 1941, Maruzen Co., Ltd, in the presence of a base such as sodium ethoxide using a solvent such as ethanol at a temperature in the range of room temperature to the solvent-reflux temperature.

Ra of the formula (vi-c) represents a suitable substituent or leaving group of L1 to L4 described above.

Step <7-2>

A compound represented by formula (vii-a) can be produced by a process similar to that described in published documents, for example, *Journal of Medicinal Chemistry*, 48, 14, pp 4541, 2005, using a compound represented by formula (viii-a) in the presence of hydradine or hydroxylamine using a solvent such as ethanol at a temperature in the range of room temperature to the solvent-reflux temperature.

Furthermore, in the case of some of the compounds according to the invention the possibility arises of employing diastereomerically or enantiomerically pure starting products for the preparation of the ring structures. By this means, other or simplified processes can be employed for the purification of the final products. These starting products were prepared beforehand in enantiomerically or diastereomerically pure form according to processes known from the literature. This can mean, in particular, that in the synthesis of the scaffold structures either enantioselective processes are used, or else an enantiomeric (or diastereomeric) separation is carried out at an earlier stage of the synthesis and not only at the stage of the final products. Likewise, a simplification of the separations can be achieved by proceeding in two or more stages.

atmosphere, using a solvent which is inactive to the reaction, such as an alcoholic solvent, e.g., methanol, ethanol, or 2-propanol, an ethereal solvent, e.g., diethyl ether or tetrahydrofuran, 1,2-dimethoxyethane, or 1,4-dioxane, a polar solvent, e.g., ethyl acetate or methyl acetate, or a mixed solvent thereof at a temperature in the range of room temperature to the solvent-reflux temperature.

Alternatively, a compound represented by formula (viii-b) can be produced from (viii-a) by using Fe, or Sn, in hydrochloric acid or acetic acid, at a temperature in the range of 0° C. to the solvent-reflux temperature. Furthermore, a compound represented by formula (viii-b) can also be produced from (viii-a) by using sodium borohydride in the presence of Lewis Acid, e.g., Nickel(II)chloride ($NiCl_2$), Tin(II)chloride ($SnCl_2$) using a solvent which is inactive to the reaction, such as an alcoholic solvent, e.g., methanol, ethanol, or 2-propanol, an ethereal solvent, e.g., diethyl ether or tetrahydrofuran, 1,2-dimethoxyethane, or 1,4-dioxane, or a mixed solvent thereof at a temperature in the range of 0° C. to the solvent-reflux temperature.

Step <8-2>

A compound represented by formula (viii-d) can be produced by conducting a reaction using a compound represented by formula (viii-b) by a process of reductive amination. After a compound represented by formula (viii-c) is converted to an imine with a suitable amine (viii-b) using a solvent which is inactive to the reaction, such as an alcoholic solvent, e.g., methanol, ethanol, or 2-propanol, such as a halogenated solvent, e.g., dichloromethane or chloroform, an ethereal solvent, e.g., diethyl ether, tetrahydrofuran, 1,2-

Scheme 4
Synthetic route of intermediate compounds (viii-d)
(Reaction scheme 4)

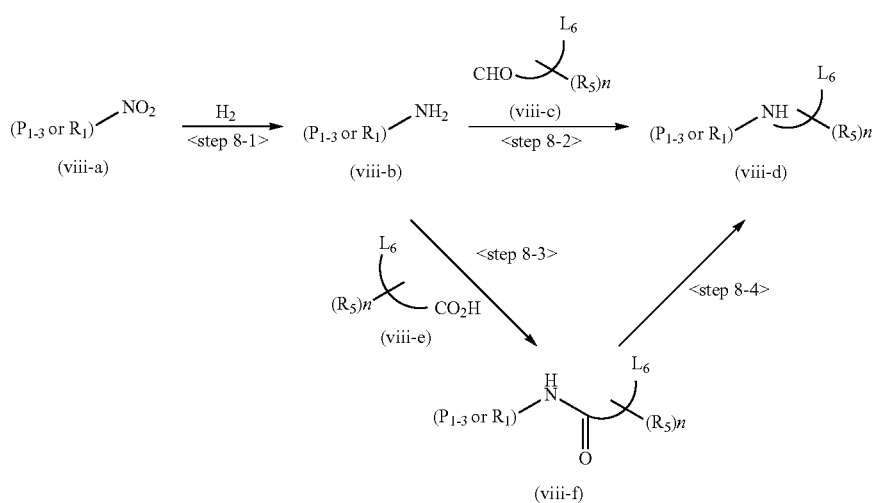

Step <8-1>

A compound represented by formula (viii-b) can be produced from (viii-a) by conducting a reaction using the compound represented by formula (viii-a) by a process similar to that described in published documents, for example, Jikken Kagaku Koza (Experimental Chemistry Series), 4th edition, 26, *Organic synthesis VIII*, Asymmetric synthesis, reduction, sugar, and labeled compound, pp. 159-266, 1992, Maruzen Co., Ltd., in the presence of a catalyst such as palladium-carbon (Pd—C), Raney-Ni, platinum oxide (PtO2), or dichloro triphenyl phosphine ruthenium, under hydrogen dimethoxyethane, 1,4-dioxane, or an aromatic hydrocarbon solvent, e.g., toluene or benzene or a mixed solvent thereof at a temperature in the range of 0° C. to the solvent-reflux temperature, a compound represented by formula (viii-d) can be produced by a process similar to that described in published documents, for example, *Journal of Medical Chemistry*, 23(12), pp. 1405-1410, 1980 in the presence of a reductive reagent such as sodium borohydride or sodium triacetoxy borohydride in the presence of acid such as acetyl alcohol, using a solvent which is inactive to the reaction, such as an alcoholic solvent, e.g., methanol, ethanol, 2-propanol, an ethereal solvent, e.g., diethyl ether, tetrahydrofuran, 1,2-dimethoxyethane, 1,4-dioxane, or an aromatic hydrocarbon solvent, e.g., toluene or benzene or a mixed solvent thereof at a temperature in the range of 0° C. to the solvent-reflux temperature.

Alternatively, hydrogen gas can be used to hydrogenate an imine with a suitable process similar to that described in published documents, for example, *Jikken Kagaku Koza* (*Experimental Chemistry Series*), 4th edition, 26, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide ($PtO_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid at a temperature in the range of room temperature to the solvent-reflux temperature, thereby producing a compound represented by formula (viii-d).

Step <8-3>

A compound represented by formula (viii-f) can be produced by the similar process as that used in <Step 5-1> of (Reaction Scheme 2) using a compound represented by formula (viii-e).

Step <8-4>

A compound represented by formula (viii-d) can be produced by a process similar to that described in published documents, for example, *Jikken Kagaku Koza* (*Experimental Chemistry Series*), 4th edition, 26, Reduction by borane, hydrazine or diimide pp 237-248, using a compound represented by formula (viii-f) in the presence of hydradine or hydroxylamine using a solvent such as ethanol at a temperature in the range of room temperature to the solvent-reflux temperature.

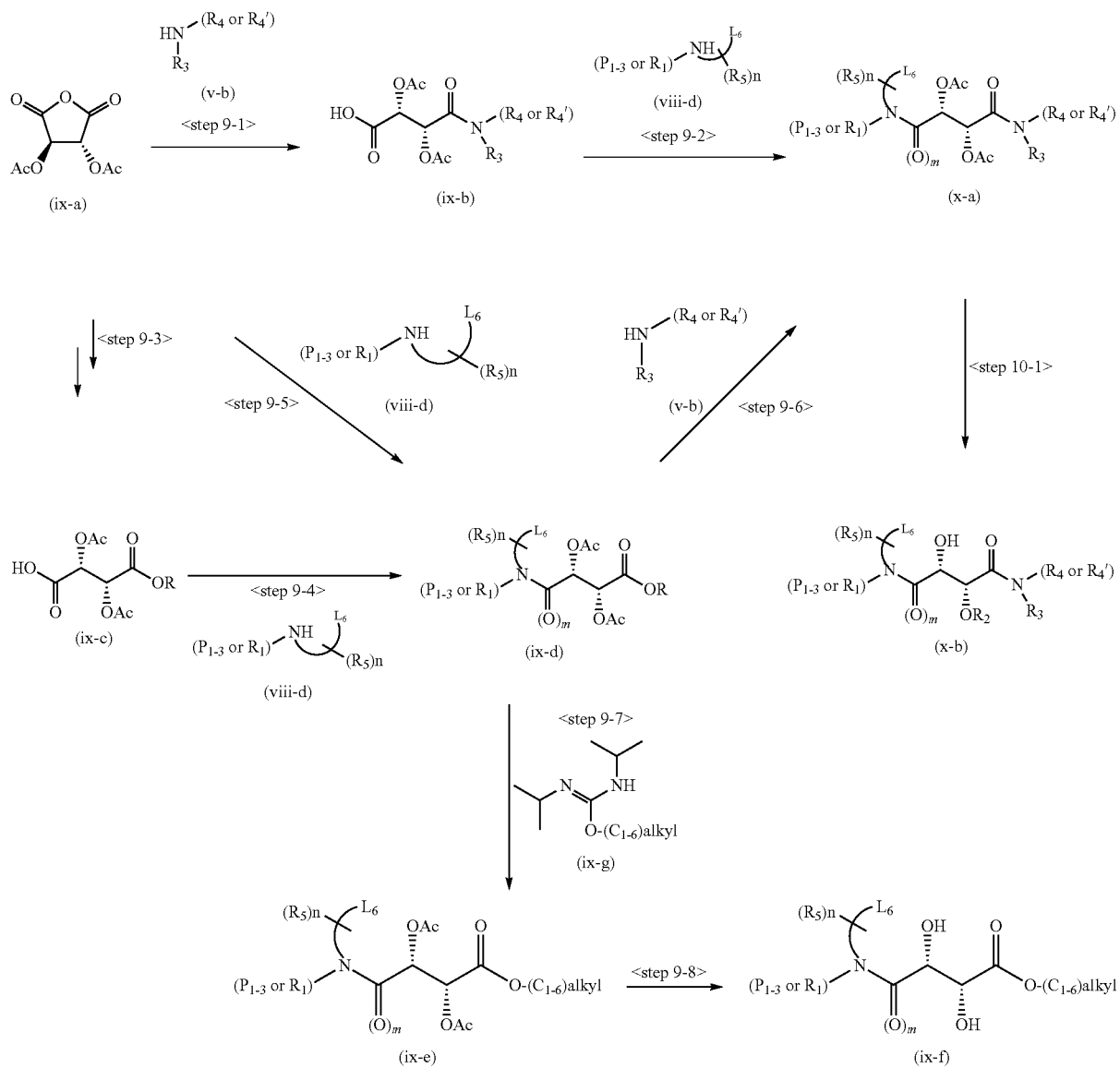

Scheme 5 Synthetic route of optically active compounds (x-b) (Reaction scheme 5)

Step <9-1>

A compound represented by formula (ix-b) can be produced by conducting a reaction using (2R,3R)-2,3-diacetoxysuccinic anhydride represented by formula (ix-a) in the presence of amine (v-b) by a process similar to that described in published documents, for example, *Organic Synthesis, Collective Vol.* 3, pp. 169 1955, using a solvent which is inactive to the reaction, such as tetrahydrofuran, N, N-dimethylformamide, dioxane, CH2Cl2 or a mixed solvent thereof at a temperature in the range of room temperature to the solvent-reflux temperature.

Step <9-2>

A compound represented by formula (x-a) can be produced by allowing a compound represented by formula (ix-b) to react with a compound represented by formula (viii-d) by a process similar to that described in published documents, for example, *Jikken Kagaku Koza (Experimental Chemistry Series)*, 4th edition, 26, Acids, amino acids, and peptides, pp. 193-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of −78° C. to the solvent-reflux temperature. When a compound represented by formula (ix-b) is converted to an acid halide, a compound represented by formula (x-a) can be similarly produced by conducting a reaction by a process similar to that described in, for example, *Jikken Kagaku Koza (Experimental Chemistry Series)*, 4th edition, 26, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of −78° C. to the solvent-reflux temperature.

Alternatively, a compound represented by formula (x-a) can be produced by using triphosgene with (ix-b) by a process similar to that described in published documents, for example, *Letters in Organic Chemistry*, 4, 20-22, 2007, in the presence of a base such as triethyl amine using a solvent which is inactive to the reaction, such as tetrahydrofuran, N,N-dimethylformamide, dioxane, CH2Cl2 or a mixed solvent thereof at a temperature in the range of room temperature to the solvent-reflux temperature.

Step <9-3>

A compound represented by formula (ix-c), wherein R represents hydrogen or C1-6 alkyl group, can be produced by conducting a reaction using (2R,3R)-2,3-diacetoxysuccinic anhydride represented by formula (ix-a) in the presence of suitable alcoholic solvent by a process similar to that described in published documents, for example, *Organic Synthesis, Collective Vol.* 3, pp 169 1955, using a solvent, such as an alcoholic solvent, e.g., benzyl alcohol, tert-butyl alcohol, methanol, ethanol, 2-propanol, or tetrahydrofuran, N,N-dimethylformamide, dioxane, $CH_2Cl_2$ or a mixed solvent thereof in the presence of DMAP at a temperature in the range of 0° C. to the solvent-reflux temperature.

Step <9-4>

A compound represented by formula (ix-d) can be produced by the same process as that used in <Step 9-2> of (Reaction Scheme 5) using a compound represented by formula (ix-c).

Step <9-5>

A compound represented by formula (ix-d) wherein R represents hydrogen atom can be produced by allowing (2R, 3R)-2,3-diacetoxysuccinic anhydride represented by formula (ix-a) to react with a compound represented by formula (viii-d) by a process similar to that described in published documents, for example, *Organic Synthesis, Collective Vol.* 3, pp. 169 1955, *Organic Synthesis, Collective Vol.* 5, pp. 944, 1973, Vol. 41, 93, 1961, or *Jikken Kagaku Koza (Experimental Chemistry Series)*, 4th edition, 26, Acids, amino acids, and peptides, pp. 146-148, 1992, Maruzen Co., Ltd., using a solvent, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., DMF, ethyl acetate or acetonitrile, an aromatic hydrocarbon solvent, e.g., toluene or benzene, or an acid solvent, e.g., acetic acid or a mixed solvent thereof in the presence of DMAP, Pyridine or sulfuric acid as a catalyst if needed at a temperature in the range of 0° C. to the solvent-reflux temperature.

Step <9-6>

A compound represented by formula (x-a) can also be produced by the same process as that used in <Step 4-3> of (Reaction Scheme 2) using a compound represented by formula (ix-d) wherein R represents C1-6 alkyl group in the presence of amine (v-b), and also be produced by the same process as that used in <step 5-1> of (Reaction scheme 2) or <step 13-3> and <step 13-4> of (Reaction scheme 11) using a compound represented by formula (ix-d) wherein R represents hydrogen atom, in the presence of amine (v-b).

Protective groups of a compound in the process of producing a compound represented by formula (x-a) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <9-7>

A compound represented by formula (ix-e) can be produced by allowing a compound represented by formula (ix-d) to react with a compound represented by formula (ix-g) by a process similar to that described in published documents, for example, Jikken Kagaku Kozo (Experimental Chemistry Series), 4th edition, 22, Organic synthesis IV, Acids, amino acids, and peptides, pp. 1-82, 1992, Maruzen Co., Ltd., in the presence of an acidic reagent such as hydrochloric acid, sulfuric acid, thionyl chloride, or acetyl chloride, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

Step <9-8>

A compound represented by formula (ix-d) can be produced by conducting a reaction using a compound represented by formula (ix-e) by a process similar to that described in published documents, for example, *Can. J. Chem.,* 49, 493 (1971) or Greene, T. W., et. al., *Protective Groups in Organic Synthesis* (2007), 4th Ed., in the presence of ammonia, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

Step <10-1>

A compound represented by formula (x-b) can be produced by the similar process as that used in <Step 9-8> of (Reaction Scheme 6) using a compound represented by formula (x-a).

Protective groups of a compound in the process of producing a compound represented by formula (x-b) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Scheme 6
Synthetic route of optically active compounds (x-c) and (x-e)
(Reaction scheme 6)

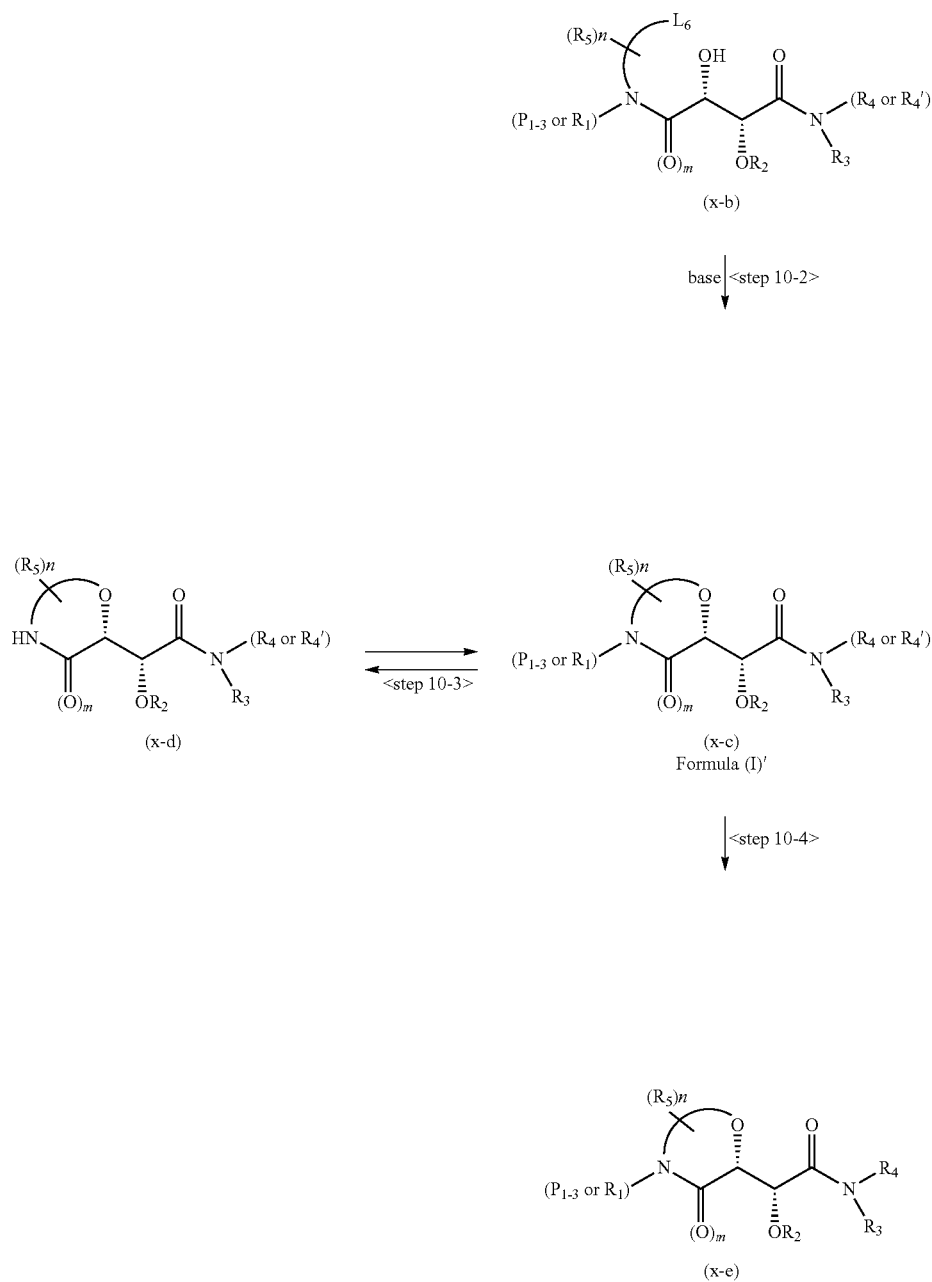

Step <10-2>

A compound represented by formula (x-c) can be produced by allowing a compound represented by formula (x-b) by a process similar to that described in published documents, for example, *Organic Synthesis, Collective Vol.* 6, pp. 301, 395, 1988, or *Jikken Kagaku Koza (Experimental Chemistry Series)*, 4th edition, 20, alcohol and amine, pp. 187-194, 1992, Maruzen Co., Ltd., in the presence of a base such as potassium tert-buthoxide, sodium hydride, lithium hydroxide, sodium hydroxide, potassium hydroxide, lithium carbonate, sodium carbonate, or potassium carbonate using a solvent which is inactive to the reaction, such as an alcoholic solvent, e.g., methanol, ethanol, or 2-propanol, tert-buthanol, or a polar solvent, e.g., DMF, DMSO, ethyl acetate, or acetonitril, or an aromatic hydrocarbon solvent, e.g., toluene or benzene, or acetone, dioxane or tetrahydrofuran, or a mixed solvent thereof at a temperature in the range of 0° C. to the solvent-reflux temperature.

Step <10-3>

Protective groups of a compound represented by formula (x-c) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <10-4>

When R4' is used as a precursor for R4 representing 4-amidino-phenyl group or its analogue, R4' represents 4-cyano-phenyl group or 1,2,4-oxadiazol-5-one-3-yl phenyl group or their analogues, which can be converted to 4-amidino-phenyl group R4 or its analogue by techniques which are well-known or described:

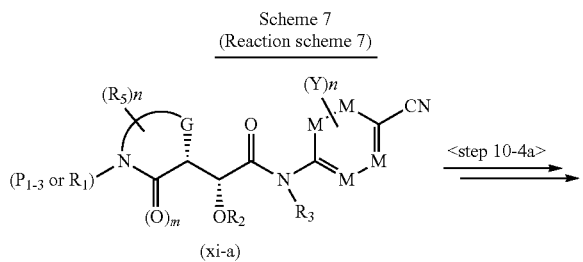

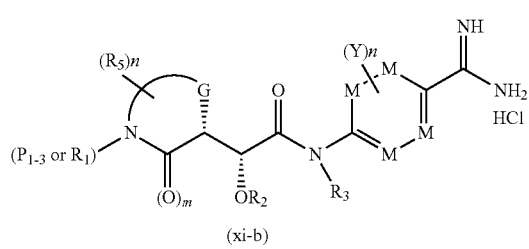

G represents O, S, NH, or CH$_2$, and M represents independently CH or N, and n represents 1 to 4 in the Scheme 7

Step <10-4a>

When R4' of a compound represented by formula (x-c) of Scheme 6 represents 4-cyano-(aryl or heteroaryl) group or its analogue wherein 4-cyano-(aryl or heteroaryl) ring is optionally substituted with one to four Y, a compound represented by formula (xi-a) which corresponds to a compound (x-c) can be converted to a compound represented by formula (xi-b) via its imidate compound.

4-cyano-(aryl or heteroaryl) group or, R4' of a compound represented by formula (xi-a), can be converted to its imidate by allowing a compound represented by formula (xi-a) to acidic condition such as HCl gas solution of, such as an alcoholic solvent, e.g., methanol, ethanol, or 2-propanol, a halogenated solvent, e.g., dichloromethane or chloroform, or a mixed solvent thereof at a temperature in the range of 0° C. to the room temperature.

Resulting imidate compound is converted to 4-amidino-(aryl or heteroaryl) compound (xi-b) or its analogue by conducting an imidate compound to ammonium or ammonium carbonate alcoholic solvent, e.g. methanol, ethanol, tert-buthanol or in a mixed solvent thereof at a temperature in the range of 0° C. to the solvent-reflux temperature in a sealed tube.

Alternatively, when R4' represents 4-cyano-(aryl or heteroaryl) group or its analogue wherein 4-cyano-(aryl or heteroaryl) is optionally substituted with one to four Y, a compound represented by formula (xi-a) can be converted to 4-amidino-(aryl or heteroaryl) group R4 via its N-hydroxy amidine compound.

4-cyano group, R4' of a compound represented by formula (xi-a), can be converted to its N-hydroxy amidino group by allowing a compound (xi-a) in the presence of a base such as triethyl amine, hunig base, potassium tert-buthoxide, sodium hydride, lithium hydroxide, sodium hydroxide, potassium hydroxide, lithium carbonate, sodium carbonate, or potassium carbonate using a solvent which is inactive to the reaction, such as water, methanol, ethanol, acetone, N,N-dimethylformamide, dioxane or tetrahydrofuran, or a mixed solvent thereof at a temperature in the range of 0° C. to the solvent-reflux temperature in a sealed tube.

Resulting N-hydroxy amidino group can be converted to its amidine compound represented by formula (xi-b) by a suitable process similar to that described in published documents, for example, Jikken Kagaku Koza (Experimental Chemistry Series), 4th edition, 26, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide (PtO$_2$) in a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid or a mixed solvent thereof at a temperature in the range of room temperature to the solvent-reflux temperature.

Scheme 8
(Reaction scheme 8)

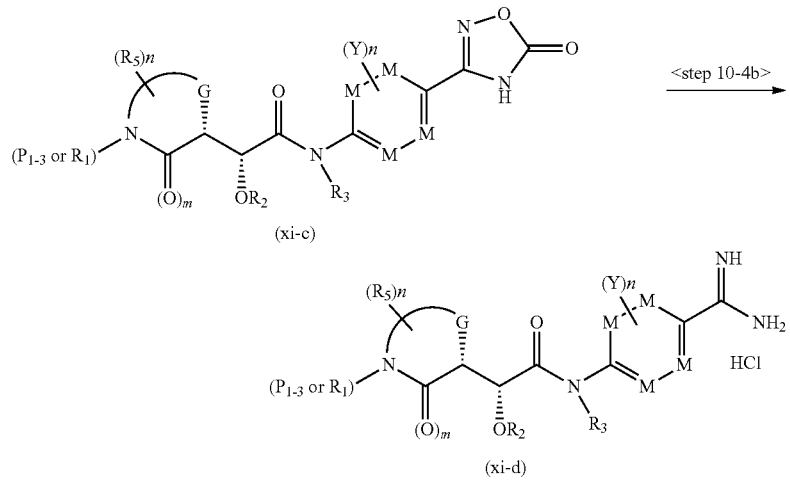

G represents O, S, NH, or CH₂, and M represents independently CH or N, and n represents 1 to 4 in the Scheme 8

Step <10-4b>

When R4' is used as a precursor for R4 representing 4-amidino-(aryl or heteroaryl) group or its analogue wherein 4-amidino-(aryl or heteroaryl) group is optionally substituted with one to four Y, R4' also represents 1,2,4-oxadiazol-5-one-3-yl (aryl or heteroaryl) group or its analogues wherein phenyl group is optionally substituted with one to four Y, which can be converted to 4-amidino-(aryl or heteroaryl) group R4 by techniques which are well-known or described here.

A compound represented by formula (xi-d) can be produced by the same process as that used in <Step 8-1> of (Reaction Scheme 4) using a compound represented by formula (xi-c).

When G in the formula (xi-c) represents sulfur atom, sulfur can be oxidized to its sulfone or sulfoxide with Oxone® by a process similar to that described in published documents, for example, Shin-Jikken Kagaku Kouza, Vol. 14-III, p 1759, R. J. Kennedy, *J. Org. Chem.*, 25, 1901 (1960), B. M. Trost, *Tetrahedron Lett.*, 22, 1287 (1981), in the presence of Oxone® using a solvent which is inactive to the reaction, such as water, or an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of 0° C. to the solvent-reflux temperature.

Scheme 9
(Reaction scheme 9)

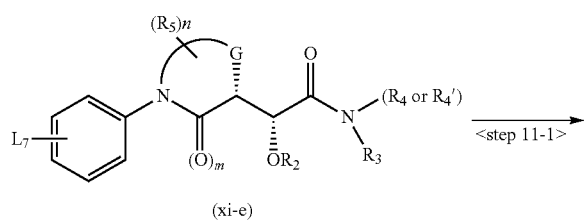

-continued

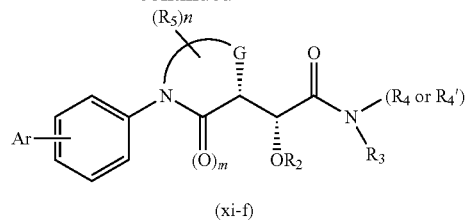

G represents O, S, NH, or CH₂ in the Scheme 9

Step <11-1>

When R1 in the Formula (I) represents biaryl groups optionally substituted with one to four Y, such as, for example, 4-thienyl phenyl group or 4-phenyl phenyl group, a compound represented by formula (xi-f) can be produced by conducting a reaction using a compound represented by formula (xi-e) by a process of Suzuki-Miyaura coupling similar to that described in published documents, for example, Miyaura, N, et. al., *Tetrahedron Lett.*, 1979, 3437, 1 *Chem. Soc. Chem. Commun.*, 1979, 866, *Chem. Rev.* 1995, 95, 2457, in the presence of catalyst such as palladium-carbon (Pd—C), Raney-Ni, or platinum oxide (PtO₂), and in the presence of a base such as potassium tert-buthoxide, sodium hydride, lithium hydroxide, sodium hydroxide, potassium hydroxide, lithium carbonate, sodium carbonate, or potassium carbonate with a corresponding arylboronic acid using a solvent which is inactive to the reaction, such as water, acetone, toluene, dioxane or tetrahydrofuran, or a mixed solvent thereof at a temperature in the range of room temperature to the solvent-reflux temperature.

Scheme 10
(Reaction scheme 10)

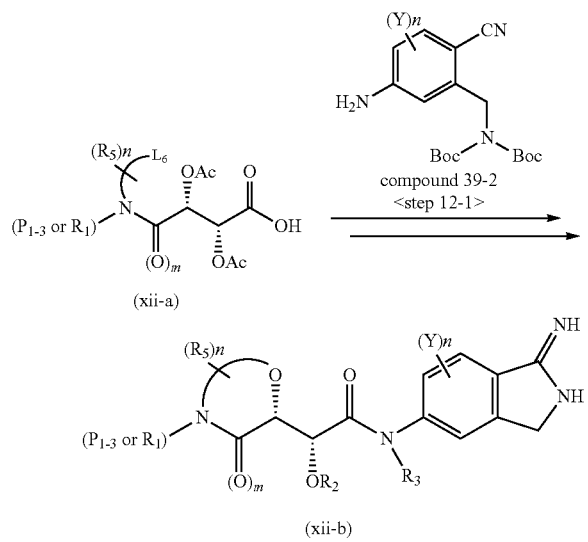

Step <12-1>

When R4 represents 1-imino-2,3-dihydroisoindol-5-yl group, or its heteroaryl analogue wherein M represents nitrogen atom, are optionally substituted with one to four Y, which is shown as a partial structure of a compound represented by formula (xii-b) in Scheme 10 or its analogue, a compound represented by formula (xii-b) can be produced from a compound represented by formula (xii-a) which is identical to the compound represented by formula (ix-d) in the Scheme 5, wherein its R is hydrogen atom, and from a compound 39-2 (N-[(5-Amino-2-cyanophenyl)-methyl]-N-[(2-methylpropan-2-yl)oxycarbonyl]carbamate) which is described in Experimental section 39. A compound represented by formula (ix-d) is converted to its analogous compound of 39-3 in the Example 39 procedure similar to that used in <Step 5-1> of (Reaction Scheme 2), which is followed by the conversion to compounds analogous to compounds 39-4, 39-5 and 39-6 by a process similar to that used in <Step 10-1> of (Reaction Scheme 5), <Step 10-2> of (Reaction Scheme 6) and deprotection of Boc group by a process similar to that used in the Experimental section Example 38-6 or by techniques which are well-known or described here (see Greene, T. W., et. al., *Protective Groups in Organic Synthesis* (2007), 4th Ed., Wiley, New York, or Kocienski, P., *Protecting Groups* (1994), Thieme). A compound represented by formula (xii-b) can be produced with resulting amine compound analogous to the compound 39-6 by a process similar to that described in the Experimental section 39 [step 39-7] using alcoholic solvent, other solvent or a mixed solvent thereof at a temperature in the range of room temperature to the solvent-reflux temperature.

Scheme 11 Alternative synthetic route of optically active compounds (xiii-f) subset of compounds (x-e)
(Reaction scheme 11)

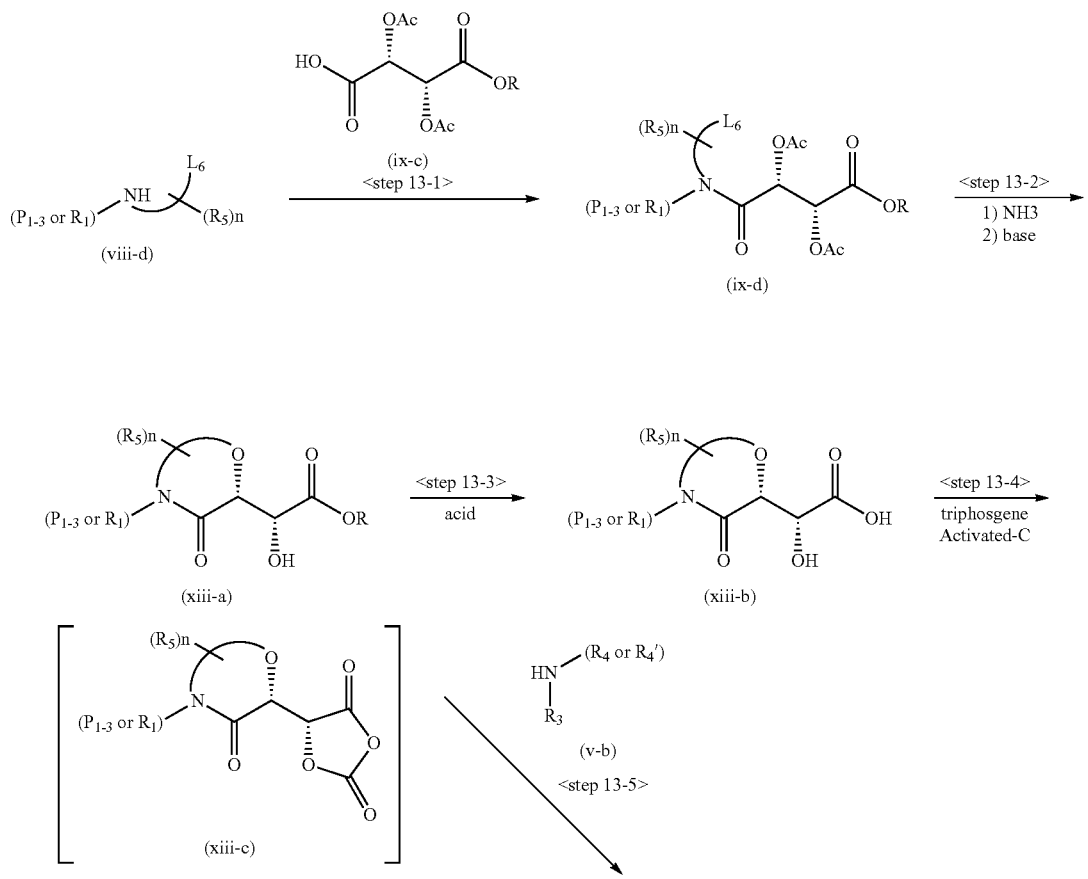

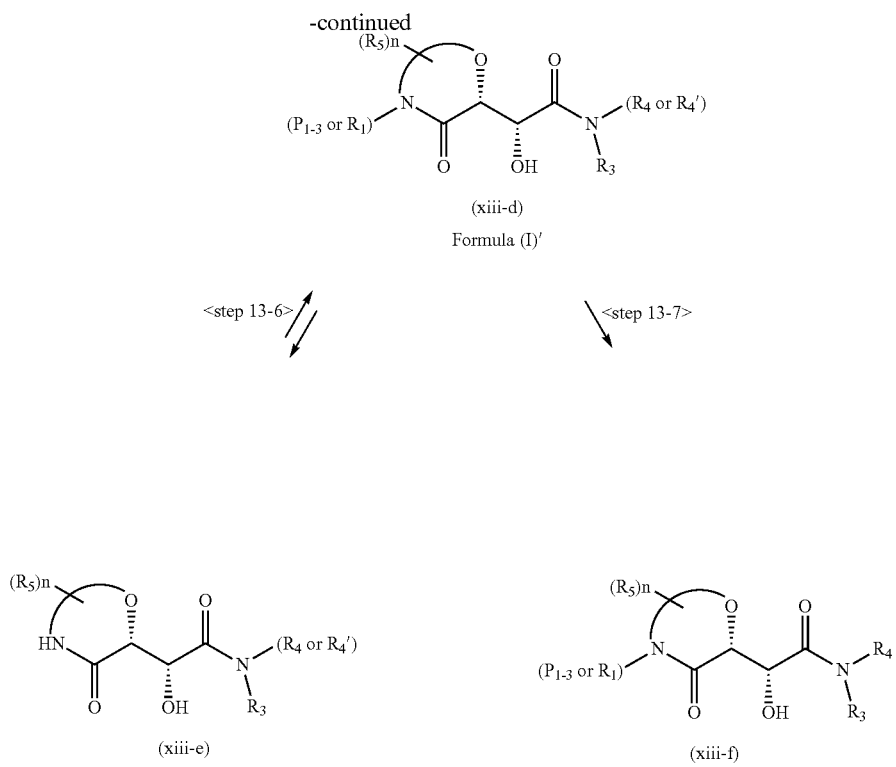

Step <13-1>

A compound represented by formula (ix-d) can be produced by the similar process as that used in <Step 5-1> of (Reaction Scheme 2) using compounds represented by formula (viii-d) and represented by formula (ix-c). When R represents tert-butyl group, a compound represented by formula (ix-c) could be prepared by a similar process that described in published document, for example, *Tetrahedron*, 45, 3071-3080, 1989.

Step <13-2>

A compound represented by formula (xiii-a) can be produced by the similar process as that used in <Step 10-1> of (Reaction Scheme 5) using a compound represented by formula (ix-d), and followed by the similar process as that used in <step 10-2> of (Reaction Scheme 6) using the resulting alcoholic compound from a compound represented by formula (ix-d).

Step <13-3>

A compound represented by formula (xiii-b) can be produced from a compound represented by formula (xiii-a) by a well-known or similar process that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of inorganic or organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid using water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

Step <13-4> and <Step 13-5>

A compound represented by formula (xiii-d) can be produced by the similar process as that used in <Step 5-1> of (Reaction Scheme 2) using a compound represented by formula (xiii-b) via its intermediate represented by formula (xiii-c), with a compound represented by formula (v-b).

Step <13-6>

Protective groups of a compound represented by formula (xiii-d) can be introduced and removed between (xiii-d) and (xiii-e) by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <13-7>

A compound represented by formula (xiii-f), which is identical to the compound represented by formula (x-e) in Scheme 6 wherein m is 1 and R is hydrogen atom, can be produced by a similar process as that used in <Step 10-4> of (Reaction Scheme 6) using a compound represented by formula (xiii-d).

Scheme 12 Synthetic route of R1 aniline derivative compounds (xiv-b), (xiv-c), and (xiv-d) from aniline analogue compound represented by formula (xiv-a)
(Reaction scheme 12)

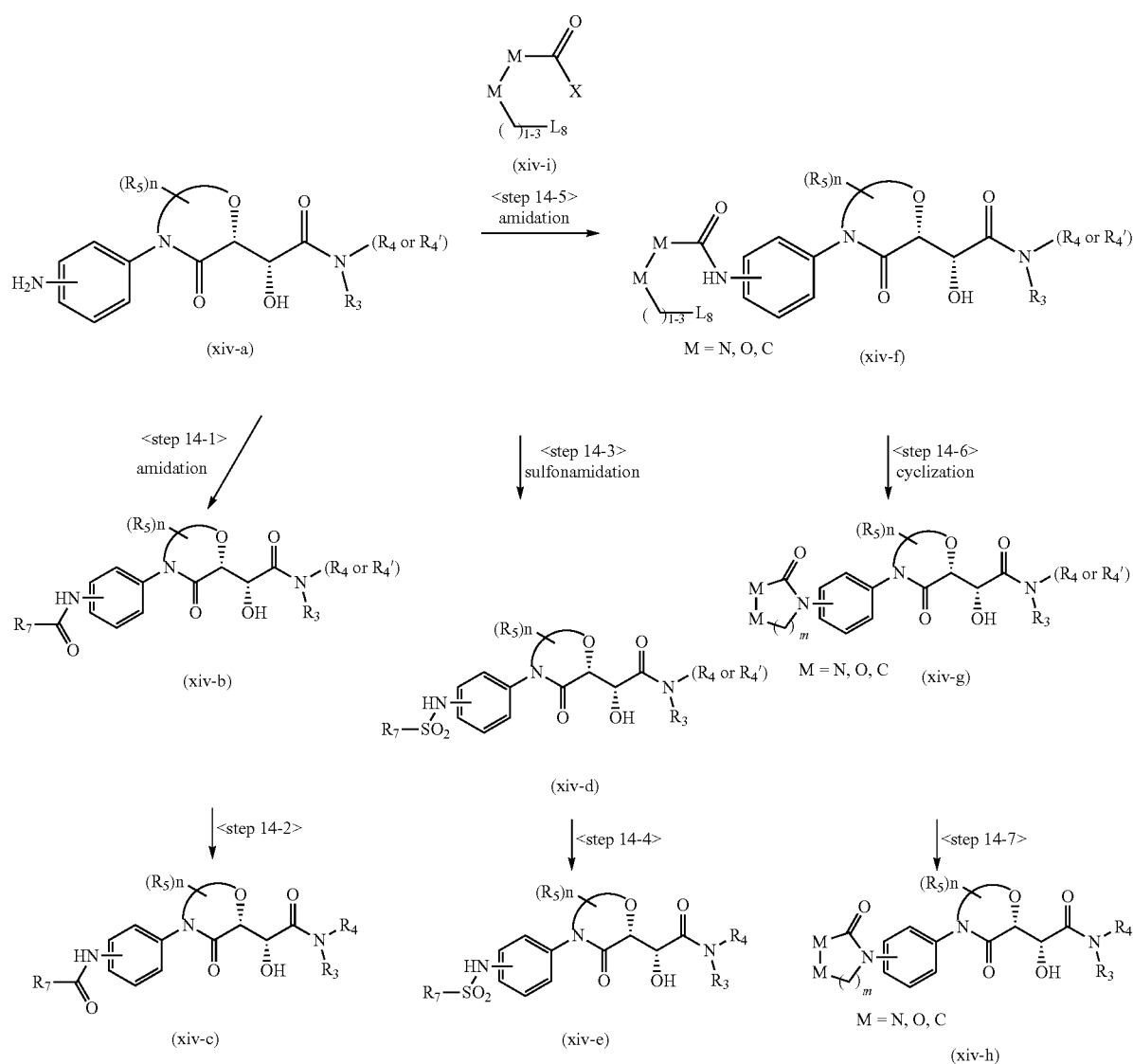

Step <14-1>

A compound represented by formula (xiv-b) can be produced by the similar process as that used in <Step 5-1> of (Reaction Scheme 2) using a compound represented by formula (xiv-a).

Step <14-2>

A compound represented by formula (xiv-c) can be produced by the similar process as that used in <Step 10-4> of (Reaction Scheme 6) using a compound represented by formula (xiv-b).

Step <14-3>

A compound represented by formula (xiv-d) can be produced by the similar process as that used in <Step 5-1> of (Reaction Scheme 2) using a compound represented by formula (xiv-a) and corresponding sulfonyl halide such as sulfonyl chloride reagent.

Step <14-4>

A compound represented by formula (xiv-e) can be produced by the similar process as that used in <Step 10-4> of (Reaction Scheme 6) using a compound represented by formula (xiv-d).

Step <14-5>

A compound represented by formula (xiv-f) wherein each M represents independently oxygen atom, nitrogen atom or carbon atom, can be produced with step by step cyclization process as that used in <Step 5-1> of (Reaction Scheme 2) using a compound represented by formula (xiv-a) and a compound represented by formula (xiv-i) denoting acid halide or acid reagent wherein X represents halogen or hydroxyl group, such as 2-chloroethoxy acetic acid.

Step <14-6>

The resulting compound represented by formula (xiv-f) can be cyclized to produce a compound represented by formula (xiv-g) by the same process as that used in <Step 10-2> of (Reaction Scheme 6).

Step <14-7>

A compound represented by formula (xiv-g) can be produced by the similar process as that used in <Step 10-4> of (Reaction Scheme 6) using a compound represented by formula (xiv-f).

Scheme 13 Alternative synthetic route of optically active compounds represented by a formula (xv-f) which is a subset of compounds represented by a formula (x-e) via key intermediate compound represented by formula (xv-b).
(Reaction scheme 13)

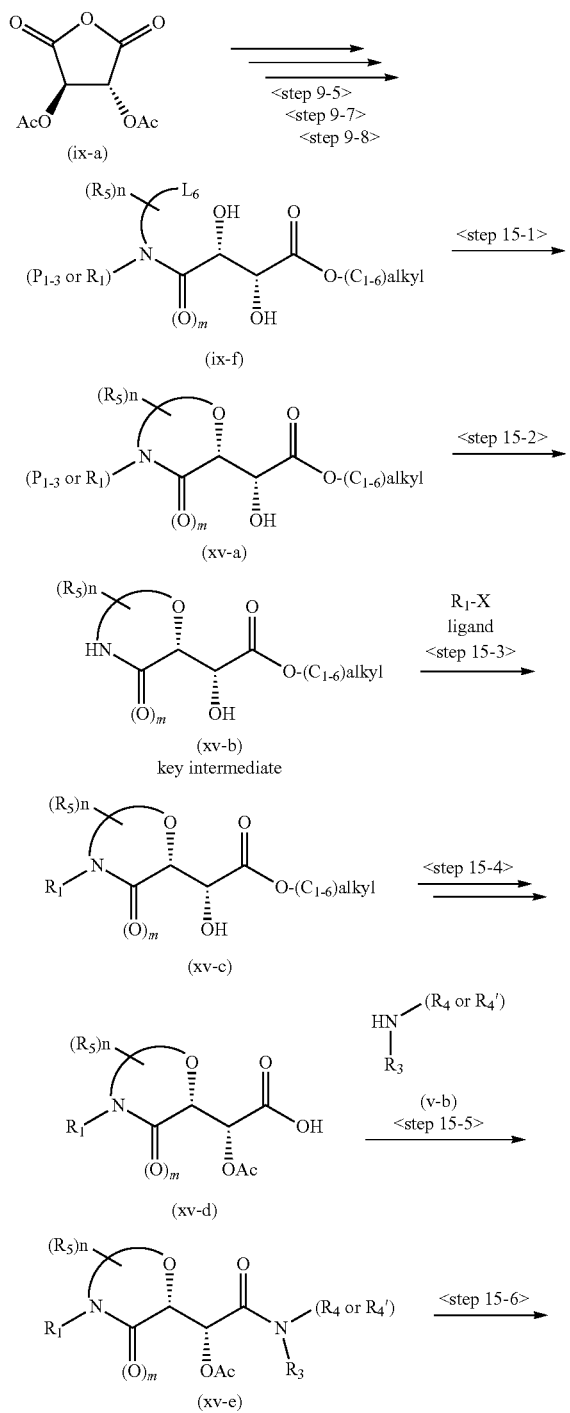

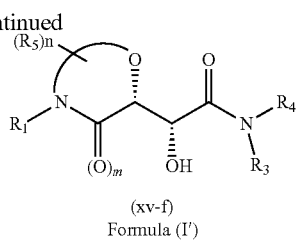

(xv-f)
Formula (I')

Step <15-1>

A compound represented by formula (xv-a) can be produced by the similar process as that used in <Step 10-2> of (Reaction Scheme 6) using a compound represented by formula (ix-f) in the Scheme 5.

Step <15-2>

A compound represented by formula (xv-b), a key intermediate to produce compounds represented by formula (xv-f) which corresponds to the compounds represented by Formula (I), can be produced by deprotection of the compound represented by formula (xv-a) using CAN (ceric ammonium nitrate) using a solvent which is inactive to the reaction, such as a polar solvent, e.g., DMF, DMSO, ethyl acetate, water, or acetonitril, or an ethereal solvent, e.g., diethyl ether, tetrahydrofuran, 1,2-dimethoxyethane, 1,4-dioxane, or a mixed solvent thereof at a temperature in the range of 0° C. to the solvent-reflux temperature, or by techniques which are well-known or described here (see Greene, T. W., et. al., *Protective Groups in Organic Synthesis* (2007), 4th Ed., Wiley, New York, or Kocienski, P., *Protecting Groups* (1994), Thieme).

Step <15-3>

A compound represented by formula (xv-c) can be produced by allowing a key intermediate compound represented by formula (xv-b) to react with a compound represented by R1-X (aryl halide or heteroaryl halide, wherein X represents halogen atom) by a process known as Goldberg reaction which are similar to that described in published documents, for example, *JACS*, 2002, 124, 7421 in the presence of a base such as potassium phosphate, cesium carbonate, potassium tert-buthoxide, sodium hydride, lithium hydroxide, sodium hydroxide, potassium hydroxide, lithium carbonate, sodium carbonate, or potassium carbonate in the presence of 1,2-diamine ligand such as trans-1,2-cyclohexanediamine, trans-N,N'-dimethylcyclohexane-1,2-diamine, or ethylene diamine, and in the presence of catalytic amount of cupper iodide using a solvent which is inactive to the reaction, such as an ethereal solvent, e.g., diethyl ether, tetrahydrofuran, 1,2-dimethoxyethane, 1,4-dioxane, polar solvents such as DMF, and DMSO; or an aromatic hydrocarbon solvent, e.g., toluene or benzene or a mixed solvent thereof at a temperature in the range of room temperature to the solvent-reflux temperature.

Step <15-4>

A compound represented by formula (xv-c) can be produced by allowing a compound represented by formula (xv-b) to react with acetic anhydride by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd., and resulting acetylated alcohol compound can be hydrolyzed by the similar process as that used in <Step 4-2> of (Reaction Scheme 2).

Step <15-5>

A compound represented by formula (xv-e) can be produced by the similar process as that used in <Step 5-1> of (Reaction Scheme 2) using a compound represented by formula (xv-d) in the Scheme 13 and a compound represented by formula (v-b).

Step <15-6>

A compound represented by formula (xv-f) can be produced by a similar process as that used in <Step 10-4> of (Reaction Scheme 6) using a compound represented by formula (xv-e).

(Reaction Scheme 1) using a compound represented by formula (xvi-a) in the Scheme 14.

Step <16-2>

A compound represented by formula (xvi-c) can be produced by a similar process as that used in <Step 2-2> of (Reaction Scheme 1) using a compound represented by formula (xvi-b) in the Scheme 14.

Scheme 14 Alternative synthetic route of compounds (xvi-h) identical to the compound represented Formula (I) wherein G represents nitrogen group.
(Reaction scheme 14)

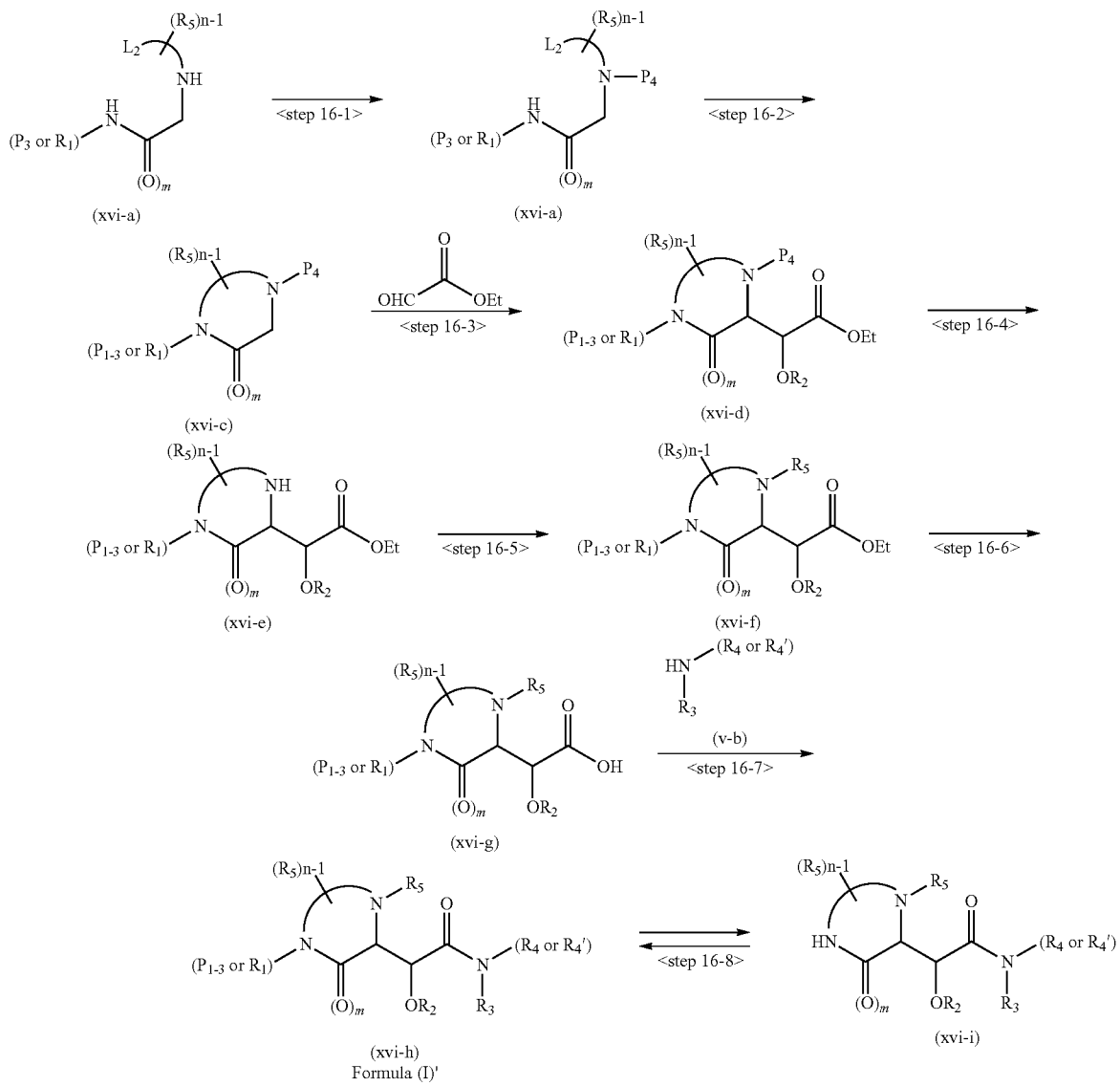

Step <16-1>

A compound represented by formula (xvi-a) are commercially available, or capable of being readily synthesized by the method as identical to the route described in Scheme 1 to synthesize a compound represented by formula (ii-b), or commonly used in the organic chemistry from commercially available products.

A compound represented by formula (xvi-b) can be produced by the similar process as that used in <Step 2-3> of Step <16-3>

A compound represented by formula (xvi-d) can be produced by the similar process as that used in <Step 3-1> of (Reaction Scheme 2) using a compound represented by formula (xvi-c) in the Scheme 14.

Step <16-4>

A compound represented by formula (xvi-e) can be produced by a similar process as that used in <Step 2-2> of (Reaction Scheme 1) using a compound represented by formula (xvi-d) in the Scheme 14.

Step <16-5>

A compound represented by formula (xvi-f) can be produced by the similar process as that used in <Step 5-1> of (Reaction Scheme 2) using a compound represented by formula (xvi-e) in the Scheme 14 when R5 represents acyl group such as, for example, acetyl group or benzyl group.

(Reaction Scheme 2) using a compound represented by formula (xvi-g) in the Scheme 14.

Step <16-8>

A compound represented by formula (xvi-i) can be produced by a similar process as that used in <Step 5-2> of (Reaction Scheme 2) using a compound represented by formula (xvi-h) in the Scheme 14.

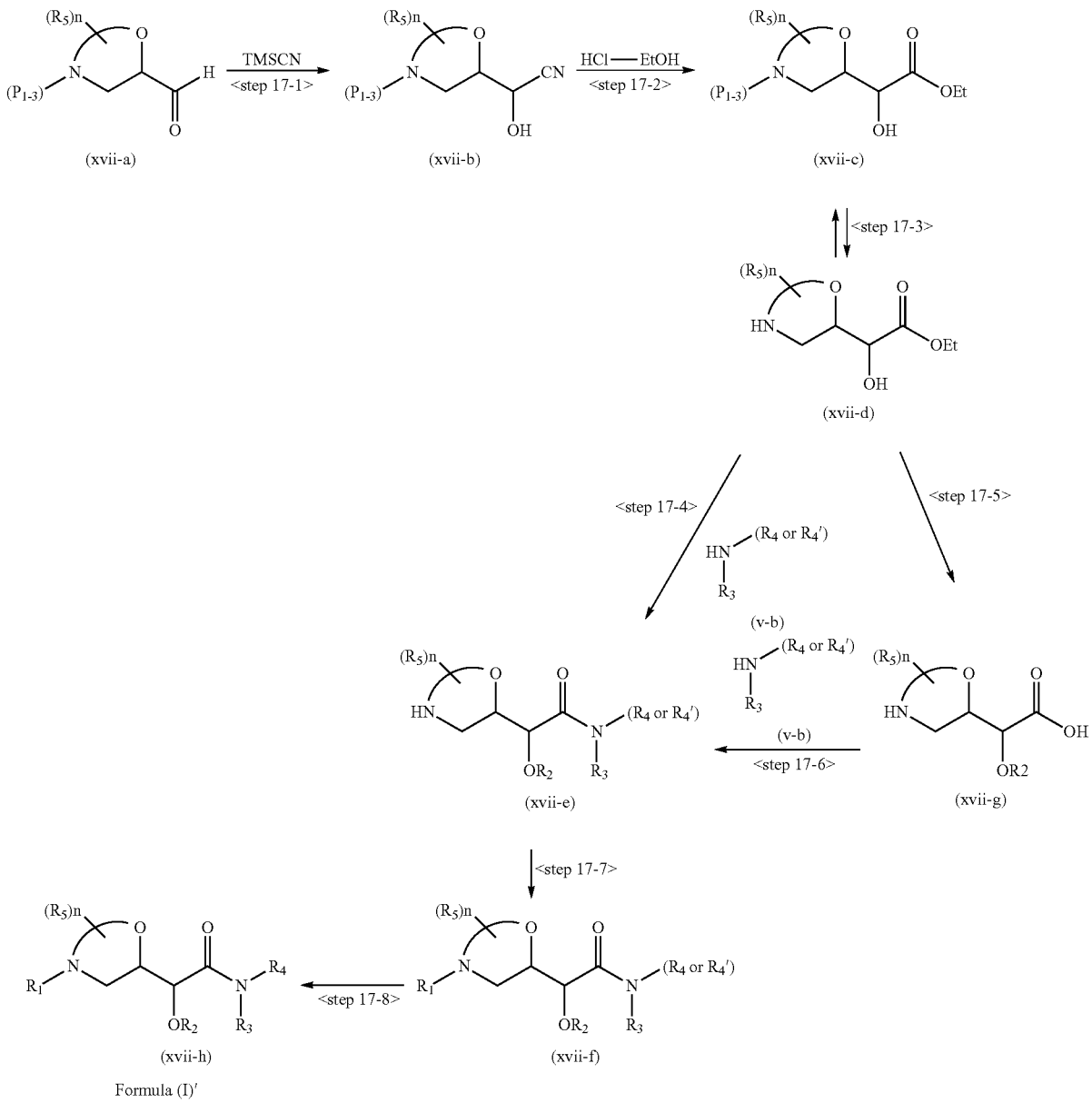

Scheme 15 Alternative synthetic route of morpholine compounds.

Step <16-6>

A compound represented by formula (xvi-g) can be produced by a similar process as that used in <Step 1-6> of (Reaction Scheme 1) using a compound represented by formula (xvi-f) in the Scheme 14.

Step <16-7>

A compound represented by formula (xvi-h) can be produced by a similar process as that used in <Step 5-1> of Step <17-1>

A compound represented by formula (xvii-b) can be produced by allowing a compound represented by formula (xvii-a) to react with TMSCN (trimethylsilyl cyanide) by a process similar to that described in published documents, for example, Organic synthesis Collective Vol. 1, pp. 336 (1941), Collective Vol. 2, pp. 7 (1943), Collective Vol. 7, pp. 521 (1990) using a solvent which is inactive to the reaction, such as an alcoholic solvent, e.g., methanol, ethanol, 2-propanol, or a mixed solvent thereof at a temperature in the range of −78° C. to the solvent-reflux temperature. $P_{1-3}$ represents typically a benzyl group and deprotection of benzyl group can be reductive deprotection by a similar process of <step 8-1>.
Step <17-2>

A compound represented by formula (xvii-c) can be produced by allowing a compound represented by formula (xvii-b) by a process similar to that described in published documents, for example, Organic synthesis Collective Vol. 1, pp. 270 (1941), Collective Vol. 2, pp. 310 (1943) in the presence of concentrated HCl using a solvent such as an alcoholic solvent containing hydrogen chloride, e.g., methanol-HCl, ethanol-HCl, or a mixed solvent thereof at a temperature in the range of 0° C. to the solvent-reflux temperature.
Step <17-3>

Protective groups of a compound represented by formula (xvii-c) can be introduced and removed by techniques which are well-known or described here (see Greene, T. W., et. al., *Protective Groups in Organic Synthesis* (2007), 4th Ed., Wiley, New York, or Kocienski, P., *Protecting Groups* (1994), Thieme).
Step <17-4>

A compound represented by formula (xvii-e) can be produced by the same process as that used in <Step 4-3> of (Reaction Scheme 2) using a compound represented by formula (xvii-c) and a compound represented by formula (v-b).
Step <17-5>

A compound represented by formula (xvii-g) can be produced by a similar process as that used in <Step 1-6> of (Reaction Scheme 1) using a compound represented by formula (xvii-c) in the Scheme 15.
Step <17-6>

A compound represented by formula (xvii-e) can be produced by the same process as that used in <Step 5-1> of (Reaction Scheme 2) using a compound represented by formula (xvii-g) and a compound represented by formula (v-b).
Step <17-7>

A compound represented by formula (xvii-f) can be produced by the same process as that used in <step 14-1> or <step 14-3> of (Reaction Scheme 12), or <step 15-3> of (Reaction Scheme 13) using a compound represented by formula (xvii-f).
Step <17-8>

A compound represented by formula (xvii-h) can be produced by a similar process as that used in <Step 10-4> of (Reaction Scheme 6) using a compound represented by formula (xvii-g).

(S,S), (R,S) and (S,R) forms of compounds represented by Formula (I) can also be made from corresponding starting materials. The required starting materials for the synthesis of (S,S), (R,S) and (S,R) isoforms of compound (ix-a) are either commercially available, or capable of being readily synthesized by the method commonly used in the organic chemistry from commercially available products.

Acidic or basic products of the compound of the Formula (I) can be present in the form of their salts or in free form. Pharmacologically acceptable salts are preferred, for example alkali metal or alkaline earth metal salts such as hydrochlorides, hydrobromides, sulfates, hemisulfates, all possible phosphates, and salts of the amino acids, natural bases or carboxylic acids.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

EXAMPLES

The present invention will now be described in more detail using examples, but the present invention is not limited to the examples.

The measurement of nuclear magnetic resonance (NMR) spectrum (Table 3) was performed using a JEOL JNM-ECX300 FT-NMR (manufactured by JEOL Ltd.) or a JEOL JNM-ECX400 FT-NMR (manufactured by JEOL Ltd.).

Liquid chromatography-mass spectrometry (LC-MS, Table 4) was performed using a Waters FractionLynx MS system (manufactured by Waters Corporation) from the Example 1 to Example 67. A SunFire Column™ (4.6 mm×5 cm, 5 microm) (manufactured by Waters Corporation) was used as an analytical column. A SunFire Column™ (19 mm×5 cm, 5 microm) (manufactured by Waters Corporation) was used as a preparative column. Acetonitrile and a 0.05% aqueous acetic acid solution or 0.05% aqueous trifluoroacetic acid solution were used as the mobile phase. Methanol and 0.05% aqueous acetic acid solution or 0.05% aqueous trifluoroacetic acid solution were also used as the mobile phase. The analysis was performed under the following gradient conditions: acetonitrile: 0.05% aqueous acetic acid solution or 0.05% aqueous trifluoroacetic acid solution=1:9 (0 minutes), 9:1 (5 minutes), and 9:1 (7 minutes). Methanol: 0.05% aqueous acetic acid solution or 0.05% aqueous trifluoroacetic acid solution=1:9 (0 minutes), 10:0 (5 minutes), and 10:0 (7 minutes). The solvent systems are described as the followings: A indicates MeCN—AcOH, B indicates MeCN-TFA, C indicates MeOH—AcOH, and D indicates MeOH-TFA.
Method E:
Electro Spray Ionization Liquid Chromatography-Mass Spectrometry (ESI-LC/MS)
Column: Phenomenex Gemini C18, 50×4.6 Mm, 5 Micron
Mobile Phase: A: 0.05% Trifluoroacetic acid in water
  B: 0.05% Trifluoroacetic acid in acetonitrile
Gradient: 90% A and 10% B to 5% A and 95% B over 5 minutes
Flow rate: 1.0 ml/min
UV detection: 254 nM
Spectrometer: PE SCIEX API-150EX, single quadrupole mass spectrometer
Method F:
Column: Zorbax SB-C-18; 1.8 micron
Mobile Phase: A: 0.1% Trifluoroacetic acid in water
  B: 0.1% Trifluoroacetic acid in acetonitrile
Gradient: 0 min=10% B
  1.3 min=55% B
  2.7 min=95% B
  2.8 min=10% B Flow rate: 1.0 ml/min
UV detection: 254 nM
Spectrometer: Agilent 6140 Quadrapole LC-MS, single quadrupole mass spectrometer
Solvent G: Column: Agilent SBC (3.0×50 mm, 1.8 u); Flow: 1.0 ml/min; solvent A: H2O-0.1% TFA: Solvent B: ACN-0.1% TFA; Gradient Table: 0.1 min: 5% B, 2.3 min: 99% B, 2.90 min: 99% B, 3.0 min: 5% B stop time 3.50 min.
Solvent H: Column: Agilent SBC (3.0×50 mm, 1.8 u); Flow: 1.0 ml/min; solvent A: H2O-0.1% TFA: Solvent B: ACN-0.1% TFA; Gradient Table: 0 min: 10% B, 1.5 min: 95% B, 2.76 min: 10% B, stop time 3.60 min, Post Time 0.70 min.
I: Instrument: Agilent Technologies 6140; Column: Agilent SBC (3.0×50 mm, 1.8 u);
Flow: 1.0 mL/min; solvent A: H2O-0.1% TFA: Solvent B: ACN-0.1% TFA; Gradient
Table: 0.1 min: 5% B, 2.3 min: 99% B, 2.90 min: 99% B, 3.0 min: 5% B stop time 3.50 min.
J: Agilent Technologies 6140; Column: Agilent SBC (3.0×50 mm, 1.8 u); Flow: 1.0 ml/min; solvent A: H2O-0.1% TFA: Solvent B: ACN-0.1% TFA; Gradient Table: 0 min: 10% B, 1.5 min: 95% B, 2.76 min: 10% B, stop time 3.60 min, Post Time 0.70 min.
K: Instrument: PE-Sciex API 150 EX; Column: Alltech Platinum C18, 33×7 mm, 3 micron; Solvent A: Water w/0.05% TFA; Solvent B: Acetonitrile w/0.05% TFA;
Flow rate: 1 mL/min; Gradient: 0 min: 10% B, 5 min: 95% B, 7 min: 95% B, 7.5 min: 10, 9 min: stop.
Method A for EX118 to EX131
Electro Spray Ionization Liquid Chromatography-Mass Spectrometry (ESI-LC/MS)
Column: Phenomenex Gemini C18, 50×4.6 Mm, 5 Micron
Mobile Phase: A: 0.05% Trifluoroacetic acid in water
   B: 0.05% Trifluoroacetic acid in acetonitrile
Gradient: 90% A and 10% B to 5% A and 95% B over 5 minutes
Flow rate: 1.0 ml/min
UV detection: 254 nM
Spectrometer: PE SCIEX API-150EX, single quadrupole mass spectrometer
Method B for EX118 to EX131
Column: Zorbax SB-C-18; 1.8 micron
Mobile Phase: A: 0.1% Trifluoroacetic acid in water
   B: 0.1% Trifluoroacetic acid in acetonitrile
Gradient: 0 min=10% B
   1.3 min=55% B
   2.7 min=95% B
   2.8 min=10% B
Flow rate: 1.0 ml/min
UV detection: 254 nM
Spectrometer: Agilent 6140 Quadrapole LC-MS, single quadrupole mass spectrometer
Solvent A for Ex 139-141
Column: Agilent SBC (3.0×50 mm, 1.8 u); Flow: 1.0 ml/min; solvent A: H2O-0.1%
TFA: Solvent B: ACN-0.1% TFA; Gradient Table: 0.1 min: 5% B, 2.3 min: 99% B, 2.90 min: 99% B, 3.0 min: 5% B stop time 3.50 min.

Deuterated starting materials are capable of being used in certain Examples.

Example 1

Synthesis of N-(1-aminoisoquinolin-6-yl)-2-hydroxy-2-(3-oxo-4-p-tolylmorpholin-2-yl)acetamide trifluoroacetate

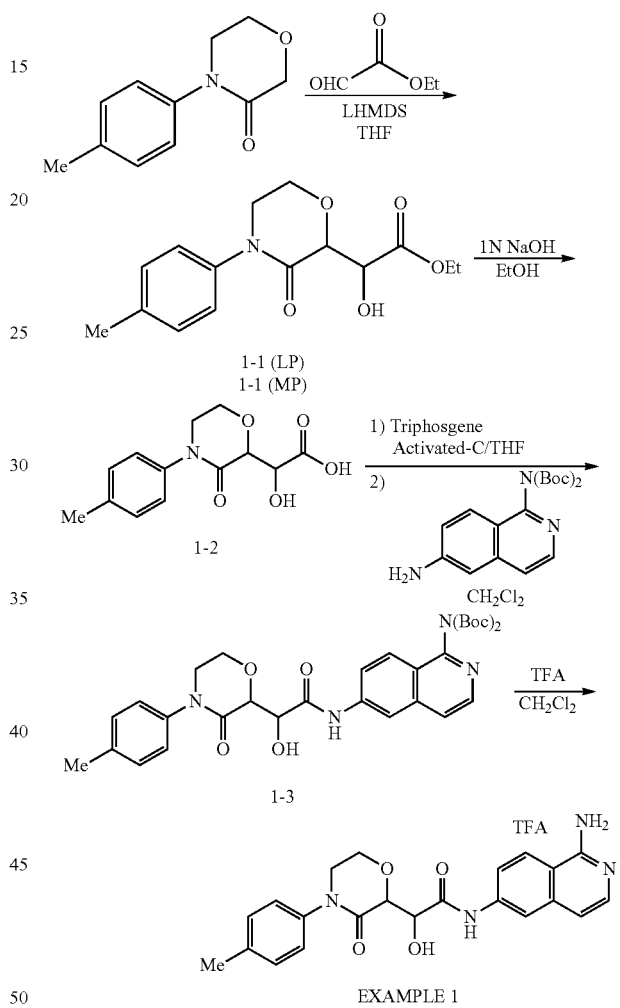

Step 1-1

Synthesis of ethyl 2-hydroxy-2-(3-oxo-4-p-tolylmorpholin-2-yl)acetate (Compound 1-1 (LP) and compound 1-1 (MP))

To a solution of 4-(4-Methylphenyl)-3-morpholinone (Zhurnal Organicheskoi Khimii, 6(6), 1305-8, 1970) (1.08 g) in THF (21.6 ml), was added 1 M lithium hexamethyldisilazide solution (7.34 ml) in THF at −78° C. The mixture was stirred at −78° C. for 15 minutes then 0° C. for 1 hour. Then the reaction mixture was cooled down at −78° C. and ethyl glyoxylate solution (1.84 ml) in toluene was added into the reaction mixture. The reaction mixture was stirred at 0° C. overnight. At the end of the reaction, saturated NH₄Cl aqueous solution was added into the reaction mixture. The mixture was concentrated in vacuo and the resulting mixture was extracted with AcOEt. The organic layer was washed with brine and dried with anhydrous Na₂SO₄. The solvent was removed under reduced pressure and the resulting residue was purified by silica gel flash column chromatography (eluent: n-Hex/AcOEt=50/50–0/100) to obtain two diastereomers, compound 1-1 (LP) (405 mg; Rf value=0.36 on TLC (n-Hex/AcOEt=1/2)) as a pale yellow amorphous solid and 1-1 (MP) (287 mg; Rf value=0.27 on TLC (n-Hex/AcOEt=1/2)) as yellow oil. LP indicates a less polar spot on TLC, MP indicates a more polar spot on TLC.

Step 1-2

Synthesis of 2-hydroxy-2-(3-oxo-4-p-tolylmorpholin-2-yl)acetic acid (Compound 1-2)

To a solution of compound 1-1 (LP) (100 mg) in EtOH (1 mL), was added 1 N NaOH aqueous solution (1 mL) at 0° C. The reaction mixture was stirred at room temperature for 1 hour. Then DowEx®-50Wx8-200 was added into the reaction mixture, then the mixture was filtered to remove DowEx®-50Wx8-200. The filtrate was concentrated in vacuo to obtain compound 1-2 (90 mg) as a colorless amorphous solid. Compound 1-2 was used in the next step without further purification.

Step 1-3

Synthesis of N—[N,N-bis(tert-butoxylcarbonyl)-1-aminoisoquinolin-6-yl]-2-hydroxy-2-(3-oxo-4-p-tolylmorpholin-2-yl)acetamide (Compound 1-3)

To a solution of compound 1-2 (90 mg) in THF (2 ml), were added activated-charcoal (4.5 mg) and triphosgene (403 mg) at 0° C. The reaction mixture was stirred at room temperature for 15 hours. Then activated-charcoal was removed by filtration and the filtrate was concentrated in vacuo. The resulting residue was resolved in CH₂Cl₂ (2 ml). 6-Amino-1-bis(tert-butoxyl carbonyl)aminoisoquinoline (146 mg) was added into the CH₂Cl₂ solution at 0° C. The reaction mixture was stirred at room temperature for 4 hours. The reaction mixture was concentrated in vacuo and a half volume of the resulting residue was purified by LC/MS to obtain compound 1-3 (30.6 mg) as a colorless amorphous solid.

Step 1-4

Synthesis of N-(1-aminoisoquinolin-6-yl)-2-hydroxy-2-(3-oxo-4-p-tolylmorpholin-2-yl)acetamide Trifluoroacetate (EXAMPLE 1)

To a solution of compound 1-3 (30.6 mg) in CH₂Cl₂ (1.5 ml), was added trifluoroacetic acid (0.5 ml) at 0° C. The reaction mixture was stirred at room temperature for 1 hour and the mixture was concentrated in vacuo. To the resulting residue, Et₂O was added and the residue was triturated. Then the precipitate was collected by filtration to obtain EXAMPLE 1 (19.3 mg) as a colorless amorphous solid.

Example 2

Synthesis of N-(4-amidinophenyl)-2-hydroxy-2-(3-oxo-4-p-tolylmorpholin-2-yl)acetamide trifluoroacetate

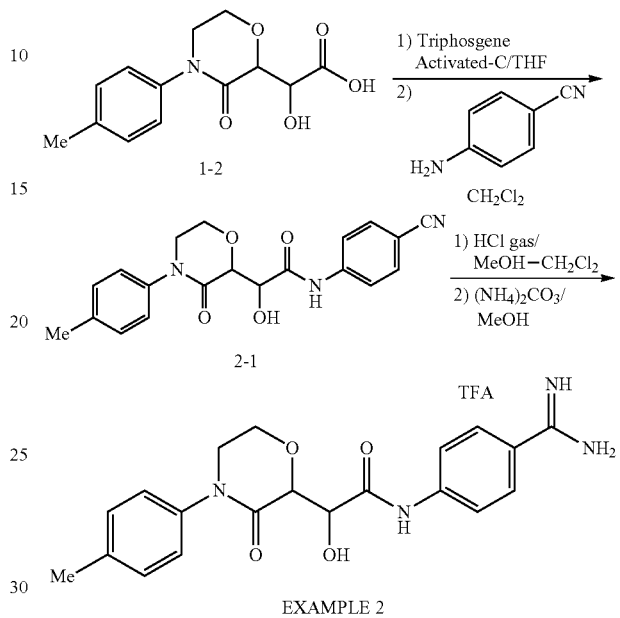

Step 2-1

Synthesis of N-(4-cyanophenyl)-2-hydroxy-2-(3-oxo-4-p-tolylmorpholin-2-yl)acetamide (Compound 2-1)

According to the Step 1-3 in synthetic method for Example 1, 4-aminobenzonitrile (17.8 mg) was used instead of 6-amino-1-bis(tert-butyl carbonyl)aminoisoquinoline to obtain compound 2-1 (24 mg) as a colorless amorphous solid.

Step 2-2

Synthesis of N-(4-amidinophenyl)-2-hydroxy-2-(3-oxo-4-p-tolylmorpholin-2-yl)acetamide Trifluoroacetate (EXAMPLE 2)

HCl gas was bubbled into a solution of compound 2-1 (15 mg) in MeOH—CH₂Cl₂ (10-6 ml) at 0° C. for 30 minutes. The reaction mixture was stirred at 0° C. overnight to form the methyl imidate. Then the mixture was concentrated in vacuo and the resulting residue was solved in MeOH (8 mL). Ammonium carbonate (39 mg) was added into the above MeOH solution at 0° C. The reaction mixture was stirred at room temperature for 24 hours. Then 8N NH₃-MeOH (2 ml) was added into the reaction mixture and the mixture was stirred at 60° C. for 6 hours until the methyl imidate intermediate disappeared. The reaction mixture was concentrated in vacuo and the resulting residue was purified by LC/MS to obtain EXAMPLE 2 (14.5 mg) as a colorless amorphous solid.

Example 3 to Example 6

The following compounds were synthesized from compound 1-2 in a similar manner to compound 1-3 using an appropriate amine instead of 6-amino-1-bis(tert-butoxycarbonyl)aminoisoquinoline, and using DMF instead of CH₂Cl₂.

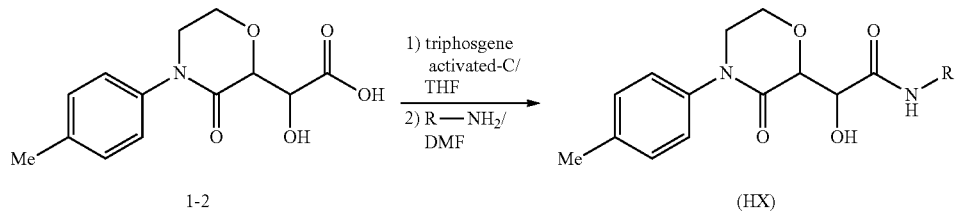
EXAMPLE 3 TO EXAMPLE 6
| EXAMPLE | STRUCTURE | NAME |
| --- | --- | --- |
| 3 | 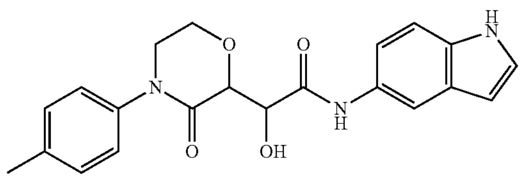 [SMILES: Cc1ccc(N2CCOC(C(O)C(=O)Nc3ccc4[nH]ccc4c3)C2=O)cc1] | 2-Hydroxy-N-(1H-indol-5-yl)-2-(3-oxo-4-p-tolylmorpholin-2-yl)acetamide |
| 4 | 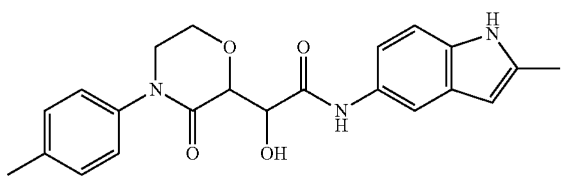 | 2-Hydroxy-N-(2-methyl-1H-indol-5-yl)-2-(3-oxo-4-p-tolylmorpholin-2-yl)acetamide |
| 5 | TFA | N-[4-(Aminomethyl)phenyl]-2-hydroxy-2-(3-oxo-4-p-tolylmorpholin-2-yl)acetamide trifluoroacetate |
| 6 | TFA | N-(2-Amino-3H-benzimidazol-5-yl)-2-hydroxy-2-(3-oxo-4-p-tolylmorpholin-2-yl)acetamide trifluoroacetate |

Example 7
Synthesis of (2R)—N-(4-amidinophenyl)-2-hydroxy-2-[(2R)-3-oxo-4-p-tolylmorpholin-2-yl]acetamide Hydrochloride (EXAMPLE 7)
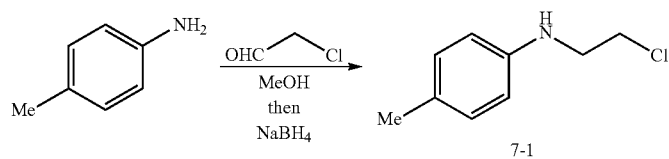
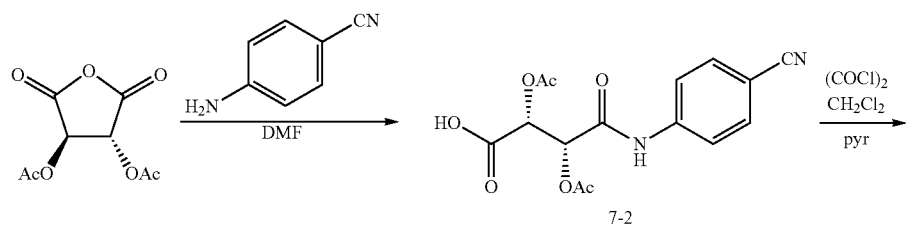
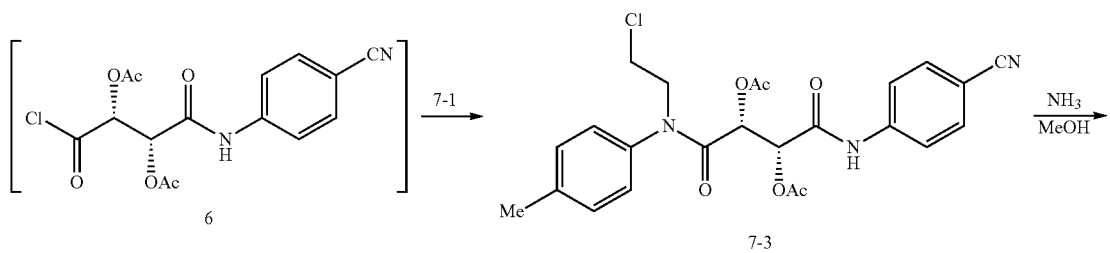
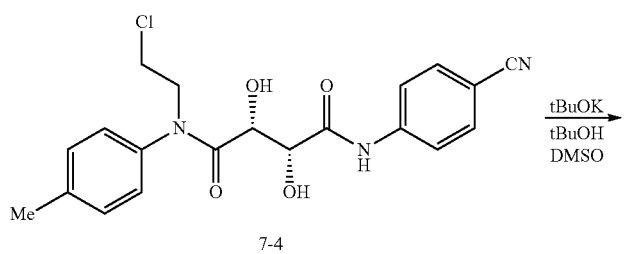
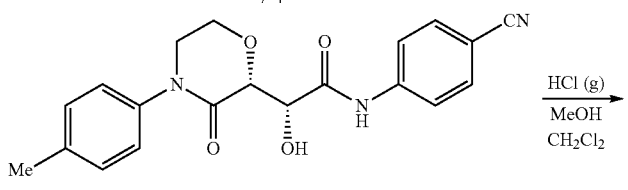
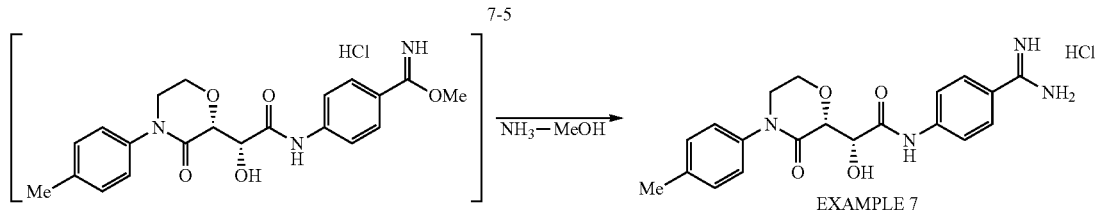
EXAMPLE 7

Step 7-1

Synthesis of N-(2-chloroethyl)-4-methylaniline (Compound 7-1)

To a solution of 4-methylaniline (100 mg) in MeOH (2.0 mL) was added 40% chroloacetaldehyde solution in water (0.17 mL) at 0° C. The mixture was stirred for 45 minutes at the same temperature, sodium borohydride (NaBH$_4$; 70.6 mg) was added into the reaction mixture at one portion and the mixture was stirred for 1 hour.

The reaction mixture was diluted with water and was extracted with EtOAc. The extract was washed with water, sat.NaHCO$_3$ and brine. The organic layer was dried with anhyd. Na$_2$SO$_4$. It was filtrated to remove insoluble matters and it was concentrated in vacuo. The residue was purified by silica gel flush chromatography (eluent:Hexane:EtOAc=95:5~75:25) to obtain 7-1 (27 mg) as brown oil.

Step 7-2

Synthesis of (2R,3R)-2,3-diacetyloxy-4-(4-cyanoanilino)-4-oxobutanoic acid (Compound 7-2)

To a solution of (+)-Diacetyl-L-tartaric anhydride (9.15 g) in dry DMF (100 mL), was added 4-aminobenzonitrile (5 g,) under ice cooling and the reaction mixture was stirred to obtain compound 7-2 at room temperature overnight. The solution of compound 7-2 was used in the next step without any treatment.

Step 7-3

Synthesis of [(2R,3R)-3-acetyloxy-1-[N-(2-chloroethyl)-4-methylanilino]-4-(4-cyanoanilino)-1,4-dioxobutan-2-yl]acetate (Compound 7-3)

The above DMF solution of 7-2 (13.8 mL) was diluted with CH$_2$Cl$_2$ (13.8 mL). The internal temperature of the mixture was kept below −60° C. over all additions with dry ice bath.

Oxalyl chloride (0.55 mL) in CH$_2$Cl$_2$ (1.7 mL) was added dropwise into the reaction mixture. After stirring for 1 hour, pyridine (1.99 mL) was added dropwise thereto and stirred for 15 min. Then 7-1 (0.99 g) in CH$_2$Cl$_2$ (6 mL) was added dropwise into the reaction mixture. The mixture was stirred below −60° C. for 20 min, then it was stirred at −30° C. for 15 hours.

The reaction mixture was quenched with water and was extracted with EtOAc. The extract was washed with water, 1N HCl, sat.NaHCO$_3$ and brine. The organic layer was dried with anhyd. Na$_2$SO$_4$. It was filtrated and was concentrated in vacuo. The residue was purified by silica gel flush chromatography (eluent: Hexane: EtOAc=75:25~25:75) to obtain 7-3 (1.70 g) as a light brown solid.

Step 7-4

Synthesis of (2R,3R)—N-(2-chloroethyl)-N'-(4-cyanophenyl)-2,3-dihydroxy-N-p-tolylbutanediamide (Compound 7-4)

To a solution of 7-3 (0.20 g) in MeOH (4 mL), was added 8N NH$_3$/MeOH (0.26 mL) at 0° C. and the mixture was stirred for 10 minutes in the same temperature. The mixture was concentrated and was dried in vacuo to obtain crude 7-4. The crude 7-4 was used in the next step without further purification.

Step 7-5

Synthesis of (2R)—N-(4-cyanophenyl)-2-hydroxy-2-[(2R)-3-oxo-4-p-tolylmorpholin-2-yl]acetamide (Compound 7-5)

The crude 7-4 was dissolved in t-BuOH (12 mL)-DMSO (8 mL), and t-BuOK (554 mg) was added portionwise into the reaction mixture at 0° C. The mixture was stirred for 10 minutes in the same temperature.

To the reaction mixture was added 1N HCl and Et$_2$O to obtain precipitate. Then the precipitate was collected by filtration, was rinsed with water, was washed with Et$_2$O and was dried in vacuo to obtain 7-5 (603 mg) as a white solid.

Step 7-6

Synthesis of (2R)—N-(4-amidinophenyl)-2-hydroxy-2-[(2R)-3-oxo-4-p-tolylmorpholin-2-yl]acetamide Hydrochloride (EXAMPLE 7)

Compound 7-5 (27 mg) was suspended in MeOH (15 mL)-CH$_2$Cl$_2$ (7 mL). The suspension was saturated with HCl gas by bubbling at 0° C. for 0.5 hours. Then the mixture was stood to form the imidate at the same temperature overnight. The reaction mixture was concentrated and was dried in vacuo to obtain crude imidate. The crude imidate was dissolved in MeOH (10 mL), then 8N NH$_3$-MeOH (2 mL) was added into the above MeOH solution. The reaction mixture was stirred in sealed tube at 80° C. for 3 hours to convert EXAMPLE 7. The reaction mixture was stirred for 1 day at room temperature then it was concentrated in vacuo. The resulting residue was dissolved in 1N HCl-MeOH, then the mixture was purified by preparative LC/MS to obtain EXAMPLE 7 (7 mg) as a colorless amorphous solid.

Example 8

Synthesis of (2R)—N-(4-amidinophenyl)-2-[(2R)-4-(2,4-dimethylphenyl)-3-oxomorpholin-2-yl]-2-hydroxyacetamide hydrochloride (EXAMPLE 8)

EXAMPLE 8

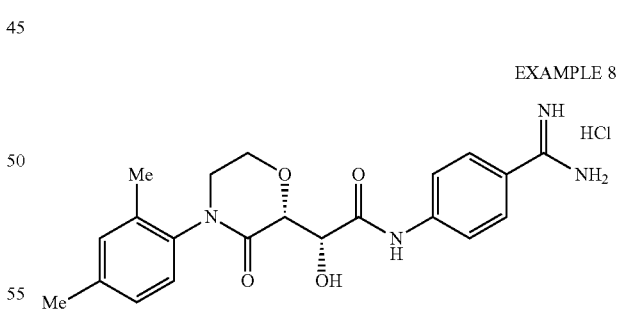

Step 8-1

Synthesis of N-(2-chloroethyl)-2,4-dimethylaniline (Compound 8-1)

According to the Step 7-1 in synthetic method for EXAMPLE 7, 2,4-dimethylaniline (7 g) was used instead of 4-methylaniline to obtain compound 8-1 (2.8 g) as pale brown oil.

159

Step 8-2

Synthesis of [(2R,3R)-3-acetyloxy-1-[N-(2-chloroethyl)-2,4-dimethylanilino]-4-(4-cyanoanilino)-1,4-dioxobutan-2-yl]acetate (Compound 8-2)

According to the Step 7-3 in synthetic method for EXAMPLE 7, compound 8-1 (1.65 g) was used instead of compound 7-1 to obtain compound 8-2 (480 mg) as a colorless amorphous solid.

Step 8-3

Synthesis of (2R,3R)—N-(2-chloroethyl)-N'-(4-cyanophenyl)-2,3-dihydroxy-N-(2,4-dimethylphenyl)-butanediamide (Compound 8-3)

According to the Step 7-4 in synthetic method for EXAMPLE 7, compound 8-2 (0.15 g) was used instead of compound 7-3 to obtain crude 8-3. The crude 8-3 was used in the next step without further purification.

Step 8-4

Synthesis of (2R)—N-(4-cyanophenyl)-2-[(2R)-4-(2,4-dimethylphenyl)-3-oxomorpholin-2-yl]-2-hydroxyacetamide (Compound 8-4)

According to the Step 7-5 in synthetic method for EXAMPLE 7, crude 8-3 was used instead of compound 7-4 to obtain compound 8-4 (70 mg) as a colorless amorphous solid.

Step 8-5

Synthesis of (2R)—N-(4-amidinophenyl)-2-[(2R)-4-(2,4-dimethylphenyl)-3-oxomorpholin-2-yl]-2-hydroxyacetamide Hydrochloride (EXAMPLE 8)

According to the Step 7-6 in synthetic method for EXAMPLE 7, compound 8-4 (50 mg) was used instead of compound 7-5 to obtain EXAMPLE 8 (11.7 mg) as a colorless amorphous solid.

Example 9

Synthesis of (2R)—N-(4-amidinophenyl)-2-hydroxy-2-[(2R)-4-[3-[(2-hydroxyacetyl)amino]-4-methylphenyl]-3-oxomorpholin-2-yl]acetamide hydrochloride (EXAMPLE 9)

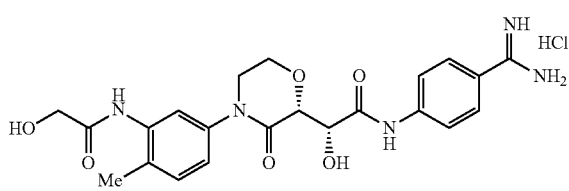

EXAMPLE 9

160

Step 9-1

Synthesis of N-(2-chloroethyl)-4-methyl-3-nitroaniline (Compound 9-1)

According to the Step 7-1 in synthetic method for EXAMPLE 7, 4-methyl-3-nitroaniline (7 g) was used instead of 4-methylaniline to obtain compound 9-1 (1.63 g) as pale yellow oil.

Step 9-2

Synthesis of [(2R,3R)-3-acetyloxy-1-[N-(2-chloroethyl)-4-methyl-3-nitroanilino]-4-(4-cyanoanilino)-1,4-dioxobutan-2-yl]acetate (Compound 9-2)

According to the Step 7-3 in synthetic method for EXAMPLE 7, compound 9-1 (1.61 g) was used instead of compound 7-1 to obtain compound 9-2 (2.88 g) as a colorless amorphous solid.

Step 9-3

Synthesis of (2R,3R)—N-(2-chloroethyl)-N'-(4-cyanophenyl)-2,3-dihydroxy-N-(4-methyl-3-nitrophenyl)butanediamide (Compound 9-3)

According to the Step 7-4 in synthetic method for EXAMPLE 7, compound 9-2 (0.9 g) was used instead of compound 7-3 to obtain crude 9-3. The crude 9-3 was used in the next step without further purification.

Step 9-4

Synthesis of (2R)—N-(4-cyanophenyl)-2-hydroxy-2-[(2R)-4-(4-methyl-3-nitrophenyl)-3-oxomorpholin-2-yl]acetamide (Compound 9-4)

According to the Step 7-5 in synthetic method for EXAMPLE 7, crude 9-3 was used instead of compound 7-4 to obtain compound 9-4 (70 mg) as a colorless amorphous solid.

Step 9-5

Synthesis of (2R)-2-[(2R)-4-(3-amino-4-methylphenyl)-3-oxomorpholin-2-yl]-N-(4-cyanophenyl)-2-hydroxyacetamide (Compound 9-5)

To a solution of compound 9-4 (70 mg) in AcOH—H$_2$O (2 mL-0.1 mL), was added electrolytic iron powder (95.3 mg). The reaction mixture was stirred at room temperature for 1 hour then at 40° C. for 2 hours to complete the reaction. The reaction mixture was filtered with Celite® pad to remove iron powder. The filtrate was concentrated in vacuo. The resulting residue was purified by amino-silica gel flash column chromatography (eluent: CH$_2$Cl$_2$/MeOH=98/2–95/5) to obtain compound 9-5 (30 mg) as a colorless amorphous solid.

Step 9-6

Synthesis of [2-[5-[(2R)-2-[(1R)-2-(4-cyanoanilino)-1-hydroxy-2-oxoethyl]-3-oxomorpholin-4-yl]-2-methylanilino]-2-oxoethyl]acetate (Compound 9-6)

To a solution of compound 9-5 (16.5 mg) in CH$_2$Cl$_2$ (1 mL), were added triethylamine (6.7 microL) and acetoxyacetyl chloride (5.1 microL) at 0° C. The reaction mixture was stirred at room temperature for 30 minutes. Then EtOAc and water were added into the mixture and it was extracted with EtOAc. The organic layer was washed with H₂O, 1N HCl, sat. NaHCO₃ aq. and brine, respectively and dried with anhydr. Na₂SO₄. The solvent was removed under reduced pressure to obtain compound 9-6 (20 mg) as a pale yellow amorphous solid.

Step 9-7

Synthesis of (2R)—N-(4-amidinophenyl)-2-hydroxy-2-[(2R)-4-[3-[(2-hydroxyacetyl)amino]-4-methylphenyl]-3-oxomorpholin-2-yl]acetamide hydrochloride (EXAMPLE 9)

According to the Step 7-6 in synthetic method for EXAMPLE 7, compound 9-6 (20 mg) was used instead of compound 7-5 to obtain EXAMPLE 9 (0.8 mg) as a colorless amorphous solid.

Example 10

Synthesis of (2R)—N-(4-amidinophenyl)-2-hydroxy-2-[(2R)-3-oxo-4-(4-thiophen-3-ylphenyl)morpholin-2-yl]acetamide hydrochloride (EXAMPLE 10)

EXAMPLE 10

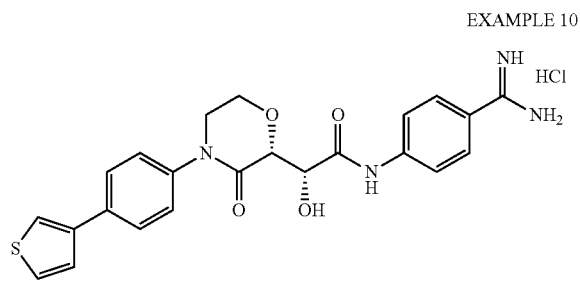 [SMILES: N=C(N)c1ccc(NC(=O)[C@H](O)[C@H]2OCCN(c3ccc(-c4ccsc4)cc3)C2=O)cc1 ; Cl]

Step 10-1

Synthesis of N-(2-chloroethyl)-4-thiophen-3-ylaniline (Compound 10-1)

According to the Step 7-1 in synthetic method for EXAMPLE 7, 4-(thiophen-3-yl)aniline (50 mg) was used instead of 4-methylaniline to obtain compound 10-1 (15 mg) a pale yellow amorphous solid.

Step 10-2

Synthesis of [(2R,3R)-3-acetyloxy-1-[N-(2-chloroethyl)-4-thiophen-3-ylanilino]-4-(4-cyanoanilino)-1,4-dioxobutan-2-yl]acetate (Compound 10-2)

According to the Step 7-3 in synthetic method for EXAMPLE 7, compound 10-1 (160 mg) was used instead of compound 7-1 to obtain compound 10-2 (122 mg) as a colorless amorphous solid.

Step 10-3

Synthesis of (2R,3R)—N-(2-chloroethyl)-N-(4-cyanophenyl)-2,3-dihydroxy-N-(4-thiophen-3-ylphenyl)butanediamide (Compound 10-3)

According to the Step 7-4 in synthetic method for EXAMPLE 7, compound 10-2 (115 mg) was used instead of compound 7-3 to obtain crude 10-3. The crude 10-3 was used in the next step without further purification.

Step 10-4

Synthesis of (2R)—N-(4-cyanophenyl)-2-hydroxy-2-[(2R)-3-oxo-4-(4-thiophen-3-ylphenyl)morpholin-2-yl]acetamide (Compound 10-4)

According to the Step 7-5 in synthetic method for EXAMPLE 7, crude 10-3 was used instead of compound 7-4 to obtain compound 10-4 (46 mg) as a pale brown amorphous solid.

Step 10-5

Synthesis of (2R)—N-(4-amidinophenyl)-2-hydroxy-2-[(2R)-3-oxo-4-(4-thiophen-3-ylphenyl)morpholin-2-yl]acetamide hydrochloride (EXAMPLE10)

According to the Step 7-6 in synthetic method for EXAMPLE 7, compound 10-4 (45 mg) was used instead of compound 7-5 to obtain EXAMPLE 10 (8.2 mg) as a colorless amorphous solid.

Example 11

Synthesis of (2R)—N-(4-amidinophenyl)-2-[(2R)-4-(4-tert-butylphenyl)-3-oxomorpholin-2-yl]-2-hydroxyacetamide Hydrochloride (EXAMPLE 11)

EXAMPLE 11

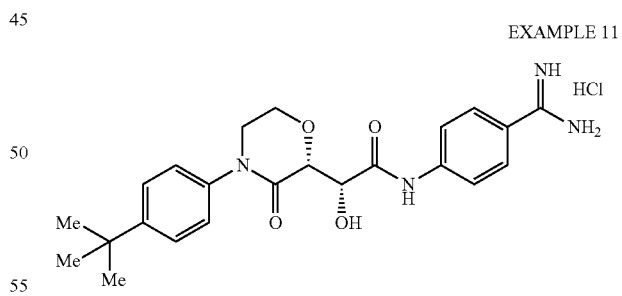

Step 11-1

Synthesis of 4-tert-butyl-N-(2-chloroethyl)aniline (Compound 11-1)

According to the Step 7-1 in synthetic method for EXAMPLE 7, 4-tert-butylaniline (5 g) was used instead of 4-methylaniline to obtain compound 11-1 (4.8 g) as pale brown oil.

Step 11-2

Synthesis of [(2R,3R)-3-acetyloxy-1-[4-tert-butyl-N-(2-chloroethyl)anilino]-4-(4-cyanoanilino)-1,4-dioxobutan-2-yl]acetate (Compound 11-2)

According to the Step 7-3 in synthetic method for EXAMPLE 7, compound 11-1 (2.28 g) was used instead of compound 7-1 to obtain compound 11-2 (1.19 g) as a colorless amorphous solid.

Step 11-3

Synthesis of (2R,3R)—N-(4-tert-Butylphenyl)-N-(2-chloroethyl)-N-(4-cyanophenyl)-2,3-dihydroxybutanediamide (Compound 11-3)

According to the Step 7-4 in synthetic method for EXAMPLE 7, compound 11-2 (0.3 g) was used instead of compound 7-3 to obtain crude 11-3. The crude 11-3 was used in the next step without further purification.

Step 11-4

Synthesis of (2R)-2-[(2R)-4-(4-tert-butylphenyl)-3-oxomorpholin-2-yl]-N-(4-cyanophenyl)-2-hydroxyacetamide (Compound 11-4)

According to the Step 7-5 in synthetic method for EXAMPLE 7, crude 11-3 was used instead of compound 7-4 to obtain compound 11-4 (115 mg) as a colorless amorphous solid.

Step 11-5

Synthesis of (2R)—N-(4-amidinophenyl)-2-[(2R)-4-(4-tert-butylphenyl)-3-oxomorpholin-2-yl]-2-hydroxyacetamide Hydrochloride (EXAMPLE 11)

According to the Step 7-6 in synthetic method for EXAMPLE 7, compound 11-4 (0.11 g) was used instead of compound 7-5 to obtain EXAMPLE 11 (30.9 mg) as a colorless amorphous solid.

Example 12

Synthesis of (2R)—N-(4-amidinophenyl)-2-hydroxy-2-[(2R)-4-[4-(hydroxymethyl)phenyl]-3-oxomorpholin-2-yl]acetamide hydrochloride (EXAMPLE 12)

Step 12-1

Synthesis of [4-(2-chloroethylamino)phenyl]methanol (Compound 12-1)

According to the Step 7-1 in synthetic method for EXAMPLE 7, 4-hydroxymethylaniline (1 g) was used instead of 4-methylaniline to obtain compound 12-1 (690 mg) as pale yellow oil.

Step 12-2

Synthesis of [(2R,3R)-3-acetyloxy-1-[N-(2-chloroethyl)-4-(hydroxymethyl)anilino]-4-(4-cyanoanilino)-1,4-dioxobutan-2-yl]acetate (Compound 12-2)

According to the Step 7-3 in synthetic method for EXAMPLE 7, compound 12-1 (2 g) was used instead of compound 7-1 to obtain compound 12-2 (1.91 g) as a colorless amorphous solid.

Step 12-3

Synthesis of (2R,3R)—N-(2-chloroethyl)-N'-(4-cyanophenyl)-2,3-dihydroxy-N-[4-(hydroxymethyl)phenyl]butanediamide (Compound 12-3)

According to the Step 7-4 in synthetic method for EXAMPLE 7, compound 12-2 (0.2 g) was used instead of compound 7-3 to obtain crude 12-3. The crude 12-3 was used in the next step without further purification.

Step 12-4

Synthesis of (2R)—N-(4-cyanophenyl)-2-hydroxy-2-[(2R)-4-[4-(hydroxymethyl)phenyl]-3-oxomorpholin-2-yl]acetamide (Compound 12-4)

According to the Step 7-5 in synthetic method for EXAMPLE 7, crude 12-3 was used instead of compound 7-4 to obtain compound 12-4 (80 mg) as a pale brown amorphous solid.

Step 12-5

Synthesis of (2R)—N-(4-amidinophenyl)-2-hydroxy-2-[(2R)-4-[4-(hydroxymethyl)phenyl]-3-oxomorpholin-2-yl]acetamide hydrochloride (EXAMPLE 12)

According to the Step 7-6 in synthetic method for EXAMPLE 7, compound 12-4 (73 mg) was used instead of compound 7-5 to obtain EXAMPLE 12 (16.6 mg) a colorless amorphous solid.

Example 13

Synthesis of (2R)—N-(4-amidinophenyl)-2-hydroxy-2-[(2R)-3-oxo-4-(2-oxo-1,3-dihydroindol-5-yl)morpholin-2-yl]acetamide hydrochloride (EXAMPLE 13)

EXAMPLE 12

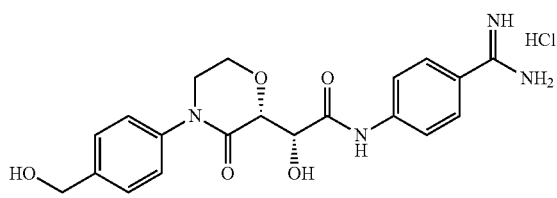

EXAMPLE 13

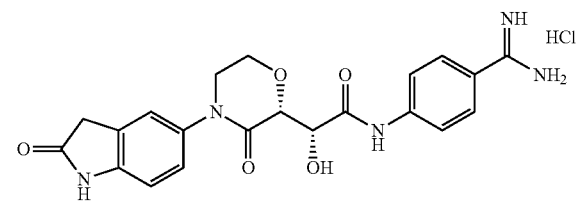

Step 13-1

5-(2-Chloroethylamino)-1,3-dihydroindol-2-one (Compound 13-1)

According to the Step 7-1 in synthetic method for EXAMPLE 7, 5-amino-2-indolinone (0.46 g) was used instead of 4-methylaniline to obtain compound 13-1 (470 mg) as a brown amorphous solid.

Step 13-2

Synthesis of [(2R,3R)-3-acetyloxy-1-[2-chloroethyl-(2-oxo-1,3-dihydroindol-5-yl)-amino]-5-(4-cyanophenyl)-1,4-dioxopentan-2-yl]acetate (Compound 13-2)

According to the Step 7-3 in synthetic method for EXAMPLE 7, compound 13-1 (0.47 g) was used instead of compound 7-1 to obtain compound 13-2 (330 mg) as a brown amorphous solid.

Step 13-3

Synthesis of (2R,3R)—N-(2-chloroethyl)-N'-(4-cyanophenyl)-2,3-dihydroxy-N-(2-oxo-1,3-dihydroindol-5-yl)butanediamide (Compound 13-3)

According to the Step 7-4 in synthetic method for EXAMPLE 7, compound 13-2 (100 mg) was used instead of compound 7-3 to obtain crude 13-3. The crude 13-3 was used in the next step without further purification.

Step 13-4

Synthesis of (2R)—N-(4-cyanophenyl)-2-hydroxy-2-[(2R)-3-oxo-4-(2-oxo-1,3-dihydroindol-5-yl)morpholin-2-yl]acetamide (Compound 13-4)

According to the Step 7-5 in synthetic method for EXAMPLE 7 crude 13-3 was used instead of compound 7-4 to obtain compound 13-4 (40 mg) as a brown amorphous solid.

Step 13-5

Synthesis of (2R)—N-(4-amidinophenyl)-2-hydroxy-2-[(2R)-3-oxo-4-(2-oxo-1,3-dihydroindol-5-yl)morpholin-2-yl]acetamide hydrochloride (EXAMPLE 13)

According to the Step 7-6 in synthetic method for EXAMPLE 7, compound 13-4 (0.76 g) was used instead of compound 7-5, to obtain EXAMPLE 13 (8 mg) as a pale yellow amorphous solid.

Example 14

Synthesis of (2R)—N-(4-amidinophenyl)-2-hydroxy-2-[(2R)-4-(4-iodophenyl)-3-oxomorpholin-2-yl]acetamide hydrochloride (EXAMPLE 14)

Step 14-1

Synthesis of N-(2-chloroethyl)-4-iodoaniline (Compound 14-1)

According to the Step 7-1 in synthetic method for EXAMPLE 7, 4-iodoaniline (10 g) was used instead of 4-methylaniline to obtain compound 14-1 (2.5 g) as colorless oil.

Step 14-2

Synthesis of [(2R,3R)-3-acetyloxy-1-[N-(2-chloroethyl)-4-iodoanilino]-4-(4-cyanoanilino)-1,4-dioxobutan-2-yl]acetate (Compound 14-2)

According to the Step 7-3 in synthetic method for EXAMPLE 7, compound 14-1 (2.39 g) was used instead of compound 7-1 to obtain compound 14-2 (2.4 g) as a colorless amorphous solid.

Step 14-3

Synthesis of (2R,3R)—N-(2-chloroethyl)-N'-(4-cyanophenyl)-2,3-dihydroxy-N-(4-iodophenyl)butane diamide (Compound 14-3)

According to the Step 7-4 in synthetic method for EXAMPLE 7, compound 14-2 (0.3 g) was used instead of compound 7-3 to obtain crude 14-3. The crude 14-3 was used in the next step without further purification.

Step 14-4

Synthesis of (2R)—N-(4-cyanophenyl)-2-hydroxy-2-[(2R)-4-(4-iodophenyl)-3-oxomorpholin-2-yl]acetamide (Compound 14-4)

According to the Step 7-5 in synthetic method for EXAMPLE 7, crude 14-3 was used instead of compound 7-4 to obtain compound 14-4 (160 mg) as a colorless amorphous solid.

Step 14-5

Synthesis of (2R)—N-(4-amidinophenyl)-2-hydroxy-2-[(2R)-4-(4-iodophenyl)-3-oxomorpholin-2-yl]acetamide hydrochloride (EXAMPLE 14)

According to the Step 7-6 in synthetic method for EXAMPLE 7, compound 14-4 (80 mg) was used instead of compound 7-5 to obtain EXAMPLE 14 (11 mg) as a pale yellow amorphous solid.

Example 15

Synthesis of (2R)—N-(4-amidinophenyl)-2-[(2R)-4-(4-cyclohexylphenyl)-3-oxomorpholin-2-yl]-2-hydroxyacetamide Hydrochloride (EXAMPLE 15)

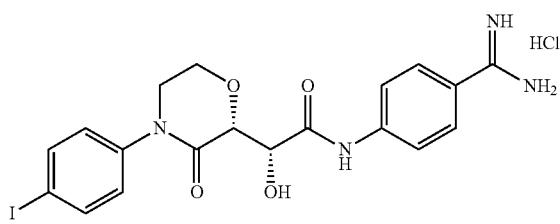

EXAMPLE 14

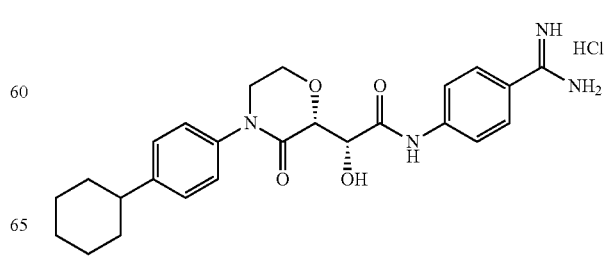

EXAMPLE 15

Step 15-1

Synthesis of N-(2-chloroethyl)-4-cyclohexylaniline (Compound 15-1)

According to the Step 7-1 in synthetic method for EXAMPLE 7, 4-cyclohexylaniline (0.9 g) was used instead of 4-methylaniline to obtain compound 15-1 (1.04 g) as brown oil.

Step 15-2

Synthesis of [(2R,3R)-3-acetyloxy-4-[N-(2-chloroethyl)-4-cyclohexylanilino]-1-(4-cyanoanilino)-1,4-dioxobutan-2-yl]acetate (Compound 15-2)

According to the Step 7-3 in synthetic method for EXAMPLE 7, compound 15-1 (1 g) was used instead of compound 7-1 to obtain compound 15-2 (1.05 g) as a colorless amorphous solid.

Step 15-3

Synthesis of (2R)—N-(4-cyanophenyl)-2-[(2R)-4-(4-cyclohexylphenyl)-3-oxomorpholin-2-yl]-2-hydroxyacetamide (Compound 15-3)

According to the Step 7-4 and 7-5 in synthetic method for EXAMPLE 7, compound 15-2 (1 g) was used instead of compound 7-3 to obtain compound 15-3 (610 mg) as a colorless amorphous solid.

Step 15-4

Synthesis of (2R)—N-(4-amidinophenyl)-2-[(2R)-4-(4-cyclohexylphenyl)-3-oxomorpholin-2-yl]-2-hydroxyacetamide Hydrochloride (EXAMPLE 15)

According to the Step 7-6 in synthetic method for EXAMPLE 7, compound 15-3 (30 mg) was used instead of compound 7-5 to obtain EXAMPLE 15 (1.8 mg) as a colorless amorphous solid.

Example 16

Synthesis of (2R)—N-(4-amidinophenyl)-2-hydroxy-2-[(2R)-3-oxo-4-(4-propan-2-ylphenyl)morpholin-2-yl]acetamide hydrochloride (EXAMPLE 16)

EXAMPLE 16

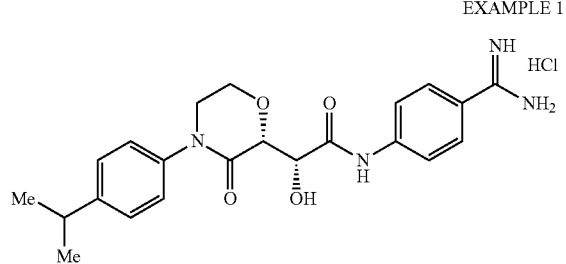

Step 16-1

Synthesis of N-(2-chloroethyl)-4-propan-2-ylaniline (Compound 16-1)

According to the Step 7-1 in synthetic method for EXAMPLE 7, 4-isopropylaniline (1 g) was used instead of 4-methylaniline to obtain compound 16-1 (1.35 g) as brown oil.

Step 16-2

Synthesis of [(2R,3R)-3-acetyloxy-4-[N-(2-chloroethyl)-4-propan-2-ylanilino]-1-(4-cyanoanilino)-1,4-dioxobutan-2-yl]acetate (Compound 16-2)

According to the Step 7-3 in synthetic method for EXAMPLE 7, compound 16-1 (1.3 g) was used instead of compound 7-1 to obtain compound 16-2 (1.27 g) as a brown amorphous solid.

Step 16-3

Synthesis of (2R)—N-(4-cyanophenyl)-2-hydroxy-2-[(2R)-3-oxo-4-(4-propan-2-ylphenyl)morpholin-2-yl]acetamide (Compound 16-3)

According to the Step 7-4 and 7-5 in synthetic method for EXAMPLE 7, compound 16-2 (1.2 g) was used instead of compound 7-3 to obtain compound 16-3 (570 mg) as a colorless amorphous solid.

Step 16-4

Synthesis of (2R)—N-(4-amidinophenyl)-2-hydroxy-2-[(2R)-3-oxo-4-(4-(propan-2-yl)phenyl)morpholin-2-yl]acetamide hydrochloride (EXAMPLE 16)

According to the Step 7-6 in synthetic method for EXAMPLE 7, compound 16-3 (30 mg) was used instead of compound 7-5 to obtain EXAMPLE 16 (1.8 mg) as a colorless amorphous solid.

Example 17

Synthesis of (2R)—N-(4-amidinophenyl)-2-[(2R)-4-(4-ethylphenyl)-3-oxomorpholin-2-yl]-2-hydroxy acetamide hydrochloride (EXAMPLE 17)

EXAMPLE 17

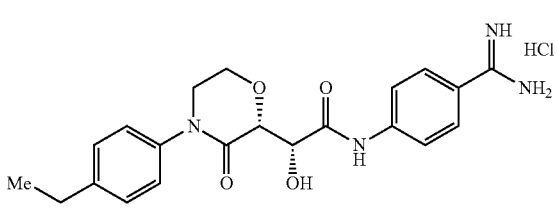

Step 17-1

Synthesis of N-(2-chloroethyl)-4-ethylaniline (Compound 17-1)

According to the Step 7-1 in synthetic method for EXAMPLE 7, 4-ethylaniline (5.15 mL) was used instead of 4-methylaniline to obtain crude 17-1. The crude 17-1 was used in the next step without further purification.

Step 17-2

Synthesis of [(2R,3R)-3-acetyloxy-4-[N-(2-chloroethyl)-4-ethylanilino]-1-(4-cyanoanilino)-1,4-dioxobutan-2-yl]acetate (Compound 17-2)

According to the Step 7-3 in synthetic method for EXAMPLE 7, crude 17-1 (2.31 g) was used instead of compound 7-1 to obtain compound 17-2 (1.57 g) as a colorless amorphous solid.

Step 17-3

Synthesis of (2R,3R)—N-(2-chloroethyl)-N'-(4-cyanophenyl)-N-(4-ethylphenyl)-2,3-dihydroxybutane diamide (Compound 17-3)

According to the Step 7-4 in synthetic method for EXAMPLE 7, compound 17-2 (1.5 g) was used instead of compound 7-3 to obtain crude 17-3. The crude 17-3 was used in the next step without further purification.

Step 17-4

Synthesis of (2R)—N-(4-cyanophenyl)-2-[(2R)-4-(4-ethylphenyl)-3-oxomorpholin-2-yl]-2-hydroxyacetamide (Compound 17-4)

According to the Step 7-5 in synthetic method for EXAMPLE 7, crude 17-3 was used instead of compound 7-4 to obtain compound 17-4 (0.76 g) as a colorless amorphous solid.

Step 17-5

Synthesis of (2R)—N-(4-amidinophenyl)-2-[(2R)-4-(4-ethylphenyl)-3-oxomorpholin-2-yl]-2-hydroxy acetamide hydrochloride (EXAMPLE 17)

According to the Step 7-6 in synthetic method for EXAMPLE 7, compound 17-4 (0.1 g) was used instead of compound 7-5 to obtain EXAMPLE 17 (5 mg) as a colorless amorphous solid.

Example 18

Synthesis of Synthesis of (2R)—N-(4-amidinophenyl)-2-hydroxy-2-[(2R)-4-(1H-indol-6-yl)-3-oxomorpholin-2-yl]acetamide trifluoroacetate (EXAMPLE 18)

EXAMPLE 18

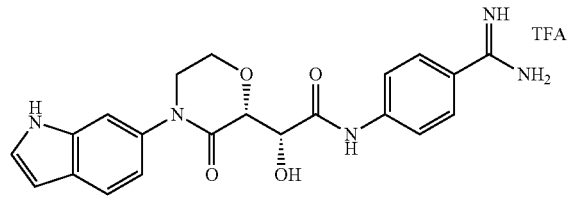

Step 18-1

Synthesis of [(2R,3R)-3-acetyloxy-4-(4-cyanoanilino)-1-[2-hydroxyethyl(1H-indol-6-yl)amino]-1,4-dioxobutan-2-yl]acetate (Compound 18-1)

According to the Step 7-3 in synthetic method for EXAMPLE 7, 6-(2-hydroxyethyl)aminoindole (1.99 g; EP424261A1) was used instead of compound 7-1 to obtain compound 18-1 (620 mg) as a colorless amorphous solid.

Step 18-2

Synthesis of [(2R,3R)-3-acetyloxy-4-(4-cyanoanilino)-1-[1H-indol-6-yl(2-methylsulfonyloxyethyl)amino]-1,4-dioxobutan-2-yl]acetate (Compound 18-2)

To a solution of compound 18-1 (0.3 g) in $CH_2Cl_2$ (9 mL), were added triethylamine (127 microL) and mesylchloride (51.9 microL) at 0° C. The reaction mixture was stirred at 0° C. for 20 minutes. Then EtOAc and water were added into the mixture and it was extraceted with EtOAc. The organic layer was washed with $H_2O$, 1N HCl, sat. $NaHCO_3$ aq, and brine. Then it was dried with anhyd. $Na_2SO_4$. The solvent was removed under reduced pressure to obtain compound 18-2 (350 mg) as a pale yellow amorphous solid. Compound 18-2 was used in the next step without further purification.

Step 18-3

Synthesis of (2R)—N-(4-cyanophenyl)-2-hydroxy-2-[(2R)-4-(1H-indol-6-yl)-3-oxomorpholin-2-yl]acetamide (Compound 18-3)

To a solution of compound 18-2 (0.34 g) in MeOH (10.2 mL), was added $K_2CO_3$ (272 mg) at 0° C. The reaction mixture was stirred at 0° C. overnight. Then 1N HCl (2 mL), $H_2O$ (5 mL) and $Et_2O$ (15 mL) were added into the reaction mixture. The precipitate was collected by filtration and was rinsed with $H_2O$ and $Et_2O$ to obtain compound 18-3 (40 mg) as a colorless amorphous solid.

Step 18-4

Synthesis of (2R)—N-(4-amidinophenyl)-2-hydroxy-2-[(2R)-4-(1H-indol-6-yl)-3-oxomorpholin-2-yl]acetamide trifluoroacetate (EXAMPLE 18)

To a solution of compound 18-3 (50 mg) in EtOH—$H_2O$ (10 mL-2.5 mL), were added triethylamine (143 microL) and hydroxyl-amine hydrochloride salt (71.2 mg). The reaction mixture was stirred at 80° C. in a sealed tube for 20 hours. Then the reaction mixture was concentrated in vacuo. The resulting residue which include hydroxyamidine compound (54 mg) was solved in AcOH-MeOH (1 mL-9 mL) and 10% palladium-charcaol (54 mg) was added into the above mixture. The reaction mixture was stirred under hydrogen gas atmosphere at room temperature overnight. After confirming the completion of the reaction by LC/MS, Pd—C was removed by filtration with Celite® pad. The filtrate was concentrated in vacuo and the resulting residue was purified by prep LC/MS to obtain EXAMPLE 18 (4.2 mg) as a pale yellow amorphous solid.

Example 19

Synthesis of (2R)—N-(4-amidinophenyl)-2-[(2R)-4-(3,3-dimethyl-2-oxo-1H-indol-6-yl)-3-oxomorpholin-2-yl]-2-hydroxyacetamide hydrochloride (EXAMPLE 19)

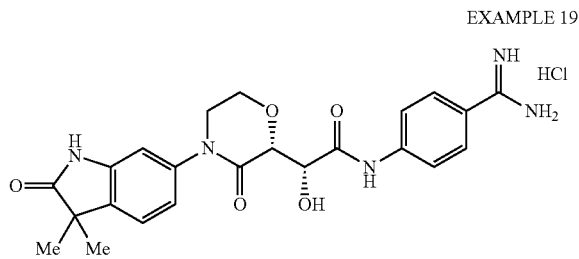 [SMILES: CC1(C)C(=O)Nc2cc(N3CCO[C@H]([C@@H](O)C(=O)Nc4ccc(C(=N)N)cc4)C3=O)ccc21 ; Cl]

EXAMPLE 19

Step 19-1

Synthesis of 6-(2-chloroethylamino)-3,3-dimethyl-1H-indol-2-one 19-1

According to the Step 7-1 in synthetic method for EXAMPLE 7, 6-amino-1,3-dihydro-3,3-dimethyl-2H-indol-2-one (1 g) was used instead of 4-methylaniline to obtain compound 19-1 (1.05 g) as a brown amorphous solid.

Step 19-2

Synthesis of [(2R,3R)-3-acetyloxy-1-[2-chloroethyl-(3,3-dimethyl-2-oxo-1H-indol-6-yl)amino]-4-(4-cyanoanilino)-1,4-dioxobutan-2-yl]acetate (Compound 19-2)

According to the Step 7-3 in synthetic method for EXAMPLE 7, compound 19-1 (1 g) was used instead of compound 7-1 to obtain compound 19-2 (0.39 g) as a yellow amorphous solid.

Step 19-3

Synthesis of (2R,3R)—N-(2-chloroethyl)-N'-(4-cyanophenyl)-N-(3,3-dimethyl-2-oxo-1H-indol-6-yl)-2,3-dihydroxybutanediamide (Compound 19-3)

According to the Step 7-4 in synthetic method for EXAMPLE 7, compound 19-2 (0.38 g) was used instead of compound 7-3 to obtain crude 19-3. The crude 19-3 was used in the next step without further purification.

Step 19-4

Synthesis of (2R)—N-(4-cyanophenyl)-2-[(2R)-4-(3,3-dimethyl-2-oxo-1H-indol-6-yl)-3-oxomorpholin-2-yl]-2-hydroxyacetamide (Compound 19-4)

According to the Step 7-5 in synthetic method for EXAMPLE 7, crude 19-3 was used instead of compound 7-4 to obtain compound 19-4 (190 mg) as a colorless amorphous solid.

Step 19-5

Synthesis of (2R)—N-(4-amidinophenyl)-2-[(2R)-4-(3,3-dimethyl-2-oxo-1H-indol-6-yl)-3-oxomorpholin-2-yl]-2-hydroxyacetamide hydrochloride (EXAMPLE 19)

According to the Step 7-6 in synthetic method for EXAMPLE 7, compound 19-4 (50 mg) was used instead of compound 7-5 to obtain EXAMPLE 19 (18 mg) as a pale yellow amorphous solid.

Example 20

(2R)—N-(4-Amidinophenyl)-2-hydroxy-2-[(2R)-3-oxo-4-(2-oxo-1,3-dihydrobenzimidazol-5-yl)morpholin-2-yl]acetamide hydrochloride (EXAMPLE 20)

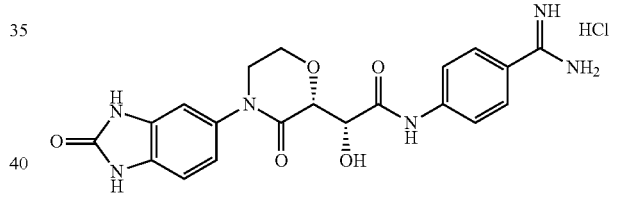

EXAMPLE 20

Step 20-1

Synthesis of 2-chloro-N-(2-oxo-1,3-dihydrobenzimidazol-5-yl)acetamide 20-1

To a suspension of 5-amino-1,3-dihydro-2H-benzimidazol-2-one (1 g) and $K_2CO_3$ (1.02 g) in DMF (20 mL), was added dropwise a solution of chloroacetylchloride (0.59 mL) in DMF (10 mL) at 0° C. The reaction mixture was stirred at room temperature for 3 hours. Then the mixture was diluted with water to precipitate. The precipitate was collected by filtration, rinsed with $H_2O$ to obtain compound 20-1 (1.2 g) as a colorless amorphous solid.

Step 20-2

Synthesis of 5-(2-chloroethylamino)-1,3-dihydrobenzimidazol-2-one (Compound 20-2)

To a suspension of compound 20-1 (1 g) in THF (10 mL), was added dropwise 1M $BH_3$-THF complex at 0° C. The reaction mixture was stirred at room temperature for 3 hours to complete the reaction. Then MeOH was carefully added to decompose an excess of $BH_3$ and then conc. HCl was added at 0° C. After stirring under reflux condition for 20 minutes, the mixture was diluted with water. It was extracted with EtOAc and the organic layer was washed with brine and dried with anhyd. $Na_2SO_4$. The solvent was removed under reduced pressure to obtain compound 20-2 (0.85 g) as a colorless amorphous solid.

Step 20-3

Synthesis of [(2R,3R)-3-acetyloxy-4-[2-chloroethyl-(2-oxo-1,3-dihydrobenzimidazol-5-yl)amino]-1-(4-cyanoanilino)-1,4-dioxobutan-2-yl]acetate (Compound 20-3)

According to the Step 7-3 in synthetic method for EXAMPLE 7, compound 20-2 (0.8 g) was used instead of compound 7-2 to obtain compound 20-3 (1.6 g) as a colorless amorphous solid.

Step 20-4

Synthesis of (2R,3R)—N-(2-chloroethyl)-N'-(4-cyanophenyl)-2,3-dihydroxy-N-(2-oxo-1,3-dihydrobenzimidazol-5-yl)butanediamide (Compound 20-4)

According to the Step 7-4 in synthetic method for EXAMPLE 7, compound 20-3 (1.6 g) was used instead of compound 7-3 to obtain crude 20-4. The crude 20-4 was used in the next step without further purification.

Step 20-5

Synthesis of (2R)—N-(4-cyanophenyl)-2-hydroxy-2-[(2R)-3-oxo-4-(2-oxo-1,3-dihydrobenzimidazol-5-yl)morpholin-2-yl]acetamide (Compound 20-5)

According to the Step 7-5 in synthetic method for EXAMPLE 7, crude 20-4 was used instead of compound 7-4 to obtain compound 20-5 (100 mg) as a brown amorphous solid.

Step 20-6

Synthesis of (2R)—N-(4-amidinophenyl)-2-hydroxy-2-[(2R)-3-oxo-4-(2-oxo-1,3-dihydrobenzimidazo1-5-yl)morpholin-2-yl]acetamide hydrochloride (EXAMPLE 20)

According to the Step 7-6 in synthetic method for EXAMPLE 7, compound 20-5 (50 mg) was used instead of compound 7-5 to obtain EXAMPLE 20 (8 mg) as a pale yellow amorphous solid.

Example 21

Synthesis of (2R)—N-(4-amidinophenyl)-2-hydroxy-2-[(2R)-3-oxo-4-methylphenylmethylmorpholin-2-yl]acetamide hydrochloride (EXAMPLE 21)

EXAMPLE 21

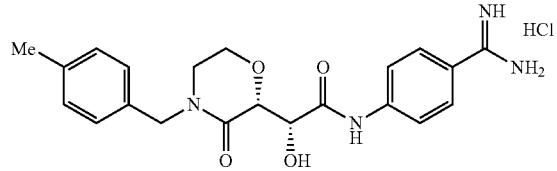

Step 21-1

Synthesis of [(2R,3R)-3-acetyloxy-1-(2-chloroethylmethylphenylmethylamino)-4-(4-cyanoanilino)-1,4-dioxobutan-2-yl]acetate (Compound 21-1)

According to the Step 7-1 and 7-3 in synthetic method for EXAMPLE 7, 4-methylbenzylamine (1.04 mL) was used instead of 4-methylaniline to obtain compound 21-1 (62 mg) as a colorless amorphous solid.

Step 21-2

Synthesis of (2R,3R)—N-(2-chloroethyl)-N'-(4-cyanophenyl)-2,3-dihydroxy-N-methylphenylmethylbutanediamide (Compound 21-2)

According to the Step 7-4 in synthetic method for EXAMPLE 7, compound 21-1 (60 mg) was used instead of compound 7-3 to obtain crude 21-2. The crude 21-2 was used in the next step without further purification.

Step 21-3

Synthesis of (2R)—N-(4-cyanophenyl)-2-hydroxy-2-[(2R)-3-oxo-4-methylphenylmethylmorpholin-2-yl] acetamide (Compound 21-3)

According to the Step 7-5 in synthetic method for EXAMPLE 7, crude 21-2 was used instead of compound 7-4 to obtain compound 21-3 (13 mg) as a colorless amorphous solid.

Step 21-4

Synthesis of (2R)—N-(4-amidinophenyl)-2-hydroxy-2-[(2R)-3-oxo-4-methylphenylmethylmorpholin-2-yl]acetamide hydrochloride (EXAMPLE 21)

According to the Step 7-6 in synthetic method for EXAMPLE 7, compound 21-3 (12 mg) was used instead of compound 7-5 to obtain EXAMPLE 21 (2 mg) as a pale yellow amorphous solid.

Example 22

Synthesis of (2R)—N-(4-amidinophenyl)-2-hydroxy-2-[(2R)-3-oxo-4-(4-(thiophen-2-yl)phenyl)morpholin-2-yl]acetamide hydrochloride (EXAMPLE 22)

EXAMPLE 22

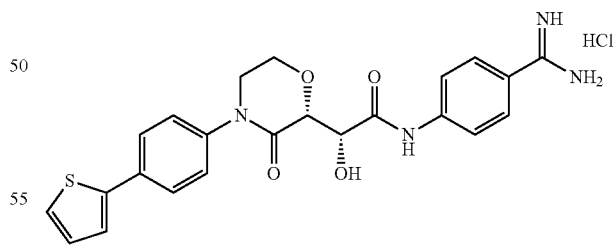

Step 22-1

Synthesis of (2R)—N-(4-cyanophenyl)-2-hydroxy-2-[(2R)-3-oxo-4-(4-(thiophen-2-yl)phenyl)morpholin-2-yl]acetamide (Compound 22-1)

To a suspension of compound 14-4 (80 mg) in THF—$H_2O$ (2 mL-0.67 mL), were added 2-thiopheneboronic acid (43 mgl), $Cs_2CO_3$ (0.44 g), and $Pd(Ph_3P)_4$ (19.4 mg). The mixture was stirred at 80° C. for 15 hours. The reaction mixture was filtered with Celite® pad and rinsed with the mixed solvent (EtOAc-MeOH=1-1). The filtrate was concentrated in vacuo and the resulting residue was washed with $H_2O$ and $Et_2O$. The precipitate was collected by filtration to obtain compound 22-1 (35 mg) as a pale brown amorphous solid.

Step 22-2

Synthesis of (2R)—N-(4-amidinophenyl)-2-hydroxy-2-[(2R)-3-oxo-4-(4-thiophen-2-ylphenyl)morpholin-2-yl]acetamide hydrochloride (EXAMPLE 22)

According to the Step 7-6 in synthetic method for EXAMPLE 7, compound 22-1 (25 mg) was used instead of compound 7-5 to obtain EXAMPLE 22 (1.4 mg) a brown amorphous solid.

Example 23

Synthesis of (2R)—N-(4-amidinophenyl)-2-[(2R)-4-biphenyl-3-oxomorpholin-2-yl]-2-hydroxyacetamide Hydrochloride (EXAMPLE 23)

EXAMPLE 23

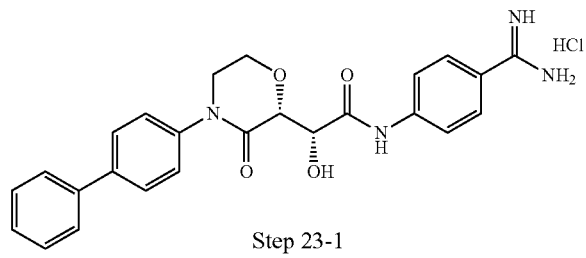

Step 23-1

Synthesis of (2R)-2-[(2R)-4-biphenyl-3-oxomorpholin-2-yl]-N-(4-cyanophenyl)-2-hydroxyacetamide (Compound 23-1)

According to the Step 22-1 in synthetic method for EXAMPLE 22, phenyl boronic acid (41 mg) was used instead of 2-thiopheneboronic acid to obtain compound 23-1 (42 mg) as a pale brown amorphous solid.

Step 23-2

Synthesis of (2R)—N-(4-amidinophenyl)-2-[(2R)-4-biphenyl-3-oxomorpholin-2-yl]-2-hydroxyacetamide Hydrochloride (EXAMPLE 23)

According to the Step 7-6 in synthetic method for EXAMPLE 7, compound 23-1 (25 mg) was used instead of compound 7-5 to obtain EXAMPLE 23 (4.2 mg) as a colorless amorphous solid.

Example 24

Synthesis of (2R)—N-(4-amidinophenyl)-2-[(2R)-4-(4'-tert-butylbiphenyl)-3-oxomorpholin-2-yl]-2-hydroxyacetamide Hydrochloride (EXAMPLE 24)

EXAMPLE 24

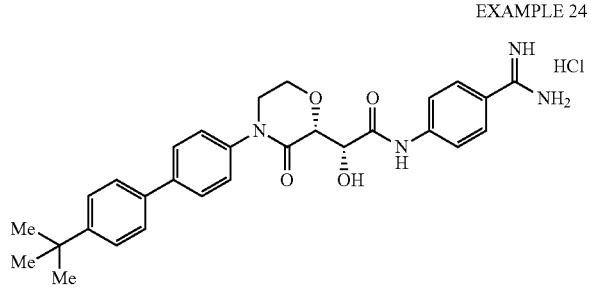 [SMILES: CC(C)(C)c1ccc(-c2ccc(N3CCO[C@H]([C@@H](O)C(=O)Nc4ccc(C(=N)N)cc4)C3=O)cc2)cc1 ; Cl]

Step 24-1

Synthesis of (2R)-2-[(2R)-4-(4'-tert-butylbiphenyl)-3-oxomorpholin-2-yl]-N-(4-cyanophenyl)-2-hydroxyacetamide (Compound 24-1)

According to the Step 22-1 in synthetic method for EXAMPLE 22, 4-tert-butylphenyl boronic acid (60 mg) was used instead of 2-thiopheneboronic acid to obtain compound 24-1 (65 mg) as a pale brown amorphous solid.

Step 24-2

Synthesis of (2R)—N-(4-amidinophenyl)-2-[(2R)-4-(4'-tert-butylbiphenyl)-3-oxomorpholin-2-yl]-2-hydroxyacetamide Hydrochloride (EXAMPLE 24)

According to the Step 7-6 in synthetic method for EXAMPLE 7, compound 24-1 (35 mg) was used instead of compound 7-5 to obtain EXAMPLE 24 (8 mg) as a colorless amorphous solid.

Example 25

Synthesis of (2R)—N-(4-amidinophenyl)-2-hydroxy-2-[(2R)-3-oxo-4-[4-(1H-pyrazol-4-yl)phenyl]morpholin-2-yl]acetamide dihydrochloride (EXAMPLE 25)

EXAMPLE 25

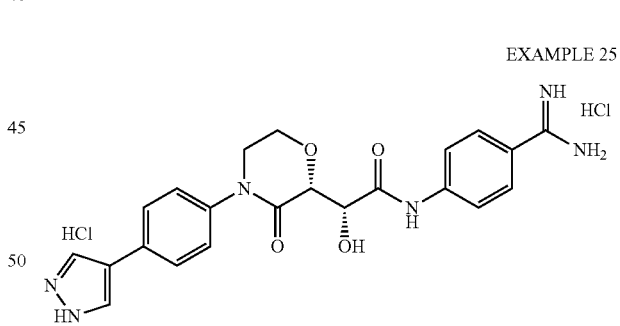

Step 25-1

Synthesis of (2R)—N-(4-cyanophenyl)-2-hydroxy-2-[(2R)-3-oxo-4-[4-(1H-pyrazol-4-yl)phenyl]morpholin-2-yl]acetamide (Compound 25-1)

According to the Step 22-1 in synthetic method for EXAMPLE 22, 1-Boc-4-(4,4,5,5-tetramethyl-1,3,2-dioxaborolan-2-yl)pyrazole (98 mg) was used instead of 2-thipheneboronic acid to obtain compound 25-1 (36 mg) as a pale brown amorphous solid.

Step 25-2

Synthesis of (2R)—N-(4-amidinophenyl)-2-hydroxy-2-[(2R)-3-oxo-4-[4-(1H-pyrazol-4-yl)phenyl]morpholin-2-yl]acetamide dihydrochloride (EXAMPLE 25)

According to the Step 7-6 in synthetic method for EXAMPLE 7, compound 25-1 (32 mg) was used instead of compound 7-5 to obtain EXAMPLE 25 (6.4 mg) as a colorless amorphous solid.

Example 26

Synthesis of (2R)-2-[(2R)-4-(4-acetamidophenyl)-3-oxomorpholin-2-yl]-N-(4-amidinophenyl)-2-hydroxyacetamide Hydrochloride (EXAMPLE 26)

EXAMPLE 26

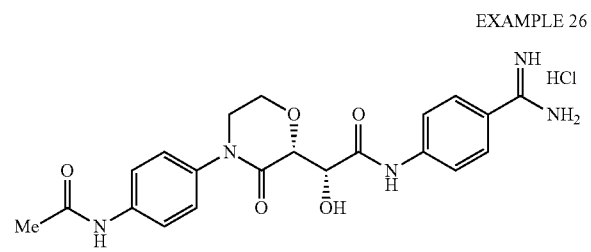 [SMILES: CC(=O)Nc1ccc(N2CCO[C@H]([C@@H](O)C(=O)Nc3ccc(C(=N)N)cc3)C2=O)cc1 ; Cl]

Method A

Step 26-1

Synthesis of tert-butyl N-[4-(2-chloroethylamino)phenyl]carbamate (Compound 26-1)

According to the Step 7-1 in synthetic method for EXAMPLE 7, 4-(tert-butoxycarbonylamino)aniline (11.6 g) was used instead of 4-methylaniline to obtain compound 26-1 (3.2 g) as a yellow brown amorphous solid.

Step 26-2

Synthesis of [(2R,3R)-3-acetyloxy-1-[N-(2-chloroethyl)-4-[(2-methylpropan-2-yl)oxycarbonylamino]anilino]-4-(4-cyanoanilino)-1,4-dioxobutan-2-yl]acetate (Compound 26-2)

According to the Step 7-3 in synthetic method for EXAMPLE 7, compound 26-1 (3.2 g) was used instead of compound 7-1 to obtain compound 26-2 (3.2 g) as colorless amorphous solid.

Step 26-3

Synthesis of tert-butyl N-[4-[2-chloroethyl-[(2R,3R)-4-(4-cyanoanilino)-2,3-dihydroxy-4-oxobutanoyl]amino]phenyl]carbamate (Compound 26-3)

According to the Step 7-4 in synthetic method for EXAMPLE 7, compound 26-2 (3.2 g) was used instead of compound 7-3 to obtain crude 26-3. The crude 26-3 was used in the next step without further purification.

Step 26-4

Synthesis of tert-butyl N-[4-[(2R)-2-[(1R)-2-(4-cyanoanilino)-1-hydroxy-2-oxoethyl]-3-oxomorpholin-4-yl]phenyl]carbamate (Compound 26-4)

According to the Step 7-5 in synthetic method for EXAMPLE 7, crude 26-3 was used instead of compound 7-4 to obtain compound 26-4 (1.68 g) as a colorless amorphous solid.

Step 26-5

Synthesis of (2R)-2-[(2R)-4-(4-aminophenyl)-3-oxomorpholin-2-yl]-N-(4-cyanophenyl)-2-hydroxyacetamide (Compound 26-5)

To compound 26-4 (1.65 g), was added trifluoroacetic acid (10 mL) with anisole (0.2 mL) at 0° C. The reaction mixture was stirred at 0° C. for 1 hour then $Et_2O$ was added into the mixture to precipitate. The precipitate was collected by filtration and washed with $Et_2O$. Then the precipitate was solved in water and the solution was basified with sat. $NaHCO_3$ aq. The precipitate was collected by filtration and washed with $H_2O$ to obtain compound 26-5 (1.2 g) as a pale brown amorphous solid.

Step 26-6

Synthesis of [(1R)-1-[(2R)-4-(4-acetamidophenyl)-3-oxomorpholin-2-yl]-2-(4-cyanoanilino)-2-oxoethyl] acetate (Compound 26-6)

To a suspension of compound 26-5 (70 mg) in pyridine (1 mL), was added $Ac_2O$ (43.4 microL). The mixture was stirred at room temperature overnight. The reaction mixture was diluted with water to precipitate. The precipitate was collected by filtration and rinsed with water to obtain compound 26-6 (85 mg) as a colorless amorphous solid.

Step 26-A

Synthesis of (2R)-2-[(2R)-4-(4-acetamidophenyl)-3-oxomorpholin-2-yl]-N-(4-amidinophenyl)-2-hydroxyacetamide Hydrochloride (EXAMPLE 26)

According to the Step 7-6 in synthetic method for EXAMPLE 7, compound 26-6 (50 mg) was used instead of compound 7-5 to obtain EXAMPLE 26 (2 mg) as a colorless amorphous solid.

Method B

Step 26-7

Synthesis of tert-butyl N-[4-[(2-chloroacetyl)amino]phenyl]carbamate (Compound 26-7)

According to the Step 20-1 in synthetic method for EXAMPLE 20, 4-(tert-butoxycarbonylamino)aniline (15 g) was used instead of 5-amino-1,3-dihydro-2H-benzimidazol-2-one to obtain compound 26-7 (19.5 g) as a gray amorphous solid.

Step 26-8

Synthesis of tert-butyl N-[4-(2-chloroethylamino)phenyl]carbamate (Compound 26-1)

According to the Step 20-2 in synthetic method for EXAMPLE 20, compound 26-7 (4 g) was used instead of compound 20-1 to obtain compound 26-1 (3.84 g).

Step 26-9

Synthesis of (2R,3R)-2,3-diacetyloxy-4-[N-(2-chloroethyl)-4-[(2-methylpropan-2-yl)oxycarbonylamino]anilino]-4-oxobutanoic acid (Compound 26-9)

To a solution of (+)-diacetyl-L-tartaric anhydride (3.01 g) in $CH_2Cl_2$ (40 mL), was added compound 26-1 (3.77 g) at 0° C. The mixture was stirred at room temperature for 1 hour. The solvent was removed under reduced pressure to obtain compound 26-9 (7.41 g) as a gray amorphous solid.

Step 26-10

Synthesis of [(2R,3R)-3-acetyloxy-4-[N-(2-chloroethyl)-4-[(2-methylpropan-2-yl)oxycarbonylamino]anilino]-1,4-dioxo-1-[4-(5-oxo-4H-1,2,4-oxadiazol-3-yl)anilino]butan-2-yl]acetate (Compound 26-10)

To a solution of compound 26-9 (4 g) in $CH_2Cl_2$ (40 mL), were added 3-(4-aminophenyl)-1,2,4-oxadiazol-5 (2H)-one (1.46 g; EP1574516 A1), 1-hydroxybenzotriazole hydrate (HOBt-$H_2O$; 0.13 g), and WSC-HCl (1.73 g). The reaction mixture was stirred at room temperature for 1.5 hours and it was concentrated in vacuo. The resulting residue was solved in EtOAc, the organic layer was washed with brine and dried with anhyd. $Na_2SO_4$. The solvent was removed under reduced pressure and the resulting residue was suspended in Hex-$Et_2O$=1-1. The precipitate was collected by filtration and rinsed with the above solvent to obtain compound 26-10 (4.45 g) as a pale brown amorphous solid.

Step 26-11

Synthesis of tert-butyl N-[4-[2-chloroethyl-[(2R,3R)-2,3-dihydroxy-4-oxo-4-[4-(5-oxo-4H-1,2,4-oxadiazol-3-yl)anilino]butanoyl]amino]phenyl]carbamate ammonium salt (Compound 26-11)

According to the Step 7-4 in synthetic method for EXAMPLE 7, compound 26-10 (3.5 g) was used instead of compound 7-3 to obtain compound 26-11 (3.04 g) as a pale brown amorphous solid.

Step 26-12

Synthesis of tert-butyl N-[4-[(2R)-2-[(1R)-1-Hydroxy-2-oxo-2-[4-(5-oxo-4H-1,2,4-oxadiazol-3-yl)anilino]ethyl]-3-oxomorpholin-4-yl]phenyl]carbamate (Compound 26-12)

According to the Step 7-5 in synthetic method for EXAMPLE 7, compound 26-11 (2.8 g) was used instead of compound 7-4 to obtain compound 26-12 (1.24 g) as an ivory weight amorphous solid.

Step 26-13

Synthesis of (2R)-2-[(2R)-4-(4-aminophenyl)-3-oxomorpholin-2-yl]-2-hydroxy-N-[4-(5-oxo-4H-1,2,4-oxadiazol-3-yl)phenyl]acetamide hydrochloride (Compound 26-13)

According to the Step 26-5 in synthetic method for EXAMPLE 26, compound 26-12 (1 g) was used instead of compound 26-4 to obtain compound 26-13 (830 mg) as a pale brown amorphous solid.

Step 26-14

Synthesis of (2R)-2-[(2R)-4-(4-acetamidophenyl)-3-oxomorpholin-2-yl]-2-hydroxy-N-[4-(5-oxo-4H-1,2,4-oxadiazol-3-yl)phenyl]acetamide (Compound 26-14)

According to the Step 26-6 in synthetic method for EXAMPLE 26, compound 26-13 (0.1 g) was used instead of compound 26-5 to obtain compound 26-14 (83 mg) as a colorless amorphous solid.

Step 26-B

Synthesis of (2R)-2-[(2R)-4-(4-acetamidophenyl)-3-oxomorpholin-2-yl]-N-(4-amidinophenyl)-2-hydroxyacetamide Hydrochloride (EXAMPLE 26)

To a suspension of compound 26-14 (80 mg) in MeOH-1N HCl (8 mL-8 mL), was added 10% Pd—C (80 mg) at room temperature. The reaction mixture was stirred under $H_2$ gas atmosphere at room temperature overnight. The reaction mixture was filtered with Celite® pad. The Celite® pad was washed with DMF and the filtrate was concentrated in vacuo. The resulting residue was suspended in MeOH and the precipitate was collected by filtration to obtain EXAMPLE 26 (38 mg) as a colorless amorphous solid.

Example 27

Synthesis of (2R)—N-(4-amidinophenyl)-2-[(2R)-4-[4-(carbamoylamino)phenyl]-3-oxomorpholin-2-yl]-2-hydroxyacetamide hydrochloride (EXAMPLE 27)

EXAMPLE 27

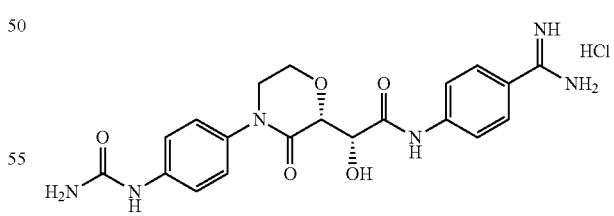

Step 27-1

Synthesis of (2R)-2-[(2R)-4-[4-(carbamoylamino)phenyl]-3-oxomorpholin-2-yl]-N-(4-cyanophenyl)-2-hydroxyacetamide (Compound 27-1)

To a solution of compound 26-5 (70 mg) in AcOH—$H_2O$ (6 mL-2 mL), was added a solution of potassium cyanate (KOCN; 31 mg) in water (2 mL). The reaction mixture was stirred at 40-50° C. for 3 hours and at room temperature overnight to precipitate. The resulting precipitate was collected by filtration, rinsed with waster and dried in vacuo to obtain compound 27-1 (70 mg) as a colorless amorphous solid.

Step 27-2

Synthesis of (2R)—N-(4-amidinophenyl)-2-[(2R)-4-[4-(carbamoylamino)phenyl]-3-oxomorpholin-2-yl]-2-hydroxyacetamide hydrochloride (EXAMPLE 27)

According to the Step 7-6 in synthetic method for EXAMPLE 7, compound 27-1 (50 mg) was used instead of compound 7-5 to obtain EXAMPLE 27 (3 mg) as a colorless amorphous solid.

Example 28

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

EXAMPLE 28

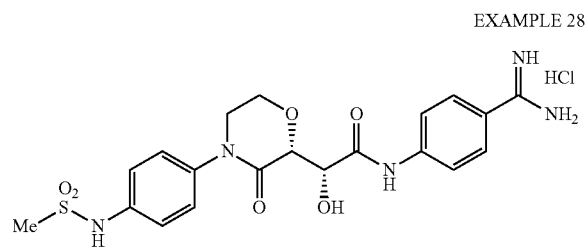 [SMILES: CS(=O)(=O)Nc1ccc(N2CCO[C@H]([C@@H](O)C(=O)Nc3ccc(C(=N)N)cc3)C2=O)cc1 ; Cl]

Method A

Step 28-1

Synthesis of (2R)—N-(4-cyanophenyl)-2-hydroxy-2-[(2R)-4-[4-(methanesulfonamido)phenyl]-3-oxo morpholin-2-yl]acetamide (Compound 28-1)

To a solution of compound 26-5 (70 mg) in DMF-pyridine (2 mL-2 mL), was added mesyl chloride (16.3 microL). The reaction mixture was stirred at room temperature overnight. The mixture was diluted with water then it was extracted with EtOAc. The extract was washed with water, 1N HCl and brine. The organic layer was dried with anhyd. $Na_2SO_4$ and the solvent was removed under reduced pressure to obtain compound 28-1 (30 mg) as a pale yellow amorphous solid.

Step 28-A

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

According to the Step 7-6 in synthetic method for EXAMPLE 7, compound 28-1 (28 mg) was used instead of compound 7-5 to obtain EXAMPLE 28 (4.9 mg) as a pale yellow amorphous solid.

Method B

Step 28-2

Synthesis of (2R)-2-hydroxy-2-[(2R)-4-[4-(methanesulfonamido)phenyl]-3-oxomorpholin-2-yl]-N-[4-(5-oxo-4H-1,2,4-oxadiazol-3-yl)phenyl]acetamide (Compound 28-2)

According to the Step 28-1 in synthetic method for EXAMPLE 28, compound 26-13 (0.1 g) was used instead of compound 26-5 to obtain compound 28-2 (50 mg) as a pale pink amorphous solid.

Step 28-B

Synthesis of (2R)—N-(4-amidinophenyl)-2-hydroxy-2-[(2R)-4-[4-(methanesulfonamido)phenyl]-3-oxomorpholin-2-yl]acetamide hydrochloride (EXAMPLE 28)

According to the Step 26-B in synthetic method for EXAMPLE 26, compound 28-2 (50 mg) was used instead of compound 26-14 to obtain EXAMPLE 28 (32 mg) as a pale yellow amorphous solid.

Example 29

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

EXAMPLE 29

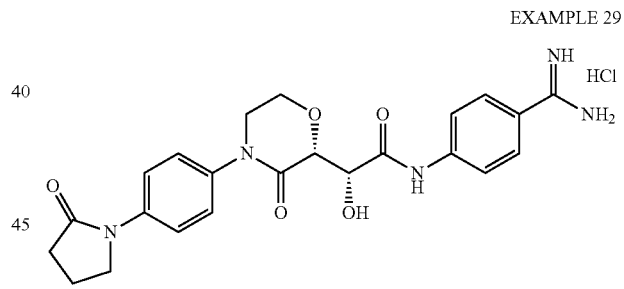

Method A

Step 29-1

Synthesis of (2R)—N-(4-cyanophenyl)-2-hydroxy-2-[(2R)-3-oxo-4-[4-(2-oxopyrrolidin-1-yl)phenyl]morpholin-2-yl]acetamide (Compound 29-1)

According to the Step 26-6 in synthetic method for EXAMPLE 26, chlorobutyryl chloride (33.6 microL) was used instead of acetyl chloride to obtain an acylated intermediate. After confirming the formation of it by LC/MS, tBuOK (91.9 mg) was added to the above solution. The reaction mixture was stirred at room temperature and for 2 hours. Then the mixture was diluted with water and it was extracted with EtOAc. The organic layer was washed with $H_2O$, 1N HCl, and brine. The organic layer was dried with anhyd. $Na_2SO_4$. The solvent was removed under reduced pressure to obtain compound 29-1 (73 mg) as a pale yellow amorphous solid.

Step 29-A

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

According to the Step 7-6 in synthetic method for EXAMPLE 7, compound 29-1 (67 mg) was used instead of compound 7-5 to obtain EXAMPLE 29 (6.6 mg) as a colorless amorphous solid.

Method B

Step 29-2

Synthesis of (2R)-2-hydroxy-N-[4-(5-oxo-4H-1,2,4-oxadiazol-3-yl)phenyl]-2-[(2R)-3-oxo-4-[4-(2-oxopyrrolidin-1-yl)phenyl]morpholin-2-yl]acetamide (Compound 29-2)

According to the Step 29-1 in synthetic method for EXAMPLE 29, compound 26-13 (0.1 g) was used instead of compound 26-5 to obtain compound 29-2 (68 mg) as a pale brown amorphous solid.

Step 29-B

Synthesis of (2R)—N-(4-amidinophenyl)-2-hydroxy-2-[(2R)-3-oxo-4-[4-(2-oxopyrrolidin-1-yl)phenyl]morpholin-2-yl]acetamide hydrochloride (EXAMPLE 29)

According to the Step 26-B in synthetic method for EXAMPLE 26, compound 29-2 (65 mg) was used instead of compound 26-14 to obtain EXAMPLE 29 (23 mg) as a colorless amorphous solid.

Example 30

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

EXAMPLE 30

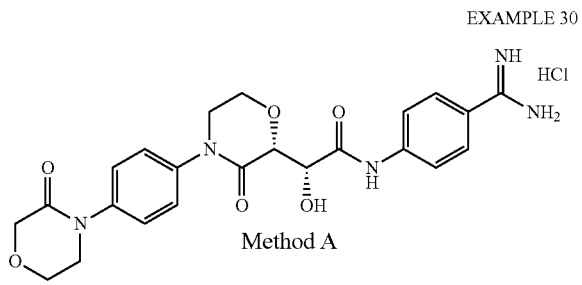 [SMILES: N=C(N)c1ccc(NC(=O)[C@H](O)[C@H]2OCCN(c3ccc(N4CCOCC4=O)cc3)C2=O)cc1 ; Cl]

Method A

Step 30-1

Synthesis of (2R)—N-(4-cyanophenyl)-2-hydroxy-2-[(2R)-3-oxo-4-[4-(3-oxomorpholin-4-yl)phenyl]morpholin-2-yl]acetamide (Compound 30-1)

To a suspension of compound 26-5 (0.1 g) and 2-chloroethoxy acetic acid (45.4 mg) in DMF (2 mL), was added 4-(4,6-dimethoxy-1,3,5-triazin-2-yl)-4-methylmorpholinium chloride (DMT-MM; 87.7 mg). The reaction mixture was stirred at room temperature overnight. Then, according to the Step 29-1 in synthetic method for EXAMPLE 29, cyclization reaction was pursued to obtain compound 30-1 (90 mg) as a colorless amorphous solid.

Step 30-A

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

According to the Step 7-6 in synthetic method for EXAMPLE 7, compound 30-1 (85 mg) was used instead of compound 7-5 to obtain EXAMPLE 30 (15.7 mg) as a colorless amorphous solid.

Method B

Step 30-2

Synthesis of (2R)-2-hydroxy-N-[4-(5-oxo-4H-1,2,4-oxadiazol-3-yl)phenyl]-2-[(2R)-3-oxo-4-[4-(3-oxomorpholin-4-yl)phenyl]morpholin-2-yl]acetamide (Compound 30-2)

According to the Step 30-1 in synthetic method for EXAMPLE 30, compound 26-13 (0.1 g) was used instead of compound 26-5 to obtain compound 30-2 (42 mg) as a colorless amorphous solid.

Step 30-B

Synthesis of (2R)—N-(4-amidinophenyl)-2-hydroxy-2-[(2R)-3-oxo-4-[4-(3-oxomorpholin-4-yl)phenyl]morpholin-2-yl]acetamide hydrochloride (EXAMPLE 30)

According to the Step 26-B in synthetic method for EXAMPLE 26, compound 30-2 (40 mg) was used instead of compound 26-14 to obtain EXAMPLE 30 (26.7 mg) as a colorless amorphous solid.

Example 31

Synthesis of (2R)—N-(4-amidinophenyl)-2-hydroxy-2-[(2R)-3-oxo-4-[4-(2-oxo-1,3-oxazolidin-3-yl)phenyl]morpholin-2-yl]acetamide hydrochloride (EXAMPLE 31)

EXAMPLE 31

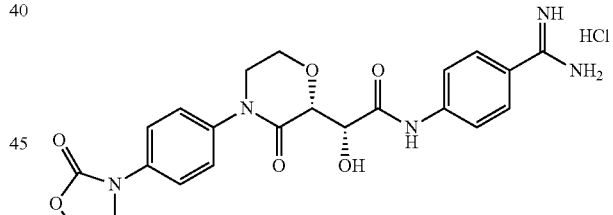

Step 31-1

Synthesis of (2R)—N-(4-cyanophenyl)-2-hydroxy-2-[(2R)-3-oxo-4-[4-(2-oxo-1,3-oxazolidin-3-yl)phenyl]morpholin-2-yl]acetamide (Compound 31-1)

According to the Step 29-1 in synthetic method for EXAMPLE 29, 2-chloroethyl chloroformate (31 microL) was used instead of chlorobutyryl chloride to obtain compound 31-1 (76 mg) as a colorless amorphous solid.

Step 31-2

Synthesis of (2R)—N-(4-amidinophenyl)-2-hydroxy-2-[(2R)-3-oxo-4-[4-(2-oxo-1,3-oxazolidin-3-yl)phenyl]morpholin-2-yl]acetamide hydrochloride (EXAMPLE 31)

According to the Step 7-6 in synthetic method for EXAMPLE 7, compound 31-1 (70 mg) was used instead of compound 7-5 to obtain EXAMPLE 31 (10.1 mg) as a colorless amorphous solid.

Example 32

Synthesis of (2R)—N-(4-amidinophenyl)-2-hydroxy-2-[(2R)-3-oxo-4-[4-[(2-phenylmethoxyacetyl)amino]phenyl]morpholin-2-yl]acetamide hydrochloride (EXAMPLE 32)

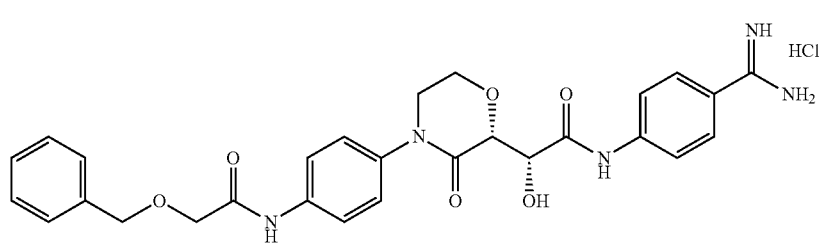

EXAMPLE 32

Step 32-1

Synthesis of (2R)—N-(4-cyanophenyl)-2-hydroxy-2-[(2R)-3-oxo-4-[4-[(2-phenylmethoxyacetyl)amino]phenyl]morpholin-2-yl]acetamide (Compound 32-1)

According to the Step 28-1 in synthetic method for EXAMPLE 28, (benzyloxy)acetyl chloride (94.8 microL) was used instead of mesyl chloride to obtain compound 32-1 (160 mg) as a colorless amorphous solid.

Step 32-2

Synthesis of (2R)—N-(4-amidinophenyl)-2-hydroxy-2-[(2R)-3-oxo-4-[4-[(2-phenylmethoxyacetyl)amino]phenyl]morpholin-2-yl]acetamide hydrochloride (EXAMPLE 32)

According to the Step 7-6 in synthetic method for EXAMPLE 7, compound 32-1 (150 mg) was used instead of compound 7-5 to obtain EXAMPLE 32 (150 mg) as a colorless amorphous solid.

Example 33

Synthesis of (2R)—N-(4-amidinophenyl)-2-hydroxy-2-[(2R)-4-[4-[(2-hydroxyacetyl)amino]phenyl]-3-oxomorpholin-2-yl]acetamide hydrochloride (EXAMPLE 33)

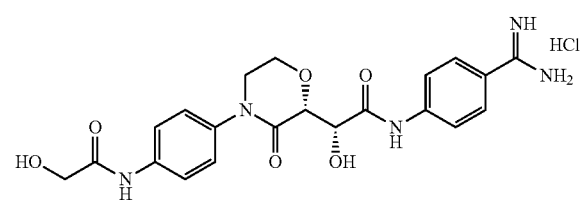

EXAMPLE 33

Step 33-1

Synthesis of (2R)—N-(4-amidinophenyl)-2-hydroxy-2-[(2R)-4-[4-[(2-hydroxyacetyl)amino]phenyl]-3-oxomorpholin-2-yl]acetamide hydrochloride (EXAMPLE 33)

To a solution of EXAMPLE 32 (0.12 g) in MeOH—AcOH (20 mL-1 mL), was added 10% Pd—C (20 mg). The reaction mixture was stirred under $H_2$ gas atmosphere at room temperature overnight. The reaction mixture was filtered to remove Pd—C and the filtrate was purified by prep. LC/MS. Before collecting the fractions, conc. HCl was added into each fraction to obtain EXAMPLE 33 (2 mg) as a colorless amorphous solid.

Example 34

Synthesis of (2R)—N-(4-amidinophenyl)-2-[(2R)-4-(3,3-dimethyl-2-oxo-1H-indol-5-yl)-3-oxomorpholin-2-yl]-2-hydroxyacetamide hydrochloride (EXAMPLE 34)

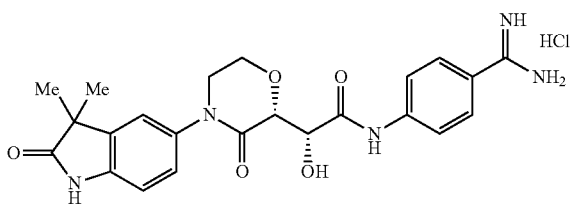

EXAMPLE 34

Step 34-1

5-(2-Chloroethylamino)-3,3-dimethyl-1H-indol-2-one (Compound 34-1)

According to the Step 7-1 in synthetic method for EXAMPLE 7, 3,3-dimethyl-1H-indol-2-one (0.5 g; *J. Med. Chem.*, 51, 4465-4475, 2008) was used instead of 4-methylaniline to obtain compound 34-1 (0.68 g) as a pale brown amorphous solid.

Step 34-2

Synthesis of (2R,3R)-2,3-diacetyloxy-4-[2-chloroethyl-(3,3-dimethyl-2-oxo-1H-indol-5-yl)amino]-4-oxobutanoic acid (Compound 34-2)

According to the Step 26-9 in synthetic method for EXAMPLE 26, compound 34-1 (680 mg) was used instead of compound 26-1 to obtain crude 34-2. The crude 34-2 was used in the next step without further purification.

Step 34-3

Synthesis of [(2R,3R)-3-acetyloxy-1-[2-chloroethyl-(3,3-dimethyl-2-oxo-1H-indol-5-yl)amino]-1,4-dioxo-4-[4-(5-oxo-4H-1,2,4-oxadiazol-3-yl)anilino]butan-2-yl]acetate (compound 34-3)

According to the Step 26-10 in synthetic method for EXAMPLE 26, crude 34-2 was used instead of compound 26-9 to obtain compound 34-3 (1.26 g) as a pale brown amorphous solid.

Step 34-4

Synthesis of (2R,3R)—N-(2-chloroethyl)-N-(3,3-dimethyl-2-oxo-1H-indol-5-yl)-2,3-dihydroxy-N-[4-(5-oxo-4H-1,2,4-oxadiazol-3-yl)phenyl]butanediamide ammonium salt (Compound 34-4)

According to the Step 7-4 in synthetic method for EXAMPLE 7, compound 34-3 (0.4 g) was used instead of compound 7-3 to obtain compound 34-4 (356 mg) as a colorless amorphous solid.

Step 34-5

Synthesis of (2R)-2-[(2R)-4-(3,3-dimethyl-2-oxo-1H-indol-5-yl)-3-oxomorpholin-2-yl]-2-hydroxy-N-[4-(5-oxo-4H-1,2,4-oxadiazol-3-yl)phenyl]acetamide (Compound 34-5)

According to the Step 7-5 in synthetic method for EXAMPLE 7, compound 34-4 (0.12 g) was used instead of compound 7-4 to obtain compound 34-5 (20.1 mg) as a pale yellow amorphous solid.

Step 34-6

Synthesis of (2R)—N-(4-amidinophenyl)-2-[(2R)-4-(3,3-dimethyl-2-oxo-1H-indol-5-yl)-3-oxomorpholin-2-yl]-2-hydroxyacetamide hydrochloride (EXAMPLE 34)

According to the Step 26-B in synthetic method for EXAMPLE 26, compound 34-5 (19 mg) was used instead of compound 26-14 to obtain EXAMPLE 34 (16.4 mg) as a pale yellow amorphous solid.

Example 35

Synthesis of (2R)—N-(4-amidinophenyl)-2-hydroxy-2-[(2R)-4-(1H-indol-5-yl)-3-oxomorpholin-2-yl]acetamide acetate (EXAMPLE 35)

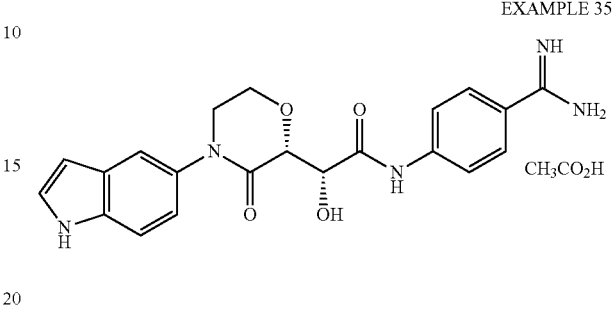

EXAMPLE 35

Step 35-1

Synthesis of 2-chloro-N-(1H-indol-5-yl)acetamide (Compound 35-1)

According to the Step 20-1 in synthetic method for EXAMPLE 20, 5-aminoindole (5.31 g) was used instead of 5-amino-1,3-dihydro-2H-benzimidazol-2-one to obtain compound 35-1 (8.38 g) as a brown amorphous solid.

Step 35-2

Synthesis of N-(2-chloroethyl)-1H-indol-5-amine (Compound 35-2)

According to the Step 20-2 in synthetic method for EXAMPLE 20, compound 35-1 (1 g) was used instead of compound 20-1 to obtain compound 35-2 (930 mg) as brown oil.

Step 35-3

Synthesis of (2R,3R)-2,3-diacetyloxy-4-[2-chloroethyl(1H-indol-5-yl)-amino]-4-oxobutanoic acid (Compound 35-3)

According to the Step 26-9 in synthetic method for EXAMPLE 26, compound 35-2 (327 mg) was used instead of compound 26-8 to obtain crude 35-3. The crude 35-3 was used in the next step without further purification.

Step 35-4

Synthesis of [(2R,3R)-3-acetyloxy-1-[2-chloroethyl(1H-indol-5-yl)amino]-1,4-dioxo-4-[4-(5-oxo-4H-1,2,4-oxadiazol-3-yl)anilino]butan-2-yl]acetate (Compound 35-4)

According to the Step 26-10 in synthetic method for EXAMPLE 26, crude 35-3 was used instead of compound 26-9 to obtain compound 35-4 (0.47 g) as a pale brown amorphous solid.

Step 35-5

Synthesis of (2R,3R)—N-(2-chloroethyl)-2,3-dihydroxy-N-(1H-indol-5-yl)-N'-[4-(5-oxo-4H-1,2,4-oxadiazol-3-yl)phenyl]butanediamide ammonium salt (Compound 35-5)

According to the Step 7-4 in synthetic method for EXAMPLE 7, compound 35-4 (0.2 g) was used instead of compound 7-3 to obtain crude 35-5. The crude 35-5 was used in the next step without further purification.

Step 35-6

Synthesis of (2R)-2-hydroxy-2-[(2R)-4-(1H-indol-5-yl)-3-oxomorpholin-2-yl]-N-[4-(5-oxo-4H-1,2,4-oxadiazol-3-yl)phenyl]acetamide (Compound 35-6)

According to the Step 7-5 in synthetic method for EXAMPLE 7, crude 35-5 was used instead of compound 7-4 to obtain 35-6 (65 mg) as a pale brown amorphous solid.

Step 35-7

Synthesis of (2R)—N-(4-amidinophenyl)-2-hydroxy-2-[(2R)-4-(1H-indol-5-yl)-3-oxomorpholin-2-yl]acetamide acetate (EXAMPLE 35)

According to the Step 26-B in synthetic method for EXAMPLE 26, compound 35-6 (20 mg) was used instead of compound 26-14 to obtain EXAMPLE 35 (13.6 mg) as pale brown amorphous solid.

Example 36

Synthesis of (2R)—N-(4-amidinophenyl)-2-hydroxy-2-[(2R)-3-oxo-4-(2-oxo-3H-1,3-benzoxazol-6-yl) morpholin-2-yl]acetamide hydrochloride (EXAMPLE 36)

EXAMPLE 36

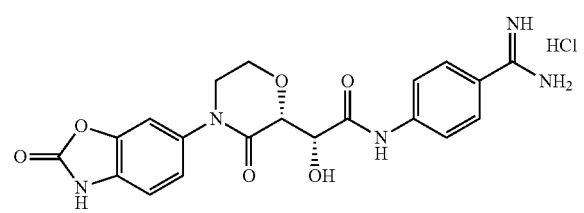

Step 36-1

Synthesis of 6-(2-chloroethylamino)-3H-1,3-benzoxazol-2-one (Compound 36-1)

According to the Step 7-1 in synthetic method for EXAMPLE 7, 6-amino-2-benzoxazolinone (0.5 g) was used instead of 4-methylaniline to obtain compound 36-1 (0.68 g) as brown oil.

Step 36-2

Synthesis of (2R,3R)-2,3-diacetyloxy-4-[2-chloroethyl-(2-oxo-3H-1,3-benzoxazol-6-yl)amino]-4-oxobutanoic acid (Compound 36-2)

According to the Step 26-9 in synthetic method for EXAMPLE 26, compound 36-1 (0.67 g) was used instead of compound 26-8 to obtain crude 36-2. The crude 36-2 was used in the next step without further purification.

Step 36-3

Synthesis of [(2R,3R)-3-acetyloxy-1-[2-chloroethyl-(2-oxo-3H-1,3-benzoxazol-6-yl)amino]-1,4-dioxo-4-[4-(5-oxo-4H-1,2,4-oxadiazol-3-yl)anilino]butan-2-yl]acetate (Compound 36-3)

According to the Step 26-10 in synthetic method for EXAMPLE 26, crude 36-2 was used instead of compound 26-9 to obtain compound 36-3 (0.1 g) as a pale brown amorphous solid.

Step 36-4

Synthesis of (2R,3R)—N-(2-chloroethyl)-2,3-dihydroxy-N-(2-oxo-3H-1,3-benzoxazol-6-yl)-N'-[4-(5-oxo-4H-1,2,4-oxadiazol-3-yl)phenyl]butanediamide ammonium salt (Compound 36-4)

According to the Step 7-4 in synthetic method for EXAMPLE 7, compound 36-3 (98 mg) was used instead of compound 7-3 to obtain crude 36-4. The crude 36-4 was used in the next step without further purification.

Step 36-5

Synthesis of (2R)-2-hydroxy-N-[4-(5-oxo-4H-1,2,4-oxadiazol-3-yl)phenyl]-2-[(2R)-3-oxo-4-(2-oxo-3H-1,3-benzoxazol-6-yl)morpholin-2-yl]acetamide (Compound 36-5)

According to the Step 7-5 in synthetic method for EXAMPLE 7, crude 36-4 was used instead of compound 7-4 to obtain 36-5 (23 mg) as a pale brown amorphous solid.

Step 36-6

Synthesis of (2R)—N-(4-amidinophenyl)-2-hydroxy-2-[(2R)-3-oxo-4-(2-oxo-3H-1,3-benzoxazol-6-yl)morpholin-2-yl]acetamide hydrochloride (EXAMPLE 36)

According to the Step 26-B in synthetic method for EXAMPLE 26, compound 36-5 (21 mg) was used instead of compound 26-14 to obtain EXAMPLE 36 (15.5 mg) as a yellow-green amorphous solid.

Example 37

Synthesis of (2R)—N-(4-amidinophenyl)-2-hydroxy-2-[(2R)-3-oxo-4-(3-oxo-1,2-dihydroisoindol-5-yl)morpholin-2-yl]acetamide hydrochloride (EXAMPLE 37)

EXAMPLE 37

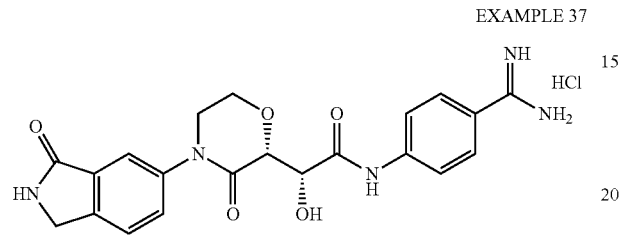

Step 37-1

Synthesis of 6-(2-chloroethylamino)-2,3-dihydroisoindol-1-one (Compound 37-1)

According to the Step 7-1 in synthetic method for EXAMPLE 7, 6-amino-2,3-dihydro-1H-isoindol-1-one, (0.8 g) was used instead of 4-methylaniline to obtain compound 37-1 (0.36 g) as a orange amorphous solid.

Step 37-2

Synthesis of (2R,3R)-2,3-diacetyloxy-4-[2-chloroethyl-(3-oxo-1,2-dihydroisoindol-5-yl)amino]-4-oxobutanoic acid (Compound 37-2)

According to the Step 26-9 in synthetic method for EXAMPLE 26, compound 37-1 (353 mg) was used instead of compound 26-8 to obtain crude 37-2. The crude 37-2 was used in the next step without further purification.

Step 37-3

Synthesis of [(2R,3R)-3-acetyloxy-1-[2-chloroethyl-(3-oxo-1,2-dihydroisoindol-5-yl)amino]-1,4-dioxo-4-[4-(5-oxo-4H-1,2,4-oxadiazol-3-yl)anilino]butan-2-yl]acetate (Compound 37-3)

According to the Step 26-10 in synthetic method for EXAMPLE 26, crude 37-2 was used instead of compound 26-9 to obtain compound 37-3 (419 mg) as a brown solid.

Step 37-4

Synthesis of (2R,3R)—N-(2-chloroethyl)-2,3-dihydroxy-N-(3-oxo-1,2-dihydroisoindol-5-yl)-N'-[4-(5-oxo-4H-1,2,4-oxadiazol-3-yl)phenyl]butanediamide ammonium salt (Compound 37-4)

According to the Step 7-4 in synthetic method for EXAMPLE 7, compound 37-3 (0.3 g) was used instead of compound 7-3 to obtain crude 37-4. The crude 37-4 was used in the next step without further purification.

Step 37-5

Synthesis of (2R)-2-hydroxy-N-[4-(5-oxo-4H-1,2,4-oxadiazol-3-yl)phenyl]-2-[(2R)-3-oxo-4-(3-oxo-1,2-dihydroisoindol-5-yl)morpholin-2-yl]acetamide (Compound 37-5)

According to the Step 7-5 in synthetic method for EXAMPLE 7, crude 37-4 was used instead of compound 7-4 to obtain compound 37-5 (38 mg) as a pale brown amorphous solid.

Step 37-6

Synthesis of (2R)—N-(4-amidinophenyl)-2-hydroxy-2-[(2R)-3-oxo-4-(3-oxo-1,2-dihydroisoindol-5-yl)morpholin-2-yl]acetamide hydrochloride (EXAMPLE 37)

According to the Step 26-B in synthetic method for EXAMPLE 26, compound 37-5 (32.9 mg) was used instead of compound 26-14 to obtain EXAMPLE 37 (21.4 mg) as a colorless amorphous solid.

Example 38

Synthesis of (2R)-2-[(2R)-4-(4-acetamidophenyl)-3-oxomorpholin-2-yl]-N-(1-aminoisoquinolin-6-yl)-2-hydroxyacetamide hydrochloride (EXAMPLE 38)

EXAMPLE 38

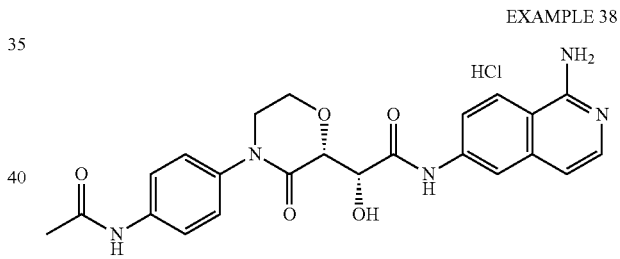

Step 38-1

Synthesis of N-[4-(2-chloroethylamino)phenyl]acetamide (Compound 38-1)

According to the Step 7-1 in synthetic method for EXAMPLE 7, N-(4-aminophenyl)acetamide (10 g) was used instead of 4-methylaniline to obtain compound 38-1 (7.9 g) as a pale yellow amorphous solid.

Step 38-2

Synthesis of (2R,3R)-4-[4-acetamido-N-(2-chloroethyl)anilino]-2,3-diacetyloxy-4-oxobutanoic acid (Compound 38-2)

According to the Step 26-9 in synthetic method for EXAMPLE 26, compound 38-1 (7.5 g) was used instead of compound 26-1 to obtain compound 38-2 (15.1 g) as a beige amorphous solid.

Step 38-3

Synthesis of [(2R,3R)-1-[4-acetamido-N-(2-chloro-ethyl)anilino]-3-acetyloxy-4-[[1-[bis[(2-methylpropan-2-yl)oxycarbonyl]amino]isoquinolin-6-yl]amino]-1,4-dioxobutan-2-yl]acetate (Compound 38-3)

To a solution of compound 38-2 (0.7 g) in $CH_2Cl_2$-DMF (30-2 mL), was added oxalyl chloride (0.25 mL) at 0° C. The reaction mixture was stirred for 1 hour in the same temperature. Then the mixture was concentrated in vacuo to remove excess oxalyl chloride. The resulting residue was resolved in $CH_2Cl_2$ (20 mL) and pyridine (0.19 mL) was added to the above solution at 0° C. The mixture was stirred for 10 minutes at the same temperature and then a solution of 6-amino-1-bis(tert-butoxy carbonyl)aminoisoquinoline (0.52 g) in $CH_2Cl_2$ (10 mL) was added to the mixture at 0° C. The reaction mixture was stirred for 1 hour at 0° C., then for 2 days at room temperature. MeOH was added to the reaction mixture and the mixture was concentrated in vacuo. Then sat. $NaHCO_3$ aq. was added to residue and the mixture was extracted with EtOAc. The organic layer was washed with water, brine and dried with anhyd. $Na_2SO_4$. The solvent was removed under reduced pressure and the resulting residue was purified by silica gel flash chromatography (eluent: Hexane/EtOAc=1/4) to obtain compound 38-3 (0.52 g) as a pale yellow amorphous solid.

Step 38-4

Synthesis of tert-butyl N-[6-[[(2R,3R)-4-[4-acetamido-N-(2-chloroethyl)anilino]-2,3-dihydroxy-4-oxobutanoyl]amino]isoquinolin-1-yl]-N-[(2-methylpropan-2-yl)oxycarbonyl]carbamate (Compound 38-4)

According to the Step 7-4 in synthetic method for EXAMPLE 7, compound 38-3 (0.5 g) was used instead of 7-3 to obtain compound 38-4 (0.42 g) as a yellow amorphous solid.

Step 38-5

Synthesis of (2R)-2-[(2R)-4-(4-acetamidophenyl)-3-oxomorpholin-2-yl]-N—[N,N-bis(tert-butoxycarbonyl)-1-aminoisoquinolin-6-yl]-2-hydroxyacetamide (Compound 38-5)

According to the Step 7-5 in synthetic method for EXAMPLE 7, compound 38-4 (0.4 g) and DMF were used instead of 7-4 and t-BuOH-DMSO to obtain compound 38-5 (0.13 g) as a yellow amorphous solid.

Step 38-6

Synthesis of (2R)-2-[(2R)-4-(4-acetamidophenyl)-3-oxomorpholin-2-yl]-N-(1-aminoisoquinolin-6-yl-2-hydroxyacetamide hydrochloride (EXAMPLE 38)

To a solution of compound 38-5 (40 mg) in MeOH (0.4 mL), was added 4N-HCl/EtOAc (1 mL) at 0° C. The reaction mixture was stirred for 21 hours at room temperature. After the reaction, the precipitate was collected by filtration to obtain EXAMPLE 38 (22 mg) as a pale yellow amorphous solid.

Example 39

Synthesis of (2R)-2-[(2R)-4-(4-acetamidophenyl)-3-oxomorpholin-2-yl]-2-hydroxy-N-(1-imino-2,3-dihydroisoindol-5-yl)acetamide hydrochloride (EXAMPLE 39)

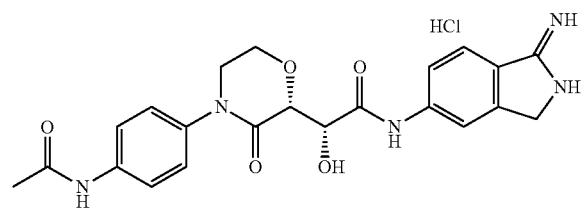

EXAMPLE 39

Step 39-1

Synthesis of tert-butyl N-[(2-cyano-5-nitrophenyl)methyl]-N-[(2-methylpropan-2-yl)oxycarbonyl]carbamate (Compound 39-1)

To a suspension of 2-(bromomethyl)-4-nitro-benzonitrile (1.0 g: WO 2005082368 A1) and $K_2CO_3$ (1.1 g) in DMF (15 mL), were added di-tert-butyl imidodicarboxylate (1.17 g) and tetrabutylammonium iodide (0.15 g) at room temperature. The reaction mixture was stirred at room temperature overnight. Water was added into the mixture and it was extracted with EtOAc. The organic layer was washed with brine and dried with anhyd. $Na_2SO_4$. The solvent was removed under reduced pressure and the resulting residue was purified by silica gel flash chromatography (eluent: Hexane/EtOAc=100/0–3/1) to obtain compound 39-1 (1.29 g) as a colorless amorphous solid.

Step 39-2

Synthesis of tert-butyl N-[(5-Amino-2-cyanophenyl)methyl]-N-[(2-methylpropan-2-yl)oxycarbonyl]carbamate (Compound 39-2)

To a solution of compound 39-1 (0.3 g) in MeOH-THF (3 mL-3 mL), was added 10% Pd/C (30 mg). The reaction mixture was stirred under hydrogen atmosphere for 3 hours at room temperature. Then the reaction mixture was filtered with Celite® pad to remove catalyst. The filtrate was concentrated in vacuo to obtain compound 39-2 (0.27 g) as pale brown oil.

Step 39-3

Synthesis of [(2R,3R)-1-[4-acetamido-N-(2-chloroethyl)anilino]-3-acetyloxy-4-[3-[[bis[(2-methylpropan-2-yl)oxycarbonyl]amino]methyl]-4-cyanoanilino]-1,4-dioxobutan-2-yl]acetate (Compound 39-3)

According to the Step 26-10 in synthetic method for EXAMPLE 26, compound 38-2 (3.0 g) and 39-2 (2.43 g)

were used instead of 26-9 and 3-(4-Aminophenyl)-1,2,4-oxadiazol-5(2H)-one to obtain compound 39-3 (5.25 g) as a beige amorphous solid.

Step 39-4

Synthesis of tert-butyl N-[[5-[[(2R,3R)-4-[4-acetamido-N-(2-chloroethyl)anilino]-2,3-dihydroxy-4-oxobutanoyl]amino]-2-cyanophenyl]methyl]-N-[(2-methylpropan-2-yl)oxycarbonyl]carbamate (Compound 39-4)

According to the Step 7-4 in synthetic method for EXAMPLE 7, compound 39-3 (5.2 g) was used instead of 7-3 to obtain compound 39-4 (4.3 g) as a beige amorphous solid.

Step 39-5

Synthesis of tert-butyl N-[[5-[[(2R)-2-[(2R)-4-(4-acetamidophenyl)-3-oxomorpholin-2-yl]-2-hydroxyacetyl]amino]-2-cyanophenyl]methyl]-N-[(2-methylpropan-2-yl)oxycarbonyl]carbamate (Compound 39-5)

According to the Step 7-5 in synthetic method for EXAMPLE 7, compound 39-4 (4.3 g) and DMF were used instead of 7-4 and t-BuOH-DMSO to obtain compound 39-5 (1.46 g) as a colorless amorphous solid.

Step 39-6

Synthesis of (2R)-2-[(2R)-4-(4-acetamidophenyl)-3-oxomorpholin-2-yl]-N-[3-(aminomethyl)-4-cyanophenyl]-2-hydroxyacetamide hydrochloride (Compound 39-6)

According to the Step 38-6 in synthetic method for EXAMPLE 38, compound 39-5 (1.45 g) was used instead of 38-5 to obtain compound 39-6 (1.2 g) as a colorless amorphous solid.

Step 39-7

Synthesis of (2R)-2-[(2R)-4-(4-acetamidophenyl)-3-oxomorpholin-2-yl]-2-hydroxy-N-(1-imino-2,3-dihydroisoindol-5-yl)acetamide hydrochloride (EXAMPLE 39)

Compound 39-6 (1.2 g) was suspended in EtOH (30 mL) and the mixture was refluxed for 6 hours. After cooling, the precipitate was collected by filtration to obtain EXAMPLE 39 (0.95 g) as a colorless amorphous solid.

Example 40

Synthesis of N-[4-[(2R)-2-[(1R)-2-(4-amidinoanilino)-1-hydroxy-2-oxoethyl]-3-oxomorpholin-4-yl]phenyl]propanamide hydrochloride (EXAMPLE 40)

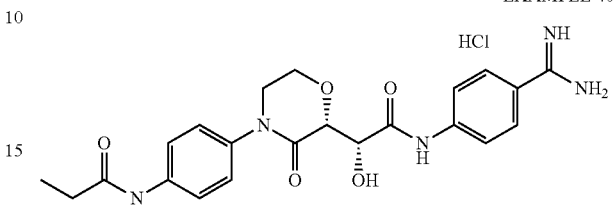

EXAMPLE 40

Step 40-1

Synthesis of N-[4-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]propanamide (Compound 40-1)

According to the Step 28-1 in synthetic method for EXAMPLE 28, propionyl chloride (15.1 microL) was used instead of mesyl chloride to obtain compound 40-1 (80.3 mg) as a colorless amorphous solid.

Step 40-2

Synthesis of N-[4-[(2R)-2-[(1R)-2-(4-amidinoanilino)-1-hydroxy-2-oxoethyl]-3-oxomorpholin-4-yl]phenyl]propanamide hydrochloride (EXAMPLE 40)

According to the Step 26-B in synthetic method for EXAMPLE 26, compound 40-1 (70 mg) was used instead of 26-14 to obtain EXAMPLE 40 (53.5 mg) as a pale beige amorphous solid.

Example 41

Synthesis of (2R)—N-(4-amidinophenyl)-2-[(2R)-4-[4-[(2-cyclopropylacetyl)amino]phenyl]-3-oxomorpholin-2-yl]-2-hydroxyacetamide hydrochloride (EXAMPLE 41)

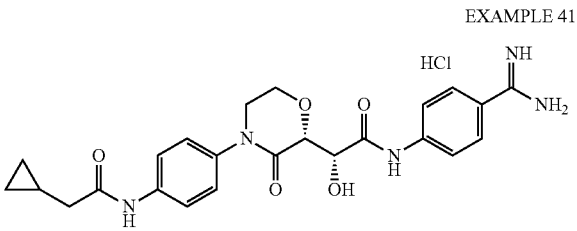 [SMILES: N=C(N)c1ccc(NC(=O)[C@H](O)[C@H]2OCCN(c3ccc(NC(=O)CC4CC4)cc3)C2=O)cc1 ; Cl]

EXAMPLE 41

Step 41-1

Synthesis of (2R)-2-[(2R)-4-[4-[(2-cyclopropylacetyl)amino]phenyl]-3-oxomorpholin-2-yl]-2-hydroxy-N-[4-(5-oxo-4H-1,2,4-oxadiazol-3-yl)phenyl]acetamide (Compound 41-1)

According to the Step 28-1 in synthetic method for EXAMPLE 28, an acid chloride derived from cyclopropylacetic acid (15.2 mg) was used instead of mesyl chloride to obtain compound 41-1 (53.5 mg) as a pale beige amorphous solid.

Step 41-2

Synthesis of (2R)—N-(4-amidinophenyl)-2-[(2R)-4-[4-[(2-cyclopropylacetyl)amino]phenyl]-3-oxomorpholin-2-yl]-2-hydroxyacetamide hydrochloride (EXAMPLE 41)

According to the Step 26-B in synthetic method for EXAMPLE 26, 41-1 (50 mg) was used instead of 26-14 to obtain EXAMPLE 41 (45.5 mg) as a colorless amorphous solid.

Example 42

Synthesis of N-[4-[(2R)-2-[(1R)-2-(4-amidinoanilino)-1-hydroxy-2-oxoethyl]-3-oxomorpholin-4-yl]phenyl]cyclohexanecarboxamide hydrochloride (EXAMPLE 42)

EXAMPLE 42

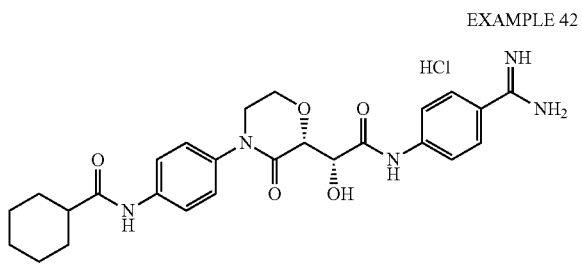 [SMILES: N=C(N)c1ccc(NC(=O)[C@H](O)[C@H]2OCCN(c3ccc(NC(=O)C4CCCCC4)cc3)C2=O)cc1 ; Cl]

Step 42-1

Synthesis of N-[4-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]cyclohexanecarboxamide (Compound 42-1)

According to the Step 28-1 in synthetic method for EXAMPLE 28, cyclohexanecarbonyl chloride (20.6 microL) was used instead of mesyl chloride to obtain compound 42-1 (57.7 mg) as a pale beige amorphous solid.

Step 42-2

Synthesis of N-[4-[(2R)-2-[(1R)-2-(4-amidinoanilino)-1-hydroxy-2-oxoethyl]-3-oxomorpholin-4-yl]phenyl]cyclohexanecarboxamide hydrochloride (EXAMPLE 42)

According to the Step 26-B in synthetic method for EXAMPLE 26, 42-1 (50 mg) was used instead of 26-14 to obtain EXAMPLE 42 (35 mg) as a colorless amorphous solid.

Example 43

Synthesis of Synthesis of (2R)—N-(4-amidinophenyl)-2-[(2R)-4-(4-aminophenyl)-3-oxomorpholin-2-yl]-2-hydroxyacetamide Dihydrochloride (EXAMPLE 43)

EXAMPLE 43

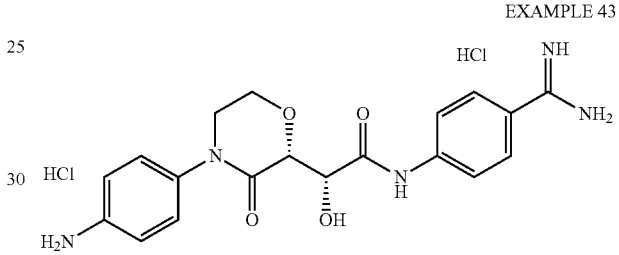

Step 43-1

Synthesis of (2R)—N-(4-amidinophenyl)-2-[(2R)-4-(4-aminophenyl)-3-oxomorpholin-2-yl]-2-hydroxyacetamide Dihydrochloride (EXAMPLE 43)

According to the Step 26-B in synthetic method for EXAMPLE 26, 26-13 (49.7 mg) was used instead of 26-14 to obtain EXAMPLE 43 (37.9 mg) as a pale yellow amorphous solid.

Example 44

Synthesis of (2R)—N-(4-amidinophenyl)-2-[(2R)-4-(3-aminophenyl)-3-oxomorpholin-2-yl]-2-hydroxyacetamide Dihydrochloride (EXAMPLE 44)

EXAMPLE 44

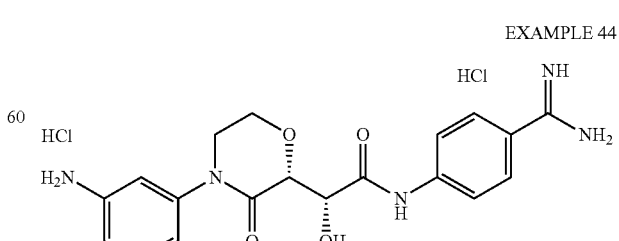

Step 44-1

Synthesis of tert-butyl N-[3-[(2-chloroacetyl)amino]phenyl]carbamate (compound 44-1)

According to the Step 20-1 in synthetic method for EXAMPLE 20, N-Boc-m-phenylenediamine (2 g) was used instead of 5-amino-1,3-dihydro-2H-benzimidazol-2-one to obtain compound 44-1 (2.35 g) as a gray amorphous solid.

Step 44-2

Synthesis of tert-butyl N-[3-(2-chloroethylamino)phenyl]carbamate (Compound 44-2)

According to the Step 20-2 in synthetic method for EXAMPLE 20, compound 44-1 (11.4 g) was used instead of 20-1 to obtain compound 44-2 (10.9 g) as a colorless amorphous solid.

Step 44-3

Synthesis of (2R,3R)-2,3-diacetyloxy-4-[N-(2-chloroethyl)-3-[(2-methylpropan-2-yl)oxycarbonylamino]anilino]-4-oxobutanoic acid (Compound 44-3)

According to the Step 26-9 in synthetic method for EXAMPLE 26, 44-2 (10.8 g) was used instead of 26-1 to obtain compound 44-3 (20.7 g) as a colorless amorphous solid.

Step 44-4

Synthesis of [(2R,3R)-3-acetyloxy-4-[N-(2-chloroethyl)-3-[(2-methylpropan-2-yl)oxycarbonylamino]anilino]-1,4-dioxo-1-[4-(5-oxo-4H-1,2,4-oxadiazol-3-yl)anilino]butan-2-yl]acetate (Compound 44-4)

According to the Step 26-10 in synthetic method for EXAMPLE 26, compound 44-3 (10 g) was used instead of 26-9 to obtain compound 44-4 (13.5 g) as a beige amorphous solid.

Step 44-5

Synthesis of tert-butyl N-[3-[2-chloroethyl-[(2R,3R)-2,3-dihydroxy-4-oxo-4-[4-(5-oxo-4H-1,2,4-oxadiazol-3-yl)anilino]butanoyl]amino]phenyl]carbamate (Compound 44-5)

According to the Step 7-4 in synthetic method for EXAMPLE 7, 44-4 (13.4 g) was used instead of 7-3 to obtain compound 44-5 (12.9 g) as a beige amorphous solid.

Step 44-6

Synthesis of tert-butyl N-[3-[(2R)-2-[(1R)-1-hydroxy-2-oxo-2-[4-(5-oxo-4H-1,2,4-oxadiazol-3-yl)anilino]ethyl]-3-oxomorpholin-4-yl]phenyl]carbamate (Compound 44-6)

According to the Step 7-5 in synthetic method for EXAMPLE 7, 44-5 (1 g) and DMF were used instead of 7-4 and t-BuOH-DMSO to obtain compound 44-6 (0.66 g) as a beige amorphous solid.

Step 44-7

Synthesis of (2R)-2-[(2R)-4-(3-aminophenyl)-3-oxomorpholin-2-yl]-2-hydroxy-N-[4-(5-oxo-4H-1,2,4-oxadiazol-3-yl)phenyl]acetamide hydrochloride (Compound 44-7)

According to the Step 38-6 in synthetic method for EXAMPLE 38, 44-6 (6.0 g) was used instead of 38-5 to obtain compound 44-7 (6.3 g) as a beige amorphous solid.

Step 44-8

Synthesis of (2R)—N-(4-amidinophenyl)-2-[(2R)-4-(3-aminophenyl)-3-oxomorpholin-2-yl]-2-hydroxylacetamide Dihydrochloride (EXAMPLE 44)

According to the Step 26-B in synthetic method for EXAMPLE 26, compound 44-7 (75 mg) was used instead of 26-14 to obtain EXAMPLE 44 (32.3 mg) as a colorless amorphous solid.

Example 45

Synthesis of (2R)-2-[(2R)-4-(3-acetamidophenyl)-3-oxomorpholin-2-yl]-N-(4-amidinophenyl)-2-hydroxyacetamide Hydrochloride (EXAMPLE 45)

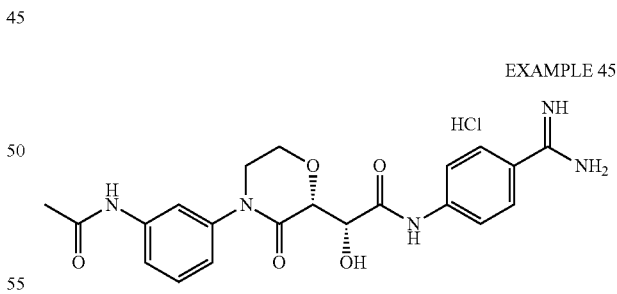

EXAMPLE 45

Step 45-1

(2R)-2-[(2R)-4-(3-acetamidophenyl)-3-oxomorpholin-2-yl]-2-hydroxy-N-[4-(5-oxo-4H-1,2,4-oxadiazol-3-yl)phenyl]acetamide (Compound 45-1)

According to the Step 26-6 in synthetic method for EXAMPLE 26, 44-7 (150 mg) was used instead of 26-5 to obtain compound 45-1 (80.8 mg) as a beige amorphous solid.

Step 45-2

Synthesis of (2R)-2-[(2R)-4-(3-acetamidophenyl)-3-oxomorpholin-2-yl]-N-(4-amidinophenyl)-2-hydroxyacetamide Hydrochloride (EXAMPLE 45)

According to the Step 26-B in synthetic method for EXAMPLE 26, compound 45-1 (65 mg) was used instead of 26-14 to obtain EXAMPLE 45 (34.9 mg) as a colorless amorphous solid.

Example 46

Synthesis of (2R)—N-(4-amidinophenyl)-2-hydroxy-2-[(2R)-3-oxo-4-[3-(2-oxopyrrolidin-1-yl)phenyl]morpholin-2-yl]acetamide hydrochloride (EXAMPLE 46)

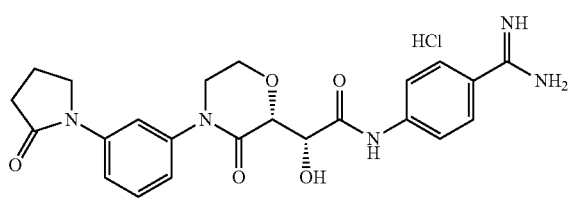

EXAMPLE 46

Step 46-1

Synthesis of (2R)-2-hydroxy-N-[4-(5-oxo-4H-1,2,4-oxadiazol-3-yl)phenyl]-2-[(2R)-3-oxo-4-[3-(2-oxopyrrolidin-1-yl)phenyl]morpholin-2-yl]acetamide (Compound 46-1)

According to the Step 29-1 in synthetic method for EXAMPLE 29, compound 44-7 (150 mg) was used instead of 26-5 to obtain compound 46-1 (74.7 mg) as a beige amorphous solid.

Step 46-2

Synthesis of (2R)—N-(4-amidinophenyl)-2-hydroxy-2-[(2R)-3-oxo-4-[3-(2-oxopyrrolidin-1-yl)phenyl]morpholin-2-yl]acetamide hydrochloride (EXAMPLE 46)

According to the Step 26-B in synthetic method for EXAMPLE 26, compound 46-1 (65 mg) was used instead of 26-14 to obtain EXAMPLE 46 (20.9 mg) as a colorless amorphous solid.

Example 47

Synthesis of (2R)—N-(4-amidinophenyl)-2-[(2R)-4-[3-(carbamoylamino)phenyl]-3-oxomorpholin-2-yl]-2-hydroxyacetamide hydrochloride (EXAMPLE 47)

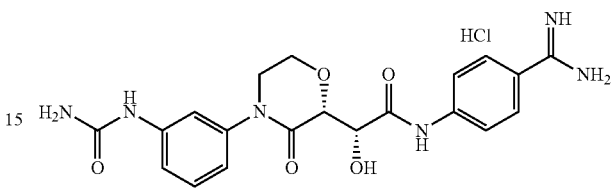

EXAMPLE 47

Step 47-1

Synthesis of (2R)-2-[(2R)-4-[3-(carbamoylamino)phenyl]-3-oxomorpholin-2-yl]-2-hydroxy-N-[4-(5-oxo-4H-1,2,4-oxadiazol-3-yl)phenyl]acetamide (Compound 47-1)

According to the Step 27-1 in synthetic method for EXAMPLE 27, compound 44-7 (150 mg) was used instead of 26-5 to obtain compound 47-1 (51.3 mg) as a colorless amorphous solid.

Step 47-2

Synthesis of (2R)—N-(4-amidinophenyl)-2-[(2R)-4-[3-(carbamoylamino)phenyl]-3-oxomorpholin-2-yl]-2-hydroxyacetamide hydrochloride (EXAMPLE 47)

According to the Step 26-B in synthetic method for EXAMPLE 26, compound 47-1 (45 mg) was used instead of 26-14 to obtain EXAMPLE 47 (23 mg) as a colorless amorphous solid.

Example 48

Synthesis of (2R)—N-(4-amidinophenyl)-2-hydroxy-2-[(2R)-3-oxo-4-[3-(2-oxo-1,3-oxazolidin-3-yl)phenyl]morpholin-2-yl]acetamide hydrochloride (EXAMPLE 48)

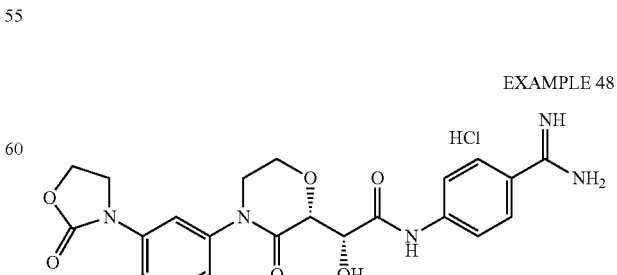

EXAMPLE 48

Step 48-1

Synthesis of (2R)-2-hydroxy-N-[4-(5-oxo-4H-1,2,4-oxadiazol-3-yl)phenyl]-2-[(2R)-3-oxo-4-[3-(2-oxo-1,3-oxazolidin-3-yl)phenyl]morpholin-2-yl]acetamide (Compound 48-1)

According to the Step 29-1 in synthetic method for EXAMPLE 29, compound 44-7 (150 mg) was used instead of 26-5 to obtain compound 48-1 (79.4 mg) as a beige amorphous solid.

Step 48-2

Synthesis of (2R)—N-(4-amidinophenyl)-2-hydroxy-2-[(2R)-3-oxo-4-[3-(2-oxo-1,3-oxazolidin-3-yl)phenyl]morpholin-2-yl]acetamide hydrochloride (EXAMPLE 48)

According to the Step 26-B in synthetic method for EXAMPLE 26, compound 48-1 (65 mg) was used instead of 26-14 to obtain EXAMPLE 48 (37.2 mg) as a colorless amorphous solid.

Example 49

Synthesis of (2R)—N-(4-amidinophenyl)-2-hydroxy-2-[(2R)-4-[3-(methanesulfonamido)phenyl]-3-oxomorpholin-2-yl]acetamide hydrochloride (EXAMPLE 49)

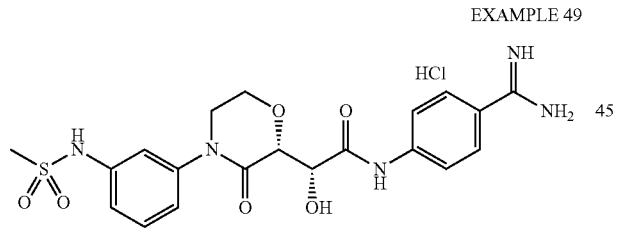

EXAMPLE 49

Step 49-1

Synthesis of (2R)-2-hydroxy-2-[(2R)-4-[3-(methanesulfonamido)phenyl]-3-oxomorpholin-2-yl]-N-[4-(5-oxo-4H-1,2,4-oxadiazol-3-yl)phenyl]acetamide (Compound 49-1)

According to the Step 28-1 in synthetic method for EXAMPLE 28, compound 44-7 (150 mg) was used instead of 26-5 to obtain compound 49-1 (28.6 mg) as a pale pink amorphous solid.

Step 49-2

Synthesis of (2R)—N-(4-amidinophenyl)-2-hydroxy-2-[(2R)-4-[3-(methanesulfonamido)phenyl]-3-oxomorpholin-2-yl]acetamide hydrochloride (EXAMPLE 49)

According to the Step 26-B in synthetic method for EXAMPLE 26, compound 49-1 (25 mg) was used instead of 26-14 to obtain EXAMPLE 49 (10.1 mg) as a colorless amorphous solid.

Example 50

Synthesis of (2R)—N-(4-amidinophenyl)-2-hydroxy-2-[(2R)-4-[3-[(2-hydroxyacetyl)amino]phenyl]-3-oxomorpholin-2-yl]acetamide hydrochloride (EXAMPLE 50)

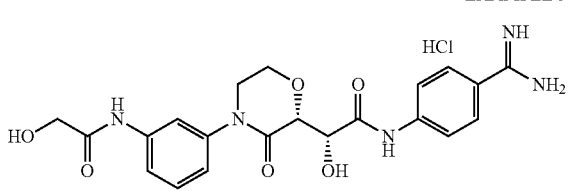

EXAMPLE 50

Step 50-1

Synthesis of (2R)-2-hydroxy-N-[4-(5-oxo-4H-1,2,4-oxadiazol-3-yl)phenyl]-2-[(2R)-3-oxo-4-[3-[(2-phenylmethoxyacetyl)amino]phenyl]morpholin-2-yl]acetamide (Compound 50-1)

According to the Step 28-1 in synthetic method for EXAMPLE 28, compound 44-7 (150 mg) was used instead of 26-5 to obtain compound 50-1 (41.4 mg) as a pale pink amorphous solid.

Step 50-2

Synthesis of (2R)—N-(4-amidinophenyl)-2-hydroxy-2-[(2R)-4-[3-[(2-hydroxyacetyl)amino]phenyl]-3-oxomorpholin-2-yl]acetamide hydrochloride (EXAMPLE 50)

According to the Step 26-B in synthetic method for EXAMPLE 26, compound 50-1 (38 mg) was used instead of 26-14 to obtain EXAMPLE 50 (15 mg) as a colorless amorphous solid.

Example 51

Synthesis of (2R)—N-(4-amidinophenyl)-2-hydroxy-2-[(2R)-3-oxo-4-[3-(3-oxomorpholin-4-yl)phenyl]morpholin-2-yl]acetamide hydrochloride (EXAMPLE 51)

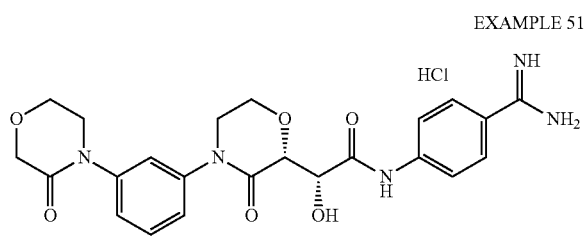 [SMILES: N=C(N)c1ccc(NC(=O)[C@H](O)[C@H]2OCCN(c3cccc(N4CCOCC4=O)c3)C2=O)cc1 ; Cl]

EXAMPLE 51

Step 51-1

Synthesis of (2R)-2-hydroxy-N-[4-(5-oxo-4H-1,2,4-oxadiazol-3-yl)phenyl]-2-[(2R)-3-oxo-4-[3-(3-oxomorpholin-4-yl)phenyl]morpholin-2-yl]acetamide (Compound 51-1)

According to the Step 30-1 in synthetic method for EXAMPLE 30, 44-7 (150 mg) was used instead of 26-5 to obtain compound 51-1 (46.8 mg) as a beige amorphous solid.

Step 51-2

Synthesis of (2R)—N-(4-amidinophenyl)-2-hydroxy-2-[(2R)-3-oxo-4-[3-(3-oxomorpholin-4-yl)phenyl]morpholin-2-yl]acetamide hydrochloride (EXAMPLE 51)

According to the Step 26-B in synthetic method for EXAMPLE 26, compound 51-1 (43 mg) was used instead of 26-14 to obtain EXAMPLE 51 (9.8 mg) as a pale beige amorphous solid.

Example 52

Synthesis of (2R)—N-(1-aminoisoquinolin-6-yl)-2-[(2R)-4-(4-tert-butylphenyl)-3-oxomorpholin-2-yl]-2-hydroxyacetamide hydrochloride (EXAMPLE 52)

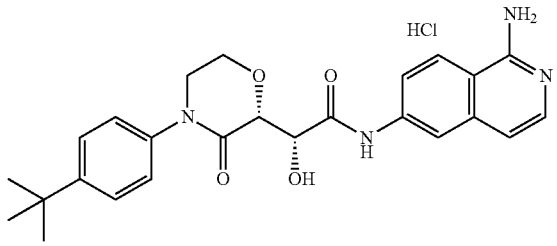

EXAMPLE 52

Step 52-1

Synthesis of tert-butyl (2R,3R)-2,3-diacetyloxy-4-[4-tert-butyl-N-(2-chloroethyl)anilino]-4-oxobutanoate (Compound 52-1)

To a solution of (R,R)-2,3-bis(acetyloxy)-butanedioic acid mono tert-butyl ester (9 g: Tetrahedron, 45, 3071-3080, 1989) in $CH_2Cl_2$ (90 mL), were added compound 11-1 (6.6 g) and 1-ethyl-3-(3'-dimethylaminopropyl)carbodiimide hydrochloride at 0° C. The reaction mixture was stirred for 5 hours at room temperature.

Then water was added into the mixture and it was extracted with $CH_2Cl_2$. The organic layer was washed with brine, dried with anhyd. $Na_2SO_4$. The solvent was removed under reduced pressure to obtain compound 52-1 (15.8 g) as a brown amorphous solid.

Step 52-2

Synthesis of tert-butyl (2R,3R)-4-[4-tert-butyl-N-(2-chloroethyl)anilino]-2,3-dihydroxy-4-oxobutanoate (Compound 52-2)

According to the Step 7-4 in synthetic method for EXAMPLE 7, compound 52-1 (15.5 g) was used instead of 7-3 to obtain compound 52-2 (13 g) as a brown oil.

Step 52-3

Synthesis of tert-butyl (2R)-2-[(2R)-4-(4-tert-butylphenyl)-3-oxomorpholin-2-yl]-2-hydroxyacetate (Compound 52-3)

According to the Step 7-5 in synthetic method for EXAMPLE 7, compound 52-2 (12.8 g) was used instead of 7-4 to obtain compound 52-3 (4.85 g) as a pale yellow amorphous solid.

Step 52-4

Synthesis of (2R)-2-[(2R)-4-(4-tert-butylphenyl)-3-oxomorpholin-2-yl]-2-hydroxyacetic acid (Compound 52-4)

Compound 52-3 (1.5 g) was resolved in 4N HCl-dioxane (30 mL). The reaction mixture was stirred at room temperature overnight. The mixture was concentrated in vacuo to obtain compound 52-4 (1.44 g) as a beige amorphous hygroscopic solid.

Step 52-5

Synthesis of (2R)—N—[N,N-bis(tert-butoxycarbonyl)-1-aminoisoquinolin-6-yl]-2-[(2R)-4-(4-tert-butyl phenyl)-3-oxomorpholin-2-yl]-2-hydroxyacetamide (Compound 52-5)

According to the Step 1-3 in synthetic method for EXAMPLE 1, 52-4 (0.38 g) was used instead of 1-2 to obtain compound 52-5 (92 mg) as a colorless amorphous solid.

Step 52-6

Synthesis of (2R)—N-(1-aminoisoquinolin-6-yl)-2-[(2R)-4-(4-tert-butylphenyl)-3-oxomorpholin-2-yl]-2-hydroxyacetamide hydrochloride (EXAMPLE 52)

According to the Step 38-6 in synthetic method for EXAMPLE 38, 52-5 (91 mg) was used instead of 38-5 to obtain EXAMPLE 52 (60 mg) as a colorless amorphous solid.

Example 53

Synthesis of (2R)-2-[(2R)-4-(4-tert-butylphenyl)-3-oxomorpholin-2-yl]-2-hydroxy-N-(1-imino-2,3-dihydroisoindol-5-yl)acetamide hydrochloride (EXAMPLE 53)

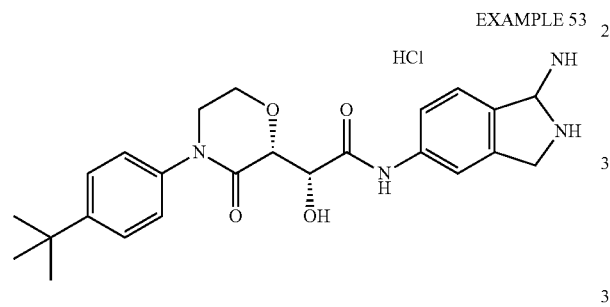

EXAMPLE 53

Step 53-1

Synthesis of tert-butyl N-[[5-[[(2R)-2-[(2R)-4-(4-tert-butylphenyl)-3-oxomorpholin-2-yl]-2-hydroxyacetyl]amino]-2-cyanophenyl]methyl]-N-[(2-methylpropan-2-yl)oxycarbonyl]carbamate (Compound 53-1)

According to the Step 1-3 in synthetic method for EXAMPLE 1, 52-4 (0.38 g) and compound 39-2 (0.1 g) were used instead of 1-2 and 6-amino-1-bis(tert-butoxy carbonyl) aminoisoquinoline to obtain compound 53-1 (96 mg) as a colorless amorphous solid.

Step 53-2

Synthesis of (2R)—N-[3-(aminomethyl)-4-cyanophenyl]-2-[(2R)-4-(4-tert-butylphenyl)-3-oxomorpholin-2-yl]-2-hydroxyacetamide hydrochloride (Compound 53-2)

According to the Step 38-6 in synthetic method for EXAMPLE 38, compound 53-1 (95 mg) was used instead of 38-5 to obtain compound 53-2 (63 mg) as a colorless amorphous solid.

Step 53-3

Synthesis of (2R)-2-[(2R)-4-(4-tert-butylphenyl)-3-oxomorpholin-2-yl]-2-hydroxy-N-(1-imino-2,3-dihydroisoindol-5-yl)acetamide hydrochloride (EXAMPLE 53)

According to the Step 39-7 in synthetic method for EXAMPLE 39, compound 53-2 (63 mg) was used instead of 39-6 to obtain EXAMPLE 53 (52 mg) as a colorless amorphous solid.

Example 54

Synthesis of (2R)—N-(1-aminoisoquinolin-6-yl)-2-hydroxy-2-[(2R)-3-oxo-4-[4-(trifluoromethyl)phenyl]morpholin-2-yl]acetamide hydrochloride (EXAMPLE 54)

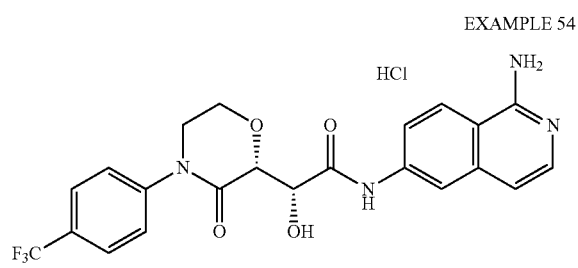 [SMILES: Nc1nccc2cc(NC(=O)[C@H](O)[C@H]3OCCN(c4ccc(C(F)(F)F)cc4)C3=O)ccc12 ; Cl]

EXAMPLE 54

Step 54-1

Synthesis of N-(2-chloro-N-[4-(trifluoromethyl)phenyl]acetamide (Compound 54-1)

According to the Step 20-1 in synthetic method for EXAMPLE 20, 4-trifluoromethyl aniline (5 g) was used instead of 5-amino-1,3-dihydro-2H-benzimidazol-2-one to obtain compound 54-1 (6.94 g) as a brown amorphous solid.

Step 54-2

Synthesis of N-(2-chloroethyl)-4-(trifluoromethyl) aniline (Compound 54-2)

According to the Step 20-2 in synthetic method for EXAMPLE 20, compound 54-1 (3.5 g) was used instead of 20-1 to obtain compound 54-2 (3.36 g) as brown oil.

Step 54-3

Synthesis of tert-butyl (2R,3R)-2,3-diacetyloxy-4-[N-(2-chloroethyl)-4-(trifluoromethyl)anilino]-4-oxobutanoate (Compound 54-3)

To a solution of (R,R)-2,3-bis(acetyloxy)-butanedioic acid mono tert-butyl ester (3.25 g: *Tetrahedron*, 45, 3071-3080, 1989) in $CH_2Cl_2$ (65 mL), were added oxalyl chloride (1.06 mL) and DMF (50 microL) at 0° C. The reaction mixture was stirred at 0° C. for 30 minutes then pyridine (3.82 mL) was added into the mixture at the same temperature. The reaction mixture was stirred at the same temperature for 5 minutes. To the mixture, was added a solution of compound 54-2 (2.5 g) in CH$_2$Cl$_2$ (12.5 mL) at 0° C. The mixture was stirred for 1 hour at the same temperature. Then the mixture was concentrated in vacuo and the resulting residue was suspended in water. The mixture was extracted with EtOAc and the organic layer was washed with 1N HCl aq., sat. NaHCO$_3$ aq., brine, and it was dried with anhyd. Na$_2$SO$_4$. The solvent was removed under reduced pressure to obtain compound 54-3 (5.7 g) as brown oil.

Step 54-4

Synthesis of tert-butyl (2R,3R)-4-[N-(2-chloroethyl)-4-(trifluoromethyl)anilino]-2,3-dihydroxy-4-oxobutanoate (Compound 54-4)

According to the Step 7-4 in synthetic method for EXAMPLE 7, compound 54-3 (5.5 g) was used instead of 7-3 to obtain compound 54-4 (4.57 g) as a brown amorphous solid.

Step 54-5

Synthesis of tert-butyl (2R)-2-hydroxy-2-[(2R)-3-oxo-4-[4-(trifluoromethyl)phenyl]morpholin-2-yl]acetate (Compound 54-5)

According to the Step 7-5 in synthetic method for EXAMPLE 7, compound 54-4 (3 g) was used instead of 7-4 to obtain compound 54-5 (220 mg) as a pale yellow amorphous solid.

Step 54-6

Synthesis of (2R)-2-hydroxy-2-[(2R)-3-oxo-4-[4-(trifluoromethyl)phenyl]morpholin-2-yl]acetic acid (Compound 54-6)

According to the Step 52-4 in synthetic method for EXAMPLE 52, compound 54-5 (0.2 g) was used instead of 52-3 to obtain compound 54-6 (128 mg) as a colorless amorphous solid.

Step 54-7

Synthesis of (2R)—N—[N,N-bis(tert-butoxycarbonyl)-1-aminoisoquinolin-6-yl]-2-hydroxy-2-[(2R)-3-oxo-4-[4-(trifluoromethyl)phenyl]morpholin-2-yl]acetamide (Compound 54-7)

According to the Step 1-3 in synthetic method for EXAMPLE 1, compound 54-6 (128 mg) was used instead of 1-2 to obtain compound 54-7 (107 mg) as a beige amorphous solid.

Step 54-8

Synthesis of (2R)—N-(1-aminoisoquinolin-6-yl)-2-hydroxy-2-[(2R)-3-oxo-4-[4-(trifluoromethyl)phenyl]morpholin-2-yl]acetamide hydrochloride (EXAMPLE 54)

According to the Step 38-6 in synthetic method for EXAMPLE 38, 54-7 (50 mg) was used instead of 38-5 to obtain EXAMPLE 54 (28.3 mg) as a leaf green amorphous solid.

Example 55

Synthesis of (2R)—N-(1-aminoisoquinolin-6-yl)-2-hydroxy-2-[(2R)-3-oxo-4-[4-(trifluoromethoxy)phenyl]morpholin-2-yl]acetamide hydrochloride (EXAMPLE 55)

EXAMPLE 55

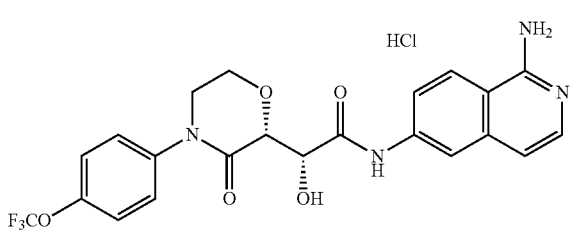

Step 55-1

Synthesis of 2-chloro-N-[4-(trifluoromethoxy)phenyl]acetamide (Compound 55-1)

According to the Step 20-1 in synthetic method for EXAMPLE 20, 4-trifluoromethoxyaniline (5 was used instead of 5-amino-1,3-dihydro-2H-benzimidazol-2-one to obtain compound 55-1 (6.67 g) as a khaki amorphous solid.

Step 55-2

Synthesis of N-(2-chloroethyl)-4-(trifluoromethoxy)aniline (Compound 55-2)

According to the Step 20-2 in synthetic method for EXAMPLE 20, compound 55-1 (3.3 g) was used instead of 20-1 to obtain compound 55-2 (3.21 g) as brown oil.

Step 55-3

Synthesis of tert-butyl (2R,3R)-2,3-diacetyloxy-4-[N-(2-chloroethyl)-4-(trifluoromethoxy)anilino]-4-oxobutanoate (Compound 55-3)

According to the Step 54-3 in synthetic method for EXAMPLE 54, compound 55-2 (3.05 g) was used instead of 54-2 to obtain compound 55-3 (6.51 g) as brown oil.

Step 55-4

Synthesis of tert-butyl (2R,3R)-4-[N-(2-chloroethyl)-4-(trifluoromethoxy)anilino]-2,3-dihydroxy-4-oxobutanoate (Compound 55-4)

According to the Step 7-4 in synthetic method for EXAMPLE 7, compound 55-3 (6.45 g) was used instead of 7-3 to obtain compound 55-4 (5.39 g) as brown amorphous solid.

Step 55-5

Synthesis of tert-butyl (2R)-2-hydroxy-2-[(2R)-3-oxo-4-[4-(trifluoromethoxy)phenyl]morpholin-2-yl]acetate (Compound 55-5)

According to the Step 7-5 in synthetic method for EXAMPLE 7, compound 55-4 (3 g) was used instead of 7-4 to obtain compound 55-5 (0.81 g) as a brown amorphous solid.

Step 55-6

Synthesis of (2R)-2-hydroxy-2-[(2R)-3-oxo-4-[4-(trifluoromethoxy)phenyl]morpholin-2-yl]acetic acid (Compound 55-6)

According to the Step 52-4 in synthetic method for EXAMPLE 52, compound 55-5 (0.6 g) was used instead of 52-3 to obtain compound 55-6 (0.7 g) as brown oil.

Step 55-7

Synthesis of (2R)—N—[N,N-bis(tert-butoxycarbonyl)-1-aminoisoquinolin-6-yl]-2-hydroxy-2-[(2R)-3-oxo-4-[4-(trifluoromethoxy)phenyl]morpholin-2-yl]acetamide (Compound 55-7)

According to the Step 1-3 in synthetic method for EXAMPLE 1, compound 55-6 (0.3 g) was used instead of 1-2 to obtain compound 55-7 (157 mg) as a beige powder.

Step 55-8

Synthesis of (2R)—N-(1-aminoisoquinolin-6-yl)-2-hydroxy-2-[(2R)-3-oxo-4-[4-(trifluoromethoxy)phenyl]morpholin-2-yl]acetamide hydrochloride (EXAMPLE 55)

According to the Step 38-6 in synthetic method for EXAMPLE 38, compound 55-7 (50 mg) was used instead of 38-5 to obtain EXAMPLE 55 (28.5 mg) as a leaf green amorphous solid.

Example 56

Synthesis of (2R)—N-(4-amidinophenyl)-2-hydroxy-2-[(2R)-3-oxo-4-[4-(trifluoromethoxy)phenyl]morpholin-2-yl]acetamide hydrochloride (EXAMPLE 56)

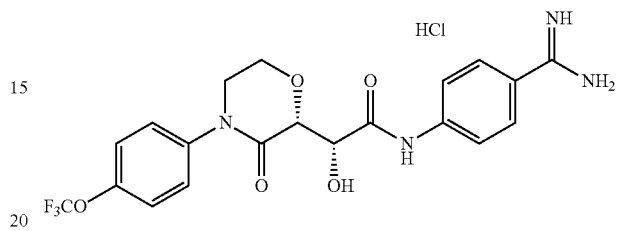

EXAMPLE 56

Step 56-1

Synthesis of (2R)-2-hydroxy-N-[4-(5-oxo-4H-1,2,4-oxadiazol-3-yl)phenyl]-2-[(2R)-3-oxo-4-[4-(trifluoromethoxy)phenyl]morpholin-2-yl]acetamide (Compound 56-1)

According to the Step 1-3 in synthetic method for EXAMPLE 1, compound 55-6 (0.3 g) and 3-(4-aminophenyl)-1,2,4-oxadiazol-5(2H)-one with DMF were used instead of 1-2 and 6-amino-1-bis(tert-butoxycarbonyl)aminoisoquinoline to obtain compound 56-1 (26 mg) as a colorless amorphous solid.

Step 56-2

Synthesis of (2R)—N-(4-amidinophenyl)-2-hydroxy-2-[(2R)-3-oxo-4-[4-(trifluoromethoxy)phenyl]morpholin-2-yl]acetamide hydrochloride (EXAMPLE 56)

According to the Step 26-B in synthetic method for EXAMPLE 26, compound 56-1 (23 mg) was used instead of 26-14 to obtain EXAMPLE 56 (13.5 mg) as a pale yellow amorphous solid.

Example 57

Synthesis of (2R)-2-hydroxy-N-(1-imino-2,3-dihydroisoindol-5-yl)-2-[(2R)-3-oxo-4-[4-(trifluoromethoxy)phenyl]morpholin-2-yl]acetamide hydrochloride (EXAMPLE 57)

Example 58

Synthesis of (2R)—N-(1-aminoisoquinolin-6-yl)-2-[(2R)-4-(4-bromophenyl)-3-oxomorpholin-2-yl]-2-hydroxyacetamide hydrochloride (EXAMPLE 58)

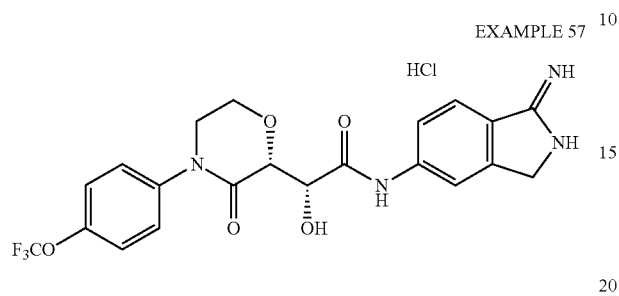

EXAMPLE 57

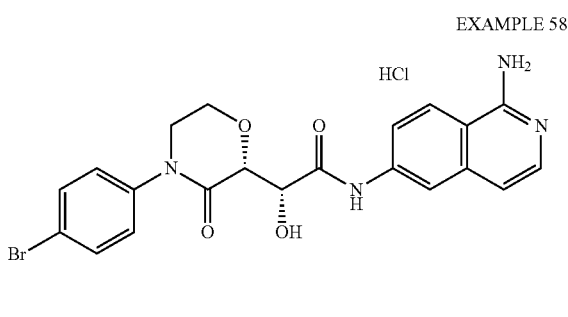 [SMILES: Nc1nccc2cc(NC(=O)[C@H](O)[C@H]3OCCN(c4ccc(Cl)cc4)C3=O)ccc12 ; Cl]

EXAMPLE 58

Step 57-1

Synthesis of N-[[2-cyano-5-[[(2R)-2-hydroxy-2-[(2R)-3-oxo-4-[4-(trifluoromethoxy)phenyl]morpholin-2-yl]acetyl]amino]phenyl]methyl]-N-[(2-methylpropan-2-yl)oxycarbonyl]carbamate (Compound 56-1)

According to the Step 1-3 in synthetic method for EXAMPLE 1, a cyclic carbonate analogue (0.15 g) derived from compound 55-6 and 39-2 (0.14 g) were used instead of 1-2 and 6-amino-1-bis(tert-butoxycarbonyl)aminoisoquinoline to obtain compound 57-1 (147 mg) as a pale yellow amorphous solid.

Step 57-2

Synthesis of (2R)—N-[3-(aminomethyl)-4-cyanophenyl]-2-hydroxy-2-[(2R)-3-oxo-4-[4-(trifluoromethoxy)phenyl]morpholin-2-yl]acetamide hydrochloride (Compound 57-2)

According to the Step 38-6 in synthetic method for EXAMPLE 38, 57-1 (0.14 g) was used instead of 38-5 to obtain compound 57-2 (93 mg) as a pale yellow amorphous solid.

Step 57-3

Synthesis of (2R)-2-hydroxy-N-(1-imino-2,3-dihydroisoindol-5-yl)-2-[(2R)-3-oxo-4-[4-(trifluoromethoxy)phenyl]morpholin-2-yl]acetamide hydrochloride (EXAMPLE 57)

According to the Step 39-7 in synthetic method for EXAMPLE 39, 57-3 (89 mg) was used instead of 39-6 to obtain EXAMPLE 57 (66.4 mg) as a pale yellow amorphous solid.

Step 58-1

Synthesis of N-(4-bromophenyl)-2-chloroacetamide (Compound 58-1)

According to the Step 20-1 in synthetic method for EXAMPLE 20, 4-bromoaniline (5 g) was used instead of 5-amino-1,3-dihydro-2H-benzimidazol-2-one to obtain compound 58-1 (7.28 g) as a gray amorphous solid.

Step 58-2

Synthesis of 4-bromo-N-(2-chloroethyl)aniline (Compound 58-2)

According to the Step 20-2 in synthetic method for EXAMPLE 20, compound 58-1 (7 g) was used instead of 20-1 to obtain compound 58-2 (6.81 g) as brown oil.

Step 58-3

Synthesis of tert-butyl (2R,3R)-2,3-diacetyloxy-4-[4-bromo-N-(2-chloroethyl)anilino]-4-oxobutanoate (Compound 58-3)

According to the Step 54-3 in synthetic method for EXAMPLE 54, compound 58-2 (6.06 g) was used instead of 54-2 to obtain compound 58-3 (13.2 g) as brown oil.

Step 58-4

Synthesis of tert-butyl (2R,3R)-4-[4-bromo-N-(2-chloroethyl)anilino]-2,3-dihydroxy-4-oxobutanoate (Compound 58-4)

According to the Step 7-4 in synthetic method for EXAMPLE 7, compound 58-3 (12.5 g) was used instead of 7-3 to obtain compound 58-4 (10.7 g) as brown oil.

Step 58-5

Synthesis of tert-butyl (2R)-2-[(2R)-4-(4-bromophenyl)-3-oxomorpholin-2-yl]-2-hydroxyacetate (compound 58-5)

According to the Step 7-5 in synthetic method for EXAMPLE 7, compound 58-4 (4 g) was used instead of 7-4 to obtain compound 58-5 (242 mg) as a colorless amorphous solid.

Step 58-6

Synthesis of (2R)-2-[(2R)-4-(4-bromophenyl)-3-oxomorpholin-2-yl]-2-hydroxyacetic acid (Compound 58-6)

According to the Step 52-4 in synthetic method for EXAMPLE 52, compound 58-5 (0.22 g) was used instead of 52-3 to obtain compound 58-6 (188 mg) as a colorless amorphous solid.

Step 58-7

Synthesis of (2R)—N—[N,N-bis(tert-Butoxycarbonyl)-1-aminoisoquinolin-6-yl]-2-[(2R)-4-(4-bromophenyl)-3-oxomorpholin-2-yl]-2-hydroxyacetamide (Compound 58-7)

According to the Step 1-3 in synthetic method for EXAMPLE 1, compound 58-6 (150 mg) was used instead of 1-2 to obtain compound 58-7 (110 mg) as a colorless amorphous solid.

Step 58-8

Synthesis of (2R)—N-(1-aminoisoquinolin-6-yl)-2-[(2R)-4-(4-bromophenyl)-3-oxomorpholin-2-yl]-2-hydroxyacetamide hydrochloride (EXAMPLE 58)

According to the Step 38-6 in synthetic method for EXAMPLE 38, compound 58-7 (50 mg) was used instead of 38-5 to obtain EXAMPLE 58 (29.3 mg) as a pale yellow amorphous solid.

Example 59

Synthesis of (2R)—N-(1-aminoisoquinolin-6-yl)-2-[(2R)-4-(4-fluorophenyl)-3-oxomorpholin-2-yl]-2-hydroxyacetamide hydrochloride (EXAMPLE 59)

EXAMPLE 59

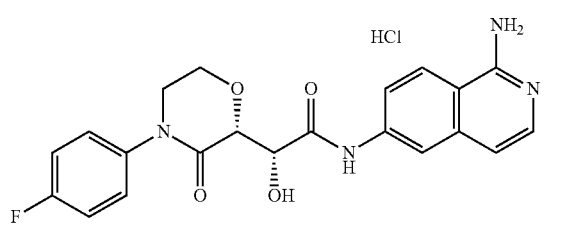

Step 59-1

Synthesis of 2-chloro-N-(4-fluorophenyl)acetamide (Compound 59-1)

According to the Step 20-1 in synthetic method for EXAMPLE 20, 4-fluoroaniline (2.65 g) was used instead of 5-amino-1,3-dihydro-2H-benzimidazol-2-one to obtain compound 59-1 (3.4 g) as a colorless amorphous solid.

Step 59-2

Synthesis of N-(2-chloroethyl)-4-fluoroaniline (Compound 59-2)

According to the Step 20-2 in synthetic method for EXAMPLE 20, compound 59-1 (2 g) was used instead of 20-1 to obtain compound 59-2 (1.95 g) as colorless oil.

Step 59-3

Synthesis of tert-butyl (2R,3R)-2,3-diacetyloxy-4-[N-(2-chloroethyl)-4-fluoroanilino]-4-oxobutanoate (Compound 59-3)

According to the Step 54-3 in synthetic method for EXAMPLE 54, compound 59-2 (1.57 g) was used instead of 54-2 to obtain compound 59-3 (2.1 g) as a colorless amorphous solid.

Step 59-4

Synthesis of tert-butyl (2R,3R)-4-[N-(2-chloroethyl)-4-fluoroanilino]-2,3-dihydroxy-4-oxobutanoate (Compound 59-4)

According to the Step 7-4 in synthetic method for EXAMPLE 7, compound 59-3 (2.1 g) was used instead of 7-3 to obtain compound 59-4 (1.62 g) as a colorless amorphous solid.

Step 59-5

Synthesis of tert-butyl (2R)-2-[(2R)-4-(4-fluorophenyl)-3-oxomorpholin-2-yl]-2-hydroxyacetate (Compound 59-5)

According to the Step 7-5 in synthetic method for EXAMPLE 7, compound 59-4 (1.62 g) and DMF were used instead of 7-4 and t-BuOH-DMSO to obtain compound 59-5 (400 mg) as a colorless amorphous solid.

Step 59-6

Synthesis of (2R)-2-[(2R)-4-(4-fluorophenyl)-3-oxomorpholin-2-yl]-2-hydroxyacetic acid (Compound 59-6)

According to the Step 52-4 in synthetic method for EXAMPLE 52, compound 59-5 (0.39 g) was used instead of 52-3 to obtain compound 59-6 (330 mg) as a colorless amorphous solid.

Step 59-7

Synthesis of (2R)—N—[N,N-bis(tert-butoxycarbonyl)-1-aminoisoquinolin-6-yl]-2-[(2R)-4-(4-fluorophenyl)-3-oxomorpholin-2-yl]-2-hydroxyacetamide (Compound 59-7)

According to the Step 1-3 in synthetic method for EXAMPLE 1, compound 59-6 (0.1 g) was used instead of 1-2 to obtain compound 59-7 (85 mg) as a beige amorphous solid.

Step 59-8

Synthesis of (2R)—N-(1-aminoisoquinolin-6-yl)-2-[(2R)-4-(4-fluorophenyl)-3-oxomorpholin-2-yl]-2-hydroxyacetamide hydrochloride (EXAMPLE 59)

According to the Step 38-6 in synthetic method for EXAMPLE 38, compound 59-7 (75 mg) was used instead of 38-5 to obtain EXAMPLE 59 (43 mg) as a beige amorphous solid.

Example 60

Synthesis of (2R)—N-(1-aminoisoquinolin-6-yl)-2-[(2R)-4-(4-chlorophenyl)-3-oxomorpholin-2-yl]-2-hydroxyacetamide hydrochloride (EXAMPLE 60)

EXAMPLE 60

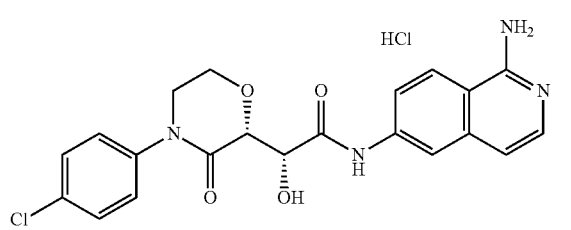

Step 60-1

Synthesis of 2-chloro-N-(4-chlorophenyl)acetamide (Compound 60-1)

According to the Step 20-1 in synthetic method for EXAMPLE 20, 4-chloroaniline (3.04 was used instead of 5-amino-1,3-dihydro-2H-benzimidazol-2-one to obtain compound 60-1 (4 g) as a colorless amorphous solid.

Step 60-2

Synthesis of 4-chloro-N-(2-chloroethyl)aniline (Compound 60-2)

According to the Step 20-2 in synthetic method for EXAMPLE 20, compound 60-1 (2 g) was used instead of 20-1 to obtain compound 60-2 (1.95 g) as colorless oil.

Step 60-3

Synthesis of tert-butyl (2R,3R)-2,3-diacetyloxy-4-[4-chloro-N-(2-chloroethyl)anilino]-4-oxobutanoate (Compound 60-3)

According to the Step 54-3 in synthetic method for EXAMPLE 54, compound 60-2 (1.87 g) was used instead of 54-2 to obtain compound 60-3 (2.2 g) as a light pink amorphous solid.

Step 60-4

Synthesis of tert-butyl (2R,3R)-4-[4-chloro-N-(2-chloroethyl)anilino]-2,3-dihydroxy-4-oxobutanoate (Compound 60-4)

According to the Step 7-4 in synthetic method for EXAMPLE 7, compound 60-3 (2.2 g) was used instead of 7-3 to obtain compound 60-4 (1.78 g) as a light yellow amorphous solid.

Step 60-5

Synthesis of tert-butyl (2R)-2-[(2R)-4-(4-chlorophenyl)-3-oxomorpholin-2-yl]-2-hydroxyacetate (compound 60-5)

According to the Step 7-5 in synthetic method for EXAMPLE 7, compound 60-4 (1.78 g) and DMF were used instead of 7-4 and t-BuOH-DMSO to obtain compound 60-5 (400 mg) as a pale yellow amorphous solid.

Step 60-6

Synthesis of (2R)-2-[(2R)-4-(4-Chlorophenyl)-3-oxomorpholin-2-yl]-2-hydroxyacetic acid (Compound 60-6)

According to the Step 52-4 in synthetic method for EXAMPLE 52, compound 60-5 (0.39 g) was used instead of 52-3 to obtain compound 60-6 (310 mg) as a pale yellow amorphous solid.

Step 60-7

Synthesis of (2R)—N—[N,N-bis(tert-butoxycarbonyl)-1-aminoisoquinolin-6-yl]-2-[(2R)-4-(4-chlorophenyl)-3-oxomorpholin-2-yl]-2-hydroxyacetamide (Compound 60-7)

According to the Step 1-3 in synthetic method for EXAMPLE 1, compound 60-6 (0.1 g) was used instead of 1-2 to obtain compound 60-7 (75 mg) as a beige amorphous solid.

Step 60-8

Synthesis of (2R)—N-(1-aminoisoquinolin-6-yl)-2-[(2R)-4-(4-chlorophenyl)-3-oxomorpholin-2-yl]-2-hydroxyacetamide hydrochloride (EXAMPLE 60)

According to the Step 38-6 in synthetic method for EXAMPLE 38, compound 60-7 (65 mg) was used instead of 38-5 to obtain EXAMPLE 60 (40 mg) as a beige amorphous solid.

Example 61

Synthesis of (2R)—N-(1-aminoisoquinolin-6-yl)-2-hydroxy-2-[(2R)-4-(4-isopropyloxyphenyl)-3-oxo morpholin-2-yl]acetamide hydrochloride (EXAMPLE 61)

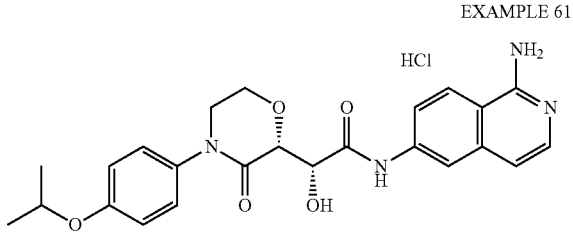 [SMILES: CC(C)Oc1ccc(N2CCO[C@H]([C@@H](O)C(=O)Nc3ccc4c(N)nccc4c3)C2=O)cc1 ; Cl]

EXAMPLE 61

Step 61-1

Synthesis of 2-chloro-N-(4-isopropyloxyphenyl)acetamide (Compound 61-1)

According to the Step 20-1 in synthetic method for EXAMPLE 20, 4-isopropoxyaniline (3.61 g) was used instead of 5-amino-1,3-dihydro-2H-benzimidazol-2-one to obtain compound 61-1 (3.6 g) as a beige amorphous solid.

Step 61-2

Synthesis of -(2-chloroethyl)-4-isopropyloxyaniline (Compound 61-2)

According to the Step 20-2 in synthetic method for EXAMPLE 20, compound 61-1 (1.8 g) was used instead of 20-1 to obtain compound 61-2 (1.7 g) as colorless oil.

Step 61-3

Synthesis of tert-butyl (2R,3R)-2,3-diacetyloxy-4-[N-(2-chloroethyl)-4-isopropyloxyanilino]-4-oxobutanoate (Compound 61-3)

According to the Step 54-3 in synthetic method for EXAMPLE 54, compound 61-2 (1.69 g) was used instead of 54-2 to obtain compound 61-3 (2.86 g) as colorless oil.

Step 61-4

Synthesis of tert-butyl (2R,3R)-4-[N-(2-chloroethyl)-4-isopropyloxyanilino]-2,3-dihydroxy-4-oxobutanoate (Compound 61-4)

According to the Step 7-4 in synthetic method for EXAMPLE 7, compound 61-3 (2.8 g) was used instead of 7-3 to obtain compound 61-4 (2.13 g) as pale yellow oil.

Step 61-5

Synthesis of tert-butyl (2R)-2-hydroxy-2-[(2R)-4-(4-isopropyloxyphenyl)-3-oxomorpholin-2-yl]acetate (Compound 61-5)

According to the Step 7-5 in synthetic method for EXAMPLE 7, compound 61-4 (0.8 g) was used instead of 7-4 to obtain compound 61-5 (220 mg) as a colorless amorphous solid.

Step 61-6

Synthesis of (2R)-2-hydroxy-2-[(2R)-4-(4-isopropyloxyphenyl)-3-oxomorpholin-2-yl]acetic acid (Compound 61-6)

According to the Step 52-4 in synthetic method for EXAMPLE 52, compound 61-5 (0.21 g) was used instead of 52-3 to obtain compound 61-6 (112 mg) as a colorless amorphous solid.

Step 61-7

Synthesis of (2R)—N—[N,N-bis(tert-Butoxycarbonyl)-1-aminoisoquinolin-6-yl]-2-hydroxy-2-[(2R)-4-(4-isopropyloxlphenyl)-3-oxomorpholin-2-yl]acetamide (Compound 61-7)

According to the Step 1-3 in synthetic method for EXAMPLE 1, compound 61-6 (0.1 g) was used instead of 1-2 to obtain compound 61-7 (71 mg) as a pale brown amorphous solid.

Step 61-8

Synthesis of (2R)—N-(1-aminoisoquinolin-6-yl)-2-hydroxy-2-[(2R)-4-(4-isopropyloxyphenyl)-3-oxo morpholin-2-yl]acetamide hydrochloride (EXAMPLE 61)

According to the Step 38-6 in synthetic method for EXAMPLE 38, compound 61-7 (59 mg) was used instead of 38-5 to obtain EXAMPLE 61 (19 mg) as a pale brown amorphous solid.

Example 62

Synthesis of (2R)—N-(1-aminoisoquinolin-6-yl)-2-hydroxy-2-[(2R)-3-oxo-4-p-tolylmorpholin-2-yl]acetamide Hydrochloride (EXAMPLE 62)

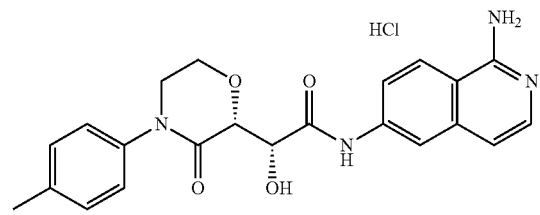

EXAMPLE 62

Step 62-1

Synthesis of tert-butyl (2R,3R)-2,3-diacetyloxy-4-[N-(2-chloroethyl)-4-methylanilino]-4-oxobutanoate (Compound 62-1)

According to the Step 52-1 in synthetic method for EXAMPLE 52, compound 7-1 (3 g) was used instead of 11-1 to obtain compound 62-1 (5.81 g) as pale yellow oil.

Step 62-2

Synthesis of tert-butyl (2R,3R)-4-[N-(2-chloroethyl)-4-methylanilino]-2,3-dihydroxy-4-oxobutanoate (Compound 62-2)

According to the Step 7-4 in synthetic method for EXAMPLE 7, compound 62-1 (5.45 g) was used instead of 7-3 to obtain compound 62-2 (4.7 g) as pale yellow oil.

Step 62-3

Synthesis of tert-butyl (2R)-2-hydroxy-2-[(2R)-3-oxo-4-p-tolylmorpholin-2-yl]acetate (Compound 62-3)

According to the Step 7-5 in synthetic method for EXAMPLE 7, compound 62-2 (2.5 g) was used instead of 7-4 to obtain compound 62-3 (1.02 g) as a pale brown amorphous solid.

Step 62-4

Synthesis of (2R)-2-hydroxy-2-[(2R)-3-oxo-4-p-tolylmorpholin-2-yl]acetic acid (Compound 62-4)

According to the Step 52-4 in synthetic method for EXAMPLE 52, compound 62-3 (1 g) was used instead of 52-3 to obtain compound 62-4 (777 mg) as a pale purple amorphous solid.

Step 62-5

Synthesis of (2R)—N—[N,N-bis(tert-butoxycarbonyl)-1-aminoisoquinolin-6-yl]-2-hydroxy-2-[(2R)-3-oxo-4-p-tolylmorpholin-2-yl]acetamide (Compound 62-5)

According to the Step 1-3 in synthetic method for EXAMPLE 1, compound 62-4 (0.2 g) was used instead of 1-2 to obtain compound 62-5 (0.11 g) as a pale brown solid.

Step 62-6

Synthesis of (2R)—N-(1-aminoisoquinolin-6-yl)-2-hydroxy-2-[(2R)-3-oxo-4-p-tolylmorpholin-2-yl]acetamide Hydrochloride (EXAMPLE 62)

According to the Step 38-6 in synthetic method for EXAMPLE 38, compound 62-5 (0.1 g) was used instead of 38-5 to obtain EXAMPLE 62 (51.5 mg) as a pale yellow amorphous solid.

Example 63

Synthesis of (2R)—N-(1-aminoisoquinolin-6-yl)-2-[(2R)-4-(4-fluoro-o-tolyl)-3-oxomorpholin-2-yl]-2-hydroxyacetamide hydrochloride (EXAMPLE 63)

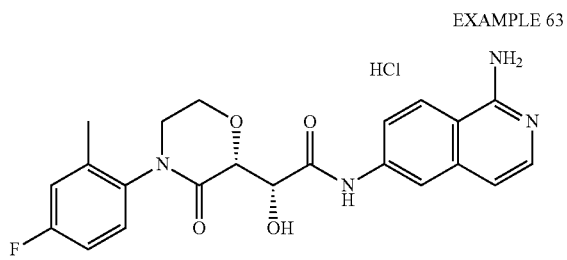

EXAMPLE 63

Step 63-1

Synthesis of 2-chloro-N-(4-fluoro-o-tolyl)acetamide (Compound 63-1)

According to the Step 20-1 in synthetic method for EXAMPLE 20, 4-fluoro-2-methylaniline (5 g) was used instead of 5-amino-1,3-dihydro-2H-benzimidazol-2-one to obtain compound 63-1 (8 g) as a gray amorphous solid.

Step 63-2

Synthesis of N-(2-chloroethyl)-4-fluoro-2-methylaniline (Compound 63-2)

According to the Step 20-2 in synthetic method for EXAMPLE 20, compound 63-1 (8 g) was used instead of 20-1 to obtain compound 63-2 (7.87 g) as brown oil.

Step 63-3

Synthesis of tert-butyl (2R,3R)-2,3-diacetyloxy-4-[N-(2-chloroethyl)-4-fluoro-2-methylanilino]-4-oxobutanoate (Compound 63-3)

According to the Step 54-3 in synthetic method for EXAMPLE 54, compound 63-2 (7.37 g) was used instead of 54-2 to obtain compound 63-3 (10.4 g) as pale yellow oil.

Step 63-4

Synthesis of tert-butyl (2R,3R)-4-[N-(2-chloroethyl)-4-fluoro-2-methylanilino]-2,3-dihydroxy-4-oxobutanoate (Compound 63-4)

According to the Step 7-4 in synthetic method for EXAMPLE 7, compound 63-3 (10.4 g) was used instead of 7-3 to obtain compound 63-4 (8 g) as a pale yellow amorphous solid.

Step 63-5

Synthesis of tert-butyl (2R)-2-[(2R)-4-(4-fluoro-o-tolyl)-3-oxomorpholin-2-yl]-2-hydroxyacetate (compound 63-5)

According to the Step 7-5 in synthetic method for EXAMPLE 7, compound 63-4 (3 g) was used instead of 7-4 to obtain compound 63-5 (710 mg) as a colorless amorphous solid.

Step 63-6

Synthesis of (2R)-2-[(2R)-4-(4-fluoro-o-tolyl)-3-oxomorpholin-2-yl]-2-hydroxyacetic acid (Compound 63-6)

According to the Step 52-4 in synthetic method for EXAMPLE 52, compound 63-5 (0.7 g) was used instead of 52-3 to obtain compound 63-6 (0.72 g) as a colorless amorphous solid.

Step 63-7

Synthesis of (2R)—N—[N,N-bis(tert-butoxycarbonyl)-1-aminoisoquinolin-6-yl]-2-[(2R)-4-(4-fluoro-o-tolyl)-3-oxomorpholin-2-yl]-2-hydroxyacetamide (Compound 63-7)

According to the Step 1-3 in synthetic method for EXAMPLE 1, compound 63-6 (0.3 g) was used instead of 1-2 to obtain compound 63-7 (198 mg) as a pale yellow amorphous solid.

Step 63-8

Synthesis of (2R)—N-(1-aminoisoquinolin-6-yl)-2-[(2R)-4-(4-fluoro-o-tolyl)-3-oxomorpholin-2-yl]-2-hydroxyacetamide Hydrochloride (EXAMPLE 63)

According to the Step 38-6 in synthetic method for EXAMPLE 38, compound 63-7 (57.2 mg) was used instead of 38-5 to obtain EXAMPLE 63 (28.8 mg) as a pale yellow amorphous solid.

Example 64

Synthesis of (2R)—N-(4-amidinophenyl)-2-[(2R)-4-(4-fluoro-o-tolyl)-3-oxomorpholin-2-yl]-2-hydroxy-acetamide Hydrochloride (EXAMPLE 64)

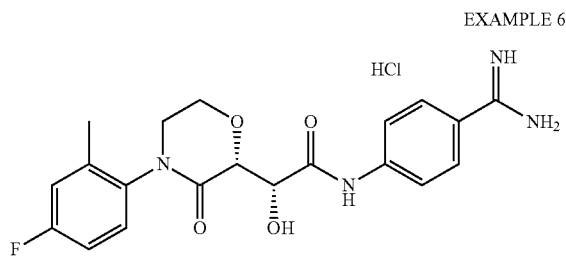

EXAMPLE 64

Step 64-1

Synthesis of (2R)-2-[(2R)-4-(4-fluoro-o-tolyl)-3-oxomorpholin-2-yl]-2-hydroxy-N-[4-(5-oxo-4H-1,2,4-oxadiazol-3-yl)phenyl]acetamide (Compound 64-1)

According to the Step 1-3 in synthetic method for EXAMPLE 1, a cyclic carbonate analogue (0.11 g) derived from compound 63-6 and 3-(4-aminophenyl)-1,2,4-oxadiazol-5(2H)-one with DMF were used instead of 1-2 and 6-amino-1-bis(tert-butoxycarbonyl)aminoisoquinoline to obtain compound 64-1 (43.2 mg) as a pale pink amorphous solid.

Step 64-2

Synthesis of (2R)—N-(4-amidinophenyl)-2-[(2R)-4-(4-fluoro-o-tolyl)-3-oxomorpholin-2-yl]-2-hydroxy-acetamide Hydrochloride (EXAMPLE 64)

According to the Step 26-B in synthetic method for EXAMPLE 26, compound 64-1 (28.2 mg) was used instead of 26-14 to obtain EXAMPLE 64 (15.7 mg) as a pale yellow amorphous solid.

Example 65

Synthesis of (2R)—N-(4-amidino-o-tolyl)-2-[(2R)-4-(4-tert-butylphenyl)-3-oxomorpholin-2-yl]-2-hydroxyacetamide (EXAMPLE 65)

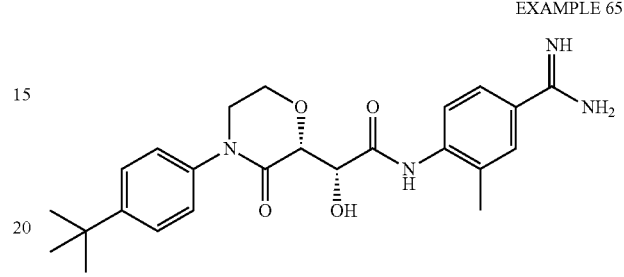

EXAMPLE 65

Step 65-1

Synthesis of (2R)-2-[(2R)-4-(4-tert-butylphenyl)-3-oxomorpholin-2-yl]-N-(4-cyano-o-tolyl)-2-hydroxy-acetamide (Compound 65-1)

According to the Step 1-3 in synthetic method for EXAMPLE 1, a cyclic carbonate analogue (0.2 g) derived from compound 52-4 and 4-amino-3-methylbenzonitrile (79.3 mg) were used instead of 1-2 and 6-amino-1-bis(tert-butoxy carbonyl)aminoisoquinoline, under high concentration condition (1M), to obtain compound 65-1 (129 mg) as a colorless amorphous solid.

Step 65-2

Synthesis of (2R)—N-(4-amidino-o-tolyl)-2-[(2R)-4-(4-tert-butylphenyl)-3-oxomorpholin-2-yl]-2-hydroxyacetamide (EXAMPLE 65)

According to the Step 7-6 in synthetic method for EXAMPLE 7, compound 65-1 (60 mg) was used instead of 7-5 to obtain EXAMPLE 65 (8.3 mg) as a pale yellow amorphous solid.

Example 66

Synthesis of (2R)—N-(4-amidino-2-chlorophenyl)-2-[(2R)-4-(4-tert-butylphenyl)-3-oxomorpholin-2-yl]-2-hydroxyacetamide acetate (EXAMPLE 66)

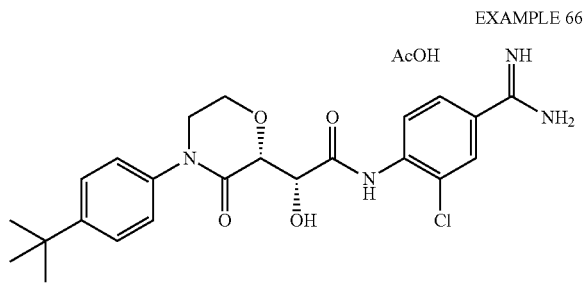 [SMILES: "AcOH" ; CC(C)(C)c1ccc(N2CCO[C@H]([C@@H](O)C(=O)Nc3ccc(C(=N)N)cc3Cl)C2=O)cc1]

EXAMPLE 66

Step 66-1

Synthesis of (2R)-2-[(2R)-4-(4-tert-butylphenyl)-3-oxomorpholin-2-yl]-N-(2-chloro-4-cyanophenyl)-2-hydroxyacetamide (Compound 66-1)

According to the Step 1-3 in synthetic method for EXAMPLE 1, a cyclic carbonate analogue (0.2 g) derived from compound 52-4 and 4-amino-3-chlorobenzonitrile (91.6 mg) were used instead of 1-2 and 6-amino-1-bis(tert-butoxy carbonyl)aminoisoquinoline, under high concentration condition (1M), to obtain compound 66-1 (93.1 mg) as a colorless amorphous solid.

Step 66-2

Synthesis of (2R)-2-[(2R)-4-(4-tert-butylphenyl)-3-oxomorpholin-2-yl]-N-[2-chloro-4-(N'-hydroxyamidino)phenyl]-2-hydroxyacetamide (Compound 66-2)

To a suspension of compound 66-1 (60 mg) in EtOH (2 mL), was added 50% NH$_2$OH aq. (22.4 microL). The reaction mixture was stirred at room temperature overnight. Then the mixture was concentrated in vacuo to obtain compound 66-2 (67 mg) as a colorless amorphous solid.

Step 66-3

Synthesis of (2R)—N-(4-amidino-2-chlorophenyl)-2-[(2R)-4-(4-tert-butylphenyl)-3-oxomorpholin-2-yl]-2-hydroxyacetamide acetate (EXAMPLE 66)

To a solution of compound 66-2 (19 mg) in EtOH (3 mL), were added cat. Raney-Ni and AcOH (0.1 mL). The mixture was stirred under hydrogen atmosphere for 3 hours at room temperature. The mixture was filtered with Celite® pad to remove catalyst. The filtrate was concentrated with toluene in vacuo. The residue was dried by vacuum pump to obtain EXAMPLE 66 (15 mg) as a colorless amorphous solid.

Example 67

Synthesis of (2R)—N-(4-amidino-2-fluorophenyl)-2-[(2R)-4-(4-tert-butylphenyl)-3-oxomorpholin-2-yl]-2-hydroxyacetamide acetate (EXAMPLE 67)

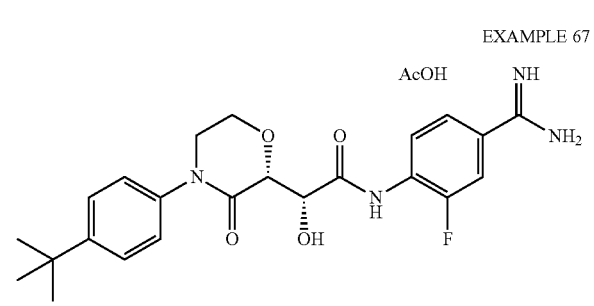 [SMILES: "AcOH" ; CC(C)(C)c1ccc(N2CCO[C@H]([C@@H](O)C(=O)Nc3ccc(C(=N)N)cc3F)C2=O)cc1]

EXAMPLE 67

Step 67-1

Synthesis of (2R)-2-[(2R)-4-(4-tert-butylphenyl)-3-oxomorpholin-2-yl]-N-(4-cyano-2-fluorophenyl)-2-hydroxyacetamide (Compound 67-1)

According to the Step 1-3 in synthetic method for EXAMPLE 1, a cyclic carbonate analogue (0.2 g) derived from compound 52-4 and 4-amino-3-fluorobenzonitrile (81.7 mg) were used instead of 1-2 and 6-amino-1-bis(tert-butoxy carbonyl)aminoisoquinoline, under high concentration condition (1M), to obtain compound 67-1 (130 mg) as a colorless amorphous solid.

Step 67-2

Synthesis of (2R)-2-[(2R)-4-(4-tert-butylphenyl)-3-oxomorpholin-2-yl]-N-[2-fluoro-4-(N'-hydroxyamidino)phenyl]-2-hydroxyacetamide (Compound 67-2)

According to the Step 66-2 in synthetic method for EXAMPLE 66, compound 67-1 (67.1 mg) was used instead of 66-1 to obtain compound 67-2 (71.9 mg) as a colorless amorphous solid.

Step 67-3

Synthesis of (2R)—N-(4-amidino-2-fluorophenyl)-2-[(2R)-4-(4-tert-butylphenyl)-3-oxomorpholin-2-yl]-2-hydroxyacetamide acetate (EXAMPLE 67)

According to the Step 66-3 in synthetic method for EXAMPLE 66, compound 67-2 (62 mg) was used instead of 66-2 to obtain EXAMPLE 67 (46.7 mg) as a colorless amorphous solid.

Example 68

Synthesis of (R)—N-(4-carbamimidoylphenyl)-2-hydroxy-2-((R)-3-oxo-4-(3-oxo-2-propylisoindolin-5-yl)morpholin-2-yl)acetamide hydrochloride (EXAMPLE 68)

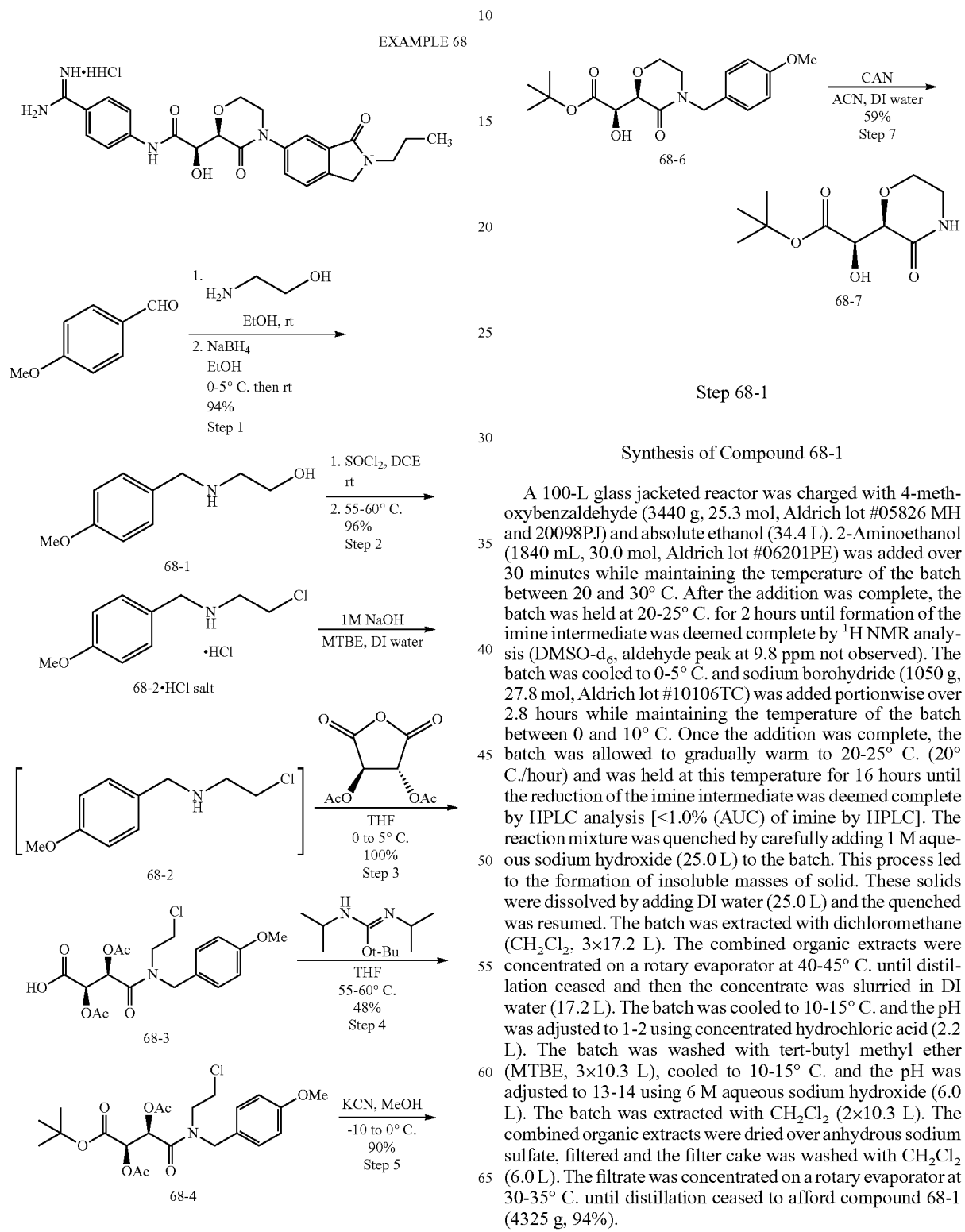

Step 68-1

Synthesis of Compound 68-1

A 100-L glass jacketed reactor was charged with 4-methoxybenzaldehyde (3440 g, 25.3 mol, Aldrich lot #05826 MH and 20098PJ) and absolute ethanol (34.4 L). 2-Aminoethanol (1840 mL, 30.0 mol, Aldrich lot #06201PE) was added over 30 minutes while maintaining the temperature of the batch between 20 and 30° C. After the addition was complete, the batch was held at 20-25° C. for 2 hours until formation of the imine intermediate was deemed complete by $^1$H NMR analysis (DMSO-$d_6$, aldehyde peak at 9.8 ppm not observed). The batch was cooled to 0-5° C. and sodium borohydride (1050 g, 27.8 mol, Aldrich lot #10106TC) was added portionwise over 2.8 hours while maintaining the temperature of the batch between 0 and 10° C. Once the addition was complete, the batch was allowed to gradually warm to 20-25° C. (20° C./hour) and was held at this temperature for 16 hours until the reduction of the imine intermediate was deemed complete by HPLC analysis [<1.0% (AUC) of imine by HPLC]. The reaction mixture was quenched by carefully adding 1 M aqueous sodium hydroxide (25.0 L) to the batch. This process led to the formation of insoluble masses of solid. These solids were dissolved by adding DI water (25.0 L) and the quenched was resumed. The batch was extracted with dichloromethane ($CH_2Cl_2$, 3×17.2 L). The combined organic extracts were concentrated on a rotary evaporator at 40-45° C. until distillation ceased and then the concentrate was slurried in DI water (17.2 L). The batch was cooled to 10-15° C. and the pH was adjusted to 1-2 using concentrated hydrochloric acid (2.2 L). The batch was washed with tert-butyl methyl ether (MTBE, 3×10.3 L), cooled to 10-15° C. and the pH was adjusted to 13-14 using 6 M aqueous sodium hydroxide (6.0 L). The batch was extracted with $CH_2Cl_2$ (2×10.3 L). The combined organic extracts were dried over anhydrous sodium sulfate, filtered and the filter cake was washed with $CH_2Cl_2$ (6.0 L). The filtrate was concentrated on a rotary evaporator at 30-35° C. until distillation ceased to afford compound 68-1 (4325 g, 94%).

Step 68-2

Synthesis of Compound 68-2

A 100-L glass jacketed reactor was charged with compound 68-1 (4325 g, 23.9 mol) and 1,2-dichloroethane (86.5 L). Thionyl chloride (1900 mL, 26.1 mol, Aldrich lot #05497DJ) was added over 50 minutes while maintaining the temperature of the batch between 20 and 30° C. Once the addition was complete, the batch was heated to 55-60° C. and held at this temperature for 5.5 hours until the reaction was deemed complete by $^1$H NMR analysis (DMSO-$d_6$, doublets at 7.3 ppm and 6.9 ppm shifted to 7.5 ppm and 7.0 ppm respectively, and doublets at 9.2 min and multiplet at 4.4 ppm disappeared). The batch was cooled to 20-25° C. and concentrated using a rotavap at 40-45° C. until distillation ceased. The concentrate was swapped once with MTBE (22.0 L), slurried in MTBE (21.7 L) and filtered to afford 68-2.HCl (5420 g, 96%) as white solids after drying in a vacuum oven at 20-30° C. for 17 hours.

Step 68-3

Synthesis of Compound 68-3

A 50-L glass jacketed reactor was charged with compound 68-2.HCl (1940 g, 8.2 mol), DI water (19.4 L) and MTBE (19.4 L). The pH of the aqueous layer was adjusted to 11-12 using 1 M aqueous sodium hydroxide (10.5 L) and maintaining the temperature of the batch between 15 and 30° C. The phases were separated and the aqueous layer was extracted with MTBE (2×9.7 L). The combined organic extracts were dried over anhydrous sodium sulfate, filtered, washed with MTBE (8.0 L) and the filtrate was concentrated on a rotary evaporator at 20-25° C. until distillation ceased, affording free amine 68-2 (1720 g, containing 6.8 wt % of MTBE by $^1$H NMR (DMSO-$d_6$), corrected weight: 1604 g, 98%)

A 50-L glass jacketed reactor was charged with di-O-acetyl-L-tartaric anhydride (1775 g, 8.2 mol, Alfa Aesar lot # E13U033) and tetrahydrofuran (17.5 L, THF). The batch was cooled to 0-5° C. and a solution of compound 68-2 (1720 g) in THF (2.0 L) was added over 1.3 hours while maintaining the temperature of the batch between 0 and 10° C. The batch was held at 0-5° C. for 18 hours until the reaction was deemed complete by HPLC analysis [2.8% (AUC) of compound 68-2 remaining] and then it was concentrated on a rotary evaporator at 20-25° C. until distillation ceased to afford compound 68-3 [4485 g, containing 22.7 wt % of THF by $^1$H NMR (DMSO-$d_6$), corrected weight: 3467 g, 102%, 86.9% (AUC) by HPLC].

Step 68-4

Synthesis of Compound 68-4

A 50-L glass jacketed reactor was charged with compound 68-3 (3520 g, assuming theoretical yield for step 3, 8.5 mol) and THF (35.0 L), and the batch was heated to 50-60° C. Two portions of O-tert-butyl-N,N-diisopropylurea (2115 g, 10.6 mol, and 1700 g, 8.9 mol) were each added dropwise over 30 minutes while maintaining the temperature of the batch between 50 and 60° C. In-process assay by HPLC analysis after these additions were complete indicated that 19.5% (AUC) of compound 68-3 remained and that 70.9% (AUC) of compound 68-4 had formed. Additional O-tert-butyl-N,N-diisopropylurea (2×425 g, 4.2 mol) was added to the batch until the reaction was deemed complete by HPLC analysis [4.4% (AUC) of compound 68-3 remaining]. The batch was cooled to 15-25° C. and MTBE (19.4 L) was added. The batch was filtered over Celite® and washed with MTBE (15.0 L). The combined filtrate and washes were concentrated on a rotary evaporator at 40-45° C. until distillation ceased to afford crude compound 68-4 [4675 g, containing 10.6 wt % of THF by $^1$H NMR (DMSO-$d_6$), corrected weight 4180 g, 105%, 55.7% (AUC) by HPLC]. This material was purified by silica-gel column chromatography (Four 1.1 to 1.3-kg batches using 5.5 kg of silica gel each, 20 to 60% EtOAc in heptane) to afford compound 68-4 [1915 g, 48%, 96.7-97.1% (AUC) by HPLC] as well as mixed fractions that were combined with other lots for further purification.

Step 68-5

Synthesis of Compound 68-5

A 50-L glass jacketed reactor was charged with compound 68-4 (1100 g, 2.3 mol) and methanol (10.2 L), and the batch was cooled to −10 to 0° C. A slurry of potassium cyanide (80 g, 1.2 mol, Aldrich lot #14614KA) in methanol (800 mL) was added over 5 minutes while maintaining the temperature of the batch between −10 and 0° C. The batch was held at −10 to 0° C. for 3.3 hours until the reaction was deemed complete by HPLC analysis [5.3% (AUC) of compound 68-4 remaining]. Solid sodium bicarbonate (200 g, 2.4 mol, Natrium Products lot #01096A) was added and the batch was concentrated on a rotary evaporator at 20-25° C. until distillation ceased. MTBE (11.0 L) and DI water (11.0 L) were added to the concentrate, and the layers were separated. The organic layer was washed with saturated aqueous sodium bicarbonate (6.0 L), dried over anhydrous sodium sulfate, filtered, washed with MTBE (7.0 L) and concentrated on a rotary evaporator at 20-25° C. until distillation ceased to yield compound 68-5 [910 g, containing 10.2 wt % of MTBE by $^1$H NMR (CDCl$_3$), corrected weight 817 g, 90%, 82.4% (AUC) by HPLC]. This material was stored in the freezer.

Step 68-6

Synthesis of Compound 68-6

A 50-L glass jacketed reactor was charged with compound 68-5 (817 g, 2.1 mol), CH$_2$Cl$_2$ (8.2 L) and deionized water (1.9 L). Benzyltrimethylammonium hydroxide (1912 mL, 40 wt % in methanol, 4.2 mol, Aldrich lot #10896HJ) was added to the batch over 10 minutes while maintaining the temperature between 20 and 25° C. The batch was held at 20-25° C. for 1.5 hours until the reaction was deemed complete by HPLC analysis [<1.0% (AUC) of compound 68-5 remaining]. At completion of the reaction, DI water (6.5 L) was added and the layers were separated. The aqueous layer was extracted with CH$_2$Cl$_2$ (8.2 L). The combined organic extracts were washed with brine (8.2 L), dried over anhydrous sodium sulfate, filtered and washed with CH$_2$Cl$_2$ (2.5 L). The combined filtrate and washes were concentrated on a rotary evaporator at 30-35° C. until distillation ceased to afford crude compound 68-6 [625 g, 84%, 82.5% (AUC) by HPLC]. This material was purified by silica-gel column chromatography [5 kg of silica gel, 20 to 60% EtOAc in heptane] and the pure fractions were slurried in 1:4 MTBE/heptane to yield compound 68-6 [Two lots: 155 g, 21%, >99% (AUC) by HPLC, and 335 g, 45%, >99% (AUC) by HPLC] as white solids.

Step 68-7

Synthesis of Compound 68-7

A 50-L glass jacketed reactor was charged with compound 68-6 (490 g, 1.4 mol), acetonitrile (10.1 L) and DI water (2.0 L). The batch was cooled to 0-5° C. and a slurry of cerium (IV) ammonium nitrate (3060 g, 5.6 mol, Alfa Aesar lot # H22T016) in acetonitrile (8.0 L) was added while maintaining the temperature of the batch between 0 and 5° C. The batch was held at 0-5° C. for 30 minutes, warmed to 20-25° C. and held at this temperature for 3.5 hours until the reaction was deemed complete by HPLC analysis. Saturated aqueous sodium bicarbonate (17.0 L) was added until the pH of the reaction mixture reached 4.5 to 5. The resulting suspension was filtered over Celite® and the filter cake was washed with CH$_2$Cl$_2$ (2×10.0 L) followed by 5% methanol in CH$_2$Cl$_2$ (10.0 L). The combined filtrate and washes were transferred to a 50-L, glass jacketed reactor and the phases were separated. The aqueous layer was extracted with CH$_2$Cl$_2$ (15.0 L). The combined organic extracts were washed with brine, dried over anhydrous sodium sulfate, filtered and the filter cake was washed with CH$_2$Cl$_2$ (10.0 L). The combined filtrate and washes were concentrated on a rotary evaporator at 30-35° C. until distillation ceased to give crude compound 68-7 [700 g, >100%]. This material was purified by silica-gel column chromatography [4 kg of silica gel, 1 to 5% methanol in dichloromethane]. The pure fractions were slurried in 1:4 CH$_2$Cl$_2$/MTBE to yield compound 68-7 [Two lots: 189 g, 59%] as white to off-white solids.

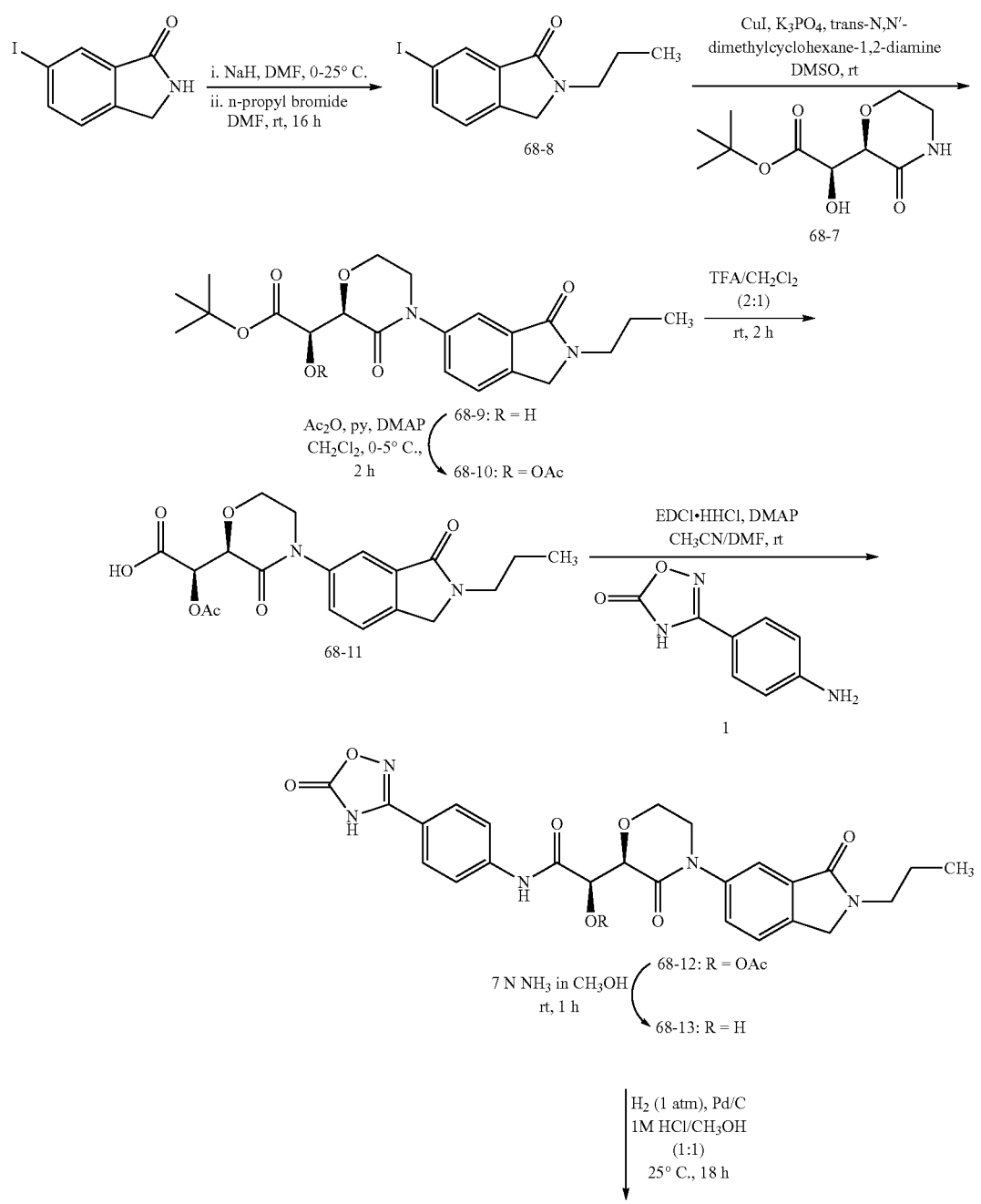

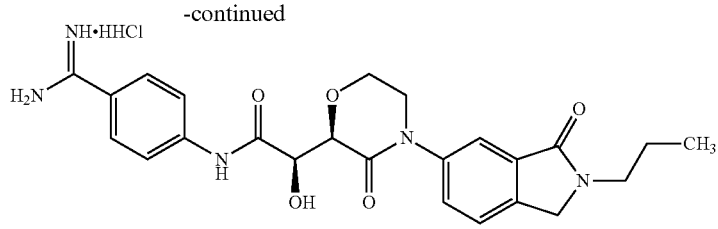

EXAMPLE 68

Step 68-8

Synthesis of Compound 68-8

To a 50 mL round bottom flask was added 5-iodo-3-oxo-isoindolin (1.00 g, 3.86 mmol) in DMF (10.0 mL) and the reaction mixture was stirred at 0-5° C. NaH (60% in oil, 186 mg, 4.65 mmol) was added, and the reaction mixture was allowed to warm to room temperature. After 20 min, the reaction obtained a green color, and a solution of n-propyl bromide (706 mg, 5.78 mmol) in DMF (2.00 mL) was added dropwise over a period of 15 min. The reaction mixture was stirred overnight at room temperature, then diluted with EtOAc (100 mL), washed with saturated aqueous NH$_4$Cl (2×25 mL), saturated aqueous LiCl (25 mL), brine (25 mL), dried over Na$_2$SO$_4$, filtered and concentrated under reduced pressure. The resulting residue was purified by CombiFlash (80 g, Hex/EtOAc, 100:0 to 30:70 over 30 min) to provide compound 68-8 (700 mg, 60%) as a white solid.[1]

Step 68-9

Synthesis of Compound 68-9

A mixture of compound 68-7 (100 mg, 0.432 mmol), aryl iodide compound 68-8 (156 mg, 0.518 mmol), CuI (8.1 mg, 43 µmol), K$_3$PO$_4$ (183 mg, 0.861 mmol), DMSO (1.5 mL), and trans-N,N'-dimethylcyclohexane-1,2-diamine (13.6 µL, 86.1 µmol) were stirred at room temperature under nitrogen in the dark. After 14 h, additional CuI (8.1 mg, 43 µmol) and trans-N,N'-dimethylcyclohexane-1,2-diamine (13.6 µL, 86.1 µmol) were added and the mixture was stirred for an additional 2.5 h. The mixture was diluted with EtOAc (100 mL), washed with water (3×25 mL), brine (25 mL), dried over Na$_2$SO$_4$, filtered, and concentrated under reduced pressure. The crude product was purified on CombiFlash (12 g SiO$_2$, Hex/EtOAc, 100:0 to 0:100 over 45 min) to provide pure product compound 68-9 (120 mg, 69%) as a yellow solid.

Step 68-10

Synthesis of Compound 68-10

To a 50 mL round bottom flask was added compound 68-9 (114 mg, 0.281 mmol), DMAP (3.4 mg, 28 µmol), pyridine (45 µL, 0.56 mmol) and CH$_2$Cl$_2$ (5.00 mL). The reaction mixture was cooled to 0-5° C., Ac$_2$O (53 µL, 0.56 mmol) was added, stirred at 0-5° C. for 2 h, and then diluted with EtOAc (40 mL), washed with saturated aqueous CuSO$_4$ (2×25 mL), brine (25 mL), dried over Na$_2$SO$_4$, filtered and concentrated under reduced pressure to provide crude compound 68-10 (125 mg, quant) as a yellow solid. The product was used in the next reaction without any further purification.

Step 68-11

Synthesis of Compound 68-11

In a 50 mL round bottom flask containing compound 68-10 (125 mg, 0.281 mmol) was added CH$_2$Cl$_2$ (1.00 mL) and TFA (2.00 mL). The reaction mixture was stirred at room temperature for 2 h, then TFA and CH$_2$Cl$_2$ were removed under reduced pressure. The crude product was triturated with ether to provide pure 68-11 (110 mg, quant.) as a yellow solid.

Step 68-12

Synthesis of Compound 68-12

To a 100 mL round bottom flask was added compound 68-11 (110 mg, 0.281 mmol), DMAP (3.4 mg, 28 µmol), and 3-(4-aminophenyl)-1,2,4-oxadiazol-5(2H)-one 1 (53.1 mg, 0.299 mmol) in CH$_3$CN (3.00 mL). The reaction mixture was cooled to 0-5° C., then EDCI.HCl (57.5 mg, 0.299 mmol) was added and the reaction mixture was warmed to room temperature. After 30 min DMF (1.00 mL) was added to dissolve the precipitate and stirring was continued for an additional 3 h. The solvents were removed under reduced pressure and the residue was triturated with ether (20.0 mL) then decanted. The undissolved material was washed with water (2×5 mL) and acetonitrile (2×5 mL) then dried on under vacuum to provide pure product 68-12 (95 mg, 62%) as off-white solid.

Step 68-13

Synthesis of Compound 68-13

To a 50 mL round bottom flask was added compound 68-12 (95 mg, 0.17 mmol), CH$_3$OH (2.00 mL) and 7 N NH$_3$ in CH$_3$OH (6.00 mL). The reaction mixture was stirred at room temperature for 1 h then the volatiles were removed under reduced pressure. Additional CH$_3$OH (2×50 mL) was used to strip off excess NH$_3$. The crude product was redissolved in CH$_3$OH (50 mL) and the solvent degassed with N$_2$ to remove trace ammonia then concentrated under reduced pressure to provide compound 68-13 (85 mg, 99%) as off-white solid.

Step 68-14

Synthesis of (R)—N-(4-carbamimidoylphenyl)-2-hydroxy-2-((R)-3-oxo-4-(3-oxo-2-propylisoindolin-5-yl)morpholin-2-yl)acetamide hydrochloride (EXAMPLE 68)

To a 250 mL round bottom flask was added compound 68-13 (84 mg, 0.17 mmol) in CH$_3$OH (6.00 mL) and 1 M HCl (6.00 mL). The solvent was degassed for 10 min with N$_2$, then 10% Pd/C (84 mg, 39 μmol) was added and the reaction mixture was hydrogenated at 1 atm overnight. The mixture was diluted with hot CH$_3$OH (250 mL), filtered and the filtrate was concentrated under reduced pressure. The residue was triturated with CH$_3$OH (5.00 mL) and filtered to provide pure product compound 68 (51 mg, 64%) as off-white solid.

Example 69

Synthesis of (R)—N-(4-carbamimidoylphenyl)-2-hydroxy-2-((R)-3-oxo-4-(3-oxo-2-(2,2,2-trifluoroethyl) isoindolin-5-yl)morpholin-2-yl)acetamide hydrochloride (EXAMPLE 69)

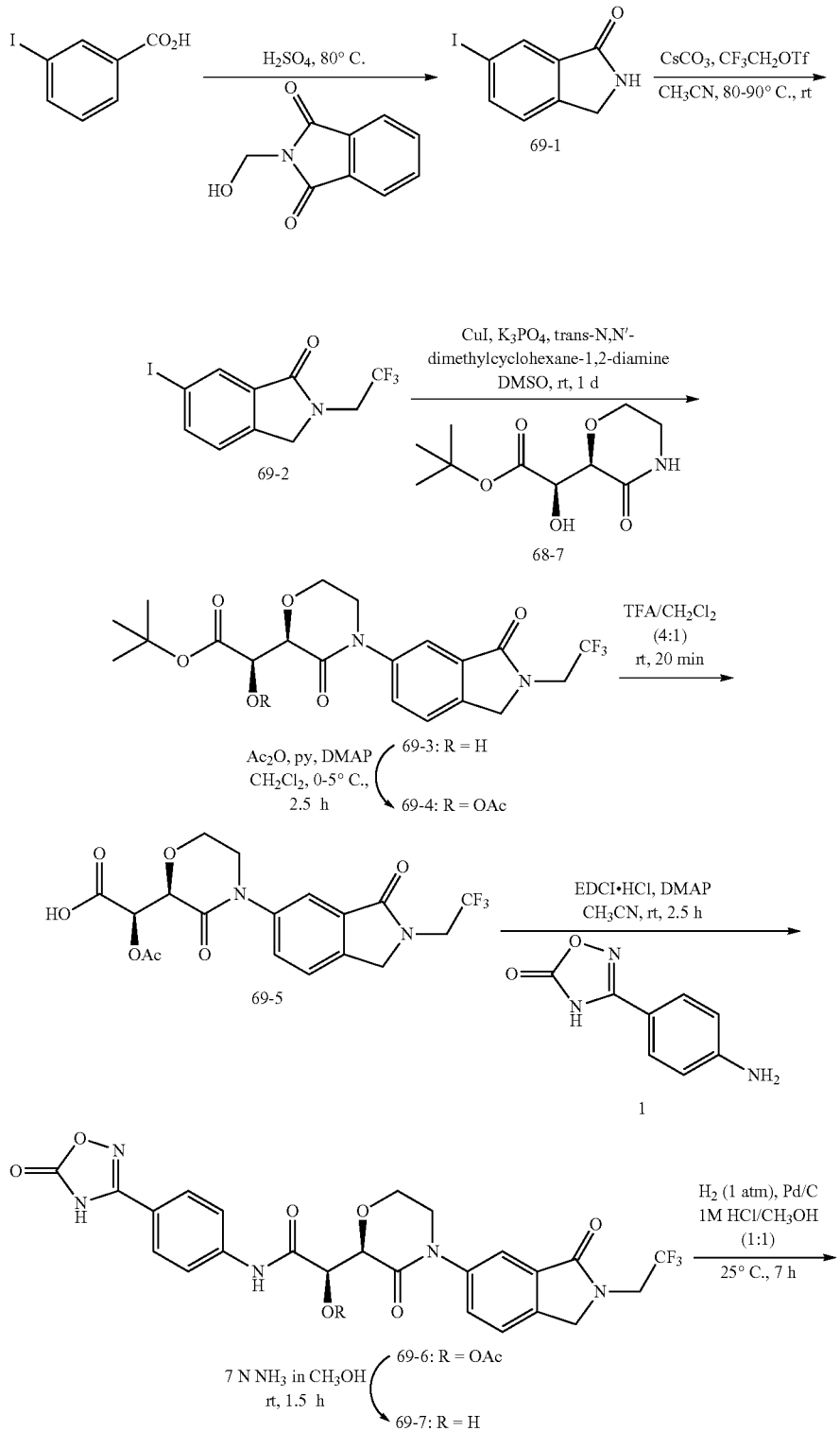

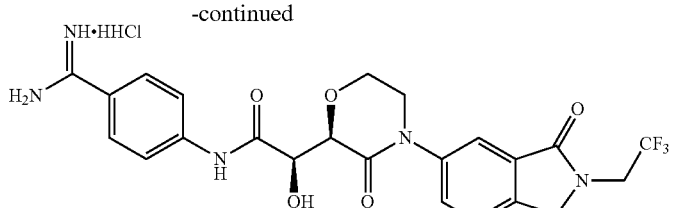

EXAMPLE 69

Step 69-1

Synthesis of Compound 69-1

A mixture of 2-(hydroxymethyl)isoindoline-1,3-dione (50.0 g, 202 mmol), 3-iodobenzoic acid (35.7 g, 202 mmol) and $H_2SO_4$ was heated at 80° C. for 3.5 h. The mixture was cooled to room temperature and then poured into ice. The precipitate was filtered off, washed with $H_2O$ (1.0 L), dilute $NH_4OH$ (500 mL) and recrystallized from EtOH (300 mL) to provide compound 69-1 (25.2 g, 48%) as an off-white solid.

Step 69-2

Synthesis of Compound 69-2

A mixture of compound 69-1 (3.00 g, 11.6 mmol), $Cs_2CO_3$ (15.1 g, 46.3 mmol), 2,2,2-trifluoroethyl trifluoromethanesulfonate (2.50 mL, 17.4 mmol) and $CH_3CN$ (120 mL) was heated at 80-90° C. for 1.5 h. Additional $Cs_2CO_3$ (7.52 g, 23.1 mmol) and 2,2,2-trifluoroethyl trifluoromethanesulfonate (1.0 mL, 6.93 mmol) were added and the mixture was heated for an additional 0.5 h. The resulting mixture was cooled to room temperature, diluted with EtOAc (250 mL), washed with saturated aqueous $NH_4Cl$ (2×20 mL), brine (3×20 mL), dried over $Na_2SO_4$, filtered and concentrated under reduced pressure. The resulting residue was purified by CombiFlash (120 g, Hex/EtOAc, 100:0 to 85:15 over 35 min) to provide compound 69-2 (1.78 g, 45%) as a brown solid.

Step 69-3

Synthesis of Compound 69-3

A mixture of compound 68-7 (215 mg, 0.929 mmol), aryl iodide 69-2 (348 mg, 1.02 mmol), CuI (8.8 mg, 46 µmol), $K_3PO_4$ (394 mg, 1.86 mmol), DMSO (3.1 mL), and trans-N,N'-dimethylcyclohexane-1,2-diamine (15 µL, 92 µmol) were stirred at room temperature under nitrogen in the dark for 4 h. Additional CuI (8.8 mg, 46 µmol) and trans-N,N'-dimethylcyclohexane-1,2-diamine (15 µL, 92 mop were added three times over the course of 20 h. After stirring for total 24 h the mixture was diluted with EtOAc (150 mL), washed with water (3×20 mL), dried over $Na_2SO_4$, filtered, and concentrated under reduced pressure. The crude product was purified on CombiFlash (40 g, Hex/EtOAc, 100:0 to 50:50 over 35 min) to provide pure product compound 69-3 (185 mg, 45%) as a yellow solid.

Step 69-4

Synthesis of Compound 69-4

To a solution of compound 69-3 (180 mg, 0.405 mmol), DMAP (4.9 mg, 40 µmol) and $CH_2Cl_2$ (4.00 mL) were added pyridine (66 µL, 0.81 mmol) and $Ac_2O$ (77 µL, 0.81 mmol) at 0-5° C. The resulting mixture was stirred for 2.5 h at 0-5° C., and then diluted with EtOAc (200 mL), washed with saturated aqueous $CuSO_4$ (2×10 mL), $H_2O$ (10 mL), brine (10 mL), dried over $Na_2SO_4$, filtered and concentrated under reduced pressure to provide crude compound 69-4 (197 mg, quant.) as a yellow solid. The product was used in the next reaction without further purification.

Step 69-5

Synthesis of Compound 69-5

In a 50 mL round bottom flask containing compound 69-4 (192 mg, 0.394 mmol) was added $CH_2Cl_2$ (1.00 mL) and TFA (4.00 mL). The reaction mixture was stirred at room temperature for 20 min, then TFA and $CH_2Cl_2$ were removed under reduced pressure. The crude product was triturated with ether and filtered to provide pure compound 69-5 (174 mg, quant.) as a yellow solid.

Step 69-6

Synthesis of Compound 69-6

A solution of compound 69-6 (165 mg, 0.383 mmol), DMAP (4.6 mg, 38 µmol), 3-(4-aminophenyl)-1,2,4-oxadiazol-5(2H)one (74.6 mg, 0.421 mmol), EDCI.HCl (80.7 mg, 0.421 mmol) and $CH_3CN$ (3 mL) was stirred at room temperature for 2.5 h. The solvent was removed under reduced pressure and the residue purified by semi-preparative HPLC to provide pure product compound 69-6 (51 mg, 23%) as an off-white solid.

Step 69-7

Synthesis of Compound 69-7

To a 50 mL round bottom flask was added compound 69-6 (51 mg, 86 mop, and 7 N $NH_3$ in $CH_3OH$ (5.00 mL). The reaction mixture was stirred at room temperature for 1.5 h then the volatiles were removed under reduced pressure. Residual ammonia was removed by evaporating with $CH_3OH$ (2×15 mL) and $CH_2Cl_2$ (2×15 mL) to provide compound 69-7 (47 mg, quant.) as an off-white solid.

Step 69-8

Synthesis of (R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide hydrochloride (EXAMPLE 69)

To a 100 mL round bottom flask was added compound 69-7 (45 mg, 82 µmol) in $CH_3OH$ (4.00 mL) and 1 M HCl (4.00 mL). The solvent was degassed for 10 min with N₂, then 10% Pd/C (45 mg, 21 μmol) was added and the reaction mixture was hydrogenated at 1 atm for 7 h. The mixture was filtered, washed with hot CH₃OH (200 mL), and the filtrate was concentrated under reduced pressure. The residue was purified by semi-preparative HPLC. The isolated product was dissolved in MeOH (5 mL) and then added 1 N HCl in Et₂O (5 mL) and stirred for 5 min. The volatiles were removed under reduced pressure to provide pure product EXAMPLE 69 (22 mg, 50%) as an off-white solid.

Example 70

Synthesis of (R)—N-(4-Carbamimidoylphenyl)-2-hydroxy-2-((R)-4-(2-methyl-3-oxoisoindolin-5-yl)-3-oxomorpholin-2-yl)acetamide hydrochloride (EXAMPLE 70)

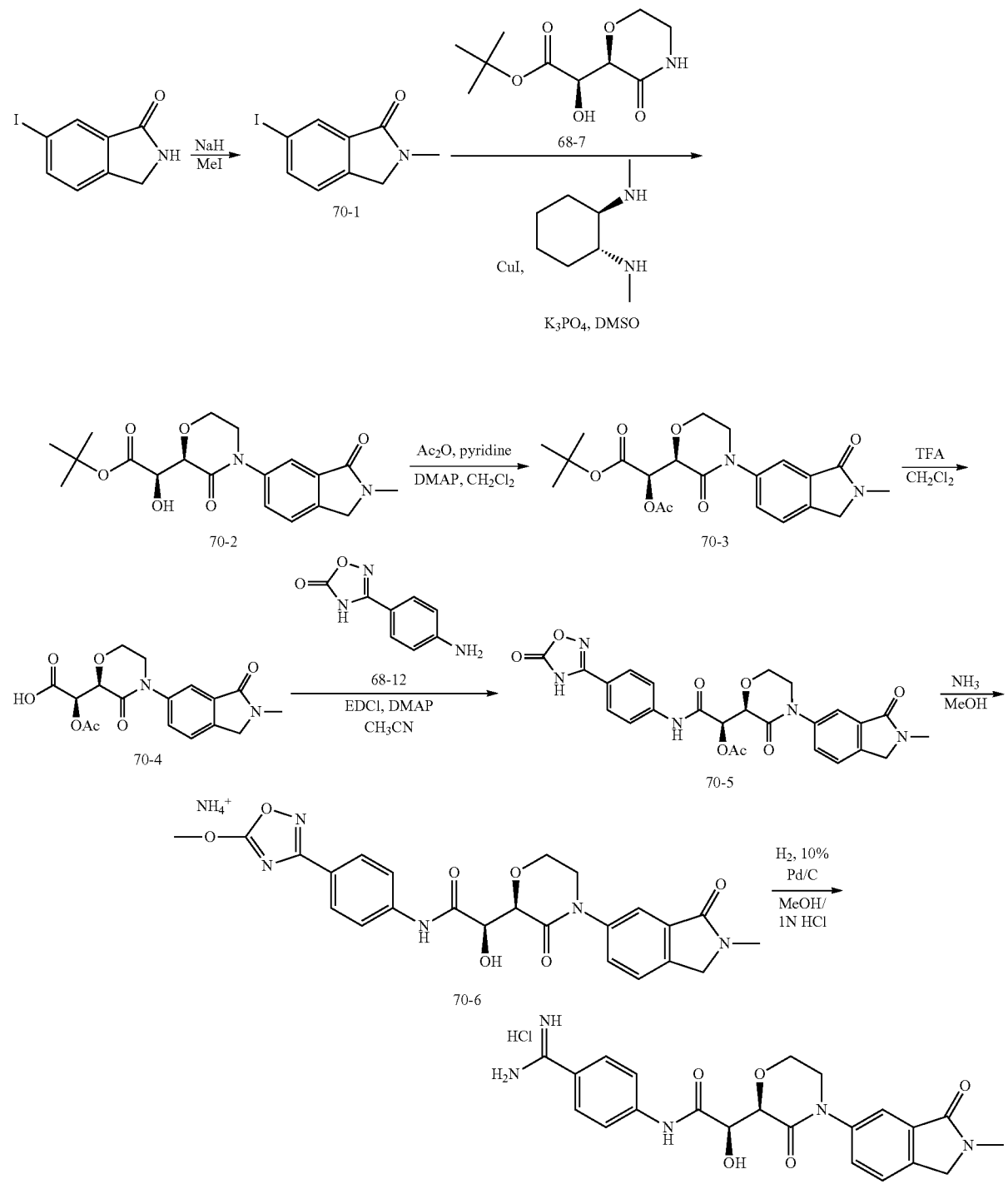

Step 70-1

Synthesis of Compound 70-1

To a mixture of 2,3-dihydro-6-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. $NH_4Cl$ (~3 mL) and was diluted with EtOAc (10 mL). The layers were separated and the aqueous layer was extracted with EtOAc. The organic layers were combined and washed sequentially with water and brine. The organic layer was dried ($Na_2SO_4$), filtered, and concentrated under reduced pressure. The crude material was purified The crude product was purified by flash chromatography (ISCO, 120 g) using a gradient of 100% hexanes to 80:20 hexanes/EtOAc to afford compound 70-1 (0.84 g) as a yellow solid. LC-MS: M+H=274.

Step 70-2

Synthesis of (R)-tert-butyl 2-hydroxy-2-((R)-4-(2-methyl-3-oxoisoindolin-5-yl)-3-oxomorpholin-2-yl)acetate (Compound 70-2)

To a round bottom flask charged with a stir bar was added morpholinone compound 68-7 (0.28 g) and compound 70-1 (0.40 g) in DMSO (8 mL) at rt was added $K_3PO_4$ (0.51 g), and CuI (23 mg) under $N_2$. trans-N,N'-Dimethylcyclohexane-1,2-diamine (37 μL) was added dropwise and the mixture was affixed with a condenser. The mixture was degassed under vacuum (~20 mm), filled with $N_2$, and heated to 80° C. The mixture stirred for 2.5 h at 80° C., cooled to rt, and was diluted with EtOAc. The mixture was then sequentially washed with conc $NH_4OH$, water, and brine. The organic layer was dried ($Na_2SO_4$), filtered, and concentrated under reduced pressure to afford a yellow oil. The crude product was purified by flash chromatography using a gradient of 100% $CH_2Cl_2$ to 60% $CH_2Cl_2$/40% MeOH to afford compound 70-2 (0.23 g) of a yellow solid. LC-MS: M+H=377.

Step 70-3

Synthesis of (R)-tert-butyl 2-acetoxy-2-((R)-4-(2-methyl-3-oxoisoindolin-5-yl)-3-oxomorpholin-2-yl)acetate (Compound 70-3)

To a solution of compound 70-2 (80 mg) in $CH_2Cl_2$ (2 ml) at 0° C. was added pyridine (26 μL), $Ac_2O$ (30 μl), and DMAP (4 mg). The mixture was stirred for 1 hour at 0° C., warmed to rt, and stirred for an additional 12 h. The mixture was diluted with EtOAc and the organic layer was washed sequentially with sat. aq. $CuSO_4$ solution, water, and brine. The organic layer was dried ($Na_2SO_4$), filtered, and concentrated under reduced pressure to afford compound 70-3 (85 mg) as a light yellow semisolid. LC-MS: M+H=419. This material was used without further purification.

Step 70-4

Synthesis of (R)-2-acetoxy-2-((R)-4-(2-methyl-3-oxoisoindolin-5-yl)-3-oxomorpholin-2-yl)acetic acid (Compound 70-4)

To a solution of compound 70-3 (85 mg) in $CH_2Cl_2$ (2.5 mL) at 0° C. was added TFA (0.5 mL) dropwise. The mixture was stirred for 1 h at 0° C. and at rt for 30 min whereupon an additional portion of TFA (0.5 mL) was added. After an additional 1 h at rt, the mixture was diluted with $CH_2Cl_2$ and concentrated to dryness under reduced pressure. The crude mixture was redissolved in $CH_2Cl_2$ and concentrated and this protocol was repeated 5 times with to afford compound 70-4 (65 mg) as a light semisolid. LC-MS: M+H=363. This material was used without further purification.

Step 70-5

Synthesis of (R)-1-((R)-4-(2-methyl-3-oxoisoindolin-5-yl)-3-oxomorpholin-2-yl)-2-oxo-2-(4-(5-oxo-4,5-dihydro-1,2,4-oxadiazol-3-yl)phenylamino)ethyl acetate (Compound 70-5)

To a solution of compound 70-4 (40 mg) in $CH_3CN$ (1 mL) at 0° C. was added 4-(5-oxo-4,5-dihydro-[1,2,4]oxadiazol-3-yl)-phenyl amide (21 mg) followed by EDCI (25 mg). The reaction mixture was warmed to rt and stirred for 72 h. The mixture was concentrated under reduced pressure and placed under high vacuum. The crude material was purified by reverse phase HPLC using a C18 column and a gradient of (89.95:9.95:0.1$H_2O$:MeCN:$HCO_2H$ to 9.95:89.95:0.1$H_2O$:MeCN:$HCO_2H$) to afford compound 70-5 (30 mg) as a white solid. LC-MS: M+H=522.

Step 70-6

Synthesis of Ammonium 3-(4-((R)-2-hydroxy-2-((R)-4-(2-methyl-3-oxoisoindolin-5-yl)-3-oxomorpholin-2-yl)acetamido)phenyl)-1,2,4-oxadiazol-5-olate (Compound 70-6)

To a solution of the compound 70-5 (30 mg) in MeOH (2 mL) at 0° C. was added 7M $NH_3$/MeOH (0.3 mL) dropwise. The mixture was stirred for 1 h at 0° C. and an additional hour at rt. The mixture was concentrated under reduced pressure and placed under high vacuum to afford compound 70-6 (27 mg) as a clear glass. LC-MS: M+H=480 (free base).

Step 70-7

Synthesis of (R)—N-(4-carbamimidoylphenyl)-2-hydroxy-2-((R)-4-(2-methyl-3-oxoisoindolin-5-yl)-3-oxomorpholin-2-yl)acetamide hydrochloride (EXAMPLE 70)

To a solution of the compound 70-6 (27 mg) in MeOH (2 mL) was added 1N HCl (2 mL) followed by 10% Pd/C (50 mg). The mixture was stirred under a $H_2$ balloon for 3 h and was filtered through a pad of Celite®. The Celite® pad was washed with MeOH and the resultant filtrate was concentrated under reduced pressure. The crude residue was treated with MeOH followed by dilution with $Et_2O$ and the resultant solid was collected by filtration and dried under vacuum to afford 17 mg of Example 70 as a maize solid. LC-MS: M+H=438 (free base).

Example 71

Synthesis of (R)—N-(4-(aminomethyl)phenyl)-2-hydroxy-2-((R)-4-(2-methyl-3-oxoisoindolin-5-yl)-3-oxomorpholin-2-yl)acetamide (EXAMPLE 71)

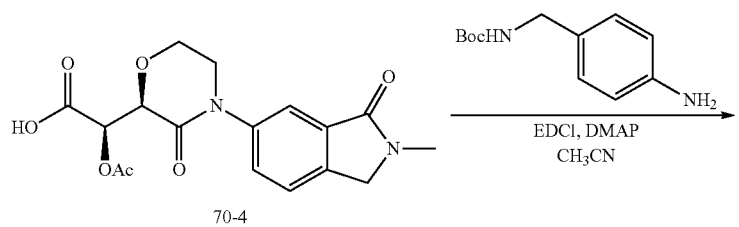

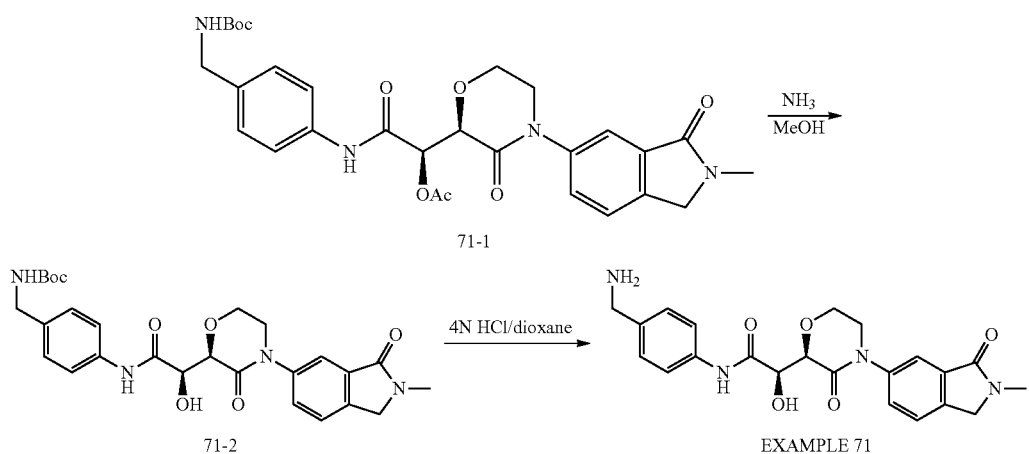

Step 71-1

Synthesis of (R)-2-(4-(((tert-butoxycarbonylamino)methyl)phenylamino)-1-((R)-4-(2-methyl-3-oxoisoindolin-5-yl)-3-oxomorpholin-2-yl)-2-oxoethyl acetate (Compound 71-1)

According to the Step 70-5 in the synthetic method for EXAMPLE 70, compound 70-4 (50 mg) was treated with tert-butyl 4-aminobenzylcarbamate (37 mg) to afford compound 71-1 (58 mg) as white solid after preparative LC purification.

Step 71-2

Synthesis of tert-butyl 4-(((R)-2-hydroxy-2-((R)-4-(2-methyl-3-oxoisoindolin-5-yl)-3-oxomorpholin-2-yl)acetamido)benzylcarbamate (Compound 71-2)

According to the Step 70-6 in the synthetic method for EXAMPLE 70, compound 71-1 (50 mg) was used instead of compound 70-5 to obtain compound 71-2 (50 mg) as a white solid. Crude compound 71-2 was used without further purification in the next step.

Step 71-3

Synthesis of (R)—N-(4-(aminomethyl)phenyl)-2-hydroxy-2-((R)-4-(2-methyl-3-oxoisoindolin-5-yl)-3-oxomorpholin-2-yl)acetamide (EXAMPLE 71)

To round bottom flask charged with the compound 71-2 (50 mg) at it was added 4 N HCl/dioxane (3 mL). The resulting solution was stirred for 3 h, concentrated under reduced pressure, and placed under high vacuum. The crude product was dissolved in MeOH and Et$_2$O and the resultant solid was collected and dried to afford EXAMPLE 71 (36 mg) as an off-white solid. LC-MS: M+H=425 (free base).

Example 72

Synthesis of (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide (EXAMPLE 72)

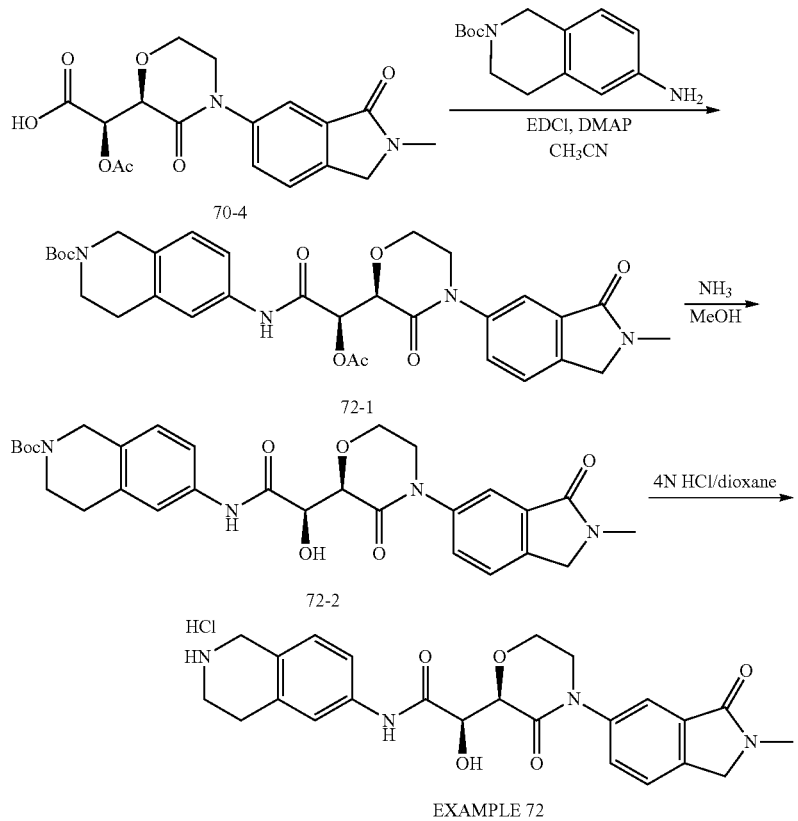

Step 72-1

Synthesis of tert-butyl 6-((R)-2-acetoxy-2-((R)-4-(2-methyl-3-oxoisoindolin-5-yl)-3-oxomorpholin-2-yl)acetamido)-3,4-dihydroisoquinoline-2(1H)-carboxylate (Compound 72-1)

According to the Step 70-5 in the synthetic method for EXAMPLE 70, compound 70-4 (50 mg) was treated with tert-butyl 6-amino-3,4-dihydroisoquinoline-2(1H)-carboxylate (30 mg) to afford compound 72-1 (52 mg) as a light yellow solid after preparative LC purification.

Step 72-2

Synthesis of tert-butyl 6((R)-2-hydroxy-2-((R)-4-(2-methyl-3-oxoisoindolin-5-yl)-3-oxomorpholin-2-yl)acetamido)-3,4-dihydroisoquinoline-2(1H)-carboxylate (Compound 72-2)

According to the Step 70-6 in the synthetic method for EXAMPLE 70, compound 72-1 (50 mg) was used instead of compound 70-5 to obtain compound 72-2 (39 mg) as an off-white solid. Crude compound 72-2 was used without further purification in the next step.

Step 72-3

Synthesis of (R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide (EXAMPLE 72)

According to the Step 71-3 in the synthetic method for EXAMPLE 71, 72-2 (39 mg) was used instead of compound 71-2 to obtain EXAMPLE 72 (26 mg) as a maize solid.

Example 73
Synthesis of (R)-2-((R)-4-(3,5-bis(trifluoromethyl)phenyl)-3-oxomorpholin-2-yl)-N-(4-carbamimidoylphenyl)-2-hydroxyacetamide hydrochloride (EXAMPLE 73)
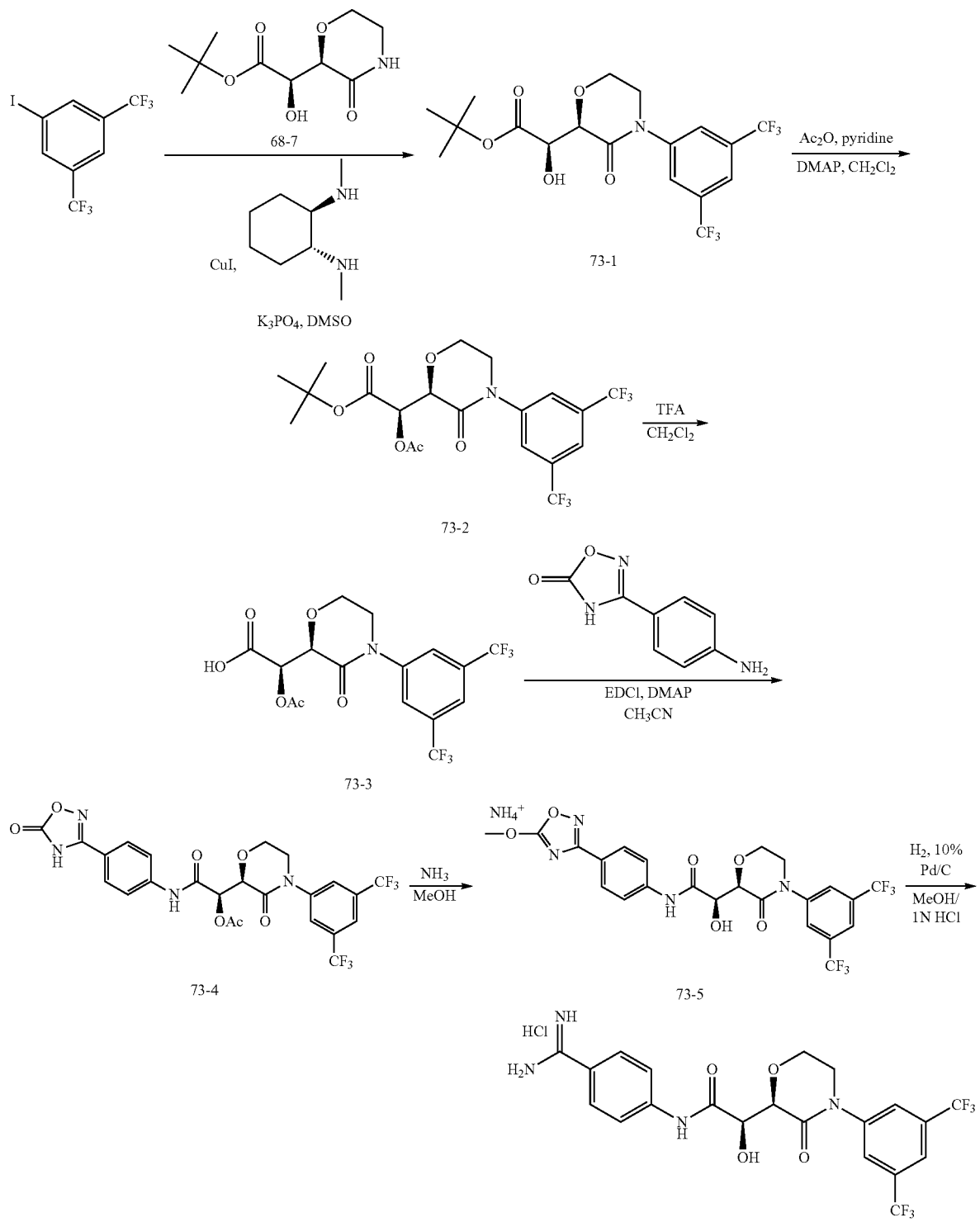

Step 73-1

Synthesis of (R)-tert-butyl 2-((R)-4-(3,5-bis(trifluoromethyl)phenyl)-3-oxomorpholin-2-yl)-2-hydroxyacetate (Compound 73-1)

According to the Step 70-2 in the synthetic method for Example 70, 3,5-(bistrifluoromethyl)iodobenzene (0.11 mL) was used instead of compound 70-1 to obtain compound 73-1 (0.13 g) as a white solid after reverse-phase (C18) purification.

Step 73-2

Synthesis of (R)-tert-butyl 2-acetoxy-2-((R)-4-(3,5-bis(trifluoromethyl)phenyl)-3-oxomorpholin-2-yl)acetate (Compound 73-2)

According to the Step 70-3 in the synthetic method for EXAMPLE 70, 73-1 (0.13 g) was used instead of compound 70-2 to obtain compound 73-2 (0.14 g) as a yellow semisolid that was used without further purification.

Step 73-3

Synthesis of (R)-2-acetoxy-2-((R)-4-(3,5-bis(trifluoromethyl)phenyl)-3-oxomorpholin-2-yl)acetic acid (Compound 73-3)

According to the Step 70-4 in the synthetic method for EXAMPLE 70, compound 73-2 (0.14 g) was used instead of compound 70-3 to afford compound 73-3 (0.12 g) as a light yellow solid that was used without further purification.

Step 73-4

Synthesis of (R)-1-((R)-4-(3,5-bis(trifluoromethyl)phenyl)-3-oxomorpholin-2-yl)-2-oxo-2-(4-(5-oxo-4,5-dihydro-1,2,4-oxadiazol-3-yl)phenylamino)ethyl acetate (Compound 73-4)

According to the Step 70-5 in the synthetic method for EXAMPLE 70, compound 73-3 (65 mg) was used instead of compound 70-4 to obtain compound 73-4 (69 mg) as a white solid after reverse-phase (C18) HPLC purification.

Step 73-5

Synthesis of Ammonium 3-(4-((R)-2-((R)-4-(3,5-bis(trifluoromethyl)phenyl)-3-oxomorpholin-2-yl)-2-hydroxyacetamido)phenyl)-1,2,4-oxadiazol-5-olate (Compound 73-5)

According to the Step 70-6 in the synthetic method for EXAMPLE 70, compound 73-4 (69 mg) was used instead of compound 70-5 to obtain compound 73-5 (58 mg) as a white solid that was used without further purification.

Step 73-6

Synthesis of (R)-2-((R)-4-(3,5-bis(trifluoromethyl)phenyl)-3-oxomorpholin-2-yl)-N-(4-carbamimidoylphenyl)-2-hydroxyacetamide hydrochloride (EXAMPLE 73)

According to the Step 70-7 in the synthetic method for EXAMPLE 70, compound 73-5 (53 mg) was used instead of compound 70-6 to obtain EXAMPLE 73 (37 mg) as a maize solid.

Example 74

Synthesis of (R)-2-((R)-4-(3,5-bis(trifluoromethyl)phenyl)-3-oxomorpholin-2-yl)-2-hydroxy-N-(1-oxoisoindolin-5-yl)acetamide (EXAMPLE 74)

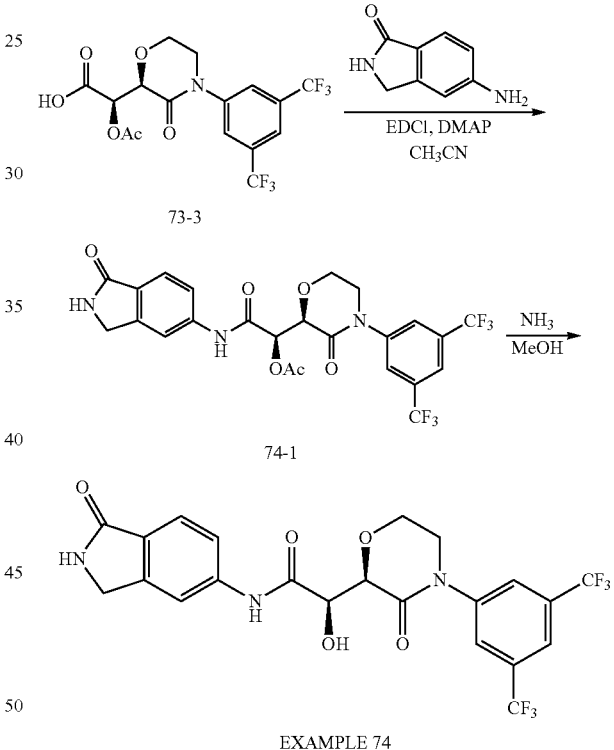

Step 74-1

Synthesis of (R)-1-((R)-4-(3,5-bis(trifluoromethyl)phenyl)-3-oxomorpholin-2-yl)-2-oxo-2-(1-oxoisoindolin-5-ylamino)ethyl acetate (Compound 74-1)

According to the Step 70-5 in the synthetic method for EXAMPLE 70, compound 73-3 (65 mg) was used instead of compound 70-4 to couple to 5-aminoisoindolin-1-one (25 mg) to obtain compound 74-1 (69 mg) as a white solid after reverse-phase (C18) purification.

Step 74-2

Synthesis of (3,5-bis(trifluoromethyl)phenyl)-3-oxo-morpholin-2-yl)-2-hydroxy-N-(1-oxoisoindolin-5-yl)acetamide (EXAMPLE 74)

According to the Step 70-6 in the synthetic method for EXAMPLE 70, compound 74-1 (50 mg) was used instead of compound 70-5 to obtain EXAMPLE 74 (48 mg) as white solid.

Example 75

Synthesis of (R)—N-(4-carbamimidoylphenyl)-2-hydroxy-2-((R)-4-(4-methoxybenzyl)-3-oxomorpholin-2-yl)acetamide hydrochloride (EXAMPLE 75)

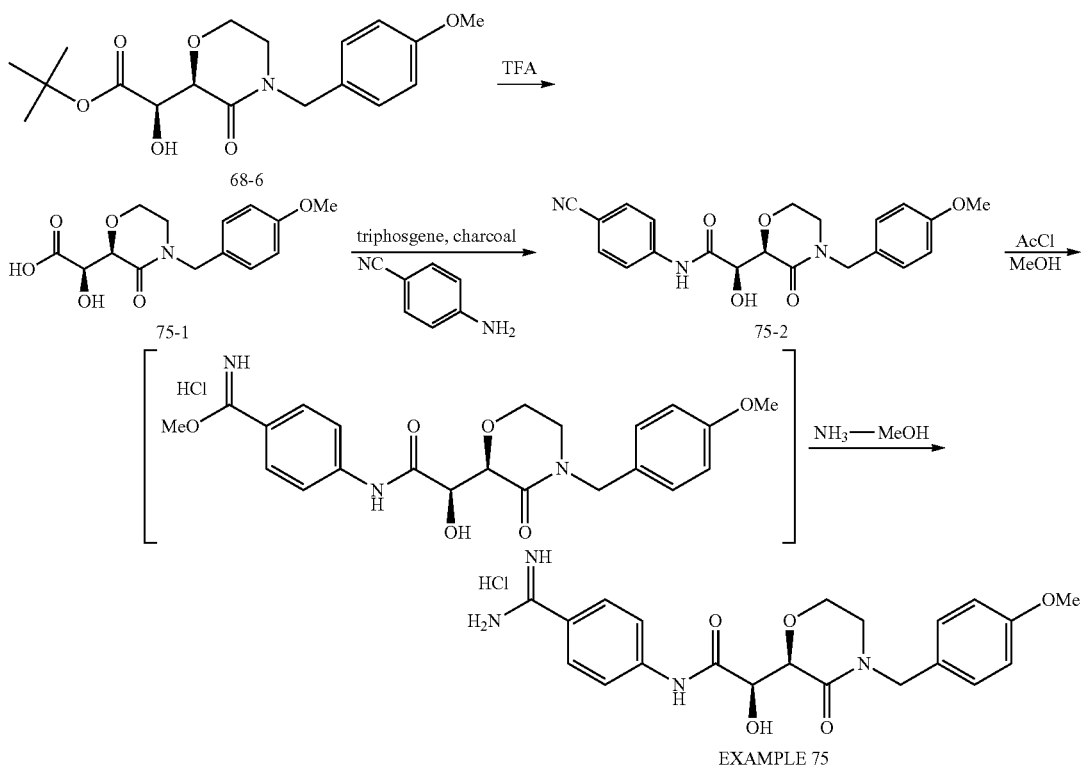

Step 75-1

Synthesis of (R)-2-hydroxy-2-((R)-4-(4-methoxybenzyl)-3-oxomorpholin-2-yl)acetic acid (Compound 75-1)

To a solution of compound 68-6 (0.10 g, 0.28 mmol) in CH$_2$Cl$_2$ (2 mL) at 0° C. was added TFA (0.6 mL) dropwise. The mixture was stirred for 1 h at 0° C., warmed to rt, and stirred for an additional 3 h. The mixture was diluted with CH$_2$Cl$_2$ and concentrated to dryness under reduced pressure. The crude mixture was redissolved in CH$_2$Cl$_2$ and concentrated and this protocol was repeated 5 times with to afford compound 75-1 (78 mg) as a light yellow oil that was used without further purification.

Step 75-2

Synthesis of (R)—N-(4-cyanophenyl)-2-hydroxy-2-((R)-4-(4-methoxybenzyl)-3-oxomorpholin-2-yl)acetamide (Compound 75-2)

To a solution of compound 75-1 (0.11 g) in THF (2.5 mL) at 0° C. was added activated charcoal (15 mg) followed by triphosgene (0.44 g). The mixture was allowed to warm to rt, stirred for 12 h, and was filtered through a pad of Celite®. The Celite® pad was washed with THF and the resultant filtrated was concentrated under reduced pressure. The crude product was dissolved in DMF (2 mL), 4-aminobenzonitrile (65 mg) was added, and the mixture was stirred for 12 h at rt. The crude mixture was purified directly by reverse phase HPLC using a C18 column and a gradient of (89.95:9.95:0.1H$_2$O:MeCN:HCO$_2$H to 9.95:89.95:0.1H$_2$O:MeCN:HCO$_2$H) to afford compound 75-2 (28%) as a white solid.

Step 75-3

Synthesis of (R)—N-(4-carbamimidoylphenyl)-2-hydroxy-2-((R)-4-(4-methoxybenzyl)-3-oxomorpholin-2-yl)acetamide hydrochloride (EXAMPLE 75)

To a pressure tube charged with compound 75-2 (35 mg) in MeOH (1.2 mL) at 0° C. was added AcCl (1.2 ml) dropwise. The tube was capped, warmed to rt, and stirred for 12 h. The mixture was concentrated to dryness and the pressure tube was charged with the crude mixture in 7M NH$_3$/MeOH (4 mL). The mixture was stirred for 3 days and was concentrated under reduced pressure. The crude mixture was purified by reverse phase HPLC using a C18 column and a gradient of

Example 76

Synthesis of (R)—N-(1-Aminoisoquinolin-6-yl)-2-hydroxy-2-((R)-4-(4-methoxybenzyl)-3-oxomorpholin-2-yl)acetamide (EXAMPLE 76)

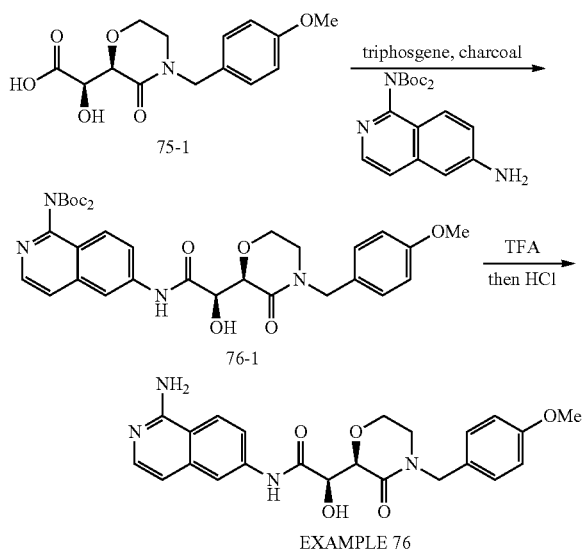

Step 76-1

Synthesis of (R)—N-(1-bis-tertbutoxycarbonyl aminoisoquinolin-6-yl)-2-hydroxy-2-((R)-4-(4-methoxybenzyl)-3-oxomorpholin-2-yl)acetamide (Compound 76-1)

According to the Step 75-2 in the synthetic method for EXAMPLE 75, compound 75-1 (0.28 was treated with di-tert-butyl(6-aminoisoquinolin-1-yl)imidocarbonate (0.51 g) from WO 2006/062972 to obtain compound 76-1 (0.23 g) as a white solid after reverse-phase purification.

Step 76-2

Synthesis of (R)—N-(1-aminoisoquinolin-6-yl)-2-hydroxy-2-((R)-4-(4-methoxybenzyl)-3-oxomorpholin-2-yl)acetamide (EXAMPLE 76)

To a solution of compound 76-1 (0.23 g) in CH$_2$Cl$_2$ (2 mL) at 0° C. was added TFA (0.6 mL) dropwise. The mixture was stirred for 1 h at 0° C., warmed to rt, and stirred for an additional 12 h. The mixture was diluted with CH$_2$Cl$_2$ and concentrated to dryness and this protocol was repeated 5 times. The crude mixture was purified by reverse phase HPLC using a C18 column and a gradient of (89.95:9.95:0.1H$_2$O:MeCN:HCO$_2$H to 9.95:89.95:0.1H$_2$O:MeCN:HCO$_2$H) to afford EXAMPLE 76 (0.10 g) as a white solid as the hydrochloride salt upon HCl treatment.

Example 77

Synthesis of (2R)—N-(4-amidinophenyl)-2-hydroxy-2-[(2R)-3-oxo-4-(3-(4,4-difluoropiperidin-1-ylcarbonyl)phenyl)morpholin-2-yl]acetamide (EXAMPLE 77)

Step 77-1

Synthesis of 4,4-difluoro-1-[(3-iodophenyl)carbonyl]piperidine (Compound 77-1)

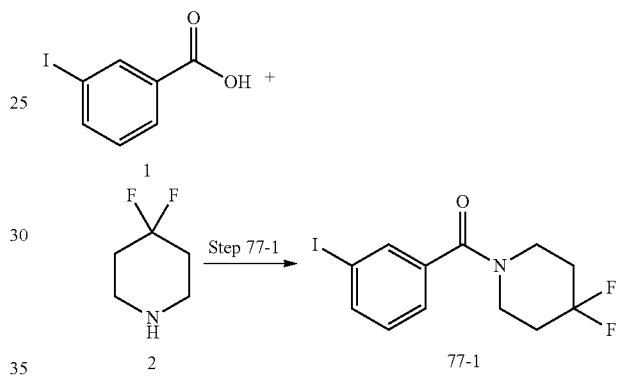

To a solution of 3-iodobenzoic acid 1 (482 mg, 1.94 mmol) in DMF (6 mL) was added 4,4-difluoropiperidine 2 (259 mg, 2.14 mmol), HATU (886 mg, 2.33 mmol) and diisopropylethylamine (750 mg, 5.81 mmol). The reaction mixture was stirred at room temperature for 1.5 hours. Ethyl acetate (100 mL) was added and the organic layer was washed with 1 N sodium hydroxide solution, 1 N hydrochloric acid, water and brine. The organic layer was dried over anhydrous sodium sulfate. The organic solvent was evaporated under reduced pressure. The crude product was purified by flash column chromatography to afford the desired 4,4-difluoro-1-[(3-iodophenyl)carbonyl]piperidine compound 77-1 (362 mg, 1.03 mmol).

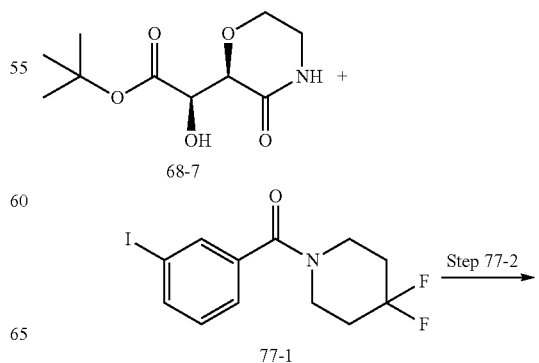

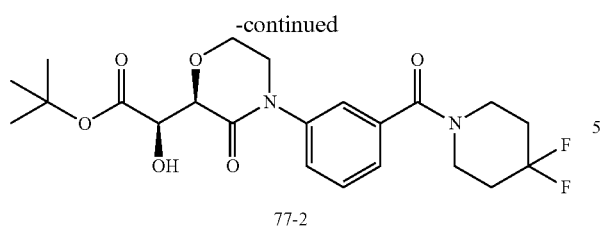

77-2

↓ Step 77-3

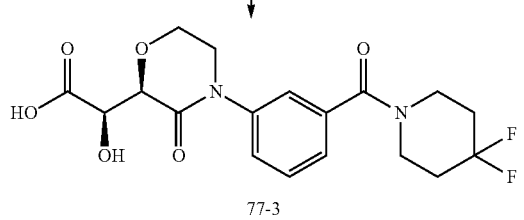

77-3

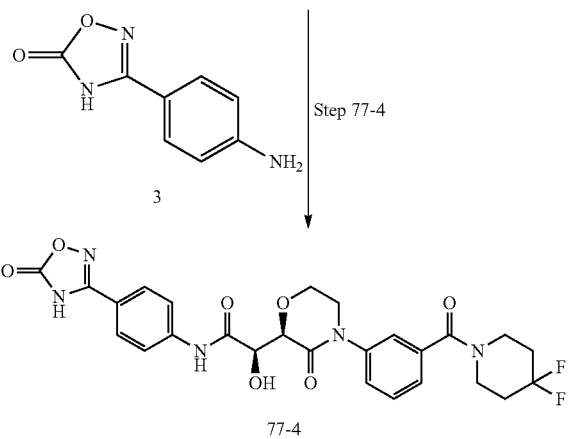

3

77-4

↓ Step 77-5

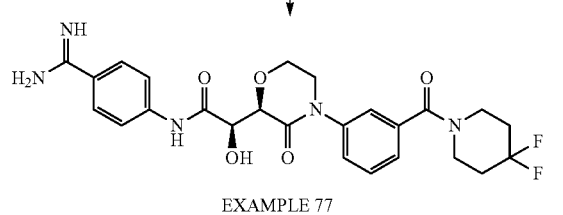

EXAMPLE 77

Step 77-2

Synthesis of Compound 77-2

To a solution of compound 68-7 (200 mg, 0.87 mmol) in anhydrous DMSO (8 mL) under a nitrogen atmosphere was added compound 77-1 (362 mg, 1.03 mmol), potassium phosphate (367 mg, 1.73 mmol), copper (I) iodide (16 mg, 0.084 mmol) and trans-N,N'-dimethylcyclohexane-1,2-diamine (24 mg, 0.17 mmol). The reaction mixture was heated at 80° C. for 2 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 77-2 (251 mg, 0.63 mmol).

Step 77-3

Synthesis of Compound 77-3

To compound 77-2 (251 mg, 0.63 mmol) was added a 50% solution of trifluoroacetic acid in dichloromethane (6 mL). The reaction mixture was stirred at room temperature for 3 hours. The organic solvent was evaporated under reduced pressure to afford the desired compound 77-3 (0.63 mmol) which was used in the next step without further purification.

Step 77-4

Synthesis of Compound 77-4

To a solution of compound 77-3 (0.63 mmol) in acetonitrile (8 mL) was added 3-(4-aminophenyl)-1,2,4-oxadiazol-5(2H)-one 1 (166 mg, 0.94 mmol), EDCI (156 mg, 0.81 mmol) and DMAP (8 mg, 0.066 mmol). The reaction mixture was stirred at room temperature for 1 hour. The organic solvent was evaporated under reduced pressure. The crude product was purified by flash column chromatography to afford the desired compound 77-4 (226 mg, 0.41 mmol).

Step 77-5

Synthesis of (2R)—N-(4-amidinophenyl)-2-hydroxy-2-[(2R)-3-oxo-4-(3-(4,4-difluoropiperidin-1-ylcarbonyl)phenyl)morpholine-2-yl]acetamide (EXAMPLE 77)

To a solution of compound 77-4 (226 mg, 0.41 mmol) in a 50% solution of 1 N hydrochloric acid in methanol (12 mL) was added palladium-charcoal (10%, 230 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 77 (204 mg, 0.37 mmol) as a white amorphous solid.

Example 78

Synthesis of (2R)—N-(4-amidinophenyl)-2-hydroxy-2-[(2R)-3-oxo-4-(4-(pyrrolidin-1-ylsulfonyl)phenyl)morpholin-2-yl]acetamide (EXAMPLE 78)

Step 78-1

Synthesis of 1-[(4-iodobenzene)sulfonyl]pyrrolidine (Compound 78-1)

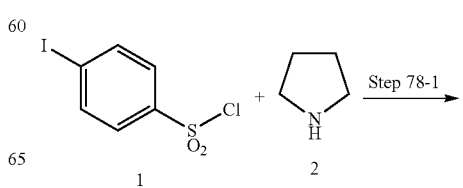

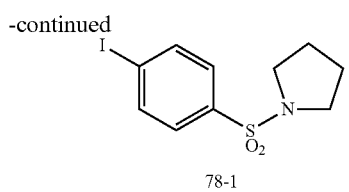

78-1

To a solution of 4-iodobenzenesulfonyl chloride 1 (500 mg, 1.66 mmol) in anhydrous acetonitrile (8 mL) under a nitrogen atmosphere was added pyrrolidine 2 (140 mg, 1.97 mmol) and pyridine (261 mg, 3.3 mmol). The reaction mixture was stirred at room temperature for 3 hours. Ethyl acetate (100 mL) was added and the organic layer was washed with 1 N hydrochloric acid, water and brine. The organic layer was dried over anhydrous sodium sulfate. The organic solvent was evaporated under reduced pressure. The crude product was purified by flash column chromatography to afford the desired 1-[(4-iodobenzene)sulfonyl]pyrrolidine compound 78-1 (487 mg, 1.45 mmol).

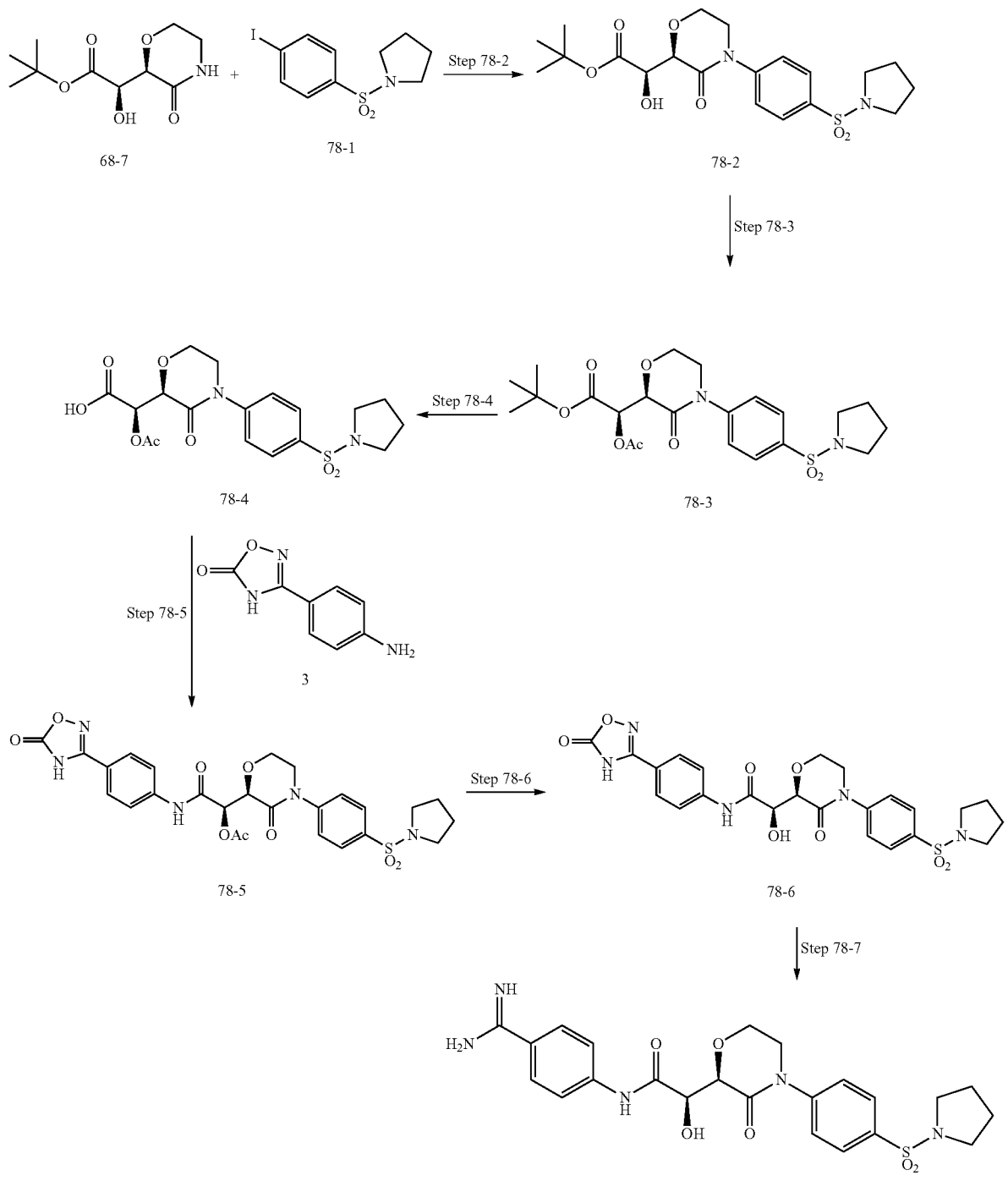

EXAMPLE 78

Step 78-2

Synthesis of Compound 78-2

To a solution of compound 68-7 (200 mg, 0.87 mmol) in anhydrous DMSO (8 mL) under a nitrogen atmosphere was added compound 78-1 (321 mg, 0.95 mmol), potassium phosphate (367 mg, 1.73 mmol), copper (I) iodide (16 mg, 0.084 mmol) and trans-N,N'-dimethylcyclohexane-1,2-diamine (24 mg, 0.17 mmol). The reaction mixture was heated at 80° C. for 3 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 78-2 (335 mg, 0.76 mmol).

Step 78-3

Synthesis of Compound 78-3

To a solution of compound 78-2 (335 mg, 0.76 mmol) in anhydrous dichloromethane (8 mL) under a nitrogen atmosphere was added acetic anhydride (154 mg, 1.51 mmol) and triethylamine (231 mg, 2.29 mmol). The reaction mixture was stirred at room temperature for 16 hours. DMAP (9.3 mg, 0.076 mmol) was added. The reaction mixture was stirred at room temperature for 2 hours. Ethyl acetate (100 mL) was added and the organic layer was washed with water and brine. The organic layer was dried over anhydrous sodium sulfate. The organic solvent was evaporated under reduced pressure. The crude product was purified by flash column chromatography to afford the desired compound 78-3 (355 mg, 0.74 mmol).

Step 78-4

Synthesis of Compound 78-4

To compound 78-3 (355 mg, 0.74 mmol) was added a 50% solution of trifluoroacetic acid in dichloromethane (6 mL). The reaction mixture was stirred at room temperature for 1.5 hours. The organic solvent was evaporated under reduced pressure to afford the desired compound 78-4 (0.74 mmol) which was used in the next step without further purification.

Step 78-5

Synthesis of Compound 78-5

To a solution of compound 78-4 (0.74 mmol) in acetonitrile (8 mL) was added 3-(4-aminophenyl)-1,2,4-oxadiazol-5 (2H)-one 1 (191 mg, 1.08 mmol), EDCI (179 mg, 0.93 mmol) and DMAP (9 mg, 0.073 mmol). The reaction mixture was stirred at room temperature for 1 hour. The organic solvent was evaporated under reduced pressure. The crude product was purified by flash column chromatography to afford the desired compound 78-5 (245 mg, 0.42 mmol).

Step 78-6

Synthesis of Compound 78-6

To compound 78-5 (245 mg, 0.42 mmol) was added a solution of 7 N ammonia in methanol (8 mL). The reaction mixture was stirred at room temperature for 40 minutes. The organic solvent was evaporated under reduced pressure to afford the desired compound 78-6 (0.42 mmol) which was used in the next step without further purification.

Step 78-7

Synthesis of (2R)—N-(4-amidinophenyl)-2-hydroxy-2-[(2R)-3-oxo-4-(4-(pyrrolidin-1-ylsulfonyl)phenyl)morpholin-2-yl]acetamide (EXAMPLE 78)

To a solution of compound 78-6 (0.42 mmol) in a 50% solution of 1 N hydrochloric acid in methanol (12 mL) was added palladium-charcoal (10%, 245 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 78 (173 mg, 0.35 mmol) as a white amorphous solid.

Example 79

Synthesis of (2R)—N-(4-amidinophenyl)-2-hydroxy-2-[(2R)-3-oxo-4-(4-(methylsulfonyl)phenyl)morpholin-2-yl]acetamide (EXAMPLE 79)

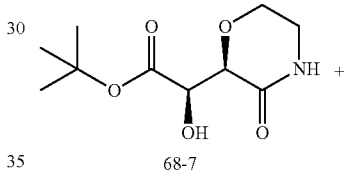

68-7

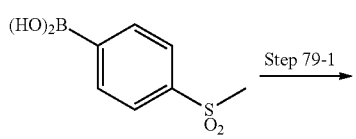

1

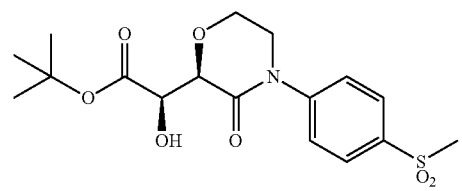

79-1

Step 79-2

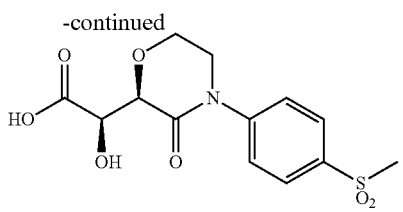

79-2

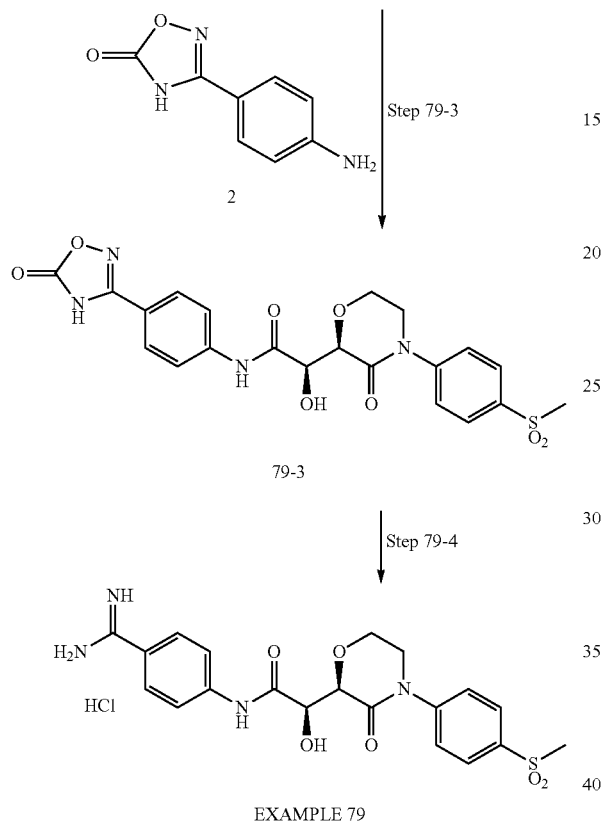

2

79-3

EXAMPLE 79

Step 79-1

Synthesis of Compound 79-1

To a solution of 68-7 (200 mg, 0.87 mmol) in anhydrous acetonitrile (4 mL) under a nitrogen atmosphere was added 4-(methylsulfonyl)phenylboronic acid 1 (346 mg, 1.73 mmol), copper (II) acetate (158 mg, 0.89 mmol), trimethylamine N-oxide (65 mg, 0.87 mmol) and triethylamine (175 mg, 1.73 mmol). The reaction mixture was stirred at room temperature for 16 hours. Ethyl acetate (100 mL) was added and the organic layer was washed with ammonium hydroxide, water and brine. The organic layer was dried over anhydrous sodium sulfate. The organic solvent was evaporated under reduced pressure. The crude product was purified by flash column chromatography to afford the desired compound 79-1 (156 mg, 0.41 mmol).

Step 79-2

Synthesis of Compound 79-2

To compound 79-1 (156 mg, 0.41 mmol) was added a 4 N solution of hydrogen chloride in dioxane (8 mL). The reaction mixture was stirred at room temperature for 16 hours. The organic solvent was evaporated under reduced pressure to afford the desired compound 79-2 (0.41 mmol) which was used in the next step without further purification.

Step 79-3

Synthesis of Compound 79-3

To a solution of compound 79-2 (0.41 mmol) in acetonitrile (4 mL) was added 3-(4-aminophenyl)-1,2,4-oxadiazol-5 (2H)-one 2 (191 mg, 1.08 mmol) and EDCI (98 mg, 0.51 mmol). The reaction mixture was stirred at room temperature for 16 hour. The organic solvent was evaporated under reduced pressure. The crude product was purified by flash column chromatography to afford the desired compound 79-3 (28 mg, 0.057 mmol).

Step 79-4

Synthesis of (2R)—N-(4-amidinophenyl)-2-hydroxy-2-[(2R)-3-oxo-4-(4-(methylsulfonyl)phenyl) morpholin-2-yl]acetamide (EXAMPLE 79)

To a solution of compound 79-3 (28 mg, 0.057 mmol) in a 50% solution of 1 N hydrochloric acid in methanol (4 mL) was added palladium-charcoal (10%, 28 mg). The reaction mixture was stirred at room temperature under a hydrogen atmosphere for 16 hours. The reaction mixture was filtered. The filtrate was evaporated under reduced pressure. The crude product was purified by RP-HPLC to afford the desired EXAMPLE 79 (5 mg, 0.011 mmol) as a white amorphous solid.

Example 80

Synthesis of (2R)—N-(4-amidinophenyl)-2-hydroxy-2-[(2R)-3-oxo-4-(3-phenylphenyl)morpholin-2-yl]Acetamide (EXAMPLE 80)

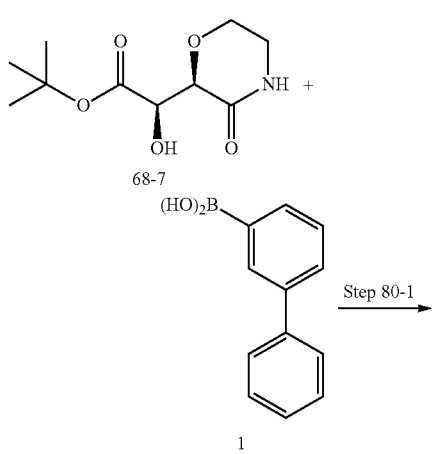

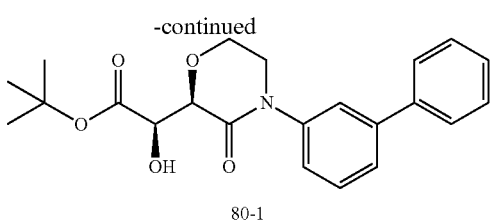

80-1

↓ Step 80-2

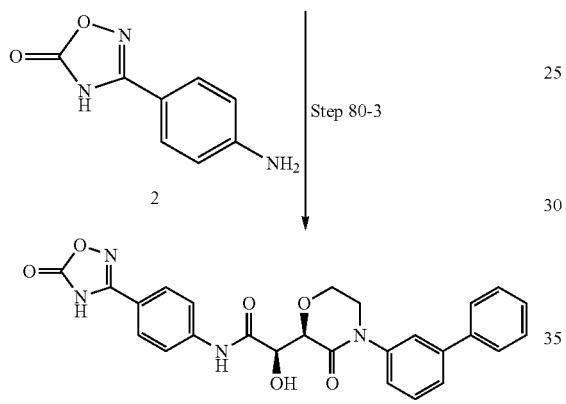

80-2

Step 80-3

80-3

↓ Step 80-4

EXAMPLE 80

Step 80-1

Synthesis of Compound 80-1

According to Step 79-1 in the synthetic method for EXAMPLE 79, 3-biphenylboronic acid 1 (342 mg, 1.73 mmol) was used instead of 4-(methylsulfonyl)phenylboronic acid to obtain compound 80-1 (47 mg, 0.12 mmol).

Step 80-2

Synthesis of Compound 80-2

According to Step 79-2 in the synthetic method for EXAMPLE 79, compound 80-1 (47 mg, 0.12 mmol) was used instead of compound 79-1 to obtain compound 80-2 (0.12 mmol) which was used in the next step without further purification.

Step 80-3

Synthesis of Compound 80-3

According to Step 79-3 in the synthetic method for EXAMPLE 79, compound 80-2 (0.12 mmol) was used instead of compound 79-2 to obtain compound 80-3 (17 mg, 0.035 mmol).

Step 80-4

Synthesis of (2R)—N-(4-amidinophenyl)-2-hydroxy-2-[(2R)-3-oxo-4-(3-phenylphenyl)morpholin-2-yl]Acetamide (EXAMPLE 80)

According to Step 79-4 in the synthetic method for EXAMPLE 79, compound 80-3 (17 mg, 0.035 mmol) was used instead of compound 79-3 to obtain EXAMPLE 80 (13 mg, 0.029 mmol) as a white amorphous solid.

Example 81

Synthesis of (2R)—N-(4-amidinophenyl)-2-hydroxy-2-[(2R)-3-oxo-4-(4-(pyrrolidin-1-ylcarbonyl)phenyl)morpholin-2-yl]acetamide (EXAMPLE 81)

Step 81-1

Synthesis of 1-[(4-iodophenyl)carbonyl]pyrrolidine compound 81-1

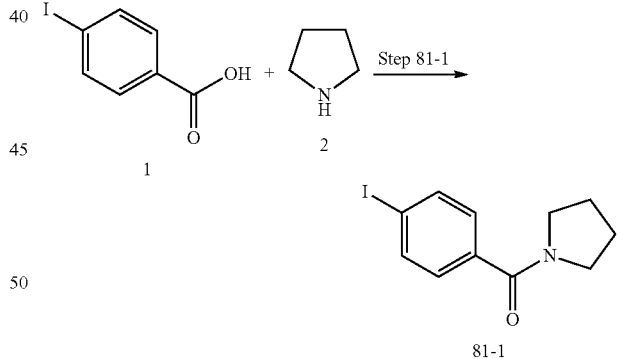

81-1

According to Step 77-2 in the synthetic method for EXAMPLE 77, 4-iodobenzoic acid 1 and pyrrolidine 2 were used to obtain compound 81-1.

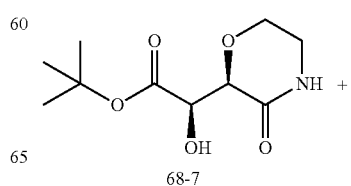

68-7

Step 81-2

Synthesis of Compound 81-2

According to Step 77-2 in the synthetic method for EXAMPLE 77, compound 81-1 (187 mg, 0.62 mmol) was used instead of compound 77-1 to obtain compound 81-2 (153 mg, 0.38 mmol).

Step 81-3

Synthesis of Compound 81-3

According to Step 77-3 in the synthetic method for EXAMPLE 77, compound 81-2 (153 mg, 0.38 mmol) was used instead of compound 77-2 to obtain compound 81-3 (0.38 mmol) which was used in the next step without further purification.

Step 81-4

Synthesis of Compound 81-4

According to Step 77-4 in the synthetic method for EXAMPLE 77, compound 81-3 (0.38 mmol) was used instead of compound 77-3 to obtain compound 81-4 (79 mg, 0.16 mmol).

Step 81-5

Synthesis of (2R)—N-(4-amidinophenyl)-2-hydroxy-2-[(2R)-3-oxo-4-(4-(pyrrolidin-1-ylcarbonyl)phenyl)morpholin-2-yl]acetamide (EXAMPLE 81)

According to Step 77-5 in the synthetic method for EXAMPLE 77, compound 81-4 (79 mg, 0.16 mmol) was used instead of compound 77-4 to obtain compound EXAMPLE 81 (72 mg, 0.15 mmol) as a white amorphous solid.

Example 82

Synthesis of (2R)—N-(4-amidinophenyl)-2-hydroxy-2-[(2R)-3-oxo-4-(4-(morpholin-4-ylcarbonyl)phenyl)morpholin-2-yl]acetamide (EXAMPLE 82)

Step 82-1

Synthesis of 1-[(4-iodophenyl)carbonyl]morpholine (Compound 82-1)

-continued

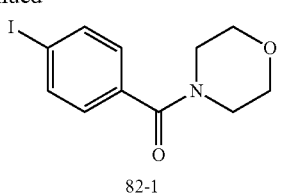
82-1

According to Step 77-1 in the synthetic method for EXAMPLE 77, 4-iodobenzoic acid 1 and morpholine 2 were used to obtain compound 82-1.

Step 82-1

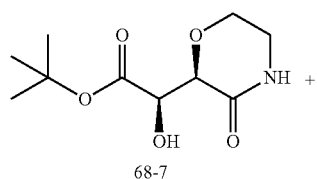
68-7

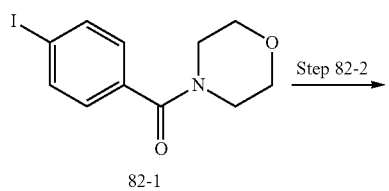
82-1

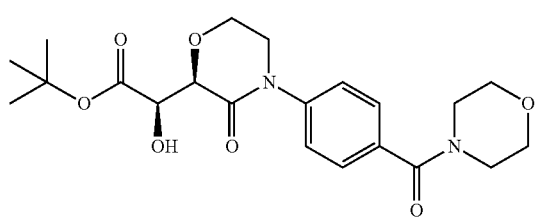
82-2

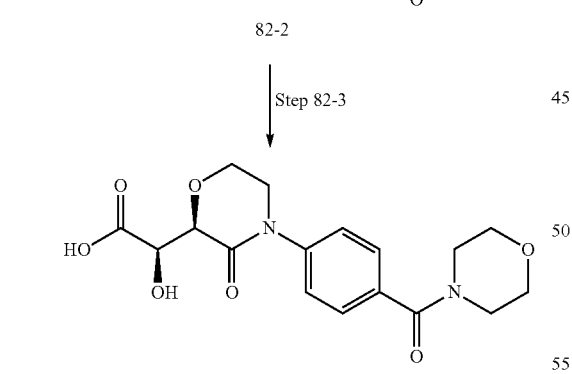
82-3

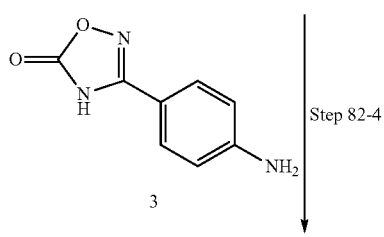
3

-continued

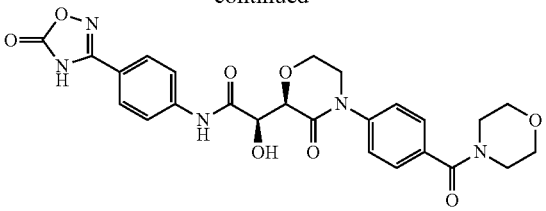
82-4

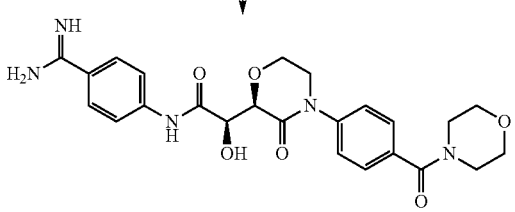
EXAMPLE 82

Step 82-2

Synthesis of Compound 82-2

According to Step 77-2 in the synthetic method for EXAMPLE 77, compound 82-1 (218 mg, 0.69 mmol) was used instead of compound 77-1 to obtain compound 82-2 (221 mg, 0.53 mmol).

Step 82-3

Synthesis of Compound 82-3

According to Step 77-3 in the synthetic method for EXAMPLE 77, compound 82-2 (221 mg, 0.53 mmol) was used instead of compound 77-2 to obtain compound 82-3 (141 mg, 0.39 mmol) which was used in the next step without further purification.

Step 82-4

Synthesis of Compound 82-4

According to Step 77-4 in the synthetic method for EXAMPLE 77, compound 82-3 (40 mg, 0.11 mmol) was used instead of compound 77-3 to obtain compound 82-4 (42 mg, 0.08 mmol).

Step 82-5

Synthesis of (2R)—N-(4-amidinophenyl)-2-hydroxy-2-[(2R)-3-oxo-4-(4-(morpholin-4-ylcarbonyl)phenyl)morpholin-2-yl]acetamide (EXAMPLE 82)

According to Step 77-5 in the synthetic method for EXAMPLE 77, compound 82-4 (42 mg, 0.08 mmol) was used instead of compound 77-4 to obtain EXAMPLE 82 (23 mg, 0.05 mmol) as a white amorphous solid.

Example 83

Synthesis of (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide (EXAMPLE 83)

Step 83-1

Synthesis of 4,4-difluoro-1-[(4-iodophenyl)carbonyl]piperidine (Compound 83-1)

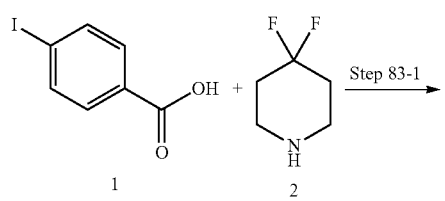

According to Step 77-1 in the synthetic method for compound 77-1, 4-iodobenzoic acid 1 and 4,4-difluoropiperidine 2 were used to obtain compound 83-1.

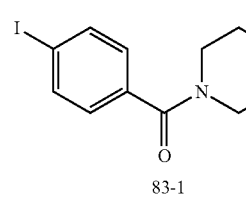

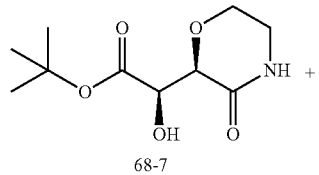

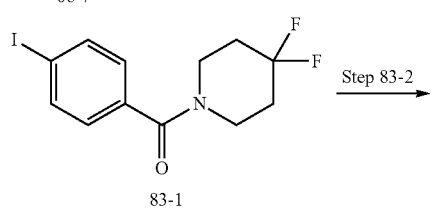

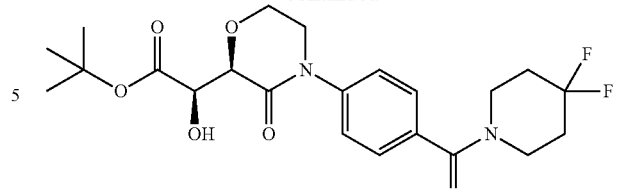

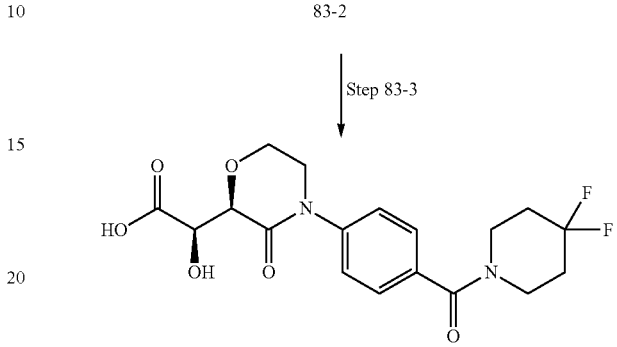

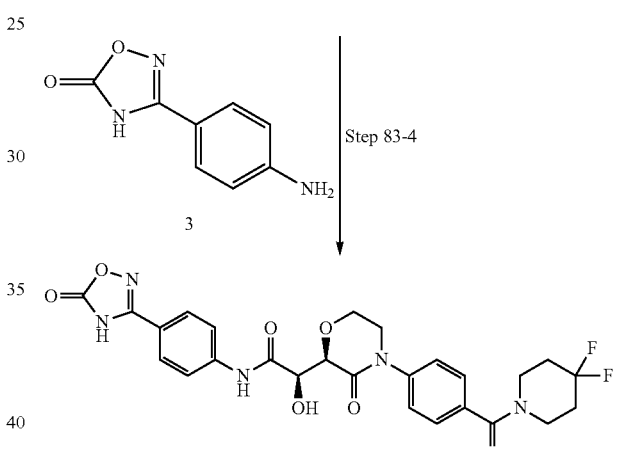

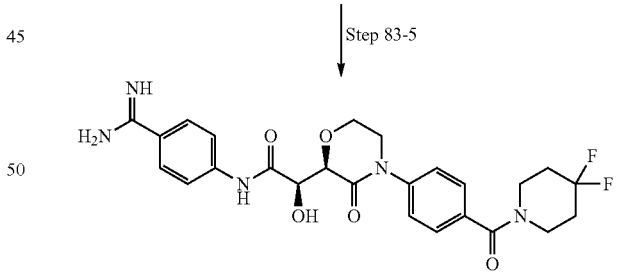

Step 83-2

Synthesis of Compound 83-2

According to Step 77-2 in the synthetic method for EXAMPLE 77, compound 83-1 (593 mg, 1.69 mmol) was used instead of compound 77-1 to obtain compound 83-2 (256 mg, 0.56 mmol).

Step 83-3

Synthesis of Compound 83-3

According to Step 77-3 in the synthetic method for EXAMPLE 77, compound 83-2 (256 mg, 0.56 mmol) was used instead of compound 77-2 to obtain compound 83-3 (0.56 mmol) which was used in the next step without further purification.

Step 83-4

Synthesis of Compound 83-4

According to Step 77-4 in the synthetic method for EXAMPLE 77, compound 83-3 (0.56 mmol) was used instead of compound 77-3 to obtain compound 83-4 (186 mg, 0.33 mmol).

Step 83-5

Synthesis of (2R)—N-(4-amidinophenyl)-2-hydroxy-2-[(2R)-3-oxo-4-(4-(4,4-difluoropiperidin-1-ylcarbonyl)phenyl)morpholin-2-yl]acetamide (EXAMPLE 83)

According to Step 77-5 in the synthetic method for EXAMPLE 77, compound 83-4 (186 mg, 0.33 mmol) was used instead of compound 77-4 to obtain EXAMPLE 83 (91 mg, 0.18 mmol) as a white amorphous solid.

Example 84

Synthesis of (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide (EXAMPLE 84)

Step 84-1

Synthesis of 2-[(3-iodophenyl)carbonyl]-1,2,3,4-tetrahydroisoquinoline 84-1

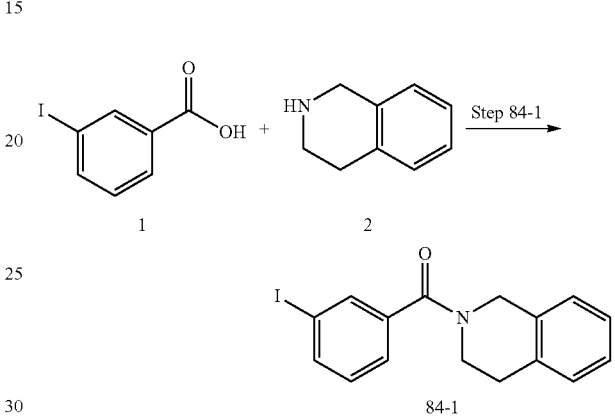

According to Step 77-1 in the synthetic method for compound 77-1, 3-iodobenzoic acid 1 and 1,2,3,4-tetrahydroisoquinoline 2 were used to obtain compound 84-1.

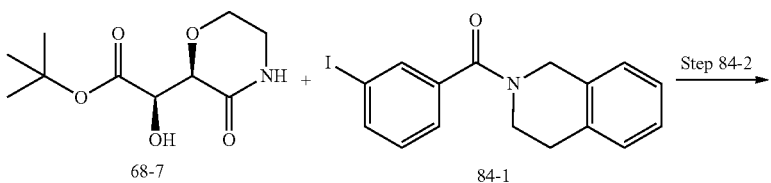

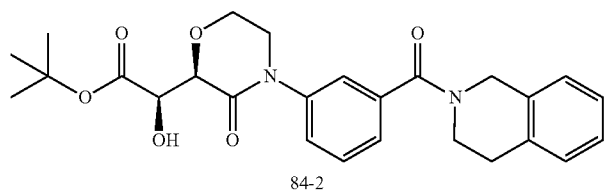

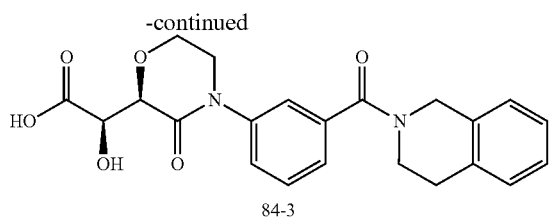

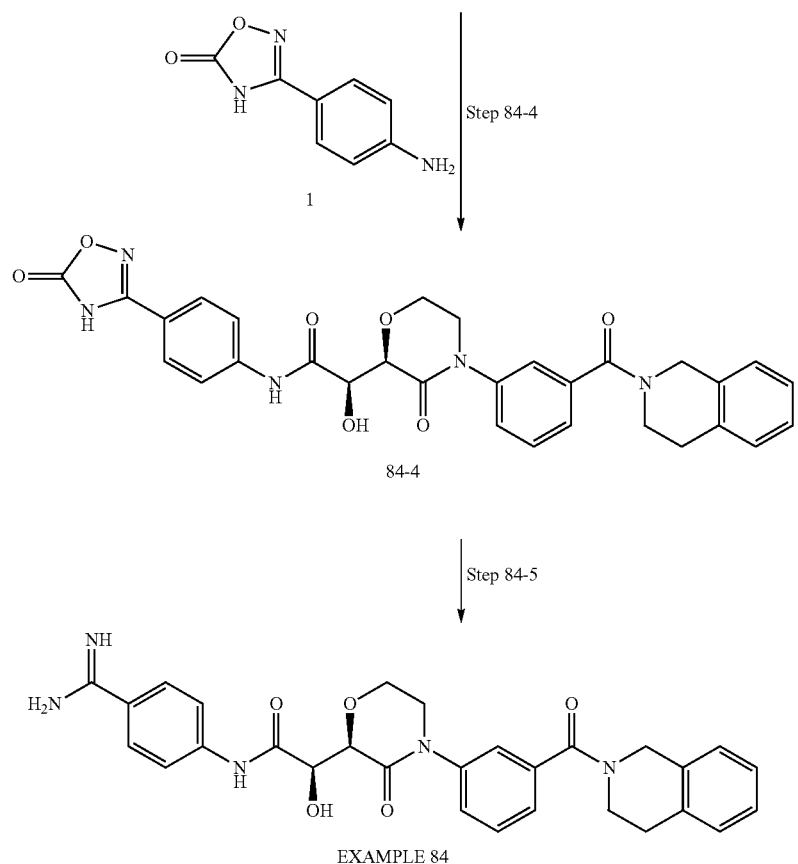

Step 84-2

Synthesis of Compound 84-2

According to Step 77-2 in the synthetic method for EXAMPLE 77, compound 84-1 (518 mg, 1.43 mmol) was used instead of compound 77-1 to obtain compound 84-2 (300 mg, 0.64 mmol).

Step 84-3

Synthesis of Compound 84-3

According to Step 77-3 in the synthetic method for EXAMPLE 77, compound 84-2 (300 mg, 0.64 mmol) was used instead of compound 77-2 to obtain compound 84-3 (0.64 mmol) which was used in the next step without further purification.

Step 84-4

Synthesis of Compound 84-4

According to Step 77-4 in the synthetic method for EXAMPLE 77, compound 84-3 (0.64 mmol) was used instead of compound 77-3 to obtain compound 84-4 (279 mg, 0.49 mmol).

Step 84-5

Synthesis of (2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide EXAMPLE 84

According to Step 77-5 in the synthetic method for EXAMPLE 77, compound 84-4 (279 mg, 0.49 mmol) was used instead of compound 77-4 to obtain EXAMPLE 84 (190 mg, 0.36 mmol) as a white amorphous solid.

Example 85

Synthesis of (2R)—N-(4-amidinophenyl)-2-hydroxy-2-[(2R)-3-oxo-4-(3-(isoindolin-2-ylcarbonyl)phenyl)morpholin-2-yl]acetamide (EXAMPLE 85)

Step 85-1

Synthesis of N-[(3-iodophenyl)carbonyl]isoindoline (Compound 85-1)

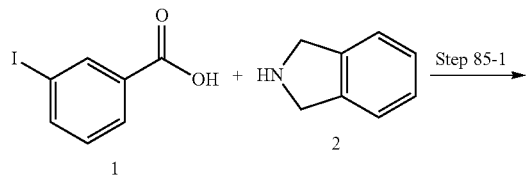

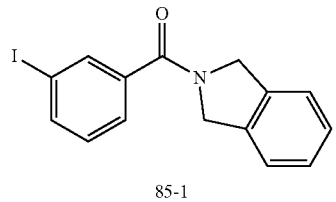

Step 85-1

Synthesis of Compound 85-1

According to Step 77-1 in the synthetic method for compound 77-1, 3-iodobenzoic acid 1 and isoindoline 2 were used to obtain compound 85-1.

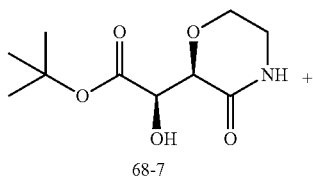

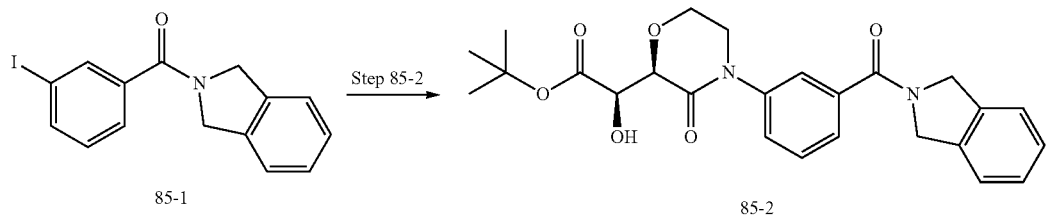

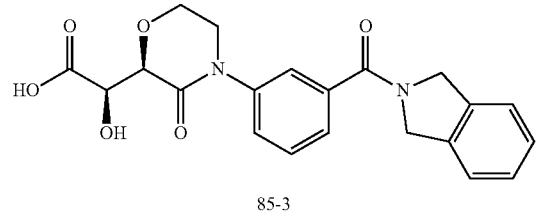

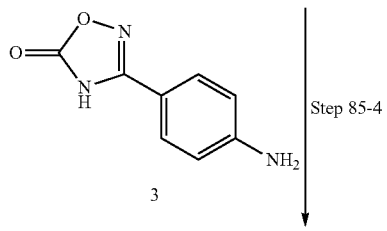

-continued

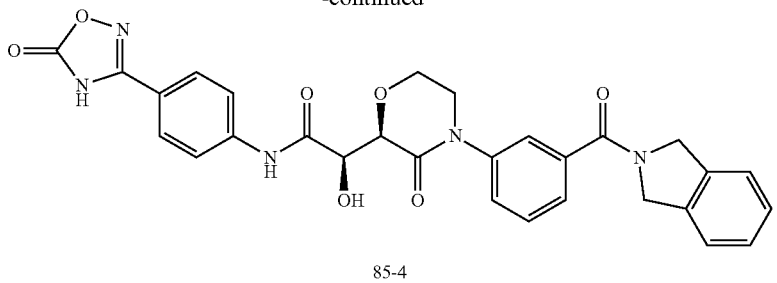

85-4

↓ Step 85-5

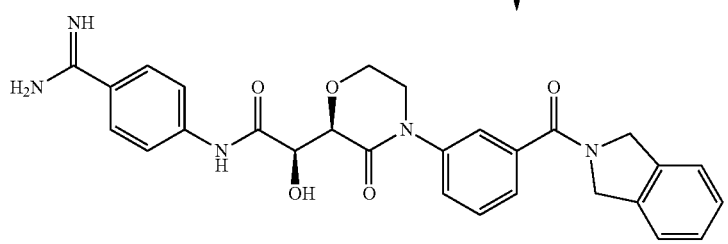

EXAMPLE 85

Step 85-2

Synthesis of Compound 85-2

According to Step 77-2 in the synthetic method for EXAMPLE 77, compound 85-1 (499 mg, 1.43 mmol) was used instead of compound 77-1 to obtain compound 85-2 (152 mg, 0.34 mmol).

Step 85-3

Synthesis of Compound 85-3

According to Step 77-3 in the synthetic method for EXAMPLE 77, compound 85-2 (152 mg, 0.34 mmol) was used instead of compound 77-2 to obtain compound 85-3 (0.34 mmol) which was used in the next step without further purification.

Step 85-4

Synthesis of Compound 85-4

According to Step 77-4 in the synthetic method for EXAMPLE 77, compound 85-3 (0.34 mmol) was used instead of compound 77-3 to obtain compound 85-4 (160 mg, 0.29 mmol).

Step 85-5

Synthesis of (2R)—N-(4-amidinophenyl)-2-hydroxy-2-[(2R)-3-oxo-4-(3-(isoindolin-2-ylcarbonyl)phenyl)morpholin-2-yl]acetamide (EXAMPLE 85)

According to Step 77-5 in the synthetic method for EXAMPLE 77, compound 85-4 (160 mg, 0.29 mmol) was used instead of compound 77-4 to obtain EXAMPLE 85 (103 mg, 0.20 mmol) as a white amorphous solid.

Example 86

Synthesis of (2R)—N-(4-amidinophenyl)-2-hydroxy-2-[(2R)-3-oxo-4-(3-(morpholin-4-ylcarbonyl)phenyl) morpholin-2-yl]acetamide (EXAMPLE 86)

Step 86-1

Synthesis of 1-[(3-iodophenyl)carbonyl]morpholine (Compound 86-1)

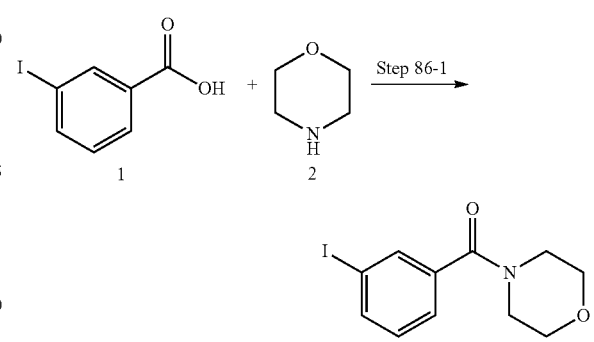

According to Step 77-1 in the synthetic method for compound 77-1, 3-iodobenzoic acid 1 and morpholine 2 were used to obtain compound 85-1.

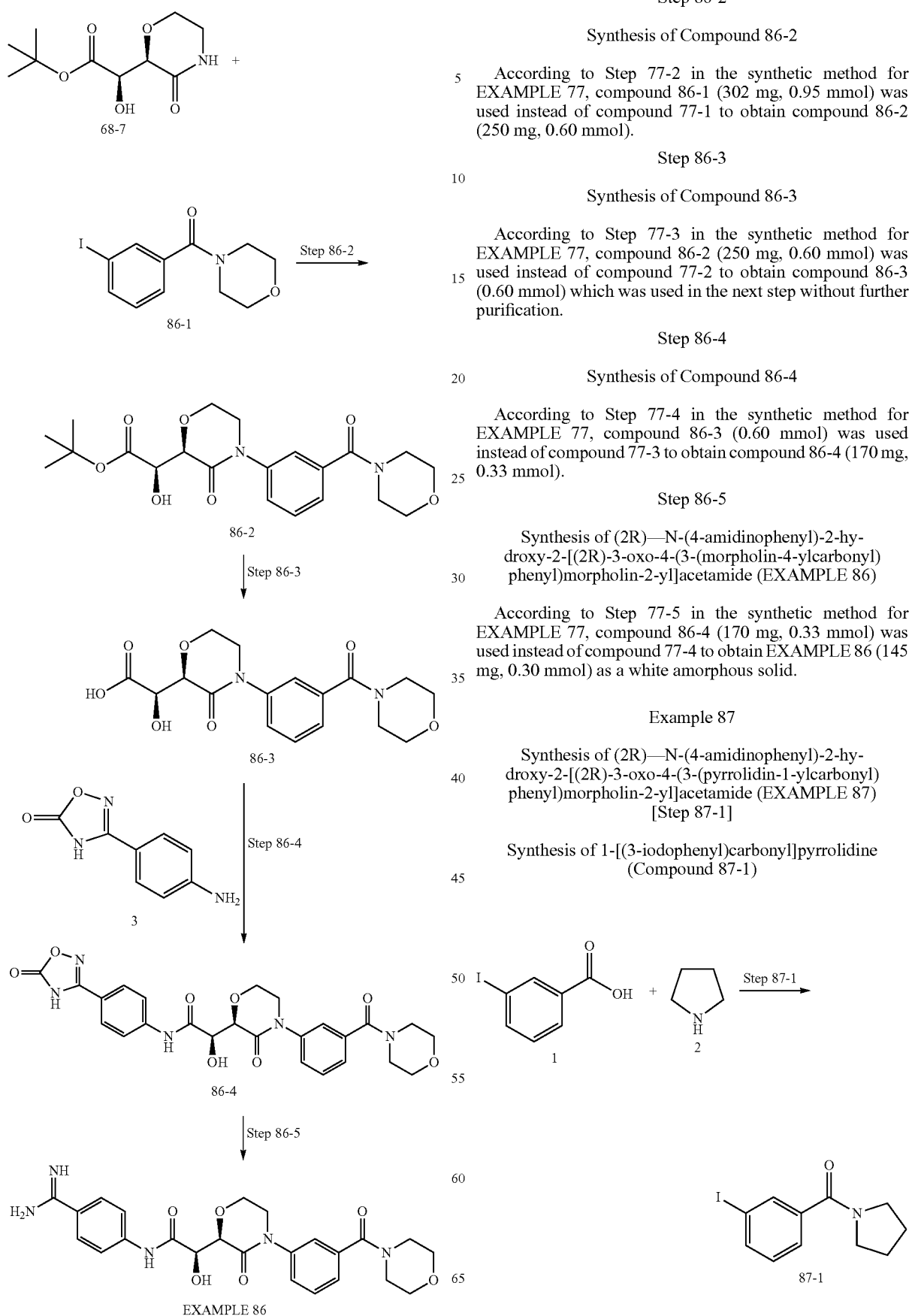

Step 86-2

Synthesis of Compound 86-2

According to Step 77-2 in the synthetic method for EXAMPLE 77, compound 86-1 (302 mg, 0.95 mmol) was used instead of compound 77-1 to obtain compound 86-2 (250 mg, 0.60 mmol).

Step 86-3

Synthesis of Compound 86-3

According to Step 77-3 in the synthetic method for EXAMPLE 77, compound 86-2 (250 mg, 0.60 mmol) was used instead of compound 77-2 to obtain compound 86-3 (0.60 mmol) which was used in the next step without further purification.

Step 86-4

Synthesis of Compound 86-4

According to Step 77-4 in the synthetic method for EXAMPLE 77, compound 86-3 (0.60 mmol) was used instead of compound 77-3 to obtain compound 86-4 (170 mg, 0.33 mmol).

Step 86-5

Synthesis of (2R)—N-(4-amidinophenyl)-2-hydroxy-2-[(2R)-3-oxo-4-(3-(morpholin-4-ylcarbonyl)phenyl)morpholin-2-yl]acetamide (EXAMPLE 86)

According to Step 77-5 in the synthetic method for EXAMPLE 77, compound 86-4 (170 mg, 0.33 mmol) was used instead of compound 77-4 to obtain EXAMPLE 86 (145 mg, 0.30 mmol) as a white amorphous solid.

Example 87

Synthesis of (2R)—N-(4-amidinophenyl)-2-hydroxy-2-[(2R)-3-oxo-4-(3-(pyrrolidin-1-ylcarbonyl)phenyl)morpholin-2-yl]acetamide (EXAMPLE 87)

[Step 87-1]

Synthesis of 1-[(3-iodophenyl)carbonyl]pyrrolidine (Compound 87-1)

According to Step 77-1 in the synthetic method for compound 77-1, 3-iodobenzoic acid 1 and pyrrolidine 2 were used to obtain compound 87-1.

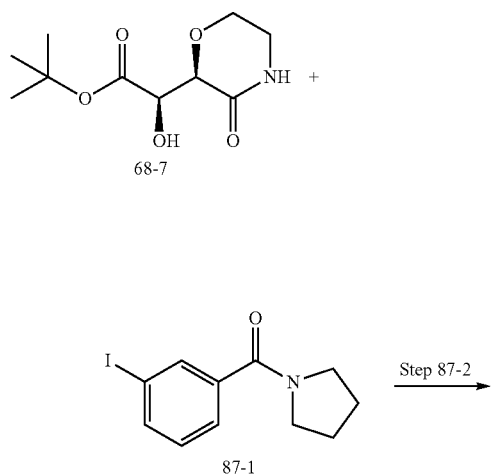

68-7

87-1

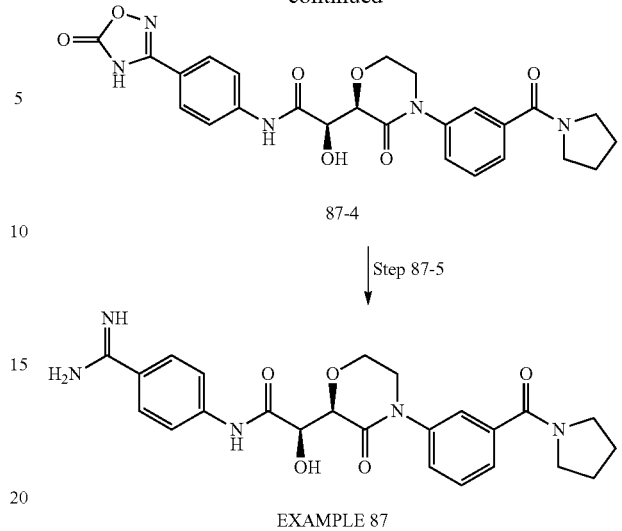

87-4

Step 87-5

EXAMPLE 87

Step 87-2

Synthesis of Compound 87-2

According to Step 77-2 in the synthetic method for EXAMPLE 77, compound 87-1 (286 mg, 0.95 mmol) was used instead of compound 77-1 to obtain compound 87-2 (218 mg, 0.54 mmol).

Step 87-3

Synthesis of Compound 87-3

According to Step 77-3 in the synthetic method for EXAMPLE 77, compound 87-2 (218 mg, 0.54 mmol) was used instead of compound 77-2 to obtain compound 87-3 (0.54 mmol) which was used in the next step without further purification.

Step 87-4

Synthesis of Compound 87-4

According to Step 77-4 in the synthetic method for EXAMPLE 77, compound 87-3 (0.54 mmol) was used instead of compound 77-3 to obtain compound 87-4 (146 mg, 0.29 mmol).

Step 87-5

Synthesis of (2R)—N-(4-amidinophenyl)-2-hydroxy-2-[(2R)-3-oxo-4-(3-(pyrrolidin-1-ylcarbonyl)phenyl)morpholin-2-yl]acetamide (EXAMPLE 87)

According to Step 77-5 in the synthetic method for EXAMPLE 77, compound 87-4 (146 mg, 0.29 mmol) was used instead of compound 77-4 to obtain EXAMPLE 87 (133 mg, 0.29 mmol) as a white amorphous solid.

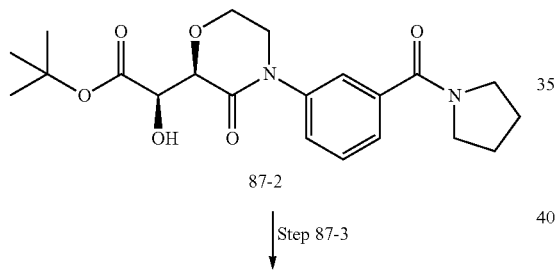

87-2

Step 87-3

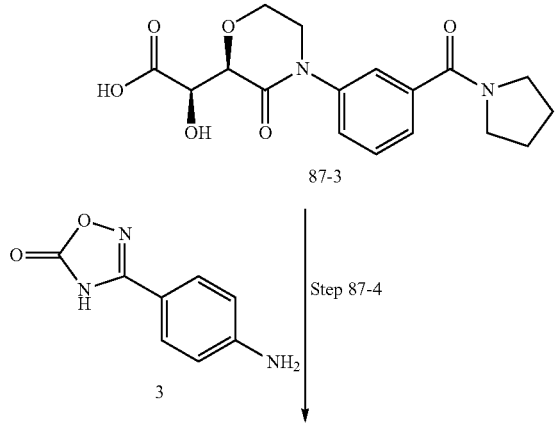

87-3

3

Step 87-4

Example 88
Synthesis of (2R)—N-(4-amidinophenyl)-2-hydroxy-2-[(2R)-3-oxo-4-(4-fluorophenyl)morpholin-2-yl]Acetamide (EXAMPLE 88)
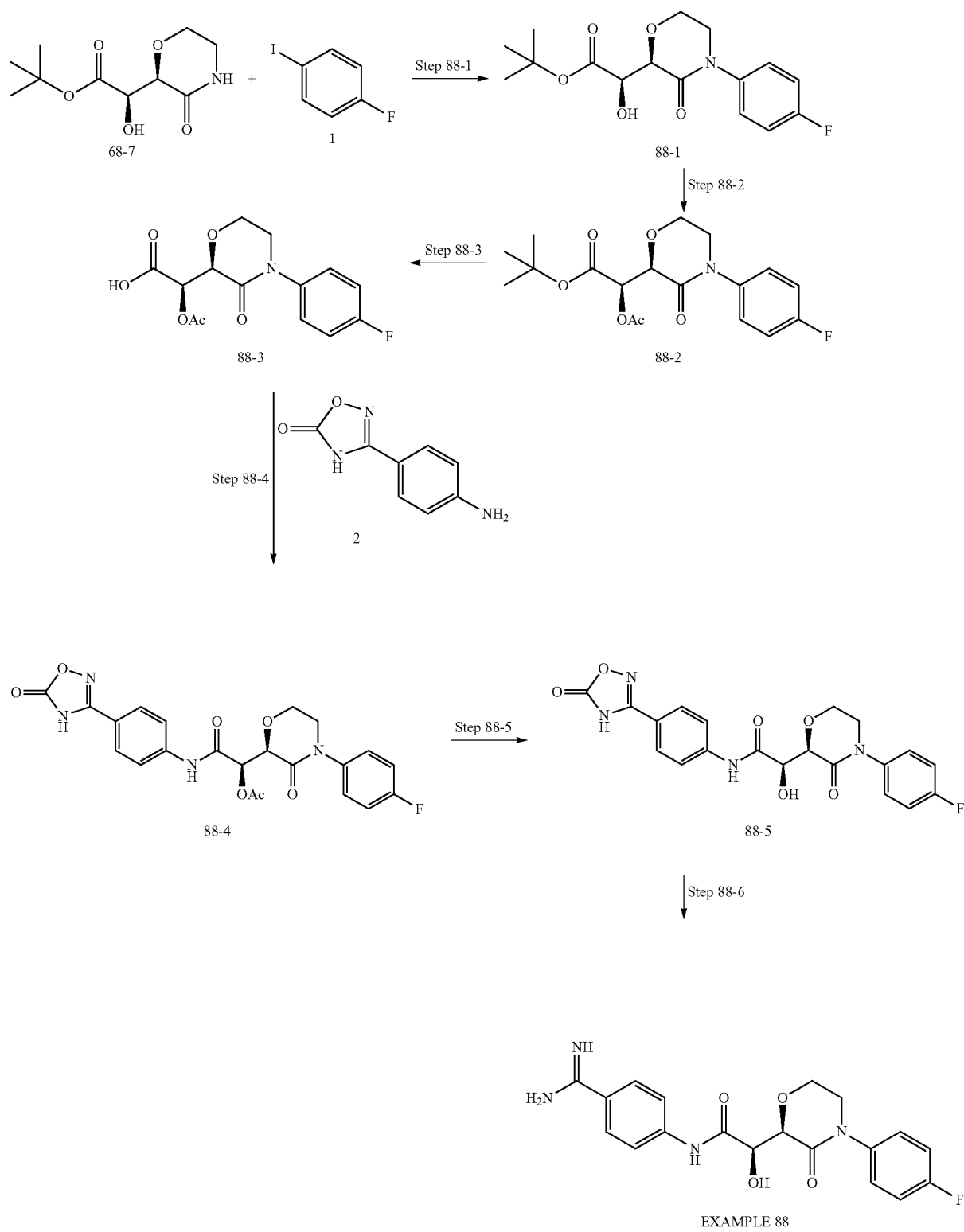

Step 88-1

Synthesis of Compound 88-1

According to Step 78-2 in the synthetic method for EXAMPLE 78, 1-fluoro-4-iodobenzene 1 (67 mg, 0.30 mmol) was used instead of compound 78-2 to obtain compound 88-1 (67 mg, 0.21 mmol).

Step 88-2

Synthesis of Compound 88-2

According to Step 78-3 in the synthetic method for EXAMPLE 78, compound 88-1 (67 mg, 0.21 mmol) was used instead of compound 78-2 to obtain compound 88-2 (77 mg, 0.21 mmol).

Step 88-3

Synthesis of Compound 88-3

According to Step 78-4 in the synthetic method for EXAMPLE 78, compound 88-2 (77 mg, 0.21 mmol) was used instead of compound 78-3 to obtain compound 88-3 (0.21 mmol) which was used in the next step without further purification.

Step 88-4

Synthesis of Compound 88-4

According to Step 78-5 in the synthetic method for EXAMPLE 78, compound 88-3 (0.21 mmol) was used instead of compound 78-4 to obtain compound 88-4 (0.21 mmol) which was used in the next step without further purification.

Step 88-5

Synthesis of Compound 88-5

According to Step 78-6 in the synthetic method for EXAMPLE 78, compound 88-4 (0.21 mmol) was used instead of compound 78-5 to obtain compound 88-5 (0.21 mmol) which was used in the next step without further purification.

Step 88-6

Synthesis of (2R)—N-(4-amidinophenyl)-2-hydroxy-2-[(2R)-3-oxo-4-(4-fluorophenyl)morpholin-2-yl]Acetamide (EXAMPLE 88)

According to Step 78-7 in the synthetic method for EXAMPLE 78, compound 88-5 (0.21 mmol) was used instead of compound 78-6 to obtain EXAMPLE 88 (45 mg, 0.12 mmol) as a white amorphous solid.

Example 89

Synthesis of (2R)—N-(4-amidinophenyl)-2-hydroxy-2-[(2R)-3-oxo-4-(3,5-difluorophenyl)morpholin-2-yl]acetamide (EXAMPLE 89)

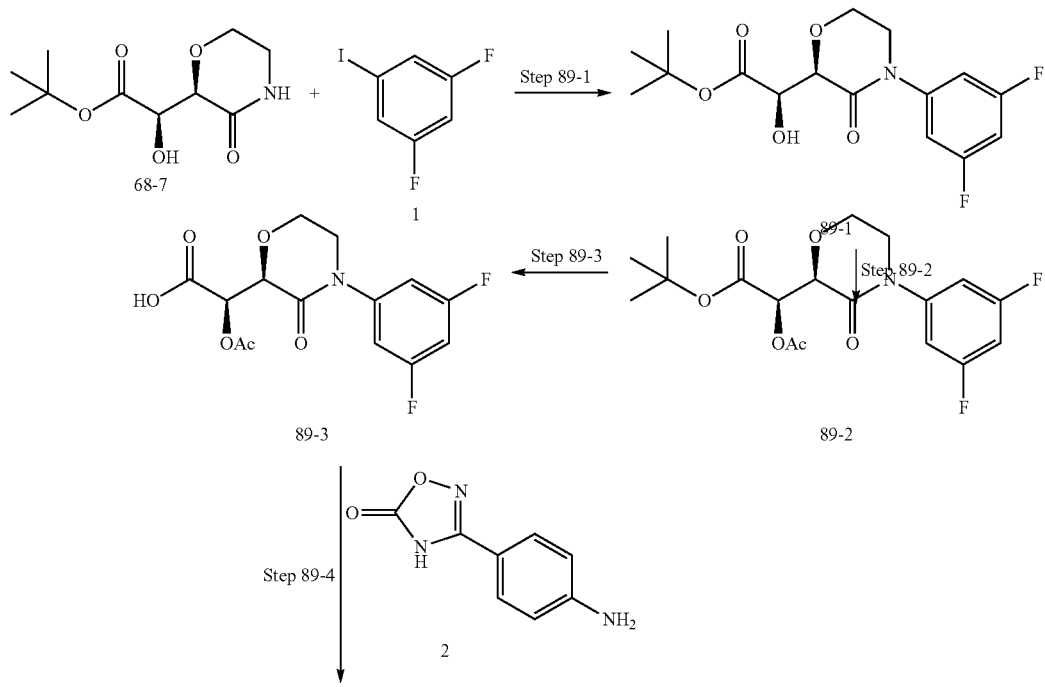

289 290

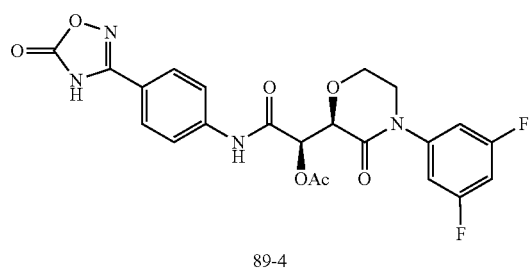

89-4

-continued

Step 89-5

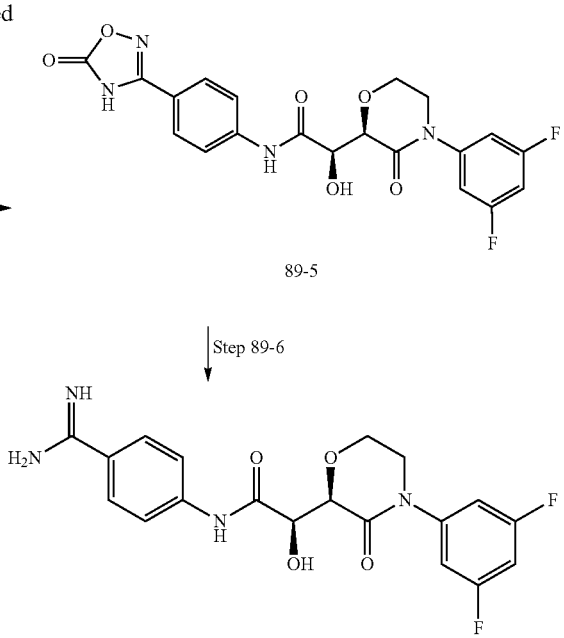

89-5

Step 89-6

EXAMPLE 89

Step 89-1

Synthesis of Compound 89-1

According to Step 78-2 in the synthetic method for EXAMPLE 78, 1,3-difluoro-5-iodobenzene 1 (87 mg, 0.37 mmol) was used instead of compound 78-1 to obtain compound 89-1 (98 mg, 0.29 mmol).

Step 89-2

Synthesis of Compound 89-2

According to Step 78-3 in the synthetic method for EXAMPLE 78, compound 89-1 (98 mg, 0.29 mmol) was used instead of compound 78-2 to obtain compound 89-2 (104 mg, 0.27 mmol).

Step 89-3

Synthesis of Compound 89-3

According to Step 78-4 in the synthetic method for EXAMPLE 78, compound 89-2 (104 mg, 0.27 mmol) was used instead of compound 78-3 to obtain compound 89-3 (0.27 mmol) which was used in the next step without further purification.

Step 89-4

Synthesis of Compound 89-4

According to Step 78-5 in the synthetic method for EXAMPLE 78, compound 89-3 (0.27 mmol) was used instead of compound 78-4 to obtain compound 89-4 (0.27 mmol) which was used in the next step without further purification.

Step 89-5

Synthesis of Compound 89-5

According to Step 78-6 in the synthetic method for EXAMPLE 78, compound 89-4 (0.27 mmol) was used instead of compound 78-5 to obtain compound 89-5 (0.27 mmol) which was used in the next step without further purification.

Step 89-6

Synthesis of (2R)—N-(4-amidinophenyl)-2-hydroxy-2-[(2R)-3-oxo-4-(3,5-difluorophenyl)morpholin-2-yl]acetamide (EXAMPLE 89)

According to Step 78-7 in the synthetic method for EXAMPLE 78, compound 89-5 (0.27 mmol) was used instead of compound 78-6 to obtain EXAMPLE 89 (38 mg, 0.094 mmol) as a white amorphous solid.

Example 90

Synthesis of (2R)—N-(4-amidinophenyl)-2-hydroxy-2-[(2R)-3-oxo-4-(4-(morpholin-1-ylsulfonyl)phenyl)morpholin-2-yl]acetamide (EXAMPLE 90)

Step 90-1

Synthesis of 1-[(4-iodobenzene)sulfonyl]morpholine (Compound 90-1)

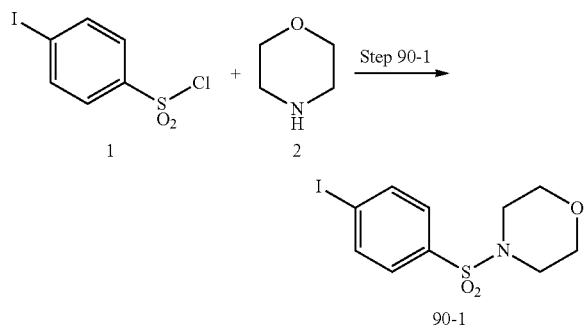

According to Step 77-2 in the synthetic method for EXAMPLE 77, 4-iodobenzenesulfonyl chloride 1 and morpholine 2 were used to obtain compound 90-1.

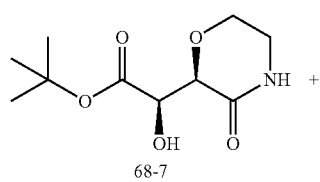

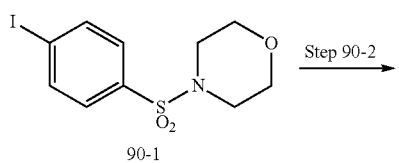

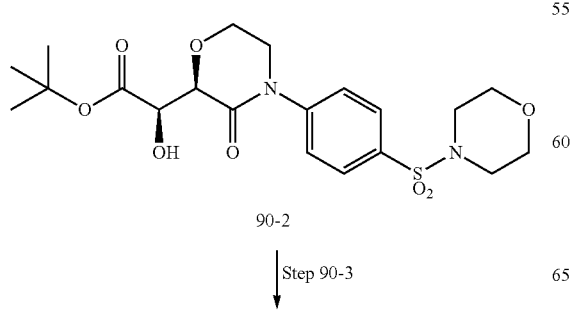

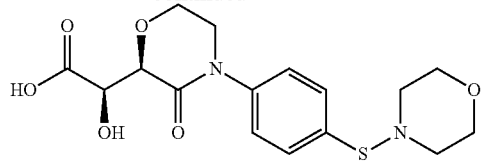

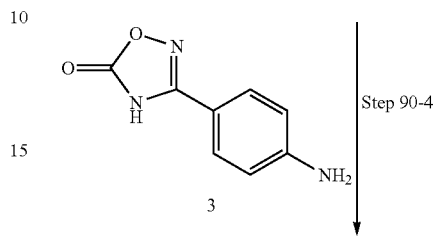

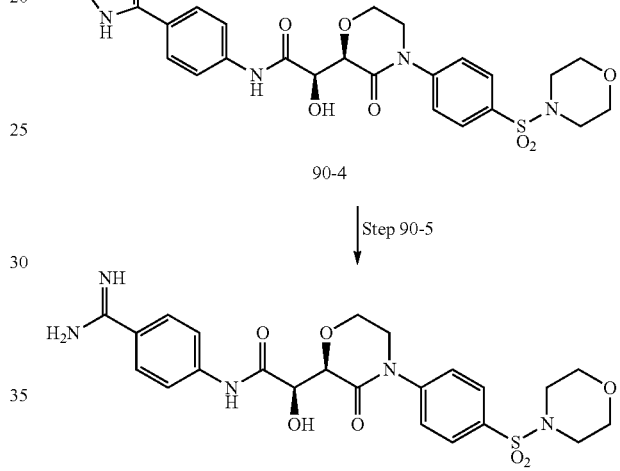

Step 90-2

Synthesis of Compound 90-2

According to Step 77-2 in the synthetic method for EXAMPLE 77, compound 90-1 (336 mg, 0.95 mmol) was used instead of compound 77-1 to obtain compound 90-2 (239 mg, 0.52 mmol).

Step 90-3

Synthesis of Compound 90-3

According to Step 77-3 in the synthetic method for EXAMPLE 77, compound 90-2 (239 mg, 0.52 mmol) was used instead of compound 77-2 to obtain compound 90-3 (208 mg, 0.52 mmol) which was used in the next step without further purification.

Step 90-4

Synthesis of Compound 90-4

According to Step 77-4 in the synthetic method for EXAMPLE 77, compound 90-3 (208 mg, 0.52 mmol) was used instead of compound 77-3 to obtain compound 90-4 (18 mg, 0.032 mmol).

Step 90-5

Synthesis of (2R)—N-(4-amidinophenyl)-2-hydroxy-2-[(2R)-3-oxo-4-(4-(morpholin-1-ylsulfonyl)phenyl)morpholin-2-yl]acetamide (EXAMPLE 90)

According to Step 77-5 in the synthetic method for EXAMPLE 77, compound 90-4 (18 mg, 0.032 mmol) was used instead of compound 77-4 to obtain EXAMPLE 90 (13 mg, 0.025 mmol).

Example 91

Synthesis of (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide (EXAMPLE 91)

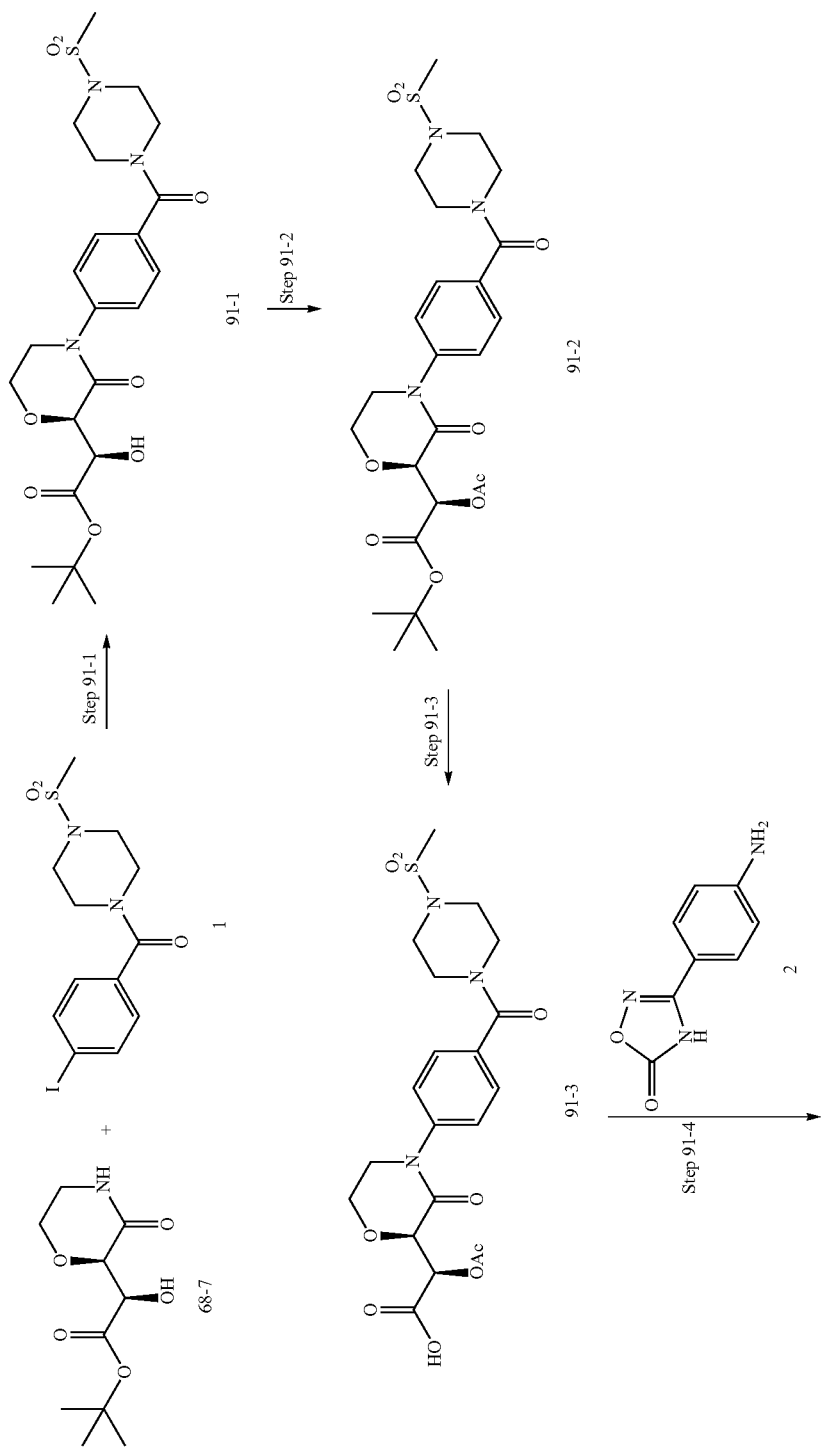

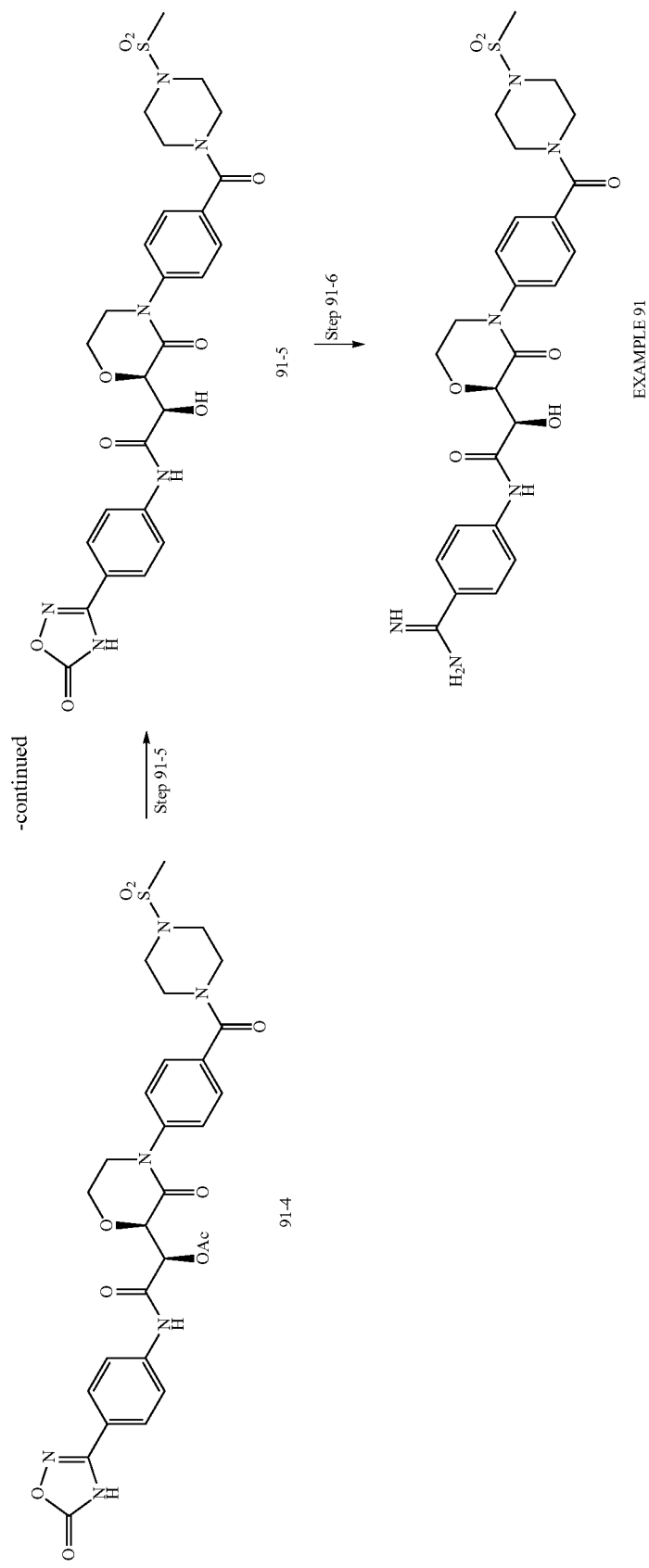

Step 91-1

Synthesis of Compound 91-1

According to Step 78-2 in the synthetic method for EXAMPLE 78, 1-[(4-iodophenyl)carbonyl]-4-methanesulfonylpiperazine 1 (375 mg, 0.95 mmol) was used instead of compound 78-1 to obtain compound 91-1 (264 mg, 0.53 mmol).

Step 91-2

Synthesis of Compound 91-2

According to Step 78-3 in the synthetic method for EXAMPLE 78, compound 91-1 (264 mg, 0.53 mmol) was used instead of compound 78-1 to obtain compound 91-2 (158 mg, 0.29 mmol).

Step 91-3

Synthesis of Compound 91-3

According to Step 78-4 in the synthetic method for EXAMPLE 78, compound 91-2 (158 mg, 0.29 mmol) was used instead of compound 78-2 to obtain compound 91-3 (141 mg, 0.29 mmol) which was used in the next step without further purification.

Step 91-4

Synthesis of Compound 91-4

According to Step 78-5 in the synthetic method for EXAMPLE 78, compound 91-3 (141 mg, 0.29 mmol) was used instead of compound 78-3 to obtain compound 91-4 (151 mg, 0.24 mmol).

Step 91-5

Synthesis of Compound 91-5

According to Step 78-6 in the synthetic method for EXAMPLE 78, compound 91-4 (151 mg, 0.24 mmol) was used instead of compound 78-4 to obtain compound 91-5 (0.24 mmol) which was used in the next step without further purification.

Step 91-6

Synthesis of (2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide (EXAMPLE 91)

According to Step 78-7 in the synthetic method for EXAMPLE 78, compound 91-5 (0.24 mmol) was used instead of compound 78-6 to obtain EXAMPLE 91 (115 mg, 0.21 mmol) as a white amorphous solid.

Example 92

Synthesis of (2R)—N-(4-amidinophenyl)-2-hydroxy-2-[(2R)-3-oxo-4-(2-fluoropyridin-5-yl)morpholin-2-yl]acetamide (EXAMPLE 92)

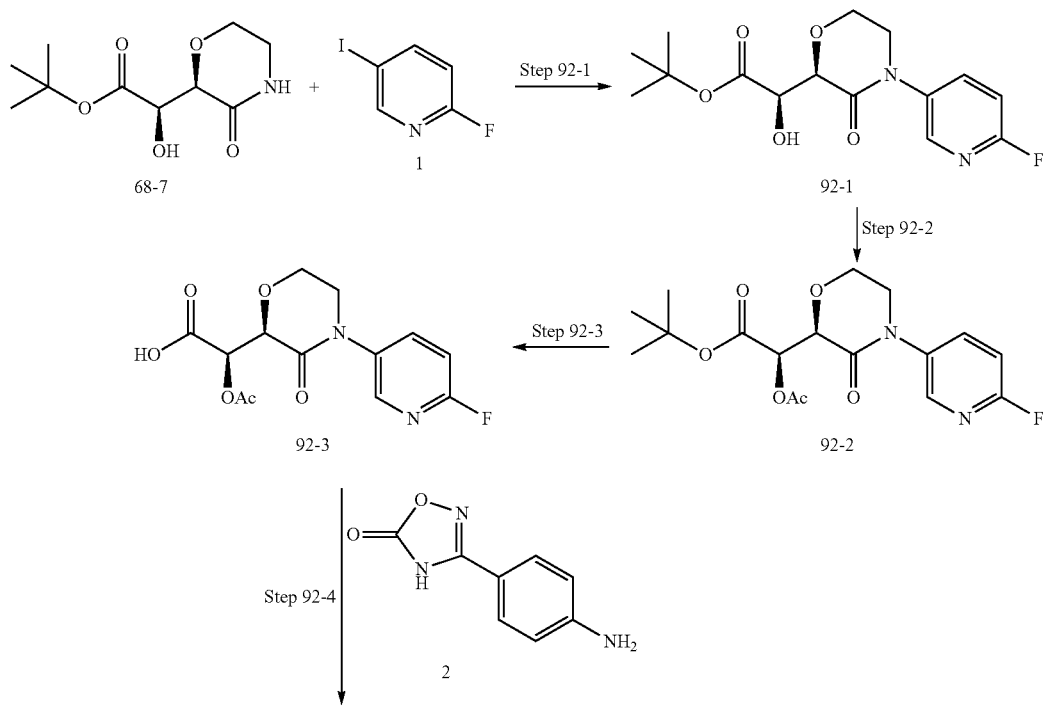

301

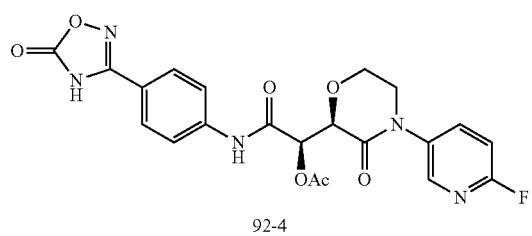

92-4

→ Step 92-5

302

-continued

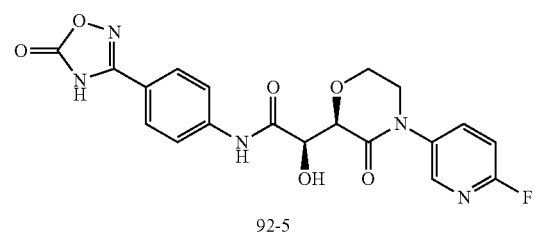

92-5

↓ Step 92-6

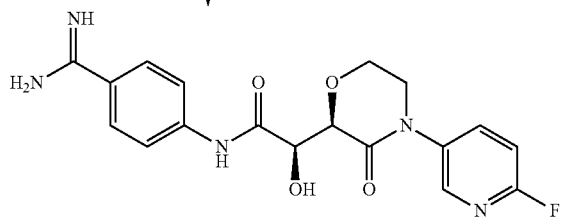

EXAMPLE 92

Step 92-1

Synthesis of Compound 92-1

According to Step 78-2 in the synthetic method for EXAMPLE 78, 2-fluoro-5-iodopyridine 1(80 mg, 0.36 mmol) was used instead of compound 78-1 to obtain compound 92-1 (94 mg, 0.29 mmol).

Step 92-2

Synthesis of Compound 92-2

According to Step 78-3 in the synthetic method for EXAMPLE 78, compound 92-1 (94 mg, 0.29 mmol) was used instead of compound 78-2 to obtain compound 92-2 (80 mg, 0.22 mmol).

Step 92-3

Synthesis of Compound 92-3

According to Step 78-4 in the synthetic method for EXAMPLE 78, compound 92-2 (80 mg, 0.22 mmol) was used instead of compound 78-3 to obtain compound 92-3 (0.22 mmol) which was used in the next step without further purification.

Step 92-4

Synthesis of Compound 92-4

According to Step 78-5 in the synthetic method for EXAMPLE 78, compound 92-3 (0.22 mmol) was used instead of compound 78-4 to obtain compound 92-4 (0.22 mmol) which was used in the next step without further purification.

Step 92-5

Synthesis of Compound 92-5

According to Step 78-6 in the synthetic method for EXAMPLE 78, compound 92-4 (0.22 mmol) was used instead of compound 78-5 to obtain compound 92-5 (0.22 mmol) which was used in the next step without further purification.

Step 92-6

Synthesis of (2R)—N-(4-amidinophenyl)-2-hydroxy-2-[(2R)-3-oxo-4-(2-fluoropyridin-5-yl)morpholin-2-yl]acetamide (EXAMPLE 92)

According to Step 78-7 in the synthetic method for EXAMPLE 78, compound 92-5 (0.22 mmol) was used instead of compound 78-6 to obtain EXAMPLE 92 (67 mg, 0.17 mmol) as a white amorphous solid.

Example 93

Synthesis of (R)—N-(3-aminobenzo[d]isoxazol-6-yl)-2-hydroxy-2-((R)-3-oxo-4-(4-(trifluoromethyl)phenyl) morpholin-2-yl)acetamide (EXAMPLE 93)

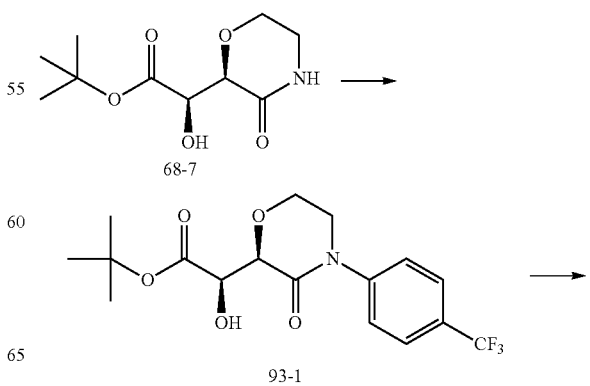

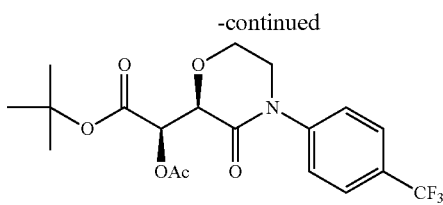

93-2

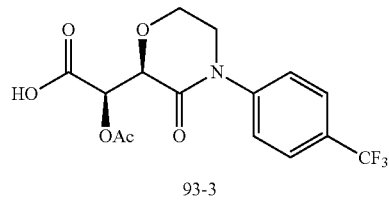

93-3

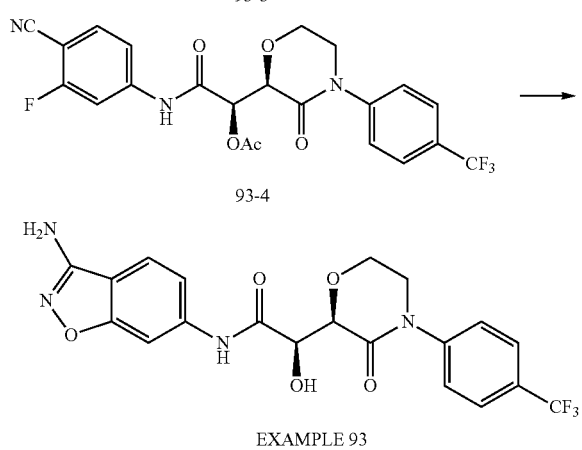

EXAMPLE 93

Step 93-1

Synthesis of (R)-tert-butyl 2-hydroxy-2-((R)-3-oxo-4-(4-(trifluoromethyl)phenyl)morpholin-2-yl)acetate (Compound 93-1)

(R)-tert-butyl 2-hydroxy-2-((R)-3-oxomorpholin-2-yl)acetate (0.5 g, 0.002162 mol) and 4-trifluoromethylphenyl iodide (0.882 g, 1.5 eq) were dissolved in 1,2-dioxane (14 ml), to this mixture were added CuI (82 mg, 0.2 eq), $K_2CO_3$ (598 mg, 2 eq), and trans-N,N-dimethylcyclohexane-1,2-diamine (0.1 ml, 0.3 eq). The resulting solution was degassed and heated at 115° C. for 5 hours. The mixture was cooled to it, the solid removed by filtration, solution washed with water, dried ($MgSO_4$), and concentrated. The resulting residue was then purified by silica gel chromatography (0-20% EtOAc in hexane) to give 477 mg of compound 93-1.

Step 93-2

Synthesis of (R)-tert-butyl 2-acetoxy-2-((R)-3-oxo-4-(4-(trifluoromethyl)phenyl)morpholin-2-yl)acetate (compound 93-2)

Compound 93-1 (350 mg, 0.932 mmol) was dissolved in $CH_2Cl_2$ (4.66 ml) and cooled to 0° C., $Ac_2O$ (0.176 ml, 2 eq), pyridine (0.151 ml, 2 eq), and DMAP (11 mg, 0.1 eq) was added. The mixture was stirred for 2 hours, diluted with EtOAc, washed with $CuSO_4$ solution, water, dried and concentrated to give 370 mg of compound 93-2.

Step 93-3

Synthesis of (R)-2-acetoxy-2-((R)-3-oxo-4-(4-(trifluoromethyl)phenyl)morpholin-2-yl)acetic acid (Compound 93-3)

Compound 93-2 (370 mg, 0.884 mmol) was dissolved in 1:1 $CH_2Cl_2$/TFA (8.8 ml) and stirred for 30 minutes. The mixture was concentrated to give 310 mg of compound 93-3.

Step 93-4

Synthesis of (R)-2-(4-cyano-3-fluorophenylamino)-2-oxo-14(R)-3-oxo-4-(4-(trifluoromethyl)phenyl)morpholin-2-yl)ethyl acetate (Compound 93-4)

Compound 93-3 (371 mg, 1.03 mmol) was dissolved in $CH_2Cl_2$ (5.13 ml), $(COCl)_2$ (0.176 ml, 2 eq), then 1 drop of DMF was added. The mixture was stirred for 1 hour, concentrated to dryness, taken up in DMF and 4-cyano-3-fluoroaniline (0.559 g, 4 eq) added. The mixture was stirred for 2 hours, $NH_4Cl_{(sat)}$ added, the mixture extracted with EtOAc, dried ($MgSO_4$), concentrated, silica gel chromatography to give 260 mg of compound 93-4.

Step 93-5

Synthesis of (R)—N-(3-aminobenzo[d]isoxazol-6-yl)-2-hydroxy-2-((R)-3-oxo-4-(4-(trifluoromethyl)phenyl)morpholin-2-yl)acetamide (EXAMPLE 93)

Compound 93-4 (160 mg, 0.334 mmol) was dissolved in 10:1 DMF/water (3.34 ml), $K_2CO_3$ (554 mg, 12 eq) and acetohydroxamic acid (150 mg, 6 eq) were added and the mixture heated at 55° C. for 4 hours. After cooling to room temperature the mixture was diluted with EtOAc, washed with water, dried ($MgSO_4$) and concentrated. The residue was purified by C18 HPLC (89.95:9.95:0.1$H_2O$:MeCN:$HCO_2H$-9.95:89.95:0.1$H_2O$:MeCN:$HCO_2H$) to give 9 mg of EXAMPLE 93.

Example 94

Synthesis of (R)—N-(3-amino-1H-indazol-6-yl)-2-hydroxy-2-((R)-3-oxo-4-(4-(trifluoromethyl)phenyl)morpholin-2-yl)acetamide (EXAMPLE 94)

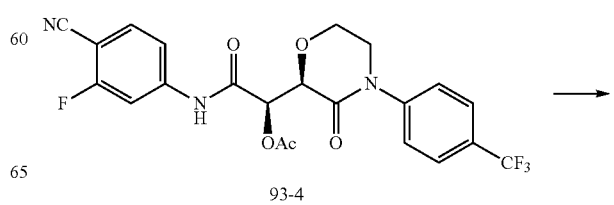

93-4

305

-continued

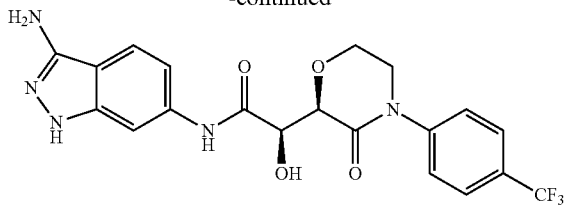

EXAMPLE 94

Compound 93-4 (20 mg, 0.042 mmol) was dissolved in n-BuOH (0.42 ml) and $NH_2NH_2$ (0.13 ml, 100 eq) was added, heated at 55° C. for 2 hours. The mixture was concentrated and purified by C18 HPLC (89.95:9.95:0.1$H_2O$:MeCN: $HCO_2H$-9.95:89.95:0.1$H_2O$:MeCN:$HCO_2H$) to give 2.6 mg EXAMPLE 94.

Example 95

Synthesis of (R)—N-(4-carbamimidoyl-3-fluorophenyl)-2-hydroxy-2-((R)-3-oxo-4-(4-(trifluoromethyl)phenyl)morpholin-2-yl)acetamide (EXAMPLE 95)

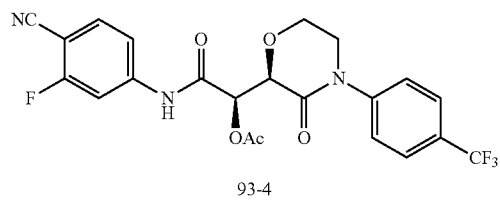

93-4

306

-continued

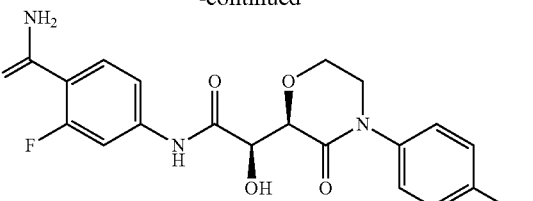

EXAMPLE 95

Compound 93-4 (30 mg, 0.063 mmol) dissolved in EtOH (7.82 ml), cooled to −78° C., HCl(g) was bubbled through for five minutes. The reaction was sealed and allowed to warm to rt with periodic venting and stirred overnight. The mixture was degassed, concentrated and taken up in 7N $NH_3$ in MeOH and stirred overnight. The mixture was concentrated and purified by C18 HPLC (89.95:9.95:0.1$H_2O$:MeCN:$HCO_2H$-9.95:89.95:0.1$H_2O$:MeCN:$HCO_2H$) to give 9 mg of EXAMPLE 95.

Example 96

Synthesis of (R)—N-(4-Carbamimidoylphenyl)-2-hydroxy-2-{(R)-3-oxo-4-[4-(trifluoromethyl)phenyl]morpholin-2-yl}acetamide (EXAMPLE 96)

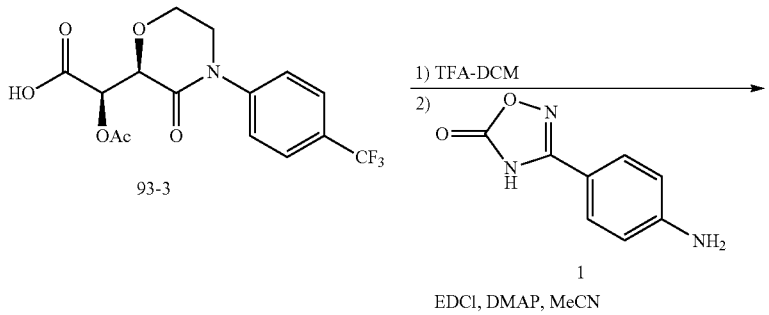

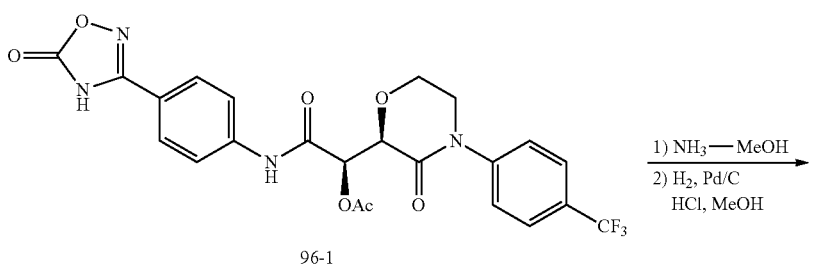

96-1

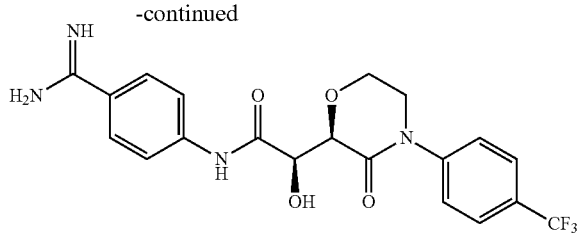

EXAMPLE 96

Step 96-1

Synthesis of (R)-2-oxo-2-(4-(5-oxo-4,5-dihydro-1,2,4-oxadiazol-3-yl)phenylamino)-1-((R)-3-oxo-4-(4-(trifluoromethyl)phenyl)morpholin-2-yl)ethyl acetate (Compound 96-1)

To a stirred mixture of compound 93-3 (175 mg, 0.50 mmol), DMAP (12 mg, 20 mmol %), and 3-(4-aminophenyl)-1,2,4-oxadiazol-5(2I)-one 1 (177 mg, 2 eq) in MeCN (2.5 ml) at 0° C., EDCI (191 mg, 2 eq) was added. The resulting mixture was stirred at RT for 2 h. The volatile materials were removed on the rotavap. The residue was purified by silica gel chromatography (MeOH/DCM 0 to 10%) to give compound 96-1 (110 mg).

Step 96-2

Synthesis of (R)—N-(4-Carbamimidoylphenyl)-2-hydroxy-2-{(R)-3-oxo-4-[4-(trifluoromethyl)phenyl]morpholin-2-yl}acetamide (EXAMPLE 96)

The compound 96-1 (110 mg) was treated with 7 M NH$_3$/MeOH (1 mL) and the mixture was stirred at RT for 1 h. After removal of the volatile materials on the rotavap, the residue was dissolved in MeOH (1 mL) and 3M HCl (0.25 ml). The resulting suspension was treated with a balloon of H$_2$ over 10% Pd/C (30 mg) and stirred at RT for 2 h. The resulting mixture was filtered through Celite® and concentrated. The residue was purified by reverse phase HPLC to give EXAMPLE 96 which was converted to the HCl salt (88 mg) by treating with one equivalent HCl in ether and concentration on a rotavap.

Example 97

Synthesis of (R)—N-(4-carbamimidoylphenyl)-2-hydroxy-2-((R)-3-oxo-4-(3-(trifluoromethyl)phenyl)morpholin-2-yl)acetamide (EXAMPLE 97)

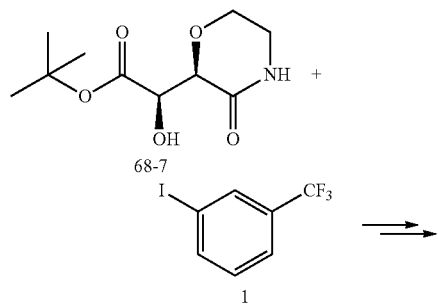

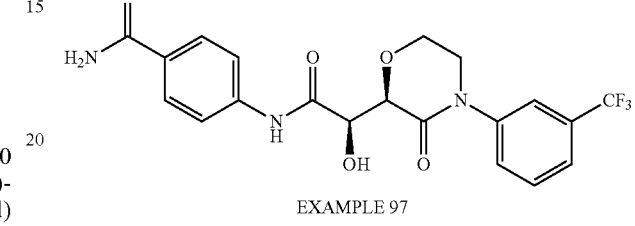

EXAMPLE 97

EXAMPLE 97 was synthesized similarly as for the synthesis of EXAMPLE 93 and EXAMPLE 96 using 1-iodo-3-(trifluoromethyl)benzene 1.

Example 98

Synthesis of N-(4-Amino-7-quinazolinyl)-alpha(R)-hydroxy-3-oxo-4-[4-(trifluoromethyl)phenyl]-2(R)-morpholineacetamide (EXAMPLE 98)

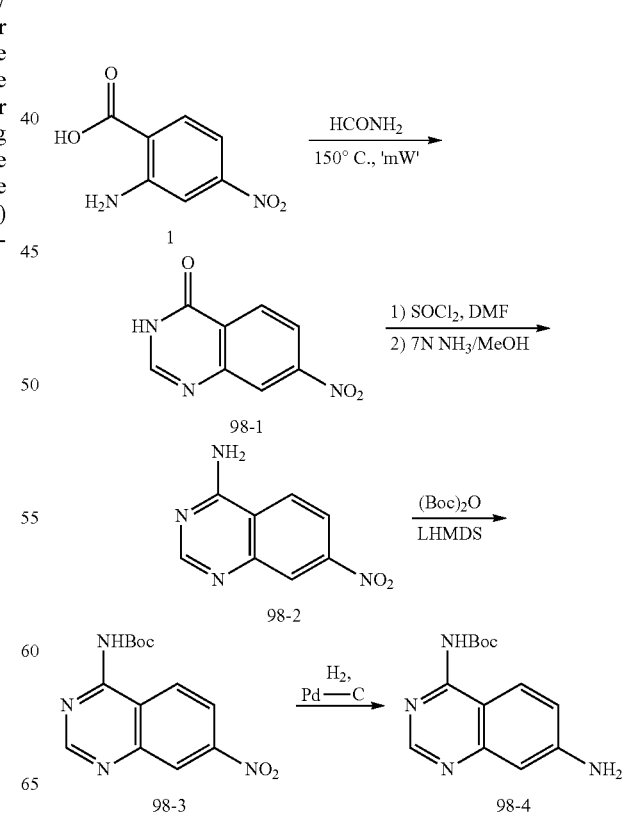

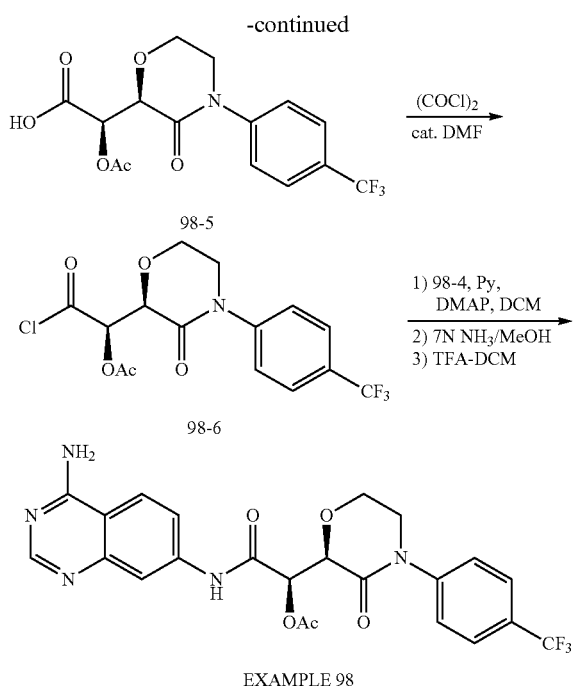

EXAMPLE 98

Step 98-1

Synthesis of 7-Nitroquinazolin-4(3H)-one (Compound 98-1)

A mixture of 2-amino-4-nitrobenzoic acid (5.0 g, 27.5 mmol) and formamide (8.0 ml, 201.5 mmol) in a microwave reaction vessel was heated in a microwave reactor at 150° C. for 1 hr. The slurry was cooled to rt, stirred with aq. NaHCO$_3$, filtered, washed with water followed by ether and dried in vacuum oven to provide 3.7 g of 7-nitroquinazolin-4(3H)-one (Compound 98-1).

Step 98-2

Synthesis of 7-Nitroquinazolin-4-amine (Compound 98-2)

To a solution of 7-nitroquinazolin-4(3H)-one (2.0 g, 10.5 mmol) in 40 ml thionyl chloride was added 0.8 ml of DMF and the mixture was heated at reflux overnight then evaporated to dryness to provide crude 4-chloro-7-nitroquinazoline.
A mixture of 1.6 g of 4-chloro-7-nitroquinazoline in 50 ml 7N ammonia in methanol was stirred overnight at rt and concentrated to dryness. The solid was suspended in water, filtered, rinsed with water followed by ether and dried overnight in vacuum oven to provide 0.98 g of 7-nitroquinazolin-4-amine (Compound 98-2).

Step 98-3

Synthesis of tert-Butyl 7-nitroquinazolin-4-ylcarbamate (Compound 98-3)

To a suspension of 7-nitroquinazolin-4-amine (0.98 g, 5.2 mmol) in 20 ml THF at it was added a 1M solution of di-tert-butyldicarbonate in THF (10.3 ml, 10.3 mmol, 2 eq.) followed by a 1M solution of LHMDS in THF (8.8 mmol, 1.7 eq.). The resultant clear solution was stirred for 10 min. quenched with aq. NH$_4$Cl, extracted 3× with ethyl acetate, the combined organic layers washed with brine, dried over MgSO$_4$, filtered, concentrated and purified by chromatography eluting with 30% ethyl acetate in hexanes to provide 713 mg of tert-butyl 7-nitroquinazolin-4-ylcarbamate (Compound 98-3).

Step 98-4

Synthesis of tert-butyl 7-aminoquinazolin-4-ylcarbamate (Compound 98-4)

A mixture of 600 mg of tert-butyl 7-nitroquinazolin-4-ylcarbamate and 150 mg of 10% Pd—C in 15 ml each of THF and MeOH was stirred overnight under a hydrogen balloon, filtered through a Celite® pad, concentrated and purified by chromatography eluting with 5% methanol in dichloromethane to provide 385 mg of tert-butyl 7-aminoquinazolin-4-ylcarbamate (Compound 98-4). MS m/e=261.1 (MH$^+$)

Step 98-5

Synthesis of Compound 98-5

Compound 98-5 was prepared using a procedure similar to the preparation of compound 93-3.

Step 98-6

Synthesis of (R)-2-chloro-2-oxo-1-((R)-3-oxo-4-(4-(trifluoromethyl)phenyl)morpholin-2-yl)ethyl acetate (Compound 98-6)

To a solution of compound 98-5 (0.30 mmol) in 4 ml of dichloromethane was added oxalylchloride (75 µl, 0.886 mmol, 3 eq.) followed by 1 drop of DMF. Stirred at rt for 1 hr, added toluene and evaporated to dryness to provide crude compound 98-6 which was used as such for the next step.

Step 98-7

Synthesis of N-(4-Amino-7-quinazolinyl)-alpha(R)-hydroxy-3-oxo-4-[4-(trifluoromethyl)phenyl]-2(R)-morpholineacetamide (EXAMPLE 98)

To a solution of compound 98-6 (~0.15 mmol) in 2 ml dichloromethane at 0° C. was added tert-butyl 7-aminoquinazolin-4-ylcarbamate (Compound 98-4) (77 mg, 0.30 mmol, 2 eq.) followed by pyridine (24 µl, 0.30 mmol, 2 eq.) and DMAP (2 mg, 0.016 mmol, 0.1 eq.). To the mixture was added 1 ml of acetonitrile and stirred overnight while warming to rt. It was diluted with ethyl acetate, washed with aq. NaHCO$_3$, water and brine, dried over MgSO$_4$, filtered, concentrated to dryness. The residue was stirred overnight with 5 ml of 7N ammonia in methanol. The methanol was evaporated and the residue was stirred with 2 ml each of dichloromethane and trifluoroacetic acid for about 75 min. The mixture was evaporated to dryness and the residue was purified by RPHPLC to provide 14 mg of EXAMPLE 98.

Example 99

Synthesis of N-[4-(aminomethyl)phenyl]-alpha(R)-hydroxy-3-oxo-4-[4-(trifluoromethyl)phenyl]-2(R)-morpholineacetamide Example (EXAMPLE 99)

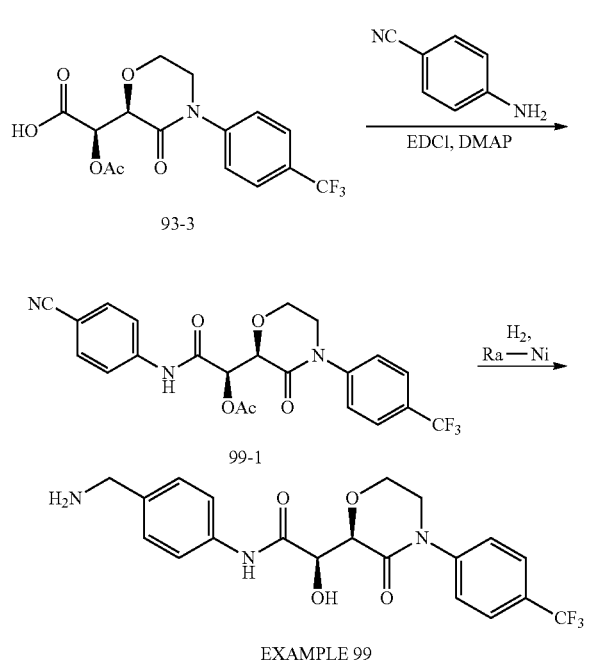

argon for two hours. The reaction mixture was poured onto water and extracted three times with ethyl acetate. The combined extracts were washed with brine, dried with $MgSO_4$, filtered and evaporated to dryness. Purification by flash chromatography yielded 151 mg of compound 99-1.

Step 99-2

Synthesis of N-[4-(aminomethyl)phenyl]-alpha(R)-hydroxy-3-oxo-4-[4-(trifluoromethyl)phenyl]-2(R)-morpholineacetamide (EXAMPLE 99)

To Compound 99-1 in 15 mL of 7M $NH_3$ in MeOH was added excess Raney Ni (an aq. suspension) and the mixture stirred under a balloon of hydrogen for two hours. The mixture was filtered and evaporated to dryness yielding a white solid. Purification by RP-HPLC yielded 34 mg of EXAMPLE 99 as a white solid after conversion to the HCl salt by the addition of 1N HCl in diethyl ether and evaporation to dryness.

Example 100

Synthesis of N-[4-(Aminoiminomethyl)phenyl]-4-[3-(aminomethyl)phenyl]-alpha(R)-hydroxy-3-oxo-2(R)-morpholineacetamide (EXAMPLE 100)

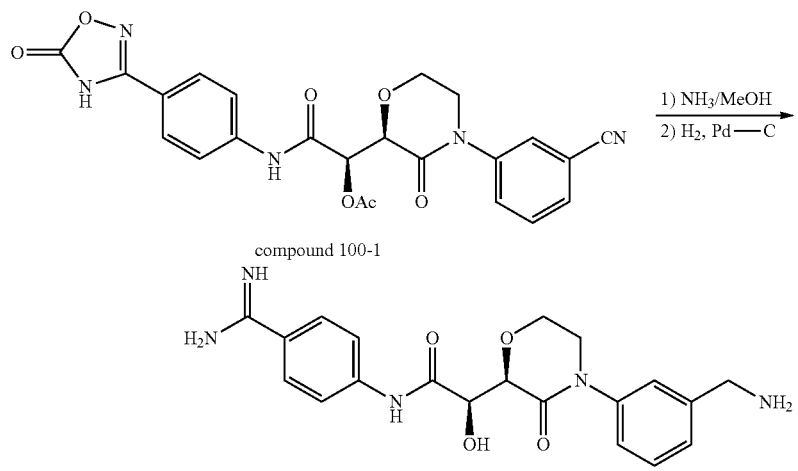

Compound 100-1 was prepared from compound 68-7 using a procedure similar to the preparation of compound 96-1.

To about 30 mL of 7N $NH_3$/MeOH was added 465 mg of compound 100-1 and the mixture was stirred in a flask sealed with a rubber stopper for 1.5 hrs. The mixture was then evaporated to dryness. To the residue in 3 mL of MeOH was added 45 mg of 10% Pd/C and 2 mL of 1N aq. HCl and the suspension stirred under a balloon of $H_2$. After about 3 hours

Step 99-1

Synthesis of (R)-2-acetoxy-2-((R)-3-oxo-4-(4-(trifluoromethyl)phenyl)morpholin-2-yl)acetic acid (Compound 99-1)

To 150 mg of compound 93-3 in 4 ml of dry acetonitrile at 0° C. was added 74 mg of 4-amino benzonitrile, 5 mg of DMAP and 103 mg of EDCI and the mixture stirred under an additional 60 mg of Pd/C was added and after a further 1 hr, the mixture was filtered and evaporated to dryness. Purification by RP-HPLC yielded 118 mg of EXAMPLE 100 as a white solid after conversion to the di-HCl salt by the addition of 1N HCl in diethyl ether and evaporation to dryness.

Example 101

Synthesis of N-[4-(Aminocarbonyl)phenyl]-alpha (R)-hydroxy-3-oxo-4-[4-(trifluoromethyl)phenyl]-2 (R)-morpholineacetamide (EXAMPLE 101)

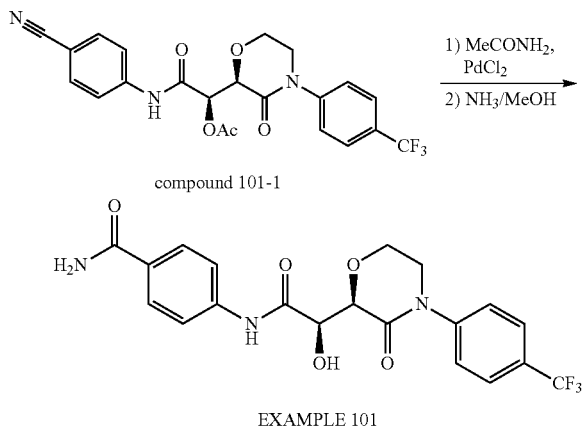

Compound 101-1 was prepared from compound 68-7 using a procedure similar to the preparation of compound 96-1.

To 25 mg of compound 101-1 in 4 ml of THF and 1 ml of $H_2O$ was added 13 mg of acetamide and 1 mg of $PdCl_2$ and the mixture stirred under argon. After 16 hrs, an additional 1 mg of $PdCl_2$ was added and after an additional 16 hrs. the reaction mixture was filtered and evaporated to dryness. To the residue was added 3 ml of 7N $NH_3$/MeOH and the flask sealed with a septa and stirred for 3 hrs. The resulting mixture was partitioned between ethyl acetate and a mixture of DMSO/water/acetonitrile. The combined ethyl acetate phases were evaporated to dryness yielding about 8 mg of EXAMPLE 101.

Example 102

Synthesis of (2R)—N-(4-amidinophenyl)-2-hydroxy-2-[(2R)-4-[3-(2-hydroxyethyl)phenyl]-3-oxomorpholin-2-yl]acetamide hydrochloride (EXAMPLE 102)

Step 102-1

Synthesis of tert-butyl (2R)-2-[(2R)-4-[3-(2-benzyloxyethyl)phenyl]-3-oxomorpholin-2-yl]-2-hydroxyacetate (Compound 102-1)

According to the Step 68-9 in synthetic method for EXAMPLE 68, 1-bromo-3-[2-(benzyloxyethyl)]benzene (0.3 g) was used instead of compound 68-8 to obtain compound 102-1 (234 mg) as colorless oil.

Step 102-2

Synthesis of (2R)-2-[(2R)-4-[3-(2-benzyloxyethyl) phenyl]-3-oxomorpholin-2-yl]-2-hydroxyacetic acid (Compound 102-2)

According to the Step 52-4 in synthetic method for EXAMPLE 52, compound 102-1 (0.13 g) was used instead of 52-3 to obtain compound 102-2 (0.11 g) as colorless oil.

Step 102-3

Synthesis of (2R)-2-[(2R)-4-[3-(2-benzyloxyethyl) phenyl]-3-oxomorpholin-2-yl]-2-hydroxy-N-[4-(5-oxo-4H-1,2,4-oxadiazol-3-yl)phenyl]acetamide (Compound 102-3)

According to the Step 1-3 in synthetic method for EXAMPLE 1, 102-2 (0.11 g) and 3-(4-aminophenyl)-1,2,4-oxadiazol-5(2H)-one (47 mg) with DMF were used instead of 1-2 and 6-Amino-1-bis(tert-butoxylcarbonyl)aminoisoquinoline to obtain compound 102-3 (38 mg) as a yellow amorphous solid.

Step 102-4

Synthesis of (2R)—N-(4-amidinophenyl)-2-hydroxy-2-[(2R)-4-[3-(2-hydroxyethyl)phenyl]-3-oxomorpholin-2-yl]acetamide hydrochloride (EXAMPLE 102)

According to the Step 26-B in synthetic method for EXAMPLE 26, compound 102-3 (30 mg) was used instead of 26-14 to obtain EXAMPLE 102 (26 mg) as a beige amorphous solid.

Example 103

Synthesis of (2R)—N-(4-amidinophenyl)-2-hydroxy-2-[(2R)-3-oxo-4-[5-(trifluoromethyl)-2-pyridyl]morpholin-2-yl]acetamide hydrochloride (EXAMPLE 103)

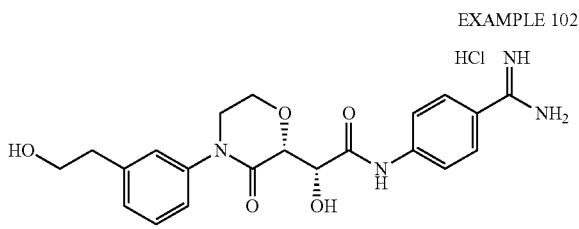 [SMILES: Cl ; N=C(N)c1ccc(NC(=O)[C@H](O)[C@H]2OCCN(c3cccc(CCO)c3)C2=O)cc1]

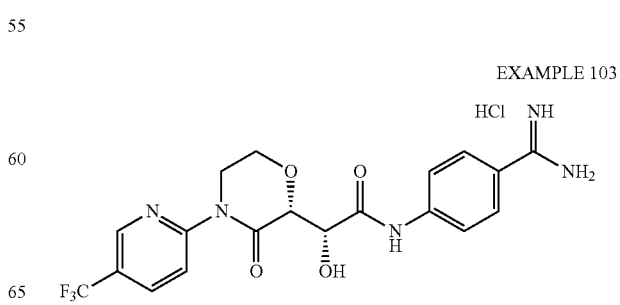

315

Step 103-1

Synthesis of tert-butyl (2R)-2-hydroxy-2-[(2R)-3-oxo-4-[5-(trifluoromethyl)-2-pyridyl]morpholin-2-yl]acetate (Compound 103-1)

According to the Step 68-9 in synthetic method for EXAMPLE 68, 2-iodo-5-trifluoromethylpyridine (0.28 g) was used instead of compound 68-8 to obtain compound 103-1 (105 mg) as a pale yellow amorphous solid.

Step 103-2

Synthesis of (2R)-2-hydroxy-2-[(2R)-3-oxo-4-[5-(trifluoromethyl)-2-pyridyl]morpholin-2-yl]acetic acid (Compound 103-2)

According to the Step 52-4 in synthetic method for EXAMPLE 52, compound 103-1 (98 mg) was used instead of 52-3 to obtain compound 103-2 (76 mg) as colorless oil.

Step 103-3

Synthesis of (2R)-2-hydroxy-N-[4-(5-oxo-4H-1,2,4-oxadiazol-3-yl)phenyl]-2-[(2R)-3-oxo-4-[5-(trifluoromethyl)-2-pyridyl]morpholin-2-yl]acetamide (Compound 103-3)

According to the Step 1-3 in synthetic method for EXAMPLE 1, 103-2 (75 mg) and 3-(4-aminophenyl)-1,2,4-oxadiazol-5(2H)-one (41 mg) were used instead of 1-2 and 6-Amino-1-bis(tert-butoxylcarbonyl)aminoisoquinoline to obtain compound 103-3 (7 mg) as pale red amorphous solid.

Step 103-4

Synthesis of (2R)—N-(4-amidinophenyl)-2-hydroxy-2-[(2R)-3-oxo-4-[5-(trifluoromethyl)-2-pyridyl]morpholin-2-yl]acetamide hydrochloride (EXAMPLE 103)

According to the Step 26-B in synthetic method for EXAMPLE 26, compound 103-3 (6 mg) was used instead of 26-14 to obtain EXAMPLE 103 (6 mg) as a pale yellow amorphous solid.

316

Example 104

Synthesis of (2R)—N-[4-amidinophenyl]-2-hydroxy-2-[(2R)-4-[3-(methylsulfonylmethyl)phenyl]-3-oxomorpholin-2-yl]acetamide hydrochloride (EXAMPLE 104)

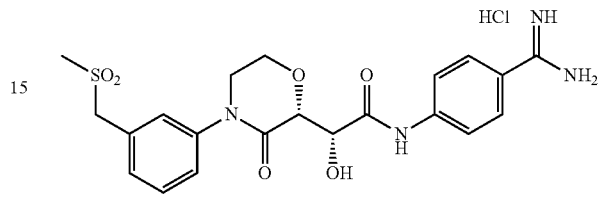

EXAMPLE 104

Step 104-1

Synthesis of tert-butyl (2R)-2-hydroxy-2-[(2R)-4-[3-(methylsulfonylmethyl)phenyl]-3-oxomorpholin-2-yl]acetate (Compound 104-1)

According to the Step 68-9 in synthetic method for EXAMPLE 68, 1-bromo-3-[(methylsulfonyl)methyl]benzene (0.39 g) was used instead of compound 68-8 to obtain compound 104-1 (0.22 g) as a colorless amorphous solid.

Step 104-2

Synthesis of (2R)-2-hydroxy-2-[(2R)-4-[3-(methylsulfonylmethyl)phenyl]-3-oxomorpholin-2-yl]acetic acid (Compound 104-2)

According to the Step 52-4 in synthetic method for EXAMPLE 52, compound 104-1 (0.2 g) was used instead of 52-3 to obtain compound 104-2 (170 mg) as colorless oil.

Step 104-3

Synthesis of (2R)-2-hydroxy-2-[(2R)-4-[3-(methylsulfonylmethyl)phenyl]-3-oxomorpholin-2-yl]-N-[4-(5-oxo-4H-1,2,4-oxadiazol-3-yl)phenyl]acetamide (Compound 104-3)

According to the Step 1-3 in synthetic method for EXAMPLE 1, 104-2 (170 mg) and 3-(4-aminophenyl)-1,2,4-oxadiazol-5(2H)-one (82 mg) with DMF were used instead of 1-2 and 6-Amino-1-bis(tert-butoxylcarbonyl)aminoisoquinoline to obtain compound 104-3 (54 mg) as a pale red amorphous solid.

Step 104-4

Synthesis of (2R)—N-[4-amidinophenyl]-2-hydroxy-2-[(2R)-4-[3-(methylsulfonylmethyl)phenyl]-3-oxomorpholin-2-yl]acetamide hydrochloride (EXAMPLE 104)

According to the Step 26-B in synthetic method for EXAMPLE 26, compound 104-3 (30 mg) was used instead of 26-14 to obtain EXAMPLE 104 (16 mg) as a colorless amorphous solid.

Example 105

Synthesis of (2R)—N-(4-amidinophenyl)-2-hydroxy-2-[(2R)-4-[4-(2-methylsulfonylphenyl)phenyl]-3-oxomorpholin-2-yl]acetamide hydrochloride (EXAMPLE 105)

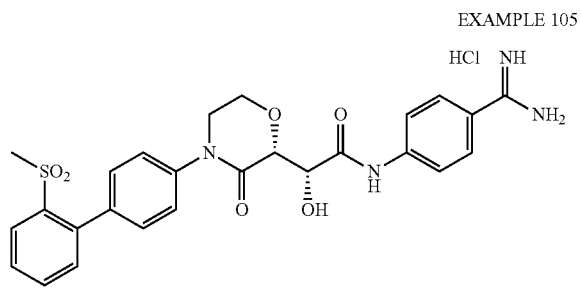 [SMILES: Cl ; CS(=O)(=O)c1ccccc1-c1ccc(N2CCO[C@H]([C@@H](O)C(=O)Nc3ccc(C(=N)N)cc3)C2=O)cc1]

EXAMPLE 105

Step 105-1

Synthesis of tert-butyl (2R)-2-hydroxy-2-[(2R)-4-(4-iodophenyl)-3-oxomorpholin-2-yl]acetate (Compound 105-1)

According to the Step 68-9 in synthetic method for EXAMPLE 68, 1,4-diiodobenzene (74.9 mg) was used instead of compound 68-8 to obtain compound 105-1 (23.1 mg) as a colorless amorphous solid.

Step 105-2

Synthesis of tert-butyl (2R)-2-hydroxy-2-[(2R)-4-[4-(2-methylsulfonylphenyl)phenyl]-3-oxomorpholin-2-yl]acetate (Compound 105-2)

According to the Step 22-1 in synthetic method for EXAMPLE 22, compound 105-1 (0.12 g) and 2-methylsulfonylphenylboronic acid (0.11 g) were used instead of 14-4 and 2-thiopheneboronic acid to obtain compound 105-2 (102 mg) as yellow oil.

Step 105-3

Synthesis of (2R)-2-hydroxy-2-[(2R)-4-[4-(2-methylsulfonylphenyl)phenyl]-3-oxomorpholin-2-yl]acetic acid (Compound 105-3)

According to the Step 52-4 in synthetic method for EXAMPLE 52, compound 105-2 (98 mg) was used instead of 52-3 to obtain compound 105-2 (87.1 mg) as a plane yellow amorphous solid.

Step 105-4

Synthesis of (2R)-2-hydroxy-2-[(2R)-4-[4-(2-methylsulfonylphenyl)phenyl]-3-oxomorpholin-2-yl]-N-[4-(5-oxo-4H-1,2,4-oxadiazol-3-yl)phenyl]acetamide (Compound 105-4)

According to the Step 1-3 in synthetic method for EXAMPLE 1, 105-3 (0.1 g) and 3-(4-aminophenyl)-1,2,4-oxadiazol-5(2H)-one (41 mg) with DMF were used instead of 1-2 and 6-Amino-1-bis(tert-butoxylcarbonyl)aminoisoquinoline to obtain compound 105-4 (52 mg) as a pale yellow amorphous solid.

Step 105-5

Synthesis of (2R)—N-(4-amidinophenyl)-2-hydroxy-2-[(2R)-4-[4-(2-methylsulfonylphenyl)phenyl]-3-oxomorpholin-2-yl]acetamide hydrochloride (EXAMPLE 105)

According to the Step 26-B in synthetic method for EXAMPLE 26, compound 105-4 (20 mg) was used instead of 26-14 to obtain EXAMPLE 105 (15 mg) as a colorless amorphous solid.

Example 106

Synthesis of (2R)—N-(4-amidinophenyl)-2-hydroxy-2-[(2R)-4-[4-[2-(2-hydroxyethyl)phenyl]phenyl]-3-oxomorpholin-2-yl]acetamide hydrochloride (EXAMPLE 106)

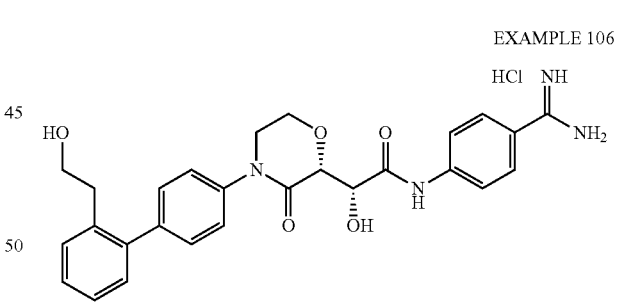

EXAMPLE 106

Step 106-1

Synthesis of (2R)-2-hydroxy-2-[(2R)-4-(4-iodophenyl)-3-oxomorpholin-2-yl]acetic acid (Compound 106-1)

According to the Step 52-4 in synthetic method for EXAMPLE 52, compound 105-1 (0.12 g) was used instead of 52-3 to obtain compound 106-1 (102 mg) as a pale yellow amorphous solid.

Step 106-2

Synthesis of (2R)-2-hydroxy-2-[(2R)-4-(4-iodophenyl)-3-oxomorpholin-2-yl]-N-[4-(5-oxo-4H-1,2,4-oxadiazol-3-yl)phenyl]acetamide (Compound 106-2)

According to the Step 1-3 in synthetic method for EXAMPLE 1, 106-1 (86 mg) and 3-(4-aminophenyl)-1,2,4-oxadiazol-5(2H)-one (38 mg) with DMF were used instead of 1-2 and 6-Amino-1-bis(tert-butoxylcarbonyl)aminoisoquinoline to obtain compound 106-2 (42 mg) as a gray amorphous solid.

Step 106-3

Synthesis of (2R)-2-hydroxy-2-[(2R)-4-[4-[2-(2-hydroxyethyl)phenyl]phenyl]-3-oxomorpholin-2-yl]-N-[4-(5-oxo-4H-1,2,4-oxadiazol-3-yl)phenyl]acetamide (Compound 106-3)

According to the Step 22-1 in synthetic method for EXAMPLE 22, compound 106-2 (30 mg) and [2-[2-[[(1,1-dimethylethyl)dimethylsilyl]oxy]ethyl]phenyl]boronic acid (31.4 mg) were used instead of 14-4 and 2-thiopheneboronic acid to obtain compound 106-3 (10 mg) as a colorless amorphous solid.

Step 106-4

Synthesis of (2R)—N-(4-amidinophenyl)-2-hydroxy-2-[(2R)-4-[4-[2-(2-hydroxyethyl)phenyl]phenyl]-3-oxomorpholin-2-yl]acetamide hydrochloride (EXAMPLE 106)

According to the Step 26-B in synthetic method for EXAMPLE 26, compound 106-3 (28 mg) was used instead of 26-14 to obtain EXAMPLE 106 (1.2 mg) as a colorless amorphous solid.

Example 107

Synthesis of (2R)—N-(4-amidinophenyl)-2-hydroxy-2-[(2R)-3-oxo-4-[3-(1H-pyrazol-4-yl)phenyl]morpholin-2-yl]acetamide dihydrochloride (EXAMPLE 107)

EXAMPLE 107

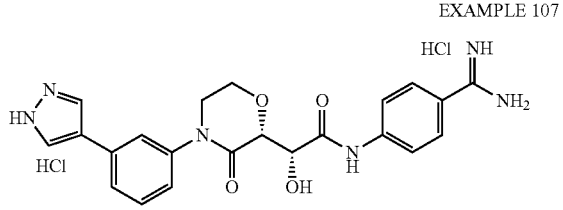 [SMILES: Cl ; N=C(N)c1ccc(NC(=O)[C@H](O)[C@H]2OCCN(c3cccc(-c4cn[nH]c4)c3)C2=O)cc1 ; Cl]

Step 107-1

Synthesis of tert-butyl (2R)-2-hydroxy-2-[(2R)-4-(3-iodophenyl)-3-oxomorpholin-2-yl]acetate (compound 107-1)

According to the Step 68-9 in synthetic method for EXAMPLE 68, 1,3-diiodobenzene (1.5 g) was used instead of compound 68-8 to obtain compound 107-1 (425 mg) as a pale yellow amorphous solid.

Step 107-2

Synthesis of tert-butyl 4-[3-[(2R)-2-[(1R)-2-tert-butoxy-1-hydroxy-2-oxoethyl]-3-oxomorpholin-4-yl]phenyl]pyrazole-1-carboxylate (Compound 107-2)

According to the Step 22-1 in synthetic method for EXAMPLE 22, compound 107-1 (0.2 g) and 3-(4,4,5,5-tetramethyl-1,3,2-dioxaborolan-2-yl)-1H-pyrazole-1-carboxylic acid 1,1-dimethylethyl ester (0.27 g) were used instead of 14-4 and 2-thiopheneboronic acid to obtain compound 107-2 (137 mg) as a pale yellow amorphous solid.

Step 107-3

Synthesis of (2R)-2-hydroxy-2-[(2R)-3-oxo-4-[3-(1H-pyrazol-4-yl)phenyl]morpholin-2-yl]acetic acid hydrochloride (Compound 107-3)

According to the Step 52-4 in synthetic method for EXAMPLE 52, compound 107-2 (0.12 g) was used instead of 52-3 to obtain compound 107-3 (89 mg) as a colorless amorphous solid.

Step 107-4

Synthesis of (2R)-2-hydroxy-N-[4-(5-oxo-4H-1,2,4-oxadiazol-3-yl)phenyl]-2-[(2R)-3-oxo-4-[3-(1H-pyrazol-4-yl)phenyl]morpholin-2-yl]acetamide (Compound 107-4)

According to the Step 77-1 in synthetic method for EXAMPLE 77, compound 107-3 (35 mg) and 5-amino-1,3-dihydro-2H-benzimidazol-2-one (17.5 mg) were used instead of 3-iodobenzoic acid and 4,4-difluoropiperidine to obtain compound 107-4 (7 mg) as a colorless amorphous solid.

Step 107-5

Synthesis of (2R)—N-(4-amidinophenyl)-2-hydroxy-2-[(2R)-3-oxo-4-[3-(1H-pyrazol-4-yl)phenyl]morpholin-2-yl]acetamide dihydrochloride (EXAMPLE 107)

According to the Step 26-B in synthetic method for EXAMPLE 26, compound 107-4 (7 mg) was used instead of 26-14 to obtain EXAMPLE 107 (7 mg) as a pale yellow amorphous solid.

Example 108

Synthesis of N-(1-amino-6-isoquinolyl)-2-hydroxy-2-[2-oxo-1-(p-tolyl)-3-piperidyl]acetamide Trifluoroacetate (EXAMPLE 108)

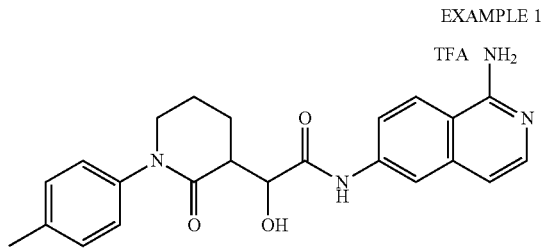

EXAMPLE 108

Step 108-1

Synthesis of ethyl 2-hydroxy-2-[2-oxo-1-(p-tolyl)-3-piperidyl]acetate (Compound 108-1)

According to the Step 1-1 in synthetic method for EXAMPLE 1, 1-(4-methylphenyl)-2-piperidinone (4 g) was used instead of 4-(4-methylphenyl)-3-morpholinone to obtain compound 108-1 (0.5 g) as a colorless amorphous solid.

Step 108-2

Synthesis of 2-hydroxy-2-[2-oxo-1-(p-tolyl)-3-piperidyl]acetic acid (Compound 108-2)

According to the Step 1-2 in synthetic method for EXAMPLE 1, compound 108-1 (0.5 g) was used instead of 1-1 (LP) to obtain compound 108-2 (0.1 g) as a colorless amorphous solid.

Step 108-3

Synthesis of tert-butyl N-tert-butoxycarbonyl-N-[6-[[2-hydroxy-2-[2-oxo-1-(p-tolyl)-3-piperidyl]acetyl]amino]-1-isoquinolyl]carbamate (Compound 108-3)

To a solution of 108-2 (0.1 g), Diisopropylethylamine (0.2 mL), HOAt (77.5 mg), 2-Chloro-1,3-dimethylimidazolidinium hexafluorophosphate (158 mg), was added 6-Amino-1-bis(tert-butoxylcarbonyl)aminoisoquinoline (164 mg) at room temperature.

The reaction mixture was stirred at room temperature for 6 hours. To the mixture, was added sat.NaHCO3 aq. and the mixture was extracted with EtOAc. The organic layer was washed with water and brine, dried with anhydr.Na2SO4. The solvent was removed under reduced pressure and the resulting residue was purified by silica gel flash column chromatography (eluent: Hex-EtOAc=1-1~1-2~1-4) to obtain compound 108-3 (53.4 mg) as a colorless amorphous solid.

Step 108-4

Synthesis of N-(1-amino-6-isoquinolyl)-2-hydroxy-2-[2-oxo-1-(p-tolyl)-3-piperidyl]acetamide Trifluoroacetate (EXAMPLE 108)

According to the Step 1-4 in synthetic method for EXAMPLE 1, compound 108-3 (34.8 mg) was used instead of 1-3 to obtain EXAMPLE 108 (17.8 mg) as a colorless amorphous solid.

Example 109

Synthesis of 2-[1-acetyl-3-oxo-4-(p-tolyl)piperazin-2-yl]-N-(1-amino-6-isoquinolyl)-2-hydroxy-acetamide Trifluoroacetate (EXAMPLE 109)

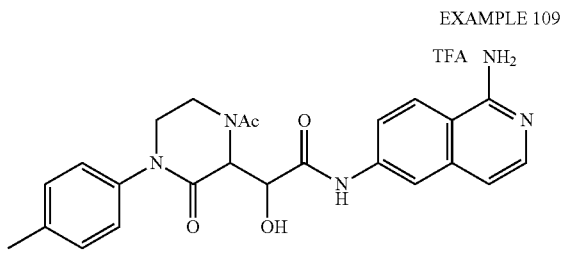

EXAMPLE 109

Step 109-1

Synthesis of Benzyl 2-(2-ethoxy-1-hydroxy-2-oxo-ethyl)-3-oxo-4-(p-tolyl)piperazine-1-carboxylate (Compound 109-1)

According to the Step 1-1 in synthetic method for EXAMPLE 1, 4-(4-methylphenyl)-3-oxopiperazine-1-carboxylic acid benzyl ester (2.3 g) was used instead of 4-(4-methylphenyl)-3-morpholinone to obtain compound 109-1 (2.2 g) as diastereomeric mixture.

Step 109-2

Synthesis of ethyl 2-hydroxy-2-[3-oxo-4-(p-tolyl)piperazin-2-yl]acetate (Compound 109-2)

According to the Step 33-1 in synthetic method for EXAMPLE 33, compound 109-1 (0.3 g) with EtOH was used instead of EXAMPLE 32 to obtain compound 109-2 (0.2 g) as a pale yellow amorphous solid.

Step 109-3

Synthesis of ethyl 2-[1-acetyl-3-oxo-4-(p-tolyl)piperazin-2-yl]-2-hydroxyacetate (Compound 109-3)

According to the Step 26-6 in synthetic method for EXAMPLE 26, compound 109-2 (0.2 g) was used instead of 26-5 to obtain compound 109-3 (0.11 g) as a colorless amorphous solid.

Step 109-4

Synthesis of 2-[1-acetyl-3-oxo-4-(p-tolyl)piperazin-2-yl]-2-hydroxyacetic acid lithium salt (Compound 109-4)

According to the Step 1-2 in synthetic method for EXAMPLE 1, compound 109-3 (0.11 g) and LiOH—H2O (13.8 mg) were used instead of 1-1 (LP) and NaOH to obtain compound 109-4 (90 mg) as a beige amorphous solid.

Step 109-5

Synthesis of tert-butyl N-[6-[[2-[1-acetyl-3-oxo-4-(p-tolyl)piperazin-2-yl]-2-hydroxyacetyl]amino]-1-isoquinolyl]-N-tert-butoxycarbonylcarbamate (Compound 109-5)

According to the Step 108-3 in synthetic method for EXAMPLE 108, compound 109-4 (90 mg) was used instead of 108-2 to obtain compound 109-5 (14.9 mg) as a pale yellow amorphous solid.

Step 109-6

Synthesis of 2-[1-acetyl-3-oxo-4-(p-tolyl)piperazin-2-yl]-N-(1-amino-6-isoquinolyl)-2-hydroxy-acetamide Trifluoroacetate (EXAMPLE 109)

According to the Step 1-4 in synthetic method for EXAMPLE 1, compound 109-5 (14.9 mg) was used instead of 1-3 to obtain EXAMPLE 109 (12.9 mg) as a beige amorphous solid.

Example 110

Synthesis of N-(1-amino-6-isoquinolyl)-2-[1-formyl-3-oxo-4-(p-tolyl)piperazin-2-yl]-2-hydroxyacetamide Trifluoroacetate (EXAMPLE 110)

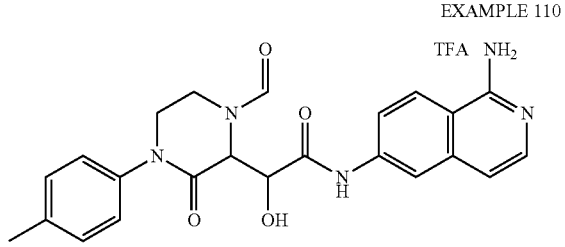 [SMILES: Cc1ccc(N2CCN(C=O)C(C(O)C(=O)Nc3ccc4c(N)nccc4c3)C2=O)cc1 ; "TFA"]

EXAMPLE 110

Step 110-1

Synthesis of ethyl 2-[1-formyl-3-oxo-4-(p-tolyl)piperazin-2-yl]-2-hydroxyacetate (Compound 110-1)

To a solution of 109-2 (0.3 g) in EtOH (10 mL), were added 4-(4,6-dimethoxy-1,3,5-triazin-2-yl)-4-methylmorpholinium chloride (426 mg) and formic acid (0.05 mL) at room temperature. The reaction mixture was stirred at room temperature for 3 hours. After the reaction, water was added into the reaction mixture. Then the mixture was extracted with EtOAc. The organic layer was washed with water, sat. NaHCO3 aq., and brine, then dried with anhyd. Na2SO4. The solvent was removed under reduced pressure to obtain 110-1 (0.14 g) as diastereomeric mixture. 110-1 was used in the next step without further purification.

Step 110-2

Synthesis of 2-[1-formyl-3-oxo-4-(p-tolyl)piperazin-2-yl]-2-hydroxyacetic acid lithium salt (Compound 110-2)

According to the Step 1-2 in synthetic method for EXAMPLE 1, compound 110-1 (0.14 g) and LiOH—H2O (18 mg) were used instead of 1-1 (LP) and NaOH to obtain compound 110-2 (0.12 g) as a colorless amorphous solid.

Step 110-3

Synthesis of tert-butyl N-tert-butoxycarbonyl-N-[6-[[2-[1-formyl-3-oxo-4-(p-tolyl)piperazin-2-yl]-2-hydroxyacetyl]amino]-1-isoquinolyl]carbamate (Compound 110-3)

According to the Step 108-3 in synthetic method for EXAMPLE 108, compound 110-2 (0.12 g) was used instead of 108-2 to obtain compound 110-3 (6.2 mg) as a colorless amorphous solid.

Step 110-4

Synthesis of N-(1-amino-6-isoquinolyl)-2-[1-formyl-3-oxo-4-(p-tolyl)piperazin-2-yl]-2-hydroxyacetamide Trifluoroacetate (EXAMPLE 110)

According to the Step 1-4 in synthetic method for EXAMPLE 1, compound 110-3 (6.2 mg) was used instead of 1-3 to obtain EXAMPLE 110 (3.8 mg) as a pale brawn amorphous solid.

Example 111

Synthesis of N-(1-amino-6-isoquinolyl)-2-[1-benzoyl-3-oxo-4-(p-tolyl)piperazin-2-yl]-2-hydroxyacetamide Trifluoroacetate (EXAMPLE 111)

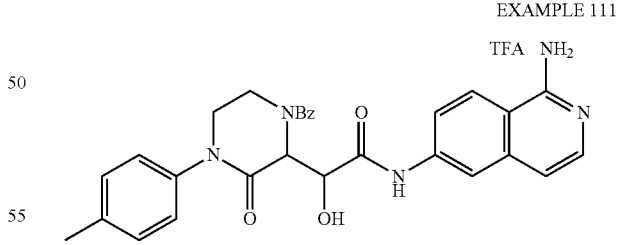

EXAMPLE 111

Step 111-1

Synthesis of ethyl 2-[1-benzoyl-3-oxo-4-(p-tolyl)piperazin-2-yl]-2-hydroxyacetate (Compound 111-1)

According to the Step 110-1 in synthetic method for EXAMPLE 110, benzoic acid (87 mg) was used instead of formic acid to obtain compound 111-1 (128 mg) as a beige amorphous solid.

Step 111-2

Synthesis of 2-[1-benzoyl-3-oxo-4-(p-tolyl)piperazin-2-yl]-2-hydroxyacetic acid (compound 111-2)

According to the Step 1-2 in synthetic method for EXAMPLE 1, compound 111-1 (128 mg) and LiOH—H2O (14.5 mg) were used instead of 1-1 (LP) and NaOH to obtain compound 111-2 (100 mg) as a beige amorphous solid.

Step 111-3

Synthesis of tert-butyl N-[6-[[2-[1-benzoyl-3-oxo-4-(p-tolyl)piperazin-2-yl]-2-hydroxyacetyl]amino]-1-isoquinolyl]-N-tert-butoxycarbonylcarbamate (compound 111-3)

According to the Step 1-3 in synthetic method for EXAMPLE 1, compound III-2 (80 mg) was used instead of 1-2 to obtain compound 111-3 (7 mg) as a pale yellow amorphous solid.

Step 111-4

Synthesis of N-(1-amino-6-isoquinolyl)-2-[1-benzoyl-3-oxo-4-(p-tolyl)piperazin-2-yl]-2-hydroxyacetamide Trifluoroacetate (EXAMPLE 111)

According to the Step 1-4 in synthetic method for EXAMPLE 1, compound III-3 (7 mg) was used instead of 1-3 to obtain EXAMPLE 111 (1.7 mg) as a beige amorphous solid.

Example 112

Synthesis of N-(4-amidinophenyl)-2-hydroxy-2-[3-oxo-4-(p-tolyl)thiomorpholin-2-yl]acetamide Acetate (EXAMPLE 112)

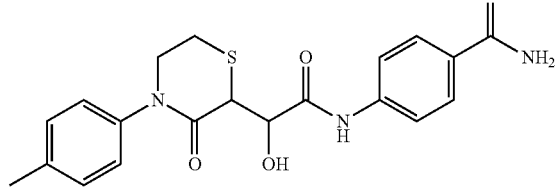

EXAMPLE 112

Step 112-1

Synthesis of ethyl 2-hydroxy-2-[3-oxo-4-(p-tolyl)thiomorpholin-2-yl]acetate (Compound 112-1)

According to the Step 1-1 in synthetic method for EXAMPLE 1, 4-(4-Methylphenyl)-thiomorpholin-3-one (3 g) was used instead of 4-(4-Methylphenyl)-3-morpholinone to obtain compound 112-1 (2 g) as a pale yellow amorphous solid.

Step 112-2

Synthesis of 2-hydroxy-2-[3-oxo-4-(p-tolyl)thiomorpholin-2-yl]acetic acid (Compound 112-2)

According to the Step 1-2 in synthetic method for EXAMPLE 1, compound 112-1 (0.88 g) was used instead of 1-1 (LP) to obtain compound 112-2 (0.59 g) as a pale yellow amorphous solid.

Step 112-3

Synthesis of 2-hydroxy-N-[4-(5-oxo-4H-1,2,4-oxadiazol-3-yl)phenyl]-2-[3-oxo-4-(p-tolyl)thiomorpholin-2-yl]acetamide (Compound 112-3)

According to the Step 77-1 in synthetic method for EXAMPLE 77, compound 112-2 (0.55 g) and 3-(4-aminophenyl)-1,2,4-oxadiazol-5(2H)-one (0.52 g) were used instead of 3-iodobenzoic acid and 4,4-difluoropiperidine to obtain compound 112-3 (0.52 g) as a pale yellow amorphous solid.

Step 112-4

Synthesis of N-(4-amidinophenyl)-2-hydroxy-2-[3-oxo-4-(p-tolyl)thiomorpholin-2-yl]acetamide Acetate (EXAMPLE 112)

To a solution of 112-3 (30 mg) in AcOH (1.5 mL), was added zinc powder (0.22 g) at room temperature. The reaction mixture was stirred at 80° C. for 3 hours. After the reaction, the mixture was filtered through Celite® pad to remove zinc powder. The filtrate was concentrated in vacuo to obtain EXAMPLE 112 (4.2 mg) as a pale brawn amorphous solid.

Example 113

Synthesis of N-(4-amidinophenyl)-2-hydroxy-2-[1,1,3-trioxo-4-(p-tolyl)-1,4-thiazinan-2-yl]acetamide Hydrochloride (EXAMPLE 113)

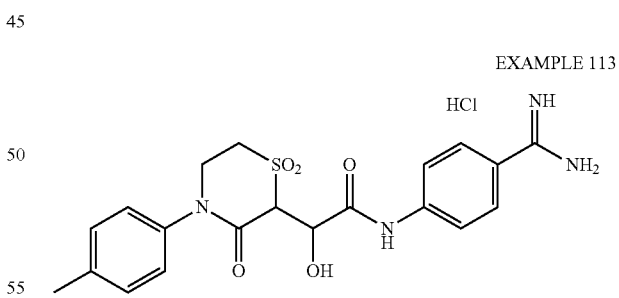

EXAMPLE 113

Step 113-1

Synthesis of 2-hydroxy-N-[4-(5-oxo-4H-1,2,4-oxadiazol-3-yl)phenyl]-2-[1,1,3-trioxo-4-(p-tolyl)-1,4-thiazinan-2-yl]acetamide (Compound 113-1)

To a solution of 112-3 (5 mg) in MeOH—H2O (1-0.5 mL), was added oxone (27.9 mg) at 0° C. The reaction mixture was stirred at room temperature overnight. Then water was added into the reaction to precipitate. The precipitate was collected by filtration and was dried to obtain 113-1 (4 mg) as a pale amorphous solid.

Step 113-2

Synthesis of N-(4-amidinophenyl)-2-hydroxy-2-[1,1,3-trioxo-4-(p-tolyl)-1,4-thiazinan-2-yl]acetamide Hydrochloride (EXAMPLE 113)

According to the Step 26-B in synthetic method for EXAMPLE 26, compound 113-1 (25 mg) was used instead of 26-14 to obtain EXAMPLE 113 (15.8 mg) as a pale green amorphous solid.

Example 114

Synthesis of (2R)—N-(4-amidinophenyl)-2-hydroxy-2-[(2R)-3-oxo-4-(p-tolyl)-1,4-oxazepan-2-yl]acetamide Hydrochloride (EXAMPLE 114)

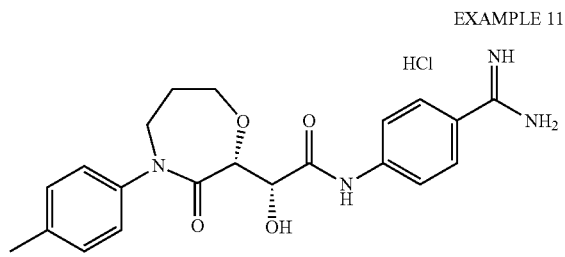

EXAMPLE 114

Step 114-1

Synthesis of (2R,3R)-2,3-diacetoxy-4-[N-(3-chloropropyl)-4-methylanilino]-4-oxobutanoic acid (Compound 114-1)

According to the Step 26-9 in synthetic method for EXAMPLE 26, N-(3-chloropropyl)-4-methylaniline (1.85 g) was used instead of 26-1 to obtain compound 114-1 (4.46 g) as a colorless amorphous solid.

Step 114-2

Synthesis of [(2R,3R)-3-acetyloxy-4-[N-(3-chloropropyl)-4-methylanilino]-1,4-dioxo-1-[4-(5-oxo-4H-1,2,4-oxadiazol-3-yl)anilino]butan-2-yl]acetate (Compound 114-2)

According to the Step 26-10 in synthetic method for EXAMPLE 26, 114-1 (3 g) was used instead of 26-9 to obtain compound 114-2 (1.17 g) as a pale pink amorphous solid.

Step 114-3

Synthesis of (2R,3R)—N-(3-chloropropyl)-2,3-dihydroxy-N'-[4-(5-oxo-4H-1,2,4-oxadiazol-3-yl)phenyl]-N-(p-tolyl)butanediamide ammonium salt (Compound 114-3)

According to the Step 7-4 in synthetic method for EXAMPLE 7, 114-2 (0.6 g) was used instead of 7-3 to obtain compound 114-3 (0.54 g) as a yellow amorphous solid.

Step 114-4

Synthesis of (2R)-2-hydroxy-N-[4-(5-oxo-4H-1,2,4-oxadiazol-3-yl)phenyl]-2-[(2R)-3-oxo-4-(p-tolyl)-1,4-oxazepan-2-yl]acetamide (Compound 114-4)

According to the Step 7-5 in synthetic method for EXAMPLE 7, 114-3 (0.2 g) was used instead of 7-4 to obtain compound 114-4 (40 mg) as a pale red amorphous solid.

Step 114-5

Synthesis of (2R)—N-(4-amidinophenyl)-2-hydroxy-2-[(2R)-3-oxo-4-(p-tolyl)-1,4-oxazepan-2-yl]acetamide Hydrochloride (EXAMPLE 114)

According to the Step 26-B in synthetic method for EXAMPLE 26, compound 114-4 (20 mg) was used instead of 26-14 to obtain EXAMPLE 114 (20 mg) as a yellow amorphous solid.

Example 115

Synthesis of N-(4-amidinophenyl)-2-hydroxy-2-[4-(4-methylbenzoyl)morpholin-2-yl]acetamide Hydrochloride (EXAMPLE 115)

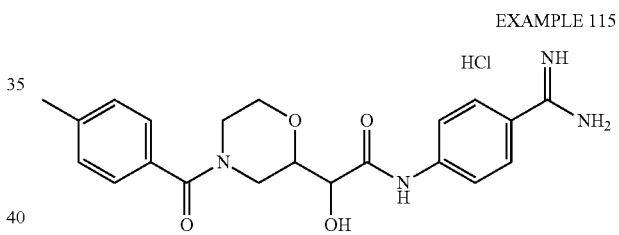

EXAMPLE 115

Step 115-1

Synthesis of 2-(4-benzylmorpholin-2-yl)-2-hydroxyacetonitrile (Compound 115-1)

To a solution of 4-(phenylmethyl)-2-morpholinecarboxaldehyde (78 mg) in MeOH (1.4 mL), was added TMSCN (0.073 mL) at room temperature. The reaction mixture was stirred at room temperature overnight. The mixture was concentrated in vacuo to obtain 115-1 (83 mg) as diastereomeric mixture.

Step 115-2

Synthesis of ethyl 2-(4-benzylmorpholin-2-yl)-2-hydroxyacetate hydrochloride (Compound 115-2)

To a solution of 115-1 (0.68 g) in HCl-EtOH (20 mL), was added conc. HCl (10 mL) at room temperature. The reaction mixture was refluxed for 2.5 hours. Then the mixture was concentrated in vacuo to obtain 115-2 (0.94 g) as a pale yellow amorphous solid.

Step 115-3

Synthesis of ethyl 2-hydroxy-2-morpholin-2-ylacetate hydrochloride (Compound 115-3)

According to the Step 33-1 in synthetic method for EXAMPLE 33, compound 115-2 (0.9 g) with EtOH was used instead of EXAMPLE 32 to obtain compound 115-3 (0.65 g) as pale yellow amorphous solid.

Step 115-4 ethyl 2-hydroxy-2-[4-(4-methylbenzoyl)morpholin-2-yl]acetate (Compound 115-4)

According to the Step 28-1 in synthetic method for EXAMPLE 28, compound 115-3 (0.2 g) and 4-methylbenzoyl chloride (164 mg) were used instead of 26-5 and mesyl chloride to obtain compound 115-4 (85 mg) as a pale yellow amorphous solid.

Step 115-5

2-hydroxy-2-[4-(4-methylbenzoyl)morpholin-2-yl]acetic acid (Compound 115-5)

According to the Step 1-2 in synthetic method for EXAMPLE 1, compound 115-4 (82.7 mg) was used instead of 1-1 (LP) to obtain compound 115-5 (87.5 mg) as a colorless amorphous solid.

Step 115-6

Synthesis of 2-hydroxy-2-[4-(4-methylbenzoyl)morpholin-2-yl]-N-[4-(5-oxo-4H-1,2,4-oxadiazol-3-yl)phenyl]acetamide (Compound 115-6)

According to the Step 77-1 in synthetic method for EXAMPLE 77, compound 115-5 (74 mg) and 3-(4-aminophenyl)-1,2,4-oxadiazol-5(2H)-one (70.4 mg) were used instead of 3-iodobenzoic acid and 4,4-difluoropiperidine to obtain compound 115-6 (75.1 mg) as a pale yellow amorphous solid.

Step 115-7

Synthesis of N-(4-amidinophenyl)-2-hydroxy-2-[4-(4-methylbenzoyl)morpholin-2-yl]acetamide Hydrochloride (EXAMPLE 115)

According to the Step 26-B in synthetic method for EXAMPLE 26, compound 115-6 (20 mg) was used instead of 26-14 to obtain EXAMPLE 115 (11.2 mg) as a brown amorphous solid.

Example 116

Synthesis of N-(4-amidinophenyl)-2-hydroxy-2-[4-(p-tolylsulfonyl)morpholin-2-yl]acetamide Hydrochloride (EXAMPLE 116)

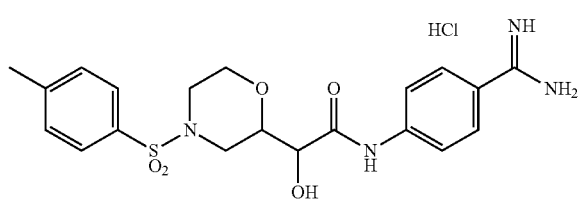

EXAMPLE 116

Step 116-1 ethyl 2-hydroxy-2-[4-(p-tolylsulfonyl)morpholin-2-yl]acetate (Compound 116-1)

According to the Step 28-1 in synthetic method for EXAMPLE 28, compound 115-3 (0.2 g) and tosylchloride (203 mg) were used instead of 26-5 and mesyl chloride to obtain compound 116-1 (108 mg) as a pale yellow amorphous solid.

Step 116-2

Synthesis of 2-hydroxy-2-[4-(p-tolylsulfonyl)morpholin-2-yl]acetic acid (Compound 116-2)

According to the Step 1-2 in synthetic method for EXAMPLE 1, compound 116-1 (108 mg) was used instead of 1-1 (LP) to obtain compound 116-2 (101 mg) as a colorless amorphous solid.

Step 116-3

Synthesis of 2-hydroxy-N-[4-(5-oxo-4H-1,2,4-oxadiazol-3-yl)phenyl]-2-[4-(p-tolylsulfonyl)morpholin-2-yl]acetamide (Compound 116-3)

According to the Step 77-1 in synthetic method for EXAMPLE 77, compound 116-2 (94 mg) and 3-(4-aminophenyl)-1,2,4-oxadiazol-5(2H)-one (79.2 mg) were used instead of 3-iodobenzoic acid and 4,4-difluoropiperidine to obtain compound 116-3 (83 mg) as a pale yellow amorphous solid.

Step 116-4

Synthesis of N-(4-amidinophenyl)-2-hydroxy-2-[4-(p-tolylsulfonyl)morpholin-2-yl]acetamide Hydrochloride (EXAMPLE 116)

According to the Step 26-B in synthetic method for EXAMPLE 26, compound 116-3 (20 mg) was used instead of 26-14 to obtain EXAMPLE 116 (16.7 mg) as a pale yellow amorphous solid.

Example 117

Synthesis of N-(1-amino-6-isoquinolyl)-2-hydroxy-2-[4-(p-tolyl)morpholin-2-yl]acetamide Ditrifluoroacetate (EXAMPLE 117)

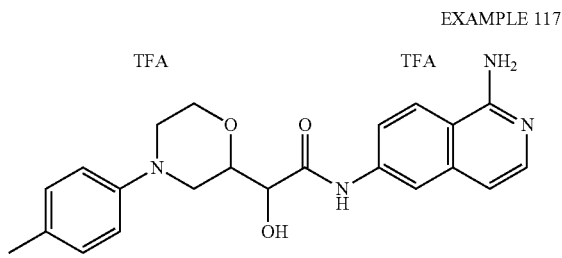 [SMILES: Cc1ccc(N2CCOC(C(O)C(=O)Nc3ccc4c(N)nccc4c3)C2)cc1]

Step 117-1

Synthesis of ethyl 2-hydroxy-2-[4-(p-tolyl)morpholin-2-yl]acetate (Compound 117-1)

According to the Step 20-2 in synthetic method for EXAMPLE 20, compound 1-1 (LP) (0.2 g) was used instead of 20-1 to obtain compound 117-1 (0.2 g) as a pale yellow amorphous solid.

Step 117-2

Synthesis of 2-hydroxy-2-[4-(p-tolyl)morpholin-2-yl]acetic acid lithium salt (Compound 117-2)

According to the Step 1-2 in synthetic method for EXAMPLE 1, compound 117-1 (45 mg) and LiOH—H2O (6.8 mg) were used instead of 1-1 (LP) and NaOH to obtain compound 117-2 (41 mg) as a pale yellow amorphous solid.

Step 117-3

Synthesis of tert-butyl N-tert-butoxycarbonyl-N-[6-[[2-hydroxy-2-[4-(p-tolyl)morpholin-2-yl]acetyl]amino]-1-isoquinolyl]carbamate (Compound 117-3)

According to the Step 1-3 in synthetic method for EXAMPLE 1, compound 117-2 (30 mg) was used instead of 1-2 to obtain compound 117-3 (4 mg) as a pale yellow amorphous solid.

Step 117-4

Synthesis of N-(1-amino-6-isoquinolyl)-2-hydroxy-2-[4-(p-tolyl)morpholin-2-yl]acetamide Ditrifluoroacetate (EXAMPLE 117)

According to the Step 1-4 in synthetic method for EXAMPLE 1, compound 117-3 (3.1 mg) was used instead of 1-3 to obtain EXAMPLE 117 (3.7 mg) as a colorless amorphous solid.

Example 118

Synthesis of (R)—N-(4-Carbamimidoylphenyl)-2-hydroxy-2-((R)-3-oxo-4-(3-(trifluoromethoxy)phenyl)morpholin-2-yl)acetamide hydrochloride (EXAMPLE 118)

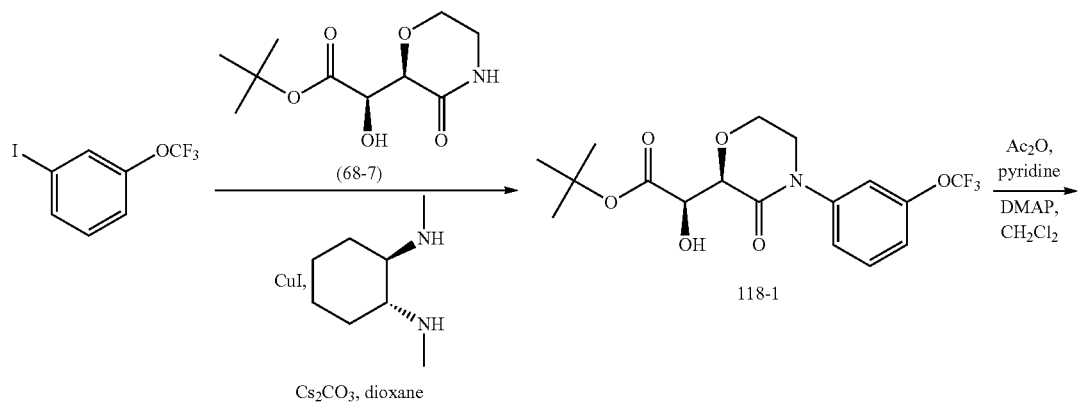

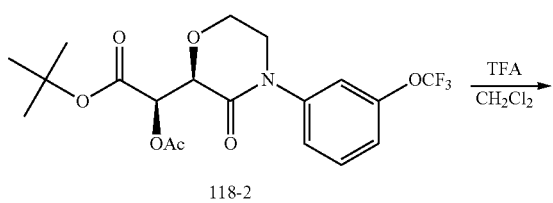

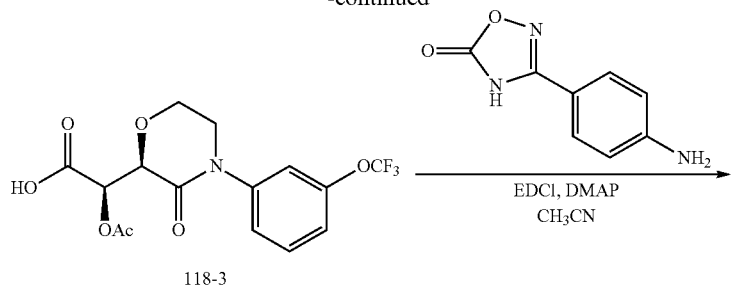

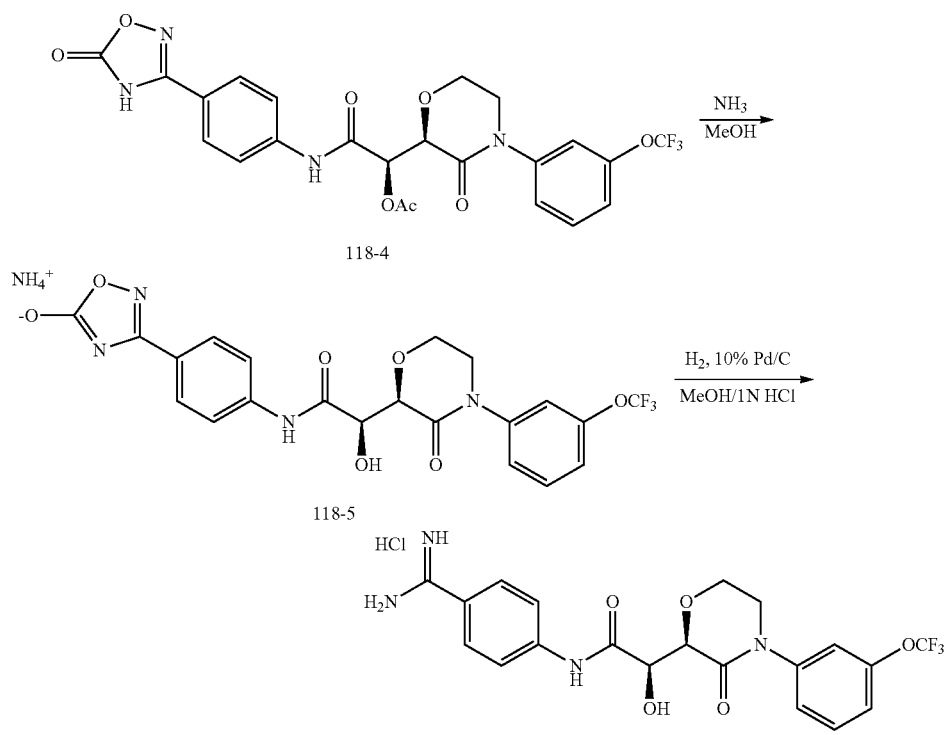

EXAMPLE 118 purified by flash chromatography using a 95% CH₂Cl₂/5% MeOH mixture to afford 118-1 (0.21 g) as a white solid.

Step 118-1

(R)-tert-Butyl 2-hydroxy-2-((R)-3-oxo-4-(3-(trifluoromethoxy)phenyl)morpholin-2-yl)acetate (Compound 118-1)

To a round bottom flask charged with a stir bar was added morpholinone (0.15 g) (68-7) and 3-trifluoromethoxyiodobenzene (0.12 mL) in dioxane (4 mL) at rt was added Cs₂CO₃ (0.42 g), and CuI (37 mg) under N₂. trans-N,N'-Dimethylcyclohexane-1,2-diamine (31 microL) was added dropwise and the mixture was affixed with a condenser. The mixture was degassed under vacuum (~20 mm), filled with N₂, and heated to 90° C. The mixture stirred for 3 h at 90° C., cooled to rt, and was diluted with conc NH₄OH and water, EtOAc. The mixture was extracted with EtOAc three times and the organic layers were combined. The organic layer was washed with brine, dried (Na₂SO₄), filtered, and concentrated under reduced pressure to afford a yellow oil. The crude product was Step 118-2

Synthesis of (R)-tert-butyl 2-acetoxy-2-((R)-3-oxo-4-(3-(trifluoromethoxy)phenyl)morpholin-2-yl)acetate (Compound 118-2)

To a solution of 118-1 (0.21 g) in CH₂Cl₂ (2.5 ml) at 0° C. was added pyridine (63 microL), Ac₂O (74 microl), and DMAP (5 mg). The mixture was stirred for 1 hour at 0° C., warmed to rt, and stirred for an additional 12 h. The mixture was diluted with EtOAc and the organic layer was washed sequentially with sat. aq. CuSO₄ solution, water, and brine. The organic layer was dried (Na₂SO₄), filtered, and concentrated under reduced pressure to afford 118-2 (0.22 g) as a light yellow semisolid. This material was used without further purification.

Step 118-3

Synthesis of (R)-2-acetoxy-2-((R)-3-oxo-4-(3-(trifluoromethoxy)phenyl)morpholin-2-yl)acetic acid (Compound 118-3)

To a solution of 118-2 (0.22 g) in CH$_2$Cl$_2$ (2 mL) at 0° C. was added TFA (0.6 mL) dropwise. The mixture was stirred for 1 h at 0° C. and at rt for 30 min whereupon an additional portion of TFA (0.4 mL) was added. After an additional 1 h at rt, the mixture was diluted with CH$_2$Cl$_2$ and concentrated to dryness under reduced pressure. The crude mixture was redissolved in a 10:1 mixture of toluene/CH$_2$Cl$_2$ and concentrated and this protocol was repeated 5 times with to afford 118-3 (0.18 g) as a light yellow solid. This material was used without further purification.

Step 118-4

Synthesis of (R)-2-oxo-2-(4-(5-oxo-4,5-dihydro-1,2,4-oxadiazol-3-yl)phenylamino)-1-((R)-3-oxo-4-(3-(trifluoromethoxy)phenyl)morpholin-2-yl)ethyl acetate (Compound 118-4)

To a solution of 118-3 (80 mg) n CH$_3$CN (1.5 mL) at 0° C. was added 4-(5-oxo-4,5-dihydro-[1,2,4]oxadiazol-3-yl)-phenyl amide (50 mg) followed by EDCI (53 mg) and DMAP (3 mg). The reaction mixture was warmed to rt and stirred for 2.5 h. The mixture was concentrated under reduced pressure and placed under high vacuum. The crude material was purified by reverse phase HPLC using a C18 column and a gradient of (89.95:9.95:0.1H$_2$O:MeCN:HCO$_2$H to 9.95:89.95:0.1H$_2$O:MeCN:HCO$_2$H) to afford 118-4 (37 mg) as a white solid.

Step 118-5

Ammonium 3-(4-((R)-2-hydroxy-2-((R)-3-oxo-4-(3-(trifluoromethoxy)phenyl)morpholin-2-yl)acetamido)phenyl)-1,2,4-oxadiazol-5-olate (Compound 118-5)

To a solution of the 118-4 (27 mg) in MeOH (1.5 mL) at 0° C. was added 7M NH$_3$/MeOH (0.5 mL) dropwise. The mixture was stirred for 1 h at 0° C. and an additional hour at rt. The mixture was concentrated under reduced pressure and placed under high vacuum to afford 118-5 (25 mg) as a white solid. This material was used without further purification.

Step 118-6

Synthesis of (R)—N-(4-Carbamimidoylphenyl)-2-hydroxy-2-((R)-3-oxo-4-(3-(trifluoromethoxy)phenyl)morpholin-2-yl)acetamide hydrochloride (EXAMPLE 118)

To a solution of the 118-5 (25 mg) in a mixture of MeOH/1N HCl (1.5 mL/1.5 mL) was added 10% Pd/C (15 mg). The mixture was stirred under a H$_2$ balloon for 3 h and was filtered thru a pad of Celite. The Celite pad was washed with MeOH and the resultant filtrate was concentrated under reduced pressure. The crude residue was treated with MeOH followed by dilution with Et$_2$O and the resultant solid was collected by filtration and dried under vacuum to afford Example 118 (24 mg) as a maize crystalline solid.

Example 119

Synthesis of (R)—N-(4-Carbamimidoylphenyl)-2-hydroxy-2-((R)-4-(2-methyl-1-oxoisoindolin-5-yl)-3-oxomorpholin-2-yl)acetamide hydrochloride (EXAMPLE 119)

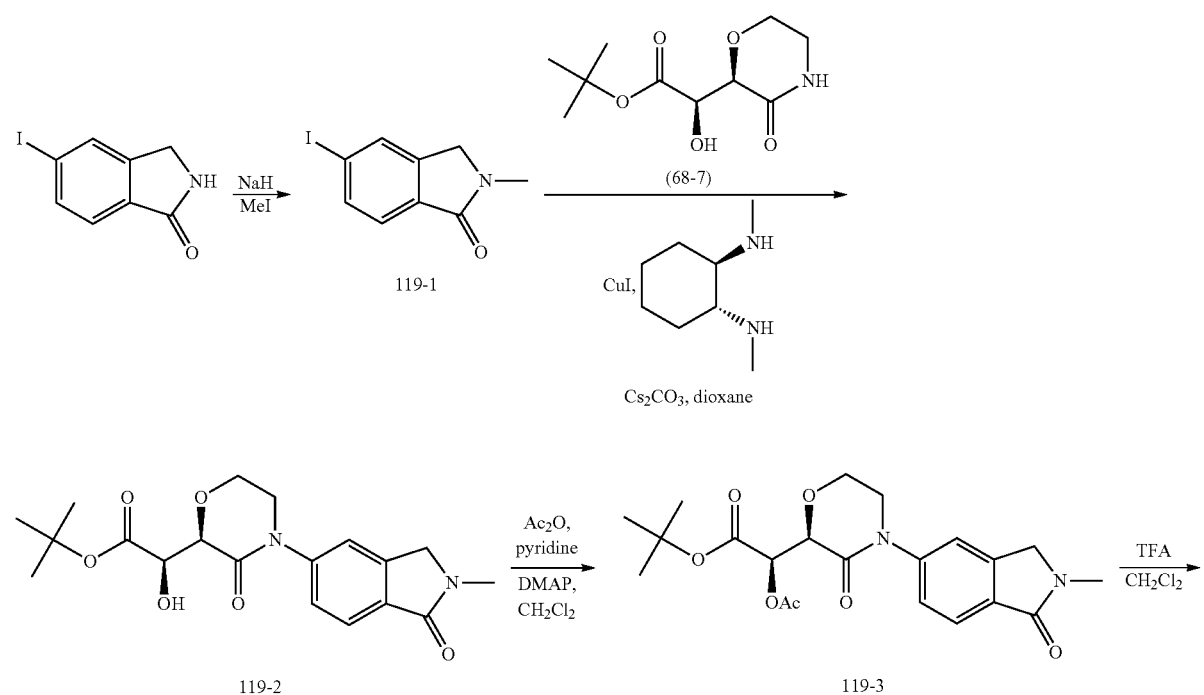

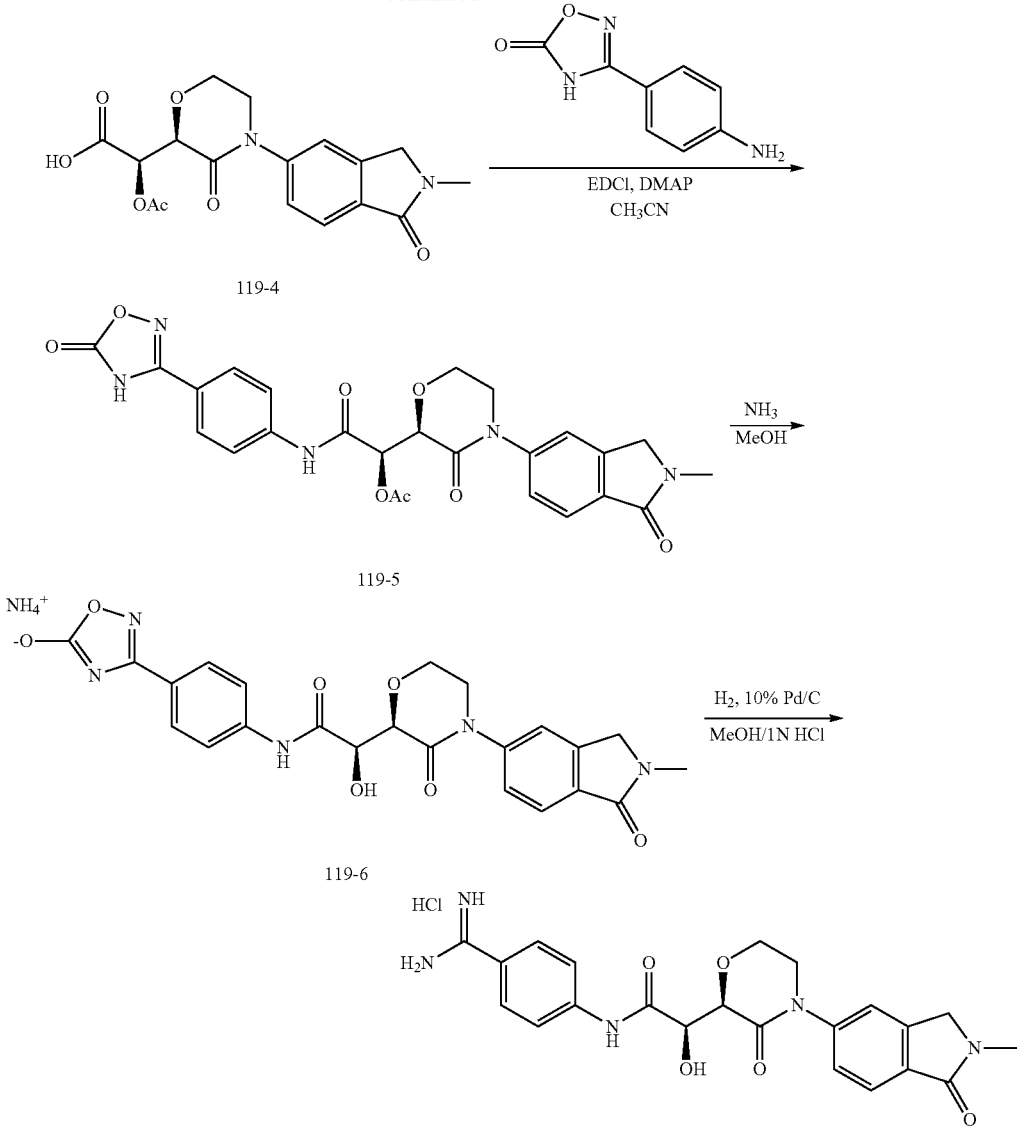

EXAMPLE 119

Step 119-1

Synthesis of 5-Iodo-2-methylisoindolin-1-one (Compound 119-1)

To a mixture of 2,3-dihydro-5-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. NH₄Cl (~3 mL) and was diluted with EtOAc (10 mL). The layers were separated and the aqueous layer was extracted with EtOAc. The organic layers were combined and washed sequentially with water and brine. The organic layer was dried (Na₂SO₄), filtered, and concentrated under reduced pressure. The crude material was purified The crude product was purified by flash chromatography (ISCO, 120 g) using a gradient of 100% hexanes to 80:20 hexanes/EtOAc to afford 119-1 (0.78 g) as a light yellow solid.

Step 119-2

Synthesis of (R)-tert-Butyl 2-hydroxy-2-((R)-4-(2-methyl-1-oxoisoindolin-5-yl)-3-oxomorpholin-2-yl)acetate (Compound 119-2)

According to the Step 118-1 in the synthetic method for EXAMPLE 118, compound 119-1 (0.20 g) was used instead of 3-trifluoromethoxy iodobenzene 118-1 to obtain 119-2 (0.29 g) as an off-white solid.

Step 119-3

Synthesis of (R)-tert-butyl 2-acetoxy-2-((R)-4-(2-methyl-1-oxoisoindolin-5-yl)-3-oxomorpholin-2-yl)acetate (Compound 119-3)

According to the Step 118-2 in the synthetic method for EXAMPLE 118, compound 119-2 (0.29 g) was used instead of 118-1 to obtain 119-3 (0.31 g) as an off-white solid which was used without further purification.

Step 119-4

Synthesis of (R)-2-acetoxy-2-((R)-4-(2-methyl-1-oxoisoindolin-5-yl)-3-oxomorpholin-2-yl)acetic acid (Compound 119-4)

According to the Step 118-3 in the synthetic method for EXAMPLE 118, compound 119-3 (0.31 g) was used instead of 118-2 to obtain 119-4 (0.27 g) as a white solid which was used without further purification.

Step 119-5

Synthesis of (R)-1)-4-(2-Methyl-1-oxoisoindolin-5-yl)-3-oxomorpholin-2-yl)-2-oxo-2-(4-(5-oxo-4,5-dihydro-1,2,4-oxadiazol-3-yl)phenylamino)ethyl acetate (Compound 119-5)

According to the Step 118-4 in the synthetic method for EXAMPLE 118, compound 119-4 (0.10 g) was used instead of 118-3 to obtain 119-5 (0.11 g) as an off-white solid which was purified by flash chromatography using 15:1 $CH_2Cl_2$/MeOH as eluent.

Step 119-6

Synthesis of Ammonium 3-(4-((R)-2-hydroxy-2-((R)-4-(2-methyl-1-oxoisoindolin-5-yl)-3-oxomorpholin-2-yl)acetamido)phenyl)-1,2,4-oxadiazol-5-olate (Compound 119-6)

According to the Step 118-5 in the synthetic method for EXAMPLE 118, compound 119-6 (0.11 g) was used instead of 118-4 to obtain 119-6 (95 mg) as a white solid which was used without further purification.

Step 119-7

Synthesis of (R)—N-(4-Carbamimidoylphenyl)-2-hydroxy-2-((R)-4-(2-methyl-1-oxoisoindolin-5-yl)-3-oxomorpholin-2-yl)acetamide hydrochloride (EXAMPLE 119)

According to the Step 118-6 in the synthetic method for EXAMPLE 118, compound 119-5 (0.11 g) was used instead of 118-5 to obtain EXAMPLE 119 (95 mg) as a white solid which was used without further purification.

Example 120

Synthesis of (R)—N-(4-(Aminomethyl)phenyl)-2-hydroxy-2-((R)-4-(2-methyl-1-oxoisoindolin-5-yl)-3-oxomorpholin-2-yl)acetamide hydrochloride (EXAMPLE 120)

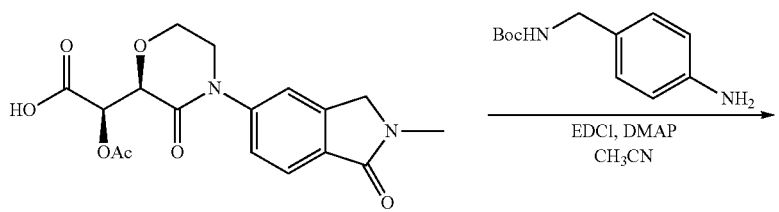

119-4

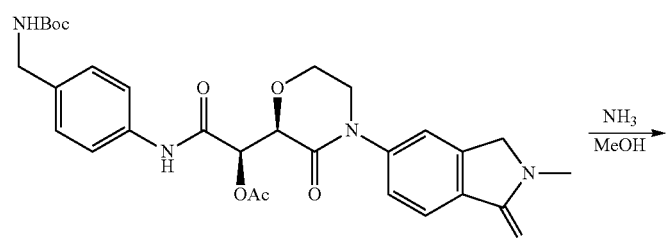

120-1

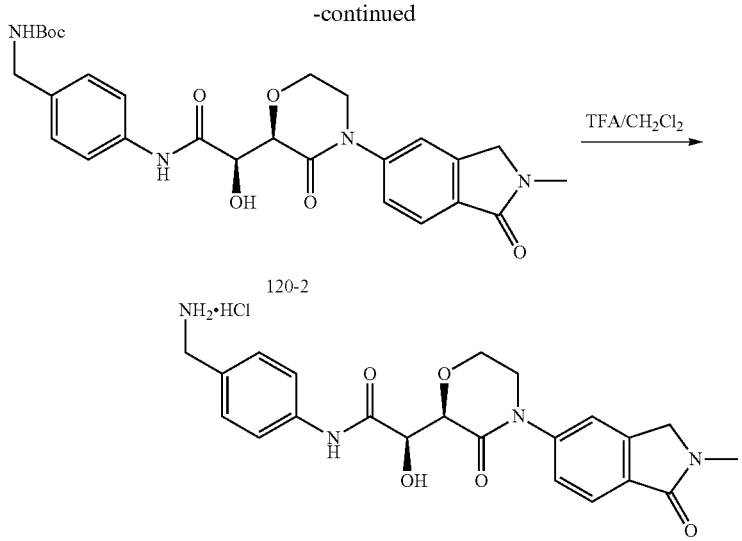

120-2

EXAMPLE 120

Step 120-1

Synthesis of (R)-2-(4-((tert-Butoxycarbonylamino)methyl)phenylamino)-1)-4-(2-methyl-1-oxoisoindolin-5-yl)-3-oxomorpholin-2-yl)-2-oxoethyl acetate (Compound 120-1)

According to the Step 118-4 in the synthetic method for EXAMPLE 118, 119-4 (0.10 g) was treated with tert-butyl 4-aminobenzylcarbamate (80 mg) to afford 120-1 (0.10 g) as yellow semisolid after reverse phase HPLC purification using a C18 column and a gradient of 89.95:9.95:0.1$H_2O$:MeCN:$HCO_2H$ to 9.95:89.95:0.1$H_2O$:MeCN:$HCO_2H$.

Step 120-2

Synthesis of tert-Butyl 4-((R)-2-hydroxy-2-((R)-4-(2-methyl-1-oxoisoindolin-5-yl)-3-oxomorpholin-2-yl)acetamido)benzylcarbamate (Compound 120-2)

According to the Step 118-5 in the synthetic method for EXAMPLE 118, 120-1 (0.10 g) was used instead of compound 118-4 to obtain 120-2 (90 mg) as a white solid. Crude 120-2 was used without further purification in the next step.

Step 120-3

Synthesis of (R)—N-(4-(Aminomethyl)phenyl)-2-hydroxy-2-((R)-4-(2-methyl-1-oxoisoindolin-5-yl)-3-oxomorpholin-2-yl)acetamide hydrochloride (EXAMPLE 120)

To round bottom flask charged with the 120-2 (90 mg) at rt in $CH_2Cl_2$ (1.5 mL) was added TFA (0.5 mL). The resulting solution was stirred for 3 h, concentrated under reduced pressure, and placed under high vacuum. The crude product was dissolved in MeOH and diluted with 1M HCl in $Et_2O$ and the resultant solid was collected and dried to afford EXAMPLE 120 (66 mg) at the hydrochloride salt as an off-white solid.

Example 121

Synthesis of (R)—N-(4-(Aminomethyl)phenyl)-2-hydroxy-2-((R)-3-oxo-4-(3-(3-oxomorpholino)phenyl)morpholin-2-yl)acetamide hydrochloride (EXAMPLE 121)

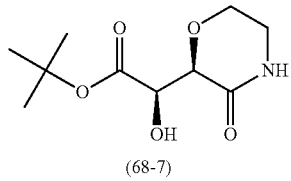

(68-7)

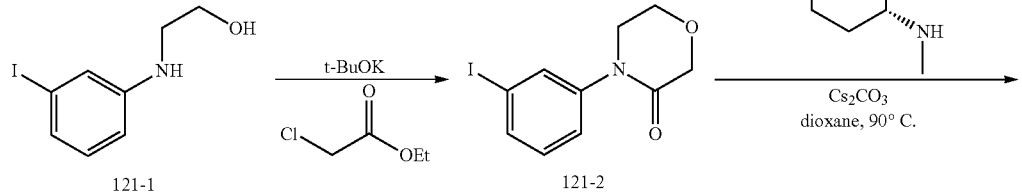

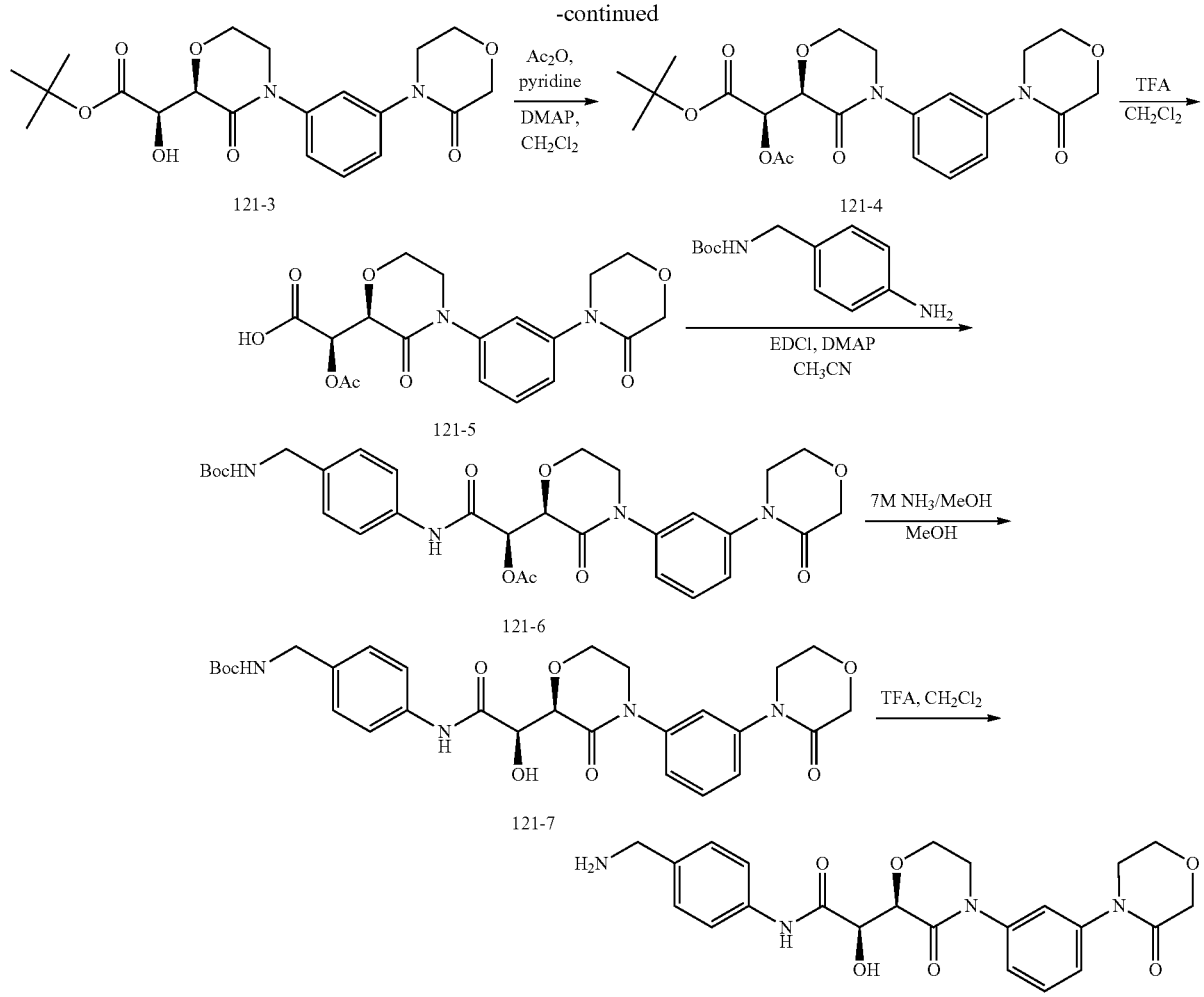

Step 121-2

Synthesis of 4-(3-Iodophenyl)morpholin-3-one (Compound 121-2)

To a solution of t-BuOK (1.3 g) in THF (15 mL) at rt was added 2-(3-iodophenylamino) ethanol 121-1 (3.0 g) prepared from US 2004/0167188 followed by ethyl chloroacetate (1.1 mL). The resulting mixture was stirred for 12 h at rt whereupon an additional portion of t-BuOK (0.6 g) and ethyl chloroacetate (0.5 mL) was added. The mixture was heated to 55° C., stirred for 12 h, and was cooled to rt. The mixture was treated with sat. aq NaHCO$_3$ and water and was extracted with EtOAc. The organic layers were combined, dried (Na$_2$SO$_4$), filtered, and concentrated under reduced pressure. The crude material was purified by flash chromatography using a gradient of 100% hexanes to 20% hexanes/80% EtOAc to afford 121-2 (1.5 g) of the title compound as a light yellow solid.

Step 121-3

Synthesis of (R)-tert-butyl 2-hydroxy-2-((R)-3-oxo-4-(3-(3-oxomorpholino)phenyl)morpholin-2-yl)acetate (Compound 121-3)

According to the Step 118-1 in the synthetic method for EXAMPLE 118, compound 121-2 (0.72 g) was used in the presence of 68-7 (0.50 g) to obtain 121-3 (0.65 g) as yellow crystalline solid after flash chromatography using a 20:1 mixture of CH$_2$Cl$_2$/MeOH.

Step 121-4

Synthesis of (R)-tert-butyl 2-acetoxy-2-((R)-3-oxo-4-(3-(3-oxomorpholino)phenyl)morpholin-2-yl)acetate (Compound 121-4)

According to the Step 118-2 in the synthetic method for EXAMPLE 118, compound 121-3 (0.65 g) was used instead of 118-1 to obtain 121-4 (0.72 g) as an off-white solid which was used without further purification.

Step 121-5

Synthesis of (R)-2-acetoxy-2-((R)-3-oxo-4-(3-(3-oxomorpholino)phenyl)morpholin-2-yl)acetic acid (Compound 121-5)

According to the Step 118-3 in the synthetic method for EXAMPLE 118, compound 121-4 (0.72 g) was used instead of 118-2 to obtain 121-5 (0.60 g) as a light yellow solid which was used without further purification.

Step 121-6

Synthesis of (R)-2-(4-((tert-butoxycarbonylamino)methyl)phenylamino)-2-oxo-1-((R)-3-oxo-4-(3-(3-oxomorpholino)phenyl)morpholin-2-yl)ethyl acetate (Compound 121-6)

According to the Step 118-4 in the synthetic method for EXAMPLE 118, 121-5 (70 mg) was treated with tert-butyl 4-aminobenzylcarbamate (60 mg) to afford 121-6 (45 mg) as an off-white solid after flash chromatography using a 20:1 mixture of $CH_2Cl_2$/MeOH as eluent.

Step 121-7

Synthesis of tert-Butyl 4-((R)-2-hydroxy-2-((R)-3-oxo-4-(3-(3-oxomorpholino)phenyl)morpholin-2-yl)acetamido)benzylcarbamate (Compound 121-7)

According to the Step 118-5 in the synthetic method for EXAMPLE 118, 121-6 (45 mg) was used instead of compound 118-4 to obtain 121-7 (43 mg) as a white solid. Crude 121-7 was used without further purification in the next step.

Step 121-8

Synthesis of (R)—N-(4-(Aminomethyl)phenyl)-2-hydroxy-2-((R)-3-oxo-4-(3-(3-oxomorpholino)phenyl)morpholin-2-yl)acetamide hydrochloride (EXAMPLE 121)

According to the Step 120-3 in the synthetic method for EXAMPLE 120, 121-7 (45 mg) was used instead of compound 120-2 to obtain EXAMPLE 121 (35 mg) as a pale yellow solid after treatment with HCl.

Example 122

Synthesis of (R)—N-(1-Aminoisoquinolin-6-yl)-2-hydroxy-2-((R)-3-oxo-4-(3-(3-oxomorpholino)phenyl)morpholin-2-yl)acetamide hydrochloride (EXAMPLE 122)

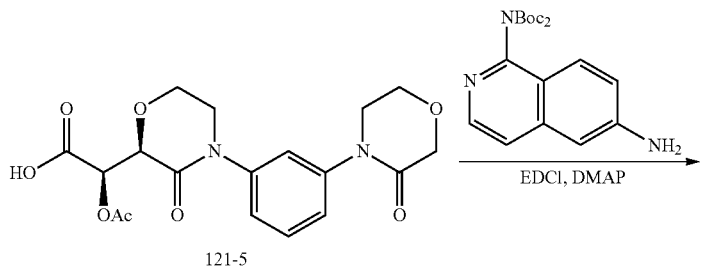

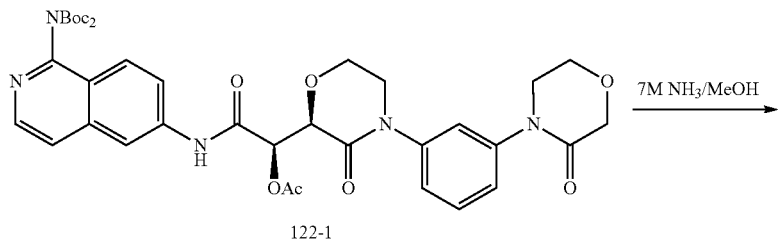

-continued

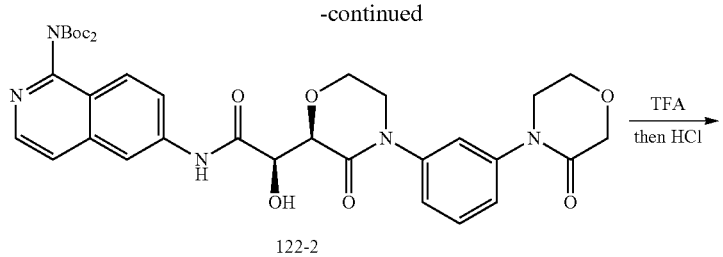

122-2

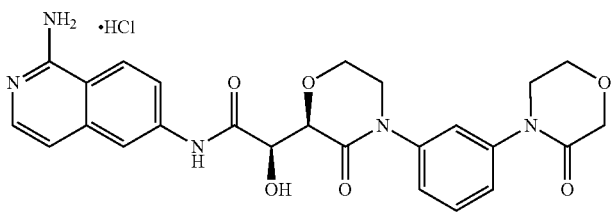

EXAMPLE 122

Step 122-1

Synthesis of (R)-2-(1-(Bis(tert-butoxycarbonyl) amino)isoquinolin-6-ylamino)-2-oxo-1-((R)-3-oxo-4-(3-(3-oxomorpholino)phenyl)morpholin-2-yl)ethyl acetate (Compound 122-1)

According to the Step 118-4 in the synthetic method for EXAMPLE 118, compound 121-5 (0.25 g) was treated with di-tert-butyl (6-aminoisoquinolin-1-yl)imidocarbonate (0.30 g) from WO 2006/062972 to obtain 122-1 (0.17 g) as a yellow semisolid after reverse-phase purification using a C18 column and a gradient of 89.95:9.95:0.1$H_2O$:MeCN:$HCO_2H$ to 9.95:89.95:0.1$H_2O$:MeCN:$HCO_2H$.

Step 122-2

Synthesis of (R)—N-(1-(Bis(tert-butoxycarbonyl) aminoisoquinolin-6-yl)-2-hydroxy-2-((R)-3-oxo-4-(3-(3-oxomorpholino)phenyl)morpholin-2-yl)acetamide (Compound 122-2)

According to the Step 118-5 in the synthetic method for EXAMPLE 118, 122-1 (0.17 g) was used instead of compound 118-4 to obtain 122-2 (0.10 g) as an off-white semisolid after reverse-phase purification using a C18 column and a gradient of 89.95:9.95:0.1$H_2O$:MeCN:$HCO_2H$ to 9.95:89.95:0.1$H_2O$:MeCN:$HCO_2H$.

Step 122-3

Synthesis of (R)—N-(1-Aminoisoquinolin-6-yl)-2-hydroxy-2-((R)-3-oxo-4-(3-(3-oxomorpholino) phenyl) morpholin-2-yl)acetamide hydrochloride (EXAMPLE 122)

To a solution of 122-2 (0.10 g) in $CH_2Cl_2$ (2 mL) at 0° C. was added TFA (0.5 mL) dropwise. The mixture was stirred for 1 h at 0° C., warmed to rt, and stirred for an additional 12 h. The mixture was diluted with $CH_2Cl_2$ and concentrated to dryness and this protocol was repeated 5 times. The crude mixture was purified by reverse phase HPLC using a C18 column and a gradient of 89.95:9.95:0.1$H_2O$:MeCN:$HCO_2H$ to 9.95:89.95:0.1$H_2O$:MeCN:$HCO_2H$ to afford EXAMPLE 122 (50 mg) as a white solid as the hydrochloride salt upon treatment with HCl.

Example 123

Synthesis of (R)—N-(4-Carbamimidoyl-3-chlorophenyl)-2-hydroxy-2-((R)-3-oxo-4-(3-(3-oxomorpholino)phenyl)morpholin-2-yl)acetamide hydrochloride (EXAMPLE 123)

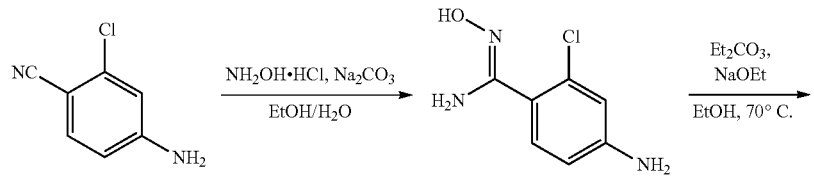

123-1

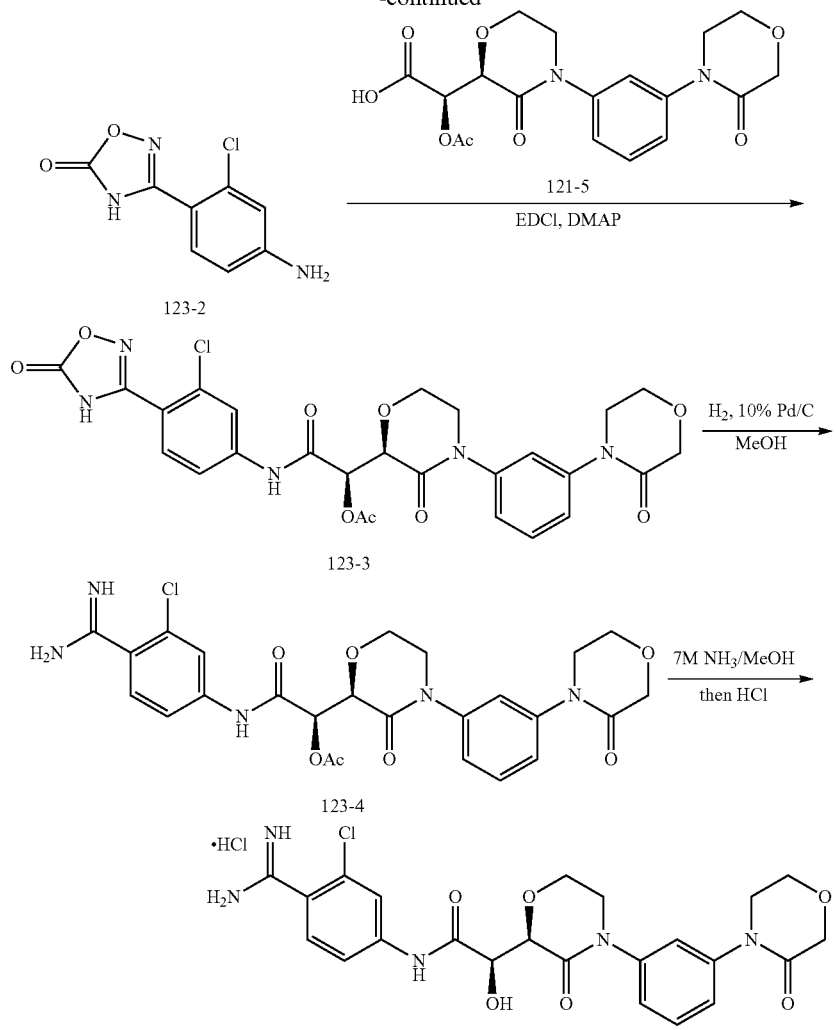

EXAMPLE 123

Step 123-1

Synthesis of 4-Amino-2-chloro-N'-hydroxybenzimidamide (Compound 123-1)

To a solution of 2-chloro-4-aminobenzonitrile (5 g) in EtOH/H₂O (22 mL/4 mL) was added Na₂CO₃ (2.3 g) and NH₂OH.HCl (2.5 g). The mixture was stirred for 8 h at 60° C. where upon an additional portion of both Na₂CO₃ (2.3 g) and NH₂OH.HCl (2.5 g) were added and continued heating at 60° C. for 72 h. The mixture was cooled to rt, filtered, and the resultant precipitate was washed with water, EtOH, and Et₂O. The crude precipitate was dried under vacuum to afford 123-1 (4.3 g) as a pale white solid which was used without further purification.

Step 123-2

Synthesis of 3-(4-Amino-2-chlorophenyl)-1,2,4-oxadiazol-5(4H)-one (Compound 123-2)

To a solution of 123-1 (2.0 g) in EtOH (10 mL) at rt was added diethyl carbonate (1.3 mL) and the mixture was heated to 65° C. A 21% wt NaOEt soln (7.31 mL) was added dropwise to the solution which was then heated to 70° C. and stirred for 2 h. The mixture was cooled to rt, concentrated to dryness, and dissolved in a minimum amount of water. Concentrated HCl was added dropwise until pH ~2 and the resultant precipitate was filtered. The precipitate was washed sequentially with water, EtOH, and Et₂O to afford 123-2 (1.7 g) as a brown solid. This material was used without further purification.

Step 123-3

Synthesis of (R)-2-(3-Chloro-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl) ethyl acetate (Compound 123-3)

According to the Step 118-4 in the synthetic method for EXAMPLE 118, compound 121-5 (0.20 g) was used instead of 118-3 to couple with 123-2 (0.13 g) to obtain 123-3 (60 mg) as an off-white solid which was purified by flash chromatography using a CH₂Cl₂/MeOH mixture.

Step 123-4

Synthesis of (R)-2-(4-Carbamimidoyl-3-chlorophenylamino)-2-oxo-1-((R)-3-oxo-4-(3-(3-oxomorpholino)phenyl)morpholin-2-yl)ethyl acetate (Compound 123-4)

To a solution of 123-3 (25 mg) in MeOH (2.5 mL) at rt was added 10% Pd/C (6 mg). The mixture was stirred under a H₂ balloon for 4.5 h whereupon the mixture was filtered thru a pad of Celite and the filtrate was concentrated under reduced pressure. The crude material was purified by reverse phase HPLC using a C18 column and a gradient of 89.95:9.95:0.1H₂O:MeCN:HCO₂H to 9.95:89.95:0.1H₂O:MeCN:HCO₂H to afford 123-4 (8 mg) as an off-white solid.

Step 123-5

Synthesis of (R)—N-(4-carbamimidoyl-3-chlorophenyl)-2-hydroxy-2-((R)-3-oxo-4-(3-(3-oxomorpholino)phenyl)morpholin-2-yl)acetamide hydrochloride (EXAMPLE 123)

To a solution of 123-4 (8 mg) in MeOH (1 mL) at rt was added 7M NH₃ in MeOH (0.3 mL). The mixture was stirred for 3 h at rt and was concentrated under reduced pressure. The crude material was taken up in MeOH and diluted with 1 M HCl/Et₂O to afford EXAMPLE 123 (1.3 mg) as a pale yellow solid.

Example 124

Synthesis of (R)—N-(4-Carbamimidoyl-3-methylphenyl)-2-hydroxy-2-((R)-3-oxo-4-(3-(3-oxomorpholino)phenyl)morpholin-2-yl)acetamide hydrochloride (EXAMPLE 124)

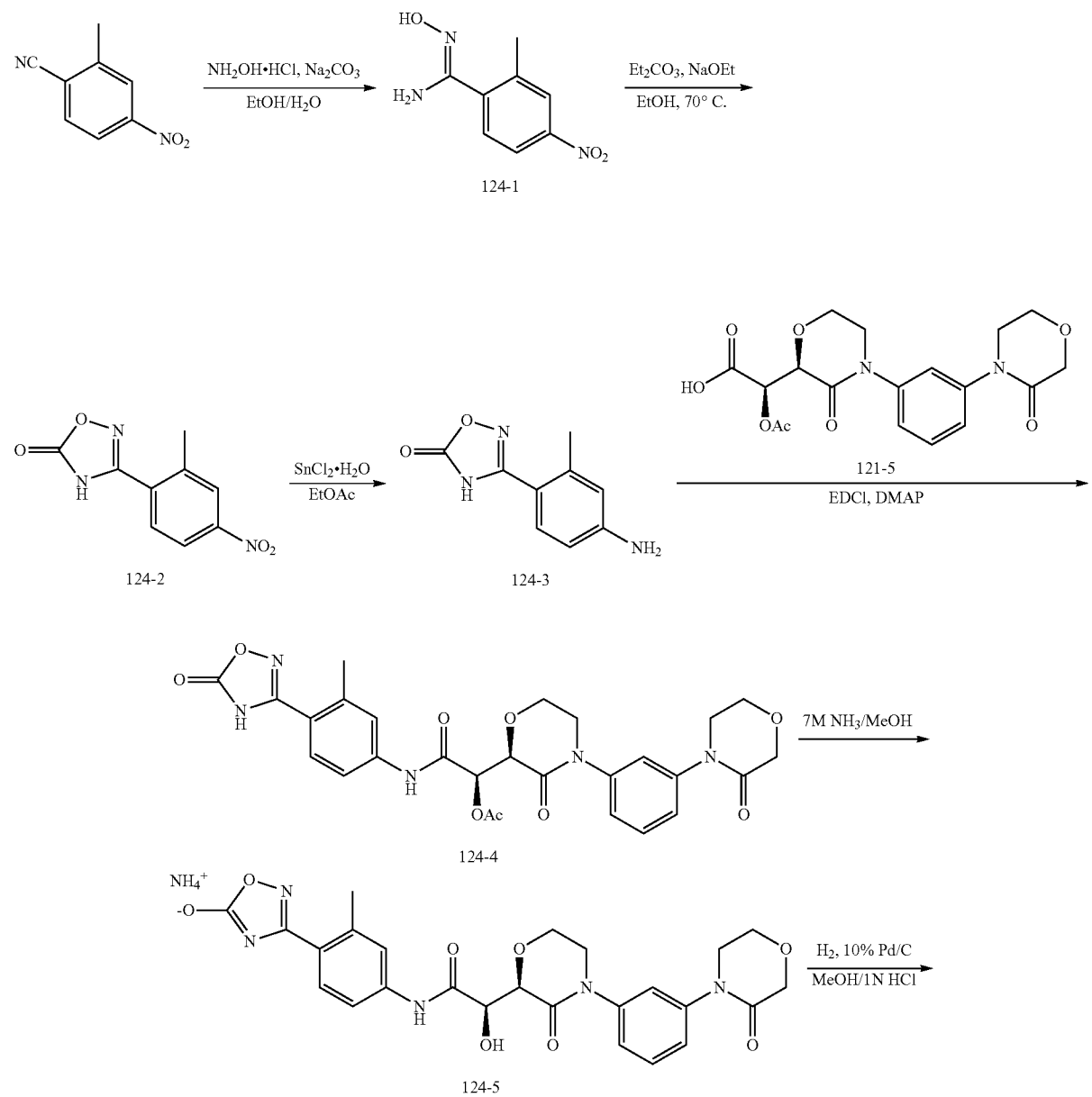

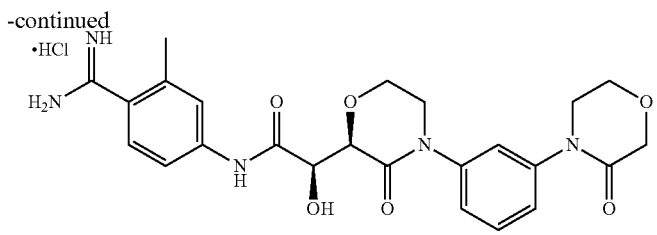

EXAMPLE 124

Step 124-1

Synthesis of N-Hydroxy-2-methyl-4-nitrobenzimidamide (Compound 124-1)

To a solution of 2-methyl-4-nitrobenzonitrile (5 g) in EtOH/$H_2O$ (30 mL/6 mL) was added $Na_2CO_3$ (3.6 g) and $NH_2OH \cdot HCl$ (4.3 g). The mixture was stirred for 8 h at 60° C. where upon an additional portion of both $Na_2CO_3$ (3.6 g) and $NH_2OH \cdot HCl$ (4.3 g) were added and continued heating at 60° C. for 72 h. The mixture was cooled to rt, filtered, and the resultant precipitate was washed with water, EtOH, and $Et_2O$. The crude precipitate was dried under vacuum to afford 124-1 (3.4 g) as a pale yellow solid which was used without further purification.

Step 124-2

Synthesis of 3-(2-Methyl-4-nitrophenyl)-1,2,4-oxadiazol-5(4H)-one (Compound 124-2)

To a solution of 124-1 (2.0 g) in EtOH (10 mL) at rt was added diethyl carbonate (1.3 mL) and the mixture was heated to 65° C. A 21% wt NaOEt soln (7.31 mL) was added dropwise to the solution which was then heated to 70° C. and stirred for 2 h. The mixture was cooled to rt, concentrated to dryness, and dissolved in a minimum amount of water. Concentrated HCl was added dropwise until pH ~2 and the resultant precipitate was filtered. The precipitate was washed sequentially with water, EtOH, and $Et_2O$ to afford a dark brown solid. The crude product was purified by flash chromatography using a mixture of $CH_2Cl_2$/MeOH to afford 124-2 (0.9 g) as a brown solid.

Step 124-3

Synthesis of 3-(4-Amino-2-methylphenyl)-1,2,4-oxadiazol-5(4H)one (Compound 124-3)

To a solution of 124-2 (0.44 g) in EtOAc (25 mL) at it was added $SnCl_2 \cdot H_2O$ (1.7 g) in one portion. The mixture was heated at 80° C. for 12 h, cooled to rt, and quenched with sat. aq $NaHCO_3$. The mixture was filtered thru a pad of Celite and the aqueous layer was extracted with EtOAc. The combined organic layers were dried over $Na_2SO_4$, filtered, and concentrated under reduced pressure to afford 124-3 (0.16 g) as a brown solid. This material was used without further purification.

Step 124-4

Synthesis of (R)-2-(3-Methyl-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl) ethyl acetate (Compound 124-4)

According to the Step 118-4 in the synthetic method for EXAMPLE 118, compound 121-5 (0.28 g) was used instead of 118-3 to couple with 124-3 (0.16 g) to obtain 124-4 (0.16 g) as an a pale yellow solid after reverse-phase HPLC purification using a C18 column and a gradient of 89.95:9.95:$0.1H_2O$:MeCN:$HCO_2H$ to 9.95:89.95:$0.1H_2O$:MeCN:$HCO_2H$.

Step 124-5

Synthesis of Ammonium 3-(4-((R)-2-hydroxy-2-((R)-3-oxo-4-(3-(3-oxomorpholino)phenyl)morpholin-2-yl)acetamido)-2-methylphenyl)-1,2,4-oxadiazol-5-olate (Compound 124-5)

According to the Step 118-5 in the synthetic method for EXAMPLE 118, compound 124-4 (0.16 g) was used instead of 118-4 to obtain 124-5 (0.15 g) as a white solid which was used without further purification.

Step 124-6

Synthesis of (R)—N-(4-Carbamimidoyl-3-methylphenyl)-2-hydroxy-2-((R)-3-oxo-4-(3-(3-oxomorpholino)phenyl)morpholin-2-yl)acetamide hydrochloride (EXAMPLE 124)

According to the Step 118-6 in the synthetic method for EXAMPLE 118, compound 124-5 (0.15 g) was used instead of 118-5 to obtain EXAMPLE 124 (90 mg) of the hydrochloride salt as a white solid which was used without further purification.

Example 125
Synthesis of (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide hydrochloride (EXAMPLE 125)
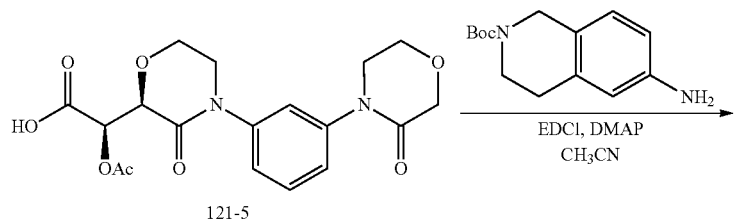
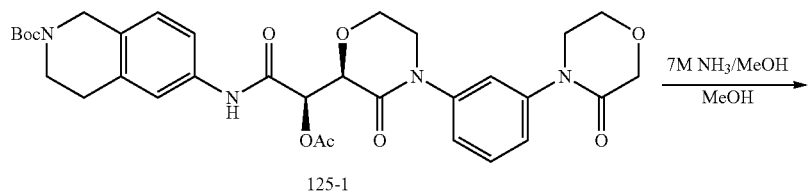
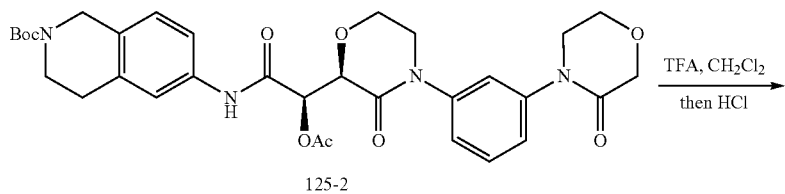
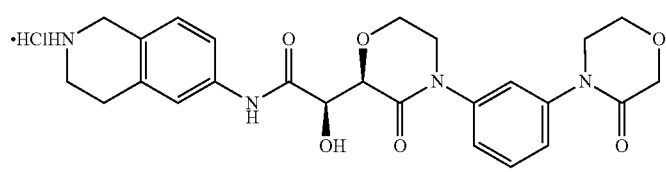
EXAMPLE 125

Step 125-1

Synthesis of tert-Butyl 6-((R)-2-acetoxy-2-((R)-3-oxo-4-(3-(3-oxomorpholino)phenyl)morpholin-2-yl)acetamido)-3,4-dihydroisoquinoline-2(1H)-carboxylate (Compound 125-1)

According to the Step 118-4 in the synthetic method for EXAMPLE 118, compound 121-5 (70 mg) was treated with tert-butyl 6-amino-3,4-dihydroisoquinoline-2(1H)-carboxylate (67 mg) to obtain 125-1 (58 mg) as a yellow solid after flash chromatography purification using a 20:1 mixture of CH$_2$Cl$_2$/MeOH as eluent.

Step 125-2

Synthesis of tert-Butyl 6-((R)-2-acetoxy-2-((R)-3-oxo-4-(3-(3-oxomorpholino)phenyl)morpholin-2-yl)acetamido)-3,4-dihydroisoquinoline-2(1H)-carboxylate (Compound 125-2)

According to the Step 118-5 in the synthetic method for EXAMPLE 118, 125-1 (58 mg) was used instead of compound 118-4 to obtain 125-2 (50 mg) as a white solid which was taken on without further purification.

Step 125-3

Synthesis of (R)-2-Hydroxy-2-((R)-3-oxo-4-(3-(3-oxomorpholino)phenyl)morpholin-2-yl)-N-(1,2,3,4-tetrahydroisoquinolin-6-yl)acetamide hydrochloride (EXAMPLE 125)

According to the Step 120-3 in the synthetic method for EXAMPLE 120, 125-2 (50 mg) was used instead of compound 120-2 to obtain EXAMPLE 125 (35 mg) as a pale yellow hydrochloride salt upon treatment with HCl.

Example 126

Synthesis of 2-(3-((R)-2-((R)-2-(4-Carbamimidoylphenylamino)-1-hydroxy-2-oxoethyl)-3-oxomorpholino)phenoxy)acetic acid hydrochloride (EXAMPLE 126)

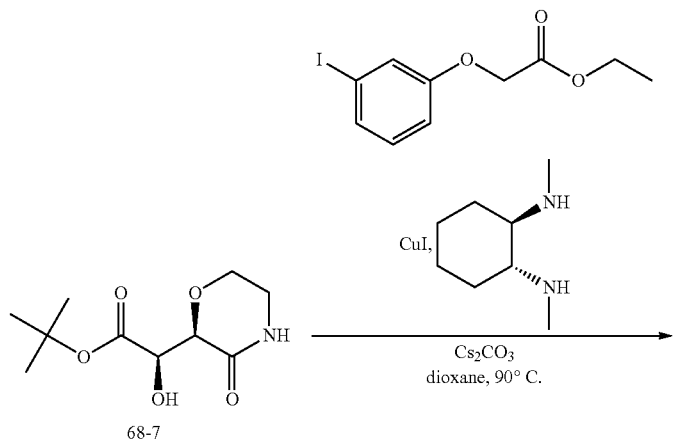

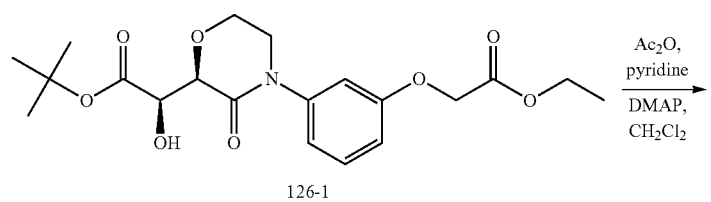

126-1

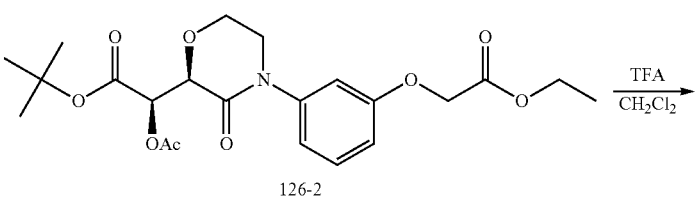

126-2

-continued

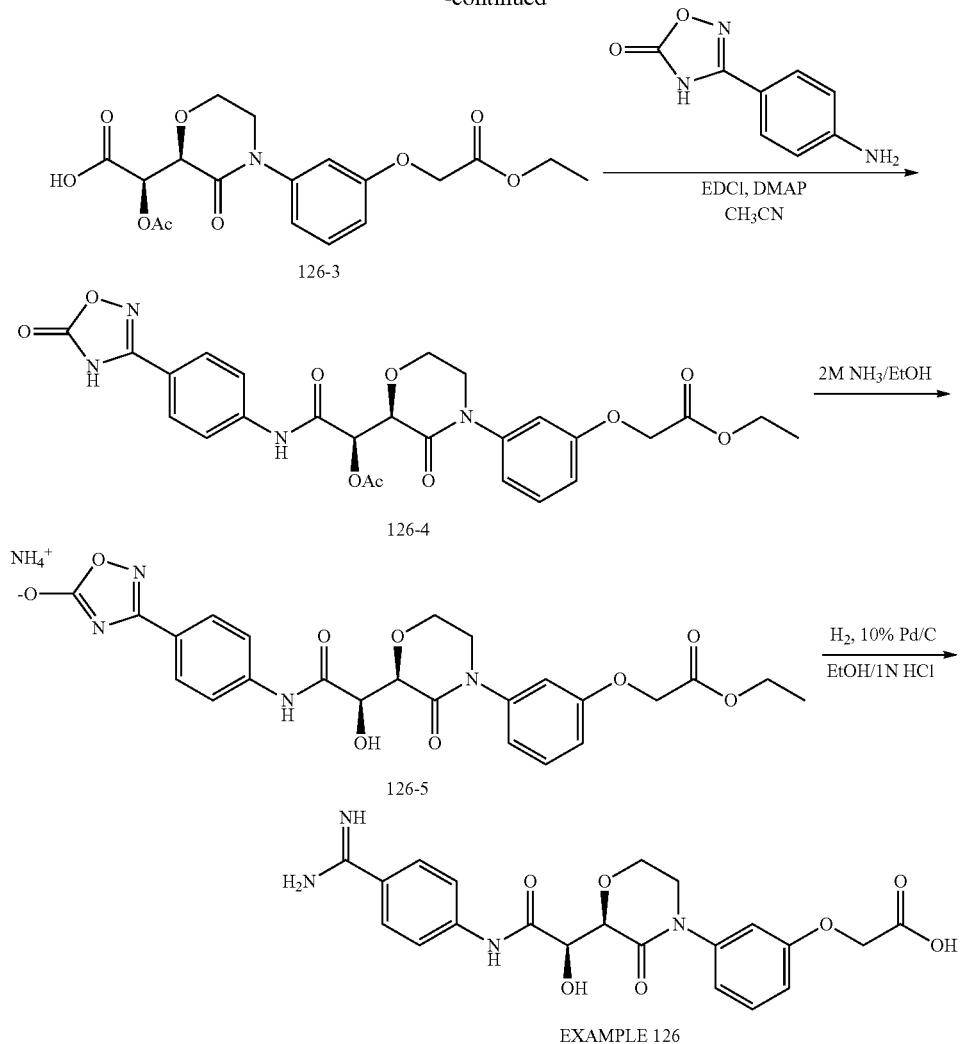

Step 126-1

Synthesis of (R)-tert-Butyl 2-((R)-4-(3-(2-ethoxy-2-oxoethoxy)phenyl)-3-oxomorpholin-2-yl)-2-hydroxyacetate (Compound 126-1)

According to the Step 118-1 in the synthetic method for EXAMPLE 118, 68-7 (0.35 g) was treated with ethyl 2-(3-iodophenoxy)acetate (0.56 g) from *Eur J. Org. Chem.* 2008, 337 to obtain 126-1 (0.54 g) as an yellow solid after flash chromatography with 40:1 $CH_2Cl_2$/MeOH as eluent.

Step 126-2

Synthesis of (R)-tert-Butyl 2-acetoxy-2-((R)-4-(3-(2-ethoxy-2-oxoethoxy)phenyl)-3-oxomorpholin-2-yl) acetate (Compound 126-2)

According to the Step 118-2 in the synthetic method for EXAMPLE 118, compound 126-1 (0.54 g) was used instead of 118-1 to obtain 126-2 (0.56 g) as a yellow oil which was used without further purification.

Step 126-3

Synthesis of (R)-2-Acetoxy-2-((R)-4-(3-(2-ethoxy-2-oxoethoxy)phenyl)-3-oxomorpholin-2-yl)acetic acid (Compound 126-3)

According to the Step 118-3 in the synthetic method for EXAMPLE 118, compound 126-2 (0.55 g) was used instead of 118-2 to obtain 126-3 (0.45 g) as a yellow solid which was used without further purification.

Step 126-4

Synthesis of Ethyl 2-(3-((R)-2-((R)-1-acetoxy-2-oxo-2-(4-(5-oxo-4,5-dihydro-1,2,4-oxadiazol-3-yl) phenyl amino)ethyl)-3-oxomorpholino)phenoxy) acetate (Compound 126-4)

According to the Step 118-4 in the synthetic method for EXAMPLE 118, compound 126-3 (0.18 g) was used instead of 118-3 to obtain 126-4 (90 mg) as an off-white solid after purification by reverse-phase HPLC using a C18 column and a gradient of 89.95:9.95:0.1H$_2$O:MeCN:HCO$_2$H to 9.95:89.95:0.1H$_2$O:MeCN:HCO$_2$H.

Step 126-5

Synthesis of Ammonium 3-(4-((R)-2-((R)-4-(3-(2-ethoxy-2-oxoethoxy)phenyl)-3-oxomorpholin-2-yl)-2-hydroxyacetamido)phenyl)-1,2,4-oxadiazol-5-olate (Compound 126-5)

According to the Step 118-5 in the synthetic method for EXAMPLE 118 except using 2M NH$_3$ in EtOH, compound 126-4 (85 mg) was used instead of 118-4 to obtain 126-5 (60 mg) as a yellow solid which was used without further purification.

Step 126-6

Synthesis of 2-(3-((R)-2-((R)-2-(4-Carbamimidoylphenylamino)-1-hydroxy-2-oxoethyl)-3-oxomorpholino)phenoxy)acetic acid hydrochloride (EXAMPLE 126)

According to the Step 118-6 in the synthetic method for EXAMPLE 118 except substituting EtOH for MeOH as solvent, compound 126-5 (58 mg) was used instead of 118-5 to obtain EXAMPLE 126 (36 mg) as a maize solid.

Example 127

Synthesis of Ethyl 2-(3-((R)-2-((R)-2-(4-(aminomethyl)phenylamino)-1-hydroxy-2-oxoethyl)-3-oxomorpholino)phenoxy)acetate Trifluoroacetate (EXAMPLE 127)

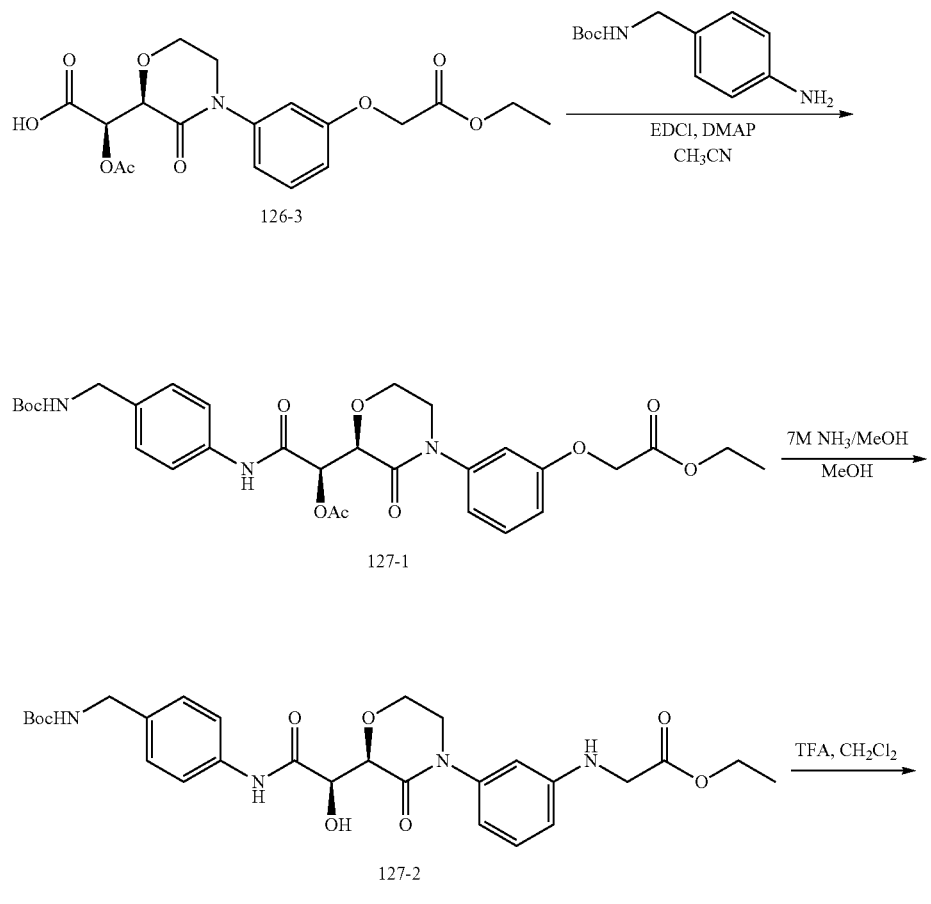

Step 127-1

Synthesis of Ethyl 2-(3-((R)-2-((R)-1-acetoxy-2-(4-((tert-butoxycarbonylamino)methyl)phenylamino)-2-oxoethyl)-3-oxomorpholino)phenoxy)acetate (Compound 127-1)

According to the Step 118-4 in the synthetic method for EXAMPLE 118, 126-3 (0.18 g) was treated with tert-butyl 4-aminobenzylcarbamate (0.13 g) to afford 127-1 (100 mg) as an yellow semisolid after purification by reverse-phase HPLC using a C18 column and a gradient of 89.95:9.95:0.1H$_2$O:MeCN:HCO$_2$H to 9.95:89.95:0.1H$_2$O:MeCN:HCO$_2$H.

Step 127-2

Synthesis of Ethyl 2-(3-((R)-2-((R)-2-(4-((tert-butoxycarbonylamino)methyl)phenylamino)-1-hydroxy-2-oxoethyl)-3-oxomorpholino)phenylamino)acetate (Compound 127-2)

According to the Step 118-5 in the synthetic method for EXAMPLE 118 except using 2M NH$_3$ in EtOH, 127-1 (0.10 g) was used instead of compound 118-4 to obtain 127-2 (90 mg) as a white solid. Crude 127-2 was used without further purification in the next step.

Step 127-3

Synthesis of Ethyl 2-(3-((R)-2-((R)-2-(4-(aminomethyl)phenylamino)-1-hydroxy-2-oxoethyl)-3-oxomorpholino)phenoxy)acetate Trifluoroacetate (EXAMPLE 127)

According to the Step 120-3 in the synthetic method for EXAMPLE 120, 127-2 (90 mg) was used instead of compound 120-2 to obtain EXAMPLE 127 (55 mg) as the trifluoroacetate salt as a white solid after purification by reverse-phase HPLC using a C18 column and a gradient of 89.95:9.95:0.1H$_2$O:MeCN:TFA to 9.95:89.95:0.1H$_2$O:MeCN:TFA.

Example 128

Synthesis of (R)—N-(4-carbamimidoyl-2-ethylphenyl)-2-hydroxy-2-((R)-4-(2-methyl-3-oxoisoindolin-5-yl)-3-oxomorpholin-2-yl)acetamide hydrochloride (EXAMPLE 128)

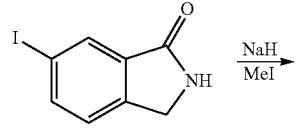

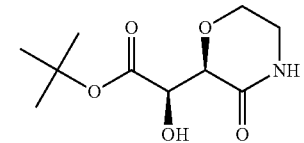

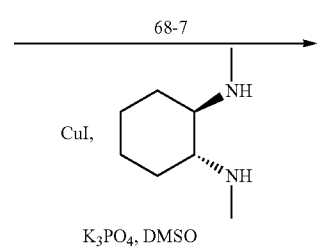

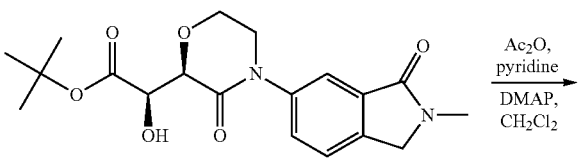

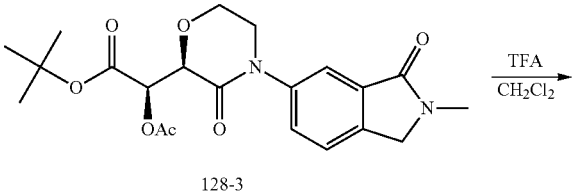

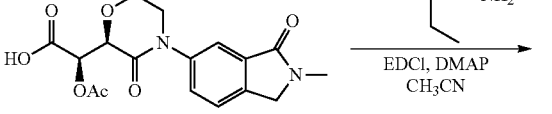

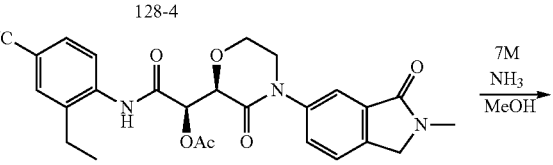

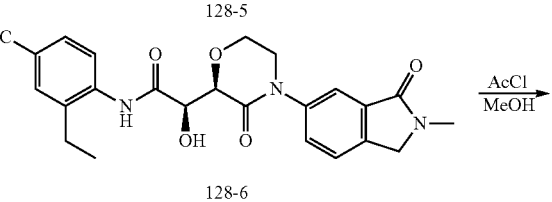

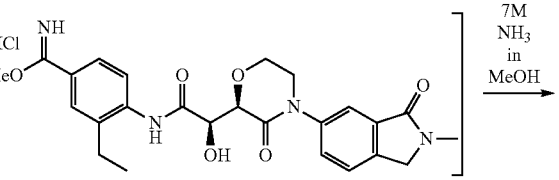

-continued

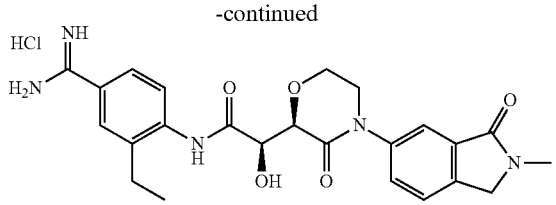

EXAMPLE 128

Step 128-1

Synthesis of 6-Iodo-2-methylisoindolin-1-one (Compound 128-1)

To a mixture of 2,3-dihydro-6-iodo-1H-isoindol-1-one (1.0 g) in DMF (20 mL) at 0° C. was added NaH (97 mg) in a single portion. The resulting mixture was stirred for 30 min at 0° C. whereupon MeI (0.25 mL) was added dropwise. The mixture was allowed to warm to rt and was stirred for 72 h. The mixture was quenched by addition of sat. aq. $NH_4Cl$ (~3 mL) and was diluted with EtOAc (10 mL). The layers were separated and the aqueous layer was extracted with EtOAc. The organic layers were combined and washed sequentially with water and brine. The organic layer was dried ($Na_2SO_4$), filtered, and concentrated under reduced pressure. The crude material was purified The crude product was purified by flash chromatography (ISCO, 120 g) using a gradient of 100% hexanes to 80:20 hexanes/EtOAc to afford 128-1 (0.84 g) as a yellow solid.

Step 128-2

Synthesis of (R)-tert-Butyl 2-hydroxy-2-((R)-4-(2-methyl-3-oxoisoindolin-5-yl)-3-oxomorpholin-2-yl)acetate (Compound 128-2)

To a round bottom flask charged with a stir bar was added 68-7 (0.28 g) and 128-1 (0.40 g) in DMSO (8 mL) at rt was added $K_3PO_4$ (0.51 g), and CuI (23 mg) under $N_2$. trans-N,N'-Dimethylcyclohexane-1,2-diamine (37 microL) was added dropwise and the mixture was affixed with a condenser. The mixture was degassed under vacuum (—20 mm), filled with $N_2$, and heated to 80° C. The mixture stirred for 2.5 h at 80° C., cooled to rt, and was diluted with EtOAc. The mixture was then sequentially washed with conc $NH_4OH$, water, and brine. The organic layer was dried ($Na_2SO_4$), filtered, and concentrated under reduced pressure to afford a yellow oil. The crude product was purified by flash chromatography using a gradient of 100% $CH_2Cl_2$ to 60% $CH_2Cl_2$/40% MeOH to afford 128-2 (0.23 g) as a yellow solid.

Step 128-3

Synthesis of (R)-tert-Butyl 2-acetoxy-2-((R)-4-(2-methyl-3-oxoisoindolin-5-yl)-3-oxomorpholin-2-yl)acetate (Compound 128-3)

According to the Step 118-2 in the synthetic method for EXAMPLE 118, compound 128-2 (80 mg) was used instead of 118-1 to obtain 128-3 (85 mg) as an off-white solid which was used without further purification.

Step 128-4

Synthesis of (R)-2-Acetoxy-2-((R)-4-(2-methyl-3-oxoisoindolin-5-yl)-3-oxomorpholin-2-yl)acetic acid (Compound 128-4)

According to the Step 118-3 in the synthetic method for EXAMPLE 118, compound 128-3 (85 mg) was used instead of 118-2 to obtain 128-4 (65 mg) as a light yellow semisolid solid which was used without further purification.

Step 128-5

Synthesis of (R)-2-(4-Cyano-2-ethylphenylamino)-1)-4-(2-methyl-3-oxoisoindolin-5-yl)-3-oxo morpholin-2-yl)-2-oxoethyl acetate (Compound 128-5)

According to the Step 118-4 in the synthetic method for EXAMPLE 118, compound 128-4 (75 mg) was used instead of 118-3 to in the presence of 4-amino-3-ethylbenzonitrile (46 mg) to obtain 128-5 (50 mg) as an off-white solid which was purified by flash chromatography using 20:1 $CH_2Cl_2$/MeOH as eluent.

Step 128-6

Synthesis of (R)—N-(4-Cyano-2-ethylphenyl)-2-hydroxy-2-((R)-4-(2-methyl-3-oxoisoindolin-5-yl)-3-oxomorpholin-2-yl)acetamide (Compound 128-6)

According to the Step 118-5 in the synthetic method for EXAMPLE 118, compound 128-5 (50 mg) was used instead of 118-4 to obtain 128-6 (49 mg) as a white solid which was used without further purification.

Step 128-7

Synthesis of (R)—N-(4-Carbamimidoyl-2-ethylphenyl)-2-hydroxy-2-((R)-4-(2-methyl-3-oxoisoindolin-5-yl)-3-oxomorpholin-2-yl)acetamide hydrochloride (EXAMPLE 128)

To a pressure tube charged with 128-6 (45 mg) in MeOH (3 mL) at 0° C. was added AcCl (3 ml) dropwise. The tube was capped, warmed to rt, and stirred for 12 h. The mixture was concentrated to dryness and the pressure tube was charged with the crude mixture in 7M $NH_3$/MeOH (4 mL). The mixture was stirred for 3 days and was concentrated under reduced pressure. The crude mixture was purified by reverse phase HPLC using a C18 column and a gradient of 89.95:9.95:0.1$H_2O$:MeCN:$HCO_2H$ to 9.95:89.95:0.1$H_2O$:MeCN:$HCO_2H$ to afford EXAMPLE 128 (6 mg) as a white solid as the hydrochloride salt after HCl treatment.

Example 129
Synthesis of (R)-2-Hydroxy-N-(2-methyl-1H-indol-5-yl)-2-((R)-3-oxo-4-(3-(3-oxomorpholino)phenyl)morpholin-2-yl)acetamide (EXAMPLE 129)
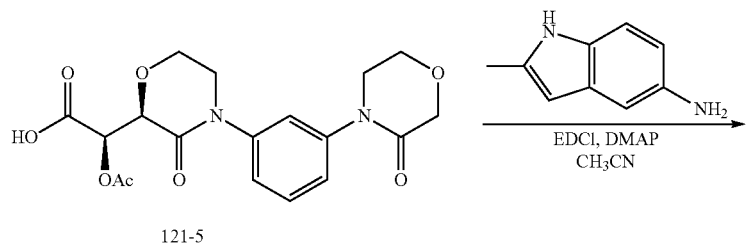
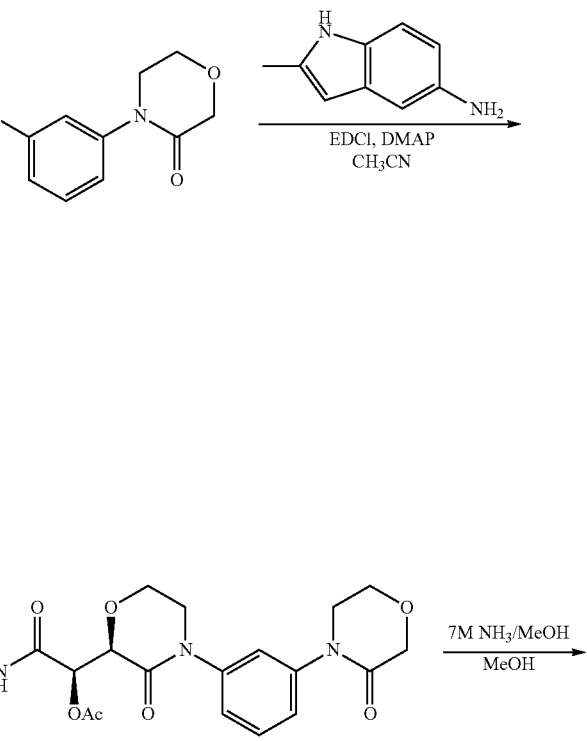
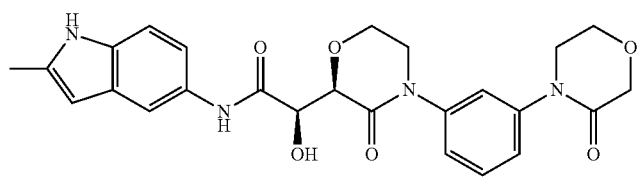
EXAMPLE 129

Step 129-1

Synthesis of (R)-2-(2-Methyl-1H-indol-5-ylamino)-2-oxo-1-((R)-3-oxo-4-(3-(3-oxomorpholino)phenyl)morpholin-2-yl)ethyl acetate (Compound 129-1)

According to the Step 118-4 in the synthetic method for EXAMPLE 118, compound 121-5 (70 mg) was treated with 2-methyl-1H-indol-5-amine (34 mg) to obtain 129-1 (73 mg) as a brown solid after flash chromatography purification using a 20:1 mixture of CH$_2$Cl$_2$/MeOH as eluent.

Step 129-2

Synthesis of (R)-2-Hydroxy-N-(2-methyl-1H-indol-5-yl)-2-((R)-3-oxo-4-(3-(3-oxomorpholino) phenyl)morpholin-2-yl)acetamide (EXAMPLE 129)

According to the Step 118-5 in the synthetic method for EXAMPLE 118, 129-1 (73 mg) was used instead of compound 118-4 to obtain EXAMPLE 129 (62 mg) as a brown solid.

Example 130

Synthesis of (R)—N-(4-Chlorophenethyl)-2-hydroxy-2-((R)-3-oxo-4-(3-(3-oxomorpholino)phenyl)morpholin-2-yl)acetamide (EXAMPLE 130)

Step 130-1

Synthesis of (R)-2-(4-Chlorophenethylamino)-2-oxo-1-((R)-3-oxo-4-(3-(3-oxomorpholino)phenyl)morpholin-2-yl)ethyl acetate (Compound 130-1)

To a solution of compound 121-5 (70 mg) in DMF (1.5 mL) was added 2-(4-chlorophenyl)ethanamine (32 mg) followed by HATU (88 mg) and NMM (32 mg). The mixture was stirred at rt for 12 h and was loaded directly onto a reverse-phase HPLC using a C18 column and gradient of 89.95:9.95:0.1H$_2$O:MeCN:HCO$_2$H to 9.95:89.95:0.1H$_2$O:MeCN:HCO$_2$H to afford 130-1 (50 mg) as a yellow semisolid.

Step 130-2

Synthesis of (R)—N-(4-Chlorophenethyl)-2-hydroxy-2-((R)-3-oxo-4-(3-(3-oxomorpholino)phenyl)morpholin-2-yl)acetamide (EXAMPLE 130)

According to the Step 118-5 in the synthetic method for EXAMPLE 118, 130-1 (73 mg) was used instead of compound 118-4 to obtain EXAMPLE 130 (42 mg) as a pale white solid.

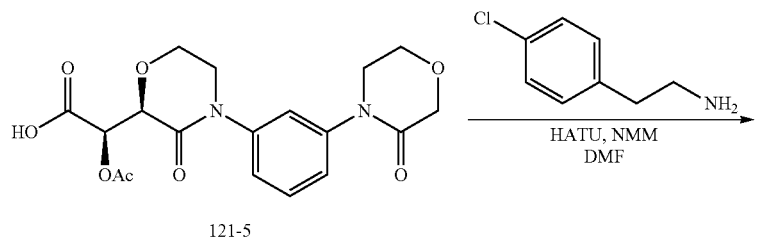

121-5

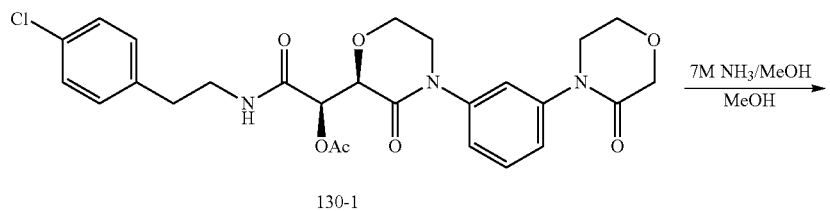

130-1

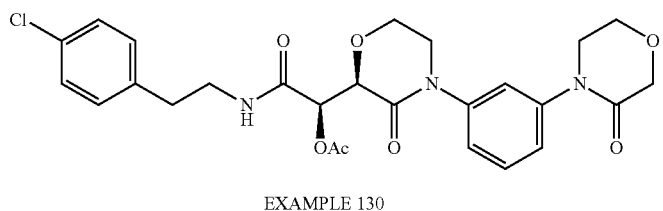

EXAMPLE 130

Example 131

Synthesis of (R)—N-(4-carbamimidoylphenyl)-2-hydroxy-2-((R)-4-(2-methoxyphenyl)-3-oxomorpholin-2-yl)acetamide (EXAMPLE 131)

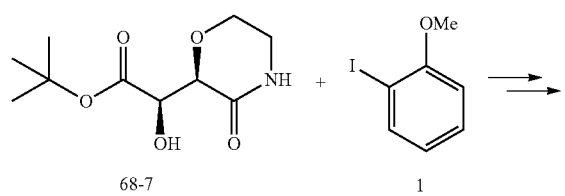

68-7 + 1

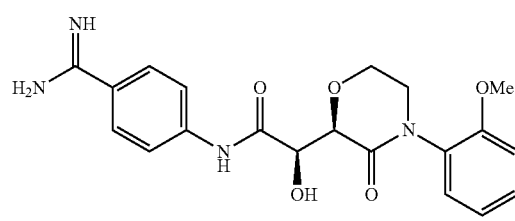

EXAMPLE 131

EXAMPLE 131 was synthesized similarly as for the synthesis of EXAMPLE 96 using 1-iodo-2-methoxybenzene 1.

Example 132

Synthesis of (R)—N-(4-carbamimidoylphenyl)-2-hydroxy-2-((R)-4-(2-fluorophenyl)-3-oxomorpholin-2-yl)acetamide (EXAMPLE 132)

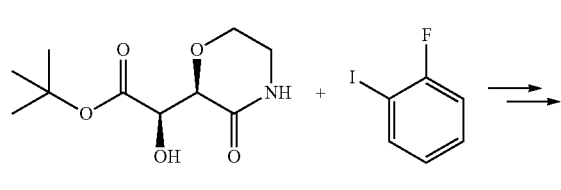

68-7 + 1

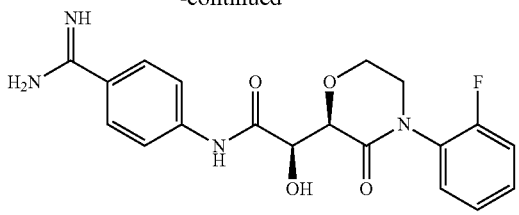

EXAMPLE 132

EXAMPLE 132 was synthesized similarly as for the synthesis of EXAMPLE 96 using 1-iodo-2-fluorobenzene 1.

Example 133

Synthesis of (R)—N-(4-carbamimidoylphenyl)-2-hydroxy-2-((R)-4-(2-(difluoromethoxy)phenyl)-3-oxomorpholin-2-yl)acetamide (EXAMPLE 133)

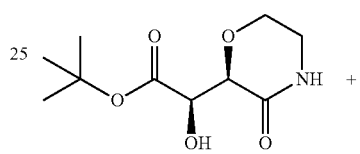

68-7

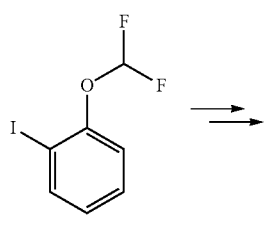

1

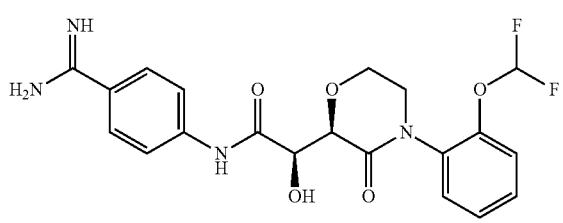

EXAMPLE 133

EXAMPLE 133 was synthesized similarly as for the synthesis of EXAMPLE 96 using 1-iodo-2-(difluoromethoxy)benzene 1.

Example 134

Synthesis of (R)—N-(6-carbamimidoylpyridin-3-yl)-2-hydroxy-2-((R)-3-oxo-4-(3-(3-oxomorpholino)phenyl)morpholin-2-yl)acetamide (EXAMPLE 134)

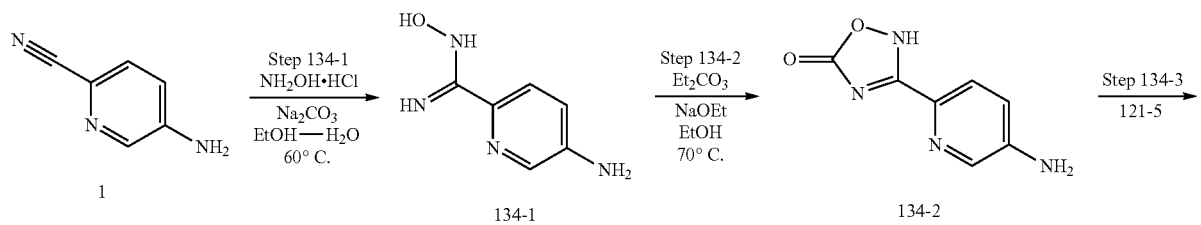

H₂O (2 mL) at 60° C. was added a mixture of hydroxylamine hydrochloride (1.85 g, 26.6 mmol) in H₂O (2 mL). The resulting mixture was stirred at 60° C. for 16 h. The mixture was cooled down to room temperature. The solids were filtered, washed with water (5 mL), EtOH (5 mL), and ether (5 mL). The solids were dried in vacuo to give 2.41 g of compound 134-1 which was used in the following step without further purification.

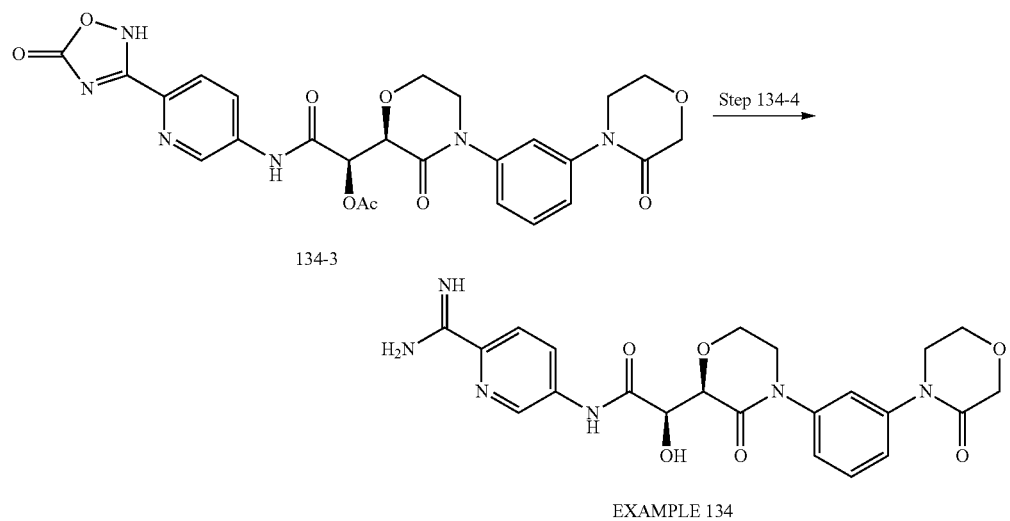

Step 134-1

Synthesis of 5-amino-N-hydroxypicolinimidamide (Compound 134-1)

To a stirred mixture of 5-aminopicolinonitrile (2.44 g, 20.5 mmol) and Na₂CO₃ (2.67 g, 25.2 mmol) in EtOH (10 mL) and

Step 134-2

Synthesis of 3-(5-aminopyridin-2-yl)-1,2,4-oxadiazol-5(2H)-one (Compound 134-2)

To a stirred mixture of compound 134-1 (1.20 g, 7.89 mmol) and Et₂CO₃ (1.1 mL, 9.5 mmol) in EtOH (8 mL) at ca 65° C. was added a solution of NaOEt (3.3 mL, 8.8 mmol, 20% in EtOH). The resulting mixture was stirred at 70° C. for 1 h. The mixture was cooled down to room temperature and concentrated. The residue was dissolved in water (5 mL) at 70° C. HCl (concentrated) was added until pH 4. The solids were filtered, washed with water (5 mL), EtOH (5 mL), and ether (5 mL). The solids were dried in vacuo to give 253 mg of Compound 134-2 which was used in the following step without further purification.

Step 134-3

Synthesis of (R)-2-oxo-2-(6-(5-oxo-2,5-dihydro-1,2,4-oxadiazol-3-yl)pyridin-3-ylamino)-1-((R)-3-oxo-4-(3-(3-oxomorpholino)phenyl)morpholin-2-yl)ethyl acetate (Compound 134-3)

Compound 134-3 was synthesized similarly as for the synthesis of Compound 91-4 using Compound 121-5 and Compound 134-2.

Step 134-4

Synthesis of (R)—N-(6-carbamimidoylpyridin-3-yl)-2-hydroxy-2-((R)-3-oxo-4-(3-(3-oxomorpholino)phenyl)morpholin-2-yl)acetamide (EXAMPLE 134)

EXAMPLE 134 was synthesized similarly as for the synthesis of Compound 96, Step 96-2, using Compound 134-3.

Example 135

Synthesis of N-[4-(aminoiminomethyl)phenyl]-4-[3-(1,1-dioxido-2-isothiazolidinyl)phenyl]-alpha(R)-hydroxy-3-oxo-2(R)-morpholineacetamide (EXAMPLE 135)

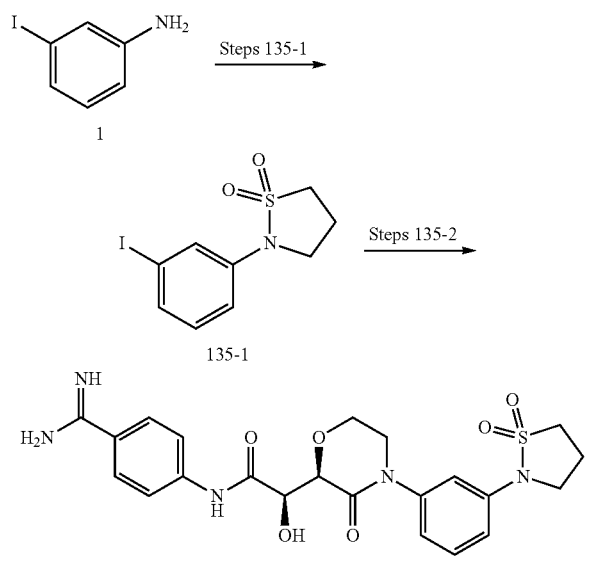

Step 135-1

Synthesis of Compound 135-1

To a solution of 3-iodoaniline (2 g, 11 mmol) and Et$_3$N (3 mL, 21 mmol) in DCM (20 mL), 3-chloropropane-1-sulfonyl chloride (1.8 mL, 14.8 mmol) was added. The mixture was stirred for 60 h at room temperature, washed with 3M HCl, and evaporated to dryness. The resulting crude mixture was dissolved in DMF (16 mL) and DBU (2 mL, 13.4 mmol) was added. After being stirred for 3 h at room temperature, the reaction mixture was poured into 400 mL of hexane/AcOEt (1/1) and washed with 3M HCl. The organic layer was dried over Na$_2$SO$_4$ and evaporated to dryness. The crude material was purified by silica gel chromatography (Acetone/Hex 0 to 25%) to give Compound 135-1 (2.4 g, 67%).

Step 135-2

N-[4-(aminoiminomethyl)phenyl]-4-[3-(1,1-dioxido-2-isothiazolidinyl)phenyl]-alpha(R)-hydroxy-3-oxo-2(R)-morpholineacetamide (EXAMPLE 135) EXAMPLE 135 was synthesized similarly as for the synthesis of Compound 91, Steps 91-1 to 91-6, using Compound 135-2.

Example 136

Synthesis of (R)—N-(4-carbamimidoylphenyl)-2-((R)-4-(4-fluoro-2-methoxyphenyl)-3-oxomorpholin-2-yl)-2-hydroxyacetamide (EXAMPLE 136)

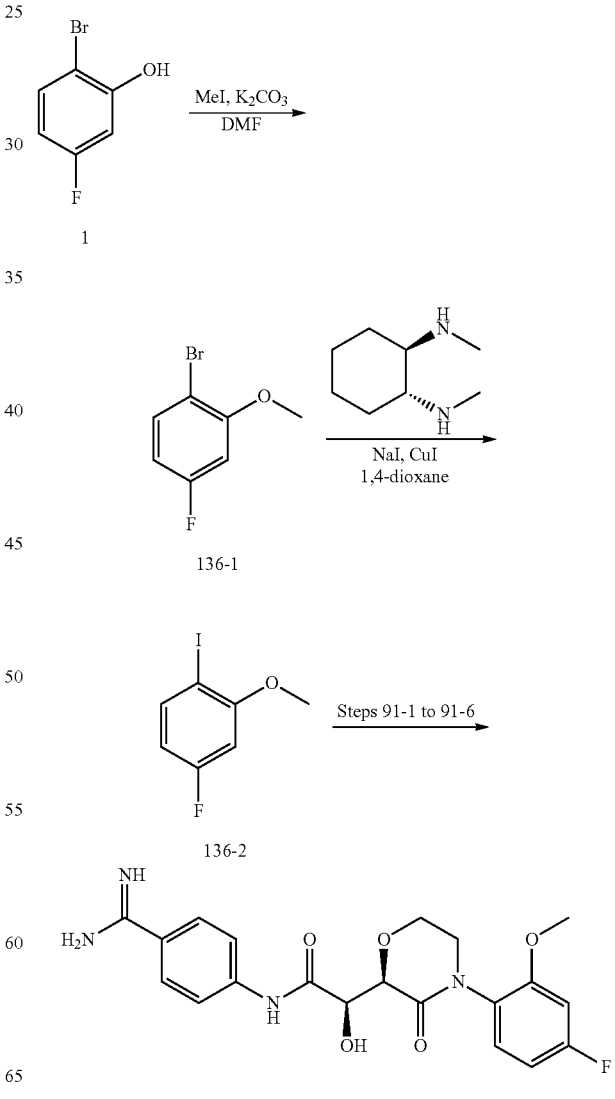

Step 136-1

Synthesis of Compound 136-1

To a mixture of 2-bromo-5-fluorophenol (2 g, 10.5 mmol) and potassium carbonate (2.9 g, 21 mmol) in DMF (10 mL), iodomethane (2.27 g, 16 mmol) was added. The mixture was heated to 55° C. and stirred for 16 h. The reaction mixture was cooled to room temperature and diluted with diethyl ether. The organics were washed with saturated aqueous ammonium chloride, water, dried with $Na_2SO_4$, and evaporated to dryness. The crude material was purified by silica gel chromatography (diethyl ether/Hex 0 to 2%) to give Compound 136-1 (1.2 g, 55%).

Step 136-2

Synthesis of Compound 136-2

To a nitrogen purged vessel, a solution of compound 136-1 (0.5 g, 2.4 mmol) in 1,4-dioxane (3 mL), sodium iodide (0.72 g, 4.8 mmol), copper iodide (0.023 g, 0.12 mmol), and trans-N,N'-dimethylcyclohexane-1,2-diamine (0.034 g, 0.24 mmol) were added. The vessel was sealed and heated to 115° C. for 65 hours. The reaction mixture was cooled to room temperature, washed with aqueous saturated ammonia chloride, and extracted with ethyl acetate. The organics were dried with $Na_2SO_4$ and evaporated to dryness to give Compound 136-2 (0.55 g, 91%) which was used without further purification in the next step.

Step 136-3

Synthesis of Example 136

EXAMPLE 136 was synthesized similarly as for the synthesis of Compound 91, Steps 91-1 to 91-6, using Compound 136-2.

Example 137

Synthesis of (R)—N-(4-carbamimidoylphenyl)-2-hydroxy-2-((R)-4-(2-isopropoxyphenyl)-3-oxomorpholin-2-yl)acetamide (EXAMPLE 137)

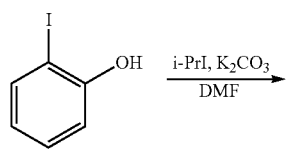

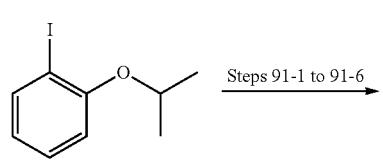

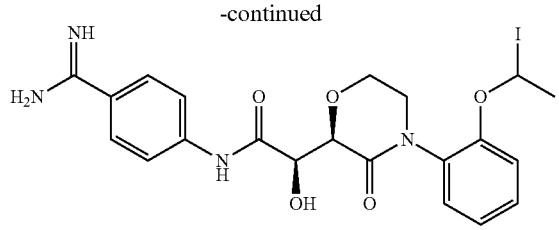

EXAMPLE 137

Step 137-1

Synthesis of Compound 137-1

Compound 137-1 was synthesized similarly as for the synthesis of EXAMPLE 136, Step 136-1, using 2-iodophenol and 2-iodopropane.

Step 137-2

Synthesis of Example 137

EXAMPLE 137 was synthesized similarly as for the synthesis of Compound 91, Steps 91-1 to 91-6, using Compound 137-1.

Example 138

Synthesis of (R)-2-((R)-4-(2-(2-amino-2-oxoethoxy)phenyl)-3-oxomorpholin-2-yl)-N-(4-carbamimidoylphenyl)-2-hydroxyacetamide (EXAMPLE 138)

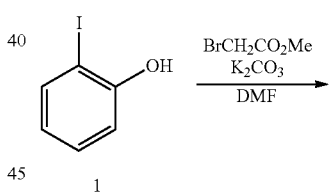

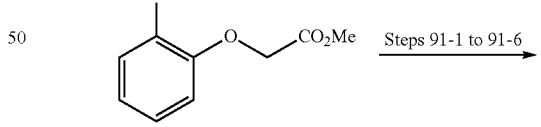

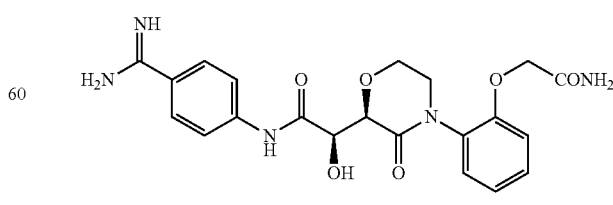

EXAMPLE 138

Step 138-1

Synthesis of Compound 138-2

Compound 138-2 was synthesized similarly as for the synthesis of EXAMPLE 136, Step 136-1, using 2-iodophenol and methyl 2-bromoacetate.

Step 138-2

Synthesis of Example 138

EXAMPLE 138 was synthesized similarly as for the synthesis of Compound 91, Steps 91-1 to 91-6, using Compound 138-2.

Example 139

Synthesis of (R)—N-(4-carbamimidoyl-3-fluorophenyl)-2-hydroxy-2-((R)-3-oxo-4-(3-(3-oxomorpholino)phenyl)morpholin-2-yl)acetamide (EXAMPLE 139)

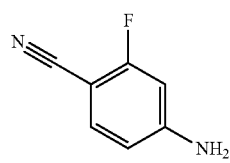

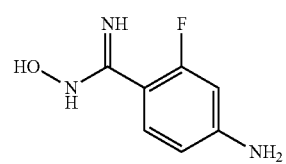

139-1

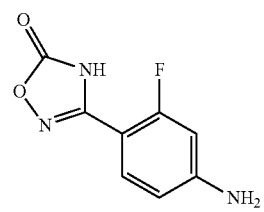

139-2

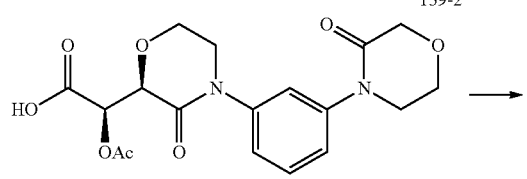

121-5

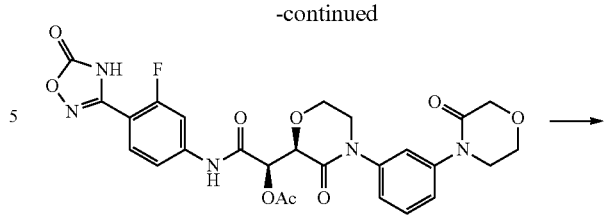

139-3

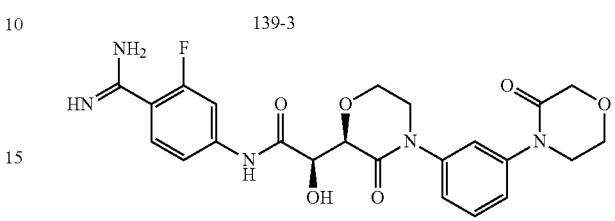

EXAMPLE 139

Step 139-1

4-amino-2-fluoro-N-hydroxybenzimidamide (Compound 139-1)

4-cyano-3-fluoroaniline (10 g, 0.0735 mol) was dissolved in EtOH (36.7 ml) and water (7.3 ml), Na$_2$CO$_3$ (5.06 g, 0.65 eq) was added. The mixture was heated at 60° C. and a solution of NH$_2$OH.HCl (5.615 g, 1.1 eq) in water (7.3 ml) was added slowly, the mixture was heated at 60° C. overnight. The mixture was cooled to 0° C., and the solid collected by filtration. Washed with water (7 ml), EtOH (7 ml), Et$_2$O (20 ml) and dried to give 7.5 g of compound 139-1.

Step 139-2

3-(4-amino-2-fluorophenyl)-1,2,4-oxadiazol-5(4H)-one (Compound 139-2)

Compound 139-1 was suspended in EtOH (26 ml), diethyl carbonate (5.344 ml, 1 eq) was added and the mixture heated at 65° C. NaOEt (16.5 g of a 21% solution in EtOH, 1.15 eq) added slowly and the mixture heated at 70° C. for 2 hours. Cooled, concentrated and taken up in water (25 ml) at 70° C., HCl(conc) was added to PH2, and the mixture cooled to 0° C. The solid was collected by filtration and washed with water (20 ml), EtOH (7 ml), and ether (20 ml) to give 6.4 g of compound 139-2.

Step 139-3

(R)-2-(3-fluoro-4-(5-oxo-4,5-dihydro-1,2,4-oxadiazol-3-yl)phenylamino)-2-oxo-1-((R)-3-oxo-4-(3-(3-oxomorpholino)phenyl)morpholin-2-yl)ethyl acetate (Compound 139-3)

121-5 (1.17 g, 0.00298 mol) and 139-2 (0.698 g, 1.2 eq) dissolved in MeCN (3.98 ml), and cooled to 0° C., EDCI.HCl (0.686 g, 1.2 eq) and DMAP (36 mg, 10%) were added and the mixture stirred overnight. The mixture was diluted with EtOAc, washed with NH$_4$Cl$_{(sat)}$, dried, concentrated, silica gel chromatography (0-5% MeOH in CH$_2$Cl$_2$) gave 1.1 g of 139-3

Step 139-4

(R)—N-(4-carbamimidoyl-3-fluorophenyl)-2-hydroxy-2-((R)-3-oxo-4-(3-(3-oxomorpholino)phenyl)morpholin-2-yl)acetamide (EXAMPLE 139)

139-3 (0.1 g, 0.000176 mol) dissolved in 5.85 ml MeOH/1 N HCl in ether (4:1), Pd(C) (35 mg) added, placed under H$_2$ 1 atm. Stirred for 4 hours, the catalyst was removed by filtration, and the filtrate concentrated. The resulting solid was dissolved in MeOH (5 ml), 7 N NH$_3$ in MeOH (0.176, 7 eq) was added and the mixture stirred for 1 hour. After cooling to rt the mixture was concentrated and then taken up in MeOH (5 ml), 1N HCl added, then the solution concentrated. Triturateion with MeOH/Ether followed by filtration gave 76 mg of EXAMPLE 139 as an HCl salt.

Example 140

(R)—N-(4-carbamimidoyl-3,5-difluorophenyl)-2-hydroxy-2-((R)-3-oxo-4-(3-(3-oxomorpholino)phenyl)morpholin-2-yl)acetamide (EXAMPLE 140)

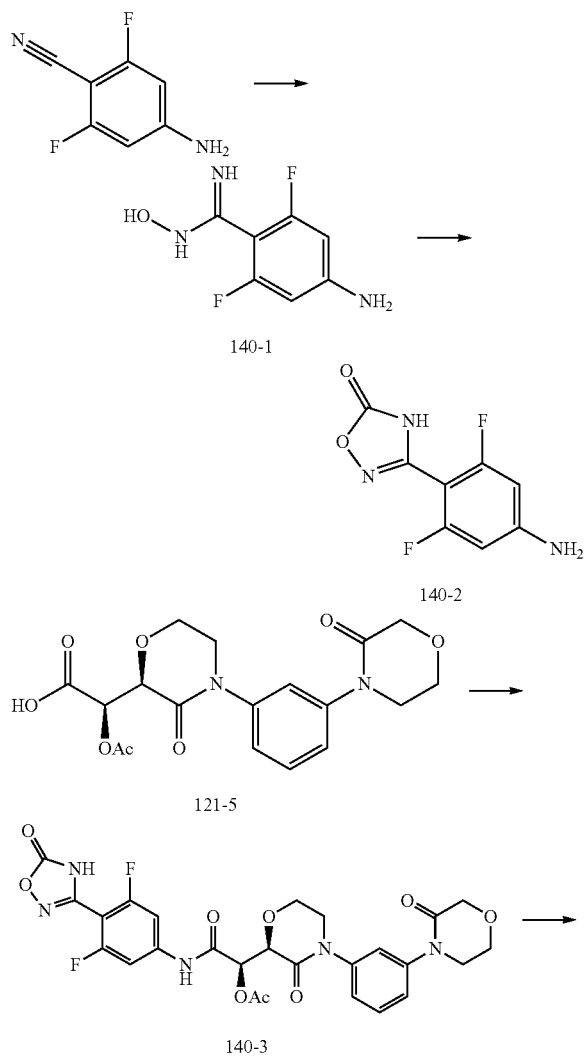

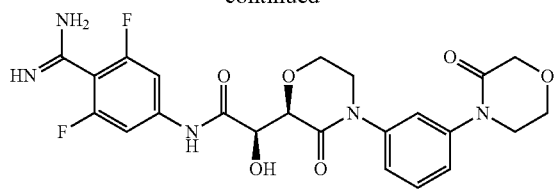

EXAMPLE 140

Step 140-1, Step 140-2

3-(4-amino-2,6-difluorophenyl)-1,2,4-oxadiazol-5(4H)-one (140-2)

Compound 140-2 was synthesized in the manner described for 139-2 as shown in the scheme above from 4-amino-2,6-difluorobenzonitrile (*J. Chem. Res.* 1998, p 144-145)

Step 140-3, Step 140-4

(R)—N-(4-carbamimidoyl-3,5-difluorophenyl)-2-hydroxy-2-((R)-3-oxo-4-(3-(3-oxomorpholino) phenyl)morpholin-2-yl)acetamide (EXAMPLE 140)

Example 140 was synthesized in the manner described for Example 139 as shown in the scheme above from 140-2 and 121-5.

Example 141

3-((R)-2-((R)-2-(4-carbamimidoyl-3-fluorophenylamino)-1-hydroxy-2-oxoethyl)-3-oxomorpholino)benzoic Acid (EXAMPLE 141)

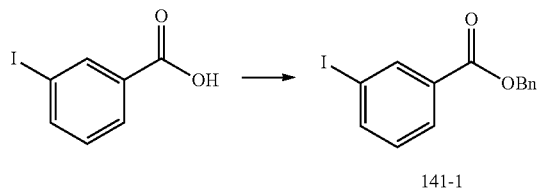

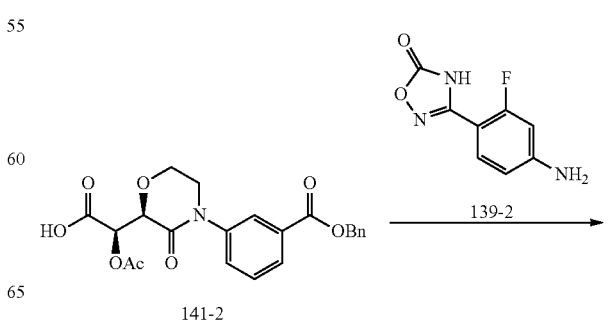

-continued

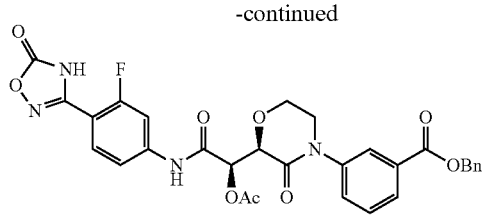

141-3

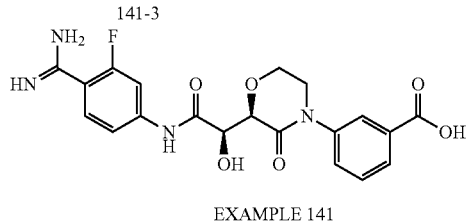

EXAMPLE 141

Step 141-1 benzyl 3-iodobenzoate (Compound 141-1)

3-iodobenzoic acid (1 g, 0.004032 mol) was dissolved in acetonitrile (20 ml), $Cs_2CO_3$ (2.63 g, 2 eq) and benzyl bromide (0.528 ml, 1.1 eq) were added. The mixture was heated at reflux overnight. Cooled to rt and concentrated. The residue was taken up in EtOAc, washed with water, dried ($MgSO_4$) and concentrated. Silica gel chromatography (0-20% EtOAc in hexane) gave 1 g of 141-1.

Step 141-2

(R)-2-acetoxy-2-((R)-4-(3-(benzyloxycarbonyl)phenyl)-3-oxomorpholin-2-yl)acetic acid (Compound 141-2)

141-2 was synthesized in a similar manner to 121-5 starting with 141-1

Step 141-3 benzyl 3-((R)-2-((R)-1-acetoxy-2-(3-fluoro-4-(5-oxo-4,5-dihydro-1,2,4-oxadiazol-3-yl)phenyl amino)-2-oxoethyl)-3-oxomorpholino)benzoate (Compound 141-3)

141-2 (1.15 g, 0.0027 mol) and 139-2 (0.63 g, 1.2 eq) dissolved in MeCN (3.6 ml), and cooled to 0° C., EDCI.HCl (0.619 g, 1.2 eq) and DMAP (33 mg, 10%) were added and the mixture stirred overnight. The mixture was diluted with EtOAc, washed with $NH_4Cl_{(sat)}$, dried, concentrated, silica gel chromatography (0-100% EtOAc in hexane) gave 1.2 g of 141-3.

Step 141-4

3-((R)-2-((R)-2-(4-carbamimidoyl-3-fluorophenylamino)-1-hydroxy-2-oxoethyl)-3-oxomorpholino) benzoic Acid (EXAMPLE 141)

141-3 (0.2 g, 0.00033 mol) was dissolved in MeOH (5.5 ml), 7N NH3 in MeOH (0.284, 6 eq) was added, stirred for 1 hour. The mixture was concentrated and taken up in MeOH (5 ml). 1 M HCl in ether (0.662, 2 eq) was then added. Pd(C) (100 mg) was added and the mixture put under H2 (1 atm) for 1 hour. The catalyst was removed by filtration and the solution concentrated. Trituration with ether/MeOH followed by filtration gave 143 mg of Example 141 as an HCl salt.

Example 142

Synthesis of N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide hydrochloride (EXAMPLE 142)

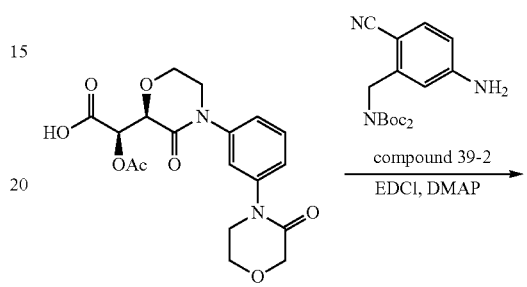

121-5

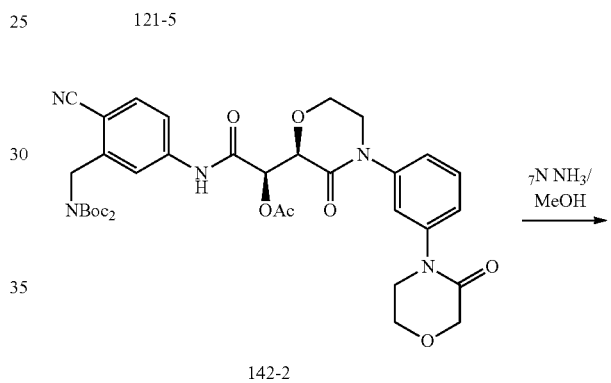

142-2

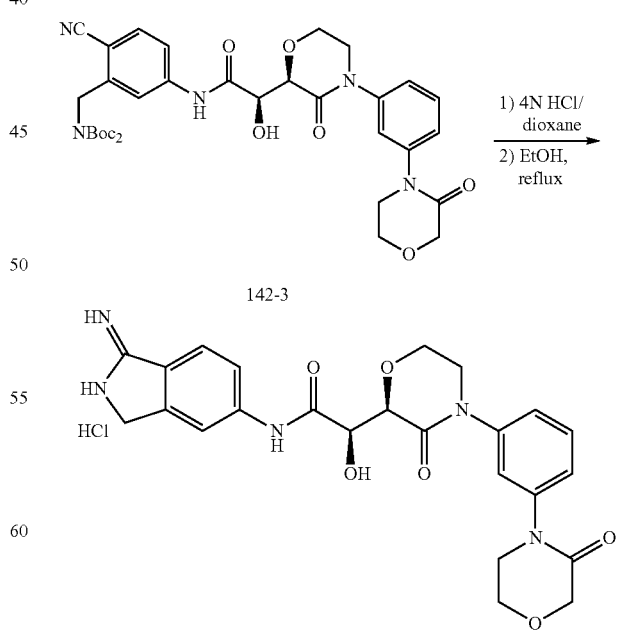

142-3

142

Step 142-1

Synthesis of (R)-2-(3-((bis(tert-butoxycarbonyl)amino)methyl)-4-cyanophenylamino)-2-oxo-1-((R)-3-oxo-4-(3-(3-oxomorpholino)phenyl)morpholin-2-yl)ethyl acetate (Compound 142-2)

To a solution of 121-5 (3.0 g, 7.65 mmol), compound 39-2 (2.7 g, 7.78 mmol, 1 eq.) and DMAP (95 mg, 0.78 mmol, 0.1 eq) in 30 ml of dichloromethane at 0° C. was added EDCI (1.9 g, 9.91 mmol, 1.3 eq) and the mixture was stirred at 0° C. for 2 hr. It was diluted with ethyl acetate, washed twice with 1N HCl then with brine. The solution was dried over anhydrous MgSO$_4$, filtered and concentrated. The resultant residue was purified by chromatography eluting with 5% methanol in dichloromethane to provide 3.5 g of 142-2.

Step 142-2 Synthesis of (Compound 142-3)

A solution of 142-2 (5.2 g, 7.20 mmol) in 50 ml of a solution of 7N NH$_3$ in methanol was stirred at rt for 30 min. and evaporated to dryness. The residue was purified by column chromatography eluting with 5% methanol in dichloromethane to provide 4.87 g of 142-3. (>theoretical weight due to the presence of solvent).

Step 142-3

Synthesis of N-(2,3-Dihydro-1-imino-1H-isoindol-5-yl)-alpha(R)-hydroxy-3-oxo-4-[3-(3-oxo-4-morpholinyl)phenyl]-2(R)-morpholineacetamide hydrochloride (EXAMPLE 142)

To a flask containing 142-3 (4.7 g, 6.92 mmol) was added 50 ml of a 4 N solution of HCl in dioxane and the resultant slurry was stirred at rt for 1 hr. It was concentrated to dryness and co-evaporated twice with anhydrous toluene. The above solid was taken in 100 ml of ethanol to give a clear solution which was heated at reflux for 10 hr to give a thick slurry. The solvent was evaporated to dryness and the solid was taken in minimum methanol to give a thick paste. To this was added anhydrous ether while being stirred vigorously. The solid was filtered off, washed with ether and dried in a vacuum oven to provide 3.05 of Example 142 as the HCl salt.

Example 143

4-(3-Cyanophenyl)-N-(2,3-dihydro-1-imino-1H-isoindol-5-yl)-alpha(R)-hydroxy-3-oxo-2(R)-morpholineacetamide (EXAMPLE 143)

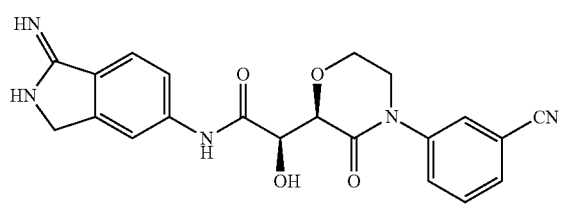 [SMILES: N#Cc1cccc(N2CCO[C@H]([C@@H](O)C(=O)Nc3ccc4c(c3)CNC4=N)C2=O)c1]

Example 143 was prepared using a procedure similar the preparation of EXAMPLE 142.

Example 144

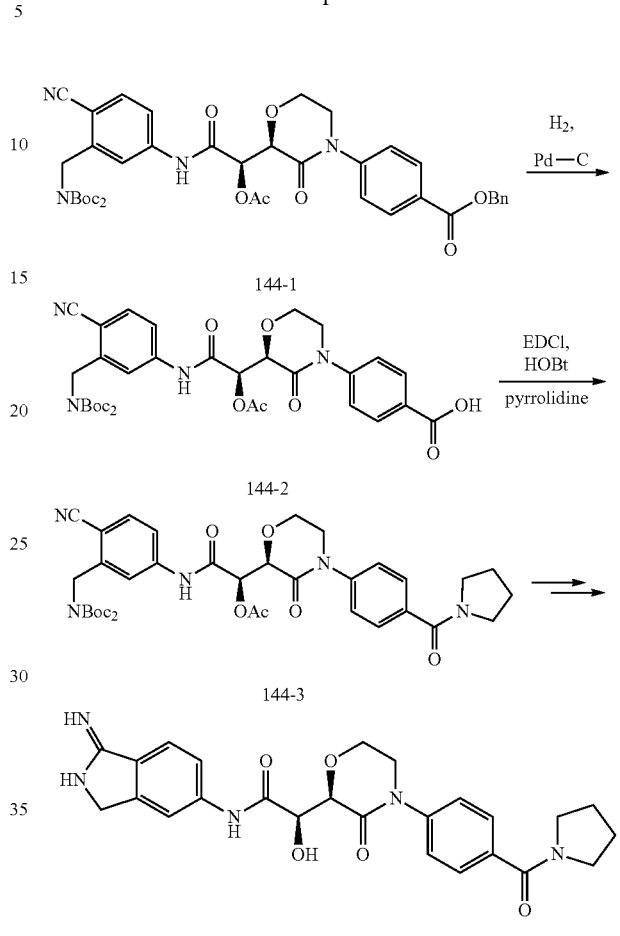

Step 144-1

Synthesis of Benzyl 3-((R)-2-((R)-1-acetoxy-2-(3-((bis(tert-butoxycarbonyl)amino)methyl)-4-cyanophenylamino)-2-oxoethyl)-3-oxomorpholino)benzoate (Compound 144-1)

Compound 144-1 was prepared using a procedure similar to the preparation of compound 142-2.

Step 144-2

Synthesis of 3-((R)-2-((R)-1-Acetoxy-2-(3-((bis(tert-butoxycarbonyl)amino)methyl)-4-cyanophenylamino)-2-oxoethyl)-3-oxomorpholino)benzoic acid (Compound 144-2)

To a solution of 144-1 (440 mg, 0.872 mmol) in 10 ml ethyl acetate was added 10% Pd—C (80 mg) and the suspension stirred under hydrogen balloon for 2.5 hr, filtered through a CELITE pad to remove the catalyst and the solvent evaporated to dryness to provide 370 mg of 144-2.

Step 144-3

Synthesis of (R)-2-(3-((Bis(tert-butoxycarbonyl)amino)methyl)-4-cyanophenylamino)-2-oxo-1-((R)-3-oxo-4-(3-(pyrrolidine-1-carbonyl)phenyl)morpholin-2-yl)ethyl acetate (Compound 144-3)

To a solution of 144-2 (180 mg, 0.27 mmol), pyrrolidine (45 ul, 0.54 mmol, 2 eq.) and hydroxybenzotriazole hydrate (62 mg, 0.41 mmol, 1.5q) in 3 ml acetonitrile at rt was added EDCI (78 mg, 0.41 mmol, 1.5 eq.) and the mixture stirred overnight at rt. It was diluted with ethyl acetate and washed twice with 1N HCl and brine. The solution was dried over MgSO$_4$, filtered, concentrated and purified by chromatography eluting with 5% methanol in dichloromethane to provide 160 mg of 144-3.

Step 144-4

Synthesis of N-(2,3-Dihydro-1-imino-1H-isoindol-5-yl)-alpha(R)-hydroxy-3-oxo-4-[4-(1-pyrrolidin ylcarbonyl)phenyl]-2(R)-morpholineacetamide (EXAMPLE 144)

Compound 144-3 was converted to EXAMPLE 144 using a procedure similar to the conversion of compound 142-2 to EXAMPLE 142 Using procedures similar to the preparation of EXAMPLE 144, the following examples were prepared:

| Example | Structure | Name |
|---|---|---|
| 145 | 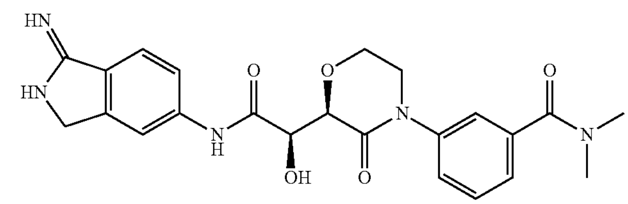 [SMILES: CN(C)C(=O)c1cccc(N2CCO[C@H]([C@@H](O)C(=O)Nc3ccc4c(c3)CNC4=N)C2=O)c1] | N-(2,3-Dihydro-1-imino-1H-isoindol-5-yl)-4-[3-[(dimethylamino)carbonyl]phenyl]-alpha(R)-hydroxy-3-oxo-2(R)-morpholineacetamide |
| 146 | 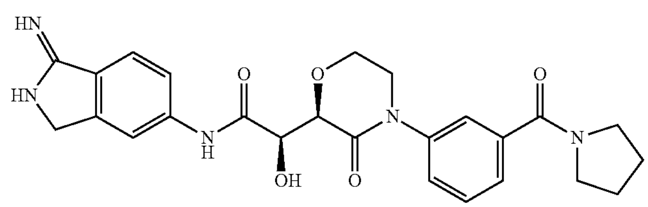 [SMILES: N=C1NCc2cc(NC(=O)[C@H](O)[C@H]3OCCN(c4cccc(C(=O)N5CCCC5)c4)C3=O)ccc21] | n-(2,3-Dihydro-1-imino-1H-isoindol-5-yl)-alpha(R)-hydroxy-3-oxo-4-[3-(1-pyrrolidinylcarbonyl)phenyl]-2(R)-morpholineacetamide |
| 147 | 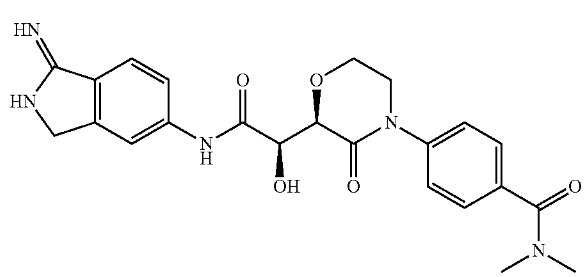 [SMILES: CN(C)C(=O)c1ccc(N2CCO[C@H]([C@@H](O)C(=O)Nc3ccc4c(c3)CNC4=N)C2=O)cc1] | N-(2,3-Dihydro-1-imino-1H-isoindol-5-yl)-4-[4-[(dimethylamino)carbonyl]phenyl]-alpha(R)-hydroxy-3-oxo-2(R)-morpholineacetamide |

Example 148

Synthesis of N-[4-(Aminoiminomethyl)phenyl]-alpha(R)-hydroxy-3-oxo-4-[3-(1h-tetrazol-5-yl)phenyl]-2(R)-morpholineacetamide EXAMPLE 148)

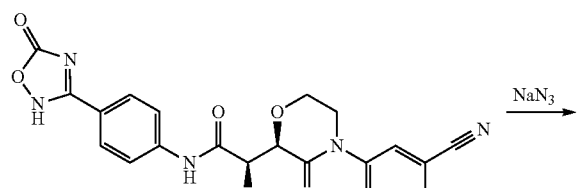

compound 100-1

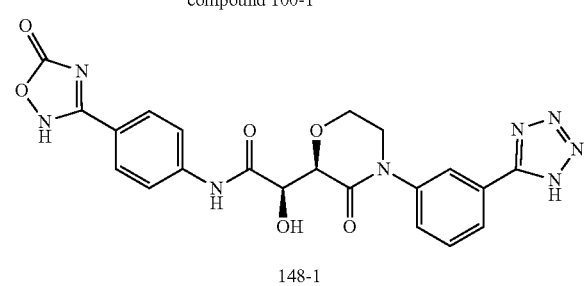

148-1

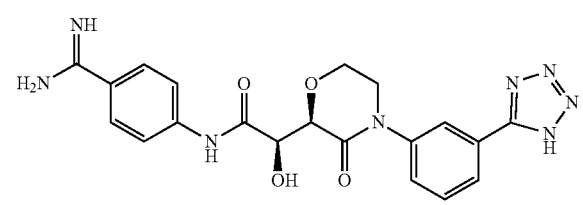

148

Step 148-1

Synthesis of (R)-2-((R)-4-(3-(1H-Tetrazol-5-yl)phenyl)-3-oxomorpholin-2-yl)-2-hydroxy-N-(4-(5-oxo-2,5-dihydro-1,2,4-oxadiazol-3-yl)phenyl)acetamide (Compound 148-1)

To 50 mg of compound 100-1 in 2 mL of dry DMF was added 68 mg (10 eq.) of sodium azide and 56 mg (10 eq.) of ammonium chloride and the mixture heated to 115° C. in a pressure tube for about 16 hours. The reaction mixture was poured onto 1N aq. HCl and extracted three times with ethyl acetate. The combined extracts were washed with brine, dried with magnesium sulfate, filtered and evaporated to dryness yielding about 20 mg of 148-1.

Step 148-2

Synthesis of N-[4-(Aminoiminomethyl)phenyl]-alpha(R)-hydroxy-3-oxo-4-[3-(1h-tetrazol-5-yl)phenyl]-2(R)-morpholineacetamide (example 148)

To about 50 mg of 148-1 in 5 mL of methanol and 3 mL of 1N aq. HCl was added 20 mg of 10% palladium on carbon and the mixture stirred under a balloon of hydrogen gas for two hours. The mixture was filtered and evaporated to dryness. Purification by reversed phase HPLC yielded 18 mg of Example 148.

Example 149

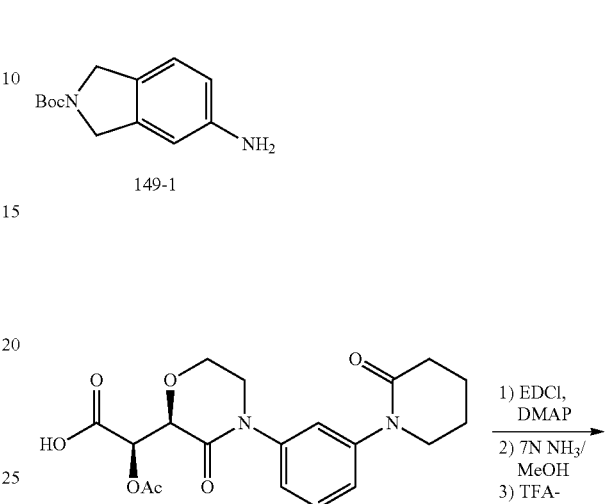

149-1

121-5

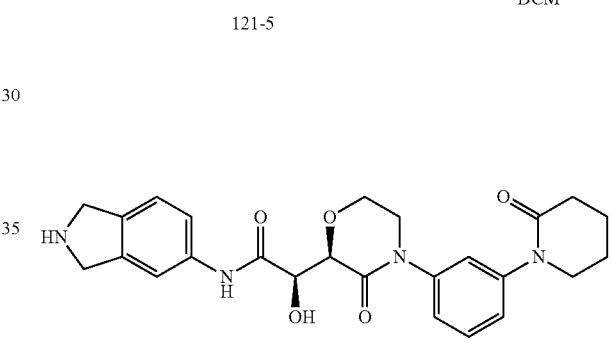

149

Step 149-1

Synthesis of N-(2,3-dihydro-1H-isoindol-5-yl)-alpha(R)-hydroxy-3-oxo-4-[3-(3-oxo-4-morpholinyl)phenyl]-2(R)-morpholineacetamide (EXAMPLE 149)

To 100 mg of 121-5 in about 5 mL of acetonitrile at 0° C. was added 66 mg (1.5 eq.) of 149-1 (WO2005059107(A2, A3)), 64 mg (1.3 eq.) of EDCI and 3 mg (10% mole) of DMAP and the mixture stirred under a balloon of argon for two hours. The reaction mixture was poured onto water and extracted three times with ethyl acetate. The combined extracts were washed with brine, dried with magnesium sulfate, filtered and evaporated to dryness. Purification by flash chromatography yielded 121 mg of amide.

To this was added about 5 mL of 7M ammonia in methanol and the mixture stirred in a flask sealed with a septa for two hours. The reaction mixture was evaporated to dryness and the residue was dissolved in 5 mL of dry DCM. The solution was cooled to 0° C. then 5 mL of trifluoroacetic acid was added and the mixture stirred under a balloon of argon for two hours. The reaction mixture was evaporated to dryness and the residue dissolved in DCM and precipitated from 1N HCl in diethyl ether yielding 71 mg of Example 149 after drying in a vacuum oven.

Example 150

Synthesis of [4-[2(R)-[2-[[4-(Aminoiminomethyl)phenyl]amino]-1(R)-hydroxy-2-oxoethyl]-3-oxo-4-morpholinyl]phenyl]pentafluorosulfur (EXAMPLE 150)

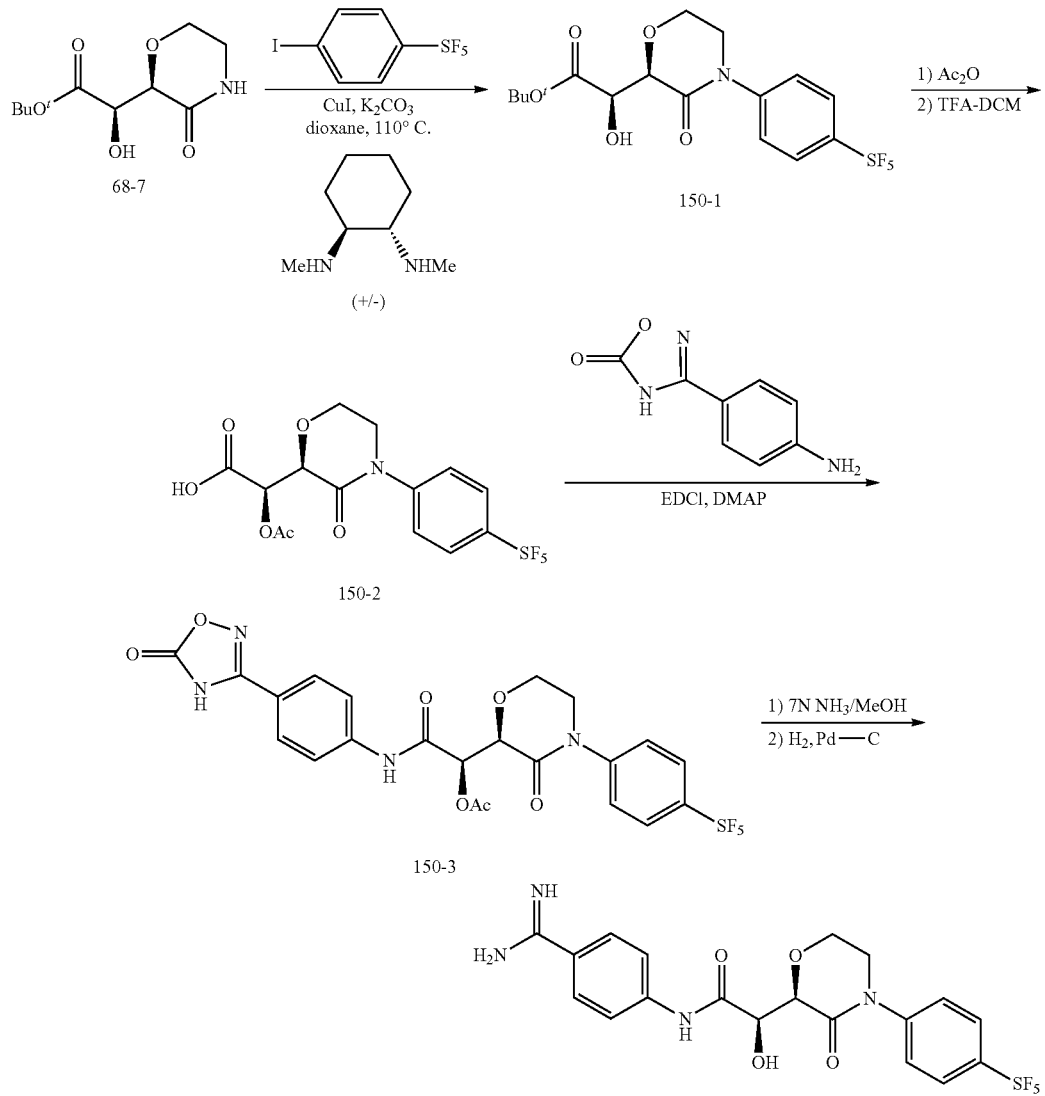

Step 150-1

(R)-tert-Butyl 2-((R)-4-((4-pentafluorosulfur)phenyl)-3-oxomorpholin-2-yl)-2-hydroxyacetate (Compound 150-1)

To a mixture of (R)-tert-butyl 2-hydroxy-2-((R)-3-oxomorpholin-2-yl)acetate (1.0 g, 4.32 mmol), pentafluoro-(4-iodophenyl)-sulfur (6.36 mmol, 1.5 eq.), powdered potassium carbonate (1.2 g, 8.68 mmol, 2 eq.) in 30 ml dioxane was added copper(I) iodide (83 mg, 0.436 mmol, 0.1 eq.) followed by trans-N,N'-dimethylcyclohexane-1,2-diamine (140 microl, 0.886 mmol, 0.2 eq.). The mixture was degassed by bubbling with argon and heated in a sealed tube 110° C. for about 10 hr. It was filtered through a CELITE pad, rinsed with ethyl acetate, concentrated and purified by chromatography eluting with a mixture of ethyl acetate-dichloromethane-hexane (1:1:3 v/v/v) to provide 1.20 g of 150-1

Step 150-2

Synthesis of (R)-2-Acetoxy-2-((R)-4-((4-pentafluorosulfur)phenyl)-3-oxomorpholin-2-yl)acetic acid (Compound 150-2)

To a solution of 150-1 (420 mg, 0.97 mmol), DMAP (12 mg, 0.098 mmol, 0.1 eq.) and pyridine (160 microl, 1.98 mmol, 2 eq.) in 10 ml dichloromethane at 0° C. was added acetic anhydride (185 microl, 1.96 mmol, 2 eq.). The mixture was stirred for 2.5 hr, diluted with ethyl acetate, washed with aqueous copper sulfate, water and brine, dried over $MgSO_4$, filtered and concentrated to provide 480 mg of the acylated product. The above product was stirred with 5 ml each of dichloromethane and trifluoroacetic acid at rt for 1 hr, added toluene and concentrated to dryness. It was evaporated once more time from toluene then twice from ether to provide 460 mg (>theoretical yield due to the presence of some solvent) of 150-2.

Step 150-3

Synthesis of (R)-1-((R)-4-((4-pentafluorosulfur)phenyl)-3-oxomorpholin-2-yl)-2-oxo-2-(4-(5-oxo-4,5-dihydro-1,2,4-oxadiazol-3-yl)phenylamino)ethyl acetate (Compound 150-3)

To solution of 150-2 (250 mg, 0.596 mmol), 3-(4-aminophenyl)-1,2,4-oxadiazol-5(4H)-one (160 mg, 0.903 mmol, 1.5 eq.), DMAP (7.3 mg, 0.050 mmol, 0.1 eq.) in 5 ml acetonitrile at 0° C. was added EDCI (150 mg 0.782 mmol, 1.3 eq.) and stirred for 2.5 hr. It was diluted with ethyl acetate, washed with aq. NaHCO₃, water, and brine, dried over MgSO₄, filtered, concentrated and purified by chromatography eluting with 5% methanol in dichloromethane to provide 225 mg of 150-3.

Step 150-4

Synthesis of [4-[2(R)-[2-[[4-(Aminoiminomethyl)phenyl]amino]-1(R)-hydroxy-2-oxoethyl]-3-oxo-4-morpholinyl]phenyl]pentafluorosulfur (EXAMPLE 150)

A solution of 150-3 (225 mg) in 10 ml of a 7N ammonia in methanol was stirred at it for 1 hr and concentrated to dryness. To this was added 210 mg of 10% Pd—C, 6 ml each of methanol and 1N hydrochloric acid. The suspension was stirred under a hydrogen balloon for 2 hr, filtered through a CELITE pad, concentrated and purified by RPHPLC to provide 130 mg of EXAMPLE 150 as the hydrochloride salt.

Example 151

Synthesis of [3-[2(R)-[2-[[4-(Aminoiminomethyl)phenyl]amino]-1(R)-hydroxy-2-oxoethyl]-oxo-4-morpholinyl]phenyl]pentafluorosulfur (EXAMPLE 151)

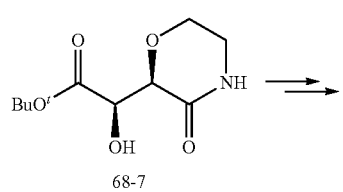
68-7

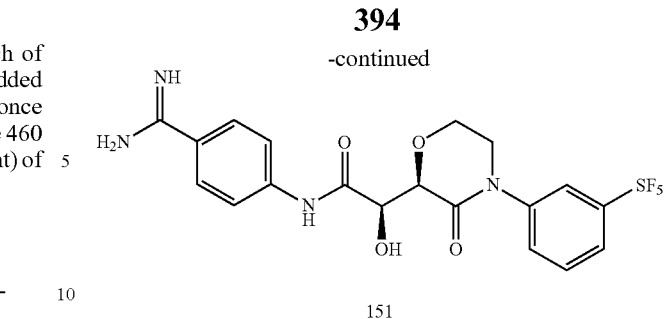
151

EXAMPLE 151 was prepared using a procedure similar to the preparation of EXAMPLE 150.

Example 152

Synthesis of (2R)—N-(4-amidinophenyl)-2-hydroxy-2-[(2R)-3-oxo-4-(4-(1,1-dioxothiomorpholin-4-ylcarbonyl)phenyl)morpholin-2-yl]acetamide (EXAMPLE 152)

Synthesis of 4-[(4-iodophenyl)carbonyl]thiomorpholine-1,1-dione 152-1

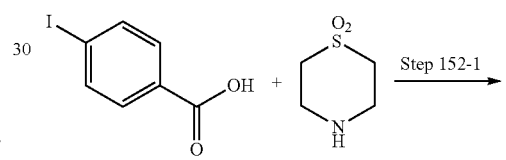

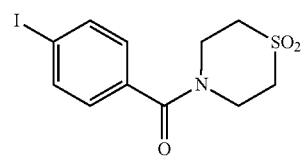
152-1

Step 152-1

According to Step 77-1 in the synthetic method for compound 77, 4-iodobenzoic acid and thiomorpholine-1,1-dione were used to obtain compound 152-1.

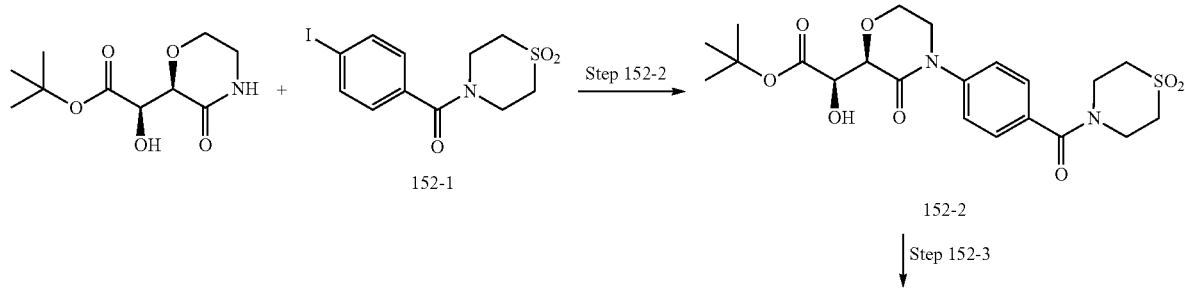
152-2

Step 152-3

395
396
-continued
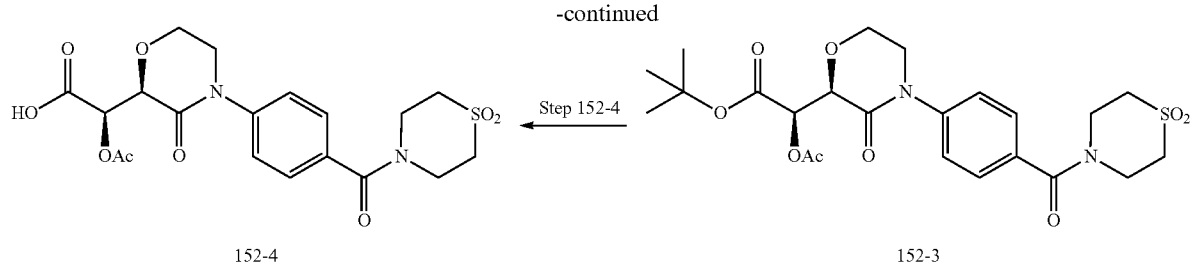
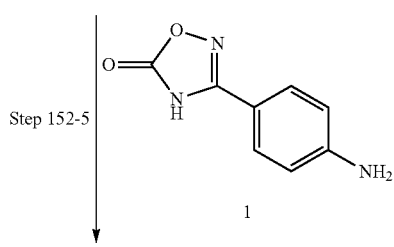
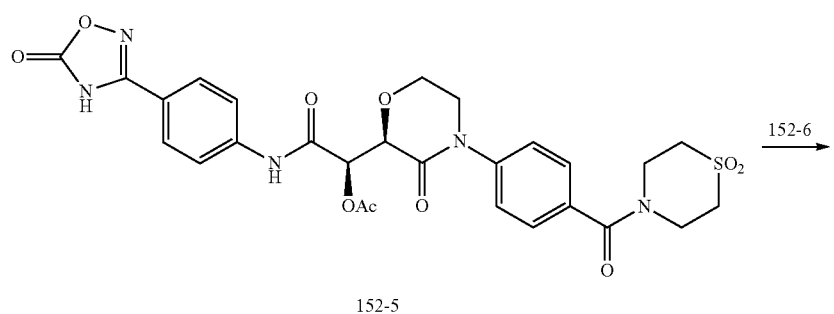
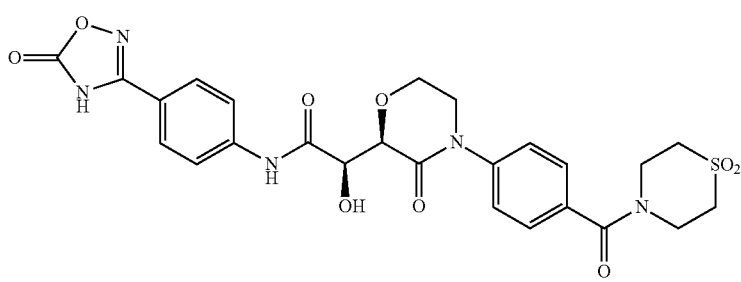
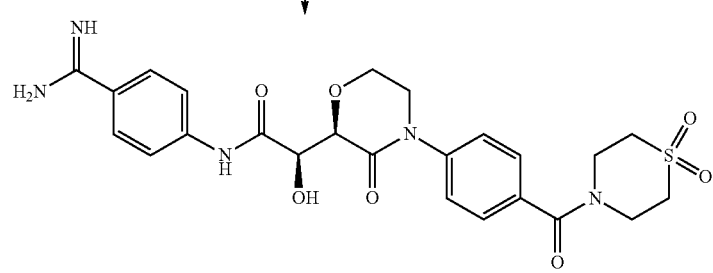
EXAMPLE 152

Step 152-2

According to Step 78-2 in the synthetic method for EXAMPLE 78, compound 152-1 (348 mg, 0.95 mmol) was used instead of compound 78-1 to obtain compound 152-2 (232 mg, 0.50 mmol).

Step 152-3

According to Step 78-3 in the synthetic method for EXAMPLE 78, compound 152-2 (232 mg, 0.50 mmol) was used instead of compound 78-2 to obtain compound 152-3 (242 mg, 0.47 mmol).

Step 152-4

According to Step 78-3 in the synthetic method for EXAMPLE 78, compound 152-2 (242 mg, 0.47 mmol) was used instead of compound 78-2 to obtain compound 152-3 (0.47 mmol) which was used in the next step without further purification.

Step 152-4

According to Step 78-4 in the synthetic method for EXAMPLE 78, compound 152-3 (0.47 mmol) was used instead of compound 78-3 to obtain compound 152-4 (0.47 mmol).

Step 152-5

According to Step 78-5 in the synthetic method for EXAMPLE 78, compound 152-4 (0.47 mmol) was used instead of compound 78-4 to obtain compound 152-5 (0.47 mmol) which was used in the next step without further purification.

Step 152-6

According to Step 78-6 in the synthetic method for EXAMPLE 78, compound 152-5 (0.47 mmol) was used instead of compound 78-5 to obtain EXAMPLE 152 (206 mg, 0.39 mmol) as a white amorphous solid.

Example 153

Synthesis of (2R)—N-(4-amidinophenyl)-2-hydroxy-2-[(2R)-3-oxo-4-(4-(dimethylaminocarbonyl)phenyl)morpholin-2-yl]acetamide (EXAMPLE 153)

Synthesis of 4-iodo-N,N-dimethylbenzamide 153-1

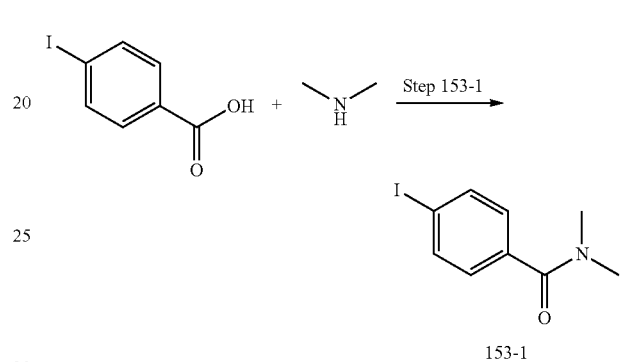

Step 153-1

According to Step 77-1 in the synthetic method for compound 77, 4-iodobenzoic acid and dimethylamine were used to obtain compound 153-1.

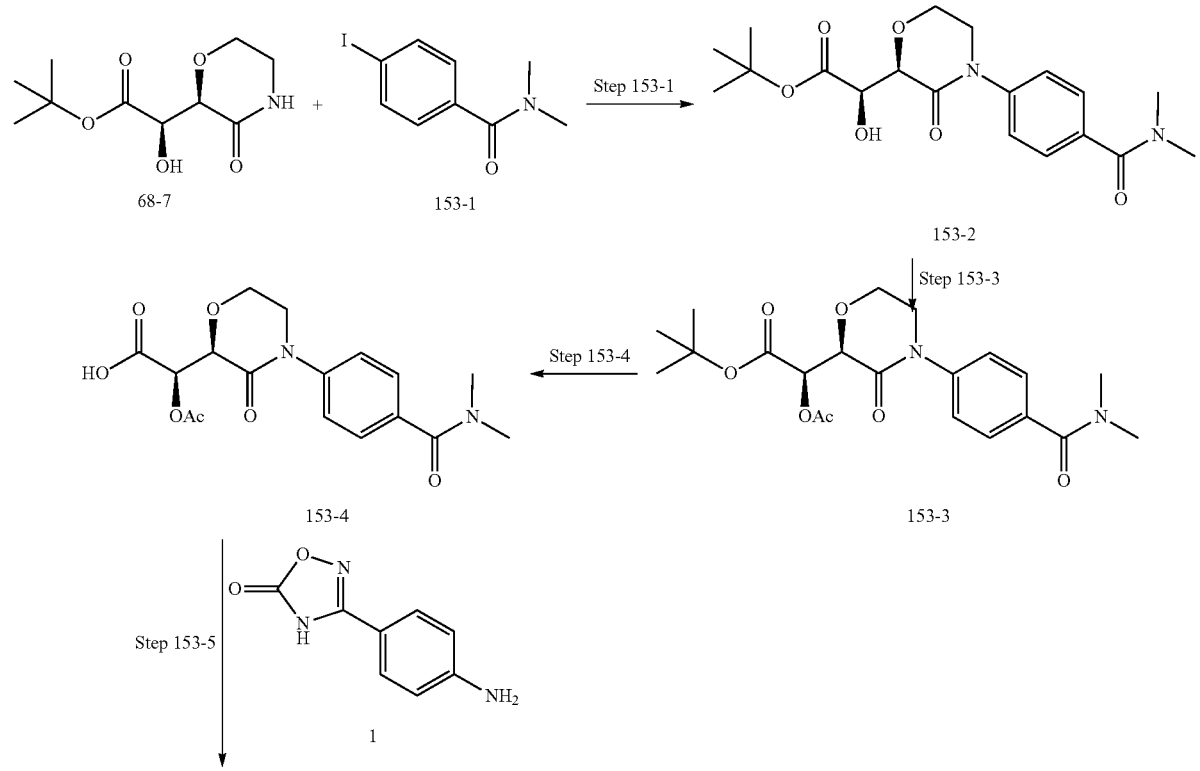

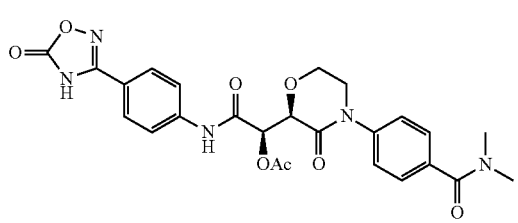

153-5

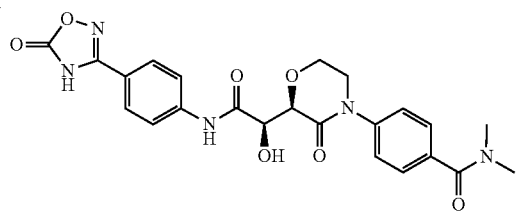

153-6

Step 153-6

-continued

Step 153-7

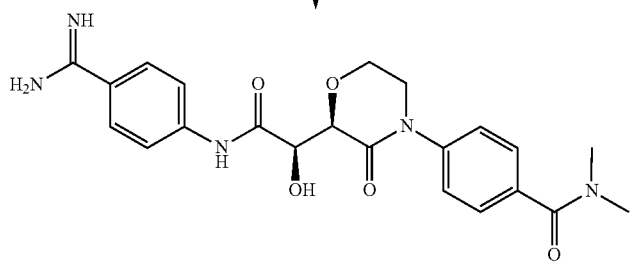

EXAMPLE 153

Step 153-2

According to Step 78-2 in the synthetic method for EXAMPLE 78, compound 153-1 (244 mg, 0.89 mmol) was used instead of compound 78-1 to obtain compound 153-2 (181 mg, 0.48 mmol).

Step 153-3

According to Step 78-3 in the synthetic method for EXAMPLE 78, compound 153-2 (181 mg, 0.48 mmol) was used instead of compound 78-2 to obtain compound 153-3 (80 mg, 0.19 mmol).

Step 153-4

According to Step 78-4 in the synthetic method for EXAMPLE 78, compound 153-3 (80 mg, 0.19 mmol) was used instead of compound 78-3 to obtain compound 153-4 (0.19 mmol) which was used in the next step without further purification.

Step 153-5

According to Step 78-5 in the synthetic method for EXAMPLE 78, compound 153-4 (0.19 mmol) was used instead of compound 78-4 to obtain compound 153-5 (77 mg, 0.15 mmol).

Step 153-6

According to Step 78-6 in the synthetic method for EXAMPLE 78, compound 153-5 (77 mg, 0.15 mmol) was used instead of compound 78-5 to obtain compound 153-6 (0.15 mmol) which was used in the next step without further purification.

Step 153-7

According to Step 78-7 in the synthetic method for EXAMPLE 78, compound 153-6 (0.15 mmol) was used instead of compound 78-6 to obtain EXAMPLE 153 (62 mg, 0.14 mmol) as a white amorphous solid.

Example 154

Synthesis of (2R)—N-(4-amidinophenyl)-2-hydroxy-2-[(2R)-3-oxo-4-(4-(dimethylaminolsulfonyl)phenyl)morpholin-2-yl]acetamide (EXAMPLE 154)

Synthesis of 4-iodo-N,N-dimethylbenzenesulfonamide 154-1

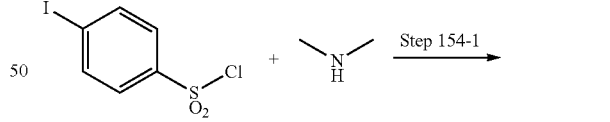

154-1

Step 154-1

According to Step 78-1 in the synthetic method for compound 78-1, 4-iodobenzenesulfonyl chloride and dimethylamine were used to obtain compound 154-1.

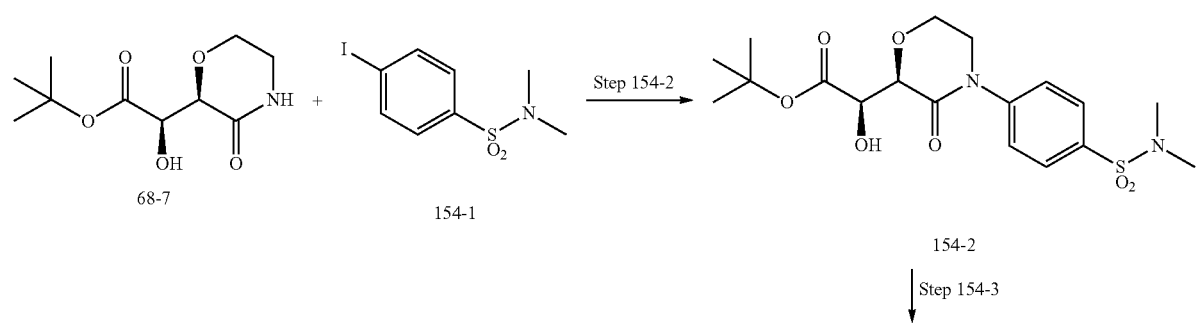
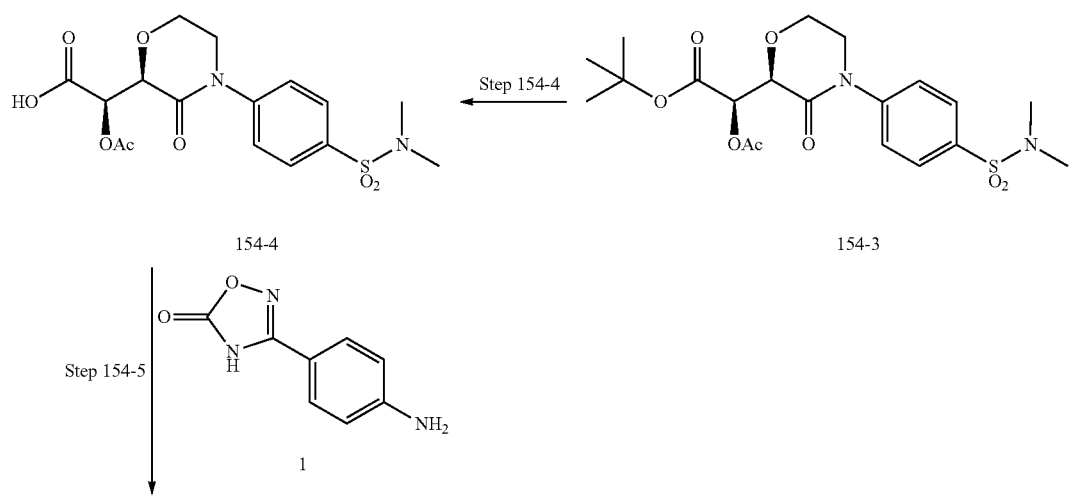
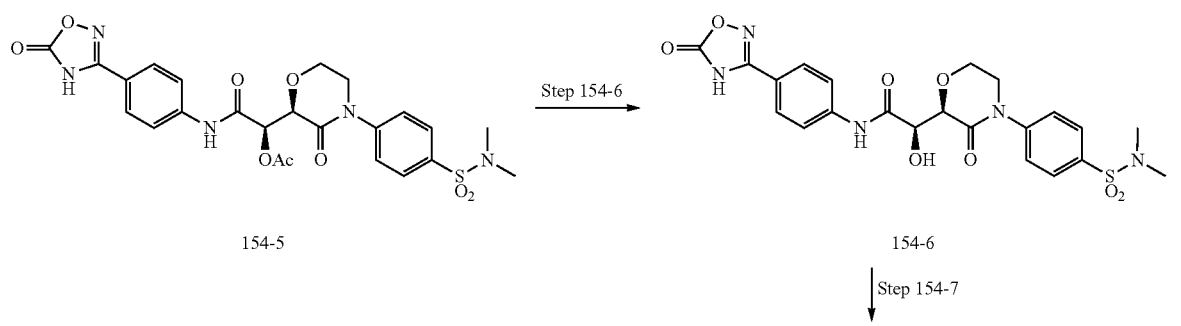
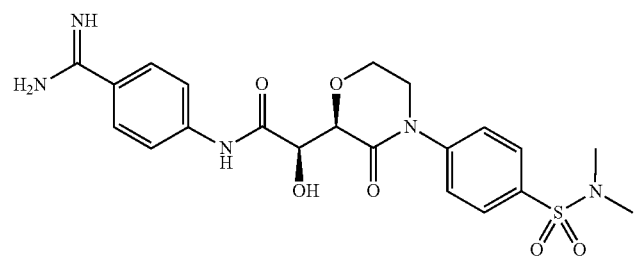
EXAMPLE 154

Step 154-2

According to Step 78-2 in the synthetic method for EXAMPLE 78, compound 154-1 (222 mg, 0.71 mmol) was used instead of compound 78-1 to obtain compound 154-2 (147 mg, 0.36 mmol).

Step 154-3

According to Step 78-3 in the synthetic method for EXAMPLE 78, compound 154-2 (147 mg, 0.36 mmol) was used instead of compound 78-2 to obtain compound 154-3 (131 mg, 0.29 mmol).

Step 154-4

According to Step 78-4 in the synthetic method for EXAMPLE 78, compound 154-3 (131 mg, 0.29 mmol) was used instead of compound 78-3 to obtain compound 154-4 (0.29 mmol) which was used in the next step without further purification.

Step 154-5

According to Step 78-5 in the synthetic method for EXAMPLE 78, compound 154-4 (0.29 mmol) was used instead of compound 78-4 to obtain compound 154-5 (120 mg, 0.21 mmol).

Step 154-6

According to Step 78-6 in the synthetic method for EXAMPLE 78, compound 154-5 (120 mg, 0.21 mmol) was used instead of compound 78-5 to obtain compound 154-6 (0.21 mmol) which was used in the next step without further purification.

Step 154-7

According to Step 78-7 in the synthetic method for EXAMPLE 78, compound 154-6 (0.21 mmol) was used instead of compound 78-6 to obtain EXAMPLE 154 (41 mg, 0.086 mmol) as a white amorphous solid.

Example 155

Synthesis of (2R)—N-(4-amidinophenyl)-2-hydroxy-2-[(2R)-3-oxo-4-(3-(dimethylaminocarbonyl)phenyl)morpholin-2-yl]acetamide (EXAMPLE 155)

Synthesis of 3-iodo-N,N-dimethylbenzamide 155-1

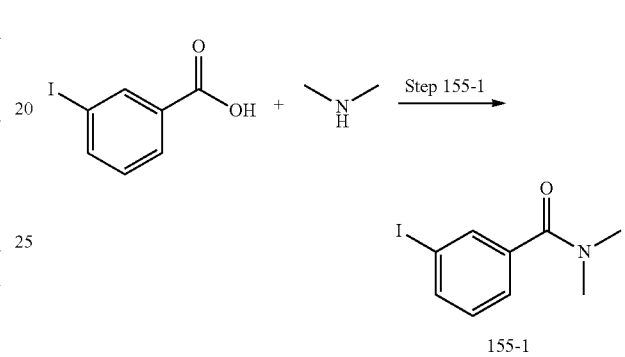

Step 155-1

According to Step 77-1 in the synthetic method for compound 77, 3-iodobenzoic acid and dimethylamine were used to obtain compound 155-1.

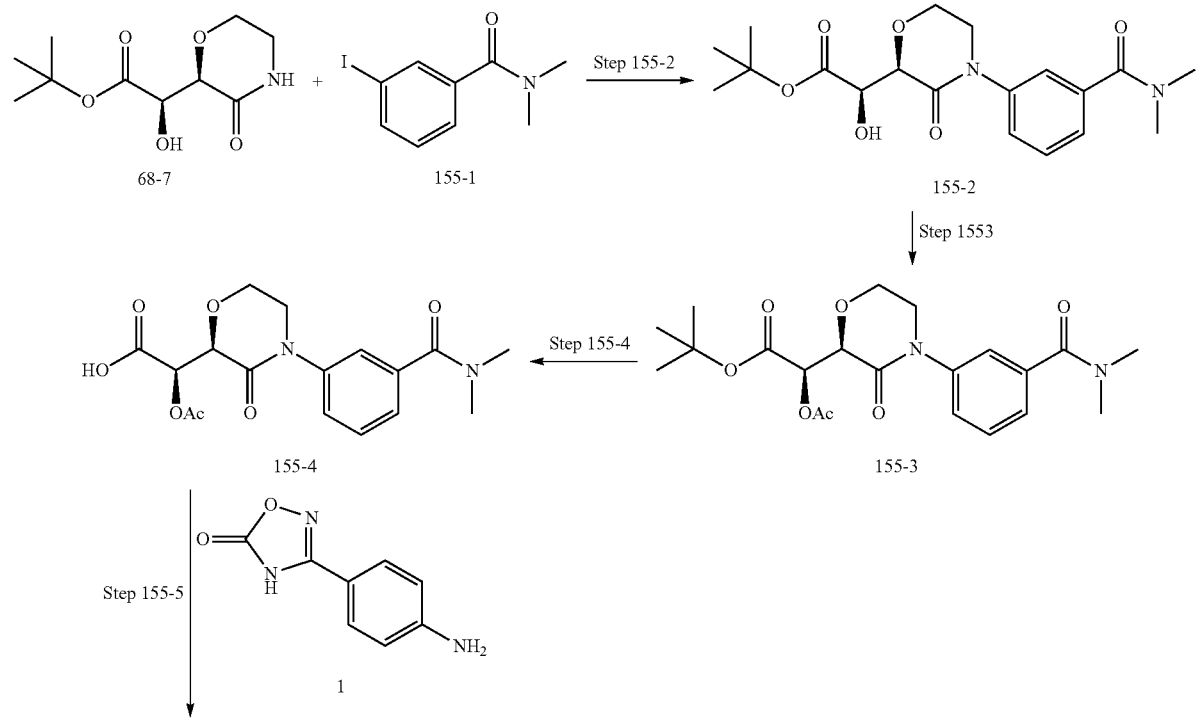

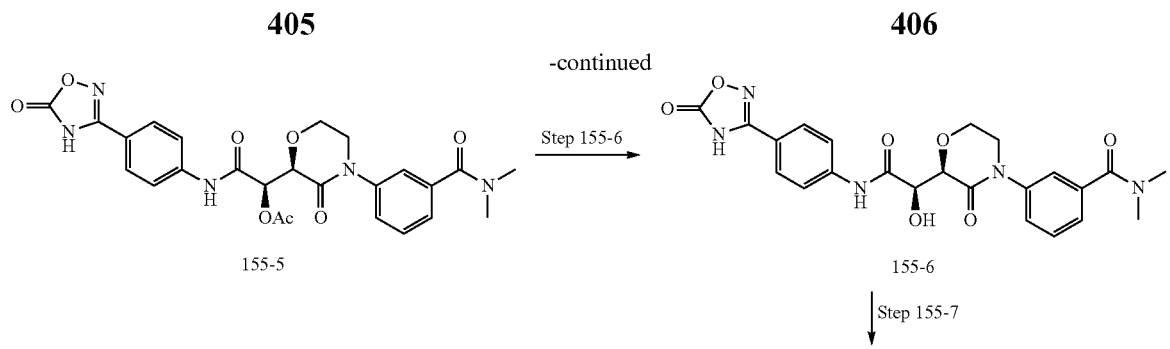

155-5

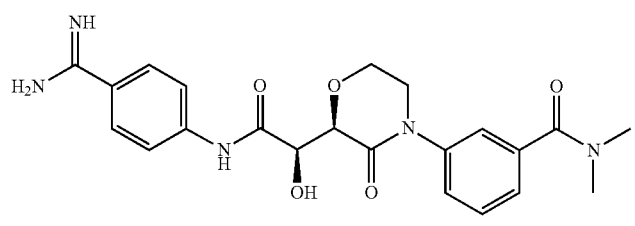

EXAMPLE 155

Step 155-2

According to Step 78-2 in the synthetic method for EXAMPLE 78, compound 155-1 (196 mg, 0.71 mmol) was used instead of compound 78-1 to obtain compound 155-2 (156 mg, 0.41 mmol).

Step 155-3

According to Step 78-3 in the synthetic method for EXAMPLE 78, compound 155-2 (156 mg, 0.41 mmol) was used instead of compound 78-2 to obtain compound 155-3 (0.41 mmol).

Step 155-4

According to Step 78-4 in the synthetic method for EXAMPLE 78, compound 155-3 (0.41 mmol) was used instead of compound 78-3 to obtain compound 155-4 (0.41 mmol) which was used in the next step without further purification.

Step 155-5

According to Step 78-5 in the synthetic method for EXAMPLE 78, compound 155-4 (0.41 mmol) was used instead of compound 78-4 to obtain compound 155-5 (171 mg, 0.33 mmol).

Step 155-6

According to Step 78-6 in the synthetic method for EXAMPLE 78, compound 155-5 (171 mg, 0.33 mmol) was used instead of compound 78-5 to obtain compound 155-6 (0.33 mmol) which was used in the next step without further purification.

Step 155-7

According to Step 78-7 in the synthetic method for EXAMPLE 78, compound 155-6 (0.33 mmol) was used instead of compound 78-6 to obtain EXAMPLE 155 (143 mg, 0.33 mmol) as a white amorphous solid. Synthesis of 4-[(2-fluoro-5-iodophenyl)carbonyl]morpholine 173-1

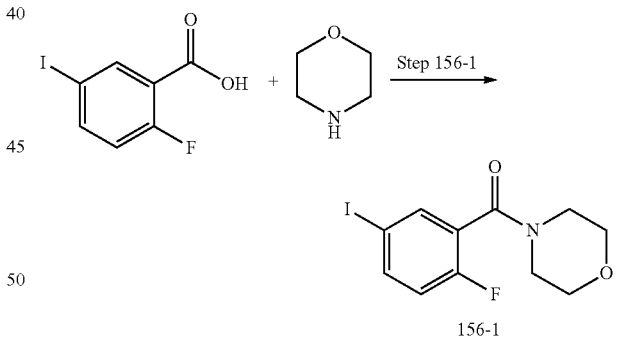

Example 156

Synthesis of (2R)—N-(4-amidinophenyl)-2-hydroxy-2-[(2R)-3-oxo-4-(4-fluoro-3-(morpholin-4-ylcarbonyl)phenyl)morpholin-2-yl]acetamide (EXAMPLE 156)

Step 156-1

According to Step 77-1 in the synthetic method for compound 77, 2-fluoro-5-iodobenzoic acid and morpholine were used to obtain compound 156-1.

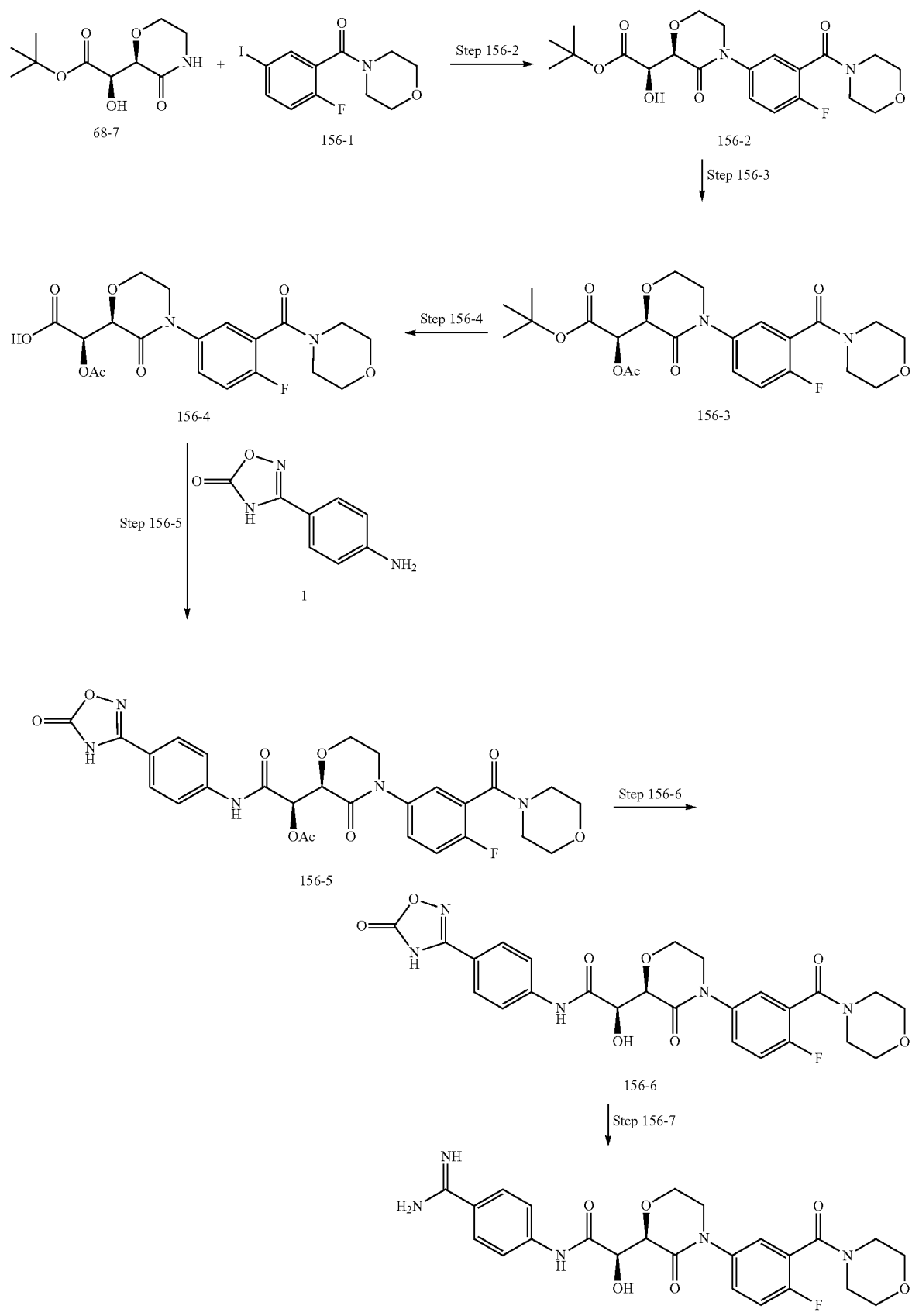

Step 156-2

According to Step 78-2 in the synthetic method for EXAMPLE 78, compound 156-1 (287 mg, 0.86 mmol) was used instead of compound 78-1 to obtain compound 156-2 (251 mg, 0.57 mmol).

Step 156-3

According to Step 78-3 in the synthetic method for EXAMPLE 78, compound 156-2 (287 mg, 0.57 mmol) was used instead of compound 78-2 to obtain compound 156-3 (0.57 mmol).

Step 156-4

According to Step 78-4 in the synthetic method for EXAMPLE 78, compound 156-3 (0.57 mmol) was used instead of compound 78-3 to obtain compound 156-4 (0.57 mmol) which was used in the next step without further purification.

Step 156-5

According to Step 78-5 in the synthetic method for EXAMPLE 78, compound 156-4 (0.57 mmol) was used instead of compound 78-4 to obtain compound 156-5 (289 mg, 0.50 mmol).

Step 156-6

According to Step 78-6 in the synthetic method for EXAMPLE 78, compound 156-5 (289 mg, 0.50 mmol) was used instead of compound 78-5 to obtain compound 156-6 (0.50 mmol) which was used in the next step without further purification.

Step 156-7

According to Step 78-7 in the synthetic method for EXAMPLE 78, compound 156-6 (0.50 mmol) was used instead of compound 78-6 to obtain EXAMPLE 156 (242 mg, 0.48 mmol) as a white amorphous solid.

Example 157

Synthesis of (2R)—N-(4-amidinophenyl)-2-hydroxy-2-[(2R)-3-oxo-4-(4-(dimethyl-$D_6$-aminocarbonyl)phenyl)morpholin-2-yl]acetamide (EXAMPLE 157)

Step 157-1

Synthesis of 4-iodo-N,N-dimethyl-$D_6$-benzmide 157-1

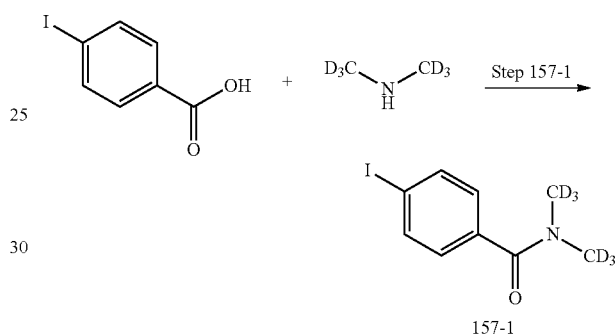

According to Step 77-1 in the synthetic method for compound 77, 4-iodobenzoic acid and dimethyl-$D_6$-amine were used to obtain compound 157-1.

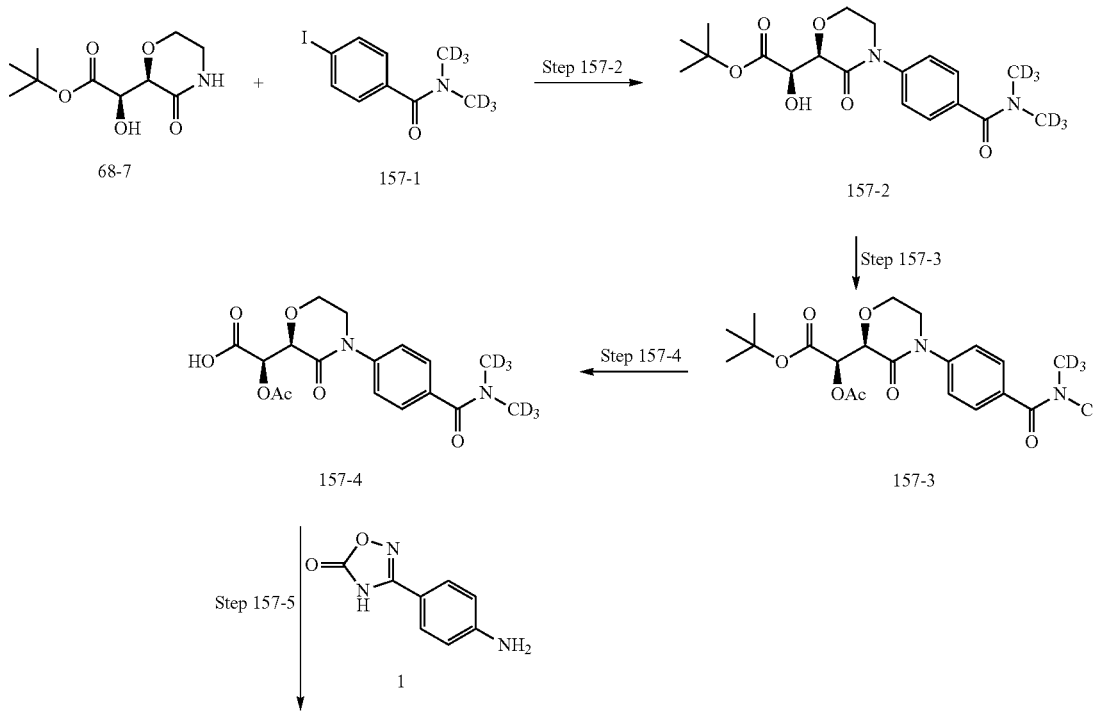

411 412

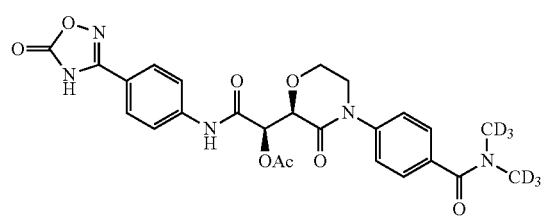

157-5

-continued

Step 157-6

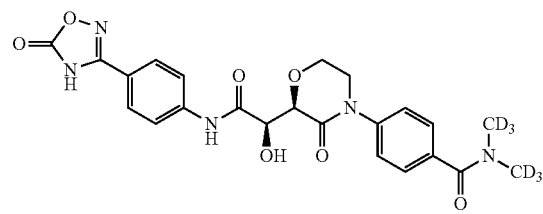

157-6

Step 157-7

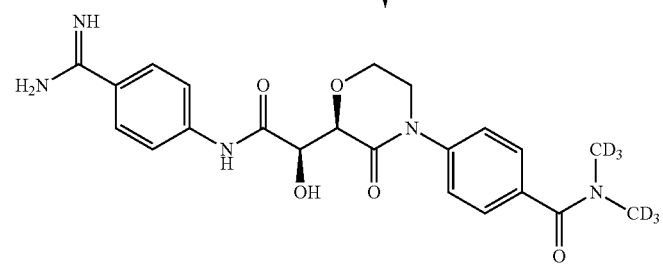

EXAMPLE 157

Step 157-2

According to Step 78-2 in the synthetic method for EXAMPLE 78, compound 157-1 (134 mg, 0.48 mmol) was used instead of compound 78-1 to obtain compound 157-2 (100 mg, 0.26 mmol).

Step 157-3

According to Step 78-3 in the synthetic method for EXAMPLE 78, compound 157-2 (100 mg, 0.26 mmol) was used instead of compound 78-2 to obtain compound 157-3 (106 mg, 0.25 mmol).

Step 157-4

According to Step 78-4 in the synthetic method for EXAMPLE 78, compound 157-3 (106 mg, 0.25 mmol) was used instead of compound 78-3 to obtain compound 157-4 (0.25 mmol) which was used in the next step without further purification.

Step 157-5

According to Step 78-5 in the synthetic method for EXAMPLE 78, compound 157-4 (0.25 mmol) was used instead of compound 78-4 to obtain compound 157-5 (0.25 mmol).

Step 157-6

According to Step 78-6 in the synthetic method for EXAMPLE 78, compound 157-5 (0.25 mmol) was used instead of compound 78-5 to obtain compound 157-6 (0.25 mmol) which was used in the next step without further purification.

Step 157-7

According to Step 78-7 in the synthetic method for EXAMPLE 78, compound 157-6 (0.25 mmol) was used instead of compound 78-6 to obtain EXAMPLE 157 (89 mg, 0.20 mmol) as a white amorphous solid.

Example 158

Synthesis of (2R)—N-(4-amidinophenyl)-2-hydroxy-2-[(2R)-3-oxo-4-(3-(dimethyl-$D_6$-aminocarbonyl)phenyl)morpholin-2-yl]acetamide (EXAMPLE 158)

Synthesis of 3-iodo-N,N-dimethyl-$D_6$-benzmide 158-1

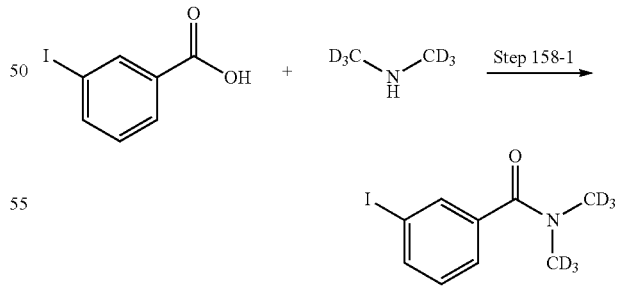

158-1

Step 158-1

According to Step 77-1 in the synthetic method for compound 77, 3-iodobenzoic acid and dimethyl-$D_6$-amine were used to obtain compound 158-1.

413 414
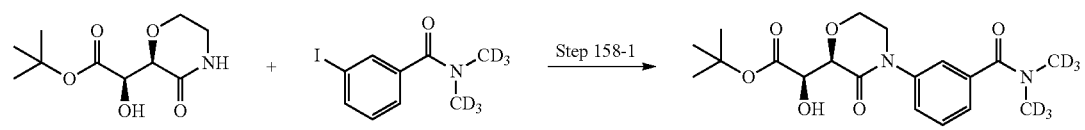
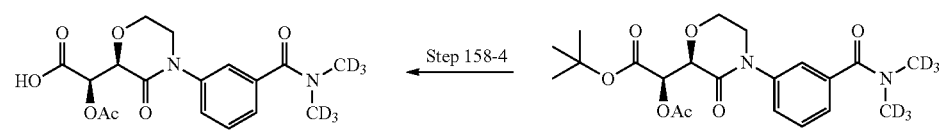
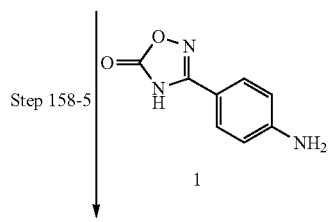
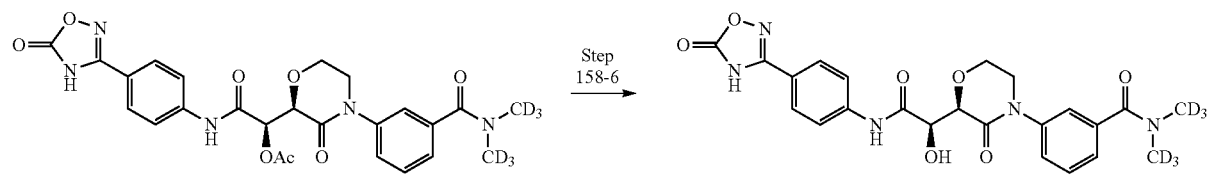
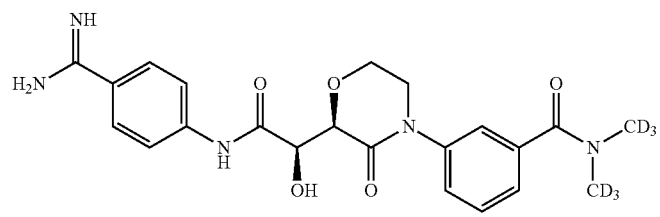
EXAMPLE 158

Step 158-2

According to Step 78-2 in the synthetic method for EXAMPLE 78, compound 158-1 (134 mg, 0.48 mmol) was used instead of compound 78-1 to obtain compound 158-2 (122 mg, 0.32 mmol).

Step 158-3

According to Step 78-3 in the synthetic method for EXAMPLE 78, compound 158-2 (122 mg, 0.32 mmol) was used instead of compound 78-2 to obtain compound 158-3 (130 mg, 0.31 mmol).

Step 158-4

According to Step 78-4 in the synthetic method for EXAMPLE 78, compound 158-3 (130 mg, 0.31 mmol) was used instead of compound 78-3 to obtain compound 158-4 (0.31 mmol) which was used in the next step without further purification.

Step 158-5

According to Step 78-5 in the synthetic method for EXAMPLE 78, compound 158-4 (0.31 mmol) was used instead of compound 78-4 to obtain compound 158-5 (72 mg, 0.14 mmol).

Step 158-6

According to Step 78-6 in the synthetic method for EXAMPLE 78, compound 158-5 (72 mg, 0.14 mmol) was used instead of compound 78-5 to obtain compound 158-6 (0.14 mmol) which was used in the next step without further purification.

Step 158-7

According to Step 78-7 in the synthetic method for EXAMPLE 78, compound 158-6 (0.14 mmol) was used instead of compound 78-6 to obtain EXAMPLE 158 (56 mg, 0.13 mmol) as a white amorphous solid.

Example 159

Synthesis of (2R)—N-(4-amidinophenyl)-2-hydroxy-2-[(2R)-3-oxo-4-(3-(dimethylaminocarbonyl)-4-fluorophenyl)morpholin-2-yl]acetamide (EXAMPLE 159)

Synthesis of 2-fluoro-5-iodo-N,N-dimethylbenzamide 159-1

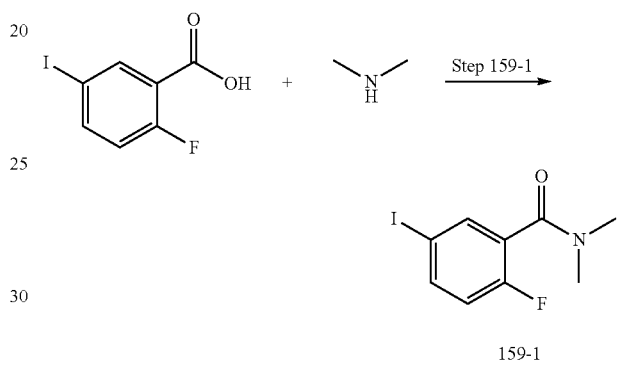

Step 159-1

According to Step 77-1 in the synthetic method for compound 77, 2-fluoro-5-iodobenzoic acid and dimethylamine were used to obtain compound 159-1.

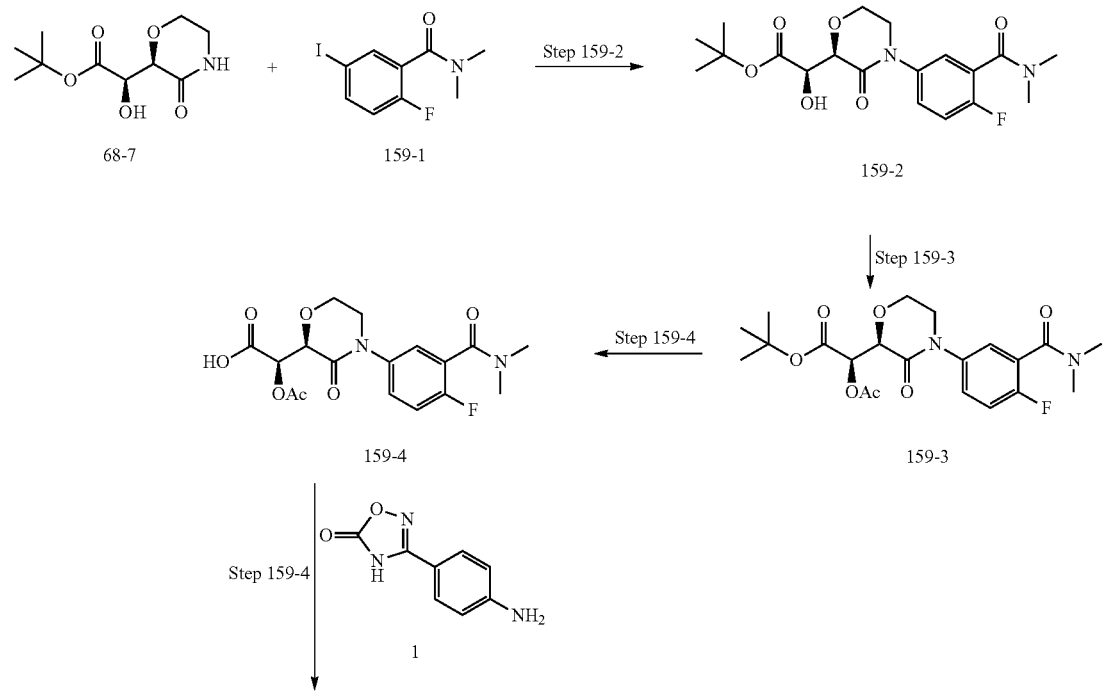

417

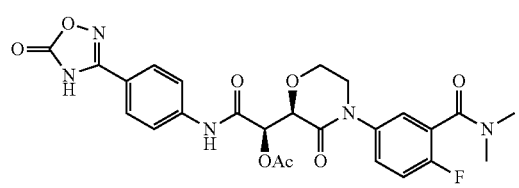

159-5

418

-continued

Step 159-6

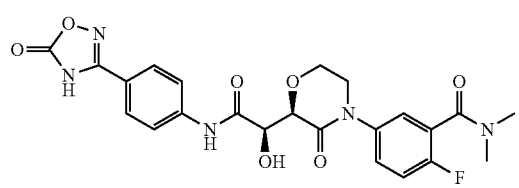

159-6

Step 159-7

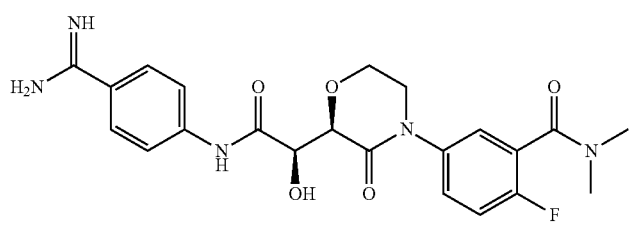

EXAMPLE 159

Step 159-2

According to Step 78-2 in the synthetic method for EXAMPLE 78, compound 159-1 (209 mg, 0.71 mmol) was used instead of compound 78-1 to obtain compound 159-2 (171 mg, 0.43 mmol).

Step 159-3

According to Step 78-3 in the synthetic method for EXAMPLE 78, compound 159-2 (171 mg, 0.43 mmol) was used instead of compound 78-2 to obtain compound 159-3 (0.43 mmol).

Step 159-4

According to Step 78-4 in the synthetic method for EXAMPLE 78, compound 159-3 (0.43 mmol) was used instead of compound 78-3 to obtain compound 159-4 (0.43 mmol) which was used in the next step without further purification.

Step 159-5

According to Step 78-5 in the synthetic method for EXAMPLE 78, compound 159-4 (0.43 mmol) was used instead of compound 78-4 to obtain compound 159-5 (170 mg, 0.31 mmol).

Step 159-6

According to Step 78-6 in the synthetic method for EXAMPLE 78, compound 159-5 (170 mg, 0.31 mmol) was used instead of compound 78-5 to obtain compound 159-6 (0.31 mmol) which was used in the next step without further purification.

Step 159-7

According to Step 78-7 in the synthetic method for EXAMPLE 78, compound 159-6 (0.31 mmol) was used instead of compound 78-6 to obtain EXAMPLE 159 (131 mg, 0.29 mmol) as a white amorphous solid.

Example 160

Synthesis of (2R)—N-(4-amidinophenyl)-2-hydroxy-2-[(2R)-3-oxo-4-(4-methoxy-D₃-phenyl)morpholin-2-yl]acetamide (EXAMPLE 160)

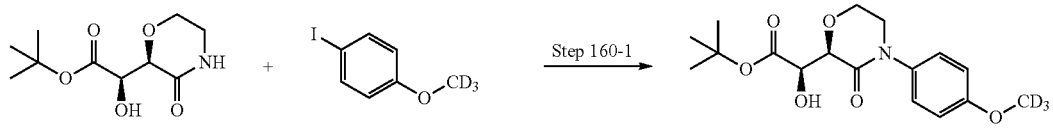

Step 160-2

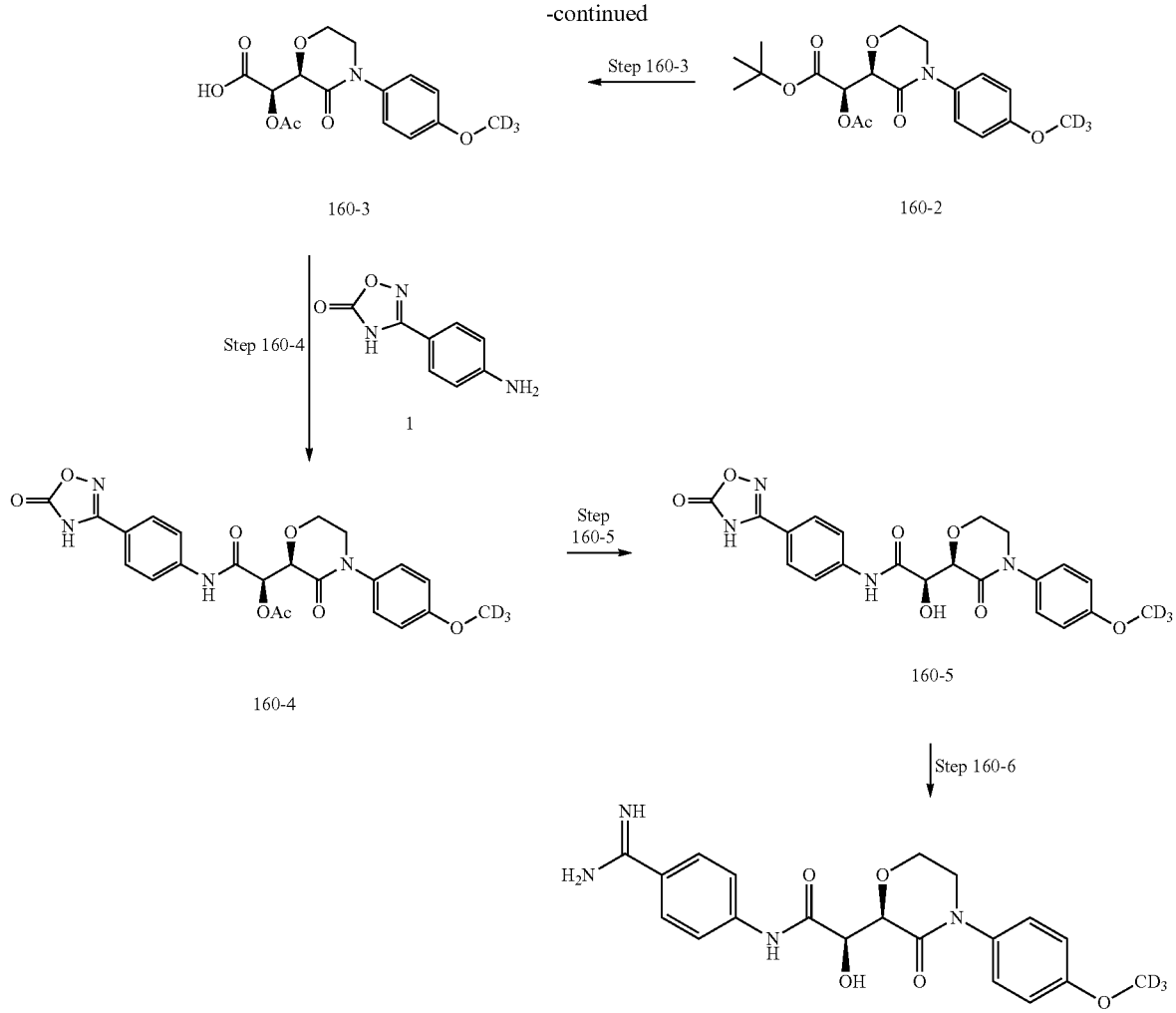

EXAMPLE 160

Step 160-1

According to Step 78-2 in the synthetic method for EXAMPLE 78, compound 2 (169 mg, 0.71 mmol) was used instead of compound 78-1 to obtain compound 160-1 (103 mg, 0.30 mmol).

Step 160-2

According to Step 78-3 in the synthetic method for EXAMPLE 78, compound 160-1 (103 mg, 0.30 mmol) was used instead of compound 78-2 to obtain compound 160-2 (112 mg, 0.29 mmol).

Step 160-3

According to Step 78-4 in the synthetic method for EXAMPLE 78, compound 160-2 (112 mg, 0.29 mmol) was used instead of compound 78-3 to obtain compound 160-3 (0.29 mmol) which was used in the next step without further purification.

Step 160-4

According to Step 78-5 in the synthetic method for EXAMPLE 78, compound 160-3 (0.29 mmol) was used instead of compound 78-3 to obtain compound 160-4 (44 mg, 0.091 mmol).

Step 160-5

According to Step 78-6 in the synthetic method for EXAMPLE 78, compound 160-4 (44 mg, 0.091 mmol) was used instead of compound 78-5 to obtain compound 160-5 (0.091 mmol) which was used in the next step without further purification.

Step 160-6

According to Step 78-7 in the synthetic method for EXAMPLE 78, compound 160-5 (0.091 mmol) was used instead of compound 78-6 to obtain EXAMPLE 160 (30 mg, 0.075 mmol) as a white amorphous solid.

Example 161
Synthesis of (2R)—N-(4-amidinophenyl)-2-hydroxy-2-[(2R)-3-oxo-4-(3-methoxy-D₃-phenyl)morpholin-2-yl]acetamide (EXAMPLE 161)
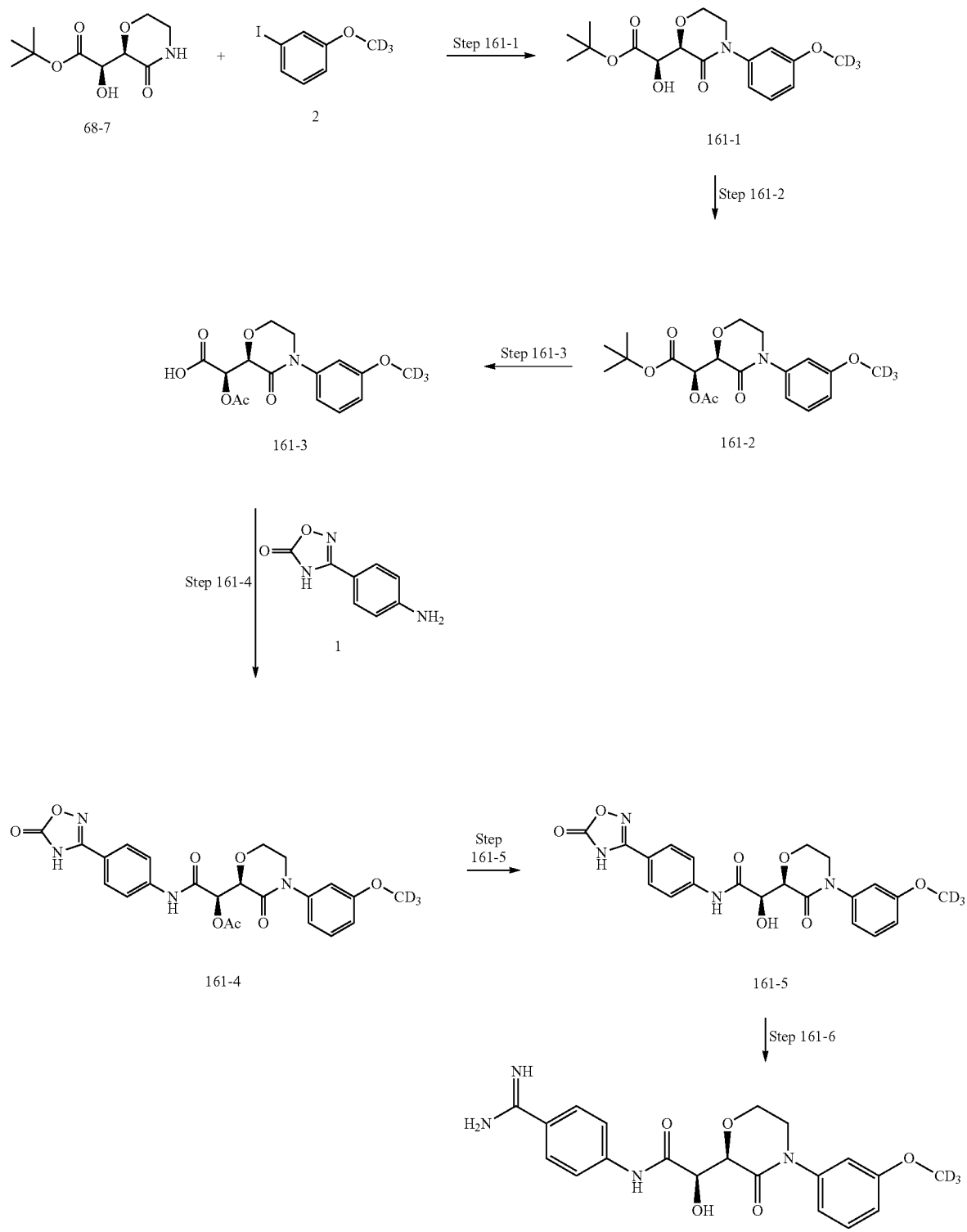

Step 161-1

According to Step 78-2 in the synthetic method for EXAMPLE 78, compound 2 (169 mg, 0.71 mmol) was used instead of compound 78-1 to obtain compound 161-1 (95 mg, 0.25 mmol).

Step 161-2

According to Step 78-3 in the synthetic method for EXAMPLE 78, compound 161-1 (95 mg, 0.25 mmol) was used instead of compound 78-2 to obtain compound 161-2 (0.25 mmol).

Step 161-3

According to Step 78-4 in the synthetic method for EXAMPLE 78, compound 161-2 (0.25 mmol) was used instead of compound 78-3 to obtain compound 161-3 (0.25 mmol) which was used in the next step without further purification.

Step 161-4

According to Step 78-5 in the synthetic method for EXAMPLE 78, compound 161-3 (0.25 mmol) was used instead of compound 78-4 to obtain compound 161-4 (64 mg, 0.13 mmol).

Step 161-5

According to Step 78-6 in the synthetic method for EXAMPLE 78, compound 161-4 (64 mg, 0.13 mmol) was used instead of compound 78-5 to obtain compound 161-5 (0.13 mmol) which was used in the next step without further purification.

Step 161-6

According to Step 78-7 in the synthetic method for EXAMPLE 78, compound 161-5 (0.13 mmol) was used instead of compound 78-6 to obtain EXAMPLE 161 (39 mg, 0.097 mmol) as a white amorphous solid.

Example 162

Synthesis of (2R)—N-(4-amidinophenyl)-2-hydroxy-2-[(2R)-3-oxo-4-(4-fluoro-3-(pyrrolidin-1-ylcarbonyl)phenyl)morpholin-2-yl]acetamide (EXAMPLE 162)

Step 162-1

Synthesis of 1-[(2-fluoro-5-iodophenyl)carbonyl]pyrrolidine 162

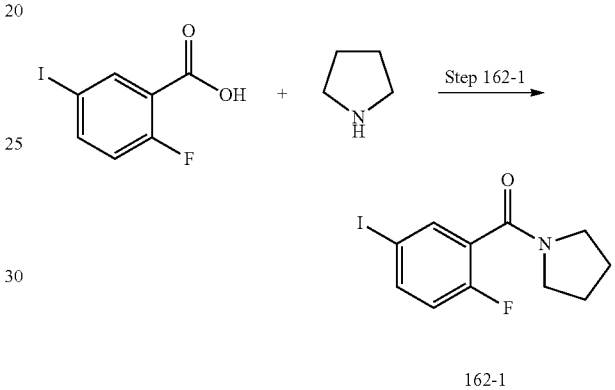

According to Step 77-1 in the synthetic method for compound 77, 2-fluoro-5-iodobenzoic acid and pyrrolidine were used to obtain compound 162-1.

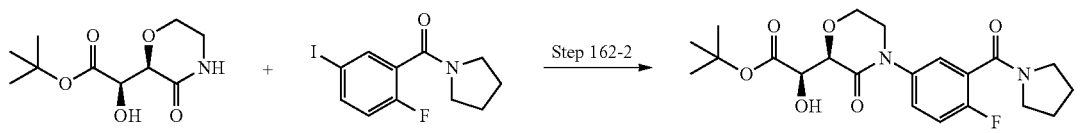

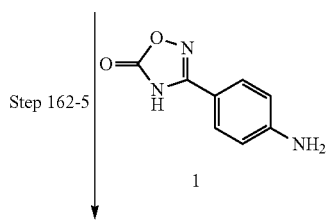

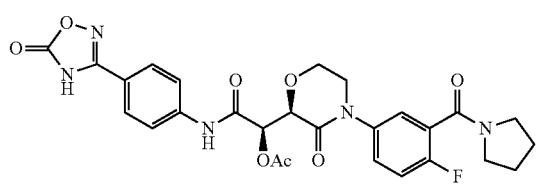

162-5

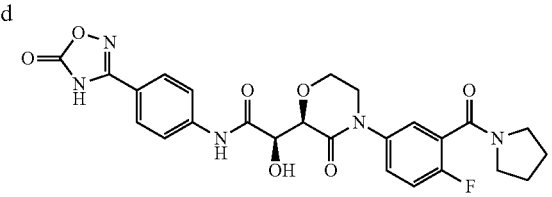

162-6

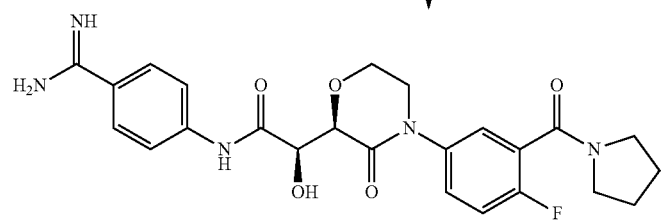

EXAMPLE 162

Step 162-2

According to Step 78-2 in the synthetic method for EXAMPLE 78, compound 162-1 (228 mg, 0.71 mmol) was used instead of compound 78-1 to obtain compound 162-2 (226 mg, 0.54 mmol).

Step 162-3

According to Step 78-3 in the synthetic method for EXAMPLE 78, compound 162-2 (226 mg, 0.54 mmol) was used instead of compound 78-2 to obtain compound 162-3 (244 mg, 0.53 mmol).

Step 162-4

According to Step 78-4 in the synthetic method for EXAMPLE 78, compound 162-3 (244 mg, 0.53 mmol) was used instead of compound 78-3 to obtain compound 162-4 (0.53 mmol) which was used in the next step without further purification.

Step 162-5

According to Step 78-5 in the synthetic method for EXAMPLE 78, compound 162-4 (0.53 mmol) was used instead of compound 78-4 to obtain compound 162-5 (281 mg, 0.50 mmol).

Step 162-6

According to Step 78-6 in the synthetic method for EXAMPLE 78, compound 162-5 (281 mg, 0.50 mmol) was used instead of compound 78-5 to obtain compound 162-6 (0.50 mmol) which was used in the next step without further purification.

Step 162-7

According to Step 78-7 in the synthetic method for EXAMPLE 78, compound 162-6 (0.50 mmol) was used instead of compound 78-6 to obtain EXAMPLE 162 (220 mg, 0.46 mmol) as a white amorphous solid.

Example 163

Synthesis of (2R)—N-(4-amidinophenyl)-2-hydroxy-2-[(2R)-3-oxo-4-(3-(dimethylaminocarbonyl)-4-methylphenyl)morpholin-2-yl]acetamide (EXAMPLE 163)

Step 163-1

Synthesis of 5-iodo-2-methyl-N,N-dimethylbenzamide 163-1

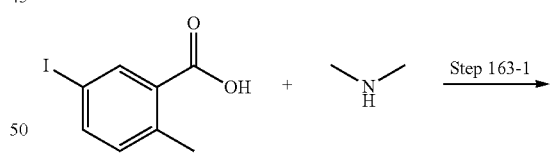

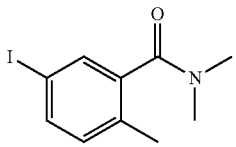

163-1

According to Step 77-1 in the synthetic method for compound 77, 5-iodo-2-methylbenzoic acid and dimethylamine were used to obtain compound 163-1.

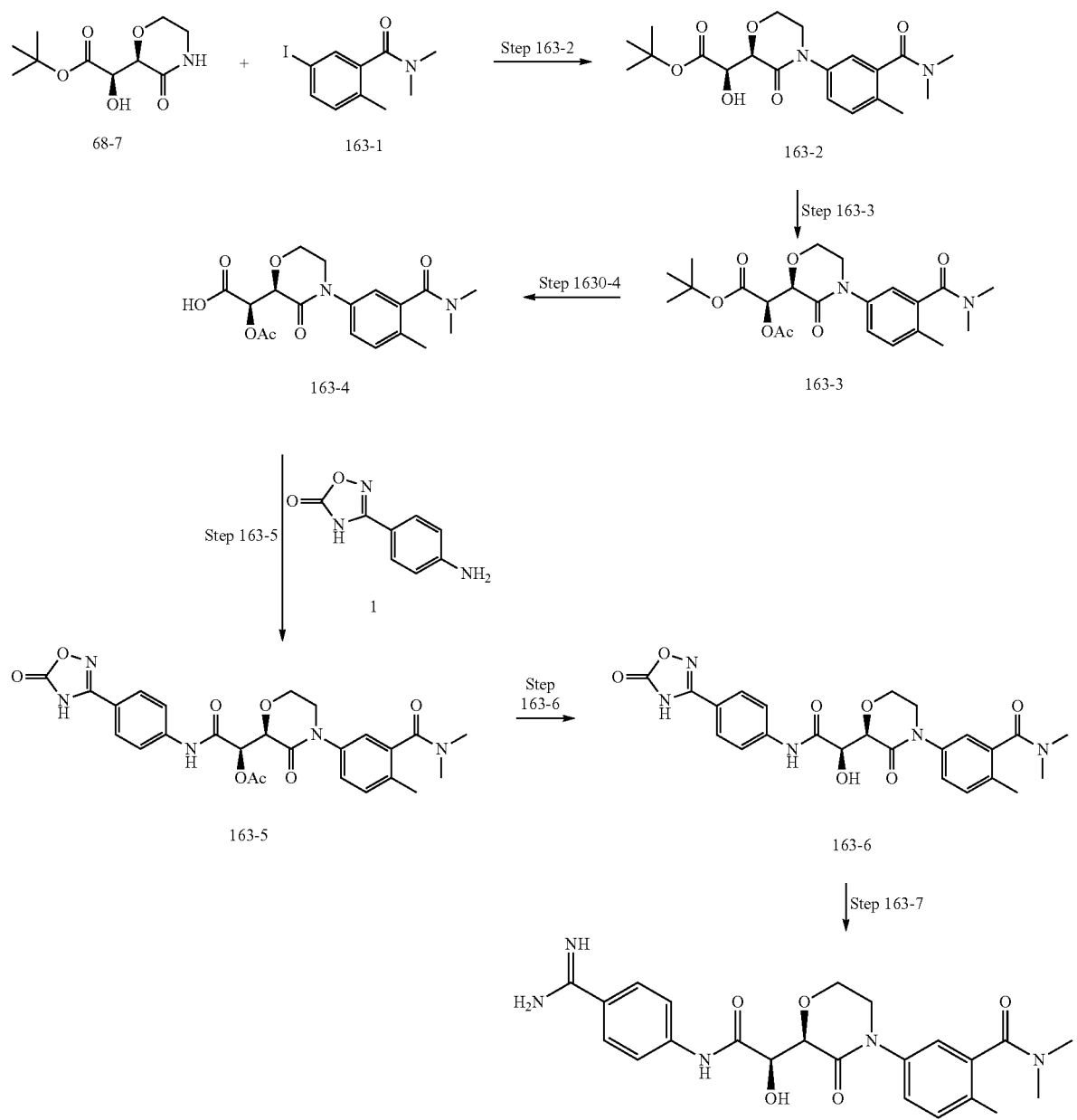

Step 163-2

According to Step 78-2 in the synthetic method for EXAMPLE 78, compound 163-1 (206 mg, 0.71 mmol) was used instead of compound 78-1 to obtain compound 163-2 (208 mg, 0.53 mmol).

Step 163-3

According to Step 78-3 in the synthetic method for EXAMPLE 78, compound 163-2 (208 mg, 0.53 mmol) was used instead of compound 78-2 to obtain compound 163-3 (232 mg, 0.53 mmol).

Step 163-4

According to Step 78-4 in the synthetic method for EXAMPLE 78, compound 163-3 (232 mg, 0.53 mmol) was used instead of compound 78-3 to obtain compound 163-4 (0.53 mmol) which was used in the next step without further purification.

Step 163-5

According to Step 78-5 in the synthetic method for EXAMPLE 78, compound 163-4 (0.53 mmol) was used instead of compound 78-4 to obtain compound 163-5 (260 mg, 0.48 mmol).

Step 163-6

According to Step 78-6 in the synthetic method for EXAMPLE 78, compound 163-5 (260 mg, 0.48 mmol) was used instead of compound 78-5 to obtain compound 163-6 (0.48 mmol) which was used in the next step without further purification.

Step 163-7

According to Step 78-7 in the synthetic method for EXAMPLE 78, compound 163-6 (0.48 mmol) was used instead of compound 78-6 to obtain EXAMPLE 163 (197 mg, 0.43 mmol) as a white amorphous solid.

Example 164

Synthesis of (2R)—N-(4-amidinophenyl)-2-hydroxy-2-[(2R)-3-oxo-4-(4-methyl-3-(morpholin-4-ylcarbonyl)phenyl)morpholin-2-yl]acetamide (EXAMPLE 164)

Step 164-1

Synthesis of 4-[(5-iodo-2-methylphenyl)carbonyl]morpholine 164-1

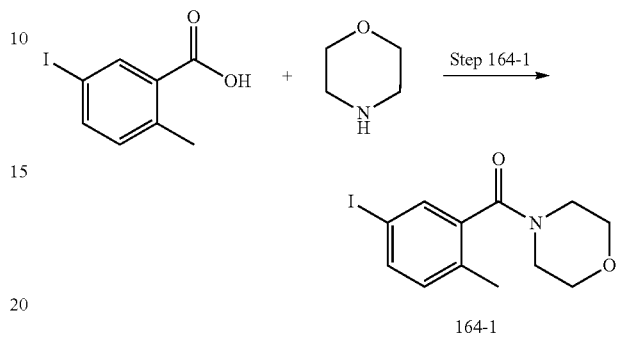

According to Step 77-1 in the synthetic method for compound 77, 5-iodo-2-methylbenzoic acid and morpholine were used to obtain compound 164-1.

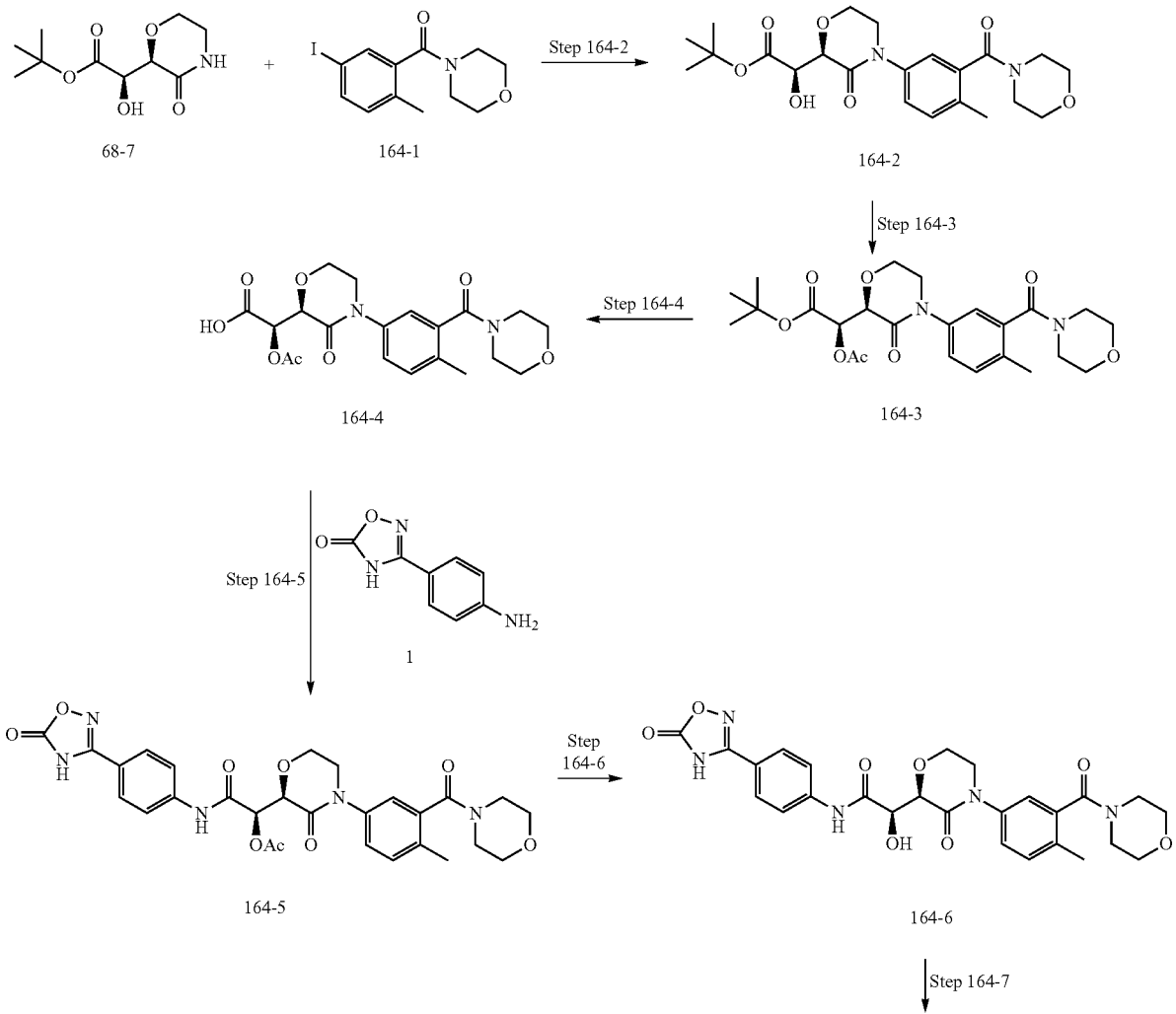

-continued

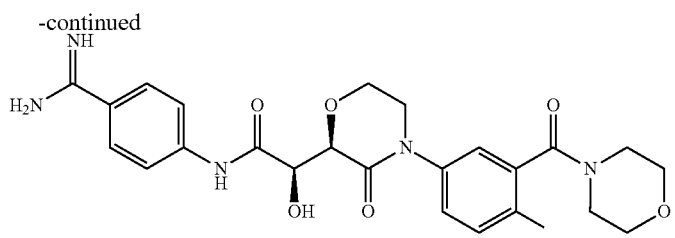

EXAMPLE 164

Step 164-2

According to Step 78-2 in the synthetic method for EXAMPLE 78, compound 164-1 (236 mg, 0.71 mmol) was used instead of compound 78-1 to obtain compound 164-2 (250 mg, 0.58 mmol).

Step 164-3

According to Step 78-3 in the synthetic method for EXAMPLE 78, compound 164-2 (250 mg, 0.58 mmol) was used instead of compound 78-2 to obtain compound 164-3 (219 mg, 0.46 mmol).

Step 164-4

According to Step 78-4 in the synthetic method for EXAMPLE 78, compound 164-3 (219 mg, 0.46 mmol) was used instead of compound 78-3 to obtain compound 164-4 (0.46 mmol) which was used in the next step without further purification.

Step 164-5

According to Step 78-5 in the synthetic method for EXAMPLE 78, compound 164-4 (0.46 mmol) was used instead of compound 78-4 to obtain compound 164-5 (240 mg, 0.41 mmol).

Step 164-6

According to Step 78-6 in the synthetic method for EXAMPLE 78, compound 164-5 (240 mg, 0.41 mmol) was used instead of compound 78-5 to obtain compound 164-6 (0.41 mmol) which was used in the next step without further purification.

Step 164-7

According to Step 78-7 in the synthetic method for EXAMPLE 78, compound 164-6 (0.41 mmol) was used instead of compound 78-6 to obtain EXAMPLE 164 (186 mg, 0.38 mmol) as a white amorphous solid.

Example 165

Synthesis of (2R)—N-(4-amidinophenyl)-2-hydroxy-2-[(2R)-3-oxo-4-(4-methyl-3-(pyrrolidin-1-ylcarbonyl)phenyl)morpholin-2-yl]acetamide (EXAMPLE 165)

Synthesis of 1-[(5-iodo-2-methylphenyl)carbonyl]pyrrolidine 165-1

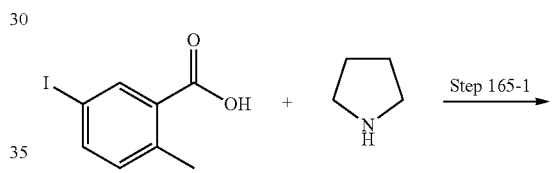

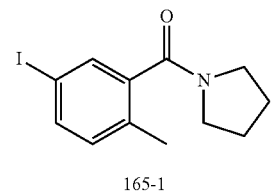

Step 165-1

According to Step 77-1 in the synthetic method for compound 77, 5-iodo-2-methylbenzoic acid and pyrrolidine were used to obtain compound 165-1.

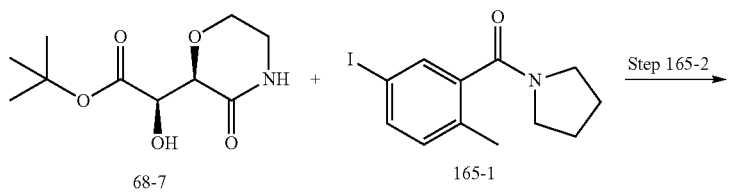

-continued
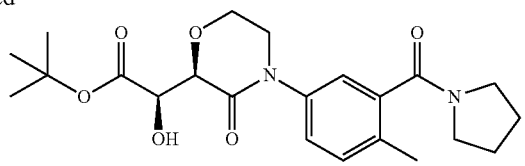
165-2
Step 165-3
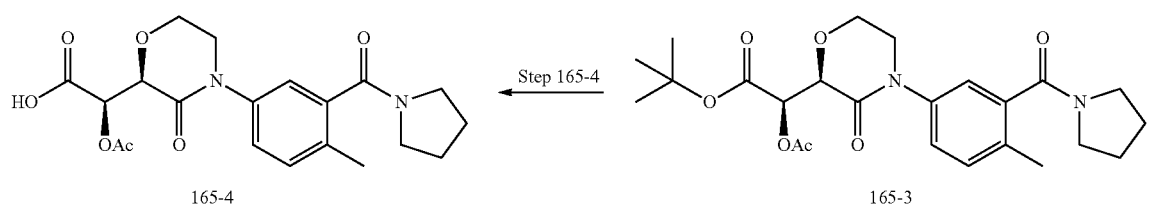
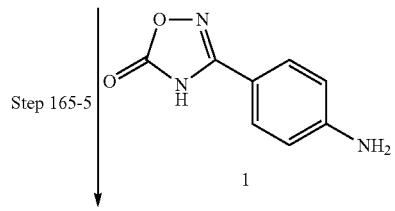
165-4
Step 165-5
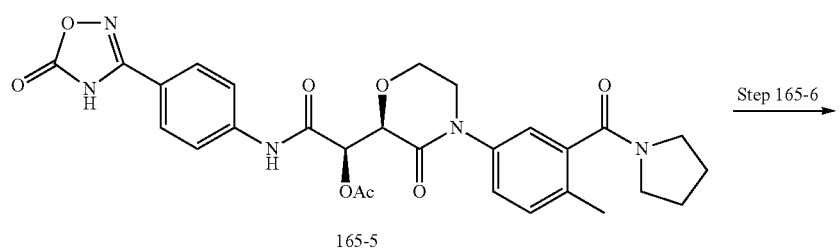
165-5
Step 165-6
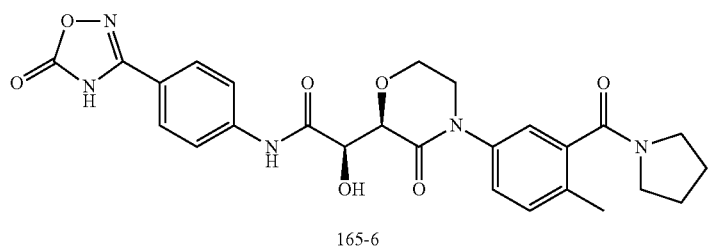
165-6
Step 165-7
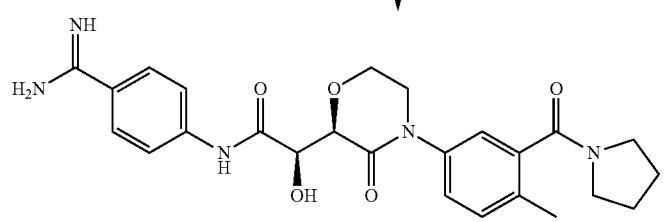
EXAMPLE 165

Step 165-2

According to Step 78-2 in the synthetic method for EXAMPLE 78, compound 165-1 (225 mg, 0.71 mmol) was used instead of compound 78-1 to obtain compound 165-2 (241 mg, 0.58 mmol).

Step 165-3

According to Step 78-3 in the synthetic method for EXAMPLE 78, compound 165-2 (241 mg, 0.58 mmol) was used instead of compound 78-2 to obtain compound 165-3 (264 mg, 0.57 mmol).

Step 165-4

According to Step 78-4 in the synthetic method for EXAMPLE 78, compound 165-3 (264 mg, 0.57 mmol) was used instead of compound 78-3 to obtain compound 165-4 (0.57 mmol) which was used in the next step without further purification.

Step 165-5

According to Step 78-5 in the synthetic method for EXAMPLE 78, compound 165-4 (0.57 mmol) was used instead of compound 78-4 to obtain compound 165-5 (247 mg, 0.44 mmol).

Step 165-6

According to Step 78-6 in the synthetic method for EXAMPLE 78, compound 165-5 (247 mg, 0.44 mmol) was used instead of compound 78-5 to obtain compound 165-6 (0.44 mmol) which was used in the next step without further purification.

Step 165-7

According to Step 78-7 in the synthetic method for EXAMPLE 78, compound 165-6 (0.44 mmol) was used instead of compound 78-6 to obtain EXAMPLE 165 (197 mg, 0.41 mmol) as a white amorphous solid.

Example 166

Synthesis of (2R)—N-(4-amidinophenyl)-2-hydroxy-2-[(2R)-3-oxo-4-(3-fluoro-5-(pyrrolidin-1-ylcarbonyl)phenyl)morpholin-2-yl]acetamide (EXAMPLE 166)

Synthesis of 1-[(3-fluoro-5-iodophenyl)carbonyl]pyrrolidine 166-1

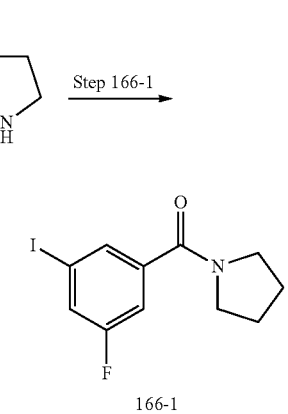

Step 166-1

According to Step 77-1 in the synthetic method for compound 77, 3-fluoro-5-iodobenzoic acid and pyrrolidine were used to obtain compound 166-1.

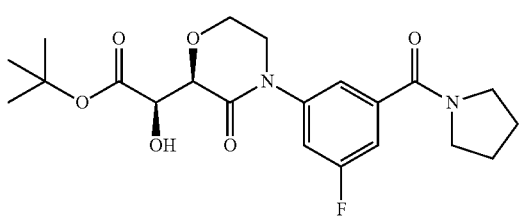

437 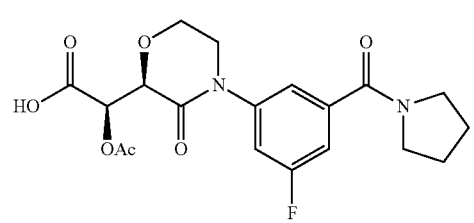 Step 166-4 ← 438 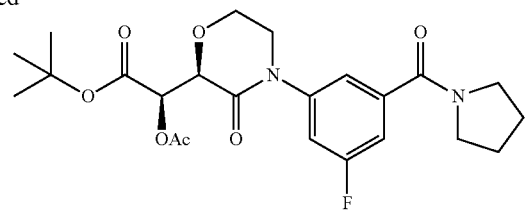
166-4 166-3
Step 166-5 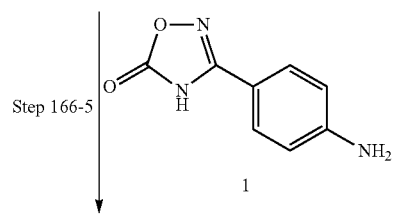
1
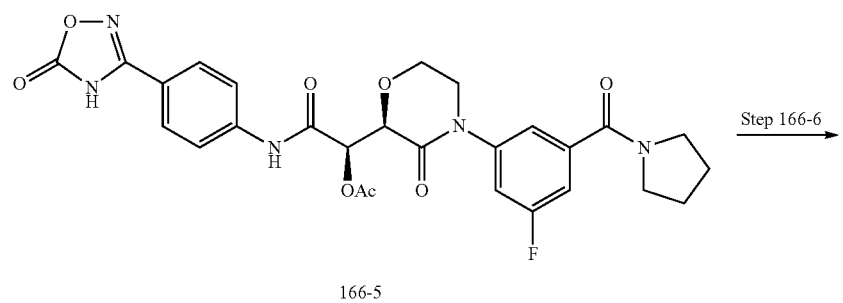 Step 166-6 →
166-5
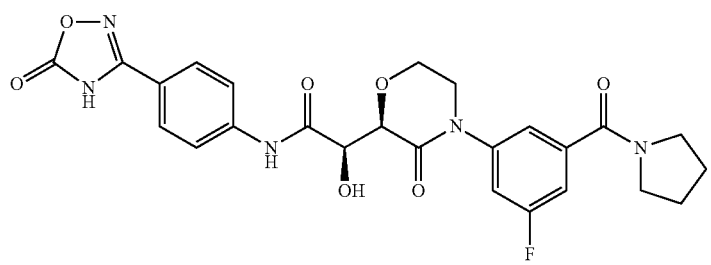
166-6
Step 166-7 ↓
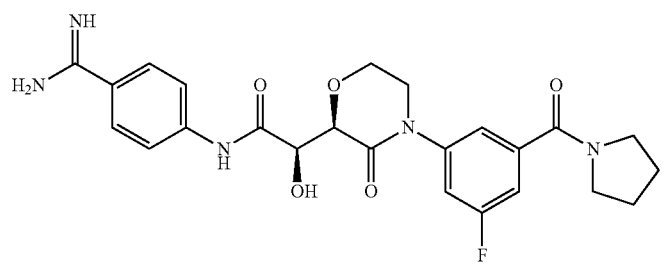
EXAMPLE 166

Step 166-2

According to Step 78-2 in the synthetic method for EXAMPLE 78, compound 166-1 (262 mg, 0.82 mmol) was used instead of compound 78-1 to obtain compound 166-2 (213 mg, 0.50 mmol).

Step 166-3

According to Step 78-3 in the synthetic method for EXAMPLE 78, compound 166-2 (213 mg, 0.50 mmol) was used instead of compound 78-2 to obtain compound 166-3 (0.50 mmol).

Step 166-4

According to Step 78-4 in the synthetic method for EXAMPLE 78, compound 166-3 (0.50 mmol) was used instead of compound 78-3 to obtain compound 166-4 (0.50 mmol) which was used in the next step without further purification.

Step 166-5

According to Step 78-5 in the synthetic method for EXAMPLE 78, compound 166-4 (0.50 mmol) was used instead of compound 78-4 to obtain compound 166-5 (275 mg, 0.49 mmol).

Step 166-6

According to Step 78-6 in the synthetic method for EXAMPLE 78, compound 169-5 (275 mg, 0.49 mmol) was used instead of compound 78-5 to obtain compound 166-6 (0.49 mmol) which was used in the next step without further purification.

Step 166-7

According to Step 78-7 in the synthetic method for EXAMPLE 78, compound 166-6 (0.49 mmol) was used instead of compound 78-6 to obtain EXAMPLE 166 (225 mg, 0.37 mmol) as a white amorphous solid.

Example 167

Synthesis of (2R)—N-(4-amidinophenyl)-2-hydroxy-2-[(2R)-3-oxo-4-(3-fluoro-5-(morpholin-4-ylcarbonyl)phenyl)morpholin-2-yl]acetamide (EXAMPLE 167)

Synthesis of 4-[(3-fluoro-5-iodophenyl)carbonyl]morpholine 167-1

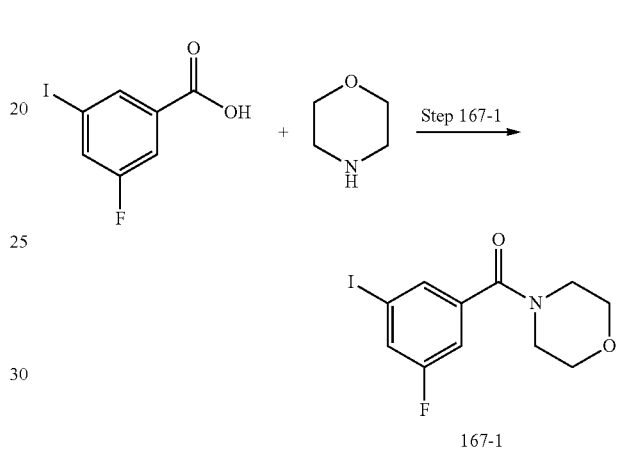

Step 167-1

According to Step 77-1 in the synthetic method for compound 77, 3-fluoro-5-iodobenzoic acid and morpholine were used to obtain compound 167-1.

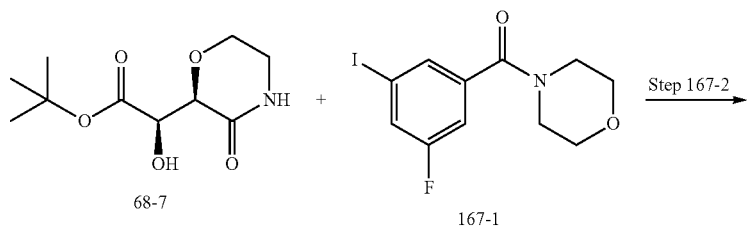

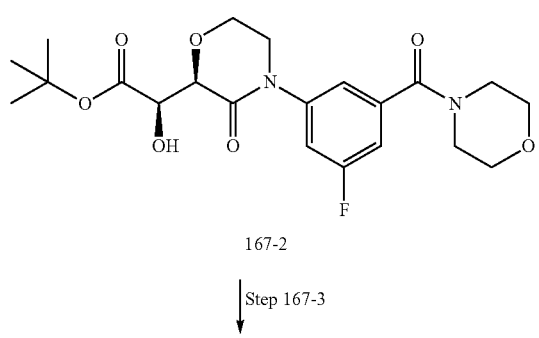

441          442
-continued
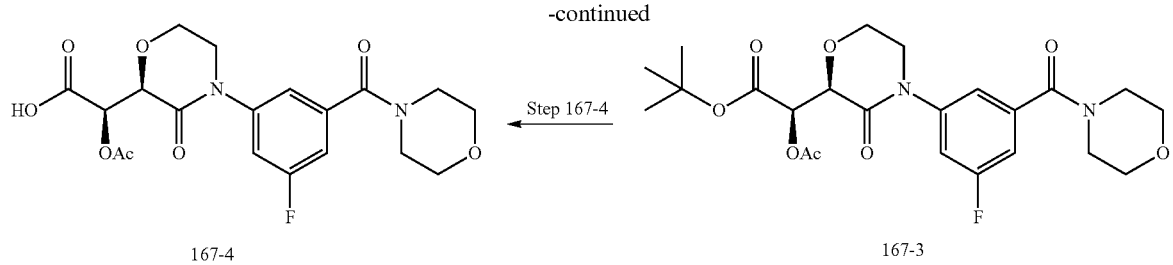
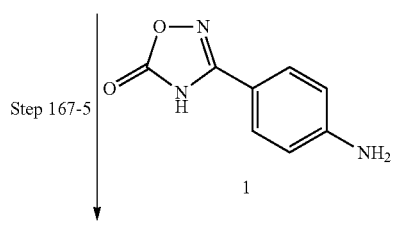
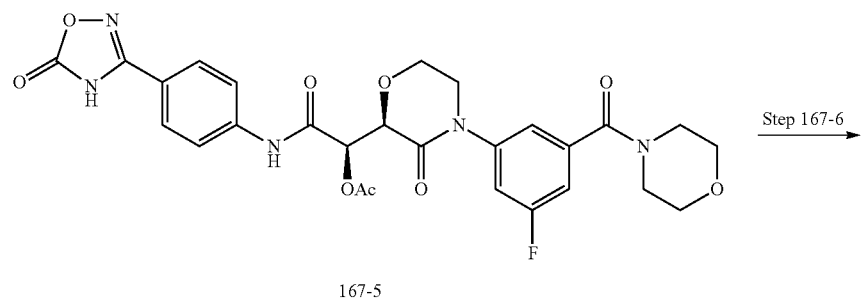
167-5
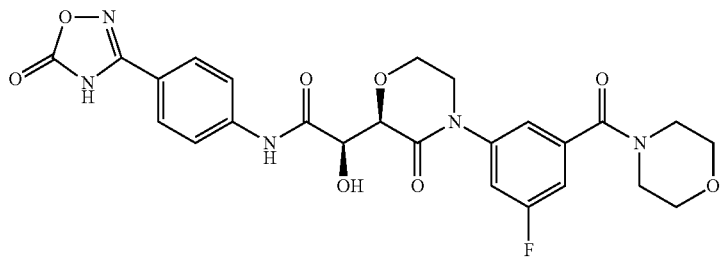
167-6
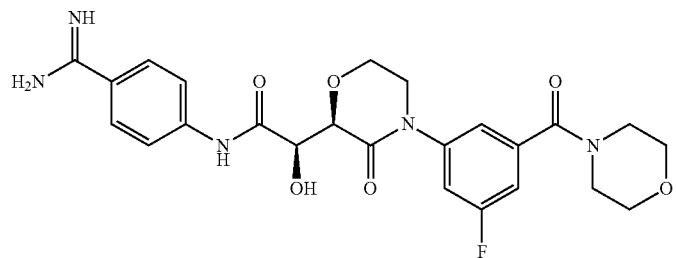
EXAMPLE 167

Step 167-2

According to Step 78-2 in the synthetic method for EXAMPLE 78, compound 167-1 (298 mg, 0.89 mmol) was used instead of compound 78-1 to obtain compound 167-2 (208 mg, 0.47 mmol).

Step 167-3

According to Step 78-3 in the synthetic method for EXAMPLE 78, compound 167-2 (208 mg, 0.47 mmol) was used instead of compound 78-2 to obtain compound 167-3 (197 mg, 0.41 mmol).

Step 167-4

According to Step 78-4 in the synthetic method for EXAMPLE 78, compound 167-3 (197 mg, 0.41 mmol) was used instead of compound 78-3 to obtain compound 167-4 (0.41 mmol) which was used in the next step without further purification.

Step 167-5

According to Step 78-5 in the synthetic method for EXAMPLE 78, compound 167-4 (0.41 mmol) was used instead of compound 78-4 to obtain compound 167-5 (221 mg, 0.38 mmol).

Step 167-6

According to Step 78-6 in the synthetic method for EXAMPLE 78, compound 167-5 (221 mg, 0.38 mmol) was used instead of compound 78-5 to obtain compound 167-6 (0.38 mmol) which was used in the next step without further purification.

Step 167-7

According to Step 78-7 in the synthetic method for EXAMPLE 78, compound 167-6 (0.38 mmol) was used instead of compound 78-6 to obtain EXAMPLE 167 (184 mg, 0.37 mmol) as a white amorphous solid.

Example 168

Synthesis of (2R)—N-(4-amidinophenyl)-2-hydroxy-2-[(2R)-3-oxo-4-(3-(dimethylaminocarbonyl)-5-fluorophenyl)morpholin-2-yl]acetamide (EXAMPLE 168)

Step 168-1

Synthesis of 3-fluoro-5-iodo-N,N-dimethylbenzamide 168-1

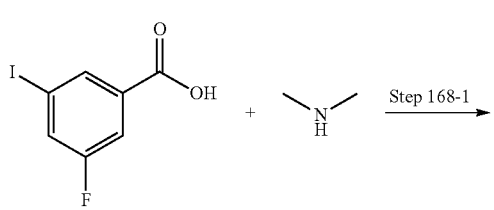

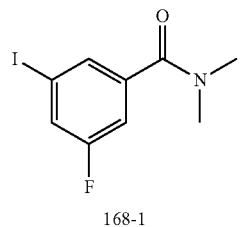

According to Step 77-1 in the synthetic method for compound 77, 3-fluoro-5-iodobenzoic acid and dimethylamine were used to obtain compound 168-1.

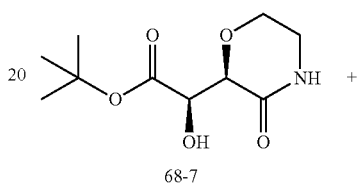

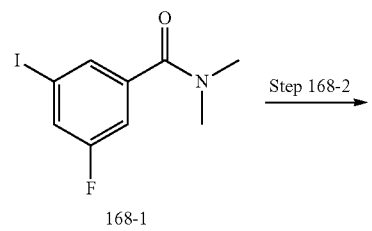

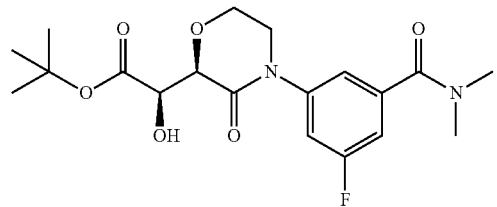

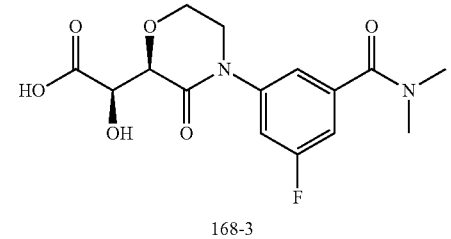

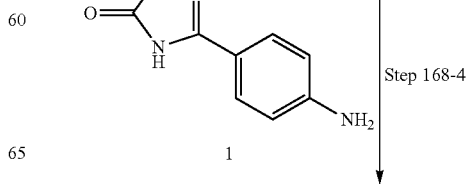

-continued

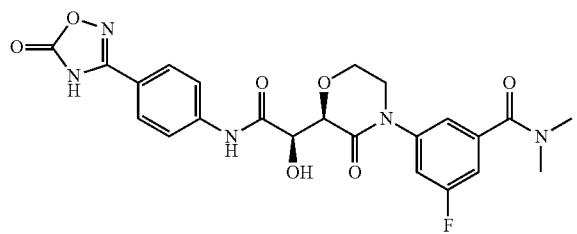

168-4

↓ Step 168-5

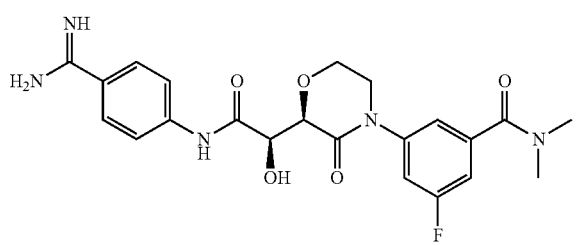

EXAMPLE 168

Step 168-2

According to Step 77-2 in the synthetic method for EXAMPLE 77, compound 168-1 (209 mg, 0.71 mmol) was used instead of compound 77-1 to obtain compound 168-2 (178 mg, 0.45 mmol).

Step 168-3

According to Step 77-3 in the synthetic method for EXAMPLE 77, compound 168-2 (178 mg, 0.45 mmol) was used instead of compound 77-2 to obtain compound 168-3 (0.45 mmol) which was used in the next step without further purification.

Step 168-4

According to Step 77-4 in the synthetic method for EXAMPLE 77, compound 168-3 (0.45 mmol) was used instead of compound 77-3 to obtain compound 168-4 (110 mg, 0.22 mmol).

Step 168-5

According to Step 77-5 in the synthetic method for EXAMPLE 77, compound 168-4 (110 mg, 0.22 mmol) was used instead of compound 77-4 to obtain compound EXAMPLE 168 (71 mg, 0.16 mmol) as a white amorphous solid.

Example 169

Synthesis of (2R)—N-(4-amidinophenyl)-2-hydroxy-2-[(2R)-3-oxo-4-(3-(dimethylaminocarbonyl)-2-methylphenyl)morpholin-2-yl]acetamide (EXAMPLE 169)

Synthesis of 3-iodo-2-methyl-N,N-dimethylbenzamide 169-1

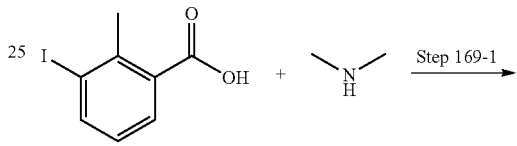

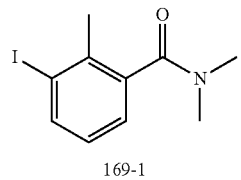

169-1

Step 169-1

According to Step 77-1 in the synthetic method for compound 77, 3-iodo-2-methylbenzoic acid and dimethylamine were used to obtain compound 169-1.

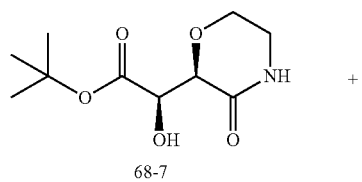 + 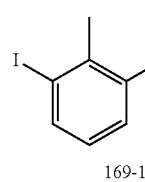 →[Step 169-2] 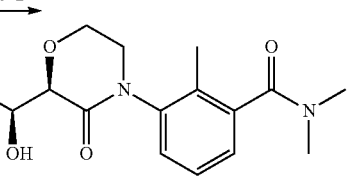

68-7    169-1    169-2

↓ Step 169-3

447 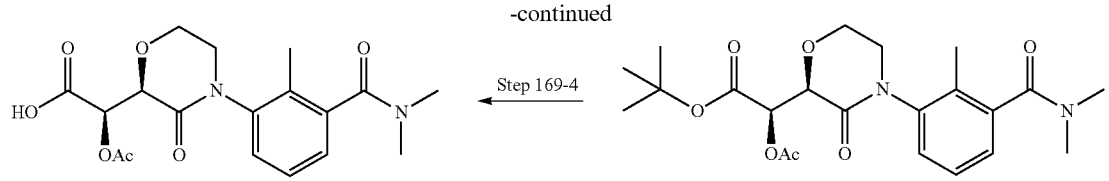 448
-continued
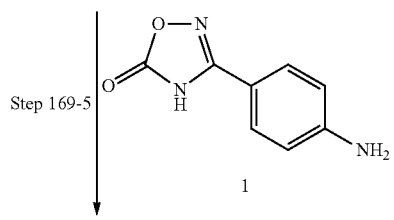
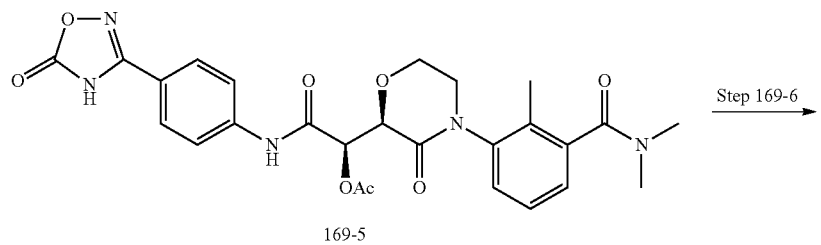
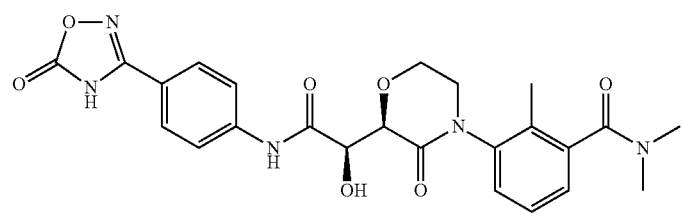
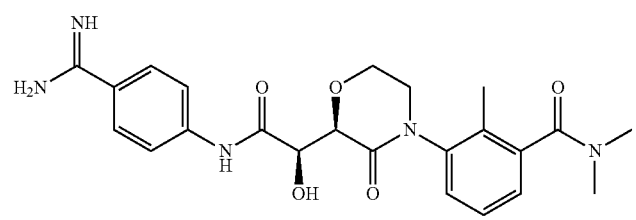
EXAMPLE 169

Step 169-2

According to Step 78-2 in the synthetic method for EXAMPLE 78, compound 169-1 (206 mg, 0.71 mmol) was used instead of compound 78-1 to obtain compound 169-2 (91 mg, 0.23 mmol).

Step 169-3

According to Step 78-3 in the synthetic method for EXAMPLE 78, compound 169-2 (91 mg, 0.23 mmol) was used instead of compound 78-2 to obtain compound 169-3 (0.23 mmol).

Step 169-4

According to Step 78-4 in the synthetic method for EXAMPLE 78, compound 169-3 (0.23 mmol) was used instead of compound 78-3 to obtain compound 169-4 (0.23 mmol) which was used in the next step without further purification.

Step 169-5

According to Step 78-5 in the synthetic method for EXAMPLE 78, compound 169-4 (0.23 mmol) was used instead of compound 78-4 to obtain compound 169-5 (80 mg, 0.15 mmol).

Step 169-6

According to Step 78-6 in the synthetic method for EXAMPLE 78, compound 169-5 (80 mg, 0.15 mmol) was used instead of compound 78-5 to obtain compound 169-6 (0.15 mmol) which was used in the next step without further purification.

Step 169-7

According to Step 78-7 in the synthetic method for EXAMPLE 78, compound 169-6 (0.15 mmol) was used instead of compound 78-6 to obtain EXAMPLE 169 (51 mg, 0.11 mmol) as a white amorphous solid.

Example 170

Synthesis of (2R)—N-(4-amidinophenyl)-2-hydroxy-2-[(2R)-3-oxo-4-(3-(piperidin-1-ylcarbonyl)phenyl)morpholin-2-yl]acetamide (EXAMPLE 170)

Synthesis of 1-[(3-iodophenyl)carbonyl]piperidine 170-1

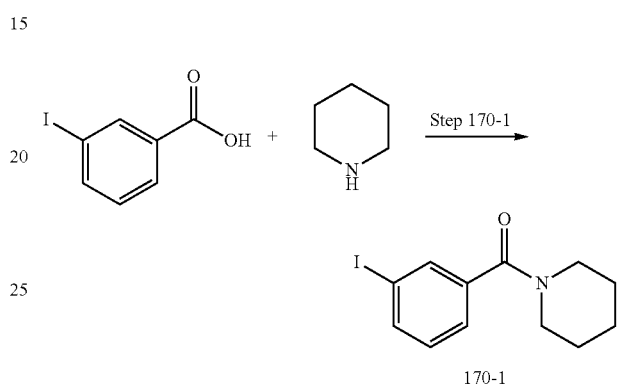

Step 170-1

According to Step 77-1 in the synthetic method for compound 77, 3-iodobenzoic acid and piperidine were used to obtain compound 170-1.

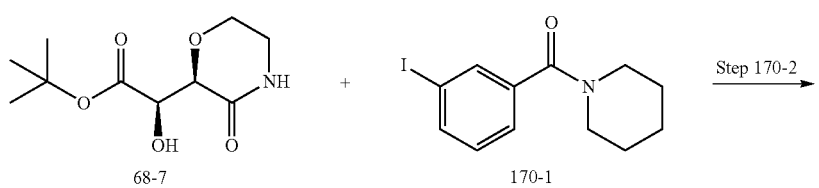

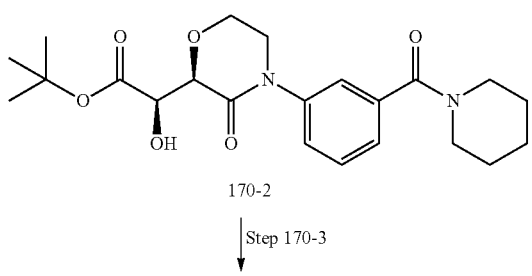

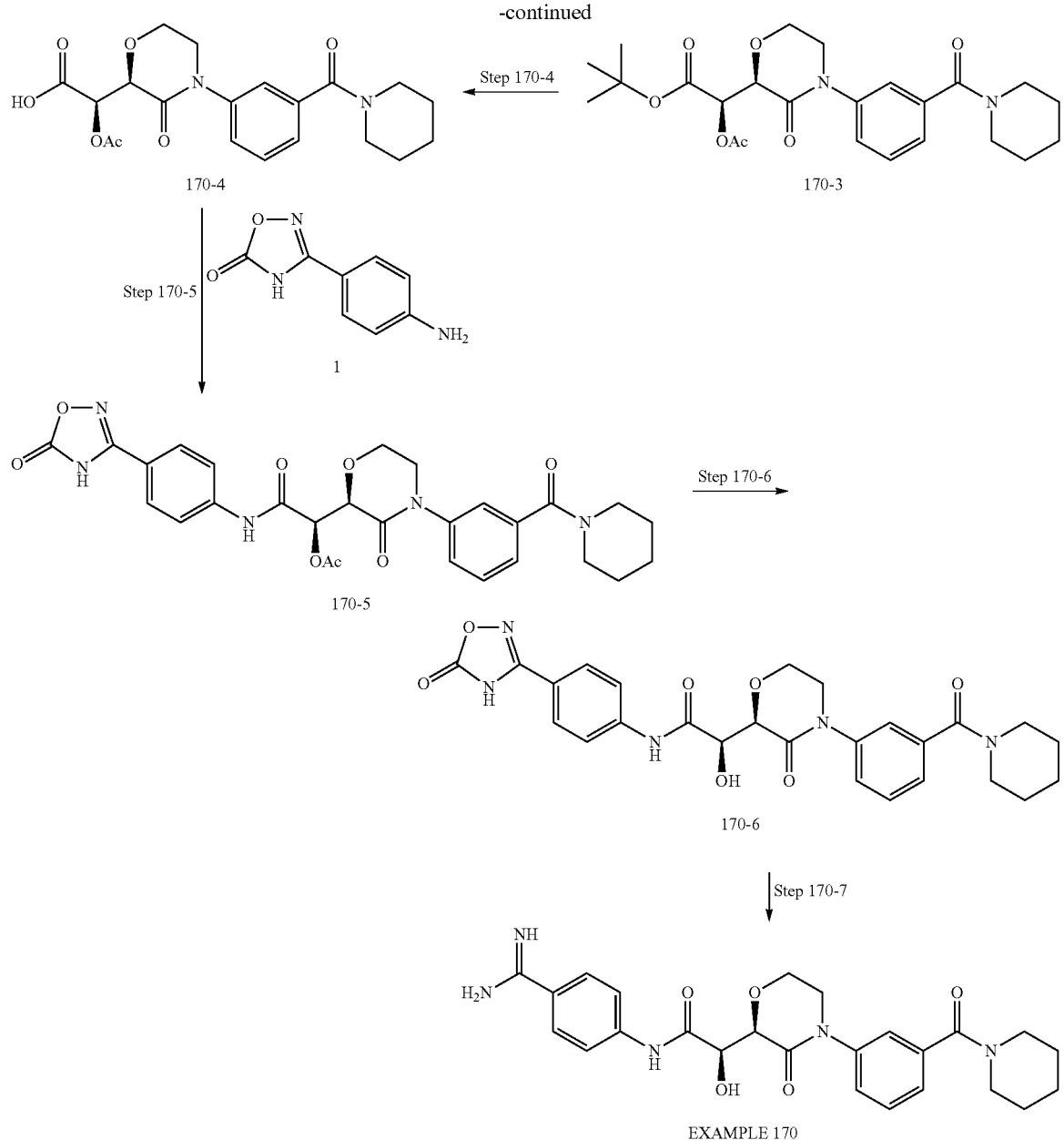

Step 170-2

According to Step 78-2 in the synthetic method for EXAMPLE 78, compound 170-1 (225 mg, 0.71 mmol) was used instead of compound 78-1 to obtain compound 170-2 (198 mg, 0.47 mmol).

Step 170-3

According to Step 78-3 in the synthetic method for EXAMPLE 78, compound 170-2 (198 mg, 0.47 mmol) was used instead of compound 78-2 to obtain compound 170-3 (0.47 mmol).

Step 170-4

According to Step 78-4 in the synthetic method for EXAMPLE 78, compound 170-3 (0.47 mmol) was used instead of compound 78-3 to obtain compound 170-4 (0.47 mmol) which was used in the next step without further purification.

Step 170-5

According to Step 78-5 in the synthetic method for EXAMPLE 78, compound 170-4 (0.47 mmol) was used instead of compound 78-4 to obtain compound 170-5 (249 mg, 0.44 mmol).

Step 170-6

According to Step 78-6 in the synthetic method for EXAMPLE 78, compound 170-5 (249 mg, 0.44 mmol) was used instead of compound 78-5 to obtain compound 170-6 (0.44 mmol) which was used in the next step without further purification.

Step 170-7

According to Step 78-7 in the synthetic method for EXAMPLE 78, compound 170-6 (0.44 mmol) was used instead of compound 78-6 to obtain EXAMPLE 170 (194 mg, 0.41 mmol) as a white amorphous solid.

Example 171

Synthesis of (2R)—N-(4-amidinophenyl)-2-hydroxy-2-[(2R)-3-oxo-4-(3-(azetidin-1-ylcarbonyl)phenyl)morpholin-2-yl]acetamide (EXAMPLE 171)

Synthesis of 1-[(3-iodophenyl)carbonyl]azetidine 171-1

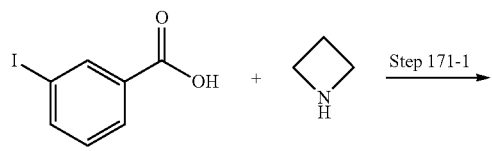

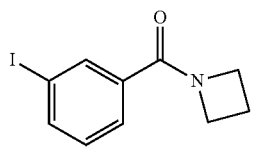

Step 171-1

According to Step 77-1 in the synthetic method for compound 77, 3-iodobenzoic acid and azetidine were used to obtain compound 171-1.

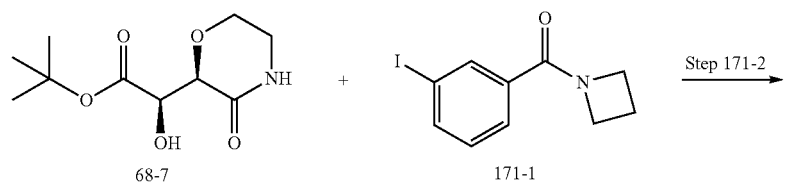

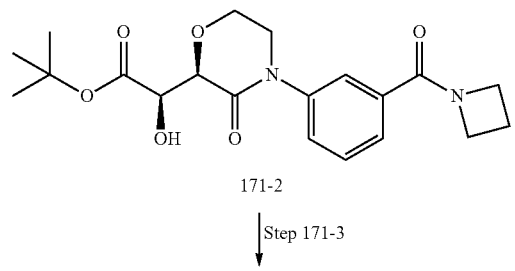

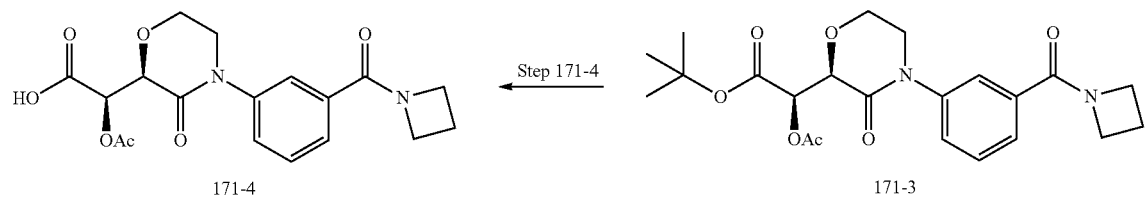

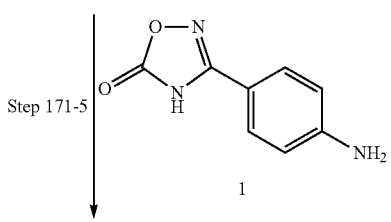

455
-continued
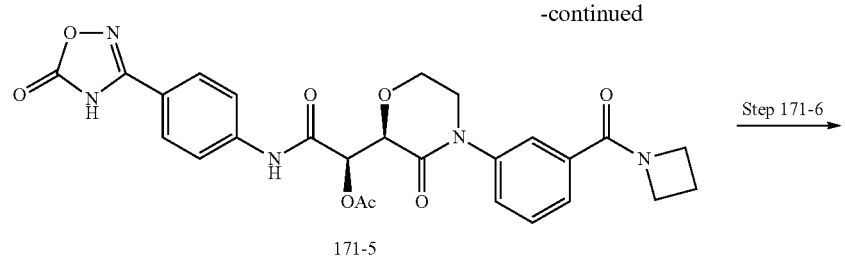
171-5
Step 171-6
456
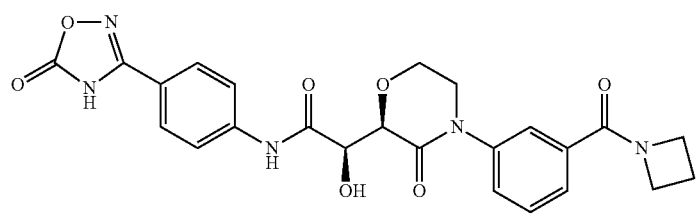
171-6
Step 171-7
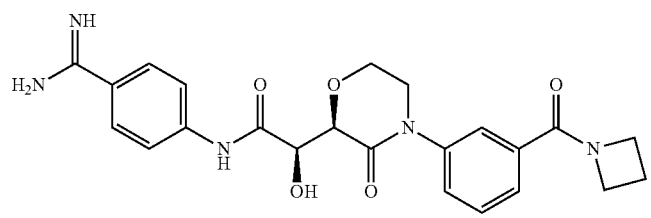
EXAMPLE 171

Step 171-2

According to Step 78-2 in the synthetic method for EXAMPLE 78, compound 171-1 (205 mg, 0.71 mmol) was used instead of compound 78-1 to obtain compound 171-2 (121 mg, 0.31 mmol).

Step 171-3

According to Step 78-3 in the synthetic method for EXAMPLE 78, compound 171-2 (121 mg, 0.31 mmol) was used instead of compound 78-2 to obtain compound 171-3 (111 mg, 0.26 mmol).

Step 171-4

According to Step 78-4 in the synthetic method for EXAMPLE 78, compound 171-3 (111 mg, 0.26 mmol) was used instead of compound 78-3 to obtain compound 171-4 (0.26 mmol) which was used in the next step without further purification.

Step 171-5

According to Step 78-5 in the synthetic method for EXAMPLE 78, compound 171-4 (0.26 mmol) was used instead of compound 78-4 to obtain compound 171-5 (112 mg, 0.21 mmol).

Step 171-6

According to Step 78-6 in the synthetic method for EXAMPLE 78, compound 171-5 (112 mg, 0.21 mmol) was used instead of compound 78-5 to obtain compound 171-6 (0.21 mmol) which was used in the next step without further purification.

Step 171-7

According to Step 78-7 in the synthetic method for EXAMPLE 78, compound 171-6 (0.21 mmol) was used instead of compound 78-6 to obtain EXAMPLE 171 (88 mg, 0.20 mmol) as a white amorphous solid.

Example 172

Synthesis of (2R)—N-(4-amidinophenyl)-2-hydroxy-2-[(2R)-3-oxo-4-(3-((2R,5R)-(−)-trans-dimethylpyrrolidin-1-ylcarbonyl)phenyl)morpholin-2-yl]acetamide (EXAMPLE 172)

Step 172-1

Synthesis of (2R,5R)-(−)-trans-dimethyl-1-[(3-iodophenyl)carbonyl]pyrrolidine 172-1

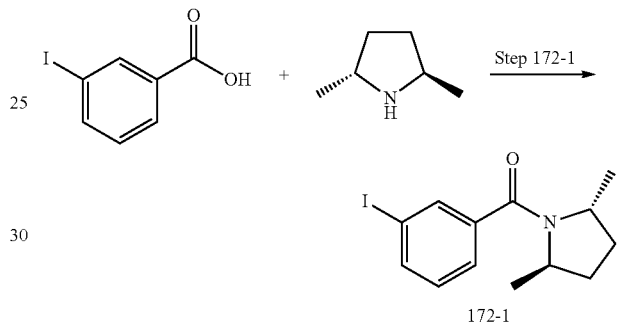

According to Step 77-1 in the synthetic method for compound 77, 3-iodobenzoic acid and (2R,5R)-(−)-trans-dimethylpyrrolidine were used to obtain compound 172-1.

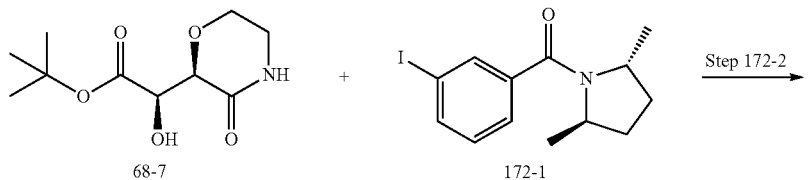

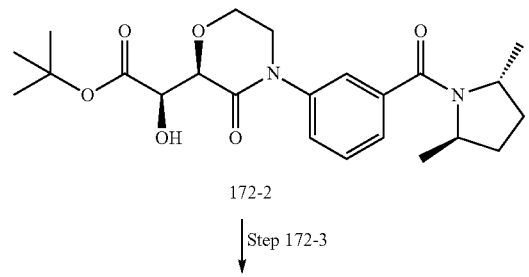

-continued

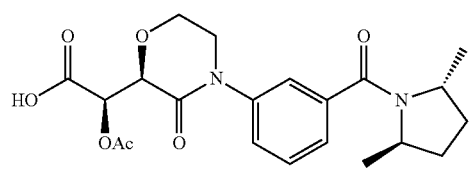
172-4

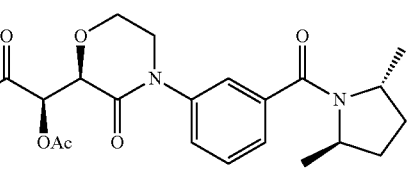
172-3

Step 172-4

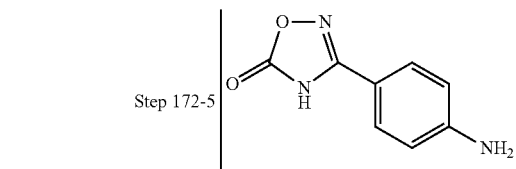

Step 172-5

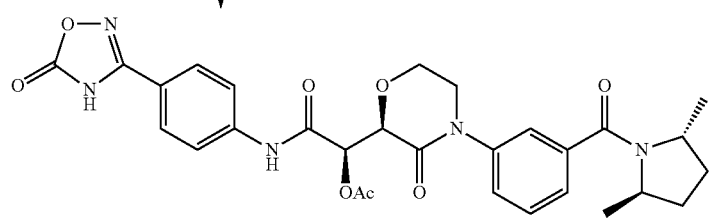
172-5

Step 172-6

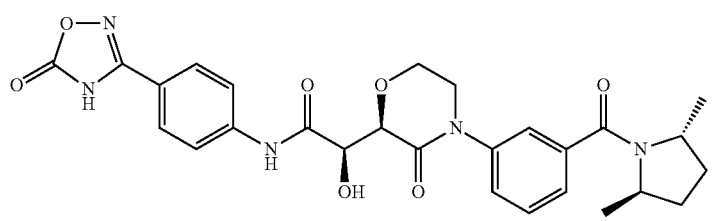
172-6

Step 172-7

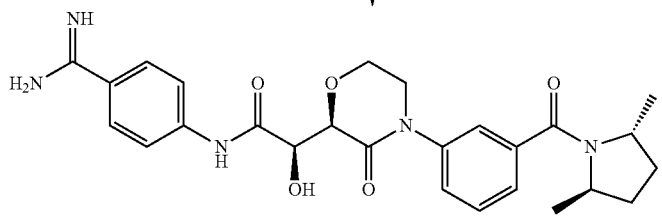
EXAMPLE 172

Step 172-2

According to Step 78-2 in the synthetic method for EXAMPLE 78, compound 172-1 (190 mg, 0.58 mmol) was used instead of compound 78-1 to obtain compound 172-2 (98 mg, 0.23 mmol).

Step 172-3

According to Step 78-3 in the synthetic method for EXAMPLE 78, compound 172-2 (98 mg, 0.23 mmol) was used instead of compound 78-2 to obtain compound 172-3 (85 mg, 0.18 mmol).

Step 172-4

According to Step 78-4 in the synthetic method for EXAMPLE 78, compound 172-3 (85 mg, 0.18 mmol) was used instead of compound 78-3 to obtain compound 172-4 (0.18 mmol) which was used in the next step without further purification.

Step 172-5

According to Step 78-5 in the synthetic method for EXAMPLE 78, compound 172-4 (0.18 mmol) was used instead of compound 78-4 to obtain compound 172-5 (103 mg, 0.18 mmol).

Step 172-6

According to Step 78-6 in the synthetic method for EXAMPLE 78, compound 172-5 (103 mg, 0.18 mmol) was used instead of compound 78-5 to obtain compound 172-6 (0.18 mmol) which was used in the next step without further purification.

Step 172-7
According to Step 78-7 in the synthetic method for EXAMPLE 78, compound 172-6 (0.18 mmol) was used instead of compound 78-6 to obtain EXAMPLE 172 (83 mg, 0.17 mmol) as a white amorphous solid.
Example 173
Synthesis of (2R)—N-(4-amidinophenyl)-2-hydroxy-2-[(2R)-3-oxo-4-(3-fluorophenyl)morpholin-2-yl]Acetamide (EXAMPLE 173)
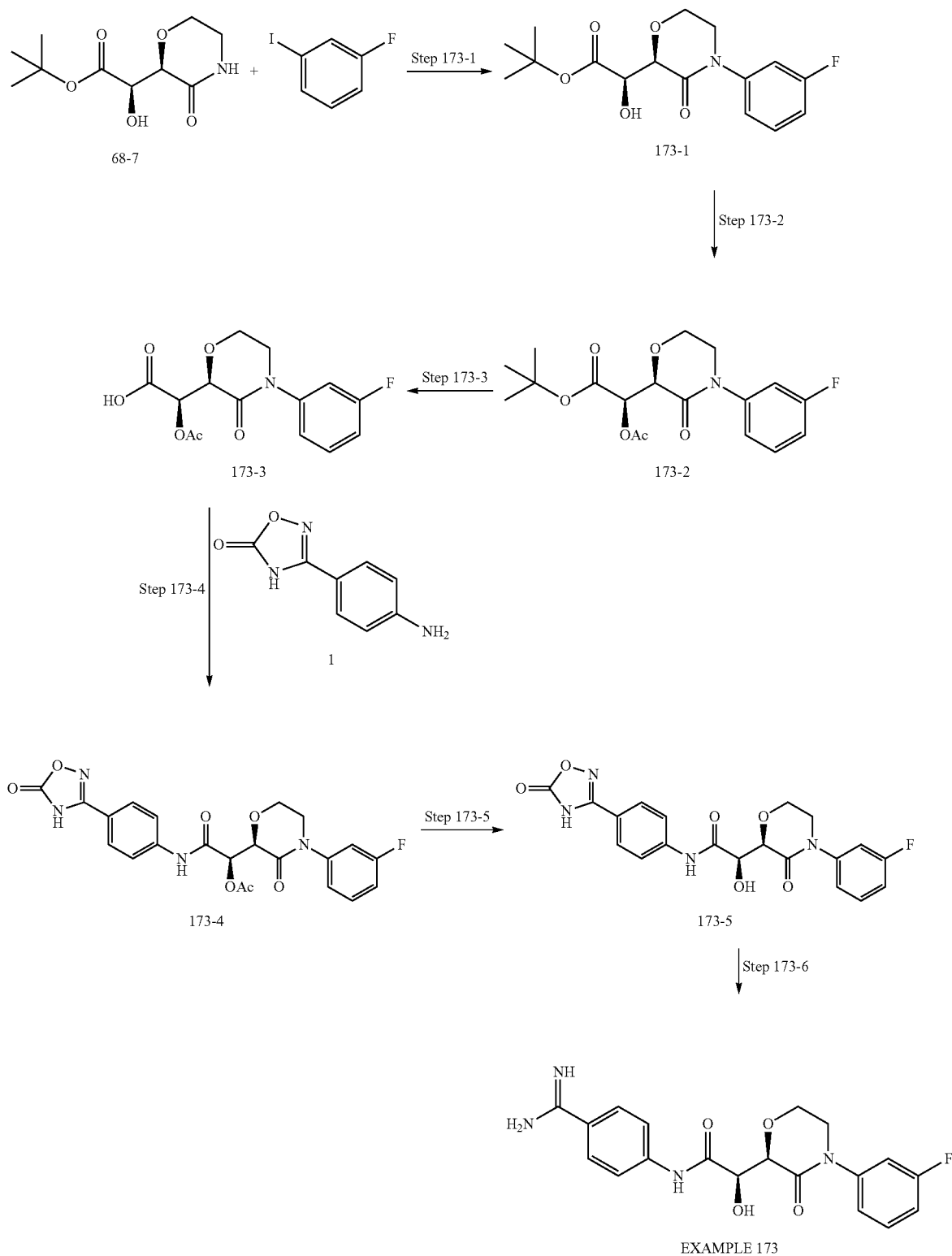

Step 173-1

According to Step 78-2 in the synthetic method for EXAMPLE 78, 3-fluoro-5-iodobenzene (79 mg, 0.36 mmol) was used instead of compound 78-1 to obtain compound 173-1 (87 mg, 0.27 mmol).

Step 173-2

According to Step 78-3 in the synthetic method for EXAMPLE 78, compound 173-1 (87 mg, 0.27 mmol) was used instead of compound 78-2 to obtain compound 173-2 (98 mg, 0.27 mmol).

Step 173-3

According to Step 78-4 in the synthetic method for EXAMPLE 78, compound 173-2 (98 mg, 0.27 mmol) was used instead of compound 78-3 to obtain compound 173-3 (0.27 mmol) which was used in the next step without further purification.

Step 173-4

According to Step 78-5 in the synthetic method for EXAMPLE 78, compound 173-3 (0.27 mmol) was used instead of compound 78-4 to obtain compound 173-4 (0.27 mmol).

Step 173-5

According to Step 78-6 in the synthetic method for EXAMPLE 78, compound 173-4 (0.27 mmol) was used instead of compound 78-5 to obtain compound 173-5 (0.27 mmol) which was used in the next step without further purification.

Step 173-6

According to Step 78-7 in the synthetic method for EXAMPLE 78, compound 173-5 (0.27 mmol) was used instead of compound 78-6 to obtain EXAMPLE 173 (81 mg, 0.21 mmol) as a white amorphous solid.

Example 174

Synthesis of (2R)—N-(4-amidinophenyl)-2-hydroxy-2-[(2R)-3-oxo-4-(3,4,5-trifluorophenyl)morpholin-2-yl]acetamide (EXAMPLE 174)

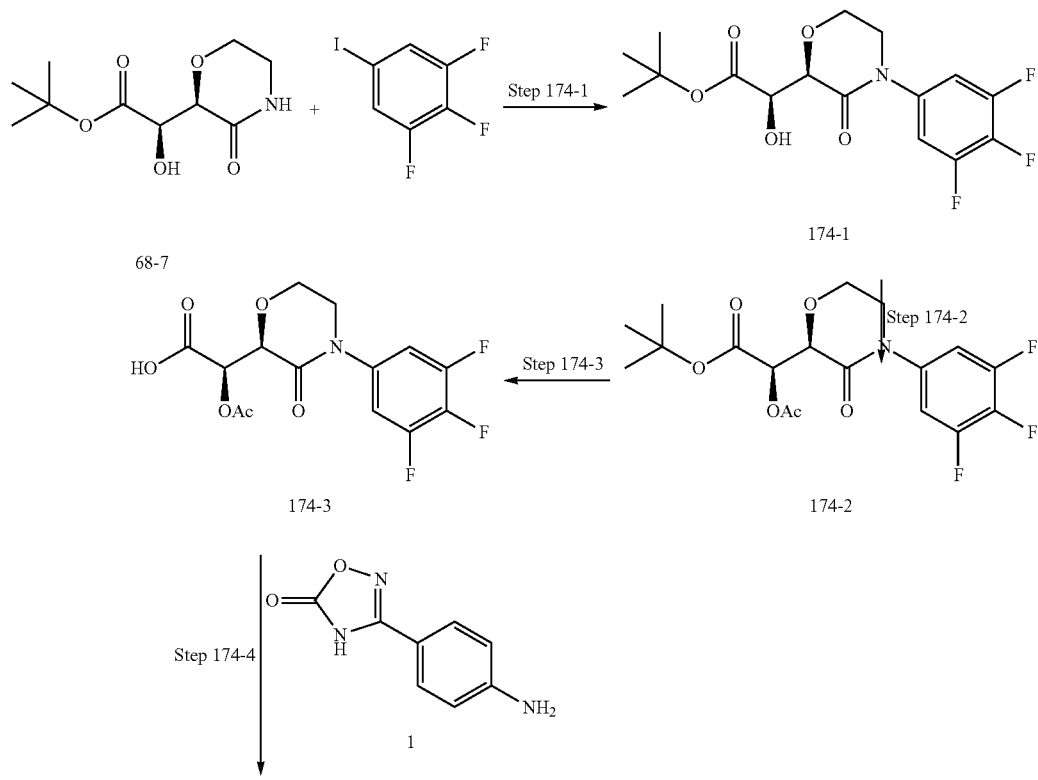

465

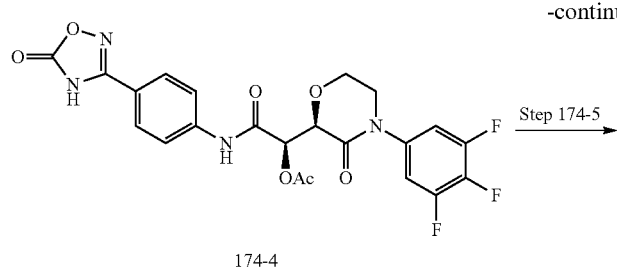

174-4

-continued

466

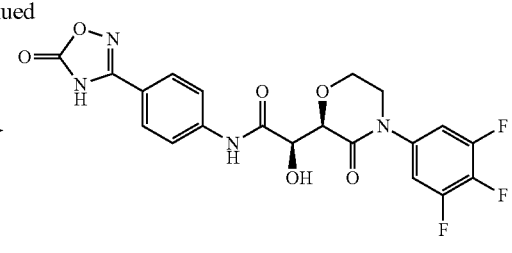

174-5

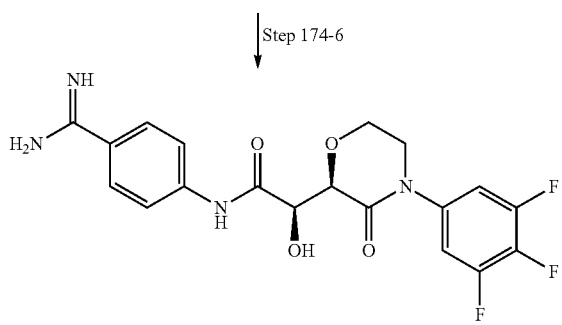

EXAMPLE 174

Step 174-1

According to Step 78-2 in the synthetic method for EXAMPLE 78, 3,4,5-trifluoro-5-iodobenzene (93 mg, 0.36 mmol) was used instead of compound 78-1 to obtain compound 174-1 (54 mg, 0.15 mmol).

Step 174-2

According to Step 78-3 in the synthetic method for EXAMPLE 78, compound 174-1 (117 mg, 0.32 mmol) was used instead of compound 78-2 to obtain compound 174-2 (121 mg, 0.30 mmol).

Step 174-3

According to Step 78-4 in the synthetic method for EXAMPLE 78, compound 174-2 (121 mg, 0.30 mmol) was used instead of compound 78-3 to obtain compound 174-3 (0.30 mmol) which was used in the next step without further purification.

Step 174-4

According to Step 78-5 in the synthetic method for EXAMPLE 78, compound 174-3 (0.30 mmol) was used instead of compound 78-4 to obtain compound 169-4 (151 mg, 0.30 mmol).

Step 174-5

According to Step 78-6 in the synthetic method for EXAMPLE 78, compound 174-4 (151 mg, 0.30 mmol) was used instead of compound 78-5 to obtain compound 174-5 (0.30 mmol) which was used in the next step without further purification.

Step 174-6

According to Step 78-7 in the synthetic method for EXAMPLE 78, compound 174-5 (0.30 mmol) was used instead of compound 78-6 to obtain EXAMPLE 174 (48 mg, 0.10 mmol) as a white amorphous solid.

Example 175

Synthesis of (2R)—N-(4-amidinophenyl)-2-hydroxy-2-[(2R)-3-oxo-4-(3,4-difluorophenyl)morpholin-2-yl]acetamide (EXAMPLE 175)

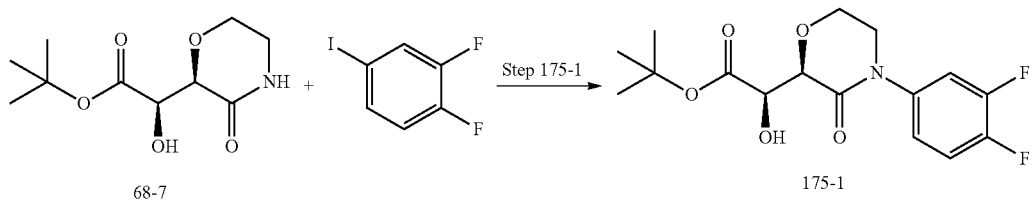

Step 175-2

-continued

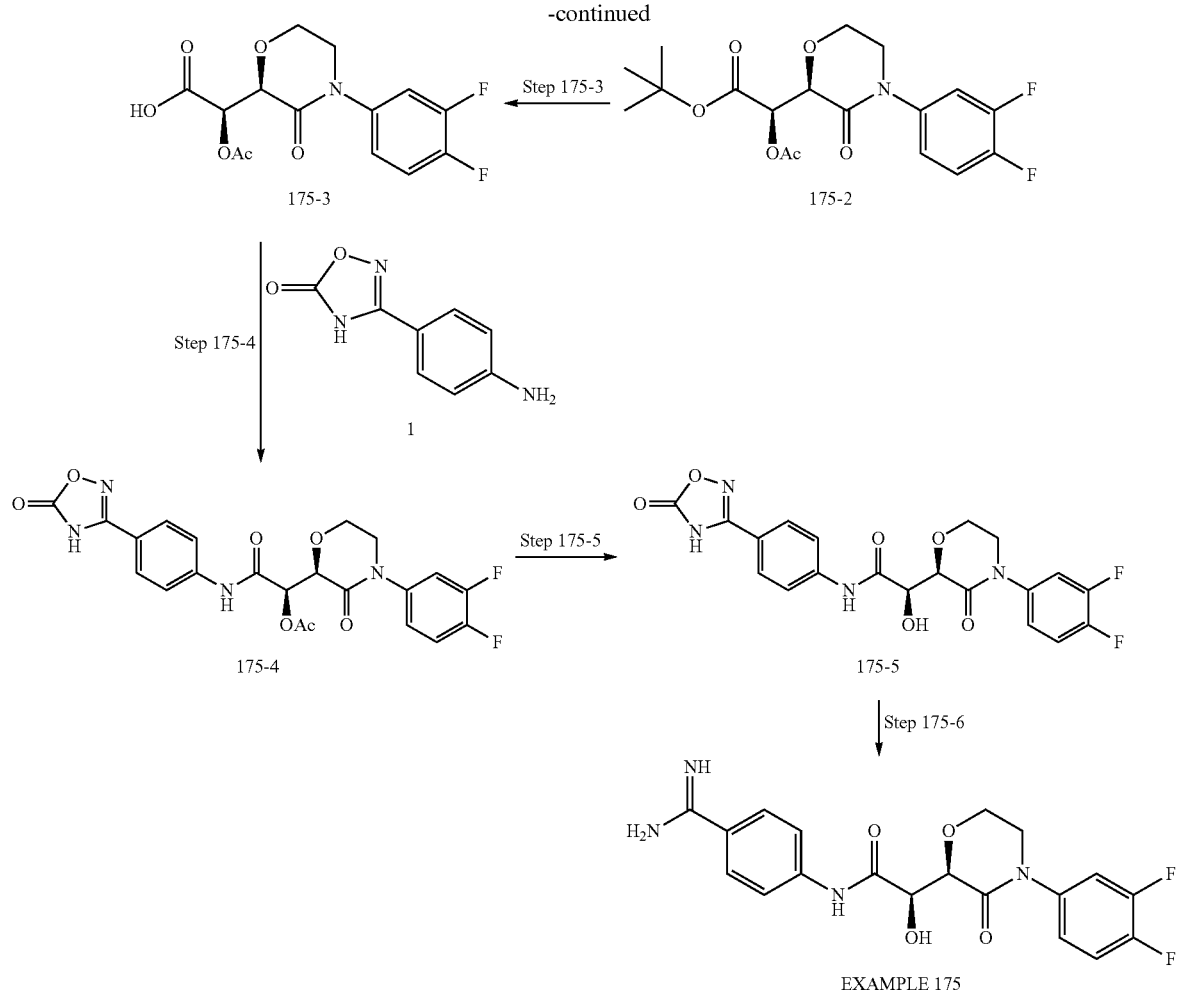

Step 175-1

According to Step 78-2 in the synthetic method for EXAMPLE 78, 3,4-difluoro-5-iodobenzene (86 mg, 0.36 mmol) was used instead of compound 78-1 to obtain compound 175-1 (54 mg, 0.13 mmol).

Step 175-2

According to Step 78-3 in the synthetic method for EXAMPLE 78, compound 175-1 (94 mg, 0.27 mmol) was used instead of compound 78-2 to obtain compound 175-2 (88 mg, 0.23 mmol).

Step 175-3

According to Step 78-4 in the synthetic method for EXAMPLE 78, compound 175-2 (88 mg, 0.23 mmol) was used instead of compound 78-3 to obtain compound 175-3 (0.23 mmol) which was used in the next step without further purification.

Step 175-4

According to Step 78-5 in the synthetic method for EXAMPLE 78, compound 175-3 (0.23 mmol) was used instead of compound 78-4 to obtain compound 175-4 (0.23 mmol).

Step 175-5

According to Step 78-6 in the synthetic method for EXAMPLE 78, compound 175-4 (0.23 mmol) was used instead of compound 78-5 to obtain compound 175-5 (0.23 mmol) which was used in the next step without further purification.

Step 175-6

According to Step 78-7 in the synthetic method for EXAMPLE 78, compound 175-5 (0.23 mmol) was used instead of compound 78-6 to obtain EXAMPLE 175 (99 mg, 0.23 mmol) as a white amorphous solid.

Example 176
Synthesis of (2R)—N-(4-amidinophenyl)-2-hydroxy-2-[(2R)-3-oxo-4-(2,4-difluoropyridin-3-yl)morpholin-2-yl]acetamide (EXAMPLE 176)
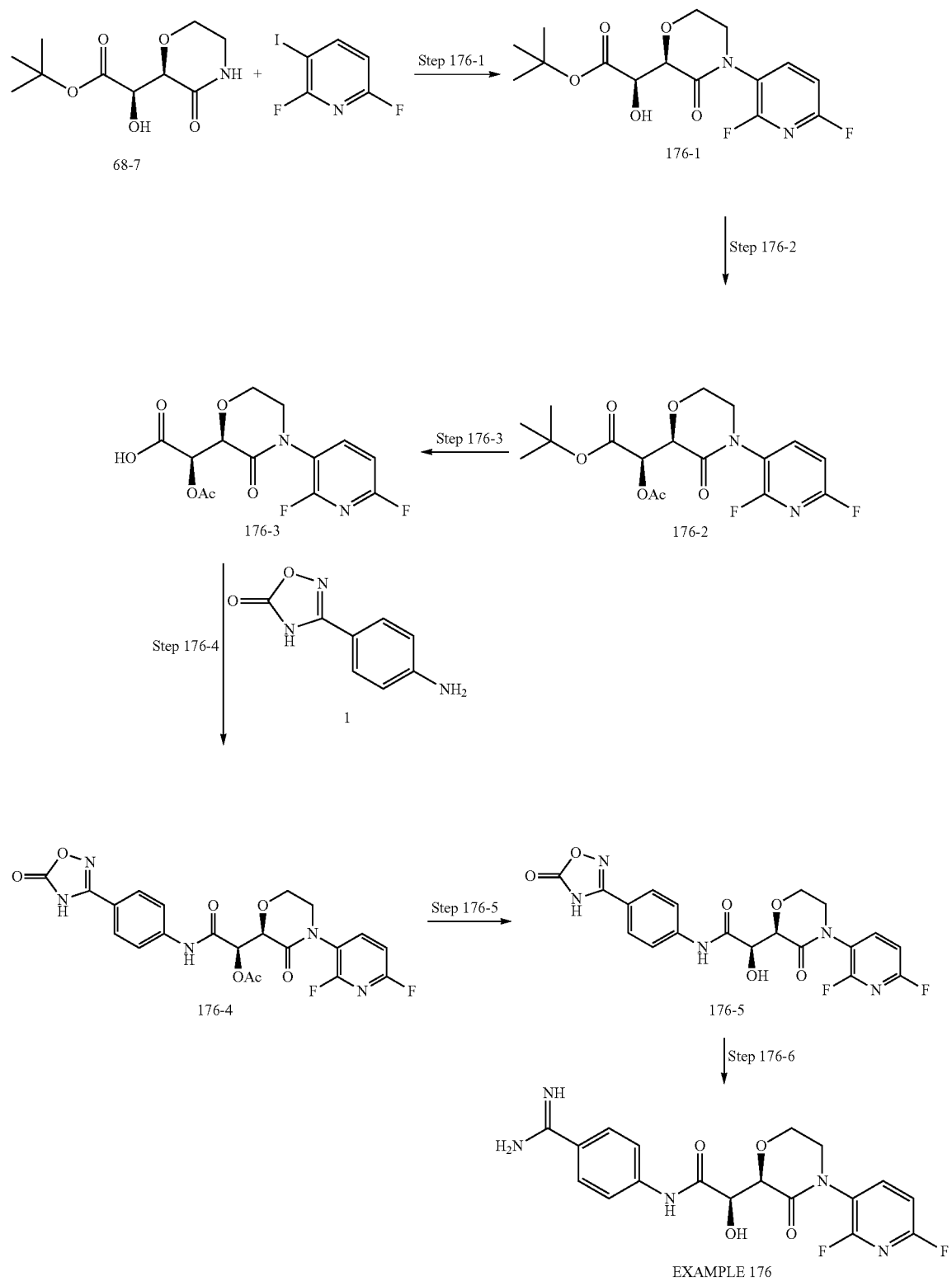

Step 176-1

According to Step 78-2 in the synthetic method for EXAMPLE 78, 2,6-difluoropyridine (174 mg, 0.72 mmol) was used instead of compound 78-1 to obtain compound 176-1 (42 mg, 0.12 mmol).

Step 176-2

According to Step 78-3 in the synthetic method for EXAMPLE 78, compound 176-1 (55 mg, 0.16 mmol) was used instead of compound 78-2 to obtain compound 176-2 (63 mg, 0.16 mmol).

Step 176-3

According to Step 78-4 in the synthetic method for EXAMPLE 78, compound 176-2 (63 mg, 0.16 mmol) was used instead of compound 78-3 to obtain compound 176-3 (0.16 mmol) which was used in the next step without further purification.

Step 176-4

According to Step 78-5 in the synthetic method for EXAMPLE 78, compound 176-3 (0.16 mmol) was used instead of compound 78-4 to obtain compound 176-4 (73 mg, 0.15 mmol).

Step 176-5

According to Step 78-6 in the synthetic method for EXAMPLE 78, compound 176-4 (73 mg, 0.15 mmol) was used instead of compound 78-5 to obtain compound 176-5 (0.15 mmol) which was used in the next step without further purification.

Step 176-6

According to Step 78-7 in the synthetic method for EXAMPLE 78, compound 176-5 (0.15 mmol) was used instead of compound 78-6 to obtain EXAMPLE 176 (13 mg, 0.032 mmol) as a white amorphous solid.

Example 177

Synthesis of (2R)—N-(4-amidinophenyl)-2-hydroxy-2-[(2R)-3-oxo-4-(4,5-difluoropyridin-3-yl)morpholin-2-yl]acetamide (EXAMPLE 177)

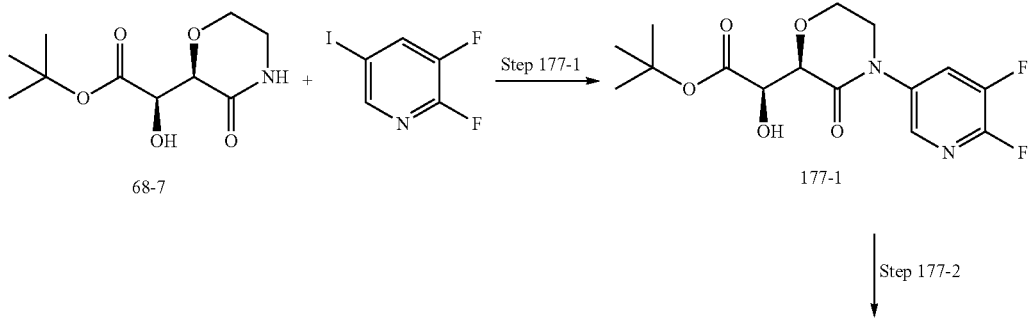

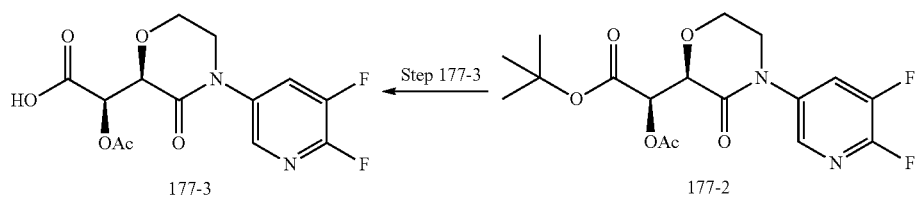

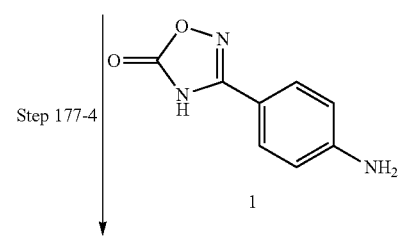

473

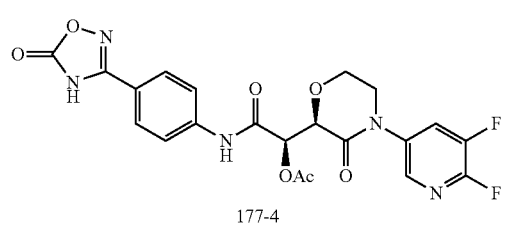

177-4

-continued

474

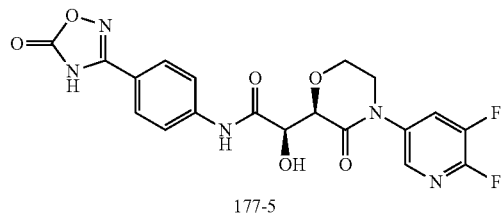

177-5

Step 177-5

Step 177-6

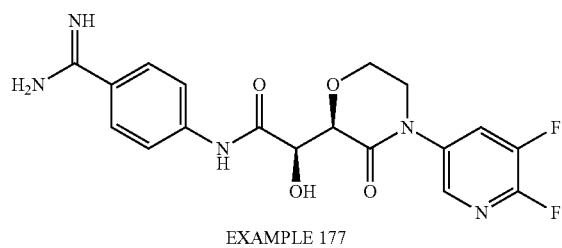

EXAMPLE 177

Step 177-1

According to Step 78-2 in the synthetic method for EXAMPLE 78, 2,3-difluoropyridine (174 mg, 0.72 mmol) was used instead of compound 78-1 to obtain compound 177-1 (106 mg, 0.31 mmol).

Step 177-2

According to Step 78-3 in the synthetic method for EXAMPLE 78, compound 177-1 (150 mg, 0.44 mmol) was used instead of compound 78-2 to obtain compound 177-2 (95 mg, 0.25 mmol).

Step 177-3

According to Step 78-4 in the synthetic method for EXAMPLE 78, compound 177-2 (95 mg, 0.25 mmol) was used instead of compound 78-3 to obtain compound 177-3 (0.25 mmol) which was used in the next step without further purification.

Step 177-4

According to Step 78-5 in the synthetic method for EXAMPLE 78, compound 177-3 (0.25 mmol) was used instead of compound 78-4 to obtain compound 177-4 (123 mg, 0.25 mmol).

Step 177-5

According to Step 78-6 in the synthetic method for EXAMPLE 78, compound 177-4 (123 mg, 0.25 mmol) was used instead of compound 78-5 to obtain compound 177-5 (0.25 mmol) which was used in the next step without further purification.

Step 177-6

According to Step 78-7 in the synthetic method for EXAMPLE 78, compound 177-5 (0.25 mmol) was used instead of compound 78-6 to obtain EXAMPLE 177 (65 mg, 0.15 mmol) as a white amorphous solid.

Example 178

Synthesis of (2R)—N-(4-amidinophenyl)-2-hydroxy-2-[(2R)-3-oxo-4-(4-carboxyphenyl)morpholin-2-yl]acetamide (EXAMPLE 178)

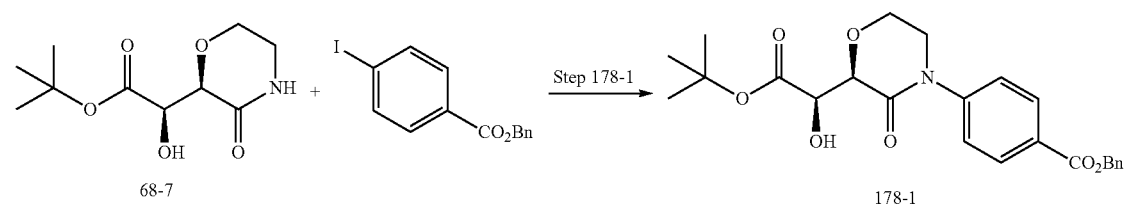

68-7

Step 178-1

178-1

Step 178-2

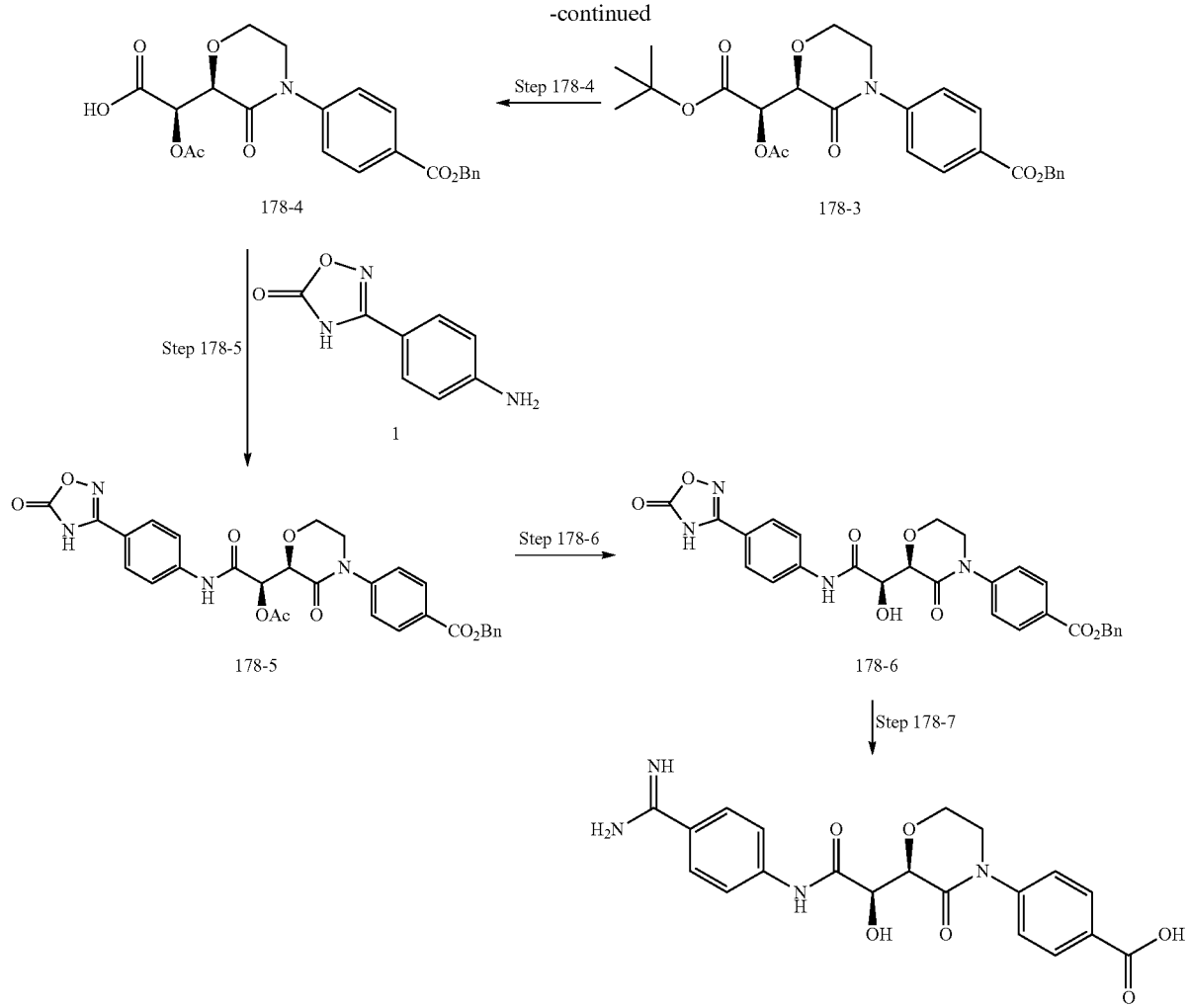

Step 178-1

According to Step 78-2 in the synthetic method for EXAMPLE 78, benzyl 4-iodobenzoate (122 mg, 0.36 mmol) was used instead of compound 78-1 to obtain compound 178-1 (110 mg, 0.25 mmol).

Step 178-2

According to Step 78-3 in the synthetic method for EXAMPLE 78, compound 178-1 (110 mg, 0.25 mmol) was used instead of compound 78-2 to obtain compound 178-2 (111 mg, 0.23 mmol).

Step 178-3

According to Step 78-4 in the synthetic method for EXAMPLE 78, compound 178-2 (111 mg, 0.23 mmol) was used instead of compound 78-3 to obtain compound 178-3 (0.23 mmol) which was used in the next step without further purification.

Step 178-4

According to Step 78-5 in the synthetic method for EXAMPLE 78, compound 178-3 (0.23 mmol) was used instead of compound 78-4 to obtain compound 169-4 (132 mg, 0.23 mmol).

Step 178-5

According to Step 78-6 in the synthetic method for EXAMPLE 78, compound 178-4 (132 mg, 0.23 mmol) was used instead of compound 78-5 to obtain compound 178-5 (0.23 mmol) which was used in the next step without further purification.

Step 178-6

According to Step 78-7 in the synthetic method for EXAMPLE 78, compound 178-5 (0.23 mmol) was used instead of compound 78-6 to obtain EXAMPLE 178 (61 mg, 0.15 mmol) as a white amorphous solid.

Example 179

Synthesis of (2R)—N-(4-amidinophenyl)-2-hydroxy-2-[(2R)-3-oxo-4-(3-(carboxymethyl)(methyl)carbamoylphenyl)morpholin-2-yl]acetamide (EXAMPLE 179)

Step 179-1

Synthesis of benzyl 2-(3-iodo-N-methylbenzamido)acetate 179-1

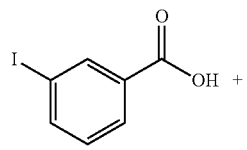

+

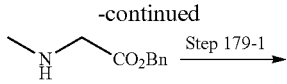

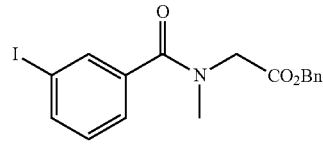

According to Step 77-1 in the synthetic method for compound 77, 3-iodobenzoic acid and sarcosine benzyl ester were used to obtain compound 179-1.

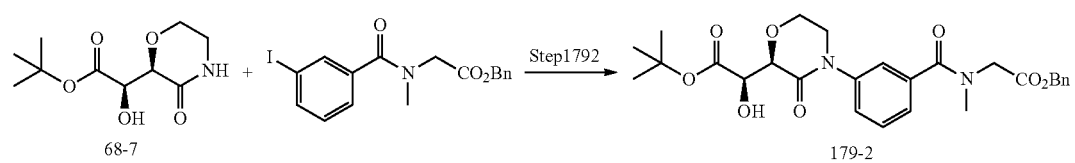

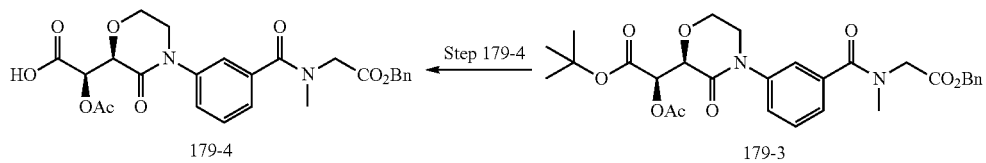

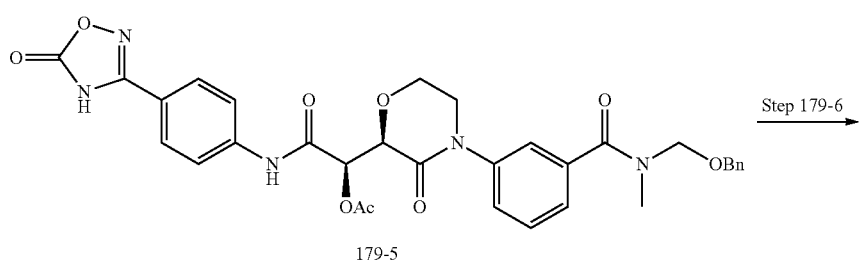

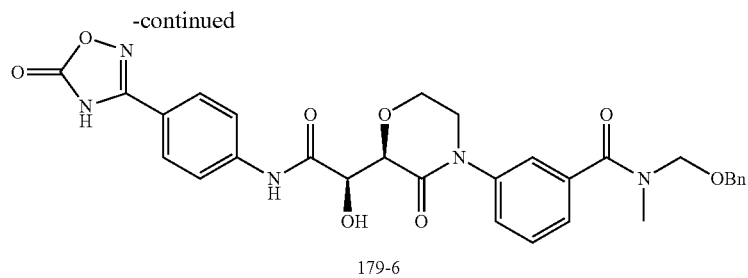

179-6

↓ Step 179-7

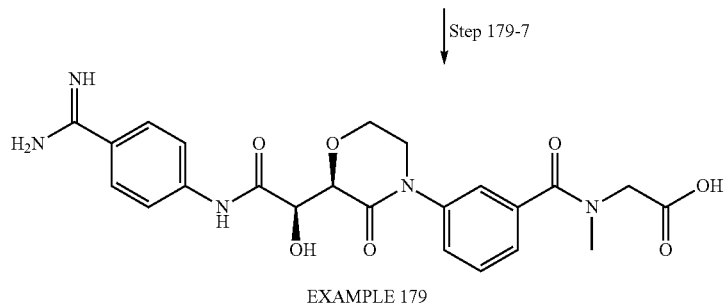

EXAMPLE 179

Step 179-2

According to Step 78-3 in the synthetic method for EXAMPLE 78, compound 179-1 (189 mg, 0.46 mmol) was used instead of compound 78-2 to obtain compound 179-2 (150 mg, 0.29 mmol).

Step 179-3

According to Step 78-2 in the synthetic method for EXAMPLE 78, compound 179-2 (150 mg, 0.29 mmol) was used instead of compound 78-2 to obtain compound 179-3 (139 mg, 0.25 mmol).

Step 179-4

According to Step 78-4 in the synthetic method for EXAMPLE 78, compound 179-3 (139 mg, 0.25 mmol) was used instead of compound 78-3 to obtain compound 179-4 (0.25 mmol) which was used in the next step without further purification.

Step 179-5

According to Step 78-5 in the synthetic method for EXAMPLE 78, compound 179-4 (0.25 mmol) was used instead of compound 78-4 to obtain compound 179-5 (166 mg, 0.25 mmol).

Step 179-6

According to Step 78-6 in the synthetic method for EXAMPLE 78, compound 179-5 (252 mg, 0.38 mmol) was used instead of compound 78-5 to obtain compound 179-6 (145 mg, 0.24 mmol) which was used in the next step without further purification.

Step 179-7

According to Step 78-7 in the synthetic method for EXAMPLE 78, compound 179-6 (145 mg, 0.24 mmol) was used instead of compound 78-6 to obtain EXAMPLE 179 (54 mg, 0.11 mmol) as a white amorphous solid.

Example 180

Synthesis of (2R)—N-(4-amidinophenyl)-2-hydroxy-2-[(2R)-3-oxo-4-(3-carboxyphenyl)morpholin-2-yl]acetamide (EXAMPLE 180)

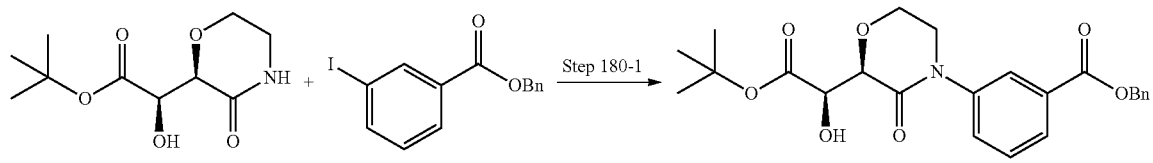

↓ Step 180-2

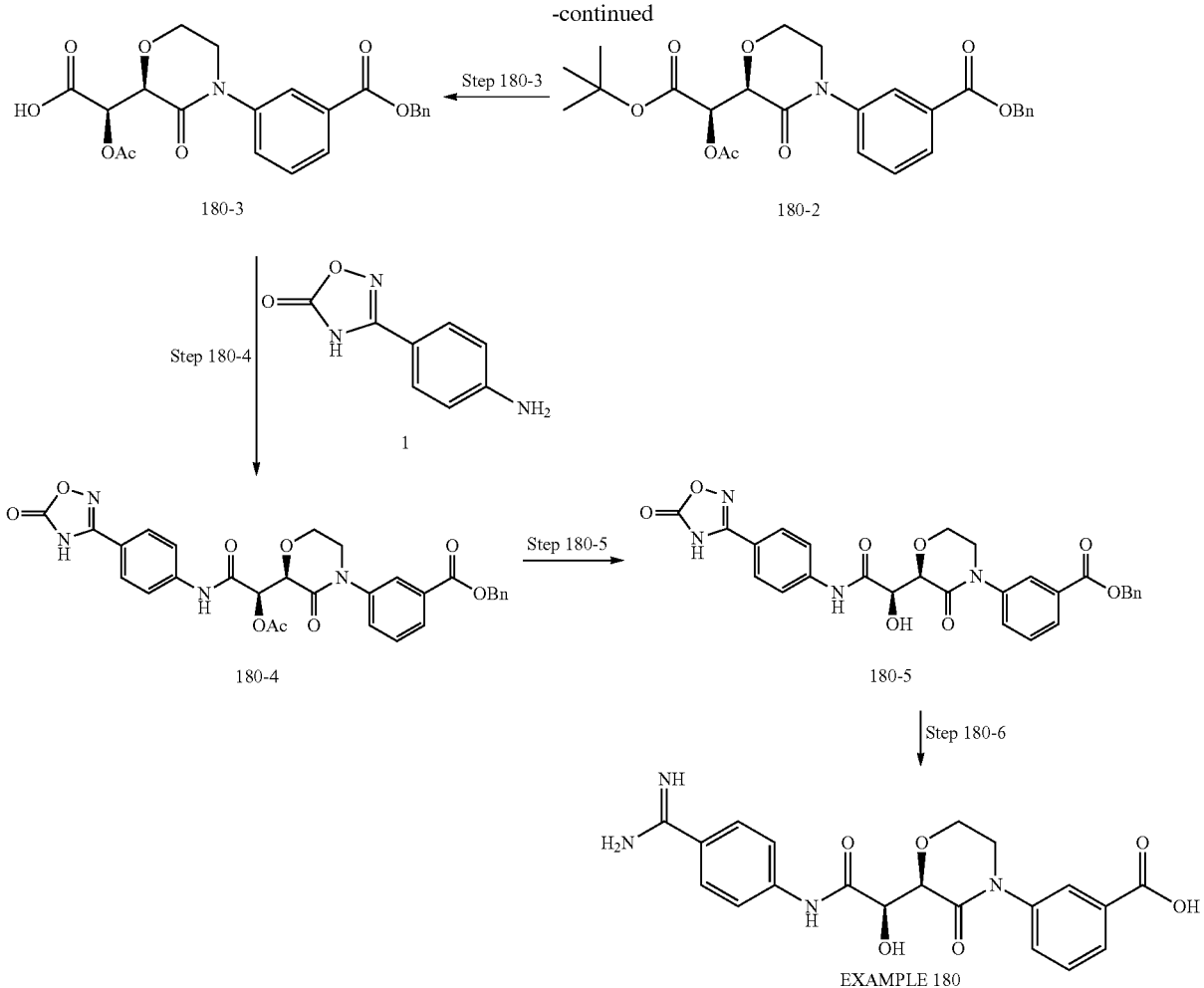

Step 180-1

According to Step 78-2 in the synthetic method for EXAMPLE 78, benzyl 3-iodobenzoate (122 mg, 0.36 mmol) was used instead of compound 78-1 to obtain compound 180-1 (127 mg, 0.29 mmol).

Step 180-2

According to Step 78-3 in the synthetic method for EXAMPLE 78, compound 180-1 (127 mg, 0.29 mmol) was used instead of compound 78-2 to obtain compound 180-2 (127 mg, 0.26 mmol).

Step 180-3

According to Step 78-4 in the synthetic method for EXAMPLE 78, compound 180-2 (127 mg, 0.26 mmol) was used instead of compound 78-3 to obtain compound 180-3 (0.26 mmol) which was used in the next step without further purification.

Step 180-4

According to Step 78-5 in the synthetic method for EXAMPLE 78, compound 180-3 (0.26 mmol) was used instead of compound 78-4 to obtain compound 180-4 (0.26 mmol) which was used in the next step without further purification.

Step 180-5

According to Step 78-6 in the synthetic method for EXAMPLE 78, compound 180-4 (0.26 mmol) was used instead of compound 78-5 to obtain compound 180-5 (130 mg, 0.24 mmol) which was used in the next step without further purification.

Step 180-6

According to Step 78-7 in the synthetic method for EXAMPLE 78, compound 180-5 (130 mg, 0.24 mmol) was used instead of compound 78-6 to obtain EXAMPLE 180 (64 mg, 0.16 mmol) as a white amorphous solid.

Example 181

Synthesis of (2R)—N-(4-amidinophenyl)-2-hydroxy-2-[(2R)-3-oxo-4-(4-methoxycarbonylphenyl)morpholin-2-yl]acetamide (EXAMPLE 181)

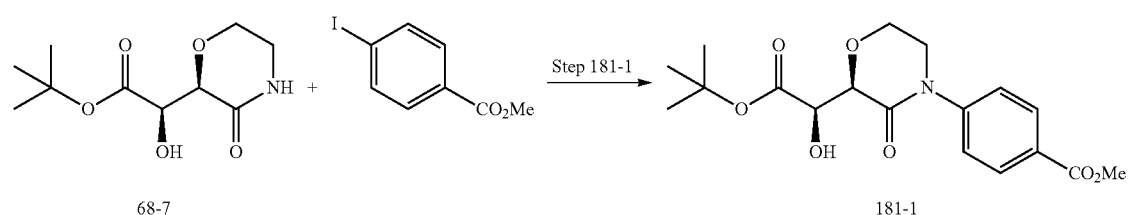
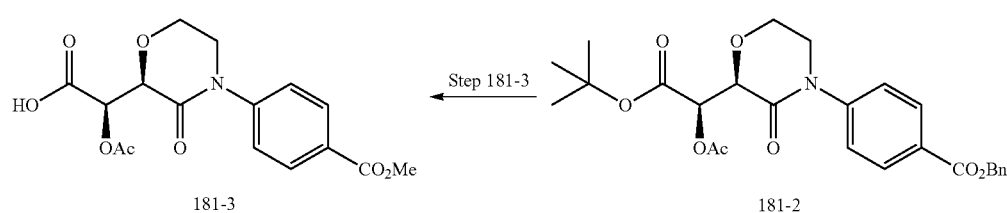
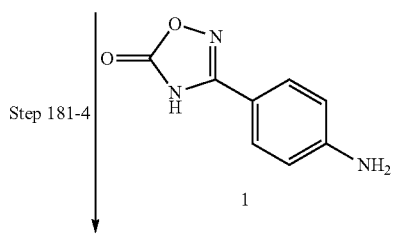
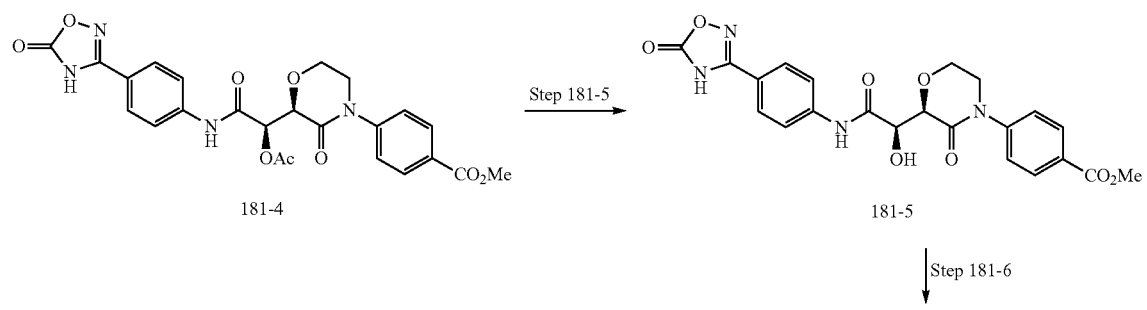

-continued

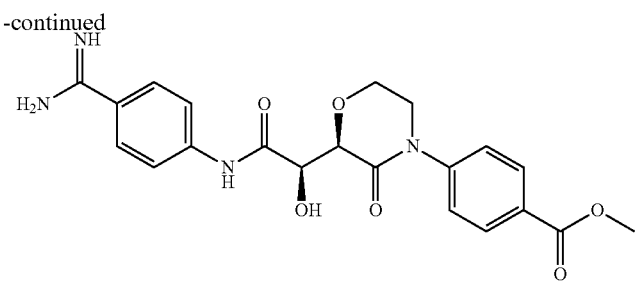

EXAMPLE 181

Step 181-1

According to Step 78-2 in the synthetic method for EXAMPLE 78, methyl 4-iodobenzoate (123 mg, 0.47 mmol) was used instead of compound 78-1 to obtain compound 181-1 (142 mg, 0.39 mmol).

Step 181-2

According to Step 78-3 in the synthetic method for EXAMPLE 78, compound 181-1 (142 mg, 0.39 mmol) was used instead of compound 78-2 to obtain compound 181-2 (145 mg, 0.37 mmol).

Step 181-3

According to Step 78-4 in the synthetic method for EXAMPLE 78, compound 181-2 (145 mg, 0.37 mmol) was used instead of compound 78-3 to obtain compound 181-3 (0.37 mmol) which was used in the next step without further purification.

Step 181-4

According to Step 78-5 in the synthetic method for EXAMPLE 78, compound 181-3 (0.37 mmol) was used instead of compound 78-4 to obtain compound 181-4 (0.37 mmol).

Step 181-5

According to Step 78-6 in the synthetic method for EXAMPLE 78, compound 181-4 (0.37 mmol) was used instead of compound 78-5 to obtain compound 181-5 (143 mg, 0.31 mmol) which was used in the next step without further purification.

Step 181-6

According to Step 78-7 in the synthetic method for EXAMPLE 78, compound 181-5 (143 mg, 0.31 mmol) was used instead of compound 78-6 to obtain EXAMPLE 181 (125 mg, 0.29 mmol) as a white amorphous solid.

Example 182

Synthesis of (2R)—N-(4-amidinophenyl)-2-hydroxy-2-[(2R)-3-oxo-4-(3-methoxycarbonylphenyl)morpholin-2-yl]acetamide (EXAMPLE 182)

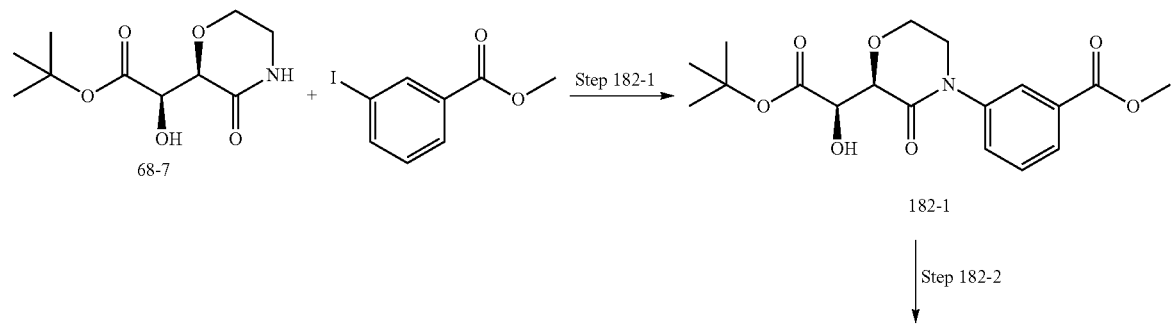

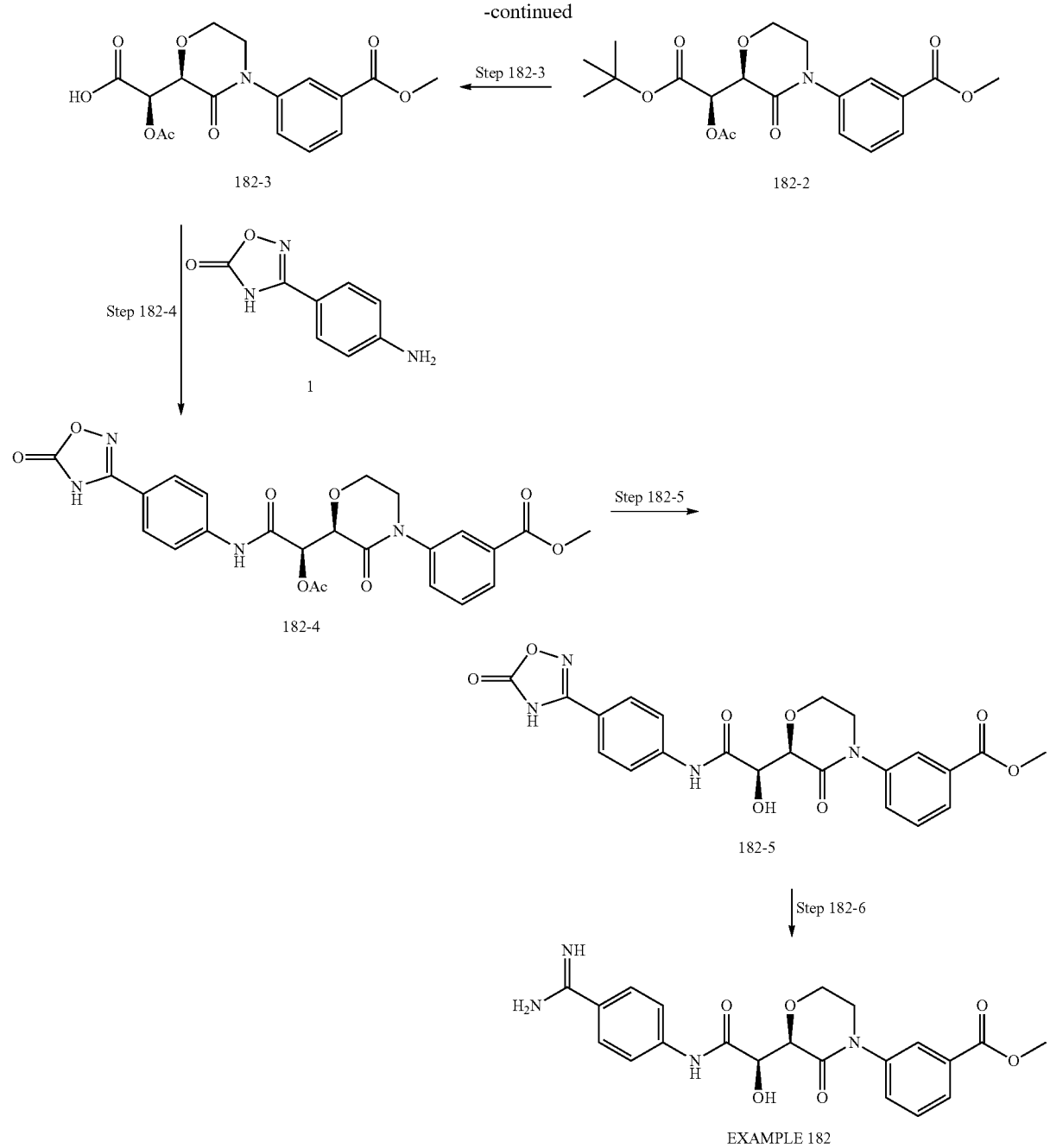

Step 182-1

According to Step 78-2 in the synthetic method for EXAMPLE 78, methyl 3-iodobenzoate (123 mg, 0.47 mmol) was used instead of compound 78-1 to obtain compound 182-1 (91 mg, 0.25 mmol).

Step 182-2

According to Step 78-3 in the synthetic method for EXAMPLE 78, compound 182-1 (91 mg, 0.25 mmol) was used instead of compound 78-2 to obtain compound 182-2 (90 mg, 0.22 mmol).

Step 182-3

According to Step 78-4 in the synthetic method for EXAMPLE 78, compound 182-2 (90 mg, 0.22 mmol) was used instead of compound 78-3 to obtain compound 182-3 (0.22 mmol) which was used in the next step without further purification.

Step 182-4

According to Step 78-5 in the synthetic method for EXAMPLE 78, compound 182-3 (0.22 mmol) was used instead of compound 78-4 to obtain compound 182-4 (106 mg, 0.21 mmol).

Step 182-5

According to Step 78-6 in the synthetic method for EXAMPLE 78, compound 182-4 (106 mg, 0.21 mmol) was used instead of compound 78-5 to obtain compound 182-5 (67 mg, 0.14 mmol) which was used in the next step without further purification.

Step 182-6

According to Step 78-7 in the synthetic method for EXAMPLE 78, compound 182-5 (67 mg, 0.14 mmol) was used instead of compound 78-6 to obtain EXAMPLE 182 (61 mg, 0.14 mmol) as a white amorphous solid.

Example 183

Synthesis of (2R)—N-(4-amidinophenyl)-2-hydroxy-2-[(2R)-3-oxo-4-(3-carboxy-4-fluorophenyl)morpholin-2-yl]acetamide (EXAMPLE 183)

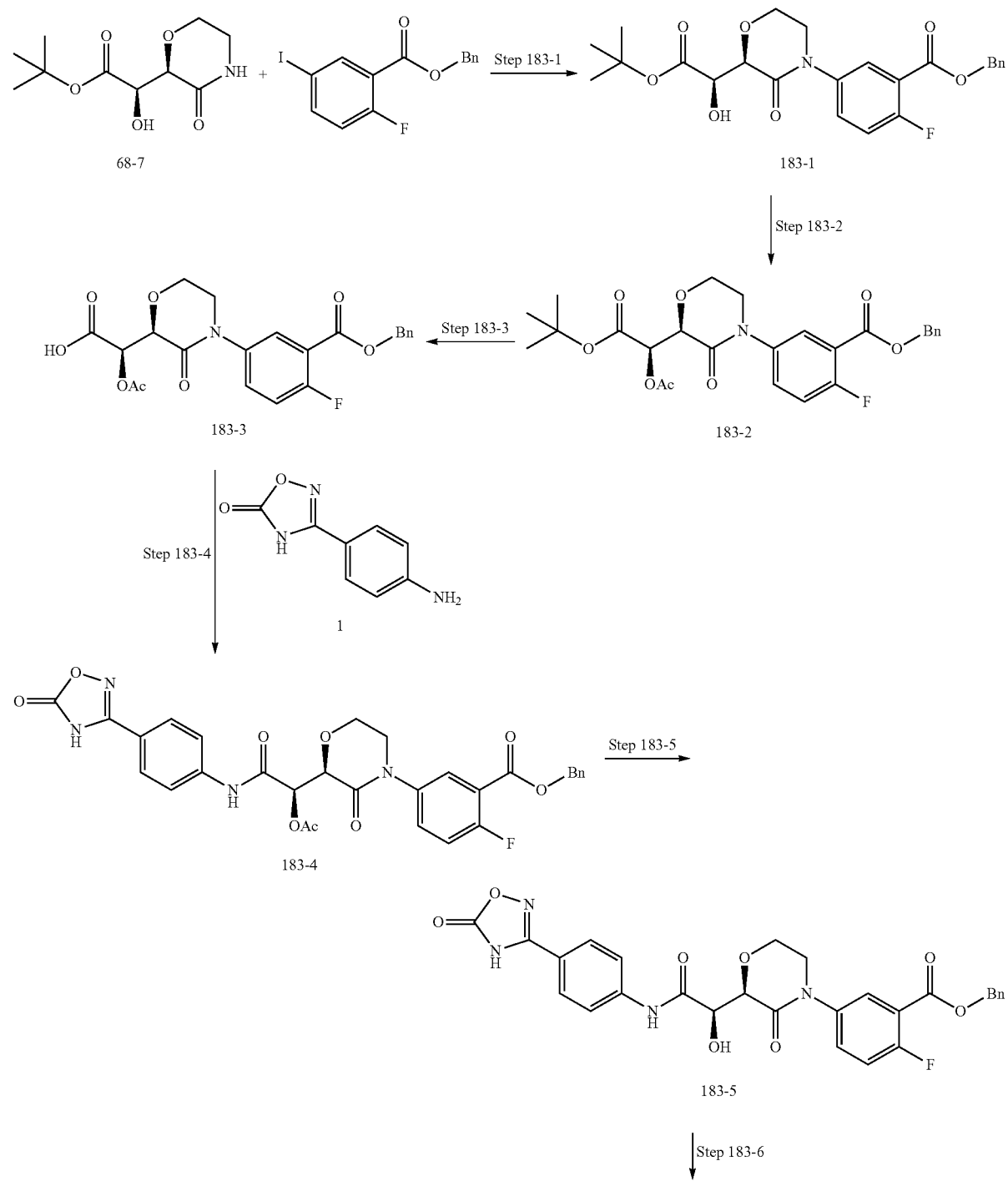

-continued

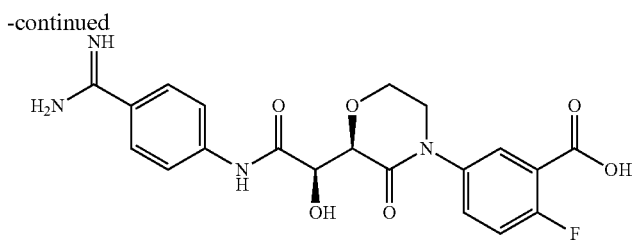

EXAMPLE 183

Step 183-1

According to Step 78-2 in the synthetic method for EXAMPLE 78, benzyl 2-fluoro-5-iodobenzoate (167 mg, 0.47 mmol) was used instead of compound 78-1 to obtain compound 183-1 (89 mg, 0.19 mmol).

Step 183-2

According to Step 78-3 in the synthetic method for EXAMPLE 78, compound 183-1 (89 mg, 0.19 mmol) was used instead of compound 78-2 to obtain compound 183-2 (91 mg, 0.18 mmol).

Step 183-3

According to Step 78-4 in the synthetic method for EXAMPLE 78, compound 183-2 (91 mg, 0.18 mmol) was used instead of compound 78-3 to obtain compound 183-3 (0.18 mmol) which was used in the next step without further purification.

Step 183-4

According to Step 78-5 in the synthetic method for EXAMPLE 78, compound 183-3 (0.18 mmol) was used instead of compound 78-4 to obtain compound 183-4 (80 mg, 0.13 mmol).

Step 183-5

According to Step 78-6 in the synthetic method for EXAMPLE 78, compound 183-4 (80 mg, 0.13 mmol) was used instead of compound 78-5 to obtain compound 183-5 (0.13 mmol) which was used in the next step without further purification.

Step 183-6

According to Step 78-7 in the synthetic method for EXAMPLE 78, compound 183-5 (0.13 mmol) was used instead of compound 78-6 to obtain EXAMPLE 183 (11 mg, 0.026 mmol) as a white amorphous solid.

Example 184

Synthesis of (2R)—N-(4-amidinophenyl)-2-hydroxy-2-[(2R)-3-oxo-4-(3-(methoxycarbonylmethyl)(methyl)carbamoylphenyl)morpholin-2-yl]acetamide (EXAMPLE 184)

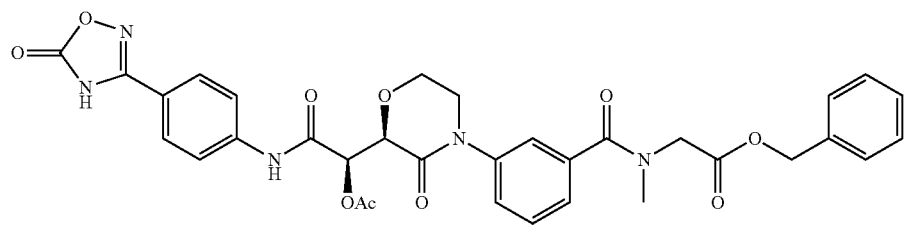

179-5

Step 184-1

-continued

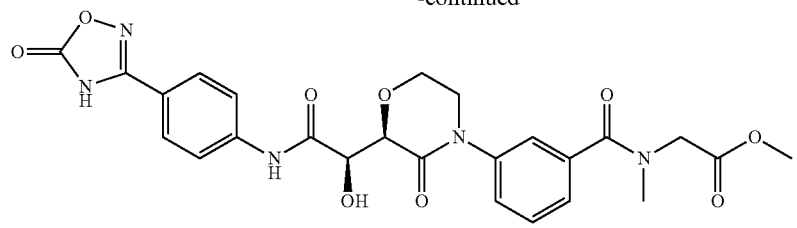

184-1

↓ Step 184-2

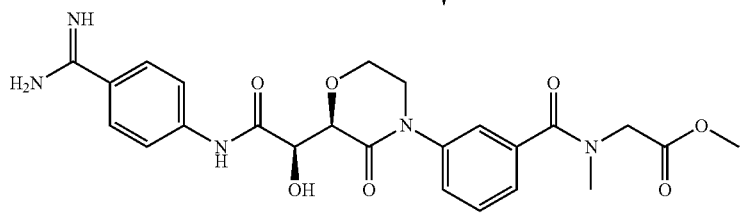

EXAMPLE 184

Step 184-1

To a solution of compound 179-5 (184 mg, 0.28 mmol) in methanol (1.4 mL) and water (1.1 mL) was added triethylamine (280 mg, 2.8 mmol). The reaction mixture was stirred at room temperature for 16 hours. Solvent was evaporated under reduced pressure. The crude product was purified by RP-HPLC to afford compound 184-1 (45 mg, 0.083 mmol).

Step 184-2

According to Step 78-7 in the synthetic method for EXAMPLE 78, compound 184-1 (45 mg, 0.083 mmol) was used instead of compound 78-6 to obtain EXAMPLE 184 (35 mg, 0.07 mmol) as a white amorphous solid.

Example 185

Synthesis of (2R)—N-(4-amidinophenyl)-2-hydroxy-2-[(2R)-3-oxo-4-(3-carboxymethylphenyl)morpholin-2-yl]acetamide (EXAMPLE 185)

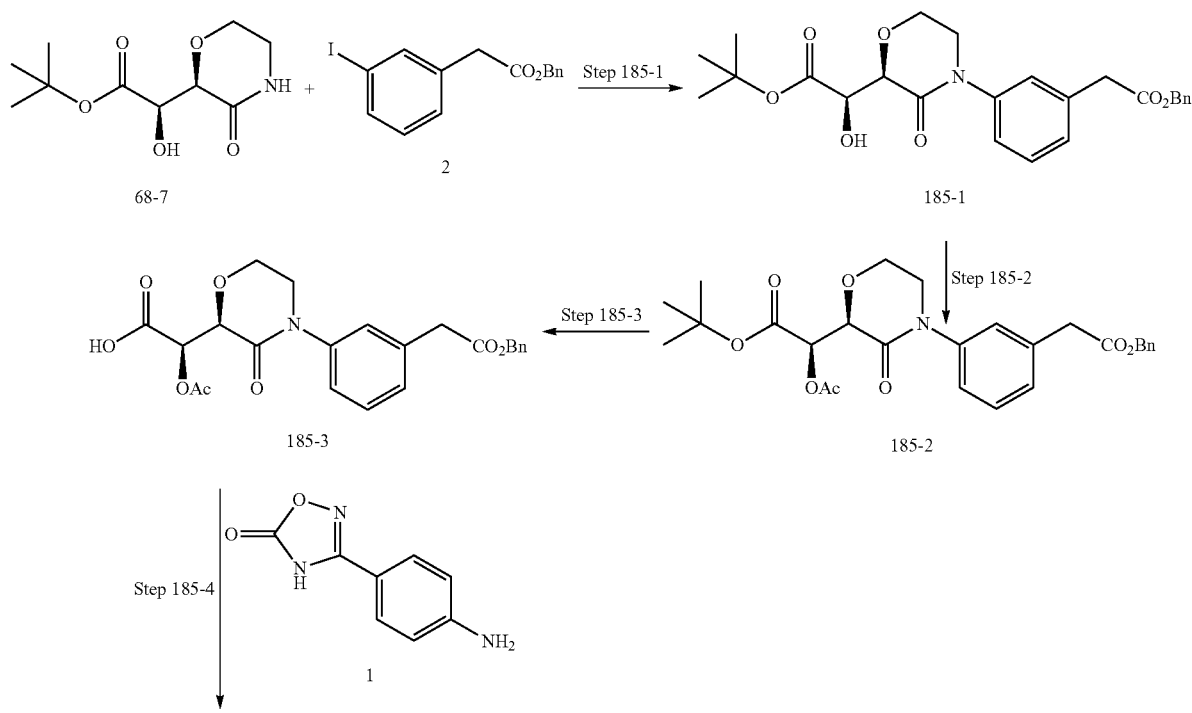

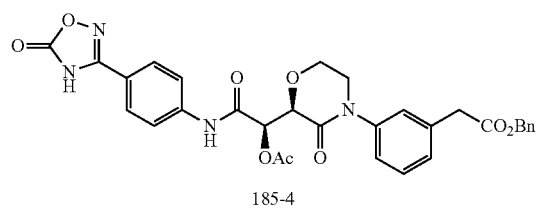

185-4

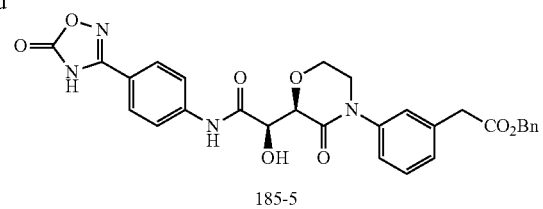

185-5

Step 185-6 ↓

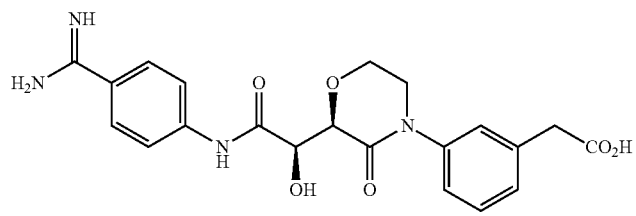

EXAMPLE 185

Step 185-1

According to Step 78-2 in the synthetic method for EXAMPLE 78, compound 2 (137 mg, 0.39 mmol) was used instead of compound 78-1 to obtain compound 185-1 (154 mg, 0.34 mmol).

Step 185-2

According to Step 78-3 in the synthetic method for EXAMPLE 78, compound 185-1 (154 mg, 0.34 mmol) was used instead of compound 78-2 to obtain compound 185-2 (77 mg, 0.31 mmol).

Step 185-3

According to Step 78-4 in the synthetic method for EXAMPLE 78, compound 185-2 (77 mg, 0.31 mmol) was used instead of compound 78-3 to obtain compound 185-3 (0.31 mmol) which was used in the next step without further purification.

Step 185-4

According to Step 78-5 in the synthetic method for EXAMPLE 78, compound 185-3 (0.31 mmol) was used instead of compound 78-4 to obtain compound 185-4 (0.31 mmol).

Step 185-5

According to Step 78-6 in the synthetic method for EXAMPLE 78, compound 185-4 (0.31 mmol) was used instead of compound 78-5 to obtain compound 185-5 (0.31 mmol) which was used in the next step without further purification.

Step 185-6

According to Step 78-7 in the synthetic method for EXAMPLE 78, compound 185-5 (0.31 mmol) was used instead of compound 78-6 to obtain EXAMPLE 185 (69 mg, 0.16 mmol) as a white amorphous solid.

Example 186
Synthesis of (2R)—N-(4-amidinophenyl)-2-hydroxy-2-[(2R)-3-oxo-4-(3-carboxy-5-fluorophenyl)morpholin-2-yl]acetamide (EXAMPLE 186)
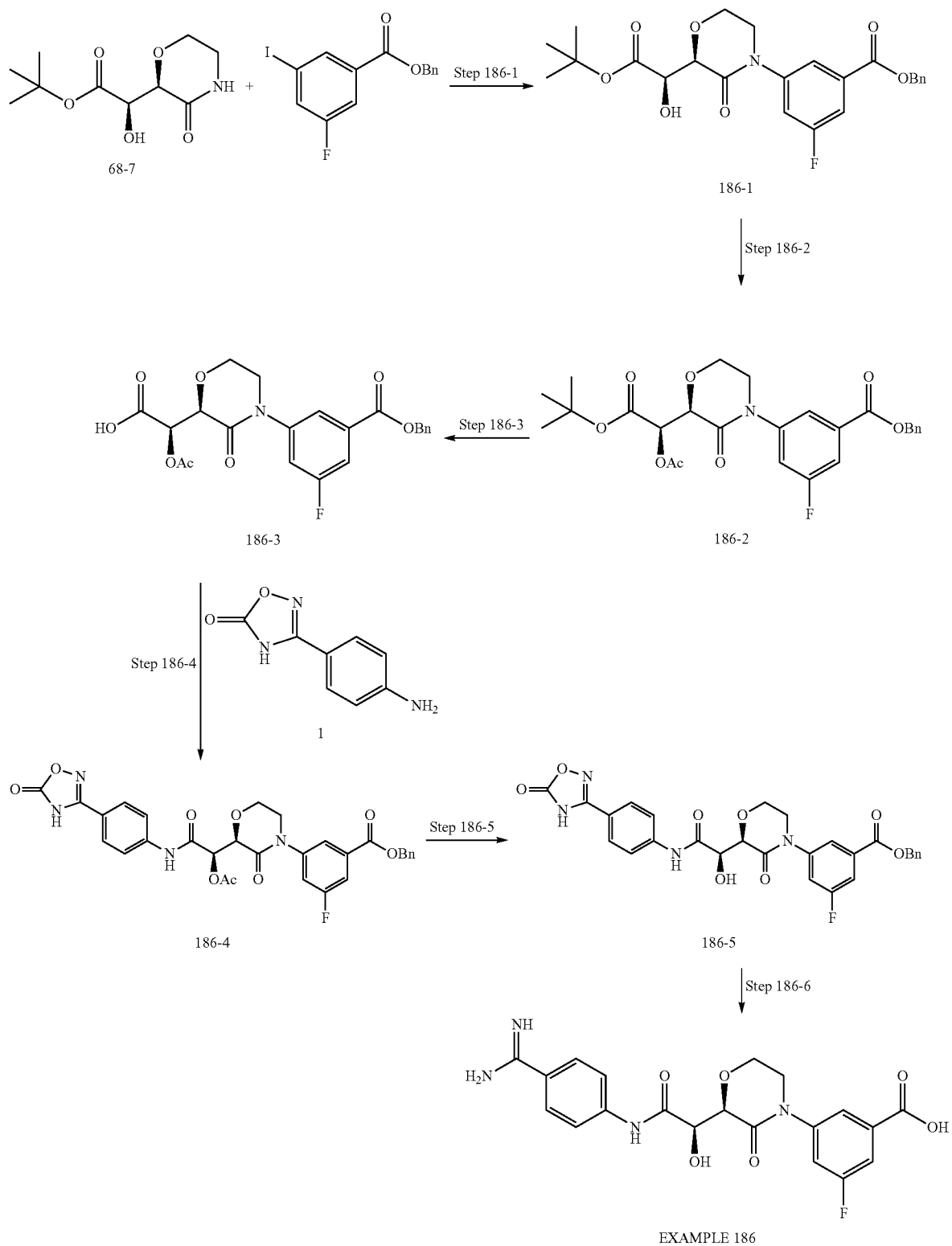

Step 186-1

According to Step 78-2 in the synthetic method for EXAMPLE 78, benzyl 3-fluoro-5-iodobenzoate (957 mg, 2.67 mmol) was used instead of compound 78-1 to obtain compound 186-1 (826 mg, 1.80 mmol).

Step 186-2

According to Step 78-3 in the synthetic method for EXAMPLE 78, compound 186-1 (826 mg, 1.80 mmol) was used instead of compound 78-1 to obtain compound 186-2 (840 mg, 1.68 mmol).

Step 186-3

According to Step 78-4 in the synthetic method for EXAMPLE 78, compound 186-2 (180 mg, 0.36 mmol) was used instead of compound 78-3 to obtain compound 186-3 (0.36 mmol) which was used in the next step without further purification.

Step 186-4

According to Step 78-5 in the synthetic method for EXAMPLE 78, compound 186-3 (0.36 mmol) was used instead of compound 78-4 to obtain compound 186-4 (208 mg, 0.34 mmol).

Step 186-5

According to Step 78-6 in the synthetic method for EXAMPLE 78, compound 186-4 (208 mg, 0.34 mmol) was used instead of compound 78-5 to obtain compound 186-5 (0.34 mmol) which was used in the next step without further purification.

Step 186-6

According to Step 78-7 in the synthetic method for EXAMPLE 78, compound 186-5 (0.34 mmol) was used instead of compound 78-6 to obtain EXAMPLE 186 (34 mg, 0.079 mmol) as a white amorphous solid.

Example 187

Synthesis of (2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide hydrochloride (EXAMPLE 187)

EXAMPLE 187

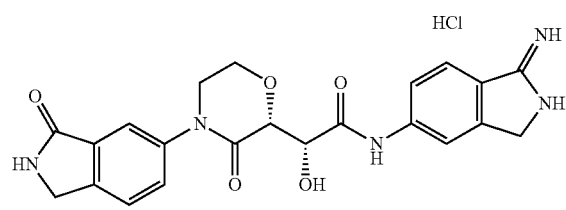

Method A

According to the synthetic method for EXAMPLE 142, EXAMPLE 187 can be prepared using corresponding carboxylic acid derived from 3-iodobenzoic acid instead of 3-iodoaniline.

Method B

According to the synthetic method for EXAMPLE 39, EXAMPLE 187 can be prepared using corresponding aniline derived from phthalimide instead of 4-(tert-butoxycarbonylamino)aniline.

Example 188

Synthesis of (2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide hydrochloride (EXAMPLE 188)

EXAMPLE 188

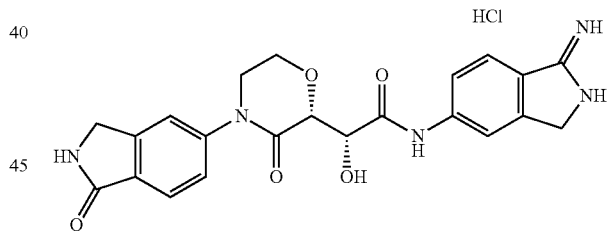

Method A

According to the synthetic method for EXAMPLE 142, EXAMPLE 188 can be prepared using corresponding carboxylic acid derived from 4-iodobenzoic acid instead of 3-iodoaniline.

Method B

According to the synthetic method for EXAMPLE 39, EXAMPLE 188 can be prepared using corresponding aniline derived from 2-methyl-4-nitro-benzoic acid instead of 4-(tert-butoxycarbonylamino)aniline.

Example 189

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide hydrochloride (EXAMPLE 189)

EXAMPLE 189

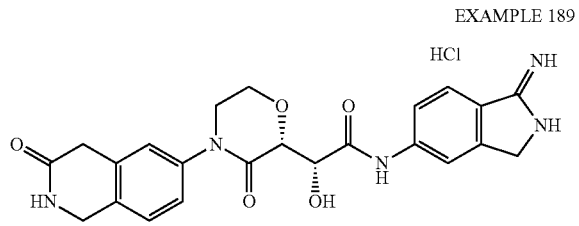 [SMILES: Cl ; N=C1NCc2cc(NC(=O)[C@H](O)[C@H]3OCCN(c4ccc5c(c4)CC(=O)NC5)C3=O)ccc21]

Method A

According to the synthetic method for EXAMPLE 142, EXAMPLE 189 can be prepared using corresponding carboxylic acid derived from 2-indanone instead of 3-iodoaniline.

Method B

According to the synthetic method for EXAMPLE 39, EXAMPLE 189 can be prepared using corresponding aniline derived from 2-indanone instead of 4-(tert-butoxycarbonylamino)aniline.

Example 190

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-7-yl)morpholin-2-yl]acetamide hydrochloride (EXAMPLE 190)

EXAMPLE 190

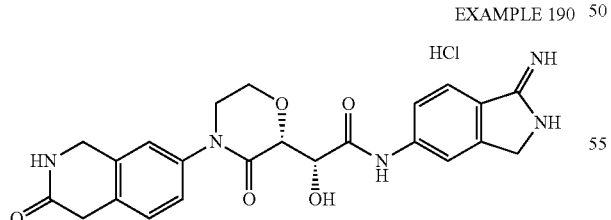

Method A

According to the synthetic method for EXAMPLE 142, EXAMPLE 190 can be prepared using corresponding carboxylic acid derived from 2-indanone instead of 3-iodoaniline.

Method B

According to the synthetic method for EXAMPLE 39, EXAMPLE 190 can be prepared using corresponding aniline derived from 2-indanone instead of 4-(tert-butoxycarbonylamino)aniline.

Example 191

Synthesis of (2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide hydrochloride (EXAMPLE 191)

EXAMPLE 191

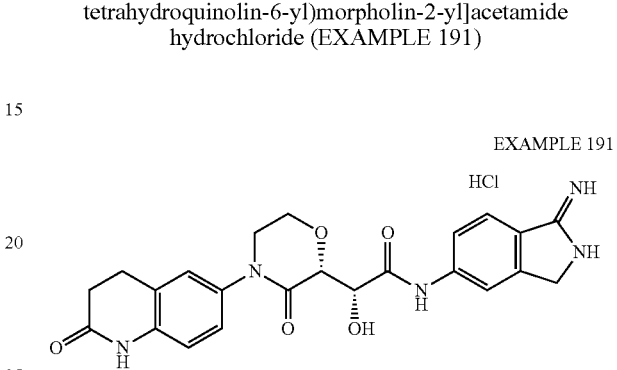

Method A

According to the synthetic method for EXAMPLE 142, EXAMPLE 208 can be prepared using corresponding carboxylic acid derived from 3,4-dihydro-2(1H)-quinolinone instead of 3-iodoaniline.

Method B

According to the synthetic method for EXAMPLE 39, EXAMPLE 191 can be prepared using corresponding aniline derived from 3,4-dihydro-2(1H)-quinolinone instead of 4-(tert-butoxycarbonylamino)aniline.

Example 192

Synthesis of (2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide hydrochloride (EXAMPLE 192)

EXAMPLE 192

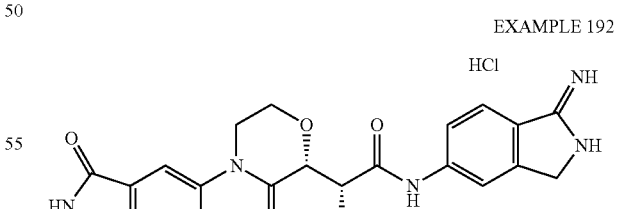

Method A

According to the synthetic method for EXAMPLE 142, EXAMPLE 192 can be prepared using corresponding carboxylic acid derived from 3-iodobenzoic acid instead of 3-iodoaniline.

Method B

According to the synthetic method for EXAMPLE 39, EXAMPLE 192 can be prepared using corresponding aniline derived from phthalimide instead of 4-(tert-butoxycarbonylamino)aniline.

Example 193

Synthesis of (2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide hydrochloride (EXAMPLE 193)

EXAMPLE 193

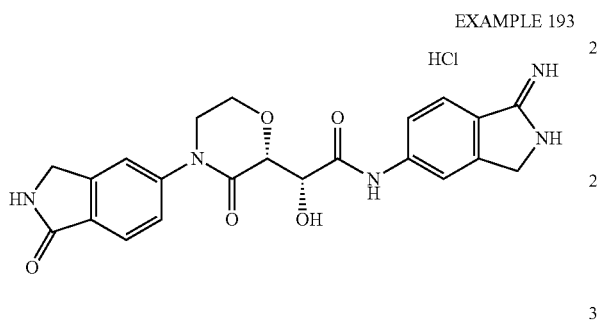

Method A

According to the synthetic method for EXAMPLE 142, EXAMPLE 193 can be prepared using corresponding carboxylic acid derived from 4-iodobenzoic acid instead of 3-iodoaniline.

Method B

According to the synthetic method for EXAMPLE 39, EXAMPLE 193 can be prepared using corresponding aniline derived from 2-methyl-4-nitro-benzoic acid instead of 4-(tert-butoxycarbonylamino)aniline.

Example 194

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide hydrochloride (EXAMPLE 194)

EXAMPLE 194

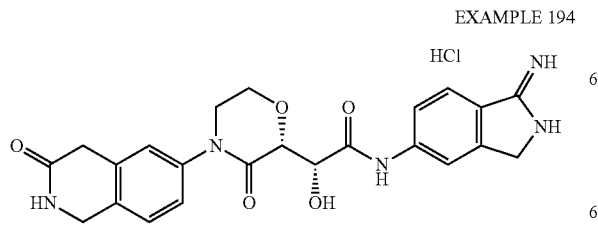

Method A

According to the synthetic method for EXAMPLE 142, EXAMPLE 194 can be prepared using corresponding carboxylic acid derived from 2-indanone instead of 3-iodoaniline.

Method B

According to the synthetic method for EXAMPLE 39, EXAMPLE 194 can be prepared using corresponding aniline derived from 2-indanone instead of 4-(tert-butoxycarbonylamino)aniline.

Example 195

Synthesis of (2R)-2-Hydroxy-N-(1-imino-2,3-dihydroisoindol-5-yl)-2-[(2R)-3-oxo-4-(3-oxo-1,2,3,4-tetrahydroisoquinolin-7-yl)morpholin-2-yl]acetamide hydrochloride (EXAMPLE 195)

EXAMPLE 195

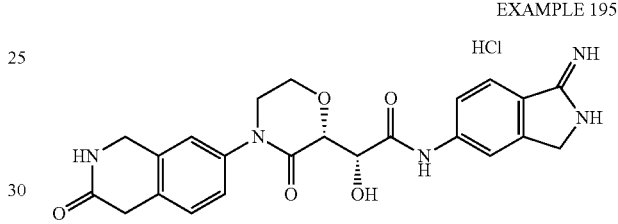

Method A

According to the synthetic method for EXAMPLE 142, EXAMPLE 195 can be prepared using corresponding carboxylic acid derived from 2-indanone instead of 3-iodoaniline.

Method B

According to the synthetic method for EXAMPLE 39, EXAMPLE 195 can be prepared using corresponding aniline derived from 2-indanone instead of 4-(tert-butoxycarbonylamino)aniline.

Example 196

Synthesis of (2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide hydrochloride (EXAMPLE 196)

EXAMPLE 196

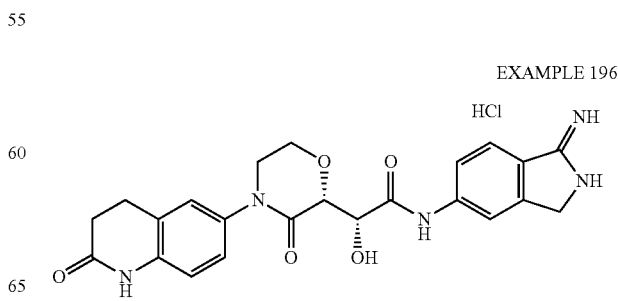

505

Method A

According to the synthetic method for EXAMPLE 142, EXAMPLE 196 can be prepared using corresponding carboxylic acid derived from 3,4-dihydro-2(1H)-quinolinone instead of 3-iodoaniline.

Method B

According to the synthetic method for EXAMPLE 39, EXAMPLE 196 can be prepared using corresponding aniline derived from 3,4-dihydro-2(1H)-quinolinone instead of 4-(tert-butoxycarbonylamino)aniline.

Example 197

Synthesis of (2R)-2-Hydroxy-N-(1-imino-2,3-dihydroisoindol-5-yl)-2-[(2R)-4-(2-methyl-3-oxo-1,2-dihydroisoindol-5-yl)-3-oxo-morpholin-2-yl]acetamide hydrochloride (EXAMPLE 197)

EXAMPLE 197

Method A

According to the synthetic method for EXAMPLE 142, EXAMPLE 197 can be prepared using corresponding carboxylic acid derived from 3-iodobenzoic acid instead of 3-iodoaniline.

Method B

According to the synthetic method for EXAMPLE 39, EXAMPLE 197 can be prepared using corresponding aniline derived from phthalimide instead of 4-(tert-butoxycarbonylamino)aniline.

506

Example 198

Synthesis of (2R)-2-Hydroxy-N-(1-imino-2,3-dihydroisoindol-5-yl)-2-[(2R)-3-oxo-4-(3-oxo-2-(2,2,2-trifluoroethyl)-1,2-dihydroisoindol-5-yl)morpholin-2-yl]acetamide hydrochloride (EXAMPLE 198)

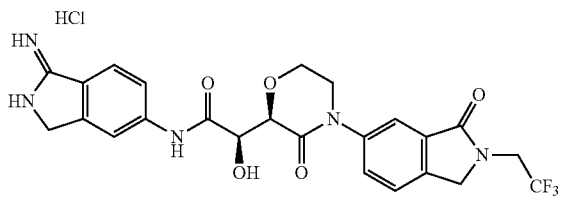

EXAMPLE 198

Method A

According to the synthetic method for EXAMPLE 142, EXAMPLE 198 can be prepared using corresponding carboxylic acid derived from 3-iodobenzoic acid instead of 3-iodoaniline.

Method B

According to the synthetic method for EXAMPLE 39, EXAMPLE 198 can be prepared using corresponding aniline derived from phthalimide instead of 4-(tert-butoxycarbonylamino)aniline.

Example 199

Synthesis of (2R)-2-Hydroxy-N-(1-imino-2,3-dihydroisoindol-5-yl)-2-[(2R)-3-oxo-4-(3-oxo-2-propyl-1,2-dihydroisoindol-5-yl)morpholin-2-yl]acetamide hydrochloride (EXAMPLE 199)

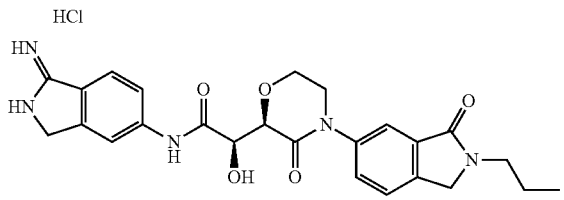

EXAMPLE 199

Method A

According to the synthetic method for EXAMPLE 142, EXAMPLE 199 can be prepared using corresponding carboxylic acid derived from 3-iodobenzoic acid instead of 3-iodoaniline.

Method B

According to the synthetic method for EXAMPLE 39, EXAMPLE 199 can be prepared using corresponding aniline derived from phthalimide instead of 4-(tert-butoxycarbonylamino)aniline.

Example 200

Synthesis of (2R)-2-Hydroxy-N-(1-imino-2,3-dihydroisoindol-5-yl)-2-[(2R)-4-(2-methyl-3-oxo-1,2-dihydroisoindol-6-yl)-3-oxo-morpholin-2-yl]acetamide hydrochloride (EXAMPLE 200)

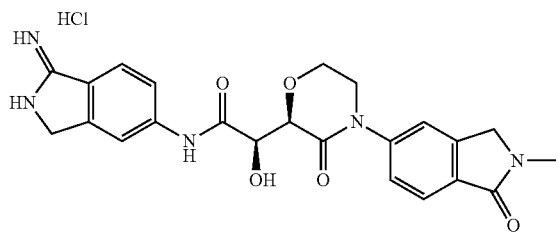

EXAMPLE 200

Method A

According to the synthetic method for EXAMPLE 142, EXAMPLE 200 can be prepared using corresponding carboxylic acid derived from 2,3-dihydro-5-iodo-1H-isoindole-1-one instead of 3-iodoaniline.

Method B

According to the synthetic method for EXAMPLE 39, EXAMPLE 200 can be prepared using corresponding aniline derived from methyl 2-methyl-4-nitrobenzoate instead of 4-(tert-butoxycarbonylamino)aniline.

Example 201

Synthesis of (2R)-2-[(2R)-4-(2-(Difluoromethoxy)phenyl)-3-oxo-morpholin-2-yl]-2-hydroxy-N-(1-imino-2,3-dihydroisoindol-5-yl)acetamide hydrochloride (EXAMPLE 201)

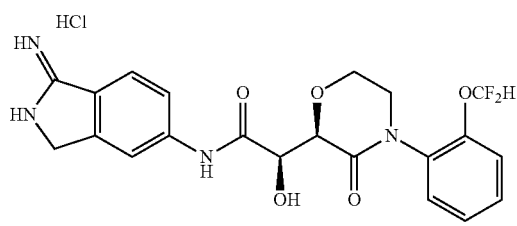

EXAMPLE 201

According to the synthetic method for EXAMPLE 142, EXAMPLE 201 can be prepared using corresponding carboxylic acid derived from 1-iodo-2-(difluoromethoxy)benzene instead of 3-iodoaniline.

Example 202

Synthesis of (2R)-2-[(2R)-4-(2-Fluorophenyl)-3-oxo-morpholin-2-yl]-2-hydroxy-N-(1-imino-2,3-dihydroisoindol-5-yl)acetamide hydrochloride (EXAMPLE 202)

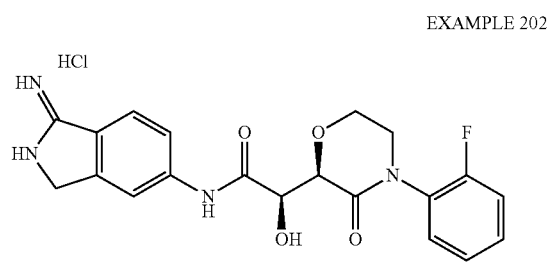 [SMILES: Cl ; N=C1NCc2cc(NC(=O)[C@H](O)[C@H]3OCCN(c4ccccc4F)C3=O)ccc21]

EXAMPLE 202

According to the synthetic method for EXAMPLE 142, EXAMPLE 202 can be prepared using corresponding carboxylic acid derived from 1-fluoro-2-iodobenzene instead of 3-iodoaniline.

Example 203

Synthesis of (2R)-2-[(2R)-4-(4-Fluorophenyl)-3-oxo-morpholin-2-yl]-2-hydroxy-N-(1-imino-2,3-dihydroisoindol-5-yl)acetamide hydrochloride (EXAMPLE 203)

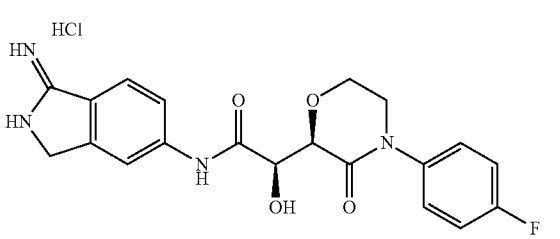

EXAMPLE 203

According to the synthetic method for EXAMPLE 142, EXAMPLE 203 can be prepared using corresponding carboxylic acid derived from 1-fluoro-4-iodobenzene instead of 3-iodoaniline.

Example 204

Synthesis of (2R)-2-[(2R)-4-(3-Fluorophenyl)-3-oxo-morpholin-2-yl]-2-hydroxy-N-(1-imino-2,3-dihydroisoindol-5-yl)acetamide hydrochloride (EXAMPLE 204)

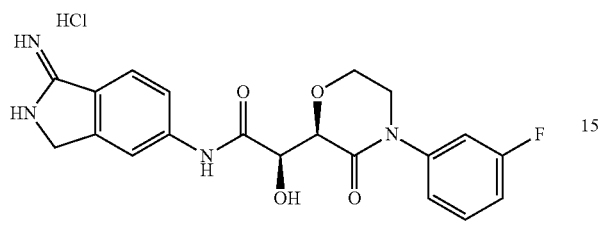

EXAMPLE 204

According to the synthetic method for EXAMPLE 142, EXAMPLE 204 can be prepared using corresponding carboxylic acid derived from 1-fluoro-3-iodobenzene instead of 3-iodoaniline.

Example 205

Synthesis of (2R)-2-[(2R)-4-(3,4-Difluorophenyl)-3-oxo-morpholin-2-yl]-2-hydroxy-N-(1-imino-2,3-dihydroisoindol-5-yl)acetamide hydrochloride (EXAMPLE 205)

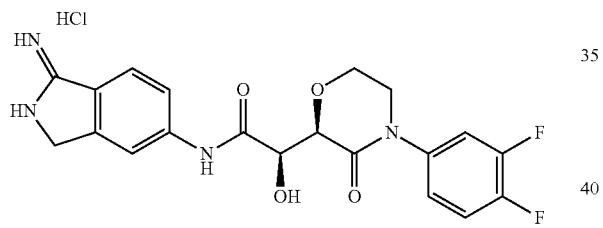

EXAMPLE 205

According to the synthetic method for EXAMPLE 142, EXAMPLE 205 can be prepared using corresponding carboxylic acid derived from 1,2-difluoro-4-iodobenzene instead of 3-iodoaniline.

Example 206

Synthesis of (2R)-2-[(2R)-4-(3,5-Difluorophenyl)-3-oxo-morpholin-2-yl]-2-hydroxy-N-(1-imino-2,3-dihydroisoindol-5-yl)acetamide hydrochloride (EXAMPLE 206)

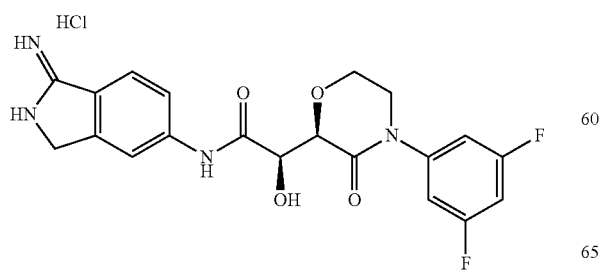

EXAMPLE 206

According to the synthetic method for EXAMPLE 142, EXAMPLE 206 can be prepared using corresponding carboxylic acid derived from 1,3-difluoro-5-iodobenzene instead of 3-iodoaniline.

Example 207

Synthesis of (2R)-2-Hydroxy-N-(1-imino-2,3-dihydroisoindol-5-yl)-2-[(2R)-3-oxo-4-(3,4,5-trifluorophenyl)morpholin-2-yl]acetamide hydrochloride (EXAMPLE 207)

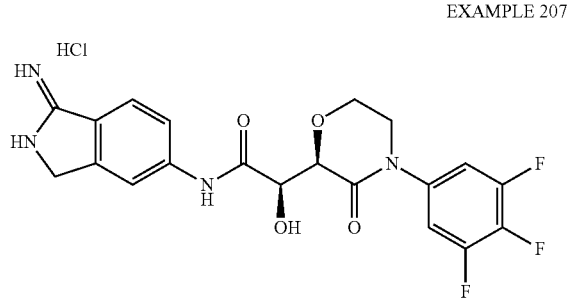 [SMILES: Cl ; N=C1NCc2cc(NC(=O)[C@H](O)[C@H]3OCCN(c4cc(F)c(F)c(F)c4)C3=O)ccc21]

EXAMPLE 207

According to the synthetic method for EXAMPLE 142, EXAMPLE 207 can be prepared using corresponding carboxylic acid derived from 1,2,3-difluoro-5-iodobenzene instead of 3-iodoaniline.

Example 208

Synthesis of (2R)-2-Hydroxy-N-(1-imino-2,3-dihydroisoindol-5-yl)-2-[(2R)-3-oxo-4-(4-trifluoromethylphenyl)morpholin-2-yl]acetamide hydrochloride (EXAMPLE 208)

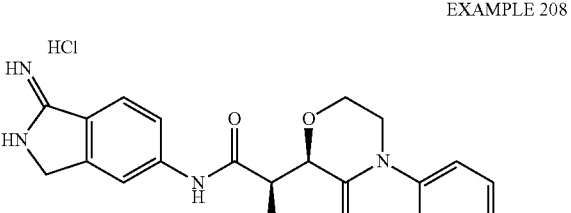

EXAMPLE 208

According to the synthetic method for EXAMPLE 142, EXAMPLE 208 can be prepared using corresponding carboxylic acid derived from 1-iodo-4-trifluoromethylbenzene instead of 3-iodoaniline.

Example 209

Synthesis of (2R)-2-Hydroxy-N-(1-imino-2,3-dihydroisoindol-5-yl)-2-[(2R)-3-oxo-4-(3-trifluoromethylphenyl)morpholin-2-yl]acetamide hydrochloride (EXAMPLE 209)

EXAMPLE 209

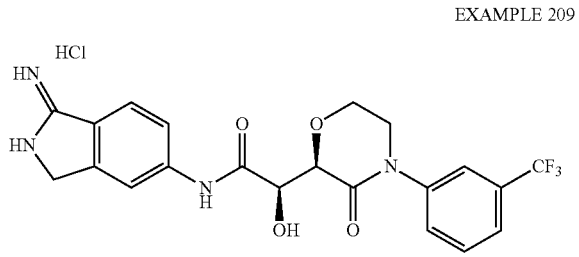 [SMILES: Cl ; N=C1NCc2cc(NC(=O)[C@H](O)[C@H]3OCCN(c4cccc(C(F)(F)F)c4)C3=O)ccc21]

According to the synthetic method for EXAMPLE 142, EXAMPLE 209 can be prepared using corresponding carboxylic acid derived from 1-iodo-3-trifluoromethylbenzene instead of 3-iodoaniline.

Example 210

Synthesis of (2R)-2-[(2R)-4-(4-Fluoro-3-(morpholin-4-ylcarbonyl)phenyl)-3-oxo-morpholin-2-yl]-2-hydroxy-N-(1-imino-2,3-dihydroisoindol-5-yl)acetamide hydrochloride (EXAMPLE 210)

EXAMPLE 210

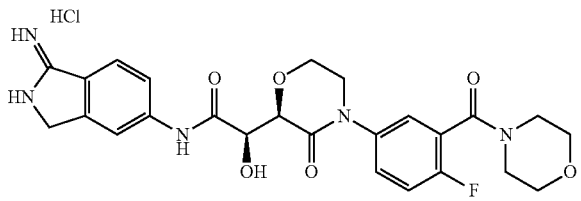

According to the synthetic method for EXAMPLE 142, EXAMPLE 210 can be prepared using corresponding carboxylic acid derived from 2-fluoro-5-iodobenzoic acid instead of 3-iodoaniline.

Example 211

Synthesis of (2R)-2-[(2R)-4-(3-(Dimethylaminocarbonyl)-4-fluorophenyl)-3-oxo-morpholin-2-yl]-2-hydroxy-N-(1-imino-2,3-dihydroisoindol-5-yl)acetamide hydrochloride (EXAMPLE 211)

EXAMPLE 211

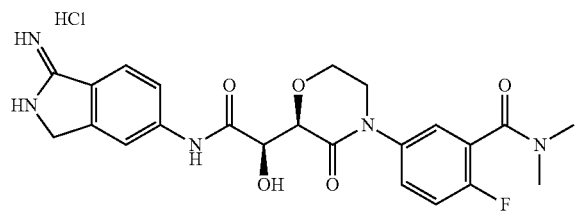

According to the synthetic method for EXAMPLE 142, EXAMPLE 211 can be prepared using corresponding carboxylic acid derived from 2-fluoro-5-iodobenzoic acid instead of 3-iodoaniline.

Example 212

Synthesis of (2R)-2-[(2R)-4-(4-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide hydrochloride (EXAMPLE 212)

EXAMPLE 212

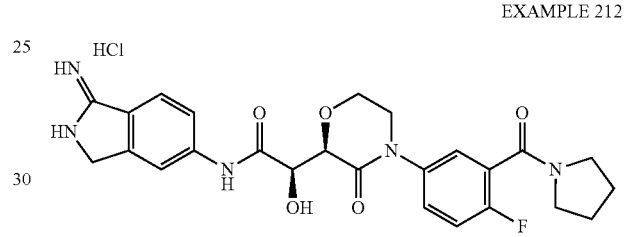

According to the synthetic method for EXAMPLE 142, EXAMPLE 212 can be prepared using corresponding carboxylic acid derived from 2-fluoro-5-iodobenzoic acid instead of 3-iodoaniline.

Example 213

Synthesis of (2R)-2-[(2R)-4-(3-(Dimethylaminocarbonyl)-5-fluorophenyl)-3-oxo-morpholin-2-yl]-2-hydroxy-N-(1-imino-2,3-dihydroisoindol-5-yl)acetamide hydrochloride (EXAMPLE 213)

EXAMPLE 213

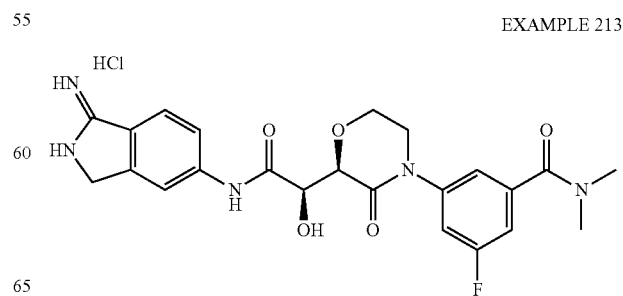

According to the synthetic method for EXAMPLE 142, EXAMPLE 213 can be prepared using corresponding carboxylic acid derived from 3-fluoro-5-iodobenzoic acid instead of 3-iodoaniline.

Example 214

Synthesis of (2R)-2-[(2R)-4-(5-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide hydrochloride (EXAMPLE 214)

EXAMPLE 214

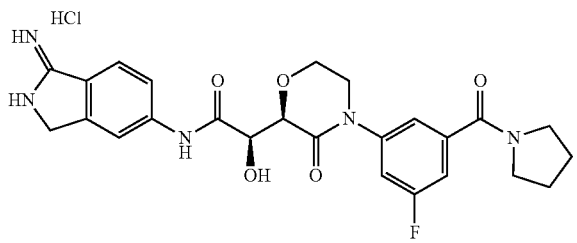

According to the synthetic method for EXAMPLE 142, EXAMPLE 214 can be prepared using corresponding carboxylic acid derived from 3-fluoro-5-iodobenzoic acid instead of 3-iodoaniline.

Example 215

Synthesis of (2R)-2-[(2R)-4-(5-Fluoro-3-(morpholin-4-ylcarbonyl)phenyl)-3-oxo-morpholin-2-yl]-2-hydroxy-N-(1-imino-2,3-dihydroisoindol-5-yl)acetamide hydrochloride (EXAMPLE 215)

EXAMPLE 215

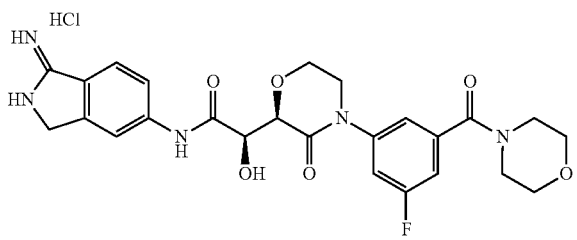

According to the synthetic method for EXAMPLE 142, EXAMPLE 215 can be prepared using corresponding carboxylic acid derived from 3-fluoro-5-iodobenzoic acid instead of 3-iodoaniline.

Example 216

Synthesis of (2R)-2-[(2R)-4-(3-Carboxyphenyl)-3-oxo-morpholin-2-yl]-2-hydroxy-N-(1-imino-2,3-dihydroisoindol-5-yl)acetamide hydrochloride (EXAMPLE 216)

EXAMPLE 216

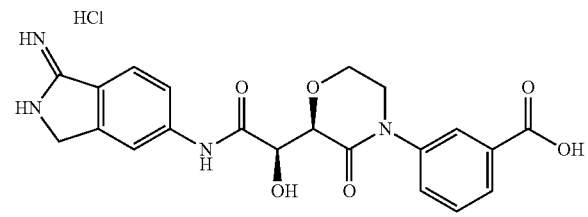

According to the synthetic method for EXAMPLE 142, EXAMPLE 216 can be prepared using corresponding carboxylic acid derived from 3-iodobenzoic acid instead of 3-iodoaniline.

Example 217

Synthesis of (2R)-2-[(2R)-4-(4-Chlorophenyl)-3-oxo-morpholin-2-yl]-2-hydroxy-N-(1-imino-2,3-dihydroisoindol-5-yl)acetamide hydrochloride (EXAMPLE 217)

EXAMPLE 217

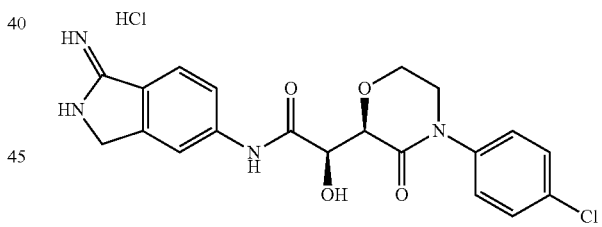

According to the synthetic method for EXAMPLE 142, EXAMPLE 217 can be prepared using corresponding carboxylic acid derived from 1-chloro-4-iodobenzene instead of 3-iodoaniline.

TABLE 3

| EXAMPLE | NMR (ppm) (No mark: 400 MHz, *: 300 MHz) |
|---|---|
| 1 | DMSO-$d_6$: 12.99 (1H, brs), 10.37 (1H, brs), 8.92 (2H, brs), 8.56-8.42 (2H, m), 8.06 (1H, d, J = 9 Hz), 7.62 (1H, d, J = 7 Hz), 7.28 (2H, d, J = 8 Hz), 7.23 (2H, d, J = 8 Hz), 7.16 (1H, d, J = 7 Hz), 6.57 (1H, brs), 4.76-4.63 (2H, m), 4.17-4.08 (1H, m), 3.98-3.89 (1H, m), 3.88-3.79 (1H, m), 3.77-3.41 (1H, m), 2.32 (3H, s) |
| 1-1 (LP) | CDCl$_3$: 7.23-7.18 (4H, m), 4.84 (1H, brs), 4.64 (1H, d, J = 2 Hz), 4.37-4.14 (3H, m), 4.00 (1H, ddd, J = 10, 10, 2 Hz), 3.95 (1H, ddd, J = 10, 10, 3 Hz), 3.60-3.52 (1H, m), 3.36 (1H, brs), 2.35 (3H, s), 1.33 (3H, t, J = 7 Hz) |

TABLE 3-continued

| EXAMPLE | NMR (ppm) (No mark: 400 MHz, *: 300 MHz) |
|---|---|
| 1-1 (MP) | CDCl$_3$: 7.23-7.16 (4H, m), 4.71 (2H, s), 4.37-4.20 (3H, m), 4.01 (1H, ddd, J = 11, 11, 2 Hz), 3.93 (1H, ddd, J = 11, 11, 4 Hz), 3.60-3.52 (1H, m), 3.38 (1H, brs), 2.34 (3H, s), 1.32 (3H, t, J = 7 Hz) |
| 1-2 | *CDCl$_3$: 7.22-7.12 (4H, m), 4.73-4.62 (2H, m), 4.21-4.10 (1H, m), 4.01-3.86 (2H, m), 3.50-3.38 (1H, m), 2.33 (3H, s) |
| 1-3 | *CDCl$_3$: 9.04 (1H, s), 8.52 (1H, d, J = 2 Hz), 8.42 (1H, d, J = 6 Hz), 7.96 (1H, d, J = 9 Hz), 7.70 (1H, d, J = 6 Hz), 7.60 (1H, dd, J = 9, 2 Hz), 7.21-7.15 (4H, m), 4.88 (1H, d, J = 2 Hz), 4.69 (1H, d, J = 2 Hz), 4.24-4.16 (1H, m), 4.12-3.96 (2H, m), 3.55-3.47 (1H, m), 2.16 (3H, s), 1.32 (18H, s) |
| 2 | DMSO-d$_6$: 10.19 (1H, s), 9.18 (2H, s), 8.77 (2H, brs), 8.03 (2H, d, J = 9 Hz), 7.79 (2H, d, J = 9 Hz), 7.27 (2H, d, J = 9 Hz), 7.22 (2H, d, J = 9 Hz), 6.49 (1H, brs), 4.66 (2H, s), 4.15-4.08 (1H, m), 3.97-3.88 (1H, m), 3.86-3.78 (1H, m), 3.64-3.57 (1H, m), 2.32 (3H, s) |
| 2-1 | *DMSO-d$_6$: 10.22 (1H, s), 8.01 (2H, d, J = 9 Hz), 7.78 (2H, d, J = 9 Hz), 7.27 (2H, d, J = 9 Hz), 7.24-7.18 (2H, m), 6.48 (1H, brs), 4.65 (2H, s), 4.15-4.07 (1H, m), 3.97-3.75 (2H, m), 3.63-3.55 (1H, m), 2.31 (3H, s) |
| 3 | DMSO-d$_6$: 11.01 (1H, s), 9.42 (1H, s), 7.98 (1H, d, J = 2 Hz), 7.36 (1H, dd, J = 9, 2 Hz), 7.32-7.26 (4H, m), 7.22 (2H, d, J = 8 Hz), 6.37 (1H, dd, J = 2, 2 Hz), 6.27 (1H, d, J = 7 Hz), 4.66 (1H, d, J = 2 Hz), 4.61 (1H, dd, J = 7, 2 Hz), 4.13 (1H, ddd, J = 11, 3, 3 Hz), 3.92 (1H, ddd, J = 11, 11, 3 Hz), 3.87-3.78 (1H, m), 3.60 (1H, ddd, J = 12, 3, 3 Hz), 2.32 (3H, s) |
| 7 | *DMSO-d$_6$: 10.21 (1H, s), 9.25 (2H, s), 8.94 (2H, s), 8.04 (2H, d, J = 9 Hz), 7.82 (2H, d, J = 9 Hz), 7.29 (2H, d, J = 9 Hz), 7.24 (2H, d, J = 9 Hz), 4.68 (2H, s), 4.18-4.08 (1H, m), 4.00-3.77 (2H, m), 3.67-3.57 (1H, m), 2.33 (3H, s) |
| 7-1 | *CDCl$_3$: 7.02 (2H, d, J = 8 Hz), 6.62 (2H, d, J = 8 Hz), 3.71 (2H, t, J = 6 Hz), 3.49 (2H, t, J = 6 Hz), 2.25 (3H, s) |
| 7-3 | *CDCl$_3$: 8.09 (1H, s), 7.63-7.59 (4H, m), 7.38 (2H, d, J = 9 Hz), 7.32-7.27 (2H, m), 5.59 (1H, d, J = 3 Hz), 5.42 (1H, d, J = 3 Hz), 3.99-3.84 (2H, m), 3.65-3.52 (2H, m), 2.41 (3H, s), 2.29 (3H, s), 2.05 (3H, s) |
| 7-5 | *DMSO-d$_6$: 10.22 (1H, brs), 8.01 (2H, d, J = 9 Hz), 7.78 (2H, d, J = 9 Hz), 7.27 (2H, d, J = 9 Hz), 7.22 (2H, d, J = 9 Hz), 6.47 (1H, brs), 4.65 (2H, s), 4.16-4.08 (1H, m), 3.97-3.75 (2H, m), 3.63-3.56 (1H, m), 2.31 (3H, s) |
| 8 | *DMSO-d$_6$ (100degC): 9.98 (1H, brs), 9.02 (4H, brs), 7.96 (2H, d, J = 8 Hz), 7.83 (2H, d, J = 8 Hz), 7.17-6.94 (3H, m), 6.09 (1H, brs), 4.67 (2H, s), 4.23-4.07 (1H, m), 4.01-3.86 (1H, m), 3.81-3.63 (1H, m), 3.49-3.33 (1H, m), 2.28 (3H, s), 2.17 (3H, s) |
| 9-5 | DMSO-d$_6$: 10.23 (1H, brs), 8.01 (2H, d, J = 9 Hz), 7.78 (2H, d, J = 9 Hz), 6.92 (1H, d, J = 8 Hz), 6.57 (1H, d, J = 2 Hz), 6.50-6.39 (1H, m), 6.41 (1H, dd, J = 8, 2 Hz), 4.96 (2H, s), 4.63 (1H, d, J = 2 Hz), 4.60 (1H, d, J = 2 Hz), 4.13-4.05 (1H, m), 3.93-3.84 (1H, m), 3.80-3.70 (1H, m), 3.52-3.45 (1H, m), 2.04 (3H, s) |
| 9-6 | DMSO-d$_6$: 10.21 (1H, s), 9.55 (1H, s), 8.01 (2H, d, J = 9 Hz), 7.78 (2H, d, J = 9 Hz), 7.43 (1H, d, J = 2 Hz), 7.27 (1H, d, J = 8 Hz), 7.16-7.12 (1H, m), 6.47 (1H, d, J = 8 Hz), 4.72-4.62 (4H, m), 4.16-4.08 (1H, m), 3.97-3.89 (1H, m), 3.85-3.75 (1H, m), 3.63-3.56 (1H, m), 2.19 (3H, s), 2.13 (3H, s) |
| 10 | *DMSO-d$_6$: 10.22 (1H, s), 9.04 (4H, brs), 8.05 (2H, d, J = 9 Hz), 7.92 (1H, dd, J = 3, 1 Hz), 7.82 (2H, d, J = 9 Hz), 7.79 (2H, d, J = 9 Hz), 7.67 (1H, dd, J = 5, 3 Hz), 7.59 (1H, dd, J = 5, 1 Hz), 7.47 (2H, d, J = 9 Hz), 6.52 (1H, brs), 4.74-4.68 (2H, m), 4.21-4.08 (1H, m), 4.03-3.84 (2H, m), 3.74-3.64 (1H, m) |
| 11 | *DMSO-d$_6$: 10.20 (1H, s), 9.21 (2H, s), 8.87 (2H, s), 8.03 (2H, d, J = 9 Hz), 7.80 (2H, d, J = 9 Hz), 7.44 (2H, d, J = 9 Hz), 7.31 (2H, d, J = 9 Hz), 6.47 (1H, brs), 4.67 (2H, s), 4.17-4.08 (1H, m), 3.98-3.77 (2H, m), 3.66-3.58 (1H, m), 1.30 (9H, s) |
| 12 | *DMSO-d$_6$: 10.20 (1H, s), 9.21 (2H, s), 8.86 (2H, s), 8.03 (2H, d, J = 9 Hz), 7.80 (2H, d, J = 9 Hz), 7.38-7.29 (4H, m), 4.67 (2H, s), 4.50 (2H, s), 4.17-4.08 (1H, m), 3.98-3.52 (3H, m) |
| 13 | DMSO-d$_6$: 10.50 (1H, s), 10.22 (1H, s), 9.26 (2H, s), 8.97 (2H, s), 8.04 (2H, d, J = 9 Hz), 7.83 (2H, d, J = 9 Hz), 7.25-7.10 (2H, m), 6.85 (1H, d, J = 8 Hz), 6.50 (1H, brs) 4.70-4.63 (2H, m), 4.16-4.08 (1H, m), 3.98-3.88 (1H, m), 3.84-3.75 (1H, m), 3.62-3.55 (1H, m), 3.53 (2H, s) |
| 14 | *DMSO-d$_6$: 10.18 (1H, s), 8.99 (4H, brs), 8.02 (2H, d, J = 9 Hz), 7.84-7.73 (4H, m), 7.25 (2H, d, J = 8 Hz), 6.50 (1H, brs), 4.73-4.61 (2H, m), 4.18-4.07 (1H, m), 3.99-3.78 (2H, m), 3.68-3.58 (1H, m) |
| 15 | DMSO-d$_6$: 10.17 (1H, s), 9.22 (2H, s), 8.93 (2H, s), 7.99 (2H, d, J = 9 Hz), 7.78 (2H, d, J = 9 Hz), 7.27-7.21 (4H, m), 6.44 (1H, d, J = 7 Hz), 4.65-4.58 (2H, m), 4.11-4.03 (1H, m), 3.93-3.84 (1H, m), 3.83-3.74 (1H, m), 3.62-3.54 (1H, m), 2.53-2.43 (1H, m), 1.82-1.63 (5H, m), 1.44-1.14 (5H, m) |
| 16 | DMSO-d$_6$: 10.18 (1H, s), 9.24 (2H, s), 8.99 (2H, s), 7.99 (2H, d, J = 9 Hz), 7.79 (2H, d, J = 9 Hz), 7.31-7.19 (4H, m), 6.45 (1H, d, J = 7 Hz), 4.67-4.59 (2H, m), 4.13-4.03 (1H, m), 3.94-3.84 (1H, m), 3.83-3.73 (1H, m), 3.62-3.54 (1H, m), 2.92-2.81 (1H, m), 1.17 (6H, d, J = 7 Hz) |
| 17 | *DMSO-d$_6$: 10.22 (1H, s), 9.24 (2H, s), 8.91 (2H, s), 8.04 (2H, d, J = 9 Hz), 7.82 (2H, d, J = 9 Hz), 7.31 (2H, d, J = 9 Hz), 7.27 (2H, d, J = 9 Hz), 6.52 (1H, brs), 4.68 (2H, s), 4.18-4.08 (1H, m), 4.01-3.78 (2H, m), 3.68-3.59 (1H, m), 2.63 (2H, q, J = 8 Hz), 1.20 (3H, t, J = 8 Hz) |
| 18 | DMSO-d$_6$: 11.21 (1H, s), 10.21 (1H, s), 9.19 (2H, s), 8.87-8.78 (2H, m), 8.04 (2H, d, J = 9 Hz), 7.80 (2H, d, J = 9 Hz), 7.55 (1H, d, J = 8 Hz), 7.40 (1H, t, J = 3 Hz), 7.39-7.35 (1H, m), 6.99-6.93 (1H, m), 6.53 (1H, d, J = 6 Hz), 6.47-6.43 (1H, m), 4.73-4.66 (2H, m), 4.17-4.09 (1H, m), 4.02-3.93 (1H, m), 3.91-3.82 (1H, m), 3.68-3.62 (1H, m) |
| 18-1 | DMSO-d$_6$: 11.34 (1H, brs), 10.33-10.18 (1H, m), 7.75 (2H, d, J = 9 Hz), 7.70 (2H, d, J = 9 Hz), 7.60 (1H, d, J = 8 Hz), 7.47-7.42 (1H, m), 7.41 (1H, s), 6.97 (1H, d, J = 8 Hz), 6.50-6.46 (1H, m), 5.61-5.42 (2H, m), 4.65 (1H, t, J = 5 Hz), 3.84-3.56 (2H, m), 3.49-3.42 (1H, m), 2.15 (3H, s), 1.88 (3H, s) |
| 18-2 | DMSO-d$_6$: 11.46-11.30 (1H, m), 10.34-1018 (1H, m), 7.75 (2H, d, J = 9 Hz), 7.70 (2H, d, J = 9 Hz), 7.68-7.59 (1H, m), 7.50-7.39 (2H, m), 7.05-6.96 (1H, m), 6.52-6.47 (1H, m), 5.61-5.42 (2H, m), 4.30-4.19 (2H, m), 4.05-3.82 (2H, m), 3.15 (3H, s), 2.17 (3H, s), 1.93-1.86 (3H, m) |
| 18-3 | DMSO-d$_6$: 11.20 (1H, s), 10.24 (1H, s), 8.03 (2H, d, J = 9 Hz), 7.79 (2H, d, J = 9 Hz), 7.55 (1H, d, J = 8 Hz), 7.40 (1H, d, J = 3 Hz), 7.38-7.35 (1H, m), 6.95 (1H, dd, J = 8, 2 Hz), 6.52 (1H, brs), 6.44 (1H, d, J = 3 Hz), 4.72-4.65 (2H, m), 4.16-4.08 (1H, m), 4.01-3.93 (1H, m), 3.88-3.81 (1H, m), 3.66-3.61 (1H, m) |
| 19 | DMSO-d$_6$: 10.51 (1H, s), 10.23 (1H, s), 9.25 (2H, brs), 8.93 (2H, brs), 8.04 (2H, d, J = 9 Hz), 7.82 (2H, d, J = 9 Hz), 7.35 (1H, d, J = 8 Hz), 6.95 (1H, dd, J = 8 Hz, 2 Hz), 6.91 (1H, d, J = 2 Hz), 6.49 (1H, d, J = 6 Hz), 4.72-4.63 (2H, m), 4.17-4.08 (1H, m), 3.98-3.90 (1H, m), 3.89-3.79 (1H, m), 3.66-3.59 (1H, m), 1.28 (6H, s) |
| 20 | DMSO-d$_6$: 10.76 (1H, brs), 10.71 (1H, brs), 10.19 (1H, s), 9.19 (2H, brs), 8.82 (2H, brs), 8.02 (2H, d, J = 9 Hz), 7.82-7.76 (2H, m), 6.93 (1H, d, J = 8 Hz), 6.92 (1H, d, J = 2 Hz), 6.88 (1H, dd, J = 8, 2 Hz), 6.50 (1H, d, J = 6 Hz), 4.68-4.63 (2H, m), 4.14-4.06 (1H, m), 3.97-3.88 (1H, m), 3.83-3.75 (1H, m), 3.61-3.55 (1H, m) |
| 20-1 | *DMSO-d$_6$: 10.59 (1H, s), 10.55 (1H, s), 10.17 (1H, s), 7.45 (1H, brs), 7.01 (1H, dd, J = 8, 2 Hz), 6.86 (1H, d, J = 8 Hz), 4.22 (2H, s) |
| 20-2 | *DMSO-d$_6$: 10.26 (1H, s), 10.11 (1H, s), 6.66 (1H, d, J = 8 Hz), 6.29-6.20 (2H, m), 5.46 (1H, t, J = 6 Hz), 3.69 (2H, t, J = 6 Hz), 3.40-3.30 (2H, m) |
| 21 | *DMSO-d$_6$: 10.20 (1H, s), 9.22 (2H, s), 8.85 (2H, s), 8.04 (2H, d, J = 9 Hz), 7.80 (2H, d, J = 9 Hz), 7.21 (2H, d, J = 8 Hz), 7.18-7.08 (2H, m), 6.52 (1H, brs), 4.84 (1H, d, J = 15 Hz), 4.69 (1H, brs), 4.62 (1H, s), 4.34 (1H, d, J = 15 Hz), 4.05-3.94 (1H, m), 3.82-3.69 (1H, m), 3.55-3.08 (2H, m), 2.31 (3H, s) |
| 22 | DMSO-d$_6$: 10.21 (1H, s), 9.19 (2H, brs), 8.79 (2H, brs), 8.04 (2H, d, J = 9 Hz), 7.80 (2H, d, J = 9 Hz), 7.71 (2H, d, J = 9 Hz), 7.57 (1H, dd, J = 5, 1 Hz), 7.54 (1H, dd, J = 4, 1 Hz), 7.47 (2H, d, J = 9 Hz), 7.15 (1H, dd, J = 5, 4 Hz), 6.52 (1H, d, |

TABLE 3-continued

| EXAMPLE | NMR (ppm) (No mark: 400 MHz, *: 300 MHz) |
|---|---|
| | J = 7 Hz), 4.73-4.61 (2H, m), 4.18-4.11 (1H, m), 4.00-3.84 (2H, m), 3.72-3.64 (1H, m) |
| 22-1 | *DMSO-d$_6$: 10.23 (1H, s), 8.03 (2H, d, J = 9 Hz), 7.80 (2H, d, J = 9 Hz), 7.77-7.69 (2H, m), 7.58 (1H, d, J = 5 Hz), 7.55 (1H, d, J = 3 Hz), 7.48 (2H, d, J = 9 Hz), 7.19-7.14 (1H, m), 6.50 (1H, d, J = 6 Hz), 4.73-4.66 (2H, m), 4.20-4.11 (1H, m), 4.01-3.83 (2H, m), 3.72-3.64 (1H, m) |
| 23 | DMSO-d$_6$: 10.21 (1H, s), 8.99 (4H, brs), 8.03 (2H, d, J = 9 Hz), 7.80 (2H, d, J = 9 Hz), 7.73 (2H, d, J = 9 Hz), 7.69 (2H, dd, J = 8, 1 Hz), 7.54-7.43 (4H, m), 7.40-7.35 (1H, m), 6.54 (1H, brs), 4.71 (1H, d, J = 3 Hz), 4.70-4.67 (1H, m), 4.18-4.12 (1H, m), 4.01-3.86 (2H, m), 3.74-3.68 (1H, m) |
| 24 | DMSO-d$_6$: 10.21 (1H, s), 9.00 (4H, brs), 8.04 (2H, d, J = 9 Hz), 7.80 (2H, d, J = 9 Hz), 7.70 (2H, d, J = 9 Hz), 7.61 (2H, d, J = 8 Hz), 7.52-7.47 (4H, m), 6.52 (1H, brs), 4.72-4.67 (2H, m), 4.18-4.11 (1H, m), 4.01-3.85 (2H, m), 3.74-3.67 (1H, m), 1.32 (9H, s) |
| 25 | DMSO-d$_6$: 10.21 (1H, s), 9.29-9.17 (2H, m), 9.01-8.75 (2H, m), 8.08 (2H, s), 8.04 (2H, d, J = 9 Hz), 7.85-7.78 (2H, m), 7.65 (2H, d, J = 9 Hz), 7.38 (2H, d, J = 9 Hz), 6.54 (1H, brs), 4.68 (2H, s), 4.18-4.10 (1H, m), 4.00-3.82 (2H, m), 3.69-3.63 (1H, m) |
| 26A | DMSO-d$_6$: 10.20 (1H, s), 10.05 (1H, s), 9.20 (2H, s), 8.79 (2H, s), 8.04 (2H, d, J = 9 Hz), 7.81 (2H, d, J = 9 Hz), 7.61 (2H, d, J = 9 Hz), 7.32 (2H, d, J = 9 Hz), 6.50 (1H, d, J = 7 Hz), 4.72-4.65 (2H, m), 4.16-4.08 (1H, m), 3.98-3.90 (1H, m), 3.88-3.79 (1H, m), 3.64-3.56 (1H, m), 2.06 (3H, s) |
| 26-5 | *DMSO-d$_6$: 8.02 (2H, d, J = 9 Hz), 7.79 (2H, d, J = 9 Hz), 6.98 (2H, d, J = 9 Hz), 6.56 (2H, d, J = 9 Hz), 5.16 (2H, s), 4.67-2224.58 (2H, m), 4.13-4.04 (1H, m), 3.94-3.83 (1H, m), 3.79-3.68 (1H, m), 3.54-3.45 (1H, m) |
| 26-6 | *DMSO-d$_6$: 10.63 (1H, s), 10.04 (1H, s), 7.80 (4H, s), 7.61 (2H, d, J = 9 Hz), 7.32-7.22 (2H, m), 5.55 (1H, s), 4.89 (1H, s), 4.19-4.08 (1H, m), 4.05-3.92 (1H, m), 3.89-3.77 (1H, m), 3.71-3.59 (1H, m), 2.17 (3H, s), 2.05 (3H, s) |
| 26-9 | *CDCl$_3$: 7.51-7.34 (4H, m), 5.47 (1H, d, J = 3 Hz), 5.44 (1H, d, J = 3 Hz), 4.09-3.99 (1H, m), 3.89-3.78 (1H, m), 3.75-3.65 (1H, m), 3.63-3.53 (1H, m), 2.20 (3H, s), 2.12 (3H, s), 1.54 (9H, s) |
| 26-10 | *CDCl$_3$: 11.10 (1H, s), 8.52 (1H, s), 7.80 (2H, d, J = 9 Hz), 7.71 (2H, d, J = 9 Hz), 7.57-7.49 (4H, m), 7.44 (2H, d, J = 9 Hz), 6.74 (1H, s), 5.58 (1H, d, J = 3 Hz), 5.43 (1H, d, J = 3 Hz), 3.94 (2H, t, J = 7 Hz), 3.65-3.56 (2H, m), 2.26 (3H, s), 2.01 (3H, s), 1.54 (9H, s) |
| 27 | DMSO-d$_6$: 10.21 (1H, s), 9.21 (2H, s), 8.82 (2H, s), 8.67 (1H, s), 8.04 (2H, d, J = 9 Hz), 7.81 (2H, d, J = 9 Hz), 7.43 (2H, d, J = 9 Hz), 7.23 (2H, d, J = 9 Hz), 6.51 (1H, d, J = 6 Hz), 5.90 (2H, s), 4.70-4.65 (2H, m), 4.16-4.08 (1H, m), 3.98-3.89 (1H, m), 3.86-3.77 (1H, m), 3.63-3.55 (1H, m) |
| 27-1 | *DMSO-d$_6$: 10.21 (1H, s), 8.63 (1H, s), 8.01 (2H, d, J = 9 Hz), 7.78 (2H, d, J = 9 Hz), 7.42 (2H, d, J = 9 Hz), 7.25-7.17 (2H, m), 6.46 (1H, brs), 5.88 (2H, s), 4.64 (2H, s), 4.17-4.05 (1H, m), 3.98-3.73 (2H, m), 3.63-3.50 (1H, m) |
| 28A | DMSO-d$_6$: 10.21 (1H, s), 9.86 (1H, s), 9.22 (2H, s), 8.83 (2H, s), 8.04 (2H, d, J = 9 Hz), 7.81 (2H, d, J = 9 Hz), 7.38 (2H, d, J = 9 Hz), 7.25 (2H, d, J = 9 Hz), 6.50 (1H, brs), 4.70-4.63 (2H, m), 4.17-4.10 (1H, m), 3.98-3.90 (1H, m), 3.89-3.80 (1H, m), 3.66-3.58 (1H, m), 3.03 (3H, s) |
| 28-1 | *DMSO-d$_6$: 10.22 (1H, s), 9.84 (1H, s), 8.02 (2H, d, J = 9 Hz), 7.79 (2H, d, J = 9 Hz), 7.37 (2H, d, J = 9 Hz), 7.24 (2H, d, J = 9 Hz), 6.46 (1H, d, J = 7 Hz), 4.70-4.63 (2H, m), 4.19-4.09 (1H, m), 3.98-3.78 (2H, m), 3.64-3.57 (1H, m), 3.02 (3H, s) |
| 29A | DMSO-d$_6$: 10.21 (1H, s), 9.22 (2H, s), 8.83 (2H, s), 8.05 (2H, d, J = 9 Hz), 7.81 (2H, d, J = 9 Hz), 7.71 (2H, d, J = 9 Hz), 7.41 (2H, d, J = 9 Hz), 6.52 (1H, d, J = 7 Hz), 4.72-4.66 (2H, m), 4.19-4.09 (1H, m), 4.00-3.81 (4H, m), 3.68-3.60 (1H, m), 2.61-2.46 (2H, m), 2.09 (2H, tt, J = 8, 8 Hz) |
| 29-1 | *DMSO-d$_6$: 10.22 (1H, s), 8.03 (2H, d, J = 9 Hz), 7.79 (2H, d, J = 9 Hz), 7.70 (2H, d, J = 9 Hz), 7.40 (2H, d, J = 9 Hz), 6.48 (1H, d, J = 8 Hz), 4.73-4.64 (2H, m), 4.19-4.09 (1H, m), 4.00-3.79 (4H, m), 3.68-3.59 (1H, m), 2.57-2.48 (2H, m), 2.08 (2H, tt, J = 8, 8 Hz) |
| 30A | DMSO-d$_6$: 10.22 (1H, s), 9.21 (2H, s), 8.81 (2H, s), 8.04 (2H, d, J = 9 Hz), 7.81 (2H, d, J = 9 Hz), 7.46 (4H, s), 6.52 (1H, d, |
| | J = 7 Hz), 4.72-4.67 (2H, m), 4.23 (2H, s), 4.19-4.11 (2H, m), 4.03-3.92 (3H, m), 3.92-3.83 (1H, m), 3.79-3.74 (2H, m), 3.72-3.66 (1H, m) |
| 31 | DMSO-d$_6$: 10.19 (1H, s), 9.34-8.62 (4H, m), 8.02 (2H, d, J = 9 Hz), 7.79 (2H, d, J = 9 Hz), 7.60 (2H, d, J = 9 Hz), 7.41 (2H, d, J = 9 Hz), 6.51 (1H, brs), 4.67 (2H, s), 4.44 (2H, t, J = 8 Hz), 4.16-4.03 (3H, m), 3.98-3.89 (1H, m), 3.88-3.79 (1H, m), 3.66-3.59 (1H, m) |
| 32 | DMSO-d$_6$: 10.21 (1H, s), 9.92 (1H, s), 9.20 (2H, s), 8.79 (2H, s), 8.04 (2H, d, J = 9 Hz), 7.81 (2H, d, J = 9 Hz), 7.70 (2H, d, J = 9 Hz), 7.45-7.30 (7H, m), 6.51 (1H, d, J = 7 Hz), 4.70-4.66 (2H, m), 4.63 (2H, s), 4.17-4.09 (3H, m), 3.98-3.90 (1H, m), 3.89-3.80 (1H, m), 3.66-3.59 (1H, m) |
| 33 | DMSO-d$_6$: 10.20 (1H, s), 9.78 (1H, s), 9.21 (2H, s), 8.84 (2H, s), 8.03 (2H, d, J = 9 Hz), 7.80 (2H, d, J = 9 Hz), 7.74 (2H, d, J = 9 Hz), 7.32 (2H, d, J = 9 Hz), 6.50 (1H, d, J = 7 Hz), 5.74-5.69 (1H, m), 4.70-4.65 (2H, m), 4.18-4.05 (1H, m), 4.00 (2H, d, J = 6 Hz), 3.97-3.89 (1H, m), 3.88-3.79 (1H, m), 3.64-3.58 (1H, m) |
| 34 | *DMSO-d$_6$: 10.43 (1H, s), 10.18 (1H, s), 9.21 (2H, s), 8.86 (2H, s), 8.03 (2H, d, J = 9 Hz), 7.80 (2H, d, J = 9 Hz), 7.31 (1H, d, J = 2 Hz), 7.15 (1H, dd, J = 8, 2 Hz), 6.87 (1H, d, J = 8 Hz), 6.49 (1H, d, J = 7 Hz), 4.72-4.61 (2H, m), 4.17-4.05 (1H, m), 3.98-3.75 (2H, m), 3.64-3.54 (1H, m), 1.26 (3H, s), 1.26 (3H, s) |
| 35 | *DMSO-d$_6$: 11.22 (1H, brs), 10.16 (1H, brs), 7.98 (2H, d, J = 9 Hz), 7.77 (2H, d, J = 9 Hz), 7.48 (1H, d, J = 2 Hz), 7.44-7.37 (2H, m), 7.04 (1H, dd, J = 8, 2 Hz), 6.44 (1H, d, J = 3 Hz), 4.70-4.63 (2H, m), 4.17-4.07 (1H, m), 4.02-3.78 (2H, m), 3.67-3.58 (1H, m), 1.72 (3H, s) |
| 36 | DMSO-d$_6$: 11.80 (1H, s), 10.21 (1H, s), 9.24 (2H, s), 8.94 (2H, s), 8.03 (2H, d, J = 9 Hz), 7.81 (2H, d, J = 9 Hz), 7.40-7.35 (1H, m), 7.21-7.05 (2H, m), 6.52 (1H, brs), 4.67 (2H, s), 4.17-4.08 (1H, m), 3.98-3.77 (2H, m), 3.70-3.56 (1H, m) |
| 37 | DMSO-d$_6$: 10.22 (1H, s), 9.23 (2H, s), 8.90 (2H, s), 8.66 (1H, s), 8.04 (2H, d, J = 9 Hz), 7.81 (2H, d, J = 9 Hz), 7.73-7.69 (1H, m), 7.66-7.59 (2H, m), 6.55 (1H, d, J = 6 Hz), 4.74-4.66 (2H, m), 4.39 (2H, s), 4.18-4.11 (1H, m), 4.02-3.85 (2H, m), 3.75-3.68 (1H, m) |
| 38 | *DMSO-d$_6$: 12.97 (1H, brs), 10.39 (1H, s), 10.09 (1H, s), 8.95 (2H, brs), 8.56-8.49 (2H, m), 8.07 (1H, dd, J = 9, 2 Hz), 7.68-7.58 (3H, m), 7.33 (2H, d, J = 9 Hz), 7.17 (1H, d, J = 7 Hz), 4.72 (1H, d, J = 2 Hz), 4.70 (1H, d, J = 2 Hz), 4.19-4.09 (1H, m), 4.00-3.79 (2H, m), 3.66-3.58 (1H, m), 2.07 (3H, s) |
| 38-3 | *DMSO-d$_6$: 10.38 (1H, s), 10.17 (1H, s), 8.37-8.30 (1H, m), 7.88-7.67 (5H, m), 7.35 (2H, d, J = 8 Hz), 5.57 (1H, d, J = 3 Hz), 5.49 (1H, d, J = 3 Hz), 3.97-3.77 (2H, m), 3.67-3.58 (2H, m), 2.19 (3H, s), 2.08 (3H, s), 1.95 (3H, s), 1.29 (18H, s) |
| 39 | DMSO-d$_6$: 10.25 (2H, s), 10.13 (1H, s), 9.75 (1H, s), 9.21 (1H, s), 8.32 (1H, s), 8.22 (1H, d, J = 9 Hz), 7.94-7.90 (1H, m), 7.61 (2H, d, J = 9 Hz), 7.29 (2H, d, J = 9 Hz), 6.49 (1H, brs), 4.77 (2H, s), 4.68-4.64 (2H, m), 4.15-4.07 (1H, m), 3.96-3.77 (2H, m), 3.62-3.54 (1H, m), 2.04 (3H, s) |
| 39-1 | *CDCl$_3$: 8.25-8.18 (2H, m), 7.86 (1H, d, J = 8 Hz), 5.12 (2H, s), 1.51 (18H, s) |
| 39-2 | *DMSO-d$_6$: 7.36 (1H, d, J = 8 Hz), 6.51-6.45 (1H, m), 6.39-6.36 (1H, m), 6.23 (2H, s), 4.70 (2H, s), 1.39 (18H, s) |
| 40 | DMSO-d$_6$: 10.20 (1H, s), 10.01 (1H, s), 9.24 (2H, s), 8.94 (2H, s), 8.03 (2H, d, J = 9 Hz), 7.81 (2H, d, J = 9 Hz), 7.63 (2H, d, J = 9 Hz), 7.30 (2H, d, J = 9 Hz), 6.53-6.46 (1H, m), 4.66 (2H, s), 4.15-4.08 (1H, m), 3.97-3.78 (2H, m), 3.63-3.56 (1H, m), 2.33 (2H, q, J = 8 Hz), 1.08 (3H, t, J = 8 Hz) |
| 41 | *DMSO-d$_6$: 10.20 (1H, s), 9.95 (1H, s), 9.23 (2H, s), 8.91 (2H, s), 8.03 (2H, d, J = 9 Hz), 7.81 (2H, d, J = 9 Hz), 7.64 (2H, d, J = 9 Hz), 7.31 (2H, d, J = 9 Hz), 6.49 (1H, d, J = 8 Hz), 4.70-4.64 (2H, m), 4.16-4.08 (1H, m), 3.98-3.77 (2H, m), 3.64-3.55 (1H, m), 2.21 (1H, d, J = 7 Hz), 1.12-1.00 (1H, m), 0.52-0.44 (2H, m), 0.23-0.17 (2H, m) |
| 42 | *DMSO-d$_6$: 10.18 (1H, s), 9.90 (1H, s), 9.20 (2H, brs), 8.81 (2H, brs), 8.03 (2H, d, J = 9 Hz), 7.80 (2H, d, J = 9 Hz), 7.63 (2H, d, J = 9 Hz), 7.29 (2H, d, J = 9 Hz), 6.48 (1H, d, J = 8 Hz), 4.69-4.64 (2H, m), 4.16-4.07 (1H, m), 3.97-3.76 (2H, m), |

TABLE 3-continued

| EXAMPLE | NMR (ppm) (No mark: 400 MHz, *: 300 MHz) |
|---|---|
|  | 3.63-3.55 (1H, m), 2.38-2.25 (1H, m), 1.85-1.60 (5H, m), 1.49-1.13 (5H, m) |
| 43 | *DMSO-$d_6$: 10.22 (1H, s), 9.28 (2H, s), 9.02 (2H, s), 8.02 (2H, d, J = 9 Hz), 7.83 (2H, d, J = 9 Hz), 7.43 (2H, d, J = 9 Hz), 7.28 (2H, d, J = 9 Hz), 4.72-4.65 (2H, m), 4.18-4.09 (1H, m), 3.99-3.80 (2H, m), 3.68-3.59 (1H, m) |
| 44 | *DMSO-$d_6$ (100degC): 9.91 (1H, s), 8.97 (3H, brs), 7.95 (2H, d, J = 9 Hz), 7.84 (2H, d, J = 9 Hz), 7.14 (1H, dd, J = 8, 8 Hz), 6.82 (1H, s), 6.75-6.66 (2H, m), 4.70 (1H, d, J = 2 Hz), 4.66 (1H, d, J = 2 Hz), 4.20-4.12 (1H, m), 3.97-3.88 (1H, m), 3.87-3.78 (1H, m), 3.75-3.31 (1H, m) |
| 45 | *DMSO-$d_6$ (100degC): 9.90 (1H, s), 9.72 (1H, s), 8.91 (3H, brs), 7.94 (2H, d, J = 9 Hz), 7.82 (2H, d, J = 9 Hz), 7.66 (1H, dd, J = 2, 2 Hz), 7.44-7.39 (1H, m), 7.29 (1H, dd, J = 8, 8 Hz), 7.07-7.02 (1H, m), 5.98 (1H, brs), 4.71-4.66 (2H, m), 4.20-4.12 (1H, m), 3.98-3.80 (2H, m), 3.63-3.55 (1H, m), 2.04 (3H, s) |
| 46 | *DMSO-$d_6$ (100degC): 9.89 (1H, s), 8.93 (3H, brs), 7.94 (2H, d, J = 9 Hz), 7.82 (2H, d, J = 9 Hz), 7.72 (1H, dd, J = 2, 2 Hz), 7.52-7.47 (1H, m), 7.37 (1H, dd, J = 8, 8 Hz), 7.18-7.13 (1H, m), 4.71-4.67 (2H, m), 4.21-4.13 (1H, m), 3.99-3.79 (4H, m), 3.67-3.60 (1H, m), 2.52-2.45 (2H, m), 2.09 (2H, tt, J = 7, 7 Hz) |
| 47 | *DMSO-$d_6$ (100degC): 9.89 (1H, s), 8.88 (2H, brs), 8.46 (1H, s), 7.94 (2H, d, J = 9 Hz), 7.82 (2H, d, J = 9 Hz), 7.52-7.48 (1H, m), 7.26-7.21 (2H, m), 6.94-6.89 (1H, m), 5.98 (1H, brs), 5.60 (2H, brs), 4.72-4.65 (2H, m), 4.20-4.11 (1H, m), 3.98-3.79 (2H, m), 3.62-3.54 (1H, m) |
| 48 | *DMSO-$d_6$: 10.20 (1H, s), 9.20 (2H, s), 8.81 (2H, s), 8.03 (2H, d, J = 9 Hz), 7.80 (2H, d, J = 9 Hz), 7.68 (1H, s), 7.46-7.41 (2H, m), 7.18-7.12 (1H, m), 6.51 (1H, d, J = 7 Hz), 4.71-4.65 (2H, m), 4.46 (2H, t, J = 8 Hz), 4.18-3.81 (5H, m), 3.67-3.59 (1H, m) |
| 49 | *DMSO-$d_6$: 10.20 (1H, s), 9.91 (1H, s), 9.21 (2H, s), 8.84 (2H, s), 8.03 (2H, d, J = 9 Hz), 7.80 (2H, d, J = 9 Hz), 7.39 (1H, dd, J = 8, 8 Hz), 7.30-7.27 (1H, m), 7.16-7.08 (2H, m), 6.48 (1H, d, J = 6 Hz), 4.72-4.63 (2H, m), 4.16-4.08 (1H, m), 4.00-3.82 (2H, m), 3.64-3.55 (1H, m), 3.03 (3H, s) |
| 50 | *DMSO-$d_6$: 10.20 (1H, s), 9.77 (1H, s), 9.20 (2H, s), 8.83 (2H, s), 8.03 (2H, d, J = 9 Hz), 7.84-7.77 (3H, m), 7.59-7.54 (1H, m), 7.35 (1H, dd, J = 8, 8 Hz), 7.12-7.07 (1H, m), 6.48 (1H, d, J = 7 Hz), 5.69 (1H, t, J = 6 Hz), 4.71-4.64 (2H, m), 4.17-4.09 (1H, m), 4.02-3.80 (4H, m), 3.63-3.55 (1H, m) |
| 51 | *DMSO-$d_6$: 10.21 (1H, s), 9.33-9.19 (2H, m), 9.06-8.86 (2H, m), 8.03 (2H, d, J = 9 Hz), 7.82 (2H, d, J = 9 Hz), 7.52-7.43 (2H, m), 7.37-7.28 (2H, m), 6.60-6.44 (1H, m), 4.72-4.64 (2H, m), 4.22 (2H, s), 4.19-4.10 (1H, m), 4.02-3.82 (4H, m), 3.78-3.63 (3H, m) |
| 52 | *DMSO-$d_6$: 12.87 (1H, brs), 10.40 (1H, s), 8.89 (2H, brs), 8.54-8.48 (2H, m), 8.06 (1H, dd, J = 9, 2 Hz), 7.63 (1H, d, J = 7 Hz), 7.45 (2H, d, J = 9 Hz), 7.33 (2H, d, J = 9 Hz), 7.18 (1H, d, J = 7 Hz), 6.55 (1H, d, J = 7 Hz), 4.76-4.69 (2H, m), 4.19-4.10 (1H, m), 4.01-3.80 (2H, m), 3.69-3.60 (1H, m), 1.31 (9H, s) |
| 52-1 | *CDCl$_3$: 7.50 (2H, d, J = 9 Hz), 7.37 (2H, d, J = 9 Hz), 5.49 (1H, d, J = 3 Hz), 5.24 (1H, d, J = 3 Hz), 4.20-3.98 (1H, m), 3.88-3.66 (2H, m), 3.63-3.46 (1H, m), 2.20 (3H, s), 2.11 (3H, s), 1.34 (9H, s), 1.26 (9H, s) |
| 52-4 | *DMSO-$d_6$: 12.73 (1H, brs), 7.41 (2H, d, J = 9 Hz), 7.27 (2H, d, J = 9 Hz), 5.41 (1H, brs), 4.55 (1H, d, J = 2 Hz), 4.52 (1H, d, J = 2 Hz), 4.16-4.08 (1H, m), 3.96-3.77 (2H, m), 3.64-3.55 (1H, m), 1.29 (9H, s) |
| 53 | DMSO-$d_6$: 10.25 (1H, s), 10.17 (1H, brs), 9.56 (1H, brs), 9.12 (1H, brs), 8.33-8.31 (1H, m), 8.14 (1H, d, J = 9 Hz), 7.93 (1H, dd, J = 9, 2 Hz), 7.43 (2H, d, J = 9 Hz), 7.30 (2H, d, J = 9 Hz), 6.48 (1H, d, J = 7 Hz), 4.78 (2H, s), 4.69-4.65 (2H, m), 4.14-4.08 (1H, m), 3.95-3.78 (2H, m), 3.65-3.58 (1H, m), 1.29 (9H, s) |
| 54 | *DMSO-$d_6$: 12.90 (1H, brs), 10.39 (1H, s), 8.91 (2H, brs), 8.54-8.47 (2H, m), 8.05 (1H, dd, J = 9, 2 Hz), 7.82 (2H, d, J = 9 Hz), 7.70 (2H, d, J = 9 Hz), 7.62 (1H, d, J = 7 Hz), 7.16 (1H, d, J = 7 Hz), 6.59 (1H, brs), 4.79-4.70 (2H, m), 4.21-4.13 (1H, m), 4.03-3.88 (2H, m), 3.78-3.70 (1H, m) |
| 54-3 | *CDCl$_3$: 7.79 (2H, d, J = 9 Hz), 7.71-7.64 (2H, m), 5.43 (1H, d, J = 2 Hz), 5.20 (1H, d, J = 2 Hz), 4.07-3.98 (1H, m), 3.96-3.85 (1H, m), 3.79-3.58 (2H, m), 2.20 (3H, s), 2.11 (3H, s), 1.28 (9H, s) |
| 55 | *DMSO-$d_6$: 12.93 (1H, brs), 10.38 (1H, s), 8.90 (2H, brs), 8.54-8.47 (2H, m), 8.05 (1H, dd, J = 9, 2 Hz), 7.65-7.53 (3H, m), 7.45 (2H, d, J = 8 Hz), 7.16 (1H, d, J = 7 Hz), 6.56 (1H, d, J = 7 Hz), 4.76-4.68 (2H, m), 4.20-4.11 (1H, m), 4.02-3.84 (2H, m), 3.72-3.63 (1H, m) |
| 56 | *DMSO-$d_6$: 10.21 (1H, s), 9.25 (2H, s), 8.96 (2H, s), 8.03 (2H, d, J = 9 Hz), 7.82 (2H, d, J = 9 Hz), 7.56 (2H, d, J = 9 Hz), 7.45 (2H, d, J = 9 Hz), 6.50 (1H, d, J = 7 Hz), 4.74-4.63 (2H, m), 4.20-4.09 (1H, m), 4.01-3.83 (2H, m), 3.72-3.63 (1H, m) |
| 57 | DMSO-$d_6$: 10.29-10.21 (2H, m), 9.68 (1H, brs), 9.18 (1H, brs), 8.33-8.32 (1H, m), 8.19 (1H, d, J = 9 Hz), 7.93 (1H, dd, J = 9, 2 Hz), 7.56 (2H, d, J = 9 Hz), 7.48-7.42 (2H, m), 6.51 (1H, d, J = 7 Hz), 4.78 (2H, s), 4.73-4.66 (2H, m), 4.18-4.11 (1H, m), 3.99-3.85 (2H, m), 3.71-3.65 (1H, m) |
| 58 | *DMSO-$d_6$: 12.88 (1H, brs), 10.37 (1H, s), 8.86 (2H, brs), 8.53-8.46 (2H, m), 8.05 (1H, dd, J = 9, 2 Hz), 7.67-7.60 (3H, m), 7.40 (2H, d, J = 9 Hz), 7.16 (1H, d, J = 7 Hz), 6.56 (1H, d, J = 8 Hz), 4.74-4.68 (2H, m), 4.18-4.10 (1H, m), 4.00-3.82 (2H, m), 3.69-3.61 (1H, m) |
| 59 | DMSO-$d_6$: 12.82 (1H, brs), 10.36 (1H, s), 8.82 (2H, brs), 8.52-8.46 (2H, m), 8.04 (1H, dd, J = 9, 2 Hz), 7.61 (1H, d, J = 7 Hz), 7.46-7.41 (2H, m), 7.27 (2H, dd, J = 9, 9 Hz), 7.15 (1H, d, J = 7 Hz), 6.56 (1H, d, J = 7 Hz), 4.73-4.68 (2H, m), 4.16-4.09 (1H, m), 3.98-3.80 (2H, m), 3.66-3.59 (1H, m) |
| 59-2 | *CDCl$_3$: 6.92 (2H, dd, J = 9, 9 Hz), 6.63-6.56 (2H, m), 3.95 (1H, brs), 3.72 (2H, t, J = 6 Hz), 3.47 (2H, t, J = 6 Hz) |
| 60 | DMSO-$d_6$: 12.78 (1H, brs), 10.36 (1H, s), 8.81 (2H, brs), 8.51-8.45 (2H, m), 8.04 (1H, dd, J = 9, 2 Hz), 7.61 (1H, d, J = 7 Hz), 7.50 (2H, d, J = 9 Hz), 7.45 (2H, d, J = 9 Hz), 7.15 (1H, d, J = 7 Hz), 6.56 (1H, d, J = 7 Hz), 4.73-4.68 (2H, m), 4.16-4.10 (1H, m), 3.98-3.82 (2H, m), 3.68-3.61 (1H, m) |
| 60-2 | *CDCl$_3$: 7.15 (2H, d, J = 9 Hz), 6.57 (2H, d, J = 9 Hz), 4.06 (1H, brs), 3.71 (2H, t, J = 6 Hz), 3.53-3.45 (2H, m) |
| 61 | *DMSO-$d_6$: 12.94 (1H, brs), 10.39 (1H, s), 8.93 (2H, brs), 8.57-8.48 (2H, m), 8.07 (1H, dd, J = 9, 2 Hz), 7.63 (1H, d, J = 7 Hz), 7.28 (2H, d, J = 9 Hz), 7.17 (1H, d, J = 7 Hz), 6.96 (2H, d, J = 9 Hz), 6.55 (1H, brs), 4.75-4.58 (3H, m), 4.18-4.09 (1H, m), 3.99-3.77 (2H, m), 3.65-3.56 (1H, m), 1.29 (6H, d, J = 6 Hz) |
| 61-2 | *CDCl$_3$: 6.84-6.76 (2H, m), 6.65-6.57 (2H, m), 4.45-4.32 (1H, m), 3.76-3.68 (2H, m), 3.50-3.42 (2H, m), 1.34-1.28 (6H, m) |
| 62 | DMSO-$d_6$: 12.94 (1H, brs), 10.38 (1H, s), 8.92 (2H, brs), 8.54-8.48 (2H, m), 8.05 (1H, dd, J = 9, 2 Hz), 7.62 (1H, d, J = 7 Hz), 7.28 (2H, d, J = 9 Hz), 7.23 (2H, d, J = 9 Hz), 7.16 (1H, d, J = 7 Hz), 6.56 (1H, brs), 4.73-4.67 (2H, m), 4.16-4.09 (1H, m), 3.98-3.90 (1H, m), 3.87-3.78 (1H, m), 3.64-3.58 (1H, m), 2.32 (3H, s) |
| 63 | *DMSO-$d_6$(100degC): 10.11 (1H, s), 8.73 (2H, brs), 8.50 (1H, d, J = 9 Hz), 8.35 (1H, d, J = 2 Hz), 8.03 (1H, dd, J = 9, 2 Hz), 7.58 (1H, d, J = 7 Hz), 7.27-7.19 (1H, m), 7.14-6.99 (3H, m), 4.74-4.68 (2H, m), 4.22-4.12 (1H, m), 4.01-3.91 (1H, m), 3.81-3.69 (1H, m), 3.49-3.40 (1H, m), 2.23 (3H, s) |
| 64 | *DMSO-$d_6$(100degC): 9.92 (1H, s), 8.89 (4H, brs), 7.95 (2H, d, J = 9 Hz), 7.85-7.79 (2H, m), 7.26-7.18 (1H, m), 7.14-6.99 (2H, m), 4.68 (2H, s), 4.21-4.11 (1H, m), 4.00-3.90 (1H, m), 3.80-3.67 (1H, m), 3.48-3.39 (1H, m), 2.22 (1H, m) |
| 65 | DMSO-$d_6$: 9.41 (4H, brs), 7.98 (1H, d, J = 9 Hz), 7.71 (1H, s), 7.69-7.64 (1H, m), 7.44 (2H, d, J = 9 Hz), 7.32 (2H, d, J = 9 Hz), 4.72-4.65 (2H, m), 4.18-4.12 (1H, m), 4.00-3.82 (2H, m), 3.66-3.60 (1H, m), 2.31 (3H, s), 1.30 (9H, s) |
| 66 | *DMSO-$d_6$: 8.54-8.47 (1H, m), 8.04-8.00 (1H, m), 7.82 (1H, d, J = 9 Hz), 7.43 (2H, d, J = 9 Hz), 7.32 (2H, d, J = 9 Hz), 4.76-4.66 (2H, m), 4.17-4.08 (1H, m), 4.00-3.82 (2H, m), 3.65-3.56 (1H, m), 1.73 (3H, s), 1.30 (9H, s) |

TABLE 3-continued

| EXAMPLE | NMR (ppm) (No mark: 400 MHz, *: 300 MHz) |
|---|---|
| 66-2 | *DMSO-d$_6$: 9.73 (1H, s), 9.55 (1H, s), 8.35 (1H, d, J = 9 Hz), 7.81 (1H, d, J = 2 Hz), 7.68 (1H, dd, J = 9, 2 Hz), 7.43 (2H, d, J = 9 Hz), 7.31 (2H, d, J = 9 Hz), 6.95 (1H, d, J = 5 Hz), 5.89 (2H, s), 4.73-4.65 (2H, m), 4.17-4.10 (1H, m), 3.99-3.82 (2H, m), 3.63-3.56 (1H, m), 1.30 (9H, s) |
| 67 | *DMSO-d$_6$: 8.27 (1H, dd, J = 8, 8 Hz), 7.84-7.63 (2H, m), 7.43 (2H, d, J = 9 Hz), 7.31 (2H, d, J = 9 Hz), 4.72 (1H, s), 4.68 (1H, s), 4.18-4.08 (1H, m), 4.00-3.80 (2H, m), 3.66-3.56 (1H, m), 1.73 (3H, s), 1.29 (9H, s) |
| 68 | $^1$H NMR (DMSO-d$_6$, 400 MHz): δ 10.2 (s, 1H), 9.22 (s, 2H), 8.89 (s, 2H), 8.03 (d, J = 8.5 Hz, 2H), 7.81 (d, J = 8.5 Hz, 2H), 7.72 (s, 1H), 7.66-7.60 (m, 2H), 6.52 (d, J = 6.8 Hz, 1H), 4.71-4.68 (m, 2H), 4.48 (s, 2H), 4.18-4.13 (m, 1H), 4.01-3.85 (m, 2H), 3.75-3.70 (m, 1H), 3.49 (t, J = 7.2 Hz, 2H), 1.63 (sextet, J = 7.2 Hz, 2H), 0.87 (t, J = 7.2 Hz, 3H) 13C NMR (CDCl$_3$, 400 MHz): δ 171.0, 166.4, 166.2, 164.3, 143.0, 141.3, 139.4, 132.8, 128.7, 128.0, 123.5, 121.8, 119.6, 118.8, 78.6, 72.6, 62.2, 49.2, 48.8, 42.9, 20.7, 10.8; |
| 68-8 | $^1$H NMR (CDCl$_3$, 300 MHz): δ 8.19 (d, J = 1.7 Hz, 1H), 7.83 (dd, J = 8.0, 1.7 Hz 1H), 7.20 (d, J = 8.0 Hz, 1H), 4.32 (s, 2H), 3.57 (t, J = 7.3 Hz, 2H), 1.69 (sextet, J = 7.3 Hz, 2H), 0.96 (t, J = 7.3 Hz, 3H). 13C NMR (CDCl3, 400 MHz): δ 166.8, 141.4, 139.8, 135.3, 132.8, 124.5, 93.1, 49.7, 44.1, 21.7, 11.3; |
| 68-9 | CDCl$_3$, 300 MHz: δ 7.73 (d, J = 1.8 Hz, 1H), 7.64 (dd, J = 8.1 Hz, 1.8 Hz, 1H), 7.47 (d, J = 8.1 Hz, 1H), 4.73 (br, s, 1H), 4.65 (d, J = 2.1 Hz, 1H), 4.37 (s, 2H), 4.28-4.20 (m, 1H), 4.06-3.94 (m, 2H), 3.70-3.56 (m, 3H), 3.25 (br, s, 1H), 1.69 (sextet, J = 7.5 Hz, 2H), 1.52 (s, 9H), 0.96 (t, J = 7.5 Hz, 3H); |
| 68-10 | CDCl$_3$, 300 MHz: δ 7.70 (d, J = 2.1 Hz, 1H), 7.57 (dd, J = 8.1 Hz, 2.1 Hz, 1H), 7.47 (d, J = 8.1 Hz, 1H), 5.65 (d, J = 2.4 Hz, 1H), 4.88 (d, J = 2.4 Hz, 1H), 4.38 (s, 2H), 4.32-4.26 (m, 1H), 4.14-3.98 (m, 2H), 3.70-3.56 (m, 3H), 2.17 (s, 3H), 1.70 (sextet, J = 7.5 Hz, 2H), 1.50 (s, 9H), 0.96 (t, J = 7.5 Hz, 3H); |
| 68-11 | DMSO-d6, 300 MHz: δ 7.64-7.62 (m, 2H), 7.55 (dd, J = 8.1 Hz, 2.1 Hz, 1H), 5.43 (d, J = 2.4 Hz, 1H), 4.86 (d, J = 2.4 Hz, 1H), 4.48 (s, 2H), 4.19-3.90 (m, 3H), 3.75-3.68 (m, 1H), 3.48 (t, J = 7.2 Hz, 2H), 2.17 (s, 3H), 1.62 (sextet, J = 7.2 Hz, 2H), 0.96 (t, J = 7.2 Hz, 3H); |
| 68-13 | DMSO-d6, 400 MHz: δ 12.8 (s, 1H), 10.5 (s, 1H), 7.82-7.78 (m, 4H), 7.67-7.64 (m, 2H), 7.58 (dd, J = 8.1 Hz, 2.1 Hz, 1H), 5.59 (d, J = 2.4 Hz, 1H), 4.95 (d, J = 2.4 Hz, 1H), 4.48 (s, 2H), 4.20-4.14 (m, 1H), 4.07-4.00 (m, 1H), 3.98-3.90 (m, 1H), 3.78-3.72 (m, 1H), 3.49 (t, J = 7.2 Hz, 2H), 2.17 (s, 3H), 1.62 (sextet, J = 7.2 Hz, 2H), 0.87 (t, J = 7.2 Hz, 3H); |
| 68-14 | DMSO-d6, 400 MHz: δ 12.8 (br, s, 1H), 10.0 (s, 1H), 8.00-7.98 (m, 2H), 7.78-7.71 (m, 3H), 7.66-7.50 (m, 2H), 6.46 (d, J = 6.8 Hz, 1H), 4.71-4.67 (m, 2H), 4.48 (s, 2H), 4.18-4.13 (m, 1H), 4.00-3.85 (m, 2H), 3.74-3.70 (m, 1H), 3.49 (t, J = 7.2 Hz, 2H), 1.62 (sextet, J = 7.2 Hz, 2H), 0.87 (t, J = 7.2 Hz, 3H) |
| 69 | CD$_3$OD, 400 MHz: δ 9.94 (s, 1H), 9.18 (br, s, 1H), 8.64 (br, s, 1H), 7.96 (d, J = 8.8 Hz, 2H), 7.85-7.80 (m, 3H), 7.72-7.67 (m, 2H), 4.68 (s, 2H), 4.35 (q, J = 9.6 Hz), 4.27-4.20 (m, 1H), 4.10-4.02 (m, 2H), 3.75-3.69 (m, 1H); E |
| 69-1 | DMSO-d6, 300 MHz: δ 8.60 (br, s, 1H), 7.95-7.91 (m, 2H), 7.42 (d, J = 7.8 Hz, 1H), 4.32 (s, 2H). 13C NMR (CDCl3, 400 MHz) δ 168.2, 143.5, 139.5, 134.9, 130.6, 125.9, 93.2, 44.7; |
| 69-2 | $^1$H NMR (CDCl$_3$, 400 MHz): δ 8.23 (d, J = 1.6 Hz, 1H), 7.90 (dd, J = 8.0 Hz, 1.6 Hz, 1H), 7.24 (d, J = 8.0 Hz, 1H), 4.50 (s, 2H), 4.20 (q, J = 9.2 Hz, 2H) 13C NMR (CDCl3, 400 MHz): δ 167.2, 140.9, 140.5, 133.4, 133.1, 124.6, 124.1 (q, J = 280.3 Hz), 93.3, 50.5, 44.1 (q, J = 34.8 Hz). |
| 69-3 | CDCl$_3$, 400 MHz: δ 7.80 (d, J = 2.0 Hz, 1H), 7.71 (dd, J = 8.4 Hz, 2.0 Hz, 1H), 7.51 (d, J = 8.4 Hz, 1H), 4.73 (dd, J = 6.8 Hz, 2.0 Hz, 1H), 4.65 (d, J = 2.0 Hz, 1H), 4.55 (s, 2H), 4.29-4.19 (m, 3H), 4.05-3.96 (m, 2H), 3.70-3.63 (m, 3H), 3.26 (d, J = 7.2 Hz, 1H), 1.52 (s, 9H). |
| 69-4 | CDCl$_3$, 300 MHz: δ 7.76 (d, J = 2.1 Hz, 1H), 7.65 (dd, J = 8.1 Hz, 2.1 Hz, 1H), 7.52 (d, J = 8.4 Hz, 1H), 5.65 (d, J = 2.4 Hz, 1H), 4.89 (d, J = 2.4 Hz, 1H), 4.56 (s, 2H), 4.33-3.99 (m, 5H), 3.70-3.64 (m, 1H), 2.17 (s, 3H), 1.51 (s, 9H). |
| 69-5 | CDCl$_3$, 300 MHz: δ 7.79 (d, J = 2.1 Hz, 1H), 7.65 (dd, J = 8.1 Hz, 2.1 Hz, 1H), 7.53 (d, J = 8.1 Hz, 1H), 5.80 (d, J = 2.4 Hz, 1H), 4.93 (d, J = 2.4 Hz, 1H), 4.58 (s, 2H), 4.34-4.02 (m, 5H), 3.71-3.65 (m, 1H), 2.19 (s, 3H). |
| 69-6 | CD$_3$OD, 300 MHz: δ 10.2 (br, s, 1H), 7.84-7.64 (m, 8H), 5.70 (d, J = 2.7 Hz, 1H), 4.92 (s, 1H), 4.68 (s, 2H), 4.40-4.02 (m, 5H), 3.80-3.71 (m, 1H), 2.23 (s, 3H). |
| 69-7 | DMSO-d$_6$, 300 MHz: δ 10.0 (br, s, 1H), 7.98 (d, J = 9.0 Hz, 2H), 7.82-7.70 (m, 6H), 6.46 (d, J = 6.8 Hz, 1H), 4.73-4.63 (m, 4H), 4.41 (q, J = 9.6 Hz, 2H), 4.20-4.13 (m, 1H), 4.03-3.85 (m, 2H), 3.77-3.68 (m, 1H); |
| 70 | DMSO-d6: 10.2 (1H, s), 9.28 (2H, s), 9.01 (2H, s), 8.04 (2H, d, J = 7.9 Hz), 7.83 (2H, d, J = 7.5 Hz), 7.73 (1H, s), 7.66-7.63 (2H, m), 6.57 (1H, s), 4.71 (2H, s), 4.50 (2H, s), 4.17-4.14 (1H, m), 3.99-3.95 (1H, m), 3.93-3.90 (1H, m), 3.74-3.71 (1H, m), 3.09 (2H, s), 2.08 (2H, s) |
| 71 | DMSO-d6: 9.93 (1H, s), 8.22 (2H, brs), 7.83 (2H, d, J = 8.2 Hz), 7.73 (1H, s), 7.65-7.62 (2H, m), 7.41 (2H, d, J = 8.5 Hz), 6.47 (1H, d, J = 6.7 Hz), 4.70 (1H, s), 4.66-4.64 (2H, m), 4.48 (2H, s), 4.16-4.13 (1H, m), 3.98 (2H, s), 3.95-3.91 (1H, m), 3.90-3.88 (2H, m), 3.73-3.71 (1H, m), 3.52-3.45 (2H, m) |
| 72 | DMSO-d6: 9.74 (1H, s), 9.31-9.24 (2H, m), 7.72 (2H, s), 7.67-7.59 (3H, m), 7.17 (1H, d, J = 8.5 Hz), 4.69 (1H, s), 4.64 (1H, s), 4.48 (2H, s), 4.28 (2H, s), 4.15 (1H, m), 3.99-3.87 (2H, m), 3.73-3.71 (3H, m), 3.52-3.42 (3H, m), 3.42 (1H, d, J = 5.3 Hz), 3.10 (3H, s) |
| 73 | DMSO-d6: 10.4 (1H, s), 9.26 (2H, s), 8.95 (2H, s), 8.22 (2H, s), 8.04 (2H, d, J = 11.6 Hz), 7.83 (2H, d, J = 7.9 Hz), 6.58 (1H, d, J = 6.6 Hz), 4.78 (1H, s), 4.71 (1H, d, J = 5.1 Hz), 4.20-4.18 (1H, m), 3.99 (1H, m), 3.87-3.85 (1H, m) |
| 74 | MeOH-d$_4$: 8.15 (2H, s), 8.11 (1H, s), 7.93 (2H, d, J = 11.1 Hz), 7.79-7.75 (2H, m), 7.72-7.67 (2H, m), 4.64 (2H, s), 4.47 (2H, d, J = 10.9 Hz), 4.49-4.45 (1H, m), 4.35-4.32 (1H, m), 4.30-4.27 (3H, m), 3.82-3.79 (1H, m), 3.73 (1H, d, J = 6.2 Hz) |
| 75 | MeOH-d$_4$: 8.62 (1H, brs), 7.96 (2H, d, J = 10.9 Hz), 7.82 (2H, d, J = 8.9 Hz), 7.29 (2H, d, J = 8.6 Hz), 6.92 (3H, d, J = 8.9 Hz), 4.91 (1H, s), 4.85 (1H, s), 4.73 (1H, d, J = 14.4 Hz), 4.52 (1H, d, J = 14.4 Hz), 4.10-4.02 (1H, m), 3.83-3.78 (1H, m), 3.81 (3H, s), 3.54-3.49 (1H, m), 3.22-3.18 (1H, m) |
| 76 | MeOH-d$_4$: 8.37 (1H, s) 8.35-8.34 (1H, d, J = 2.1 Hz), 7.99-7.97 (1H, dd, J = 2.16 Hz), 7.50-7.48 (1H, d, J = 7.06 Hz), 7.27-7.25 (2H, d, J = 8.74 Hz), 7.13-7.11 (1H, d, J = 7.06 Hz), 6.89-6.88 (2H, d, J = 8.74 Hz), 4.91 (1H, s), 4.85 (1H, s), 4.75 (1H, d, J = 14.4 Hz), 4.52 (1H, d, J = 14.4 Hz), 4.08-4.02 (1H, m), 3.80-3.78 (1H, m), 3.79 (3H, s), 3.53-3.43 (1H, m), 3.22-3.18 (1H, m) |
| 93 | MeOH-d$_4$: 7.97 (1H, d, J = 1.2 Hz), 7.75 (2H, d, J = 8.4 Hz), 7.69 (1H, d, J = 8.4 Hz), 7.64 (2H, d, J = 8.4 Hz), 7.41 (1 H, dd, J = 8.4, 1.5 Hz), 4.84 (2H, m), 4.26-4.22 (1H, m), 4.08-4.04 (2H, m), 3.72-3.69 (1H, m) |
| 94 | MeOH-d$_4$: 7.91 (1H, m), 7.75 (2H, d, J = 8.5 Hz), 7.65-7.62 (3H, m), 7.05 (1H, dd, J = 8.7, 1.8 Hz), 4.84-4.82 (2H, m), 4.26-4.22 (1H, m), 4.08-4.04 (2H, m), 3.72-3.69 (1H, m) |
| 95 | MeOH-d$_4$: 7.96 (1H, d, J = 13.5 Hz), 7.65 (2H, d, J = 8.5 Hz), 7.66-7.63 (4H, m), 4.83 (2H, m), 4.25-4.22 (1H, m), 4.06-4.04 (2H, m), 3.73-3.70 (1H, m) |
| 96 | MeOH-d$_4$: 3.70-3.73 (m, 1H), 4.04-4.07 (m, 2H), 4.22-4.25 (m, 1H), 4.83-4.84 (m, 2H), 7.64 (d, 2H, J = 8 Hz), 7.75 (d, 2H, J = 8 Hz), 7.81 (d, 2H, J = 7 Hz), 7.96 (d, 2H, J = 7 Hz). |
| 97 | MeOH-d$_4$: 3.69-3.72 (m, 1H), 4.02-4.08 (m, 2H), 4.22-4.25 (m, 1H), 4.83-4.84 (m, 2H), 7.62-7.69 (m, 3H), 7.79-7.83 (m, 3H), 7.96 (d, 2H, J = 7 Hz), 8.45 (br s, 1H) |
| 98 | Formate salt in MeOH-d$_4$: 8.46 (1H, s), 8.37 (1H, d, J = 1.18 Hz), 8.17 (1H, d, J = 8.8 Hz), 7.82 (1H, dd, J = 9.2, 1.8 Hz), 7.75 (2H, d, J = 8.80 Hz), 7.64 (2H, d, J = 8.4 Hz), 4.87-4.85 (2H, m), 4.27-4.22 (1H, m), 4.10-4.00 (2H, m), 3.74-3.70 (1H, m) |
| 99 | HCl salt in DMSO-d$_6$: 9.79 (s, 1H), 8.25 (s, 2H), 7.79 (d, 7.66 Hz, 4H), 7.67 (d, 8.32 Hz, 2H), 7.39 (d, 8.40 Hz, 2H), 6.40 (d, |

TABLE 3-continued

| EXAMPLE | NMR (ppm) (No mark: 400 MHz, *: 300 MHz) |
|---|---|
| | 6.14 Hz, 1H), 4.70 (s, 1H), 4.61 (m, 1H), 4.17-4.08 (m, 1H), 3.99-3.85 (m, 4H), 3.73-3.67 (m, 1H) |
| 100 | HCl salt in DMSO-d$_6$: 9.32 (s, 1H), 9.15 (s, 1H), 8.85 (s, 1H), 8.65 (s, 1H), 8.61-8.47 (m, 2H), 8.01 (d, 8.92 Hz, 1H), 7.83 (d, 8.90 Hz, 1H), 7.62-7.56 (m, 2H), 7.46-7.38 (m, 3H), 7.31 (s, 1H), 7.19 (s, 1H), 6.65 (d, 8.78 Hz, 1H), 4.67 (dd, 12.34 Hz, 1.88 Hz, 2H), 4.19-3.55 (m, 4H). |
| 101 | DMSO-d$_6$: 9.94 (s, 1H), 7.85-7.86 (m, 3H), 7.68 (d, 8.38 Hz, 1H), 7.55-7.18 (m, 4H), 4.71 (d, 1.96 Hz, 1H), 4.63 (d, 1.89 Hz, 1H), 4.17-4.12 (m, 1H), 3.98-3.86 (m, 2H), 3.74-3.67 (m, 1H) |
| 102 | DMSO-d6: 10.19 (1H, s), 9.25 (2H, s), 8.95 (2H, s), 8.02 (2H, d, J = 9 Hz), 7.81 (2H, d, J = 9 Hz), 7.32 (1H, dd, J = 8.8 Hz), 7.23 (1H, s), 7.21 (1H, d, J = 8 Hz), 7.16-7.11 (1H, m), 4.66 (2H, s), 4.15-4.08 (1H, m), 3.97-3.78 (2H, m), 3.65-3.58 (3H, m), 2.73 (2H, t, J = 7 Hz) |
| 103 | DMSO-d6: 10.25 (1H, s), 9.27 (2H, s), 8.99 (2H, s), 8.39 (1H, d, J = 9 Hz), 8.30 (1H, dd, J = 9.3 Hz), 8.04 (2H, d, J = 9 Hz), 7.83 (2H, d, J = 9 Hz), 6.54 (1H, brs), 4.83 (1H, d, J = 2 Hz), 4.73 (1H, brs), 4.25-4.11 (2H, m), 4.00-3.92 (2H, m) |
| 104 | DMSO-d6 (100degC): 9.93 (1H, s), 8.97 (4H, brs), 7.96 (2H, d, J = 9 Hz), 7.85 (2H, d, J = 9 Hz), 7.50 (1H, s), 7.48-7.43 (2H, m), 7.37-7.31 (1H, m), 6.08 (1H, brs), 4.72 (2H, s), 4.47 (2H, s), 4.23-4.16 (1H, m), 4.02-3.87 (2H, m), 3.71-3.64 (1H, m), 2.91 (3H, s) |
| 105 | *DMSO-d6: 10.21 (1H, s), 9.23 (2H, s), 8.89 (2H, s), 8.10 (1H, d, J = 8 Hz), 8.04 (2H, d, J = 9 Hz), 7.85-7.65 (4H, m), 7.57-7.39 (5H, m), 6.53 (1H, d, J = 7 Hz), 4.77-4.66 (2H, m), 4.22-4.11 (1H, m), 4.03-3.90 (2H, m), 3.78-3.67 (1H, m), 2.86 (3H, s) |
| 106 | CD3OD: 9.87 (1H, s), 9.10 (1H, s), 8.57 (1H, s), 7.87 (2H, d, J = 9 Hz), 7.72 (2H, d, J = 9 Hz), 7.65-7.44 (2H, m), 7.38-7.05 (6H, m), 4.92-4.67 (2H, m), 4.19-4.10 (1H, m), 4.01-3.92 (2H, m), 3.67-3.60 (1H, m), 3.49 (2H, t, J = 7 Hz), 2.74 (2H, t, J = 7 Hz) |
| 107 | DMSO-d6: 10.23 (1H, s), 9.29 (2H, s), 9.03 (2H, s), 8.82 (1H, s), 8.54 (1H, s), 8.14-8.02 (4H, m), 7.84 (2H, d, J = 9 Hz), 7.65-7.51 (2H, m), 7.45-7.38 (1H, m), 7.27-7.13 (1H, m), 6.69-6.62 (1H, m), 4.71 (2H, s), 4.26-3.25 (4H, m) |
| 108 | DMSO-d6: 12.77 (1H, s), 10.05 (1H, s), 8.80 (2H, brs), 8.46-8.40 (2H, m), 8.00 (1H, dd, J = 9.2 Hz), 7.58 (1H, d, J = 7 Hz), 7.18-7.06 (5H, m), 6.39 (1H, d, J = 6 Hz), 4.36-4.29 (1H, m), 3.66-3.57 (1H, m), 3.53-3.45 (1H, m), 3.16-3.08 (1H, m), 2.26 (3H, m), 2.10-1.86 (4H, m) |
| 108-3 | *CDCl3: 9.09 (1H, s), 8.41-8.35 (2H, m), 7.90 (1H, d, J = 9 Hz), 7.59 (1H, d, J = 6 Hz), 7.53 (1H, dd, J = 9.2 Hz), 7.24-7.19 (2H, m), 7.08 (2H, d, J = 9 Hz), 5.32 (1H, brs), 4.63-4.54 (1H, m), 3.71-3.63 (2H, m), 3.15-3.06 (1H, m), 2.39-2.23 (4H, m), 2.19-1.84 (3H, m), 1.30 (18H, s) |
| 109 | DMSO-d6: 12.63 (1H, brs), 10.61-10.37 (1H, m), 8.76 (2H, brs), 8.52-8.26 (2H, m), 8.03-7.90 (1H, m), 7.66-7.57 (1H, m), 7.29-7.14 (5H, m), 6.85-6.30 (1H, m), 5.27-4.79 (2H, m), 4.56-3.89 (2H, m), 3.76-3.19 (2H, m), 2.35-2.29 (3H, m), 2.05-1.98 (3H, m) |
| 110 | DMSO-d6: 12.72 (1H, brs), 10.55-10.45 (1H, m), 8.81 (1H, brs), 8.52-8.27 (2H, m), 8.11-7.88 (2H, m), 7.65-7.58 (1H, m), 7.28-7.14 (5H, m), 6.98-6.38 (1H, m), 5.07-4.76 (2H, m), 4.35-3.84 (2H, m), 3.80-3.21 (2H, m), 2.35-2.29 (3H, m) |
| 110-1 | DMSO-d6: 8.22-7.94 (1H, m), 7.23-7.16 (4H, m), 6.35-5.85 (1H, m), 5.07-4.54 (2H, m), 4.36-3.47 (6H, m), 2.35-2.27 (3H, m), 1.29-1.12 (3H, m) |
| 111 | *DMSO-d6: 12.76-11.88 (1H, m), 10.53-9.88 (1H, m), 8.49-6.88 (16H, m), 6.57-6.45 (1H, m), 5.63-5.43 (1H, m), 5.01-2.19 (8H, m) |
| 112 | *CD3OD: 7.95 (2H, d, J = 9 Hz), 7.79 (2H, d, J = 9 Hz), 7.24 (2H, d, J = 9 Hz), 7.20-7.15 (2H, m), 5.06-4.78 (1H, m), 4.22-4.18 (2H, m), 4.11-3.95 (2H, m), 3.58-3.22 (1H, m), 2.94-2.82 (1H, m), 2.35 (3H, s), 1.89-1.87 (3H, m) |
| 113 | *CD3OD: 7.99-7.71 (4H, m), 7.32-7.12 (4H, m), 5.11-4.56 (2H, m), 4.21-3.93 (2H, m), 3.86-3.62 (2H, m), 2.42-2.29 (3H, m) |
| 113-1 | *DMSO-d6: 12.87 (1H, brs), 10.18-10.01 (1H, m), 7.99-7.87 (2H, m), 7.79-7.69 (2H, m), 7.28-7.00 (5H, m), 4.97-4.83 (1H, m), 4.67-4.55 (1H, m), 4.16-3.58 (4H, m), 2.35-2.27 (3H, m) |
| 114 | DMSO-d6: 10.34 (1H, s), 9.29 (2H, brs), 9.06 (2H, brs), 7.96 (2H, d, J = 8 Hz), 7.83 (2H, d, J = 8 Hz), 7.20 (2H, d, J = 8 Hz), 7.14-7.07 (2H, m), 6.22 (1H, brs), 4.69-4.62 (1H, s), 4.51-4.44 (1H, s), 4.19-3.99 (2H, m), 3.88-3.69 (2H, m), 2.31 (3H, s), 2.04-1.89 (2H, m) |
| 115 | *DMSO-d6 (100degC): 10.00-9.83 (1H, m), 8.96 (4H, brs), 7.93-7.74 (4H, m), 7.32-7.15 (4H, m), 4.17-3.39 (4H, m), 3.22-2.69 (4H, m), 2.37-2.29 (3H, m) |
| 115-1 | *CDCl3: 7.38-7.26 (5H, m), 4.45 (1H, dd, J = 9.4 Hz), 4.06-3.95 (1H, m), 3.90-3.46 (5H, m), 2.84-2.74 (1H, m), 2.72-2.61 (1H, m), 2.42-2.22 (2H, m) |
| 115-2 | *DMSO-d6: 7.66-7.56 (1H, m), 7.50-7.43 (5H, m), 4.44-4.28 (2H, m), 4.24-3.76 (6H, m), 3.53-3.15 (2H, m), 3.11-2.81 (2H, m), 1.21-1.13 (3H, m) |
| 116 | *DMSO-d6: 10.35-10.06 (1H, m), 9.23 (2H, s), 8.95 (2H, s), 7.97-7.75 (4H, m), 7.63 (2H, d, J = 8 Hz), 7.48 (2H, d, J = 8 Hz), 6.29-6.02 (1H, m), 4.25-3.70 (3H, m), 3.64-3.22 (3H, m), 2.43 (3H, s), 2.38-2.14 (2H, m) |
| 117 | DMSO-d6: 12.63 (1H, brs), 10.28 (1H, s), 8.78 (1H, brs), 8.51-8.38 (2H, m), 8.05-7.95 (1H, m), 7.64-7.52 (1H, m), 7.20-7.12 (1H, m), 7.08-6.97 (2H, m), 6.89-6.77 (2H, m), 6.20 (1H, brs), 4.27 (1H, brs), 4.01-3.85 (2H, m), 3.64-3.16 (3H, m), 2.80-2.28 (2H, m), 2.21 (3H, s) |
| 118 | CD3OD-d4: 9.21 (1H, s), 8.70 (1H, s), 7.98 (2H, d, J = 8.5 Hz), 7.84 (2H, d, J = 8.5 Hz), 7.57 (1H, t, J = 8.1 Hz), 7.45 (2H, m), 7.28 (1H, d, J = 8.3 Hz), 4.86 (1H, s), 4.85 (1H, s), 4.25 (1H, m), 4.06 (2H, m), 3.71 (1H, m). |
| 119 | DMSO-d6: 10.2 (1H, s), 9.31 (2H, s), 9.08 (2H, s), 8.04 (2H, d, J = 8.5 Hz), 7.85 (2H, d, J = 8.5 Hz), 7.72 (1H, d, J = 8.1 Hz), 7.66 (1H, m), 7.53 (1H, d, J = 8.1 Hz), 6.65 (1H, s), 4.74 (1H, s), 4.69 (1H, s), 4.49 (2H, s), 4.16 (1H, d, J = 11.0 Hz), 3.99-3.90 (2H, m), 3.72 (1H, d, J = 11.0 Hz), 3.09 (3H, s). |
| 120 | DMSO-d6: 9.83 (1H, s), 8.26 (2H, s), 7.83 (2H, d, J = 8.3 Hz), 7.72 (1H, d, J = 8.2 Hz), 7.66 (1H, m), 7.53 (1H, d, J = 9.3 Hz), 7.42 (2H, d, J = 8.3 Hz), 6.43 (1H, d, J = 6.3 Hz), 4.72 (1H, s), 4.65 (1H, s), 4.49 (2H, s), 4.16 (1H, d, J = 10.2 Hz), 3.99-3.90 (4H, m), 3.71 (1H, d, J = 10.2 Hz), 3.09 (3H, s). |
| 121 | Cd3OD-d4: 7.75-7.73 (2H, d, J = 8.6 Hz), 7.51-7.35 (6H, m), 4.80 (2H, s), 4.28 (2H, s), 4.12-4.09 (1H, m), 4.08-4.02 (8H, m), 3.79 (2H, m), 3.65-3.61 (1H, m). |
| 122 | CD3OD-d4: 8.42 (1H, s), 8.36 (2H, d, J = 9.9 Hz), 8.01 (2H, dd, J = 7.8, 13.9 Hz), 7.56-7.51 (3H, m), 7.40 (2H, dd, J = 7.8, 13.9 Hz), 4.86 (1H, s), 4.31 (2H, s), 4.28 (1H, s), 4.09-4.03 (4H, m), 3.83 (2H, m), 3.31 (1H, m). |
| 123 | Cd3OD-d4: 8.15 (1H, s), 7.97 (1H, s), 7.83-7.81 (1H, dd, J = 8.6, 10.7 Hz), 7.64 (2H, s), 7.36 (2H, t, J = 1.1 Hz), 4.81 (2H, s), 4.29 (2H, s), 4.28-4.27 (1H, m), 4.04-4.01 (3H, m), 3.81-3.80 (2H, m). |
| 124 | Cd3OD-d4: 9.2 (1H, s), 8.8 (1H, s), 7.73 (2H, s), 7.72-7.34 (5H, m), 4.81 (2H, s), 4.28 (2H, s), 4.28 (1H, d, J = 3.1 Hz), 4.04-4.01 (3H, m), 3.81-3.6 (4H, m), 2.44 (3H, s). |
| 125 | Cd3OD-d4: 7.62 (1H, s), 7.54-7.47 (3H, m), 7.36 (2H, t, J = 1.0 Hz), 7.18 (1H, d, J = 8.5 Hz), 4.79 (2H, s), 4.32 (2H, s), 4.28 (2H, s), 4.31 (1H, s), 4.28 (1H, s), 4.05-4.04 (3H, m), 3.81 (2H, t, J = 5.2 Hz), 3.70 (1H, d, J = 6.0 Hz), 3.48 (2H, t, J = 6.5 Hz), 3.3 (2H, s), 3.11 (2H, t, J = 6.4 Hz). |
| 126 | DMSO-d6: 10.2 (1H, s), 9.23 (2H, s), 8.88 (2H, s), 8.04 (2H, d, J = 8.4 Hz), 7.81 (2H, d, J = 8.4 Hz), 7.34 (1H, t, J = 7.8 Hz), 7.03 (2H, m), 6.85 (1H, d, 8.2 Hz), 6.52 (1H, s), 4.74-4.66 (4H, m), 4.13 (1H, m), 3.93 (1H, m), 3.85 (1H, m), 3.65 (1H, d, J = 12.6 Hz). |
| 127 | CD3OD-d4: 8.60 (1H, s), 7.70 (2H, d, J = 8.5 Hz), 7.46 (2H, d, J = 8.5 Hz), 7.40 (1H, m), 7.03 (2H, m), 6.93 (1H, d, J = 8.5 Hz), 4.83 (1H, s), 4.81 (1H, s), 4.75 (2H, s), 4.30-4.20 (3H, m), 4.11 (2H, s), 4.09-3.98 (2H, m), 3.65 (1H, m), 1.31 (3H, t, J = 7.4 Hz). |
| 128 | Cd3OD-d4: 8.22 (2H, d, J = 5.5 Hz), 7.77-7.60 (3H, m), 4.58 (2H, s), 4.2-4.1 (1H, m), 3.95-3.94 (1H, m), 3.90-3.85 (1H, m), 3.74-3.71 (1H, m), 3.09 (2H, s), 2.80 (3H, t, 1.1 (2H, m). |

TABLE 3-continued

| EXAMPLE | NMR (ppm) (No mark: 400 MHz, *: 300 MHz) |
|---|---|
| 129 | Cd3OD-d4: 7.66 (1H, d, J = 1.8 Hz), 7.53-7.46 (2H, m), 7.38-7.33 (2H, m), 7.22 (1H, d, J = 8.6 Hz), 7.15 (1H, d, J = 2.0 Hz), 6.1 (1H, s), 4.80 (2H, d, J = 2 Hz), 4.28 (1H, s), 4.24 (1H, d, J = 5.9 Hz), 4.04-4.01 (4H, m), 3.80 (1H, t, J = 3.7 Hz), 3.78-3.68 (1H, m), 2.39 (3H, s). |
| 130 | Cd3OD-d4: 8.1 (1H, m), 7.52-7.22 (8H, m), 4.69 (1H, d, J = 1.9 Hz), 4.63 (1H, d, J = 1.8 Hz), 4.27 (2H, s), 4.11-4.08 (1H, m), 4.04-3.96 (4H, m), 3.80 (3H, t, J = 4.4 Hz), 3.62-3.60 (1H, m), 3.50-3.40 (2H, m), 3.27 (2H, s), 2.81 (2H, t, J = 7.3 Hz). |
| 131 | (CD3OD) 3.46-3.49 (m, 1H), 3.84-3.88 (m, 1H), 3.86 (s, 3H), 3.97-4.03 (m, 1H), 4.18-4.21 (m, 1H), 4.79-4.82 (m, 2H), 7.00 (t, 1H, J = 8 Hz), 7.12 (d, 1H, J = 8 Hz), 7.24 (d, 1H, J = 8 Hz), 7.36 (t, 1H, J = 8 Hz), 7.81 (d, 2H, J = 7 Hz), 7.94 (d, 2H, J = 7 Hz). |
| 132 | (CD3OD) 7.96 (d, J = 8.8 Hz, 2H), 7.81 (d, J = 8.8 Hz, 2H), 7.38-7.46 (m, 2H), 7.22-7.31 (m, 2H), 4.84 (d, J = 3.7 Hz, 2H), 4.21-4.28 (m, 1H), 3.95-4.10 (m, 2H), 3.53-3.63 (m, 1H) |
| 133 | (CD3OD) 7.92 (d, J = 8.8 Hz, 2H), 7.77 (d, J = 8.8 Hz, 2H), 7.35-7.45 (m, 2H), 7.30 (t, J = 7.7 Hz, 2H), 6.74 (t, J = 74.3 Hz, 1H), 4.77 (s, 2H), 4.20 (d, J = 10.6 Hz, 1H), 3.88-4.04 (m, 2H), 3.49 (d, J = 9.9 Hz, 1H) |
| 134 | (DMSO-d6) 3.68-3.71 (m, 1H), 3.80-3.82 (m, 2H), 4.02-4.06 (m, 4H), 4.18-4.22 (m, 1H), 4.29 (s, 2H), 4.82 (d, 1H, J = 2 Hz), 4.87 (d, 1H, J = 2 Hz), 7.33-7.54 (m, 4H), 8.16 (d, 1H, J = 9 Hz), 8.28 (br s, 1H), 8.51 (dd, 1H, J = 9.2 Hz), 9.12 (d, 1H, J = 3 Hz). |
| 135 | (DMSO-d6) 9.20 (br. s., 2H), 8.84-9.05 (m, 2H), 8.03 (d, J = 8.8 Hz, 2H), 7.80 (d, J = 8.8 Hz, 2H), 7.43 (t, J = 8.1 Hz, 1H), 7.24 (s, 1H), 7.09-7.19 (m, 2H), 6.53 (d, J = 6.1 Hz, 1H), 4.69 (s, 1H), 4.65 (br. s, 1H), 4.13 (d, J = 11.6 Hz, 1H), 3.91-4.02 (m, 1H), 3.81-3.91 (m, 1H), 3.75 (t, J = 6.5 Hz, 2H), 3.62 (d, J = 11.7 Hz, 1H), 3.54 (t, J = 7.4 Hz, 2H), 2.42 (quin, J = 6.9 Hz, 2H) |
| 136 | (CD3OD) 7.95 (d, J = 8.6 Hz, 2H), 7.81 (d, J = 8.6 Hz, 2H), 7.26 (dd, J = 8.5, 6.1 Hz, 1H), 6.92 (dd, J = 10.7, 2.5 Hz, 1H), 6.74 (td, J = 8.3, 2.6 Hz, 1H), 4.81 (d, J = 6.8 Hz, 2H), 4.13-4.26 (m, 1H), 3.86-4.06 (m, 2H), 3.88 (s, 3H), 3.46 (d, J = 11.9 Hz, 1H) |
| 137 | (CD3OD) 7.95 (d, J = 8.8 Hz, 2H), 7.79 (d, J = 8.6 Hz, 2H), 7.32 (t, J = 7.0 Hz, 1H), 7.22 (d, J = 7.7 Hz, 1H), 7.11 (d, J = 8.4 Hz, 1H), 6.96 (t, J = 7.3 Hz, 1H), 4.80 (d, J = 1.5 Hz, 1H), 4.77 (s, 1H), 4.65 (dt, J = 12.0, 6.0 Hz, 1H), 4.20 (d, J = 11.4 Hz, 1H), 3.89-4.02 (m, 2H), 3.47 (d, J = 9.5 Hz, 1H), 1.33 (dd, J = 5.9, 2.4 Hz, 6H) |
| 138 | (CD3OD) 7.97 (d, J = 8.8 Hz, 2H), 7.82 (d, J = 8.8 Hz, 2H), 7.27-7.44 (m, 2H), 7.05-7.15 (m, 2H), 4.83 (s, 2H), 4.59-4.65 (m, 2H), 4.15-4.28 (m, 1H), 3.90-4.12 (m, 2H), 3.55 (d, J = 11.7 Hz, 1H) |
| 139 | MeOH-d4: 7.96 (1H, d, J = 13.5 Hz), 7.66 (2H, m), 7.52 (1H, t, J = 8 Hz), 7.47 (1H, m), 7.36 (2H, m), 4.81 (2H, d, J = 11 Hz), 4.29 (2H, br s) 4.23-4.21 (1H, m), 4.06-4.01 (4H, m), 3.81 (2H, m), 3.70-3.68 (1H, m) |
| 140 | MeOH-d4: 7.71 (2H, d, J = 8.5 Hz), 7.52 (1H, t, J = 8 Hz), 7.47 (1H, m), 7.36 (2H, m), 4.80 (2H, d, J = 12 Hz), 4.29 (2H, br s) –4.23-4.20 (1H, m), 4.06-4.01 (4H, m), 3.82-3.80 (2H, m), 3.70-3.68 (1H, m) |
| 141 | MeOH-d4: 7.99-7.95 (3H, m), 7.67-7.63 (3H, m), 7.56 (1H, t, J = 7.5 Hz), ), 4.83 (2H, m), 4.24-4.22 (1H, m), 4.05-4.05 (2H, m), 3.70-3.68 (1H, m) |
| 142 | HCl salt in CD3OD: 8.25 (d, J = 1.1 Hz, 1H), 8.04 (d, J = 8.1 Hz, 1H), 7.90 (dd, J = 2.0, 8.6 Hz, 1H), 7.50 (t, J = 7.9 Hz, 1H), 7.4 (t, J = 1.8 Hz, 1H), 7.39-7.33 (m, 2H), 4.87-4.84 (m, 4H), 4.29 (s, 2H), 4.23-4.21 (m, 1H), 4.06-4.01 (m, 4H), 3.82-3.80 (m, 2H), 3.70 (dd, J = 2.5, 9.1 Hz, 1H) |
| 143 | HCl salt in DMSO-d6: 10.43 (s, 2H), 9.91 (s, 1H), 9.38 (s, 1H), 8.48 (s, 1H), 8.38 (d, J = 7.7 Hz, 1H), 8.12 (s, 1H), 8.08 (d, J = 8.5 Hz, 1H), 7.97 (s, J = 8.1 Hz, 1H), 7.92 (d, J = 7.7 Hz, 1H), 7.81 (t, J = 8.1 Hz, 1H), 4.94 (s, 2H), 4.89 (s, 1H), 4.85 (s, 1H), 4.32-4.28 (m, 1H), 4.13-4.04 (m, 2H), 3.93-3.89 (m, 1H), |
| 144 | HCl salt in CD3OD: 8.2 (s, 1H), 8.06 (d, J = 8.4 Hz, 1H), 7.89-7.86 (m, 1H), 7.63 (d, J = 8.4 Hz, 2H), 7.54 (d, J = 8.1 Hz, 2H), 4.85-4.81 (m, 4H), 4.27-4.21 (m, 1H), 3.63 (t, J = 6.8 Hz, 2H), 3.52 (t, J = 6.4 Hz, 2H), 2.05-1.90 (m, 2H) |
| 145 | HCl salt in DMSO-d6: 10.24 (s, 1H), 10.21 (s, 1H), 9.65 (s, 1H), 9.15 (s, 1H), 8.31 (s, 1H), 8.16 (d, J = 8.8 Hz, 1H), 7.92 (dd, J = 1.8, 8.8 Hz, 1H), 7.48-7.46 (m, 3H), 7.31-7.28 (m, 1H), 4.76 (s, 2H), 4.67 (dd, J = 2.2, 5.1 Hz, 2H), 4.14-4.10 (m, 1H), 3.95-3.84 (m, 2H), 3.69-3.65 (m, 1H), 2.97 (s, 3H), 2.91 (s, 3H) |
| 146 | HCl salt in CD3OD: 8.25 (s, 1H), 8.05 (d, J = 8.5 Hz, 1H), 7.91-7.87 (m, 1H), 7.78-7.56 (m, 1H), 7.61-7.48 (m, 4H), 4.85-4.81 (m, 4H), 4.26-4.19 (m, 1H), 4.07-4.0 (m, 2H), 3.73-3.65 (m, 1H), 3.63-3.57 (m, 1H), 3.50 (t, J = 6.6 Hz, 2H), 2.03-2.18 (m, 4H) |
| 147 | HCl salt in DMSO-d6: 10.25 (s, 1H), 10.28 (s, 1H), 9.58 (s, 1H), 9.12 (s, 1H), 8.31 (s, 1H), 8.13 (d, J = 8.8 Hz, 1H), 7.94 (dd, J = 1.8, 8.8 Hz, 1H), 7.49-7.44 (m, 4H), 6.50 (d, J = 7.0 Hz, 1H), 4.77 (s, 2H), 4.70-4.66 (m, 2H), 4.14-4.11 (m, 1H), 3.96-3.85 (m, 2H), 3.68-3.65 (m, 1H), 2.97 (s, 3H), 2.92 (s, 3H) |
| 148 | HCl salt in DMSO-d6: 9.20-9.29 (m, 2H), 8.98-9.07 (m, 2H), 8.19 (s, 1H), 7.89-8.04 (m, 3H), 7.53-7.68 (m, 2H), 4.56-4.74 (m, 2H), 4.06-4.19 (m, 1H), 3.85-4.02 (m, 2H), 3.60-3.81 (m, 1H). |
| 149 | HCl salt in DMSO-d6: 9.86 (s, 1H), 9.52 (br. s., 2H), 7.94 (s, 1H), 7.66 (d, J = 8.8 Hz, 1H), 7.42-7.52 (m, 2H), 7.28-7.37 (m, 3H), 4.56 (d, J = 14.3 Hz, 2H), 4.47 (d, J = 15.8 Hz, 4H), 4.22 (s, 2H), 4.09-4.18 (m, 1H), 3.83-4.02 (m, 4H), 3.71-3.78 (m, 2H), 3.67 (d, J = 10.6 Hz, 1H) |
| 150 | HCl salt in CD3OD: 7.98-7.95 (2H, m), 7.92-7.89 (2H, m), 7.82-7.79 (2H, m), 7.65 (1H, d, J = 8.8 Hz), 4.84 (s, 2H); 4.25-4.21 (1H, m), 4.10-4.00 (2H, m), 3.75-3.68 (1H, m) |
| 151 | Formate salt in CD3OD: 8.00 (1H, br s), 7.47 (3H, app d, J = 7.7 Hz), 7.31 (3H, app d, J = 7.3 Hz), 7.16 (2H, br s),, 4.35-4.33 (m, 2H), 3.76-3.70 (1H, m), 3.59-3.52 (2H, m), 3.25-3.20 (1H, m) |

TABLE 4

| EXAMPLE | LC/MS m/z [M + 1]+ | RT min | Method/Solvent |
|---|---|---|---|
| 1 | 407 | 2.65 | B |
| 1-1 (LP) | 294 | 3.05 | A |
| 1-1 (MP) | 294 | 3.03 | A |
| 1-2 | 266 | 4.08 | A |
| 1-3 | 607 | 4.47 | A |
| 2 | 383 | 2.33 | B |
| 2-1 | 366 | 3.50 | A |
| 3 | 380 | 3.47 | B |
| 4 | 394 | 3.67 | B |
| 5 | 370 | 2.45 | B |
| 6 | 396 | 2.52 | B |
| 7 | 383 | 2.30 | B |
| 7-1 | 170 | 4.50 | A |
| 7-2 | 335 | 2.82 | B |
| 7-3 | 486 | 4.68 | A |
| 7-4 | 402 | 3.92 | A |
| 7-5 | 366 | 3.50 | A |
| 8 | 397 | 2.48 | B |
| 8-1 | 184 | 4.92 | A |
| 8-2 | 500 | 4.82 | A |
| 8-3 | 416 | 4.12 | A |
| 8-4 | 380 | 3.73 | A |
| 9 | 456 | 1.30 | B |
| 9-1 | 215 | 4.52 | A |
| 9-2 | 531 | 4.55 | A |
| 9-3 | 447 | 3.92 | A |
| 9-4 | 411 | 3.75 | A |
| 9-5 | 381 | 2.95 | A |

TABLE 4-continued

| EXAMPLE | LC/MS m/z [M + 1]+ | RT min | Method/ Solvent |
|---|---|---|---|
| 9-6 | 481 | 3.08 | A |
| 10 | 451 | 2.27 | A |
| 10-1 | 238 | 5.03 | A |
| 10-2 | 554 | 5.02 | A |
| 10-3 | 470 | 4.35 | A |
| 10-4 | 434 | 4.05 | A |
| 11 | 425 | 3.07 | B |
| 11-1 | 212 | 5.40 | A |
| 11-2 | 528 | 5.33 | A |
| 11-3 | 444 | 4.63 | A |
| 11-4 | 408 | 4.30 | A |
| 12 | 399 | 0.93 | B |
| 12-1 | 186 | 2.58 | A |
| 12-2 | 502 | 3.68 | A |
| 12-3 | 418 | 2.97 | A |
| 12-4 | 382 | 2.78 | A |
| 13 | 424 | 0.85 | B |
| 13-1 | 211 | 3.18 | C |
| 13-2 | 527 | 3.40 | A |
| 13-3 | 443 | 2.82 | A |
| 13-4 | 407 | 2.72 | A |
| 14 | 495 | 1.13 | A |
| 14-1 | 282 | 4.98 | A |
| 14-2 | 598 | 4.95 | A |
| 14-3 | 514 | 4.32 | A |
| 14-4 | 478 | 4.07 | A |
| 15 | 449 [M − 1]− | 2.57 | A |
| 15-1 | 238 | 6.52 | C |
| 15-2 | 554 | 6.45 | C |
| 15-3 | 434 | 4.75 | A |
| 16 | 409 [M − 1]− | 1.97 | A |
| 16-1 | 198 | 5.97 | C |
| 16-2 | 514 | 6.05 | C |
| 16-3 | 394 | 4.10 | A |
| 17 | 397 | 1.02 | A |
| 17-1 | 184 | 4.83 | A |
| 17-2 | 500 | 4.87 | A |
| 17-3 | 416 | 4.20 | A |
| 17-4 | 380 | 3.83 | A |
| 18 | 408 | 2.33 | B |
| 18-1 | 493 | 3.60 | A |
| 18-2 | 571 | 4.08 | A |
| 18-3 | 391 | 3.35 | A |
| 19 | 452 | 2.22 | B |
| 19-1 | 239 | 4.87 | C |
| 19-2 | 555 | 3.95 | A |
| 19-3 | 471 | 3.33 | A |
| 19-4 | 435 | 3.55 | A |
| 20 | 425 | 0.80 | B |
| 20-1 | 226 | 2.85 | C |
| 20-2 | 212 | 2.87 | C |
| 20-3 | 528 | 3.32 | A |
| 20-4 | 444 | 2.68 | A |
| 20-5 | 408 | 2.67 | A |
| 21 | 397 | 2.60 | B |
| 21-1 | 500 | 4.77 | A |
| 21-2 | 416 | 4.23 | A |
| 21-3 | 380 | 3.87 | A |
| 22 | 451 | 3.25 | C |
| 22-1 | 434 | 4.20 | A |
| 23 | 445 | 3.38 | C |
| 23-1 | 428 | 4.20 | A |
| 24 | 501 | 4.20 | C |
| 24-1 | 484 | 5.13 | A |
| 25 | 435 | 3.27 | D |
| 25-1 | 418 | 3.05 | A |
| 26A | 426 | 3.02 | D |
| 26-1 | 271 | 5.22 | C |
| 26-2 | 587 | 4.95 | A |
| 26-3 | 503 | 4.25 | A |
| 26-4 | 467 | 3.90 | A |
| 26-5 | 367 | 2.57 | A |
| 26-6 | 451 | 3.15 | A |
| 26B | 426 | 3.02 | D |
| 26-7 | 285 | 4.85 | C |
| 26-8 | 271 | 5.25 | C |
| 26-9 | 487 | 5.48 | D |
| 26-10 | 646 | 6.52 | C |
| 26-11 | 562 | 5.95 | C |
| 26-12 | 526 | 5.47 | C |
| 26-13 | 426 | 3.75 | C |
| 26-14 | 468 | 4.20 | C |
| 27 | 427 | 2.80 | D |
| 27-1 | 410 | 3.78 | C |
| 28A | 462 | 2.97 | D |
| 28-1 | 445 | 3.02 | A |
| 28B | 462 | 2.98 | D |
| 28-2 | 504 | 4.13 | C |
| 29A | 452 | 3.20 | D |
| 29-1 | 435 | 3.03 | A |
| 29B | 452 | 3.23 | C |
| 29-2 | 494 | 4.35 | C |
| 30A | 468 | 2.90 | D |
| 30-1 | 451 | 2.82 | A |
| 30B | 468 | 2.80 | D |
| 30-2 | 510 | 3.93 | C |
| 31 | 454 | 3.05 | D |
| 31-1 | 437 | 3.05 | A |
| 32 | 532 | 3.98 | D |
| 32-1 | 515 | 3.85 | A |
| 33 | 442 | 2.81 | D |
| 34 | 452 | 2.47 | C |
| 34-1 | 239 | 4.17 | C |
| 34-2 | 455 | 4.43 | D |
| 34-3 | 614 | 5.72 | C |
| 34-4 | 530 | 4.87 | C |
| 34-5 | 494 | 4.47 | C |
| 35 | 408 | 2.35 | C |
| 35-1 | 209 | 3.52 | C |
| 35-2 | 195 | 1.32 | C |
| 35-3 | 411 | 4.60 | D |
| 35-4 | 570 | 6.10 | C |
| 35-5 | 486 | 5.03 | C |
| 35-6 | 450 | 4.58 | C |
| 36 | 426 | 1.05 | C |
| 36-1 | 213 | 3.83 | C |
| 36-2 | 429 | 4.10 | D |
| 36-3 | 588 | 5.22 | C |
| 36-4 | 504 | 4.50 | C |
| 36-5 | 468 | 4.23 | C |
| 37 | 424 | 0.73 | C |
| 37-1 | 211 | 3.87 | C |
| 37-2 | 427 | 3.68 | D |
| 37-3 | 586 | 4.88 | C |
| 37-4 | 502 | 4.23 | C |
| 37-5 | 466 | 3.87 | C |
| 38 | 450 | 2.70 | C |
| 38-1 | 213 | 3.58 | C |
| 38-2 | 429 | 4.12 | D |
| 38-3 | 770 | 5.62 | C |
| 38-4 | 686 | 5.23 | C |
| 38-5 | 650 | 5.00 | C |
| 39 | 438 | 3.00 | D |
| 39-1 | 400 [M + Na]+ | 5.93 | C |
| 39-2 | 370 [M + Na]+ | 5.43 | C |
| 39-3 | 780 [M + Na]+ | 5.78 | C |
| 39-4 | 696 [M + Na]+ | 5.68 | C |
| 39-5 | 660 [M + Na]+ | 5.48 | C |
| 39-6 | 438 | 1.75 | C |
| 40 | 440 | 2.13 | C |
| 40-1 | 482 | 4.35 | C |
| 41 | 466 | 2.67 | C |
| 41-1 | 508 | 4.78 | C |
| 42 | 494 | 3.05 | C |
| 42-1 | 536 | 5.47 | C |
| 43 | 384 | 0.25 | C |
| 44 | 384 | 1.02 | D |
| 44-1 | 307 [M + Na]+ | 4.97 | C |
| 44-2 | 271 | 5.45 | C |
| 44-3 | 509 [M + Na]+ | 5.50 | D |

TABLE 4-continued

| EXAMPLE | LC/MS m/z [M + 1]⁺ | RT min | Method/ Solvent |
|---|---|---|---|
| 44-4 | 646 | 5.65 | D |
| 44-5 | 562 | 6.12 | C |
| 44-6 | 526 | 5.82 | C |
| 44-7 | 426 | 3.83 | C |
| 45 | 426 | 2.90 | D |
| 45-1 | 468 | 4.22 | C |
| 46 | 452 | 3.05 | D |
| 46-1 | 494 | 4.33 | C |
| 47 | 427 | 2.70 | D |
| 47-1 | 469 | 3.95 | C |
| 48 | 454 | 2.97 | D |
| 48-1 | 496 | 4.18 | C |
| 49 | 462 | 2.82 | D |
| 49-1 | 504 | 4.22 | C |
| 50 | 442 | 2.70 | D |
| 50-1 | 574 | 5.35 | C |
| 51 | 468 | 2.72 | D |
| 51-1 | 510 | 4.07 | C |
| 52 | 449 | 3.57 | C |
| 52-1 | 506 [M + Na]⁺ | 6.15 | C |
| 52-2 | 422 [M + Na]⁺ | 5.93 | C |
| 52-3 | 364 | 5.68 | C |
| 52-4 | 308 | 4.97 | D |
| 52-5 | 649 | 5.88 | C |
| 53 | 437 | 3.37 | C |
| 53-1 | 659 [M + Na]⁺ | 6.15 | C |
| 53-2 | 437 | 3.38 | C |
| 54 | 461 | 3.20 | C |
| 54-1 | 238 | 5.22 | C |
| 54-2 | 224 | 5.73 | C |
| 54-3 | 518 [M + Na]⁺ | 5.82 | C |
| 54-4 | 434 [M + Na]⁺ | 5.53 | C |
| 54-5 | 398 [M + Na]⁺ | 5.15 | C |
| 54-6 | 342 [M + Na]⁺ | 4.17 | D |
| 54-7 | 661 | 5.62 | C |
| 55 | 477 | 3.32 | C |
| 55-1 | 254 | 5.22 | C |
| 55-2 | 240 | 5.82 | C |
| 55-3 | 534 [M + Na]⁺ | 5.90 | C |
| 55-4 | 450 [M + Na]⁺ | 5.65 | C |
| 55-5 | 414 [M + Na]⁺ | 5.25 | C |
| 55-6 | 336 | 4.37 | D |
| 55-7 | 677 | 5.68 | C |
| 56 | 453 | 2.82 | C |
| 56-1 | 495 | 5.03 | D |
| 57 | 465 | 3.12 | C |
| 57-1 | 687 [M + Na]⁺ | 6.12 | C |
| 57-2 | 465 | 3.08 | C |
| 58 | 471 | 3.03 | C |
| 58-1 | 248 | 5.00 | C |
| 58-2 | 234 | 5.70 | C |
| 58-3 | 528 [M + Na]⁺ | 5.83 | C |
| 58-4 | 422 | 5.53 | C |
| 58-5 | 408 [M + Na]⁺ | 5.15 | C |
| 58-6 | 330 | 4.05 | D |
| 58-7 | 671 | 5.67 | C |
| 59 | 411 | 2.57 | C |
| 59-1 | 188 | 4.07 | C |
| 59-3 | 468 [M + Na]⁺ | 5.47 | C |
| 59-4 | 384 [M + Na]⁺ | 5.15 | C |
| 59-5 | 348 [M + Na]⁺ | 4.55 | C |
| 59-6 | 270 | 2.92 | D |
| 59-7 | 611 | 5.32 | C |
| 60 | 427 | 2.85 | C |
| 60-1 | 204 | 4.82 | C |
| 60-3 | 484 [M + Na]⁺ | 5.73 | C |
| 60-4 | 400 [M + Na]⁺ | 5.47 | C |
| 60-5 | 364 [M + Na]⁺ | 5.07 | C |
| 60-6 | 286 | 3.72 | D |
| 60-7 | 627 | 5.52 | C |
| 61 | 451 | 3.17 | C |
| 61-1 | 228 | 4.77 | C |
| 61-3 | 508 [M + Na]⁺ | 5.99 | C |
| 61-4 | 424 [M + Na]⁺ | 5.60 | C |
| 61-5 | 388 [M + Na]⁺ | 5.22 | C |
| 61-6 | 310 | 4.15 | D |
| 61-7 | 651 | 5.60 | C |
| 62 | 407 | 2.82 | C |
| 62-1 | 464 [M + Na]⁺ | 5.73 | C |
| 62-2 | 380 [M + Na]⁺ | 5.43 | C |
| 62-3 | 344 [M + Na]⁺ | 4.87 | C |
| 62-4 | 266 | 3.65 | D |
| 62-5 | 607 | 5.58 | C |
| 63 | 425 | 2.93 | C |
| 63-1 | 202 | 4.17 | C |
| 63-2 | 188 | 5.62 | C |
| 63-3 | 482 [M + Na]⁺ | 5.78 | C |
| 63-4 | 398 [M + Na]⁺ | 5.47 | C |
| 63-5 | 362 [M + Na]⁺ | 4.88 | C |
| 63-6 | 284 | 3.53 | D |
| 63-7 | 625 | 5.53 | C |
| 64 | 401 | 3.53 | D |
| 64-1 | 443 | 5.02 | C |
| 65 | 439 | 3.25 | C |
| 65-1 | 422 | 5.48 | C |
| 66 | 459 | 3.57 | C |
| 66-1 | 442 | 5.73 | C |
| 66-2 | 475 | 4.98 | C |
| 67 | 443 | 3.35 | C |
| 67-1 | 426 | 5.55 | C |
| 67-2 | 459 | 4.63 | C |
| 68 | 466 | — | — |
| 68-8 | 302 | — | — |
| 68-9 | 405 | — | — |
| 68-10 | 447 | — | — |
| 68-11 | 391 | — | — |
| 68-13 | 550 | — | — |
| 68-14 | 508 | — | — |
| 69 | 506 | — | — |
| 69-1 | 260 | — | — |
| 69-2 | 342 | — | — |
| 69-3 | 389 | — | — |
| 69-5 | 431 | — | — |
| 69-6 | 590 | — | — |
| 69-7 | 548 | — | — |
| 70 | 438 | 1.92 | E |
| 70-1 | 274 | 3.36 | E |
| 70-2 | 321 | 3.08 | E |
| 70-3 | 419 | 3.23 | E |
| 70-4 | 363 | 1.18 | F |
| 70-5 | 522 | 3 | E |
| 70-6 | 480 | 1.59 | E |
| 71 | 425 | 0.97 | E |
| 71-1 | 567 | 2.17 | E |
| 71-2 | 525 | 1.61 | F |
| 72 | 451 | 0.97 | E |
| 72-1 | 593 | 4.2 | E |
| 72-2 | 551 | 2.29 | E |
| 73 | 505 | 2 | E |
| 73-1 | 444 | 5.38 | E |
| 73-2 | 486 | 3.17 | E |
| 73-3 | 430 | 2.46 | E |
| 73-4 | 589 | 5.11 | E |
| 73-5 | 547 | 1.81 | F |
| 74 | 518 | 2.31 | E |
| 74-1 | 560 | 4.57 | E |
| 75 | 413 | 2.7 | E |
| 75-1 | 296 | 2.96 | E |
| 75-2 | 396 | 3.52 | E |
| 76 | 437 | 2.4 | E |
| 76-1 | 637 | 5.62 | E |
| 77 | 516.3 | — | — |
| 78 | 447.2 | — | — |
| 79 | 466.2 | — | — |
| 80 | 516.3 | — | — |
| 81 | 514.3 | — | — |
| 82 | 466.3 | — | — |
| 83 | 405.2 | — | — |
| 84 | 559.3 | — | — |
| 85 | 530.3 | — | — |

TABLE 4-continued

| EXAMPLE | LC/MS m/z [M + 1]+ | RT min | Method/Solvent |
|---|---|---|---|
| 86 | 502.3 | — | — |
| 87 | 445.2 | — | — |
| 88 | 482.3 | — | — |
| 89 | 528.3 | — | — |
| 90 | 482.3 | — | — |
| 91 | 387.2 | — | — |
| 92 | 518.3 | — | — |
| 93-1 | 398 (M + Na) | 2.05 | G |
| 93-2 | 440 (M + Na) | 2.12 | H |
| 93-3 | 362 | 1.77 | G |
| 93-4 | 480 | 2.11 | G |
| 93 | 451 | 1.74 | G |
| 94 | 450 | 1.61 | G |
| 95 | 455 | 1.57 | G |
| 96 | 437.2 | | |
| 97 | 437.2 | | |
| 98-1 | 192.2 | 1.47 | J |
| 98-2 | 191.2 | 0.89 | I |
| 98-3 | 291.2 | 4.33 | K |
| 98-4 | 261.1 | 1.47 | I |
| 98 | 462.2 | 1.62 | I |
| 99-2 | 484 (M + Na)+ | 2.03 | I |
| 99 | 424.2 | 2.95 | K |
| 100 | 398 | 0.6 | K |
| 101 | 438.2 | 3.45 | K |
| 102 | 413 | 3.02 | D |
| 102-1 | 442 | 5.70 | C |
| 102-2 | 386 | 4.97 | D |
| 102-3 | 545 | 5.37 | D |
| 103 | 438 | 4.00 | D |
| 103-1 | 399 [M + Na]+ | 5.43 | C |
| 103-2 | 321 | 4.42 | D |
| 103-3 | 480 | 5.08 | D |
| 104 | 461 | 2.72 | D |
| 104-1 | 400 | 4.05 | C |
| 104-2 | 344 | 1.93 | D |
| 104-3 | 503 | 3.97 | D |
| 105 | 523 | 2.80 | C |
| 105-1 | 456 [M + Na]+ | 5.20 | C |
| 105-2 | 484 [M + Na]+ | 4.88 | C |
| 105-3 | 406 | 3.88 | D |
| 105-4 | 565 | 5.03 | C |
| 106 | 489 | 3.07 | C |
| 106-1 | 378 | 4.20 | D |
| 106-2 | 537 | 5.63 | C |
| 106-3 | 531 | 5.47 | C |
| 107 | 435 | 3.25 | D |
| 107-1 | 456 [M + Na]+ | 5.15 | C |
| 107-2 | 474 | 5.40 | C |
| 107-3 | 318 | 3.30 | D |
| 107-4 | 477 | 4.43 | D |
| 108 | 405 | 2.15 | A |
| 108-1 | 292 | 3.42 | A |
| 108-2 | 264 | 2.90 | A |
| 108-3 | 605 | 4.78 | A |
| 109 | 448 | 2.48 | B |
| 109-1 | 427 | 4.27 | A |
| 109-2 | 293 | 0.73 | A |
| | | 1.40 | |
| 109-3 | 357 [M + Na]+ | 2.78 | A |
| 109-4 | 329 [M + Na]+ | 2.88 | A |
| | | 3.25 | |
| 109-5 | 648 | 4.25 | A |
| 110 | 434 | 2.47 | B |
| 110-1 | 321 | 2.78 | A |
| 110-2 | 315 [M + Na]+ | 3.08 | A |
| | | 3.47 | |
| 110-3 | 634 | 4.23 | A |
| 111 | 510 | 2.37 | A |
| 111-1 | 397 | 4.83 | D |
| 111-2 | 369 | 4.32 | A |
| 111-3 | 710 | 4.72 | A |
| 112 | 399 | 2.88 | C |
| 112-1 | 310 | 4.55 | C |
| | | 4.65 | |
| 112-2 | 282 | 4.03 | D |
| | | 4.17 | |
| 112-3 | 441 | 4.90 | D |
| | | 5.03 | |
| 113 | 431 | 3.20 | D |
| | | 3.35 | |
| 113-1 | 473 | 4.73 | C |
| 114 | 397 | 3.80 | D |
| 114-1 | 422 [M + Na]+ | 5.35 | D |
| 114-2 | 559 | 5.72 | D |
| 114-3 | 475 | 5.25 | D |
| 114-4 | 439 | 4.88 | D |
| 115 | 397 | 3.45 | D |
| 115-1 | 233 | 0.70 | C |
| | | 0.97 | |
| 115-2 | 280 | 2.40 | D |
| | | 2.67 | |
| 115-3 | 190 | 0.28 | D |
| 115-4 | 308 | 4.33 | C |
| 115-5 | 280 | 3.65 | D |
| 115-6 | 439 | 5.07 | C |
| 116 | 433 | 3.73 | D |
| 116-1 | 344 | 4.55 | C |
| 116-2 | 316 | 4.02 | D |
| 116-3 | 475 | 5.3 | C |
| 117 | 393 | 2.13 | A |
| 117-1 | 280 | 3.98 | A |
| 117-2 | 252 | 2 | B |
| 117-3 | 593 | 5.17 | A |
| 118 | 453 | 2.46 | A |
| 118-1 | 392 | 4.86 | A |
| 118-2 | 434 | 1.95 | B |
| 118-3 | 378 | 1.64 | B |
| 118-4 | 537 | 1.76 | B |
| 118-5 | 495 | 1.68 | B |
| 119 | 438 | 1.51 | A |
| 119-1 | 274 | 1.65 | B |
| 119-2 | 377 | 1.53 | B |
| 119-3 | 419 | 1.65 | B |
| 119-4 | 363 | 1.17 | B |
| 119-5 | 522 | 1.66 | B |
| 119-6 | 480 | 1.6 | B |
| 120 | 408 | 1.8 | A |
| 120-1 | 567 | 3.26 | A |
| 120-2 | 425 | 1.61 | B |
| 121 | 455 | 1.66 | A |
| 121-1 | 264 | 3.33 | A |
| 121-2 | 304 | 3.97 | A |
| 121-3 | 407 | 1.5 | B |
| 121-4 | 449 | 1.65 | B |
| 121-5 | 393 | 1.13 | B |
| 121-6 | 597 | 3.4 | A |
| 121-7 | 555 | 3.17 | A |
| 122 | 492 | 1.28 | B |
| 122-1 | 734 | 1.79 | B |
| 122-2 | 692 | 1.72 | B |
| 123 | 544 | 1.85 | A |
| 123-1 | 186 | 0.98 | B |
| 123-2 | 212 | 1.15 | B |
| 123-3 | 586 | 3.36 | A |
| 123-4 | 544 | 2.65 | A |
| 124 | 482 | 1.59 | A |
| 124-1 | 196 | 1.48 | A |
| 124-2 | 222 | 1.51 | B |
| 124-3 | 192 | 0.62 | B |
| 124-4 | 566 | 1.48 | B |
| 124-5 | 544 | 1.41 | B |
| 125 | 481 | 1.56 | A |
| 125-1 | 623 | 3.63 | A |
| 125-2 | 581 | 1.72 | B |
| 126 | 443 | 1.85 | A |
| 126-1 | 410 | 1.69 | B |
| 126-2 | 452 | 1.82 | B |
| 126-3 | 396 | 1.53 | B |
| 126-4 | 555 | 1.63 | B |

TABLE 4-continued

| EXAMPLE | LC/MS m/z [M + 1]+ | RT min | Method/Solvent |
|---|---|---|---|
| 126-5 | 513 | 1.56 | B |
| 127 | 458 | 1.37 | B |
| 127-1 | 600 | 1.8 | B |
| 127-2 | 558 | 1.76 | B |
| 128 | 468 | 1.16 | A |
| 128-1 | 274 | 3.36 | A |
| 128-2 | 321 | 3.08 | A |
| 128-3 | 419 | 3.23 | A |
| 128-4 | 363 | 1.18 | B |
| 128-5 | 491 | 1.82 | B |
| 128-6 | 449 | 1.58 | B |
| 129 | 479 | 2.71 | A |
| 129-1 | 521 | 2.97 | A |
| 130 | 488 | 3.06 | A |
| 130-1 | 530 | 3.3 | A |
| 131 | 399.2 | — | — |
| 132 | 387.2 | — | — |
| 133 | 435.2 | — | — |
| 134 | 469.2 | — | — |
| 135 | 488.2 | — | — |
| 136 | 417.2 | — | — |
| 137 | 427.2 | — | — |
| 138 | 442.2 | — | — |
| 139-2 | 196 | 1.02 | A |
| 139-3 | 570 | 1.542 | A |
| 140-2 | 214 | 1.125 | A |
| 140-3 | 605 | 1.965 | A |
| 139 | 486 | 1.2 | A |
| 140 | 504 | 1.183 | A |
| 141 | 431 | 1.198 | A |
| 142-2 | 744.2 (MNa+) | — | — |
| 142-3 | 702.2 (MNa+) | — | — |
| 142 | 480.3 | — | — |
| 143 | 406.2 | — | — |
| 144-1 | 778.6 (MNa+) | — | — |
| 144-2 | 688.6 (MNa+) | — | — |
| 144-3 | 742 (MNa+) | — | — |
| 144 | 478.2 | — | — |
| 145 | 451.8 | — | — |
| 146 | 478.2 | — | — |
| 147 | 452.2 | — | — |
| 148-1 | 479 | — | — |
| 148 | 437.2 | — | — |
| 149 | 467.3 | — | — |
| 152 | 530.3 | — | — |
| 153 | 440.2 | — | — |
| 154 | 476.3 | — | — |
| 155 | 440.2 | — | — |
| 156 | 500.3 | — | — |
| 157 | 446.2 | — | — |
| 158 | 446.2 | — | — |
| 159 | 458.3 | — | — |
| 160 | 402.2 | — | — |
| 161 | 402.2 | — | — |
| 162 | 484.3 | — | — |
| 163 | 454.2 | — | — |
| 164 | 496.3 | — | — |
| 165 | 480.3 | — | — |
| 166 | 484.3 | — | — |
| 167 | 500.3 | — | — |
| 168 | 458.3 | — | — |
| 169 | 454.2 | — | — |
| 170 | 480.3 | — | — |
| 171 | 452.2 | — | — |
| 172 | 494.3 | — | — |
| 173 | 387.2 | — | — |
| 174 | 423.2 | — | — |
| 175 | 405.2 | — | — |
| 176 | 406.2 | — | — |
| 177 | 406.2 | — | — |
| 178 | 413.2 | — | — |
| 179 | 484.3 | — | — |
| 180 | 413.2 | — | — |
| 181 | 427.2 | — | — |
| 182 | 427.2 | — | — |
| 183 | 431.2 | — | — |
| 184 | 498.3 | — | — |
| 185 | 427.2 | — | — |
| 186 | 431.2 | — | — |

UTILITY

The invention also relates to medicaments which contain an efficacious amount of at least one compound of the Formula (I) and/or of a pharmaceutically acceptable salt of the compound of the Formula (I) and/or an optionally stereoisomeric form of the compound of the Formula (I), together with a pharmaceutically suitable and pharmaceutically acceptable vehicle, additive and/or other active substances and auxiliaries.

On account of their pharmacological properties, the compounds according to the invention are suitable, for example, for the prophylaxis, secondary prevention and therapy of all those diseases which are treatable by inhibition of blood clotting factor IXa. Thus, the compounds according to the invention are suitable as inhibitors both for prophylactic and for therapeutic administration to humans. They are suitable both for acute treatment and for long-term therapy. The compounds of the Formula (I) can be employed in patients who are suffering from disorders of well-being or diseases which accompany thromboses, embolisms, hypercoagulability or fibrotic changes.

These include myocardial infarct, angina pectoris and all other forms of acute coronary syndrome, stroke, peripheral vascular diseases, deep vein thrombosis, pulmonary embolism, embolic or thrombotic events caused by cardiac arrhythmias, cardiovascular events such as restenosis after revascularization, angioplasty and similar interventions such as stent implantations and bypass operations. Furthermore, the compounds of the Formula (I) can be employed in all interventions which lead to contact of the blood with foreign surfaces, as in dialysis patients and patients with indwelling catheters. Compounds of the Formula (I) can also be employed in order to reduce the risk of thrombosis after surgical interventions such as in knee and hip joint operations.

Compounds of the Formula (I) are suitable for the treatment of patients with disseminated intravascular coagulation, sepsis and other intravascular events which accompany inflammation. Furthermore, compounds of the Formula (I) are suitable for the prophylaxis and treatment of patients with atherosclerosis, diabetes and the metabolic syndrome and their sequelae. Disorders of the hemostatic system (for example fibrin deposits) have been implicated in mechanisms which lead to tumor growth and tumor metastasis, and in the inflammatory and degenerative joint diseases such as rheumatoid arthritis and arthrosis. Compounds of the Formula (I) are suitable for the retardation or prevention of such processes.

Further indications for the use of the compounds of the Formula (I) are fibrotic changes of the lungs such as chronic obstructive pulmonary disease, adult respiratory distress syndrome (ARDS) and of the eye, such as fibrin deposits after eye operations. Compounds of the Formula (I) are also suitable for the prevention and/or treatment of scar formation.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

Preferably, the pharmaceutical preparations are prepared and administered in dose units, where each unit contains as active constituent a certain dose of the compound of the Formula (I) according to the invention. In the case of solid dose units such as tablets, capsules, coated tablets or suppositories, this dose can be approximately 1000 mg, but preferably approximately 50 to 300 mg and in the case of injection solutions in ampoule form approximately 300 mg, but preferably approximately 10 to 100 mg.

For the treatment of an adult patient weighing approximately 70 kg, depending on the efficacy of the compound according to Formula (I), daily doses of approximately 2 mg to 1000 mg of active substance, preferably approximately 50 mg to 500 mg, are indicated. Under certain circumstances, however, higher or lower daily doses may also be appropriate. The daily dose can be administered both by single administration in the form of an individual dose unit or else of a number of smaller dose units and by multiple administration of subdivided doses at certain intervals.

Compounds of the Formula (I) can be administered both as a monotherapy and in combination or together with all antithrombotics (anticoagulants and platelet aggregation inhibitors), thrombolytics (plasminogen activators of any type), other profibrinolytically active substances, hypotensives, blood sugar regulators, lipid-lowering agents and antiarrhythmics.

The inhibitatory effectiveness of compounds of the present invention to the coagulation factors XIa, VIIa, IXa, Xa, plasma kallikrein or thrombin, can be determined using a relevant purified serine protease, respectively, and an appropriate synthetic substrate.

PHARMACOLOGICAL EXAMPLES

Determination of Inhibitory Activity Against Factor IXa

Inhibitory activity against factor IXa was tested using the substrate SPECTROFLUOR FIXa (american diagnostica inc.; 500 West Avenue, Stamford, Conn. 06902 USA; Pr. No. 299F) and human factor IXa (american diagnostica inc.; Pr. No. 449b). Test substances dissolved in buffer A (50 mM α,α,α-tris(hydroxymethyl)methylamine (Tris), 100 mM NaCl, 5 mM $CaCl_2$, 15% (v/v) ethylene glycol, pH 8.0) were mixed with factor IXa (2.0 µg/ml final concentration). The enzyme reaction was started by addition of SPECTROFLUOR FIXa (100 µM final concentration). After incubation for 60 minutes at room temperature, the reaction was stopped by the addition of 20% (v/v) acetic acid solution, and then measured the fluorescence value (Excitation Wavelength:355 nm, Emission Wavelength; 460 nm) in a microtiter plate reader (ARVO 1420 Multilabel Counter; PerkinElmer).

The $IC_{50}$ was calculated from a dilution series of the test substance with the aid of the software, Symix Assay Explorer (Symyx Technologies, Inc.).

Table 5 shows the results.

TABLE 5

| Compound from Example | Factor IXa enzyme assay $IC_{50}$ [micro M] | Compound from Example | Factor IXa enzyme assay $IC_{50}$ [micro M] |
|---|---|---|---|
| 1 | 0.04 | 2 | 0.03 |
| 15 | 0.02 | 21 | 0.13 |
| 50 | 0.02 | 62 | 0.02 |
| 67 | 0.06 | 105 | 0.01 |
| 109 | 0.06 | 114 | 0.03 |

In one embodiment, the compounds of the present invention were selective factor IXa inhibitors, i.e., selective for factor IXa over other coagulation factors, such as factor Xa.

Determination of Inhibitory Activity Against Factor Xa

This measuring was performed as well as Factor IXa method excluding the following conditions. As substrate and enzyme, SPECTROFLUOR FXa (american diagnostica inc.; Pr. No. 222F, 100 µM final concentration) and human factor Xa (american diagnostica inc.; Pr. No. 526, 44 ng/ml final concentration) were used respectively. Test substances dissolved in buffer B (20 mM Tris, 200 mM NaCl, 2.5 mM $CaCl_2$, pH 8.0).

Selectivity Calculation

Selectivity for Factor IXa activity over Factor Xa activity can be determined by the following calculation.: (IC50 Factor Xa)/(IC50 Factor IXa). Similar calculations can be made for selectivity of compounds for Factor IXa compared to other coagulation factors.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

A number of references have been cited, the entire disclosures of which have been incorporated herein in their entirety.

The compounds of the present invention may also be useful as inhibitors of additional serine protease, notably human thrombin, human plasma kallikrein and human plasmin. Because of their inhibitory action, these compounds are indicated for use in the prevention or treatment of physiological reactions, as it were "Conditions" including thromboembolic disorder (arterial cardiovascular thromboembolic disorders, venous cardiovascular thromboembolic disorders, thromboembolic disorders in the chambers of the heart, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis), blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents anti-platelet or platelet inhibitory agents, anti-inflammatory agents, thrombin inhibitors, thrombolytic or fibrinolytic agents, thrombin receptor (PAR-1) antagonist, a factor VIIa inhibitor, factor VIIIa inhibitor, a factor IXa inhibitor different from the compound of claim 1, a factor Xa inhibitor, a factor XIa inhibitor, TAFI, and fibrinogen inhibitors.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds in preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANO), aprotinin, synthetic pentasaccharide, direct acting thrombin inhibitors including hirudin and argatroban, as well as other factor VIIa inhibitor, VIIIa inhibitor, IXa inhibitor, Xa inhibitor, XIa inhibitor, thrombin inhibitor, fibrinogen inhibitors, TAFI, and known in the art. Factor IXa inhibitors different from the compounds of Formula (I) include synthetic active-site blocked competitive inhibitors, oral inhibitors and RNA aptamers. These are described in the previously cited Howard et al. reference (Howard, E L, Becker K C, Rusconi, C P, Becker R C. Factor IXa Inhibitors as Novel Anticoagulents. *Arterioscler Thromb Vasc Biol.* 2007; 27: 722-727.).

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferable antagonists of the purinergic receptors P2Y1 and P2Y12 with P2Y12 being even more preferred. Preferred P2Y12 receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-I and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptiders include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term "thrombin receptor antagonists", also known as protease activated receptor (PAR) antagonists or PAR-1 antagonists, are useful in the treatment of thrombotic, inflammatory, atherosclerotic and fibroproliferative disorders, as well as other disorders in which thrombin and its receptor play a pathological role.

Thrombin receptor antagonist peptides have been identified based on structure-activity studies involving substitutions of amino acids on thrombin receptors. In Bernatowicz et al, *J Med. Chem.*, vol. 39, pp. 4879-4887 (1996), tetra- and pentapeptides are disclosed as being potent thrombin receptor antagonists, for example N-trans-cinnamoyl-p-fluoroPhe-p-guanidinoPhe-Leu-Arg-NH2 and N-trans-cinnamoyl-p-fluoroPhe-p-guanidinoPhe-Leu-Arg-Arg-NH2. Peptide thrombin receptor antagonists are also disclosed in WO 94/03479, published Feb. 17, 1994.

Substituted tricyclic thrombin receptor antagonists are disclosed in U.S. Pat. Nos. 6,063,847, 6,326,380 and WO 01/96330 and 10/271,715.

Other thrombin receptor antagonists include those disclosed in U.S. Pat. Nos. 7,304,078; 7,235,567; 7,037,920; 6,645,987; and EP Patent Nos. EP1495018 and EP1294714.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complexes, including pharmaceutically acceptable salts or prodrugs thereof. The term anistreplase, as used herein, refers to anisoylated plasminogen streptokinase activator complexes, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrhythmic agents for use in combination with the present compounds include: Class I agents (such as propafenone); Class II agents (such as carvedilol and propranolol); Class III agents (such as sotalol, dofetilide, aminodarone, azimilide and ibutilide); Class IV agents (such as ditiazem and verapamil); K+ cannel openers such as IAch inhibitors, and IKur inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil nifedipine, amlodipine and mybefradil); diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamterene, amiloride, spironolactone); rennin inhibitors; angiotensin-converting enzyme (ACE) inhibitors (e.g., captopril, Lisinopril, fosinopril, enalapril, ceranopril, cilazopril, delapril, pentopril, quinapril, ramipril, Lisinopril); angiotensin-II-receptor antagonists (e.g., irbestatin, Losartan, valsartan); ET receptor antagonists (e.g., sitaxsentan, atrsentan and compounds disclosed in U.S. Pat. Nos. 5,612, 359 and 6,043,265); Dual ET/All antagonist (e.g., compounds disclosed in WO 00/01389); neutral endopeptidase (NEP) inhibitors; vasopepsidase inhibitors (dual CCE/NEP inhibitors, e.g., omapatrilat, gemopatrilat, nitrates); and β-blockers (e.g., propranolol, nadolol, or carvedilol).

Examples of suitable cardiac glycosides for use in combination with compounds of the present invention include digitalis and ouabain.

Examples of suitable mineralocorticoid receptor antagonists for use in combination with the compounds of the present invention include spironolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atrbastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/ glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagons-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; piroxicam; naproxen; celecoxib; and/or rofecoxib.

Examples of suitable anti-osteoporosis agents for use in combination with the compounds of the present invention include alendronate and raloxifene. Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitor (such as those disclosed in WO00/ 59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporine A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

What is claimed is:

1. A compound of the Formula (I)

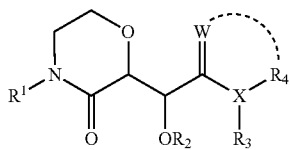

or a pharmaceutically acceptable salt thereof;
wherein:
R1 is selected from the group consisting of:
1) —($C_6$-$C_{14}$)-aryl, which is unsubstituted or substituted independently with one to four Y;
2) -(three- to fifteen-membered heterocyclic ring), which is unsubstituted or substituted independently with one to four Y;
3) —($C_6$-$C_{14}$)-aryl-U—($C_6$-$C_{14}$)-aryl, wherein each of said —($C_6$-$C_{14}$)-aryl- independently is unsubstituted or substituted independently with one to four Y;
4) —($C_6$-$C_{14}$)-aryl-U—($C_3$-$C_{12}$)-cycloalkyl, wherein said —($C_6$-$C_{14}$)-aryl and —($C_3$-$C_{12}$)-cycloalkyl independently are unsubstituted or substituted independently with one to four Y;
5) —($C_6$-$C_{14}$)-aryl-U-(three- to fifteen-membered heterocyclic ring), wherein said —($C_6$-$C_{14}$)-aryl and said (three- to fifteen-membered heterocyclic ring) are independently unsubstituted or substituted independently with one to four Y;
6) —(three- to fifteen-membered heterocyclic ring)-U-($C_6$-$C_{14}$)-aryl, wherein said —($C_6$-$C_{14}$)-aryl and said (three- to fifteen-membered heterocyclic ring) are independently unsubstituted or substituted independently with one to four Y;
7) —(three- to fifteen-membered heterocyclic ring)-U-(three- to fifteen-membered heterocyclic ring), wherein each of said -(three- to fifteen-membered heterocyclic ring)- is independently unsubstituted or substituted independently with one to four Y;
8) —(three- to fifteen-membered heterocyclic ring)-U-($C_3$-$C_{12}$)-cycloalkyl, wherein said —($C_3$-$C_{12}$)-cycloalkyl, and said -(three- to fifteen-membered heterocyclic ring)- are independently unsubstituted or substituted independently with one to four Y;
9) —V—($C_6$-$C_{14}$)-aryl, which is unsubstituted or substituted independently with one to four Y; and
10) —V-(three- to fifteen-membered heterocyclic ring), which is unsubstituted or substituted independently with one to four Y;
R2 is selected from the group consisting of hydrogen atom,
R3 is absent, or selected from the group consisting of hydrogen atom
R4 is selected from the group consisting of:
1) —($C_6$-$C_{14}$)-aryl-Z, wherein said Z is a basic nitrogen-containing group and wherein said —($C_6$-$C_{14}$)-aryl is unsubstituted or substituted independently with one to four Y;
2) —($C_3$-$C_{12}$)-cycloalkyl-Z, wherein said Z is a basic nitrogen-containing group and wherein said —($C_3$-$C_{12}$)-cycloalkyl is unsubstituted or substituted independently with one to four Y;
3) —(three- to fifteen-membered heterocyclic ring)-Z, wherein said Z is a basic nitrogen-containing group and wherein said (three- to fifteen-membered heterocyclic ring) is unsubstituted or additionally substituted independently with one to four Y;
4) —(three- to fifteen-membered heterocyclic ring)-U-(three- to fifteen-membered heterocyclic ring) -Z, wherein said Z is a basic nitrogen-containing group and wherein each of said (three- to fifteen-membered heterocyclic ring) is independently unsubstituted or additionally substituted independently with one to four Y;
5) —($C_6$-$C_{14}$)-aryl, which is unsubstituted or substituted independently with one to four Y;
6) —($C_3$-$C_{12}$)-cycloalkyl, which is unsubstituted or substituted independently with one to four Y;
7) —(three- to fifteen-membered heterocyclic ring), which is unsubstituted or substituted independently with one to four Y;
8) -(three- to fifteen-membered heterocyclic ring)-U-(three- to fifteen-membered heterocyclic ring), wherein each of said (three- to fifteen-membered heterocyclic ring) is independently unsubstituted or substituted independently with one to four Y;
each V independently is selected from the group consisting of —$SO_2$—, —C(O)—, —C(O)—NH— and —$SO_2$—NH—,
wherein the carbon atom of said —C(O)—NH— or the sulfur atom of said —$SO_2$—NH— is connected to a nitrogen atom of the morpholinone ring,
and wherein said —($C_1$-$C_4$)-alkylene is unsubstituted or substituted independently with one to four T,
or wherein geminal hydrogens in said —($C_1$-$C_4$)-alkylene can be replaced by a ($C_3$-$C_8$)-cycloalkyl to form a spiro cyclic ring;
each T independently is selected from the group consisting of:
1) halogen;
2) —($C_1$-$C_6$)-alkyl, which is unsubstituted or substituted independently with one to four substituents selected from the group consisting of OH, —O—($C_1$-$C_4$)-alkyl, —($C_1$-$C_3$)-haloalkyl, —O—($C_1$-$C_3$)-haloalkyl, —N—C(O)—OH and —N—C(O)—$C_1$-$C_4$)-alkyl;
3) —($C_1$-$C_3$)-haloalkyl;
4) —($C_3$-$C_8$)-cycloalkyl;
5) —OH;
6) —O—($C_1$-$C_4$)-alkyl, which is unsubstituted or mono substituted with OH, —O—($C_1$-$C_4$)-alkyl, —($C_1$-$C_3$)-haloalkyl, —O—($C_1$-$C_3$)-haloalkyl, —N—C(O)—OH or —N—C(O)—($C_1$-$C_4$)-alkyl;
7) —O—($C_1$-$C_3$)-haloalkyl;
8) —$NO_2$;
9) —CN;
10) —N(R7)(R8);
11) —C(O)—N(R7)(R8);
12) —N(R8)-C(O)—R7;
13) —N(R8)-$SO_2$—R7;
14) —$SO_2$—($C_1$-$C_4$)-alkyl;
15) —$SO_2$—N(R7)(R8);
16) —$SO_2$—($C_1$-$C_3$)-haloalkyl;
17) —S—($C_1$-$C_4$)-alkyl;
18) —S—($C_1$-$C_3$)-haloalkyl;
19) —($C_1$-$C_6$)-alkyl-N(R7)(R8);
20) —NH—C(O)—N(R7)(R8);
21) =O (oxo); and
22) —C(O)OR7;
23) —C(O)OR7;
24) —N—C(O)—OR7 wherein each of R7 and R8 independently is selected from the group consisting of a hydrogen atom, —(C₃-C₈)-cycloalkyl, halogen and —(C₁-C₆)-alkyl, wherein said —(C₁-C₆)-alkyl is optionally substituted with at least one substituent selected from the group consisting of OH, —O—(C₁-C₄)-alkyl, —(C₁-C₃)-fluoroalky, and —O—(C₁-C₃)-haloalkyl;

W is selected from the group consisting of oxygen atom,
X is selected from the group consisting of nitrogen atom
Y is selected from the group consisting of:
  1) halogen;
  2) —(C₁-C₆)-alkyl;
  3) —(C₁-C₃)-haloalkyl;
  4) —(C₃-C₈)-cycloalkyl;
  5) —OH;
  6) —O—(C₁-C₃)-haloalkyl;
  7) —NO₂;
  8) —CN;
  9) —N(R7)(R8);
  10) —C(O)—N(R7)(R8);
  11) —N(R8)-C(O)—R7;
  12) —N(R8)-SO₂—R7;
  13) —SO₂—(C₁-C₄)-alkyl;
  14) —SO₂—N(R7)(R8);
  15) —SO₂—(C₁-C₃)-haloalkyl;
  16) —S—(C₁-C₄)-alkyl;
  17) —S—(C₁-C₃)-haloalkyl;
  18) —(C₁-C₆)-alkyl-N(R7)(R8);
  19) —N(R8)—C(O)—N(R7)(R8);
  20) =O (oxo);
  21) —SF₅;
  22) —C(O)OR7;
  23) —N=C(O)—OR7
  24) —N(R8)—C(O)—(C₁-C₄)-alkyl-O—(C₁-C₄)-alkyl-(C₆-C₁₄)-aryl, wherein said —(C₆-C₁₄)-aryl is unsubstituted or substituted independently with one to four Y selected from (1) to (24) as set forth above;
  25) —N(R8)—C(O)—(C₁-C₄)-alkyl-O—(C₁-C₄)-alkyl-(three- to fifteen-membered heterocyclic ring), wherein said -(three- to fifteen-membered heterocyclic ring) is unsubstituted or substituted independently with one to four Y selected from (1) to (24) as set forth above;

wherein said —(C₁-C₄)-alkyl part or —(C₁-C₆)-alkyl part of 2), 6), 13), 16), 18), 24) or 25) of said Y is unsubstituted or substituted independently with one to four T;

wherein each of R7 and R8 of 9), 10), 11), 12), 14), 18), 19), 22), 23), 24) or 25) of said Y independently is selected from the group consisting of hydrogen atom, —(C₃-C₈)-cycloalkyl, and —(C₁-C₆)-alkyl, wherein said —(C₁-C₆)-alkyl is optionally substituted with OH, —O—(C₁-C₄)-alkyl, —(C₁-C₃)-fluoroalkyl, —O—(C₁-C₃)-haloalkyl, —C(O)OH, or C(O)O—(C₁-C₆)alkyl;

the dotted linkage between W and R4 of the substructure (III)

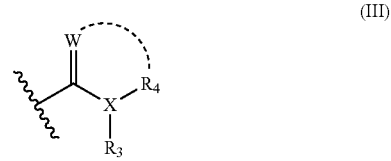

(III)

in Formula (I) is
  1) absent.

2. A compound of claim 1 or a pharmaceutically acceptable salt thereof, wherein substructure (III)

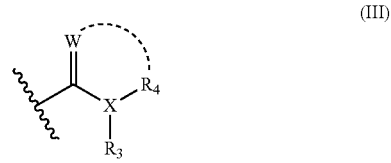

(III)

in Formula (I) is

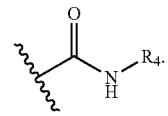

3. A compound of claim 1 or a pharmaceutically acceptable salt thereof, wherein:
  R1 is selected from the group consisting of:
  1) —(C₆-C₁₄)-aryl, which is unsubstituted or substituted independently with one to four Y;
  2) -(three- to fifteen-membered heterocyclic ring), which is unsubstituted or substituted independently with one to four Y;
  3) —(C₆-C₁₄)-aryl-U—(C₆-C₁₄)-aryl, wherein each of said —(C₆-C₁₄)-aryl independently is unsubstituted or substituted independently with one to four Y;
  5) —(C₆-C₁₄)-aryl-U-(three- to fifteen-membered heterocyclic ring), in which said —(C₆-C₁₄)-aryl and said (three- to fifteen-membered heterocyclic ring) are independently unsubstituted or substituted independently with one to four Y; and
  9) -V—(C₆-C₁₄)-aryl, wherein said —V—(C₆-C₁₄)-aryl is unsubstituted or substituted independently with one to four Y.

4. A compound of claim 1 or a pharmaceutically acceptable salt thereof, wherein R1 is (C₆-C₁₄)-aryl, which is unsubstituted or substituted independently with one to four Y.

5. A compound of claim 1 or a pharmaceutically acceptable salt thereof wherein R1 is a phenyl group, which is unsubstituted or substituted independently with one to four Y.

6. A compound of claim 1 wherein said three- to fifteen-membered heterocyclic ring of R1 is represented by the Formula (a)

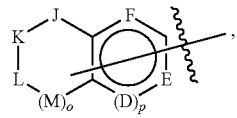

Formula (a)

wherein Formula (a) is unsubstituted or substituted independently with one to four Y; and wherein:

o and p are independently selected from 0 or 1;

J, K, L and M are independently selected from the group consisting of $CH_2$, $C(O)$, NH, O and $S(O)q$, wherein q is 0, 1 or 2;

D, E and F are independently selected from the group consisting of carbon atom, nitrogen atom, oxygen atom and sulfur atom.

7. A compound of claim 1 or a pharmaceutically acceptable salt thereof, wherein Z represents a radical selected from the group consisting of amino, imino, aminomethyl, amidino (carbamimidoyl), guanidino, azetidinyl, pyrrolidinyl, piperidinyl, pyridinyl and aminopyridinyl, and wherein any nitrogen atom of each of said aforementioned Z radicals is unsubstituted or substituted independently with one or two $(C_1-C_6)$ alkyl.

8. A compound of claim 1 wherein R4 is a (three- to fifteen-membered heterocyclic ring)-Z, wherein said Z is a basic nitrogen-containing group and wherein said (three- to fifteen-membered heterocyclic ring) is unsubstituted or additionally substituted independently with one to four Y.

9. A compound of claim 1 or a pharmaceutically acceptable salt thereof, wherein R4 is $-(C_6-C_{14})$-aryl-Z, wherein Z is a basic nitrogen-containing group and wherein said $-(C_6-C_{14})$-aryl is unsubstituted or additionally substituted independently with one to four Y.

10. A compound of claim 1 wherein R4 is -benzimidazole-Z, wherein Z is a basic nitrogen-containing group and wherein said benzimidazole is unsubstituted or additionally substituted independently with one to four Y.

11. A compound of claim 1 or a pharmaceutically acceptable salt thereof, wherein R4 is -phenyl-Z, wherein Z is a basic nitrogen-containing group and wherein said phenyl is unsubstituted or additionally substituted independently with one to four Y.

12. A compound of formula (I) of claim 1 consisting of:

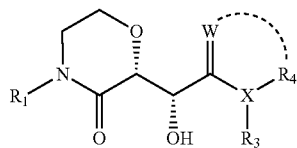

or a pharmaceutically acceptable salt thereof, wherein $R_1$ is a group selected from the group consisting of:

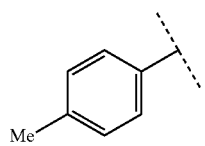 a1

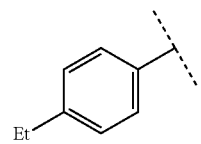 a2

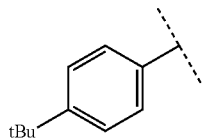 a3

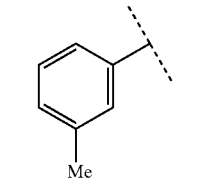 a4

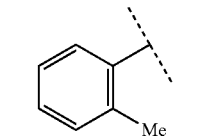 a5

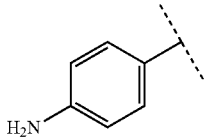 a6

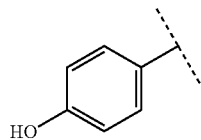 a7

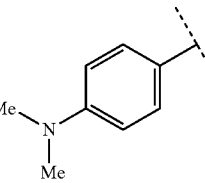 a8

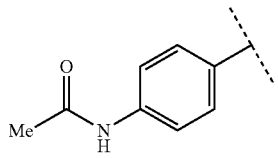 a9

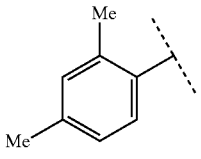 a10

547
-continued
| | |
|---|---|
| a11 | 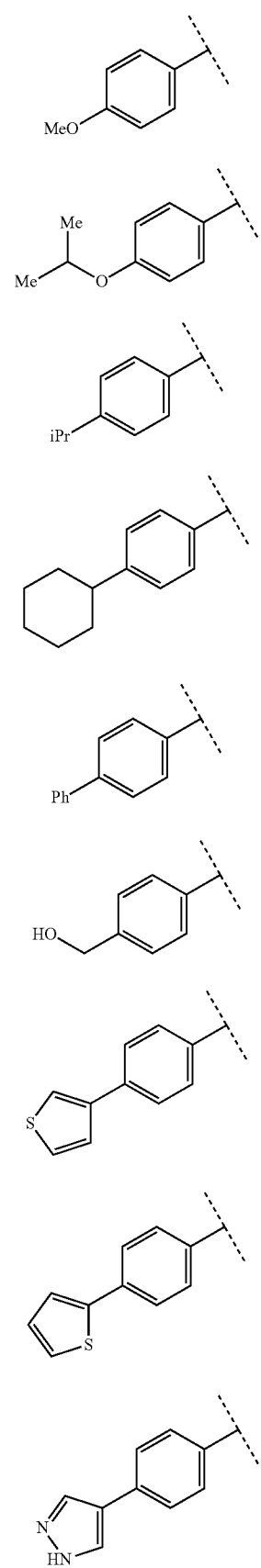 |
| a12 | |
| a13 | |
| a14 | |
| a15 | |
| a16 | |
| a17 | |
| a18 | |
| a19 | |
548
-continued
| | |
|---|---|
| a20 | 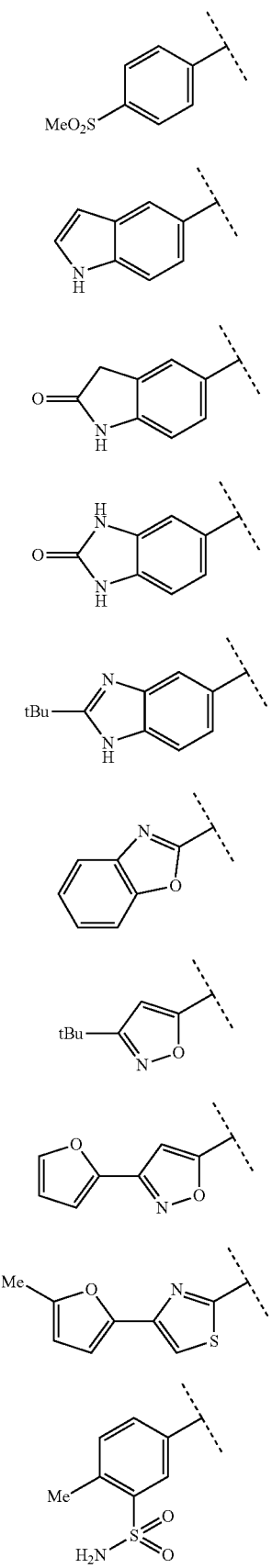 |
| a21 | |
| a22 | |
| a23 | |
| a24 | |
| a25 | |
| a26 | |
| a27 | |
| a28 | |
| a29 | |

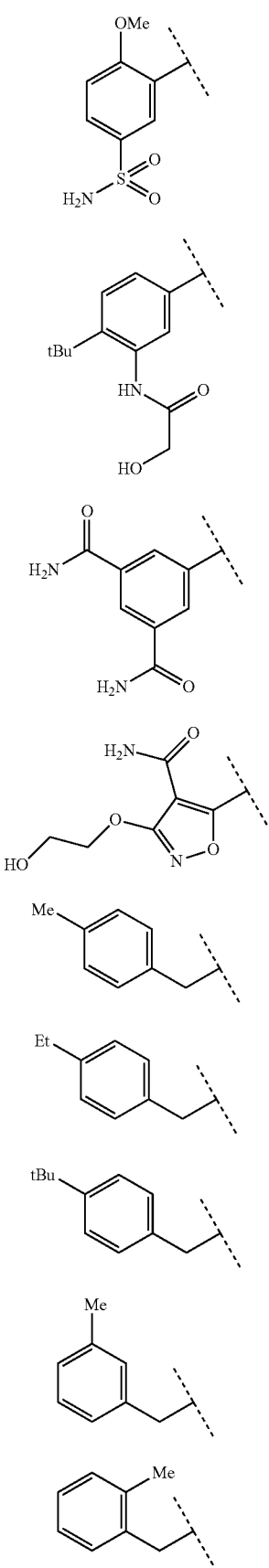
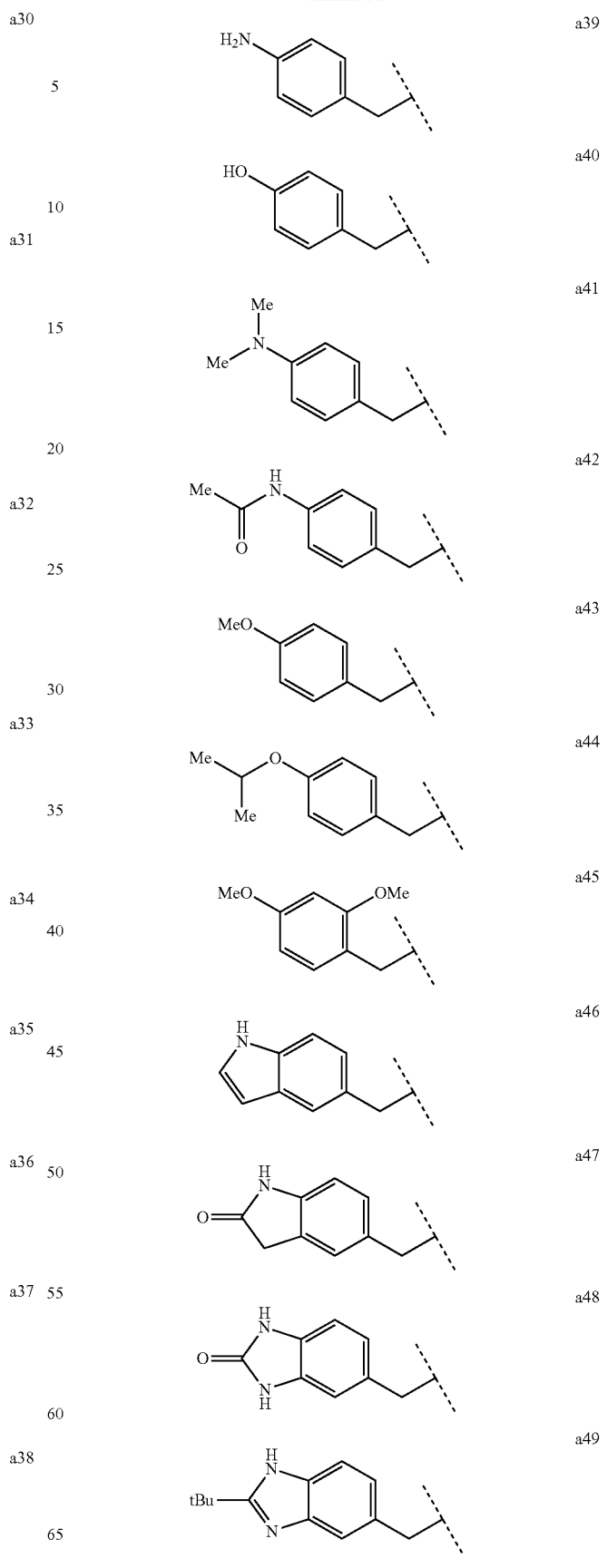

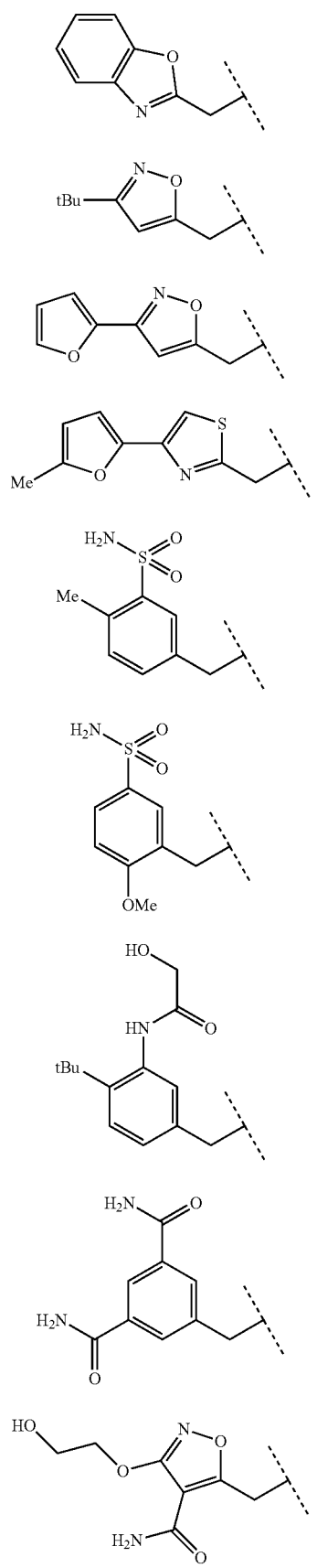
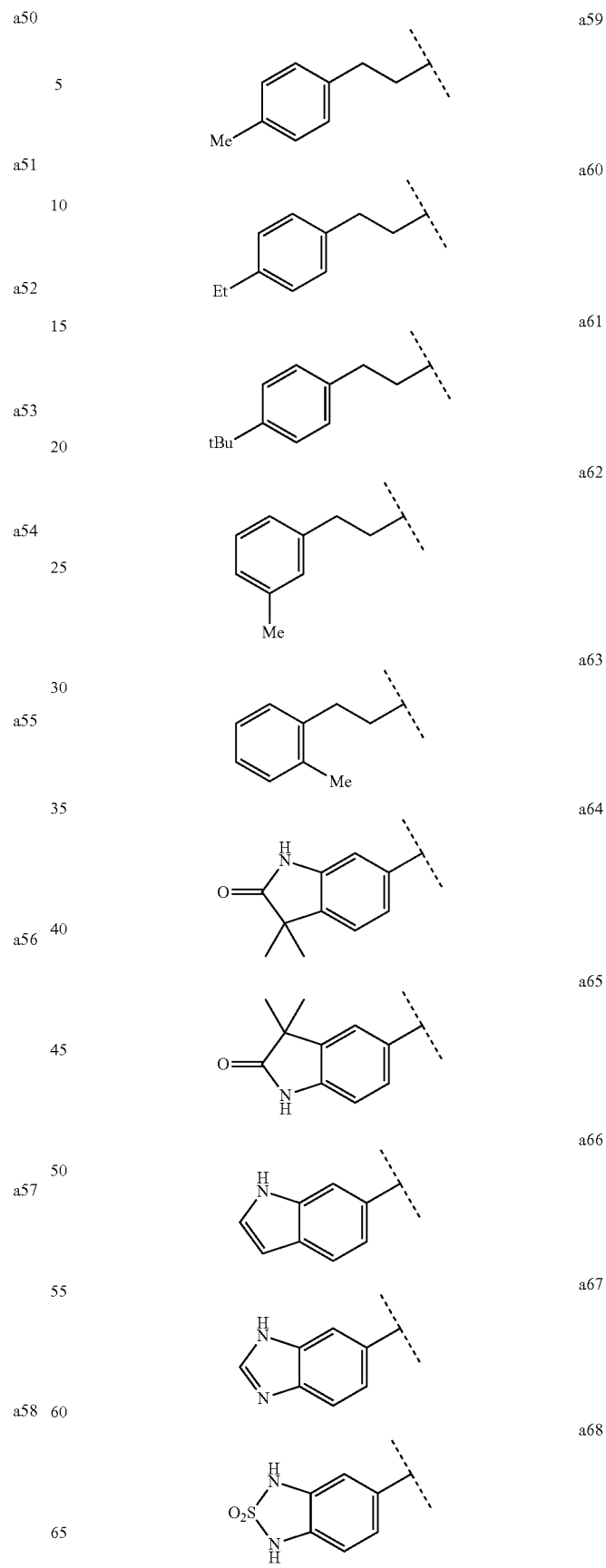

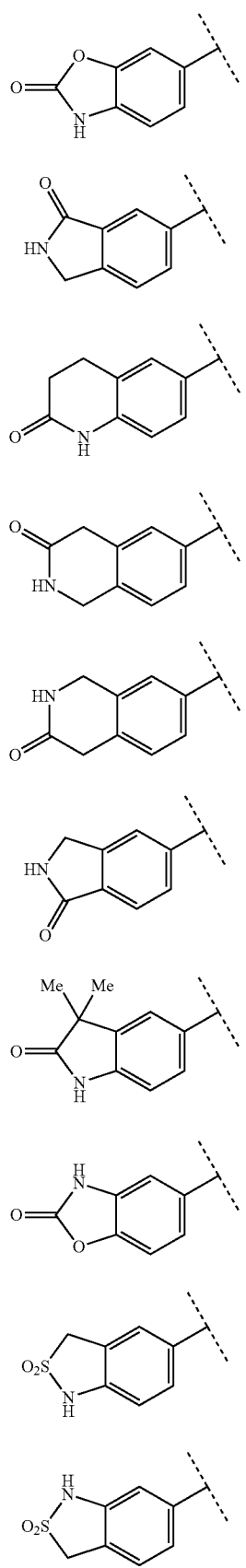
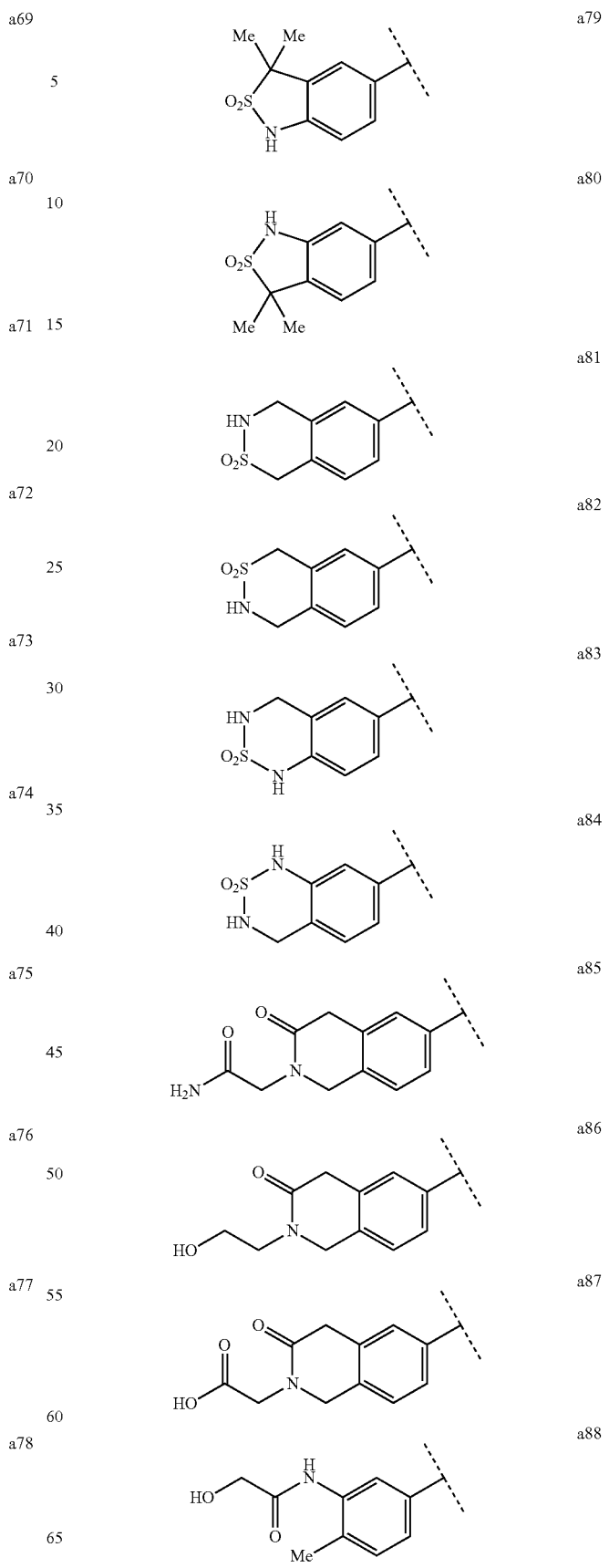

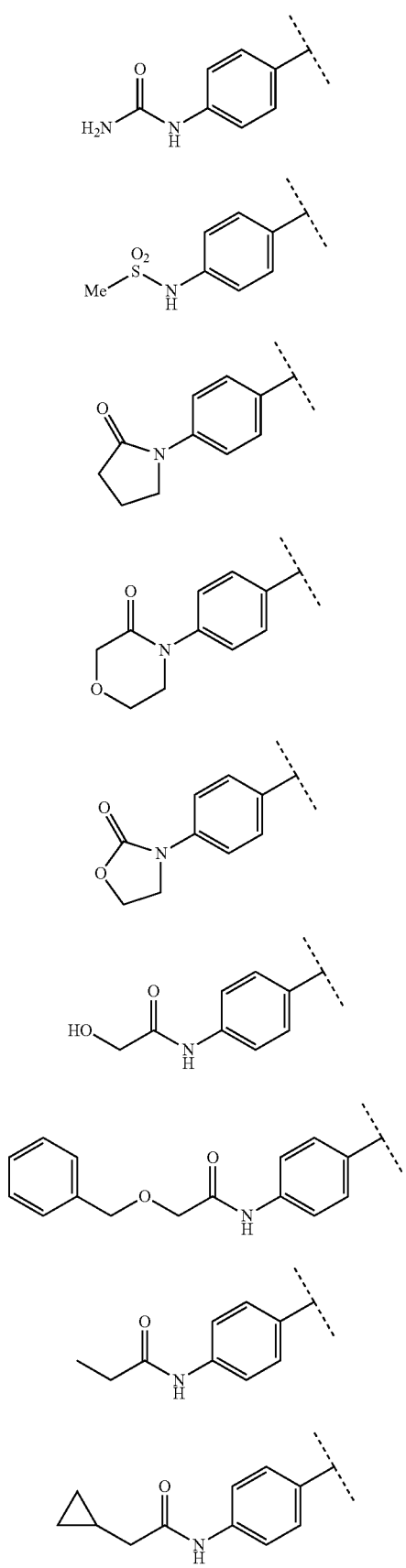
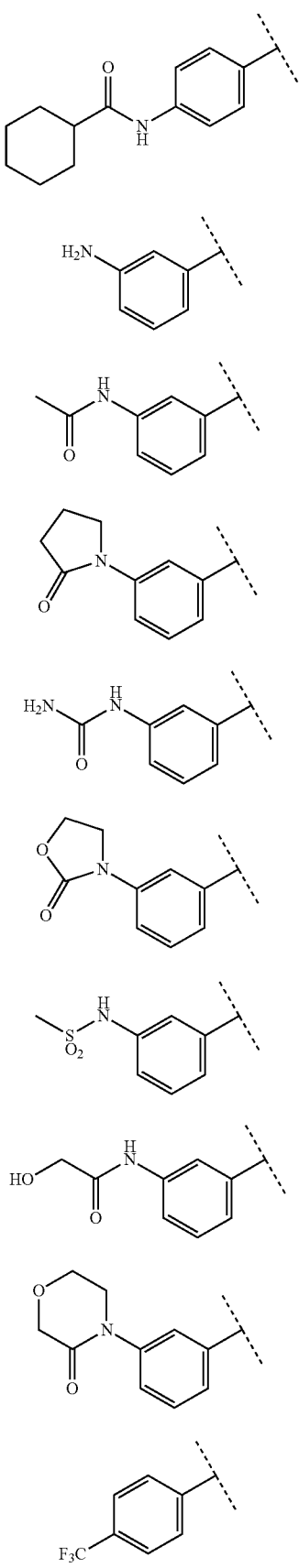

557
-continued
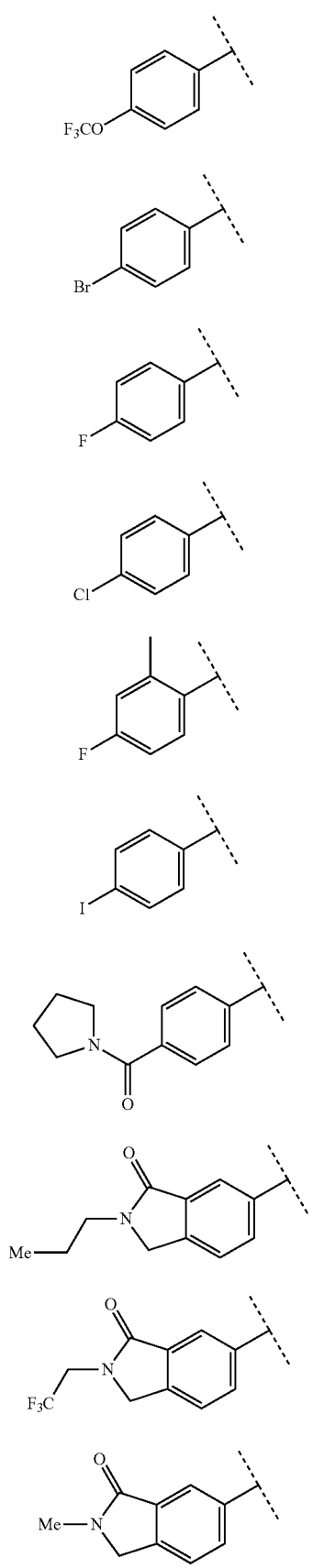
| | |
|---|---|
| a108 | |
| a109 | |
| a110 | |
| a111 | |
| a112 | |
| a113 | |
| a114 | |
| a115 | |
| a116 | |
| a117 | |
558
-continued
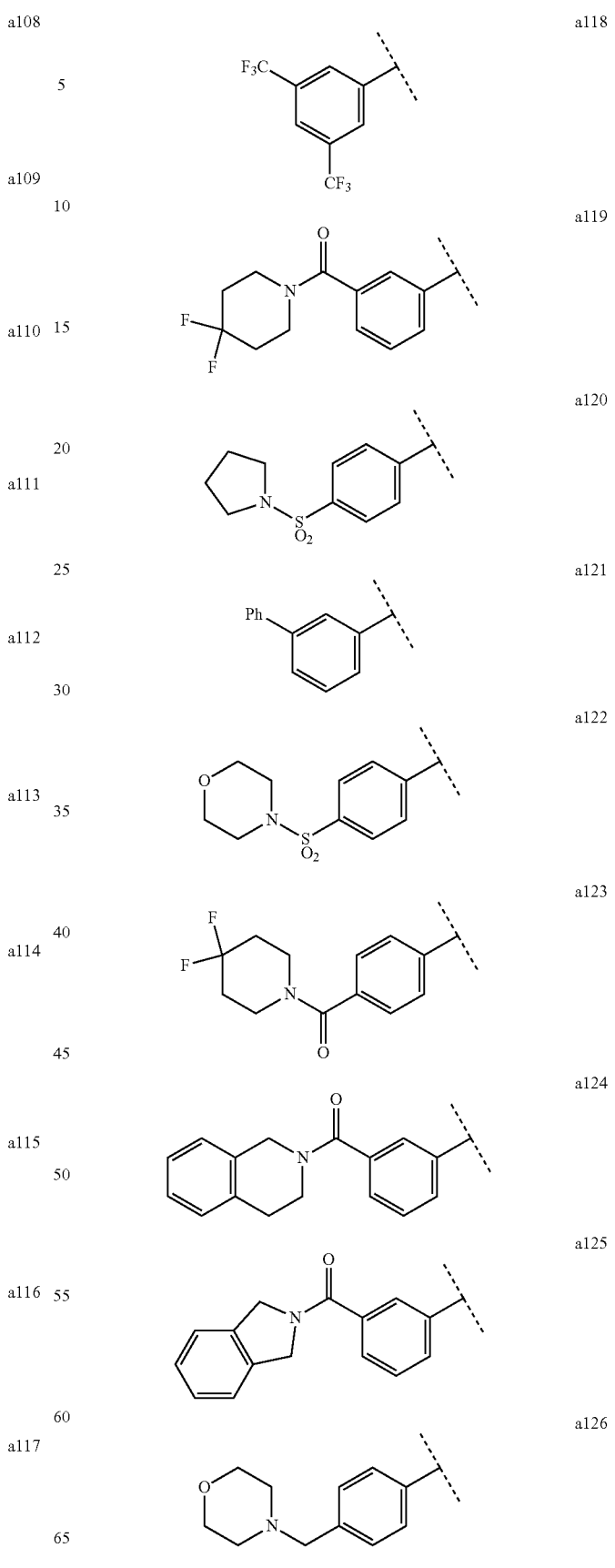
| | |
|---|---|
| a118 | |
| a119 | |
| a120 | |
| a121 | |
| a122 | |
| a123 | |
| a124 | |
| a125 | |
| a126 | |

| | |
|---|---|
| a127 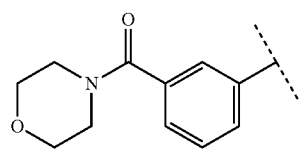 | a136 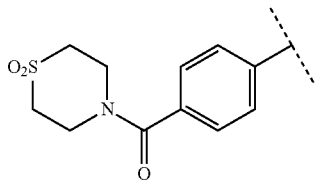 |
| a128 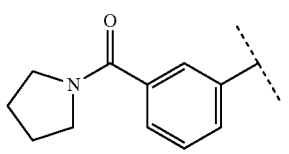 | a137 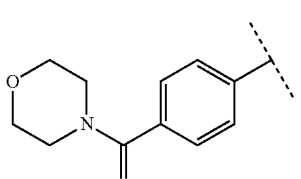 |
| a129 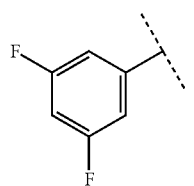 | a138 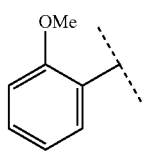 |
| a130 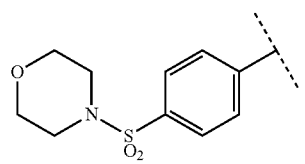 | a139 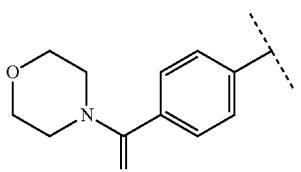 |
| a131 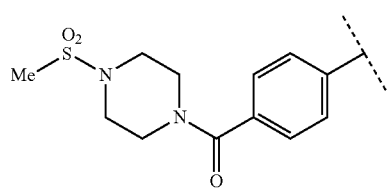 | a140 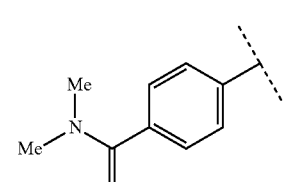 |
| a132 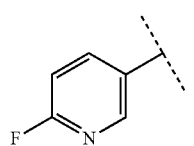 | a141 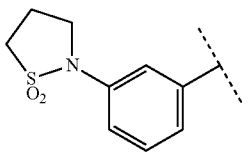 |
| a133 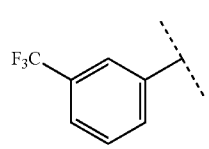 | a142 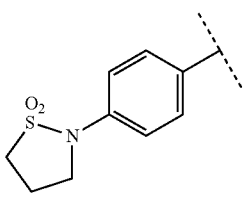 |
| a134 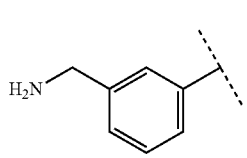 | a143 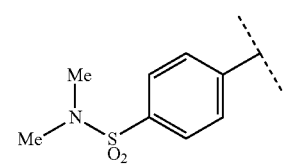 |
| a135 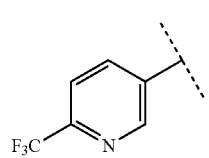 | a144 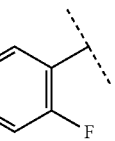 |

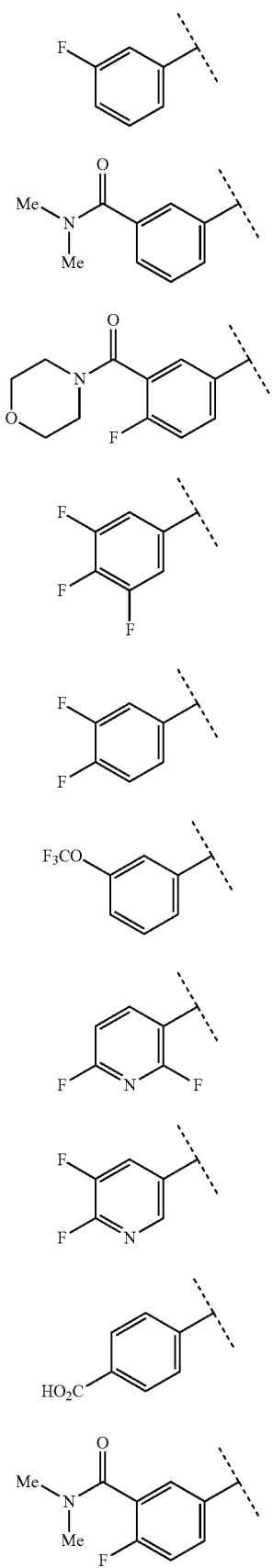
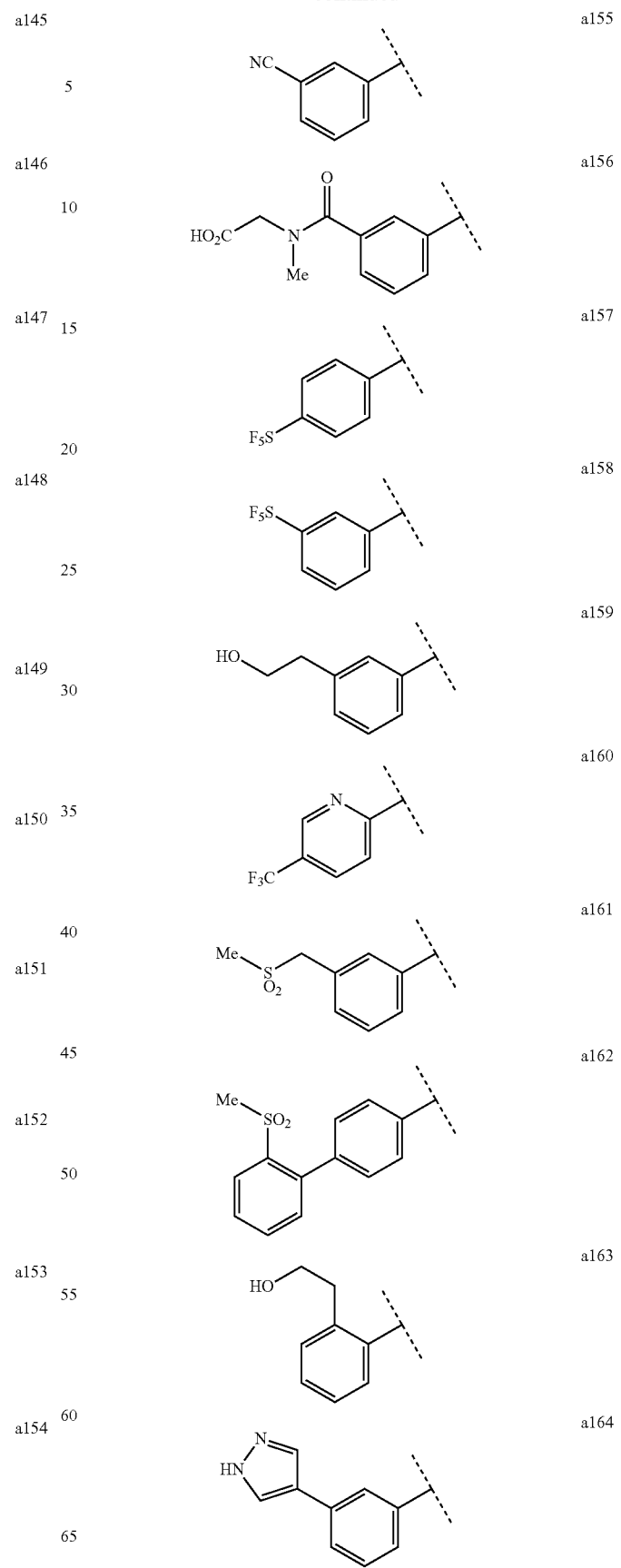

-continued

| | |
|---|---|
| a165 | a174 |
| a166 | a175 |
| a167 | a176 |
| a168 | a177 |
| a169 | a178 |
| a170 | a179 |
| a171 | a180 |
| a172 | a181 |
| a173 | a182 |

| | |
|---|---|
| 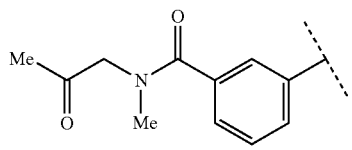 | a183 |
| 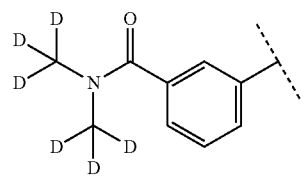 | a184 |
| 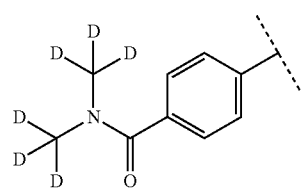 | a185 |
| 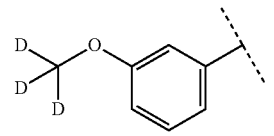 | a186 |
| 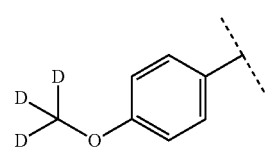 | a187 |
| 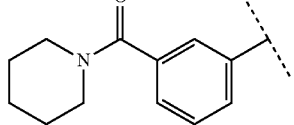 | a188 |
| 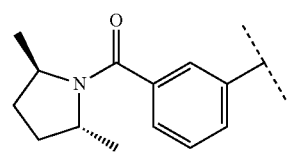 | a189 |
| 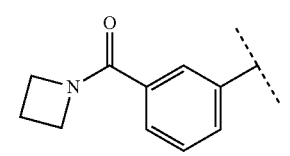 | a190 |
| 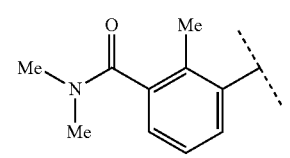 | a191 |
| 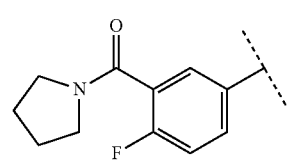 | a192 |
| | |
|---|---|
| 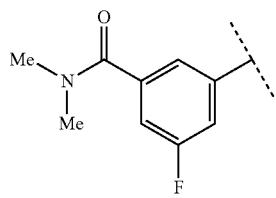 | a193 |
| 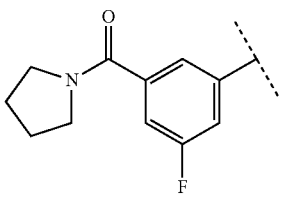 | a194 |
| 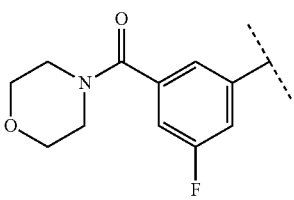 | a195 |
| 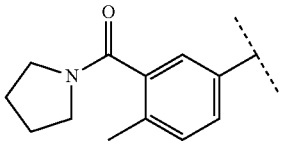 | a196 |
| 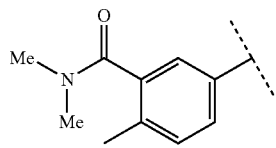 | a197 |
| 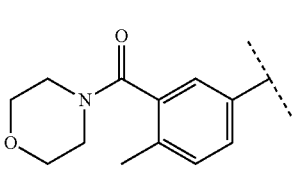 | a198 |
| 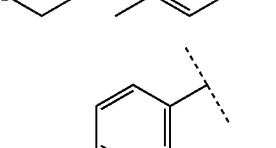 | a199 |
| 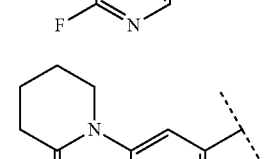 | a200 | and wherein $$\text{structure with W, X, R}_3, R_4$$

is selected from the group consisting of b1: 4-amidinophenyl amide
b2: N-hydroxy-4-amidinophenyl amide
b3: 3-amino-benzo[d]isoxazol-6-yl amide
b4: 4-(aminomethyl)phenyl amide
b5: isoindolin-5-yl amide
b6: indolin-5-yl amide
b7: 1H-indol-5-yl amide
b8: 5-chloro-1H-indol-3-yl amide
b9: 2-oxo-2,3-dihydro-1H-benzimidazol-5-yl amide
b10: 1H-benzimidazol-5-yl amide
b11: 2-amino-1H-benzimidazol-5-yl amide
b12: p-tolyl amide
b13: 4-hydroxyphenyl amide
b14: 4-chlorophenyl amide
b15: 4-carbamoylphenyl amide
b16: 4-methoxyphenyl amide
b17: 3-chlorophenyl amide

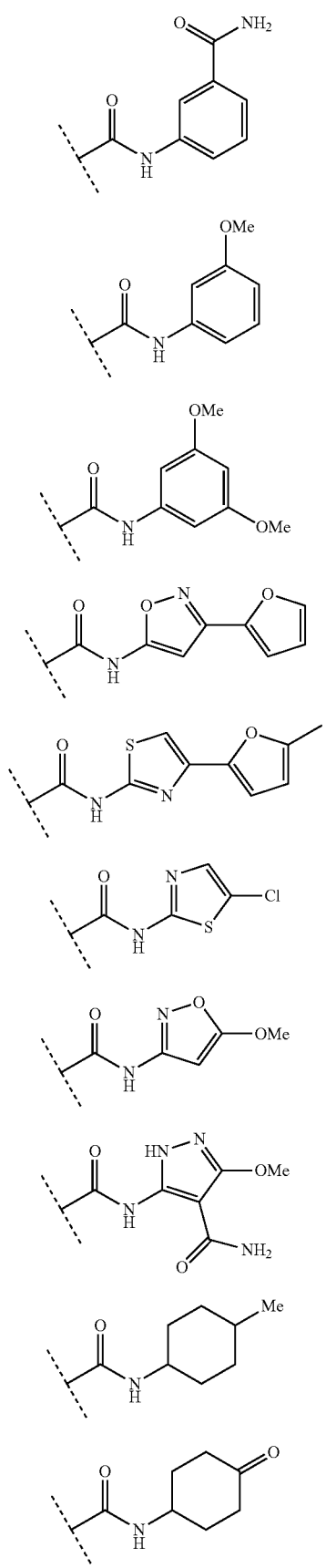
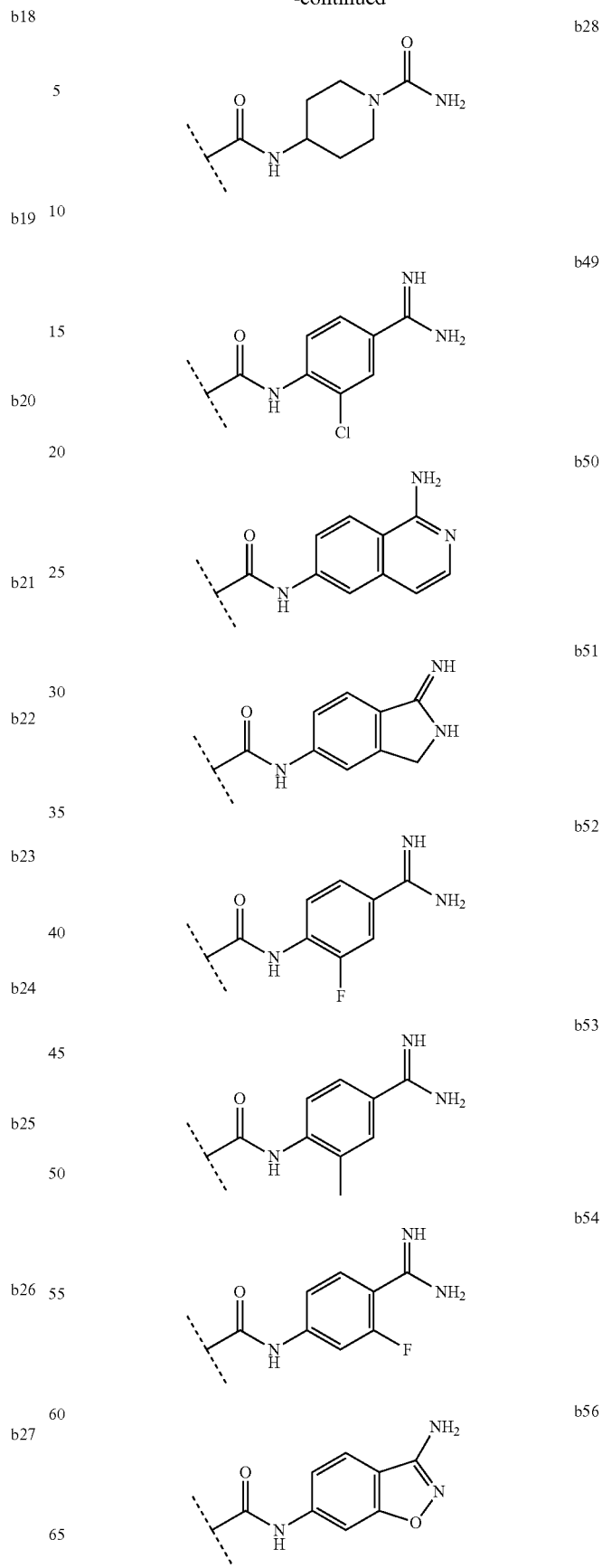

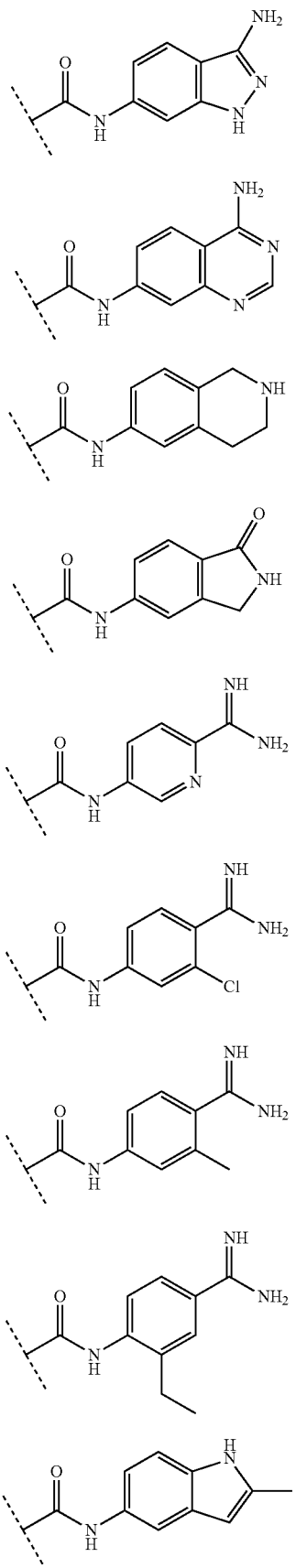

13. A compound of formula (I) of claim 1 consisting of:
N-(1-aminoisoquinolin-6-yl)-2-hydroxy-2-(3-oxo-4-p-tolylmorpholin-2-yl)-acetamide;
N-(4-amidinophenyl)-2-hydroxy-2-(3-oxo-4-p-tolylmorpholin-2-yl)acetamide;
2-hydroxy-N-(1H-indol-5-yl)-2-(3-oxo-4-p-tolylmorpholin-2-yl)acetamide;
2-hydroxy-N-(2-methyl-1H-indol-5-yl)-2-(3-oxo-4-p-tolylmorpholin-2-yl)-acetamide;
N-[4-(aminomethyl)phenyl]-2-hydroxy-2-(3-oxo-4-p-tolylmorpholin-2-yl-acetamide;
N-(2-amino-3H-benzimidazol-5-yl)-2-hydroxy-2-(3-oxo-4-p-tolylmorpholin-2-yl)-acetamide;
(2R)—N-(4-amidinophenyl)-2-hydroxy-2-[(2R)-3-oxo-4-p-tolylmorpholin-2-yl]-acetamide;
(2R)—N-(4-amidinophenyl)-2-[(2R)-4-(2,4-dimethylphenyl)-3-oxomorpholin-2-yl]-2-hydroxyacetamide;
(2R)—N-(4-amidinophenyl)-2-hydroxy-2-[(2R)-4-[3-[(2-hydroxyacetyl)amino]-4-methylphenyl]-3-oxomorpholin-2-yl]acetamide;
(2R)—N-(4-amidinophenyl)-2-hydroxy-2-[(2R)-3-oxo-4-(4-thiophen-3-ylphenyl)-morpholin-2-yl]acetamide;
(2R)—N-(4-amidinophenyl)-2-[(2R)-4-(4-tert-butylphenyl)-3-oxomorpholin-2-yl]-2-hydroxyacetamide;
(2R)—N-(4-amidinophenyl)-2-hydroxy-2-[(2R)-4-[4-(hydroxymethyl)phenyl]-3-oxomorpholin-2-yl]acetamide;
(2R)—N-(4-amidinophenyl)-2-hydroxy-2-[(2R)-3-oxo-4-(2-oxo-1,3-dihydroindol-5-yl)morpholin-2-yl]acetamide;
(2R)—N-(4-amidinophenyl)-2-hydroxy-2-[(2R)-4-(4-iodophenyl)-3-oxomorpholin-2-yl]-acetamide;
(2R)—N-(4-amidinophenyl)-2-[(2R)-4-(4-cyclohexylphenyl)-3-oxomorpholin-2-yl]-2-hydroxyacetamide;
(2R)—N-(4-amidinophenyl)-2-hydroxy-2-[2R)-3-oxo-4-(4-propan-2-ylphenyl)-morpholin-2-yl]acetamide;
(2R)—N-(4-amidinophenyl)-2-[(2R)-4-(4-ethylphenyl)-3-oxomorpholin-2-yl]-2-hydroxyacetamide;
(2R)—N-(4-amidinophenyl)-2-hydroxy-2-[(2R)-4-(1H-indol-6-yl)-3-oxomorpholin-2-yl]-acetamide;
(2R)—N-4-amidinophenyl)-2-[(2R)-4-(3,3-dimethyl-2-oxo-1H-indol-6-yl)-3-oxomorpholin-2-yl]-2-hydroxyacetamide;
(2R)—N-(4-amidinophenyl)-2-hydroxy-2-[(2R)-3-oxo-4-(2-oxo-1,3-dihydrobenz-imidazol-5-yl)morpholin-2-yl]acetamide;
(2R)—N-(4-amidinophenyl)-2-hydroxy-2-[(2R)-3-oxo-4-p-tolylmethylmorpholin-2-yl]acetamide hydrochloric salt;
(2R)—N-(4-amidinophenyl)-2-hydroxy-2-[(2R)-3-oxo-4-(4-thiophen-2-ylphenyl)-morpholin-2-yl]acetamide;
(2R)—N-(4-amidinophenyl)-2-[(2R)-4-biphenyl-3-oxomorpholin-2-yl]-2-hydroxy-acetamide;
(2R)—N-(4-amidinophenyl)-2-[(2R)-4-(4'-tert-butylbiphenyl)-3-oxomorpholin-2-yl]-2-hydroxyacetamide;

(2R)—N-(4-amidinophenyl)-2-hydroxy-2-[(2R)-3-oxo-4-[4-(1H-pyrazol-4-yl)phenyl]morpholin-2-yl]acetamide;
(2R)-2-[(2R)-4-(4-acetamidophenyl)-3-oxomorpholin-2-yl]-N-(4-amidinophenyl)-2-hydroxyacetamide;
(2R)—N-(4-amidinophenyl)-2-[(2R)-4-[4-(carbamylamino)phenyl]-3-oxomorpholin-2-yl]-2-hydroxyacetamide;
(2R)—N-(4-amidinophenyl)-2-hydroxy-2-[(2R)-4-[4-(methanesulfonamido)phenyl]-3-oxomorpholin-2-yl]acetamide;
(2R)—N-(4-amidinophenyl)-2-hydroxy-2-[(2R)-3-oxo-4-[4-(2-oxopyrrolidin-1-yl)-phenyl]morpholin-2-yl]acetamide;
(2R)—N-(4-amidinophenyl)-2-hydroxy-2-[(2R)-3-oxo-4-[4-(3-oxomorpholin-4-yl)-phenyl]morpholin-2-yl]acetamide;
(2R)—N-amidinophenyl)-2-hydroxy-2-[(2R)-3-oxo-4-[4-(2-oxo-1,3-oxazolidin-3-yl)-phenyl]morpholin-2-yl]acetamide;
(2R)—N-(4-amidinophenyl)-2-hydroxy-2-[(2R)-3-oxo-4-[4-[(2-phenylmethoxy-acetyl)amino]phenyl]morpholin-2-yl]acetamide;
(2R)—N-(4-amidinophenyl)-2-hydroxy-2-[(2R)-4-[4-[(2-hydroxyacetyl)amino]phenyl]3-oxomorpholin-2-yl]acetamide;
(2R)—N-(4-amidinophenyl)-2-[(2R)-4-(3,3-dimethyl-2-oxo-1H-indol-5-yl)-3-oxomorpholin-2-yl]-2-hydroxyacetamide;
(2R)—N-(4-amidinophenyl)-2-hydroxy-2-[(2R)-4-(1H-indol-5-yl)-3-oxomorpholin-2-yl]-acetamide;
(2R)—N-(4-amidinophenyl)-2-hydroxy-2-[(2R)-3-oxo-4-(2-oxo-3H-1,3-benzoxazol-6-yl)morpholin-2-yl]acetamide;   (2R)—N-(4-amidinophenyl)-2-hydroxy-2-[(2R)-3-oxo-4-(3-oxo-1,2-dihydroisoindol-5-yl)morpholin-2-yl]acetamide;
(2R)-2-[(2R)-4(4-Acetamidophenyl)-3-oxomorpholin-2-yl]-N-(1-aminoisoquinolin-6-yl)-2-hydroxyacetamide;
(2R)-2-[(2R)-4-(4-Acetamidophenyl)-3-oxomorpholin-2-yl]-2-hydroxy-N-(1-imino-2,3-dihydroisoindol-5-yl)acetamide;
N-[4-[(2R)-2-[(1R)-2-(4-amidinoanilino)-1-hydroxy-2-oxoethyl]-3-oxomorpholin-4-yl]phenyl]propanamide;
(2R)—N-(4-Amidinophenyl)-2-[(2R)-4-[4-[(2-cyclopropylacetyl)amino]phenyl]-3-oxomorpholin-2-yl]-2-hydroxyacetamide;
N-[4-[(2R)-2-[(1R)-2-(4-Amidinoanilino)-1-hydroxy-2-oxoethyl]-3-oxomorpholin-4-yl]phenyl]cyclohexanecarboxamide;
(2R)—N-(4-Amidinophenyl)-2-[(2R)-4-(4-aminophenyl)-3-oxomorpholin-2-yl]-2-hydroxyacetamide;
(2R)—N-(4-Amidinophenyl)-2-[(2R)-4-(3-aminophenyl)-3-oxomorpholin-2-yl]-2-hydroxyacetamide;
(2R)-2-[(2R)-4-(3-Acetamidophenyl)-3-oxomorpholin-2-yl]-N-(4-amidinophenyl)-2-hydroxyacetamide;
(2R)—N-(4-Amidinophenyl)-2-hydroxy-2-[(2R)-3-oxo-4-[3-(2-oxopyrrolidin-1-yl)phenyl]morpholin-2-yl]acetamide;
(2R)—N-(4-Amidinophenyl)-2-[(2R)-4-[3-(carbamoylamino)phenyl]-3-oxomorpholin-2-yl]-2-hydroxyacetamide;
(2R)—N-(4-Amidinophenyl)-2-hydroxy-2-[(2R)-3-oxo-4-[3-(2-oxo-1,3-oxazolidin-3-yl)phenyl]morpholin-2-yl]acetamide;
(2R)—N-(4-Amidinophenyl)-2-hydroxy-2-[(2R)-4-[3-(methanesulfonamido)phenyl]-3-oxomorpholin-2-yl]acetamide;
(2R)-N-(4-Amidinophenyl)-2-hydroxy-2-[(2R)-4-[3-[(2-hydroxyacetyl)amino]phenyl]-3-oxomorpholin-2-yl]acetamide;
(2R)—N-4-Amidinophenyl)-2-hydroxy-2-[(2R)-3-oxo-4-[3-(3-oxomorpholin-4-yl)phenyl]morpholin-2-yl]acetamide;
(2R)—N-(1-Aminoisoquinolin-6-yl)-2-[(2R)-4-(4-tert-butylphenyl)-3-oxomorpholin-2-yl]-2-hydroxyacetamide;
(2R)-2-[(2R)-4(4-tert-Butylphenyl)-3-oxomorpholin-2-yl]-2-hydroxy-N-(1-imino-2,3-dihydroisoindol-5-yl)acetamide;
(2R)—N-(1-Aminoisoquinolin-6-yl)-2-hydroxy-2-[(2R)-3-oxo-4-[4-(trifluoromethyl)phenyl]morpholin-2-yl]acetamide;
(2R)—N-(1-Aminoisoquinolin-6-yl)-2-hydroxy-2-[(2R)-3-oxo-4-[4-(trifluoromethoxy)phenyl]morpholin-2-yl]acetamide;
(2R)—N-(4-Amidinophenyl)-2-hydroxy-2-[(2R)-3-oxo-4-[4-(trifluoromethoxy)phenyl]morpholin-2-yl]acetamide;
(2R)-2-Hydroxy-N-(1-imino-2,3-dihydroisoindol-5-yl)-2-[(2R)-3-oxo-4-[4-(trifluoromethoxy)phenyl]morpholin-2-yl]acetamide;
(2R)—N-(1-Aminoisoquinolin-6-yl)-2-[(2R)-4-(4-bromophenyl)-3-oxomorpholin-2-yl]-2-hydroxyacetamide;
(2R)—N-(1-Aminoisoquinolin-6-yl)-2-[(2R)-4-(4-fluorophenyl)-3-Oxomorpholin-2-yl]-2-hydroxyacetamide;
(2R)—N-(1-Aminoisoquinolin-6-yl)-2-[(2R)-4-(4-chlorophenyl)-3-oxomorpholin-2-yl]-2-hydroxyacetamide;
(2R)—N-(1-Aminoisoquinolin-6-yl)-2-hydroxy-2-[(2R)-4-(4-isopropyloxyphenyl)-3-oxomorpholin-2-yl]acetamide;
(2R)—N-(1-Aminoisoquinolin-6-yl)-2-hydroxy-2-[(2R)-3-oxo-4-p-tolylmorpholin-2-yl]acetamide;
(2R)—N-(1-Aminoisoquinolin-6-yl)-2-[(2R)-4-4-fluoro-o-tolyl)-3-oxomorpholin-2-yl]-2-hydroxyacetamide;
(2R)—N-(4-Amidinophenyl)-2-[(2R)-4(4-fluoro-o-tolyl)-3-oxomorpholin-2-yl]-2-hydroxyacetamide;
(2R)—N-(4-Amidino-o-tolyl)-2-[(2R)-4-(4-tert-butylphenyl)-3-oxomorpholin-2-yl]-2-hydroxyacetamide;
(2R)—N-(4-Amidino-2-chlorophenyl)-2-[(2R)-4-(4-tert-butylphenyl)-3-oxomorpholin-2-yl]-2-hydroxyacetamide;
(2R)—N-(4-Amidino-2-fluorophenyl-2-[(2R)-4-(4-tert-butylphenyl)-3-oxomorpholin-2-yl]-2-hydroxyacetamide;
(2R)—N-(4-amidinophenyl)-2-hydroxy-2-[(2R)-4-[3-(2-hydroxyethyl)phenyl]-3-oxomorpholin-2-yl]acetamide;
(2R)—N-(4-amidinophenyl)-2-hydroxy-2-[(2R)-3-oxo-4-[5-trifluoromethyl)-2-pyridyl]morpholin-2-yl]acetamide;
(2R)-N-[4-amidinophenyl]-2-hydroxy-2-[2R)-4-[3-(methylsulfonyl)phenyl]-3-oxomorpholin-2-yl]acetamide;
(2R)—N-(4-amidinophenyl)-2-hydroxy-2-[(2R)-4-[4-(2-methylsulfonylphenyl)phenyl]-3-oxomorpholin-2-yl]acetamide;
(2R)—N-(4-amidinophenyl)-2-hydroxy-2-[2R)-4-[4-[2-(2-hydroxyethyl)phenyl]phenyl]-3-oxomorpholin-2-yl]acetamide;
(2R)—N-(4-amidinphenyl)-2-hydroxy-2-[2R)-3-oxo-4-[3-(1H-pyrazol-4-yl)phenyl]morpholin-2-yl]acetamide;

N-(4-amidinophenyl)-2-hydroxy-2-[4-(4-methylbenzoyl)
morpholin-2-yl]acetamide;
N-(4-amidinophenyl)-2-hydroxy-2-[4(p-tolylsulfonyl)
morpholin-2-yl]acetamide; and
N-(1-amino-6-isoquinolyl)-2-hydroxy-2-[4-(p-tolyl)morpholin-2-yl]acetamide ditrifluoroacetate;
or a pharmaceutically acceptable salt thereof.

14. A compound of formula (I) of claim 1 consisting of:
(2R)—N-(4-amidinophenyl)-2-hydroxy-2-[(2R)-3-oxo-4-(2-oxo-3,4-dihydro-1H-quinolin-6-yl)morpholin-2-yl]acetamide;
(2R)—N-(4-amidinophenyl)-2-hydroxy-2-[(2R)-3-oxo-4-(3-oxo-2,4-dihydro-1H-isoquinolin-6-yl)morpholin-2-yl]acetamide;
2-[6-[(2R)-2-[(1R)-2-(4-amidinoanilino)-1-hydroxy-2-oxoethyl]-3-oxomorpholin-4-yl]-3-oxo-1,4-dihydroisoquinolin-2-yl]acetic acid;
(2R)—N-(4-amidinophenyl)-2-hydroxy-2-[(2R)-4-[2-(2-hydroxyethyl)-3-oxo-1,4-dihydroisoquinolin-6-yl]-3-oxomorpholin-2-yl]acetamide;
(2R)—N-(4-amidinophenyl)-2-[(2R)-[2-(2-amino-2-oxoethyl)-3-oxo-1,4-dihydro-isoquinolin-6-yl]-3-oxomorpholin-2-yl]-2-hydroxyacetamide;
(2R)—N-(4-amidinophenyl)-2-hydroxy-2-[(2R)-3-oxo-4-(2-oxo-3H-1,3-benzoxazol-5-yl)morpholin-2-yl]acetamide;
(2R)—N-(4-amidinophenyl)-2-[(2R)-4-(1H-benzimidazol-5-yl)-3-oxomorpholin-2-yl]-2-hydroxyacetamide;
(2R)—N-(4-amidinophenyl)-2-[(2R)-4-(2,2-dioxo-1,3-dihydro-2,1-benzothiazol-5-yl)-3-oxomorpholin-2-yl]-2-hydroxyacetamide;
(2R)—N-(4-amidinophenyl)-2-[(2R)-4-(2,2-dioxo-1,3-dihydro-2,1-benzothiazol-6-yl)-3-oxomorpholin-2-yl]-2-hydroxyacetamide;
(2R)—N-(4-amidinophenyl)-2-[(2R)-4-(3,3-dimethyl-2,2-dioxo-1H-2,1-benzothiazol-5-yl)-3-oxomorpholin-2-yl]-2-hydroxyacetamide;
(2R)—N-(4-amidinophenyl)-2-[(2R)-4-(3,3-dimethyl-2,2-dioxo-1H-2,1-benzothiazol-6-yl)-3-oxomorpholin-2-yl]-2-hydroxyacetamide;
(2R)—N-(4-amidinophenyl)-2-[(2R)-4-(2,2-oxo-3,4-dihydro-1H-benzo[d]thiazin-6-yl)-3-oxomorpholin-2-yl]-2-hydroxyacetamide;
(2R)—N-(4-amidinophenyl)-2-[(2R)-4-(2,2-dioxo-3,4-dihydro-1H-benzo[d]thiazin-7-yl)-3-oxomorpholin-2-yl]-2-hydroxyacetamide;
(2R)—N-(4-amidinophenyl)-2-hydroxy-2-[(2R)-3-oxo-4-(1-oxo-2,3-dihydroisoindol-5-yl)morpholin-2-yl]acetamide;
(2R)—N-(4-amidinophenyl)-2-hydroxy-2-[(2R)-3-oxo-4-(3-oxo-2,4-dihydro-1H-isoquinolin-7-yl)morpholin-2-yl]acetamide;
(2R)—N-amidinophenyl)-2-hydroxy-2-[(2R)-3-oxo-4-(2-oxo-3,4-dihydro-1H-quinolin-7-yl)morpholin-2-yl]acetamide;
(2R)—N-(4-amidinophenyl)-2-[(2R)-4(2,2-dioxo-3,4-dihydro-1H-benzo[c][1,2,6]-thiadiazin-6-yl)-3-oxomorpholin-2-yl]-2-hydroxyacetamide;
(2R)—N-(4-amidinophenyl)-2-[(2R)-4-(2,2-dioxo-3,4-dihydro-1H-benzo[c][1,2,6]-thiadiazin-7-yl)-3-oxomorpholin-2-yl]-2-hydroxyacetamide;
(2R)-2-[(2R)-4-(3,3-dimethyl-2-oxo-1H-indol-5-yl)-3-oxomorpholin-2-yl]-2-hydroxy-N-(1-imino-2,3-dihydroisoindol-5-yl)acetamide;
(2R)-2-[(2R)-4-(4-tert-butylphenyl)-3-oxomorpholin-2-yl]-2-hydroxy-N-(1-imino-2,3-dihydroisoindol-5-yl)acetamide;
(2R)-2-[(2R)-4-(4-acetamidophenyl)-3-oxomorpholin-2-yl]-2-hydroxy-N-(1-imino-2,3-dihydroisoindol-5-yl)acetamide;
(2R)—N-(1-aminoisoquinolin-6-yl)-2-[(2R)-4-(3,3-dimethyl-2-oxo-1H-indol-5-yl)-3-oxomorpholin-2-yl]-2-hydroxyacetamide;
(2R)—N-(1-aminoisoquinolin-6-yl)-2-[(2R)-4-(4-tert-butylphenyl)-3-oxomorpholin-2-yl]-2-hydroxyacetamide; and
(2R)-2-[(2R)-4(4-acetamidophenyl)-3-oxomorpholin-2-yl]-N-(1-aminoisoquinolin-6-yl)-2-hydroxyacetamide;
or a pharmaceutically acceptable salt or solvate thereof.

15. A compound of formula (I) of claim 1 selected from the group consisting of:
(R)—N-(4-carbamimidoylphenyl)-2-hydroxy-2-((R)-3-oxo-4-(3-oxo-2-propylisoindolin-5-yl)morpholin-2-yl)acetamide;
(R)—N-(4-carbamimidoylphenyl)-2-hydroxy-2-((R)-3-oxo-4-(3-oxo-2-(2,2,2-trifluoroethyl)isoindolin-5-yl)morpholin-2-yl)acetamide;
(R)—N-(4-carbamimidoylphenyl)-2-hydroxy-2-((R)-4-(2-methyl-3-oxoisoindolin-5-yl)-3-oxomorpholin-2-yl)acetamide;
(R)—N-(4-(aminomethyl)phenyl)-2-hydroxy-2-((R)-4-(2-methyl-3-oxoisoindolin-5-yl)-3-oxomorpholin-2-yl)acetamide;
(R)-2-hydroxy-2-((R)-4-(2-methyl-3-oxoisoindolin-5-yl)-3-oxomorpholin-2-yl)-N-(1,2,3,4-tetrahydroisoquinolin-6-yl)acetamide;
(R)-2-((R)-4-(3,5-bis(trifluoromethyl)phenyl)-3-oxomorpholin-2-yl)-N-(4-carbamimidoylphenyl)-2-hydroxyacetamide;
(R)-2-((R)-4-(3,5-bis(trifluoromethyl)phenyl)-3-oxomorpholin-2-yl)-2-hydroxy-N-(1-oxoisoindolin-5-yl)acetamide;
(2R)—N-(4-amidinophenyl)-2-hydroxy-2-[(2R)-3-oxo-4-(3-(4,4-difluoropiperidin-1-ylcarbonyl)phenyl)morpholin-2-yl]acetamide;
(2R)—N-(4-amidinophenyl)-2-hydroxy-2-[(2R)-3-oxo-4-(4-(pyrrolidin-1-ylsulfonyl)phenyl)morpholin-2-yl]acetamide;
(2R)—N-(4-amidinophenyl)-2-hydroxy-2-[(2R)-3-oxo-4-(4-(methylsulfonyl)phenyl)morpholin-2-yl]acetamide;
(2R)—N-(4-amidinophenyl)-2-hydroxy-2-[(2R)-3-oxo-4-(3-phenylphenyl)morpholin-2-yl]acetamide;
(2R)—N-(4-amidinophenyl)-2-hydroxy-2-[(2R)-3-oxo-4-(4-(pyrrolidin-1-ylcarbonyl)phenyl)morpholin-2-yl]acetamide;
(2R)—N-(4-amidinophenyl)-2-hydroxy-2-[(2R)-3-oxo-4-(4-(morpholin-4-ylcarbonyl)phenyl)morpholin-2-yl]acetamide;
(2R)—N-(4-amidinophenyl)-2-hydroxy-2-[(2R)-3-oxo-4-(4-(4,4-difluoropiperidin-1-ylcarbonyl)phenyl)morpholin-2-yl]acetamide;
(2R)—N-(4-amidinophenyl)-2-hydroxy-2-[(2R)-3-oxo-4-(3-(1,2,3,4-tetrahydroisoquinolin-2-ylcarbonyl)phenyl)morpholin-2-yl]acetamide;
(2R)—N-(4-amidinophenyl)-2-hydroxy-2-[(2R)-3-oxo-4-(3-(isoindolin-2-ylcarbonyl)phenyl)morpholin-2-yl]acetamide;
(2R)—N-(4-aminophenyl)-2-hydroxy-2-[(2R)-3-oxo-4-(3-(morpholin-4-ylcarbonyl)phenyl)morpholin-2-yl]acetamide;
(2R)—N-(4-amidinophenyl)-2-hydroxy-2-[(2R)-3-oxo-4-(3-(pyrrolidin-1-ylcarbonyl)phenyl)morpholin-2-yl]acetamide;

(2R)—N-(4-amidinophenyl)-2-hydroxy-2-[(2R)-3-oxo-4-(4-fluorophenyl)morpholin-2-yl]acetamide;

(2R)—N-(4-amidinophenyl)-2-hydroxy-2-[(2R)-3-oxo-4-(3,5-difluorophenyl)morpholin-2-yl]acetamide;

(2R)—N-(4-amidinophenyl)-2-hydroxy-2-[(2R)-3-oxo-4-(4-(pyrrolidin-1-ylsulfonyl)phenyl)morpholin-2-yl]acetamide;

(2R)—N-(4-amidinophenyl)-2-hydroxy-2-[(2R)-3-oxo-4-(4-(4-methylsulfonylpiperazin-1-ylcarbonyl)phenyl)morpholin-2-yl]acetamide;

(2R)—N-(4-amidinophenyl)-2-hydroxy-2-[(2R)-3-oxo-4-(2-fluoropyridin-5-yl)morpholin-2-yl]acetamide;

(R)—N-(3-aminobenzo[d]isoxazol-6-yl)-2-hydroxy-2-((R)-3-oxo-4-(4-(trifluoromethyl)phenyl)morpholin-2-yl)acetamide;

(R)—N-(3-amino-1H-indazol-6-yl)-2-hydroxy-2-((R)-3-oxo-4-(4-(trifluoromethyl)phenyl)morpholin-2-yl)acetamide;

(R)—N-(4-carbamimidoyl-3-fluorophenyl)-2-hydroxy-2-((R)-3-oxo-4-(4-(trifluoromethyl)phenyl)morpholin-2-yl)acetamide;

(R)—N-(4-carbamimidoylphenyl)-2-hydroxy-2-{(R)-3-oxo-4-[4-(trifluoromethyl)phenyl]morpholin-2-yl}acetamide;

(R)—N-(4-carbamimidoylphenyl)-2-hydroxy-2-((R)-3-oxo-4-(3-(trifluoromethyl)phenyl)morpholin-2-yl)acetamide;

N-(4-amino-7-quinazolinyl)-alpha(R)-hydroxy-3-oxo-4-[4-(trifluormethyl)phenyl]-2(R)-morpholineacetamide;

N-[4-(aminomethyl)phenyl]-alpha(R)-hydroxy-3-oxo-4-[4-(trifluoromethyl)phenyl]-2(R)-morpholineacetamide;

N-[4-(aminoiminomethyl)phenyl]-4-[3-(aminomethyl)phenyl]-alpha(R)-hydroxy-3-oxo-2(R)-morpholineacetamide; and N-[4-(aminocarbonyl)phenyl]-alpha(R)-hydroxy-3-oxo-4-[4-(trifluoromethyl)phenyl]-2(R)-morpholineacetamide;

(R)—N-(4-Carbamimidoylphenyl)-2-hydroxy-2-((R)-3-oxo-4-(3-(trifluoromethoxy)phenyl)morpholin-2-yl)acetamide;

(R)—N-(4-Carbamimidoylphenyl)-2-hydroxy-2-((R)-4-(2-methyl-3-oxoisoindolin-5-yl)-3-oxomorpholin-2-yl)acetamide;

(R)—N-(4-(Aminomethyl)phenyl)-2-hydroxy-2-((R)-4-(2-methyl-1-oxoisoindolin-5-yl)-3-oxomorpholin-2-yl)acetamide;

(R) —N(Aminomethyl)phenyl)-2-hydroxy-2-((R)-3-oxo-4-(3-(3-oxomorpholino)phenyl)morpholin-2-yl)acetamide;

(R)—N-(1-Aminoisoquinolin-6-yl)-2-hydroxy-2-((R)-3-oxo-4-(3-(3-oxomorpholino)phenyl)morpholin-2-yl)acetamide;

(R)—N-(4-Carbamimidoyl-3-chlorophenyl)-2-hydroxy-2-((R)-3-oxo-4-(3-(3-oxomorpholino)phenyl)morpholin-2-yl)acetamide;

(R)—N-(4-Carbamimidoyl-3-methylphenyl)-2-hydroxy-2-((R)-3-oxo-4-(3-(3-oxomorpholino)phenyl)morpholin-2-yl)acetamide;

(R)-2-Hydroxy-2-((R)-3-oxo-4-(3-(3-oxomorpholino)phenyl)morpholin-2-yl)-N-(1,2,3,4-tetrahydroisoquinolin-6-yl)acetamide;

2-(3-((R)-2-((R)-2-(4-Carbamimidoylphenylamino)-1-hydroxy-2-oxoethyl)-3-oxomorpholino)phenoxy)acetic acid;

Ethyl 2-(3-((R)-2-((R)-2-(4-(aminomethyl)phenylamino)-1-hydroxy-2-oxoethyl)-3-oxomorpholino)phenoxy)acetate;

(R)—N-(4-carbamimidoyl-2-ethylphenyl)-2-hydroxy-2-((R)-4-(2-methyl-3-oxoisoindolin-5-yl)-3-oxomorpholin-2-yl)acetamide;

(R)-2-Hydroxy-N-(2-methyl-1H-indol-5-yl)-2-((R)-3-oxo-4-(3-(3-oxomorpholino)phenyl)morpholin-2-yl)acetamide;

(R)—N-(4-carbamimidoylphenyl)-2-hydroxy-2-((R)-4-(2-methoxyphenyl)-3-oxomorpholin-2-yl)acetamide;

(R)—N-(4-carbamimidoylphenyl)-2-hydroxy-2-((R)-4-(2-fluorophenyl)-3-oxomorpholin-2-yl)acetamide;

(R)—N-(4-carbamimidoylphenyl)-2-hydroxy-2-((R)-4-(2-(difluoromethoxy)phenyl)-3-oxomorpholin-2-yl)acetamide;

(R)—N-(6-carbamimidoylpyridin-3-yl)-2-hydroxy-2-((R)-3-oxo-4-(3-(3-oxomorpholino)phenyl)morpholin-2-yl)acetamide;

N-[4-(aminoiminomethyl)phenyl]—[3-(1,1-dioxido-2-isoizolidinyl)phenyl]-alpha(R)-hydroxy-3-oxo-2(R)-morpholineacetamide;

(R)—N-(4-carbamimidoylphenyl)-2-((R)-4-(4-fluoro-2-methoxyphenyl)-3-oxomorpholin-2-yl)-2-hydroxyacetamide;

(R)—N-(4-carbamimidoylphenyl)-2-hydroxy-2-((R)-4-(2-isopropoxyphenyl)-3-oxomorpholin-2-yl)acetamide;

(R)-2-((R)-4-(2-(2-amino-2-oxoethoxy)phenyl)-3-oxomorpholin-2-yl)-N-(4-carbamimidoylphenyl)-2-hydroxyacetamide;

(R)—N-(4-carbamimidoyl-3-fluorophenyl)-2-hydroxy-2-((R)-3-oxo-4-(3-(3-oxomorpholino)phenyl)morpholin-2-yl)acetamide;

(R)—N-(4-carbamimidoyl-3,5-difluorophenyl)-2-hydroxy-2-((R)-3-oxo-4-(3-(3-oxomorpholino)phenyl)morpholin-2-yl)acetamide;

3-((R)-2-((R)-2-(4-carbamimidoyl-3-fluorophenylamino)-1-hydroxy-2-oxoethyl)-3-oxomorpholino)benzoic acid;

N-(2,3-Dihydro-1-iminio-1H-isoindol-5-yl)-alpha(R)-hydroxy-3-oxo-4-[3-(3-oxo-4-morpholinyl)phenyl]-2(R)-morpholineacetamide;

4-(3-Cyanophenyl)-N-(2,3-dihydro-1-imino-1H-isoindol-5-yl)-alpha(R)-hydroxy-3-oxo-2(R)-morpholineacetamide;

N-(2,3-Dihydro-1-imino-1H-isoindol-5-yl)-alpha(R)-hydroxy-3-oxo-4-[4-(1-pyrrolidinylcarbonyl)phenyl]-2(R)-morpholineacetamide;

N-(2,3-Dihydro-1-imino-1H-isoindol-5-yl)-4-[3-[(dimethylamino)carbonyl]phenyl]-alpha(R)-hydroxy-3-oxo-2(R)-morpholineacetamide;

n-(2,3-Dihydro-1-imino-1H-isoindol-5-yl)-alpha(R)-hydroxy-3-oxo-4-[3-(1-pyrrolidinylcarbonyl)phenyl]-2(R)-morpholineacetamide;

N-(2,3-Dihydro-1-imino-1H-isoindol-5-yl)-4-[4[(dimethylamino)carbonyl]phenyl]-alpha(R)-hydroxy-3-oxo-2(R)-morpholineacetamide;

N-[4-(Aminoiminomethyl)phenyl]-alpha(R)-hydroxy-3-oxo-4-[3-(1 h-tetrazol-5-yl)phenyl]-2(R)-morpholineacetamide;

N-(2,3-dihydro-1H-isoindol-5-yl)-alpha(R)-hydroxy-3-oxo-4-[3-(3-oxo-4-morpholinyl)phenyl]-2(R)-morpholineacetamide;

[4-[2(R)-[2-[[4-(Aminoiminomethyl)phenyl]amino]-1(R)-hydroxy-2-oxoethyl]-3-oxo-4-morpholinyl]phenyl]pentafluorosulfur,

[3-[2(R)-[2-[[4-(Aminoiminomethyl)phenyl]amino]-1(R)-hydroxy-2-oxoethyl]-3-oxo-4-morpholinyl]phenyl]pentafluorosulfur, (2R)—N-(4-amidinophenyl)-2-hydroxy-2-[2R]-3-oxo-4-(4-(1,1-dioxothiomorpholin-4-ylcarbonyl)phenyl)morpholin-2-yl]acetamide;

(2R)—N-(4-amidinophenyl)-2-hydroxy-2-[(2R)-3-oxo-4-(4-(dimethylaminocarbonyl)phenyl)morpholin-2-yl]acetamide;

(2R)—N-(4-amidinophenyl)-2-hydroxy-2-[(2R)-3-oxo-4-(4-(dimethylamino)sulfonyl)phenyl)morpholin-2-yl]acetamide;

(2R)—N-amidinophenyl)-2-hydroxy-2-[(2R)-3-oxo-4-(3-(dimethylaminocarbonyl)phenyl)morpholin-2-yl]acetamide;

(2R)—N-amidinophenyl-2-hydroxy-2-[(2R)-3-oxo-4-(4-fluoro-3-(morpholin-4-ylcarbonyl)phenyl)morpholin-2-yl]acetamide;

(2R)—N-(4-amidinophenyl)-2-hydroxy-2-[(2R)-3-oxo-4-(4-(dimethyl-$D_6$-aminocarbonyl)phenyl)morpholin-2-yl]acetamide;

(2R)—N-(4-amidinophenyl)-2-hydroxy-2-[(2R)-3-oxo-4-(3-(dimethyl-$D_6$-aminocarbonyl)phenyl)morpholin-2-yl]acetamide;

(2R)—N-(4-amidinophenyl)-2-hydroxy-2-[(2R)-3-oxo-4-(3-(dimethylaminocarbonyl) 4-fluorophenyl)morpholin-2-yl]acetamide;

(2R)—N-(4-amidinophenyl)-2-hydroxy-2-[(2R)-3-oxo 4-(4-methoxy-$D_3$-phenyl)morpholin-2-yl]acetamide;

(2R)—N-(4-amidinophenyl)-2-hydroxy-2-[(2R)-3-oxo-4-(3-methoxy-$D_3$-phenyl)morpholin-2-yl]acetamide;

(2R)—N-(4-amidinophenyl)-2-hydroxy-2-[(2R)-3-oxo-4-(4-fluoro-3-(pyrrolidin-1-ylcarbonyl)phenyl)morpholin-2-yl]acetamide;

(2R)—N-(4-amidinophenyl)-2-hydroxy-2-[(2R)-3-oxo-4-(3-(dimethylaminocarbonyl)-4-methylphenyl)morpholin-2-yl]acetamide;

(2R)—N-(4-amidinophenyl)-2-hydroxy-2-[(2R)-3-oxo-4-(4-methyl-3-(morpholin-4-ylcarbonyl)phenyl)morpholin-2-yl]acetamide;

(2R)—N-(4-amidinophenyl)-2-hydroxy-2-[(2R)-3-oxo-4-(4-methyl-3-(pyrrolidin-1-ylcarbonyl)phenyl)morpholin-2-yl]acetamide;

(2R)—N-(4-amidinophenyl)-2-hydroxy-2-[(2R)-3-oxo-4-(3-fluoro-5-(pyrrolidin-1-ylcarbonyl)phenyl)morpholin-2-yl]acetamide;

(2R)—N-(4-amidinophenyl)-2-hydroxy-2-[(2R)-3-oxo-4-(3-fluorO-5-(morpholin-4-ylcarbonyl)phenyl)morpholin-2-yl]acetamide;

(2R)—N-(4-amidinophenyl)-2-hydroxy-2-[(2R)-3-oxo-4-(3-(dimethylaminocarbonyl)-5-fluorophenyl)morpholin-2-yl]acetamide;

(2R)—N-(4-amidinophenyl)-2-hydroxy-2-[2R]-3-oxo-(3-(dimethylaminocarbonyl)-2-methylphenyl)morpholin-2-yl]acetamide;

(2R)—N-(4-amidinophenyl)-2-hydroxy-2-[(2R)-3-oxo-4-(3-(piperidin-1-ylcarbonyl)phenyl)morpholin-2-yl]acetamide;

(2R)—N-(amidinophenyl)-2-hydroxy-2-[(2R)-3-oxo-4-(3-(azetidin-1-ylcarbonyl)phenyl)morpholin-2-yl]acetamide;

(2R)—N-(4-amidinophenyl)-2-hydroxy-2-[(2R)-3-oxo-4-(3-((2R,5R)-(−)-trans-dimethylpyrrolidin-1-ylcarbonyl)phenyl)morpholin-2-yl]acetamide;

(2R)—N-(4-amidinophenyl)-2-hydroxy-2-[(2R)-3-oxo-4-(3-fluorophenyl)morpholin-2-yl]acetamide;

(2R)—N-(4-amidinophenyl)-2-hydroxy-2-[(2R)-3-oxo-4-(3,4,5-trifluorophenyl)morpholin-2-yl]acetamide;

(2R)—N-(4-amidinophenyl)-2-hydroxy-2-[(2R)-3-oxo-4-(3,4-difluorophenyl)morpholin-2-yl]acetamide;

(2R)—N-(4-amidinophenyl)-2-hydroxy-2-[(2R)-3-oxo-4-(2,4-difluoropyridin-3-yl)morpholin-2-yl]acetamide;

(2R)—N-(4-amidinophenyl)-2-hydroxy-2-[(2R)-3-oxo-4-(4,5-difluoropyridin-3-yl)morpholin-2-yl]acetamide;

(2R)—N-(4-amidinophenyl)-2-hydroxy-2-[(2R)-3-oxo-4-(4-carboxyphenyl)morpholin-2-yl]acetamide;

(2R)—N-(4-amidinophenyl)-2-hydroxy-2-[(2R)-3-oxo-4-(3-(carboxymethyl)methyl)carbamoylphenyl)morpholin-2-yl]acetamide;

(2R)—N-(4-amidinophenyl)-2-hydroxy-2-[(2R)-3-oxo-4-(3-carboxyphenyl)morpholin-2-yl]acetamide;

(2R)—N-(4-amidinophenyl)-2-hydroxy-2-[(2R)-3-oxo-4-(4-methoxycarbonylphenyl)morpholin-2-yl]acetamide;

(2R)—N-(4-amidinophenyl)-2-hydroxy-2-[(2R)-3-oxo-4-(3-methoxycarbonylphenyl)morpholin-2-yl]acetamide;

(2R)—N-(4-amidinophenyl)-2-hydroxy-2-[(2R)-3-oxo-4-(3-carboxy-4-fluorophenyl)morpholin-2-yl]acetamide;

(2R)—N-(4-amidinophenyl)-2-hydroxy-2-[(2R)-3-oxo-4-(3-(methoxycarbonylmethyl)methyl)carbamoylphenyl)morpholin-2-yl]acetamide;

(2R)—N-amidinophenyl)-2-hydroxy-2-[(2R)-3-oxo-4-(3-carboxymethylphenyl)morpholin-2-yl]acetamide;

(2R)—N-(4-amidinophenyl)-2-hydroxy-2-[(2R)-3-oxo-4-(3-carboxy-5-fluorophenyl)morpholin-2-yl]acetamide;

(2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide;

(2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide;

(2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide;

(2R)-2-Hydroxy-N-(1-imino-2,3-dihydroisoindol-5-yl)-2-[(2R)-3-oxo-4-(3-oxo-1,2,3,4-tetrahydroisoquinolin-7-yl)morpholin-2-yl]acetamide;

(2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide;

(2R)-2-Hydroxy-N-(1-imino-2,3-dihydroisoindol-5-yl)-2-[(2R)-4-(2-methyl-3-oxo-1,2-dihydroisoindol-5-yl)-3-oxo-morpholin-2-yl]acetamide;

(2R)-2-Hydroxy-N-(1-imino-2,3-dihydroisoindol-5-yl)-2-[(2R)-3-oxo-4-(3-oxo-2-(2,2,2-trifluoroethyl)-1,2-dihydroisoindol-5-yl)morpholin-2-yl]acetamide;

(2R)-2-Hydroxy-N-(1-imino-2,3-dihydroisoindol-5-yl)-2-[(2R)-3-oxo-4-(3-oxo-2-propyl-1,2-dihydroisoindol-5-yl)morpholin-2-yl]acetamide;

(2R)-2-Hydroxy-N-(1-imino-2,3-dihydroisoindol-5-yl)-2-[(2R)-4-(2-methyl-3-oxo-1,2-dihydroisoindol-6-yl)-3-oxo-morpholin-2-yl]acetamide;

(2R)-2-[(2R)-4(2-(Difluoromethoxy)phenyl)-3-oxo-morpholin-2-yl]-2-hydroxy-N-(1-imino-2,3-dihydroisoindol-5-yl)acetamide;

(2R)-2-[(2R)-4-(2-Fluorophenyl)-3-oxo-morpholin-2-yl]-2-hydroxy-N-(1-imino-2,3-dihydroisoindol-5-yl)acetamide;

(2R)-2-[(2R)-4-(4-Fluorophenyl)-3-oxo-morpholin-2-yl]-2-hydroxy-N-(1-imino-2,3-dihydroisoindol-5-yl)acetamide;

(2R)-2-[(2R)-4-(3-Fluorophenyl)-3-oxo-morpholin-2-yl]-2-hydroxy-N-(1-imino-2,3-dihydroisoindol-5-yl)acetamide;

(2R)-2-[(2R)-4-(3,4-Difluorophenyl)-3-oxo-morpholin-2-yl]-2-hydroxy-N-(1-imino-2,3-dihydroisoindol-5-yl)acetamide;

(2R)-2-[(2R)-4-(3,5-Difluorophenyl)-3-oxo-morpholin-2-yl]-2-hydroxy-N-(1-imino-2,3-dihydroisoindol-5-yl)acetamide;

(2R)-2-Hydroxy-N-(1-imino-2,3-dihydroisoindol-5-yl)-2-[(2R)-3-oxo-4-(3,4,5-trifluorophenyl)morpholin-2-yl]acetamide;

(2R)-2-Hydroxy-N-(1-imino-2,3-dihydroisoindol-5-yl)-2-[(2R)-3-oxo-4-(4-trifluoromethylphenyl)morpholin-2-yl]acetamide;

(2R)-2-Hydroxy-N-(1-imino-2,3-dihydroisoindol-5-yl)-2-[(2R)-3-oxo-4-(3-trifluoromethylphenyl)morpholin-2-yl]acetamide;

(2R)-2-[(2R)-4-(4-Fluoro-3-(morpholin-4-ylcarbonyl)phenyl)-3-oxo-morpholin-2-yl]-2-hydroxy-N-(1-imino-2,3-dihydroisoindol-5-yl)acetamide;

(2R)-2-[(2R)-4(3-Dimethylaminocarbonyl)-4-fluorophenyl)-3-oxo-morpholin-2-yl]-2-hydroxy-N-(1-imino-2,3-dihydroisoindol-5-yl)acetamide;

(2R)-2-[(2R)-4-(4-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide;

(2R)-2-[(2R)-4-(3-(Dimethylaminocarbonyl)-5-fluorophenyl)-3-oxo-morpholin-2-yl]-2-hydroxy-N-(1-imino-2,3-dihydroisoindol-5-yl)acetamide;

(2R)-2-[(2R)-4-(5-Fluoro-3-(pyrrolidin-1-ylcarbonyl)phenyl)-3-oxo-morpholin-2-yl]-2-hydroxy-N-(1-imino-2,3-dihydroisoindol-5-yl)acetamide;

(2R)-2-[(2R)-4-(5-Fluoro-3-(morpholin-4-ylcarbonyl)phenyl)-3-oxo-morpholin-2-yl]-2-hydroxy-N-(1-imino-2,3-dihydroisoindol-5-yl)acetamide;

(2R)-2-[(2R)-4-(3-Carboxyphenyl)-3-oxo-morpholin-2-yl]-2-hydroxy-N-(1-imino-2,3-dihydroisoindol-5-yl)acetamide; and (2R)-2-[(2R)-4-(4-Chlorophenyl)-3-oxo-morpholin-2-yl]-2-hydroxy-N-(1-imino-2,3-dihydroisoindol-5-yl)acetamide;

or a pharmaceutically acceptable salt or solvate thereof.

16. A compound of formula (I) of claim 1 consisting of:

(2R)-2-Hydroxy-N-(1-imino-2,3-dihydroisoindol-5-yl)-2-[(2R)-3-oxo-4-(3-oxo-1,2-dihydroisoindol-5-yl)morpholin-2-yl]acetamide;

(2R)-2-Hydroxy-N-(1-imino-2,3-dihydroisoindol-5-yl)-2-[(2R)-3-oxo-4-(3-oxo-1,2-dihydroisoindol-6-yl)morpholin-2-yl]acetamide;

(2R)-2-Hydroxy-N-(1-imino-2,3-dihydroisoindol-5-yl)-2-[(2R)-3-oxo-4-(3-oxo-1,2,3,4-tetrahydroisoquinolin-6-yl)morpholin-2-yl]acetamide;

(2R)-2-Hydroxy-N-(1-imin-2,3-dihydroisoindol-5-yl)-2-[(2R)-3-oxo-4(3-oxo-1,2,3,4-tetrahydroisoquinolin-7-yl)morpholin-2-yl]acetamide;

(2R)-2-Hydroxy-N-(1-imino-2,3-dihydroisoindol-5-yl)-2-[(2R)-3-oxo-4-(2-oxo-1,2,3,4-tetrahydroquinolin-6-yl)morpholin-2-yl]acetamide;

or a pharmaceutically acceptable salt or solvate thereof.

17. A pharmaceutical composition comprising at least one compound of claim 1 or a pharmaceutically acceptable salt thereof and at least one pharmaceutically acceptable carrier.

18. A pharmaceutical composition comprising:
a therapeutically effective amount of at least one compound of claim 1 or a pharmaceutically acceptable salt thereof, and at least one pharmaceutically acceptable carrier, and an effective amount of at least one agent selected from the group consisting of: (a) anticoagulants, (b) anti-thrombin agents, (c) anti-platelet agents, (d) fibrinolytic, (e) hypolipidemic agents, (f) antihypertensive agents, and (g) anti-ischemic agents.

19. A pharmaceutical composition comprising:
a therapeutically effective amount of at least one compound of claim 1 or a pharmaceutically acceptable salt thereof, and at least one pharmaceutically acceptable carrier, and an effective amount of at least one agent selected from the group consisting of (a-1) warfarin, (a-2) heparin, (a-3) aprotinin, (a-4) synthetic pentasaccharide, (a-5) direct acting thrombin inhibitors including hirudin and argatroban, (a-6) a factor VIIa inhibitor, (a-7) a factor VIIIa inhibitor, (a-8) a factor IXa inhibitor different from the compounds of Formula (I), (a-9) a factor Xa inhibitor, (a-10) a factor XIa inhibitor, (a-11) a thrombin inhibitor, (a-12) a TAFI, (a-13) a fibrinogen inhibitor, (b-1) a boroarginine derivative, (b-2) a boropeptide, (b-3) heparin, (b-4) hirudin, (b-5) argatroban, (c-1) a NSAID, (c-2) a IIb/IIIa antagonist, (c-3) a thromboxane-A2-receptor antagonist, (c-4) a thromboxane-A2-synthetase inhibitor, (c-5) a PDE-III inhibitor, (c-6) a PDE V inhibitor, (c-7) a ADP receptor antagonist, (c-8) an antagonist of the purinergic receptor P2Y1, (c-9) an antagonist of the purinergic receptor P2Y12, (d-1) tissue plasminogen activator (TPA, natural or recombinant) and modified forms thereof; (d-2) anistreplase, (d-3) urokinase, (d-4) streptokinase, (d-5) tenecteplase (TNK), (d-6) lanoteplase (nPA), (d-7) a factor VIIa inhibitor, (d-8) a PAI-I inhibitor, (d-9) an alpha-2-antiplasmin inhibitor, (d-10) an anisoylated plasminogen streptokinase activator complex, (e-1) a HMG-CoA reductase inhibitor, (e-2) a squalene synthetase inhibitor, (e-3) a fibrate, (e-4) a bile acid sequestrant, (e-5) an ACAT inhibitor, (e-6) a MTP inhibitor, (e-7) a lipooxygenase inhibitor, (e-8) a cholesterol absorption inhibitor, (e-9) a cholesterol ester transfer protein inhibitor, (f-1) an alpha adrenergic blocker, (f-2) a beta adrenergic blocker, (f-3) a calcium channel blocker, (f-4) a diuretics, (f-5) a rennin inhibitor, (f-6) an angiotensin-converting enzyme inhibitor, (f-7) an angiotensin-II-receptor antagonist, (f-8) an ET receptor antagonist, (f-9) a Dual ET/AII antagonist, (f-10) a neutral endopeptidase inhibitors, (f-11) a vasopepsidase inhibitor, (g-1) a Class I agent, (g-2) a Class II agent, (g-3) a Class III agent, a (g-4) Class IV agent, (g-5) a K+ cannel opener, (g-6) an IKur inhibitor and (g-7) a cardiac glycoside.

* * * * *

UNITED STATES PATENT AND TRADEMARK OFFICE
CERTIFICATE OF CORRECTION

| | |
|---|---|
| PATENT NO. | : 8,642,582 B2 |
| APPLICATION NO. | : 12/744736 |
| DATED | : February 4, 2014 |
| INVENTOR(S) | : Nishida Hidemitsu et al. |

It is certified that error appears in the above-identified patent and that said Letters Patent is hereby corrected as shown below:

Title Page, item (73) Assignee should read as follows:

Merck Sharp & Dohme Corp.
Rahway, NJ

Mochida Pharmaceutical Co., Ltd.
Tokyo, Japan

Signed and Sealed this
Twenty-sixth Day of August, 2014

Michelle K. Lee
*Deputy Director of the United States Patent and Trademark Office*